United States Patent
Jakob et al.

(10) Patent No.: US 12,110,293 B2
(45) Date of Patent: Oct. 8, 2024

(54) SUBSTITUTED TRIAZOLO QUINOXALINE DERIVATIVES

(71) Applicant: GRÜNENTHAL GMBH, Aachen (DE)

(72) Inventors: Florian Jakob, Aachen (DE); Jo Alen, Averbode (BE); Simon Lucas, Bad König (DE); Tobias Craan, Niedernberg (DE); Ingo Konetzki, Monschau (DE); Achim Kless, Aachen (DE); Stefan Schunk, Aachen (DE); Paul Ratcliffe, Aachen (DE); Sebastian Wachten, Aachen (DE); Simon Cruwys, Aachen Aachen (DE)

(73) Assignee: GRÜNENTHAL GMBH, Aachen (DE)

( * ) Notice: Subject to any disclaimer, the term of this patent is extended or adjusted under 35 U.S.C. 154(b) by 798 days.

(21) Appl. No.: 17/152,930

(22) Filed: Jan. 20, 2021

(65) Prior Publication Data

US 2021/0139488 A1    May 13, 2021

Related U.S. Application Data

(63) Continuation of application No. PCT/EP2019/069611, filed on Jul. 22, 2019.

(30) Foreign Application Priority Data

Jul. 20, 2018  (EP) ..................................... 18184613

(51) Int. Cl.
C07D 487/04    (2006.01)

(52) U.S. Cl.
CPC .................. C07D 487/04 (2013.01)

(58) Field of Classification Search
CPC .................................................. C07D 487/04
See application file for complete search history.

(56) References Cited

U.S. PATENT DOCUMENTS

| | | | |
|---|---|---|---|
| 6,005,835 A | 12/1999 | Tsuji et al. | |
| 8,193,187 B2 | 6/2012 | Matsuda et al. | |
| 8,569,493 B2 | 10/2013 | Matsuda et al. | |
| 10,189,796 B2 | 1/2019 | Kawashima et al. | |
| 10,435,379 B2 | 10/2019 | Kawashima et al. | |
| 10,874,670 B2 | 12/2020 | Cai et al. | |
| 10,981,918 B2 * | 4/2021 | Jakob .................. | C07D 487/04 |
| 2004/0019269 A1 | 1/2004 | Schaefer et al. | |
| 2010/0137307 A1 | 6/2010 | Matsuda et al. | |
| 2012/0129866 A1 | 5/2012 | Matsuda et al. | |
| 2013/0303537 A1 | 11/2013 | Matsuda et al. | |
| 2018/0244633 A1 | 8/2018 | Kawashima et al. | |
| 2019/0106393 A1 | 8/2019 | Kawashima et al. | |
| 2019/0358225 A1 | 11/2019 | Cai et al. | |
| 2019/0359577 A1 | 11/2019 | Kawashima et al. | |

FOREIGN PATENT DOCUMENTS

| | | |
|---|---|---|
| CN | 1125446 C | 10/2003 |
| WO | 2004/093805 A2 | 11/2004 |
| WO | 2008/146871 A1 | 12/2008 |
| WO | 2009/003567 A1 | 1/2009 |
| WO | 2009/035067 A1 | 3/2009 |
| WO | 2013/034755 A1 | 3/2013 |
| WO | 2013/186666 A1 | 12/2013 |
| WO | 2017/034006 A1 | 2/2017 |
| WO | 2018/127195 A1 | 7/2018 |
| WO | 2020/016453 A1 | 1/2020 |

OTHER PUBLICATIONS

Buttgereit F. et al., "Polymyalgia Rheumatica and Giant Cell Arteritis a Systematic Review", JAMA. 2016;315 (22):2442-2458).
Buttgereit F. et al., "Novel Glucocorticoids: Where are we now and where do we want to go?", Clin. Exp. Rheumatol. 2015, vol. 33, pp. S29-S33.
De Bosscher K. et al., "Activation of the Glucocorticoid Receptor in Acute Inflammation: The SEDIGRAM Concept", Trends Pharmacol. Sci. Jan. 2016;37(1):4-16.
Cui et al., "Synthesis and Anticonvulsant Activity of 1-Substituted-7-Benzyloxy-4,5dihydro-[1,2,4]triazolo[4,3-a]quinoline", Biological and Pharmaceutical Bulletin, 2005, vol. 28, pp. 1216-1220.
Hapgood J.P. et al., "Glucocorticoid-independent Modulation of GR activity: Implications for Immunotherapy", Pharmacol. Ther. Sep. 2016; 165: 93-113.
Hartmann K. et al., "Molecular Actions of Glucocorticoids in Cartilage and Bone During Health, Disease, and Steroid Therapy", Physiol. Rev. Vol. 96, No. 2, pp. :409-447, 2016.
Liu D. et al., "A Practical guide to the monitoring and management of the complications of systemic corticosteriod therapy", Allergy Asthma Clin. Immunol. Aug. 15, 2013;9(1):30, pp. 1-25.
"Metal-Catalyzed Cross-Coupling Reactions and More", de Meijere et al., Eds., Wiley, 2014.
Nicolaou K.C. et al., "Palladiumkatalysierte Kreuzkupplungen in der Totalsynthese", Angew. Chem., 2005, 117, 4516-4563.
Reiter L.A. et al., "The Synthesis of Spirocyclic [1,2,4]Triazolo[4,3-a]Quinolines as Potential Ligands for the Benzodiazepine Receptor", Heterocycles, 1992, 34, 771-780.

(Continued)

*Primary Examiner* — Golam M Shameem
(74) *Attorney, Agent, or Firm* — Norris McLaughlin, P.A.

(57) ABSTRACT

The present invention relates to compounds according to general formula (I)

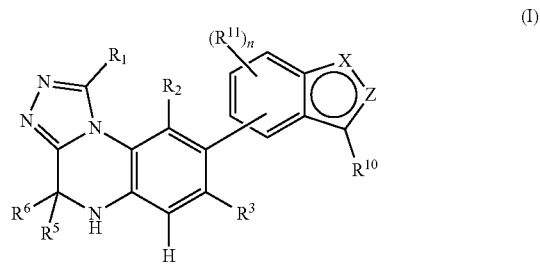

which act as modulators of the glucocorticoid receptor and can be used in the treatment and/or prophylaxis of disorders which are at least partially mediated by the glucocorticoid receptor.

18 Claims, No Drawings

(56) References Cited

OTHER PUBLICATIONS

Johansson Seechurn C.C.C. et al., "Palladium-Catalyzed Cross-Coupling: A Historical Contextual Perspective to the 2010 Nobel Prize", Angew. Chem. Int. Ed., 2012, 51, 5062-5085.
"Science of Synthesis: Compounds with One Saturated Carbon-Heteroatom Bond", vol. 35, Houben-Weyl, 2007 (Schaumann E., vol. Ed.).
Tanimori S. et al., "A General and Practical Access to Chiral Quinoxalinones with Low Copper-Catalyst Loading", Adv. Synth. Catal., 2010, 352, 2531-2537.

* cited by examiner

SUBSTITUTED TRIAZOLO QUINOXALINE DERIVATIVES

This application is a continuation of International Patent Application No. PCT/EP2019/069611, filed Jul. 22, 2019, which claims benefit of European Patent Application No. 18184613.0, filed Jul. 20, 2018, the entire disclosures of each of which are hereby incorporated herein by reference.

The present invention relates to compounds according to general formula (I)

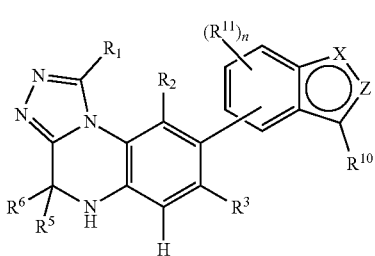

which act as modulators of the glucocorticoid receptor and can be used in the treatment and/or prophylaxis of disorders which are at least partially mediated by the glucocorticoid receptor.

Glucocorticoids (GC) exert strong anti-inflammatory, immunosuppressive and disease-modifying therapeutic effects mediated by the glucocorticoid receptor (GR). They have been widely used to treat inflammatory and immune diseases for decades and still represent the most effective therapy in those conditions. However, chronic GC treatment of inflammatory diseases is hampered by GC-associated adverse effects. These undesired side effects include insulin resistance, diabetes, hypertension, glaucoma, depression, osteoporosis, adrenal suppression and muscle wasting with osteoporosis and diabetes being the most severe ones from the physician's point of view (Hapgood J P. et al., Pharmacol Ther. 2016 September; 165: 93-113; Buttgereit F. el al, Clin Exp Rheumatol. 2015 July-August; 33(4 Suppl 92):S29-33; Hartmann K. et al, Physiol Rev. 2016 April; 96(2):409-47).

One example of an oral glucocorticoid is prednisone which is frequently prescribed for the treatment of several inflammatory disorders (De Bosscher K et al., Trends Pharmacol Sci. 2016 January; 37(1):4-16; Buttgereit F. et A., JAMA. 2016; 315(22):2442-2458). As GC cause adrenal suppression, prednisolone withdrawal symptoms can be severe if the drug is discontinued abruptly when all the signs of the disease have disappeared. Thus gradual GC tapering to physiological doses is frequently part of treatment protocols to reduce the risk of relapse and other withdrawal symptoms (Liu D. et al., Allergy Asthma Clin Immunol. 2013 Aug. 15; 9(1):30). Therefore, there is high medical need for novel potent anti-inflammatory drugs with less adverse effects.

Recent research has focused on the development of partial agonists or selective glucocorticoid receptor modulators which activate the pathways for the inhibition of inflammation but avoid targeting the pathways that lead to the GC-associated adverse effects. Most of these effects have been demonstrated to be mediated by different GR-dependent genomic mechanisms termed transactivation and transrepression. The anti-inflammatory actions of GC are mainly attributable to the transrepression of inflammatory genes while certain side effects are predominantly mediated via transactivation of several genes. According to the nature of a ligand the GR can be selectively modulated in a specific conformation which favors transrepression over transactivation resulting in an improved therapeutic benefit (De Bosscher K et al., Trends Pharmacol Sci. 2016 January; 37(1):4-16). The concept of such dissociating ligands was already defined about two decades ago and several compounds have been identified and were evaluated in preclinical and clinical testing but none of them has as yet been approved for clinical use.

Compounds which are active as modulators of the glucocorticoid receptor are also known from WO 2009/035067 and WO 2017/034006.

It was an object of the present invention to provide novel compounds which are modulators of the glucocorticoid receptor and which preferably have advantages over the compounds of the prior art. The novel compounds should in particular be suitable for use in the treatment and/or prophylaxis of disorders or diseases which are at least partially mediated by the glucocorticoid receptor.

This object has been achieved by the subject-matter of the patent claims.

It was surprisingly found that the compounds according to the present invention are highly potent modulators of the glucocorticoid receptor.

The present invention relates to a compound according to general formula (I),

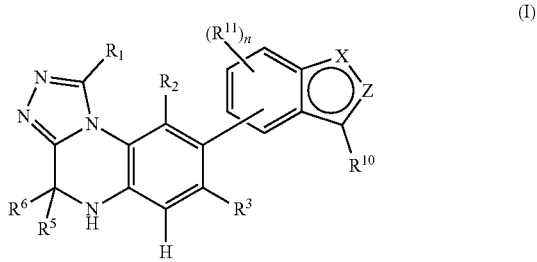

wherein
$R^1$ represents H; $C_{1-10}$-alkyl, $C_{3-10}$-cycloalkyl, 3 to 7 membered heterocycloalkyl, aryl, or 5 or 6 membered heteroaryl;
  wherein $C_{3-10}$-cycloalkyl. 3 to 7 membered heterocycloalkyl, aryl and 5 or 6-membered heteroaryl can optionally be bridged via $C_{1-6}$-alkylene:
$R^2$ represents H; F; Cl; Br; I; CN; $C_{1-10}$-alkyl; $C_{3-10}$-cycloalkyl; O—$C_{1-10}$-alkyl; N(H)($C_{1-10}$-alkyl), N($C_{1-10}$-alkyl)$_2$; C(O)—$C_{1-10}$-alkyl; C(O)—O—$C_{1-10}$-alkyl; C(O)—NH$_2$; C(O)—N(H)($C_{1-10}$-alkyl); C(O)—N($C_{1-10}$-alkyl)$_2$; O—$C_{3-10}$-cycloalkyl; N(H)($C_{3-10}$-cycloalkyl), N($C_{1-10}$-alkyl)($C_{3-10}$-cycloalkyl); C(O)—$C_{3-10}$-cycloalkyl; C(O)—O—$C_{3-10}$-cycloalkyl; C(O)—N(H)($C_{3-10}$-cycloalkyl) or C(O)—N($C_{1-10}$-alkyl)($C_{3-10}$-cycloalkyl);
  wherein $C_{3-10}$-cycloalkyl can optionally be bridged via $C_{1-6}$-alkylene:
$R^3$ represents H; F; Cl; Br; I; CN; $C_{1-10}$-alkyl; $C_{3-10}$-cycloalkyl; O—$C_{1-10}$-alkyl; N(H)($C_{1-10}$-alkyl); N($C_{1-10}$-alkyl)$_2$; C(O)—$C_{1-10}$-alkyl; C(O)—O—$C_{1-10}$-alkyl; C(O)—NH$_2$; C(O)—N(H)($C_{1-10}$-alkyl); C(O)—N($C_{1-10}$-alkyl)$_2$; O—$C_{3-10}$-cycloalkyl; N(H)($C_{3-10}$-cycloalkyl), N($C_{1-10}$-alkyl)($C_{3-10}$-cycloalkyl); C(O)—$C_{3-10}$-cycloalkyl; C(O)—O—$C_{3-10}$-cycloalkyl; C(O)—N(H)($C_{3-10}$-cycloalkyl) or C(O)—N($C_{1-10}$-alkyl)($C_{3-10}$-cycloalkyl);

wherein $C_{3-10}$-cycloalkyl can optionally be bridged via $C_{1-6}$-alkylene:

$R^5$ and $R^6$ represent independently from one another H or unsubstituted $C_{1-4}$-alkyl;

X represents N or $NR^7$;

Z represents N, $NR^7$ or $CR^9$;

with the proviso that when X represents $NR^7$, Z represents N or $CR^9$;

when X represents N, Z represents $NR^7$;

$R^7$ represents H or $L-R^8$; wherein

L represents bond; S(O); S(O)$_2$; $C_{1-6}$-alkylene; C(O); $C_{1-6}$-alkylene-C(O); C(O)—O; $C_{1-6}$-alkylene-C(O)—O; $C_{1-6}$-alkylene-N(H)—C(O); $C_{1-6}$-alkylene-N($C_{1-10}$-alkyl)-C(O); $C_{1-6}$-alkylene-N(H)—C(O)—O; $C_{1-6}$-alkylene-N($C_{1-10}$-alkyl)-C(O)—O; O; NH or N($C_{1-10}$-alkyl);

$R^8$ represents $C_{1-10}$-alkyl; $C_{3-10}$-cycloalkyl or 3 to 7 membered heterocycloalkyl; wherein $C_{3-10}$-cycloalkyl and 3 to 7 membered heterocycloalkyl can optionally be bridged via $C_{1-6}$-alkylene:

$R^9$ and $R^{10}$ represent independently from one another H; F; Cl; Br; I; CN; $C_{1-10}$-alkyl; $C_{3-10}$-cycloalkyl; 3 to 7 membered heterocycloalkyl; S(O)—($C_{1-10}$-alkyl); S(O)—($C_{3-10}$-cycloalkyl); S(O)-(3 to 7-membered heterocycloalkyl); S(O)$_2$—($C_{1-10}$-alkyl); S(O)$_2$—($C_{3-10}$-cycloalkyl); S(O)$_2$-(3 to 7 membered heterocycloalkyl); P(O)—($C_{1-10}$-alkyl)$_2$; P(O)($C_{1-10}$-alkyl)($C_{3-10}$-cycloalkyl); P(O)($C_{1-10}$-alkyl)(3 to 7-membered heterocycloalkyl); P(O)—(O—$C_{1-10}$-alkyl)$_2$; P(O)(O—$C_{1-10}$-alkyl)(O—$C_{3-10}$-cycloalkyl); P(O)(O—$C_{1-10}$-alkyl)(O-(3 to 7-membered heterocycloalkyl)); O—$C_{1-10}$-alkyl; S—$C_{1-10}$-alkyl; N(H)($C_{1-10}$-alkyl), N($C_{1-10}$-alkyl)$_2$; C(O)—$C_{1-10}$-alkyl; C(O)—O—$C_{1-10}$-alkyl; C(O)—NH$_2$; C(O)—N(H)($C_{1-10}$-alkyl); C(O)—N($C_{1-10}$-alkyl)$_2$; O—$C_{3-10}$-cycloalkyl; N(H)($C_{3-10}$-cycloalkyl), N($C_{1-10}$-alkyl)($C_{3-10}$-cycloalkyl); C(O)—$C_{3-10}$-cycloalkyl; C(O)—O—$C_{3-10}$-cycloalkyl; C(O)—N(H)($C_{3-10}$-cycloalkyl); C(O)—N($C_{1-10}$-alkyl)($C_{3-10}$-cycloalkyl); O-3 to 7-membered heterocycloalkyl; N(H)(3 to 7-membered heterocycloalkyl), N($C_{1-10}$-alkyl)(3 to 7-membered heterocycloalkyl); C(O)-3 to 7-membered heterocycloalkyl; C(O)—O-(3 to 7-membered heterocycloalkyl); C(O)—N(H)(3 to 7-membered heterocycloalkyl) or C(O)—N($C_{1-10}$-alkyl)(3 to 7-membered heterocycloalkyl);

wherein $C_{3-10}$-cycloalkyl and 3 to 7 membered heterocycloalkyl can optionally be bridged via $C_{1-6}$-alkylene;

$R^{11}$ represents F; Cl; Br; I; CN; $C_{1-10}$-alkyl; O—$C_{1-10}$-alkyl; NO$_2$; OH, NH$_2$; $C_{3-10}$-cycloalkyl; 3 to 7-membered heterocycloalkyl; S(O)—($C_{1-10}$-alkyl); S(O)—($C_{3-10}$-cycloalkyl); S(O)-(3 to 7-membered heterocycloalkyl); S(O)$_2$—($C_{1-10}$-alkyl); S(O)$_2$—($C_{3-10}$-cycloalkyl); S(O)$_2$-(3 to 7-membered heterocycloalkyl); P(O)—($C_{1-10}$-alkyl)$_2$; P(O)($C_{1-10}$-alkyl)($C_{3-10}$-cycloalkyl); P(O)($C_{1-10}$-alkyl)(3 to 7-membered heterocycloalkyl); P(O)—(O—$C_{1-10}$-alkyl)$_2$; P(O)(O—$C_{1-10}$-alkyl)(O—$C_{3-10}$-cycloalkyl); P(O)(O—$C_{1-10}$-alkyl)(O-(3 to 7-membered heterocycloalkyl)); O—$C_{1-10}$-alkyl; N(H)($C_{1-10}$-alkyl), N($C_{1-10}$-alkyl)$_2$; C(O)—$C_{1-10}$-alkyl; C(O)—O—$C_{1-10}$-alkyl; C(O)—NH$_2$; C(O)—N(H)($C_{1-10}$-alkyl); C(O)—N($C_{1-10}$-alkyl)$_2$; O—$C_{3-10}$-cycloalkyl; N(H)($C_{3-10}$-cycloalkyl), N($C_{1-10}$-alkyl)($C_{3-10}$-cycloalkyl); C(O)—$C_{3-10}$-cycloalkyl; C(O)—O—$C_{3-10}$-cycloalkyl; C(O)—N(H)($C_{3-10}$-cycloalkyl); C(O)—N($C_{1-10}$-alkyl)($C_{3-10}$-cycloalkyl); O-3 to 7-membered heterocycloalkyl; N(H)(3 to 7-membered heterocycloalkyl), N($C_{1-10}$-alkyl)(3 to 7-membered heterocycloalkyl); C(O)-3 to 7-membered heterocycloalkyl; C(O)—O-(3 to 7-membered heterocycloalkyl); C(O)—N(H)(3 to 7-membered heterocycloalkyl) or C(O)—N($C_{1-10}$-alkyl)(3 to 7-membered heterocycloalkyl);

wherein $C_{3-10}$-cycloalkyl and 3 to 7 membered heterocycloalkyl can optionally be bridged via $C_{1-6}$-alkylene;

n represents 0, 1, 2 or 3;

wherein $C_{1-10}$-alkyl, $C_{1-4}$-alkyl and $C_{1-6}$-alkylene in each case independently from one another is linear or branched, saturated or unsaturated;

wherein $C_{1-10}$-alkyl, $C_{1-4}$-alkyl, Cm-alkylene, $C_{3-10}$-cycloalkyl and 3 to 7 membered heterocycloalkyl in each case independently from one another are unsubstituted or mono- or polysubstituted with one or more substituents selected from F; Cl; Br; I; CN; Cm-alkyl; CF$_3$; CF$_2$H; CFH$_2$; CF$_2$Cl; CFCl$_2$; C(O)—$C_{1-6}$-alkyl; C(O)—OH; C(O)—O$C_{1-6}$-alkyl; C(O)—NH$_2$; C(O)—N(H)($C_{1-6}$-alkyl); C(O)—N($C_{1-6}$-alkyl)$_2$; OH; =O; OCF$_3$; OCF$_2$H; OCFH$_2$; OCF$_2$Cl; OCFCl$_2$; O—$C_{1-6}$-alkyl; O—C(O)—$C_{1-6}$-alkyl; O—C(O)—O—$C_{1-6}$-alkyl; O—(CO)—N(H)($C_{1-6}$-alkyl); O—C(O)—N($C_{1-6}$-alkyl)$_2$; O—S(O)$_2$—NH$_2$; O—S(O)$_2$—N(H)($C_{1-6}$-alkyl); O—S(O)$_2$—N($C_{1-6}$-alkyl)$_2$; NH$_2$; N(H)($C_{1-6}$-alkyl); N($C_{1-6}$-alkyl)$_2$; N(H)—C(O)—$C_{1-6}$-alkyl; N(H)—C(O)—O—$C_{1-6}$-alkyl; N(H)—C(O)—NH$_2$; N(H)—C(O)—N(H)($C_{1-6}$-alkyl); N(H)—C(O)—N($C_{1-6}$-alkyl)$_2$; N($C_{1-6}$-alkyl)-C(O)—$C_{1-6}$-alkyl; N($C_{1-6}$-alkyl)-C(O)—O—$C_{1-6}$-alkyl; N($C_{1-6}$-alkyl)-C(O)—NH$_2$; N($C_{1-6}$-alkyl)-C(O)—N(H)($C_{1-6}$-alkyl); N($C_{1-6}$-alkyl)-C(O)—N($C_{1-6}$-alkyl)$_2$; N(H)—S(O)$_2$OH; N(H)—S(O)$_2$—$C_{1-6}$-alkyl; N(H)—S(O)$_2$—O—$C_{1-6}$-alkyl; N(H)—S(O)$_2$—NH$_2$; N(H)—S(O)$_2$—N(H)($C_{1-6}$-alkyl); N(H)—S(O)$_2$N($C_{1-6}$-alkyl)$_2$; N($C_{1-6}$-alkyl)-S(O)$_2$—OH; N($C_{1-6}$-alkyl)-S(O)$_2$—$C_{1-6}$-alkyl; N($C_{1-6}$-alkyl)-S(O)$_2$—O—$C_{1-6}$-alkyl; N($C_{1-6}$-alkyl)-S(O)$_2$—NH$_2$; N($C_{1-6}$-alkyl)-S(O)$_2$—N(H)($C_{1-6}$-alkyl); N($C_{1-6}$-alkyl)-S(O)$_2$—N($C_{1-6}$-alkyl)$_2$; SCF$_3$; SCF$_2$H; SCFH$_2$; S—$C_{1-6}$-alkyl; S(O)—$C_{1-6}$-alkyl; S(O)$_2$—$C_{1-6}$-alkyl; S(O)$_2$—OH; S(O)$_2$—O—$C_{1-6}$-alkyl; S(O)$_2$—NH$_2$; S(O)$_2$—N(H)($C_{1-6}$-alkyl); S(O)$_2$—N($C_{1-6}$-alkyl)$_2$; $C_{3-6}$-cycloalkyl; 3 to 6-membered heterocycloalkyl; phenyl; 5 or 6-membered heteroaryl; O—$C_{3-6}$-cycloalkyl; O-(3 to 6-membered heterocycloalkyl); O-phenyl; O-(5 or 6-membered heteroaryl); C(O)—$C_{3-6}$-cycloalkyl; C(O)-(3 to 6-membered heterocycloalkyl); C(O)-phenyl; C(O)-(5 or 6-membered heteroaryl); S(O)$_2$—($C_{3-6}$-cycloalkyl); S(O)$_2$-(3 to 6-membered heterocycloalkyl); S(O)$_2$-phenyl or S(O)$_2$-(5 or 6-membered heteroaryl);

wherein aryl and 5 or 6-membered heteroaryl in each case independently from one another are unsubstituted or mono- or polysubstituted with one or more substituents selected from F; Cl; Br; I; CN; $C_{1-6}$-alkyl; CF$_3$; CF$_2$H; CFH$_2$; CF$_2$Cl; CFCl$_2$; $C_{1-4}$-alkylene-CF$_3$; $C_{1-4}$-alkylene-CF$_2$H; $C_{1-4}$-alkylene-CFH$_2$; C(O)—$C_{1-6}$-alkyl; C(O)—OH; C(O)—OC$_{1-6}$-alkyl; C(O)—N(H)(OH); C(O)—NH$_2$; C(O)—N(H)($C_{1-6}$-alkyl); C(O)—N($C_{1-6}$-alkyl)$_2$; OH; OCF$_3$; OCF$_2$H; OCFH$_2$; OCF$_2$Cl; OCFCl$_2$; O—$C_{1-6}$-alkyl; O—$C_{3-6}$-cycloalkyl; O-(3 to 6-membered heterocycloalkyl); NH$_2$; N(H)($C_{1-6}$-alkyl); N($C_{1-6}$-alkyl)$_2$; N(H)—C(O)—$C_{1-6}$-alkyl; N($C_{1-6}$-alkyl)-C(O)—$C_{1-6}$-alkyl; N(H)—C(O)—NH$_2$; N(H)—C(O)—N(H)($C_{1-6}$-alkyl); N(H)—C(O)—N($C_{1-6}$-alkyl)$_2$; N($C_{1-6}$-alkyl)-C(O)—N(H)($C_{1-6}$-alkyl); N($C_{1-6}$-alkyl)-C(O)—N($C_{1-6}$-alkyl)$_2$; N(H)—S(O)$_2$—$C_{1-6}$-alkyl; SCF$_3$; S—$C_{1-6}$-alkyl; S(O)—$C_{1-6}$-alkyl; S(O)$_2$—$C_{1-6}$-alkyl; S(O)$_2$—NH$_2$; S(O)$_2$—N(H)($C_{1-6}$-alkyl); S(O)$_2$—N($C_{1-6}$-alkyl)$_2$; $C_{3-6}$-cycloalkyl; $C_{1-4}$-alkylene-$C_{3-6}$-cycloalkyl; 3 to 6-membered heterocycloalkyl; $C_{1-4}$-alkylene-(3 to 6-membered heterocycloalkyl); phenyl or 5 or 6-membered heteroaryl;
in the form of the free compound or a physiologically acceptable salt thereof.

In a preferred embodiment, the compound according to the present invention is present in form of the free compound. For the purpose of specification, "free compound" preferably means that the compound according to the present invention is not present in form of a salt. Methods to determine whether a chemical substance is present as the free compound or as a salt are known to the skilled artisan such as $^{14}N$ or $^{15}N$ solid state NMR, x-ray diffraction, x-ray powder diffraction, IR, Raman, XPS. $^1H$-NMR recorded in solution may also be used to consider the presence of protonation.

In another preferred embodiment, the compound according to the present invention is present in form of a physiologically acceptable salt. For the purposes of this specification, the term "physiologically acceptable salt" preferably refers to a salt obtained from a compound according to the present invention and a physiologically acceptable acid or base.

According to the present invention, the compound according to the present invention may be present in any possible form including solvates, cocrystals and polymorphs. For the purposes of this specification, the term "solvate" preferably refers to an adduct of (i) a compound according to the present invention and/or a physiologically acceptable salt thereof with (ii) distinct molecular equivalents of one or more solvents.

Further, the compound according to the present invention may be present in form of the racemate, enantiomers, diastereomers, tautomers or any mixtures thereof.

The present invention also includes isotopic isomers of a compound of the invention, wherein at least one atom of the compound is replaced by an isotope of the respective atom which is different from the naturally predominantly occurring isotope, as well as any mixtures of isotopic isomers of such a compound. Preferred isotopes are $^2H$ (deuterium), $^3H$ (tritium), $^{13}C$ and $^{14}C$. Isotopic isomers of a compound of the invention can generally be prepared by conventional procedures known to a person skilled in the art.

According to the present invention, the terms "$C_{1-10}$-alkyl", "$C_{1-8}$-alkyl", "$C_{1-6}$-alkyl" and "$C_{1-4}$-alkyl" preferably mean acyclic saturated or unsaturated aliphatic (i.e. non-aromatic) hydrocarbon residues, which can be linear (i.e. unbranched) or branched and which can be unsubstituted or mono- or polysubstituted (e.g. di- or trisubstituted), and which contain 1 to 10 (i.e. 1, 2, 3, 4, 5, 6, 7, 8, 9 or 10), 1 to 8 (i.e. 1, 2, 3, 4, 5, 6, 7 or 8), 1 to 6 (i.e. 1, 2, 3, 4, 5 or 6) and 1 to 4 (i.e. 1, 2, 3 or 4) carbon atoms, respectively. In a preferred embodiment, $C_{1-10}$-alkyl, $C_{1-8}$-alkyl, $C_{1-6}$-alkyl and $C_{1-4}$-alkyl are saturated. In another preferred embodiment, $C_{1-10}$-alkyl, $C_{1-8}$-alkyl, $C_{1-6}$-alkyl and $C_{1-4}$-alkyl are not saturated. According to this embodiment, $C_{1-10}$-alkyl, $C_{1-8}$-alkyl, $C_{1-6}$-alkyl and $C_{1-4}$-alkyl comprise at least one C—C double bond (a C=C-bond) or at least one C—C triple bond (a C≡C-bond). In still another preferred embodiment, $C_{1-10}$-alkyl, $C_{1-8}$-alkyl, $C_{1-6}$-alkyl and $C_{1-4}$-alkyl are (i) saturated or (ii) not saturated, wherein $C_{1-10}$-alkyl, $C_{1-8}$-alkyl, $C_{1-6}$-alkyl and $C_{1-4}$-alkyl comprise at least one, preferably one, C—C triple bond (a C≡C-bond). Preferred $C_{1-10}$-alkyl groups are selected from methyl, ethyl, ethenyl (vinyl), n-propyl, 2-propyl, 1-propynyl, 2-propynyl, propenyl (—CH$_2$CH=CH$_2$, —CH=CH—CH$_3$, —C(=CH$_2$)—CH$_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; more preferably methyl, ethyl, n-propyl, 2-propyl, 1-propynyl, 2-propynyl, propenyl (—CH$_2$CH=CH$_2$, —CH=CH—CH$_3$, —C(=CH$_2$)—CH$_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, n-heptyl, n-octyl, n-nonyl and n-decyl. Preferred $C_{1-8}$-alkyl groups are selected from methyl, ethyl, ethenyl (vinyl), n-propyl, 2-propyl, 1-propynyl, 2-propynyl, propenyl (—CH$_2$CH=CH$_2$, —CH=CH—CH$_3$, —C(=CH$_2$)—CH$_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; more preferably methyl, ethyl, n-propyl, 2-propyl, 1-propynyl, 2-propynyl, propenyl (—CH$_2$CH=CH$_2$, —CH=CH—CH$_3$, —C(=CH$_2$)—CH$_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, n-heptyl and n-octyl. Preferred $C_{1-6}$-alkyl groups are selected from methyl, ethyl, ethenyl (vinyl), n-propyl, 2-propyl, n-butyl, isobutyl, sec-butyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; more preferably methyl, ethyl, n-propyl, 2-propyl, 1-propynyl, 2-propynyl, propenyl (—CH$_2$CH=CH$_2$, —CH=CH—CH$_3$, —C(=CH$_2$)—CH$_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl. Particularly preferred $C_{1-6}$-alkyl groups are selected from $C_{1-4}$-alkyl groups. Preferred $C_{1-4}$-alkyl groups are selected from methyl, ethyl, ethenyl (vinyl), n-propyl, 2-propyl, 1-propynyl, 2-propynyl, propenyl (—CH$_2$CH=CH$_2$, —CH=CH—CH$_3$, —C(=CH$_2$)—CH$_3$), n-butyl, 1-butynyl, 2-butynyl, 1-butenyl, 2-butenyl, isobutyl, sec-butyl, tert-butyl and 3-methylbut-1-ynyl.

Further according to the present invention, the terms "$C_{1-6}$-alkylene"; "$C_{1-4}$-alkylene" and "$C_{1-2}$-alkylene" relate to a linear or branched, preferably linear, and preferably saturated aliphatic residues which are preferably selected from the group consisting of methylene (—CH$_2$—), ethylene (—CH$_2$CH$_2$—), propylene (—CH$_2$CH$_2$CH$_2$— or —C(CH$_3$)$_2$—), butylene (—CH$_2$CH$_2$CH$_2$CH$_2$—), pentylene (—CH$_2$CH$_2$CH$_2$CH$_2$CH$_2$—) and hexylene (—CH$_2$CH$_2$CH$_2$CH$_2$CH$_2$CH$_2$—); more preferably methylene (—CH$_2$—) and ethylene (—CH$_2$CH$_2$—) and most preferably methylene (—CH$_2$—). Preferably, C$_{1-6}$-alkylene is selected from C$_{1-4}$-alkylene, more preferably from C$_{1-2}$-alkylene.

Still further according to the present invention, the terms "C$_{3-10}$-cycloalkyl" and "C$_{3-6}$-cycloalkyl" preferably mean cyclic aliphatic hydrocarbons containing 3, 4, 5, 6, 7, 8, 9 or 10 carbon atoms and 3, 4, 5 or 6 carbon atoms, respectively, wherein the hydrocarbons in each case can be saturated or unsaturated (but not aromatic), unsubstituted or mono- or polysubstituted. Preferably, C$_{3-10}$-cycloalkyl and C$_{3-6}$-cycloalkyl are saturated. The C$_{3-10}$-cycloalkyl and C$_{3-6}$-cycloalkyl can be bound to the respective superordinate general structure via any desired and possible ring member of the cycloalkyl group. The C$_{3-10}$-cycloalkyl and C$_{3-6}$-cycloalkyl groups can also be condensed with further saturated, (partially) unsaturated, (hetero)cyclic, aromatic or heteroaromatic ring systems, i.e. with cycloalkyl, heterocyclyl, aryl or heteroaryl residues, which in each case can in turn be unsubstituted or mono- or polysubstituted. Further, C$_{3-10}$-cycloalkyl and C$_{3-6}$-cycloalkyl can be singly or multiply bridged such as, for example, in the case of adamantyl, bicyclo[2.2.1]heptyl or bicyclo[2.2.2]octyl. However, preferably, C$_{3-10}$-cycloalkyl and C$_{3-6}$-cycloalkyl are neither condensed with further ring systems nor bridged. More preferably, C$_{3-10}$-cycloalkyl and C$_{3-6}$-cycloalkyl are neither condensed with further ring systems nor bridged and are saturated. Preferred C$_{3-10}$-cycloalkyl groups are selected from the group consisting of cyclopropyl, cyclobutyl, cyclopentyl, cyclohexyl, cycloheptyl, cyclooctyl, cyclononyl, cyclodecyl, adamantly, cyclopentenyl, cyclohexenyl, cycloheptenyl, cyclooctenyl, bicyclo[2.2.1]heptyl and bicyclo[2.2.2]octyl. Particularly preferred C$_{3-10}$-cycloalkyl groups are selected from C$_{3-6}$-cycloalkyl groups. Preferred C$_{3-6}$-cycloalkyl groups are selected from the group consisting of cyclopropyl, cyclobutyl, cyclopentyl, cyclohexyl, cyclopentenyl and cyclohexenyl. Particularly preferred C$_{3-6}$-cycloalkyl groups are selected from the group consisting of cyclopropyl, cyclobutyl, cyclopentyl and cyclohexyl, most preferably cyclopropyl.

According to the present invention, the terms "3 to 7-membered heterocycloalkyl" and "3 to 6-membered heterocycloalkyl" preferably mean heterocycloaliphatic saturated or unsaturated (but not aromatic) residues having 3 to 7, i.e. 3, 4, 5, 6 or 7 ring members and 3 to 6, i.e. 3, 4, 5 or 6 ring members, respectively, wherein in each case at least one, if appropriate also two or three carbon atoms are replaced by a heteroatom or a heteroatom group each selected independently of one another from the group consisting of O, S, S(=O), S(=O)$_2$, N, NH and N(C$_{1-4}$-alkyl) such as N(CH$_3$), wherein the carbon atoms of the ring can be unsubstituted or mono- or polysubstituted. Preferably, 3 to 7-membered heterocycloalkyl and 3 to 6-membered heterocycloalkyl are saturated. The 3 to 7-membered heterocycloalkyl and the 3 to 6-membered heterocycloalkyl groups can also be condensed with further saturated or (partially) unsaturated cycloalkyl or heterocyclyl, aromatic or heteroaromatic ring systems. However, more preferably, 3 to 7-membered heterocycloalkyl and 3 to 6-membered heterocycloalkyl are not condensed with further ring systems. Still more preferably, 3 to 7-membered heterocycloalkyl and 3 to 6-membered heterocycloalkyl are not condensed with further ring systems and are saturated. The 3 to 7-membered heterocycloalkyl and the 3 to 6-membered heterocycloalkyl group can be bound to the superordinate general structure via any desired and possible ring member of the heterocycloaliphatic residue if not indicated otherwise. In a preferred embodiment, 3 to 7-membered heterocycloalkyl and 3 to 6-membered heterocycloalkyl are bound to the superordinate general structure via a carbon atom.

Preferred 3 to 7-membered heterocycloalkyl groups are selected from the group consisting of azepanyl, dioxepanyl, oxazepanyl, diazepanyl, thiazolidinyl, tetrahydrothiophenyl, tetrahydropyridinyl, thiomorpholinyl, tetrahydropyranyl, oxetanyl, oxiranyl, tetrahydrofiiranyl, morpholinyl, pyrrolidinyl, 4-methylpiperazinyl, morpholinonyl, azetidinyl, aziridinyl, dithiolanyl, dihydropyrrolyl, dioxanyl, dioxolanyl, dihydropyridinyl, dihydrofuranyl, dihydroisoxazolyl, dihydrooxazolyl, imidazolidinyl, isoxazolidinyl, oxazolidinyl, piperazinyl, piperidinyl, pyrazolidinyl, pyranyl; tetrahydropyrrolyl, dihydroquinolinyl, dihydroisoquinolinyl, dihydroindolinyl, dihydroisoindolyl, tetrahydroquinolinyl, tetrahydroisoquinolinyl and tetrahydroindolinyl. Particularly preferred 3 to 7-membered heterocycloalkyl groups are selected from 3 to 6-membered heterocycloalkyl groups. Preferred 3 to 6-membered heterocycloalkyl groups are selected from the group consisting of tetrahydropyranyl, oxetanyl, oxiranyl, tetrahydrofuranyl, thiazolidinyl, tetrahydrothiophenyl, tetrahydropyridinyl, thiomorpholinyl, morpholinyl, pyrrolidinyl, 4-methylpiperazinyl, morpholinonyl, azetidinyl, aziridinyl, dithiolanyl, dihydropyrrolyl, dioxanyl, dioxolanyl, dihydropyridinyl, dihydrofuranyl, dihydroisoxazolyl, dihydrooxazolyl, imidazolidinyl, isoxazolidinyl, oxazolidinyl, piperazinyl, piperidinyl, pyrazolidinyl, pyranyl, tetrahydropyrrolyl, dihydroindolinyl, dihydroisoindolyl and tetrahydroindolinyl. Particularly preferred 3 to 6-membered heterocycloalkyl groups are selected from the group consisting of tetrahydropyranyl, oxetanyl, oxiranyl, and tetrahydrofuranyl.

According to the present invention, the term "aryl" preferably means aromatic hydrocarbons having 6 to 14, i.e. 6, 7, 8, 9, 10, 11, 12, 13 or 14 ring members, preferably having 6 to 10, i.e. 6, 7, 8, 9 or 10 ring members, including phenyls and naphthyls. Each aryl residue can be unsubstituted or mono- or polysubstituted. The aryl can be bound to the superordinate general structure via any desired and possible ring member of the aryl residue. The aryl residues can also be condensed with further saturated or (partially) unsaturated cycloalkyl or heterocycloalkyl, aromatic or heteroaromatic ring systems, which can in turn be unsubstituted or mono- or polysubstituted. In a preferred embodiment, aryl is condensed with a further ring system. Examples of condensed aryl residues are 2H-benzo[b][1,4]oxazin-3(4H)-onyl, 1H-benzo[d]imidazolyl, 2,3-dihydro-1H-indenyl, tetrahydronaphthalenyl, isochroman, 1,3-dihydroisobenzofuranyl, benzodioxolanyl and benzodioxanyl. Preferably, aryl is selected from the group consisting of phenyl, 1H-benzo[d]imidazolyl, 2H-benzo[b][1,4]oxazin-3 (4H)-onyl, 2,3-dihydro-1H-indenyl, tetrahydronaphthalenyl, isochroman, 1,3-dihydroisobenzofuranyl, 1-naphthyl, 2-naphthyl, fluorenyl and anthracenyl, each of which can be respectively unsubstituted or mono- or polysubstituted. In another preferred embodiment, aryl is not condensed with any further ring system. A particularly preferred aryl is phenyl, unsubstituted or mono- or polysubstituted.

According to the present invention, the term "5- to 6-membered heteroaryl" preferably means a 5 or 6-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted, if not indicated otherwise. In the case of substitution on the heteroaryl, the substituents can be the same or different and be in any desired and possible position of the heteroaryl. The binding to the superordinate general structure can be carried out via any desired and possible ring member of the heteroaryl residue if not indicated otherwise. Preferably, the 5- to 6-membered heteroaryl is bound to the suprordinate general structure via a carbon atom of the heterocycle. The heteroaryl can also be part of a bi- or polycyclic system having up to 14 ring members, wherein the ring system can be formed with further saturated or (partially) unsaturated cycloalkyl or heterocycloalkyl, aromatic or heteroaromatic ring systems, which can in turn be unsubstituted or mono- or polysubstituted, if not indicated otherwise. In a preferred embodiment, the 5- to 6-membered heteroaryl is part of a bi- or polycyclic, preferably bicyclic, system. In another preferred embodiment, the 5- to 6-membered heteroaryl is not part of a bi- or polycyclic system. Preferably, the 5- to 6-membered heteroaryl is selected from the group consisting of pyridyl (i.e. 2-pyridyl, 3-pyridyl, 4-pyridyl), pyrimidinyl, pyridazinyl, pyrazinyl, pyrrolyl, imidazolyl, pyrazolyl, oxazolyl, isoxazolyl, thiazolyl, isothiazolyl, furanyl, thienyl (thiophenyl), triazolyl, thiadiazolyl, 4,5,6,7-tetrahydro-2H-indazolyl, 2,4,5,6-tetrahydrocyclopenta[c]pyrazolyl, benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, imidazothiazolyl, indazolyl, indolizinyl, indolyl, isoquinolinyl, naphthyridinyl, oxazolyl, oxadiazolyl, phenazinyl, phenothiazinyl, phthalazinyl, purinyl, phenazinyl, tetrazolyl and triazinyl. Particularly preferred 5- to 6-membered heteroaryl are selected from the group consisting of pyridyl (i.e. 2-pyridyl, 3-pyridyl, 4-pyridyl).

The compounds according to the present invention are defined by substituents, for example by $R^1$, $R^2$ and $R^3$ ($1^{st}$ generation substituents) which may optionally be for their part themselves be substituted ($2^{nd}$ generation substituents). Depending on the definition, these substituents of the substituents can optionally be for their part resubstituted ($3^{rd}$ generation substituents). If, for example, $R^1$=a $C_{1-10}$-alkyl ($1^{st}$ generation substituent), then the $C_{1-10}$-alkyl can for its part be substituted, for example with a N(H)($C_{1-6}$-alkyl) ($2^{nd}$ generation substituent). This produces the functional group $R^1$=($C_{1-10}$-alkyl-NH—$C_{1-6}$-alkyl). The NH—$C_{1-6}$-alkyl can then for its part be resubstituted, for example with Cl ($3^{rd}$ generation substituent). Overall, this produces the functional group $R^1$=$C_{1-10}$-alkyl-NH—$C_{1-6}$-alkyl. wherein the $C_{1-6}$-alkyl of the NH—$C_{1-6}$-alkyl is substituted by Cl. However, in a preferred embodiment, the $3^{rd}$ generation substituents may not be resubstituted, i.e. there are then no $4^{th}$ generation substituents. More preferably, the $2^{nd}$ generation substituents may not be resubstituted, i.e. there are no $3^{rd}$ generation substituents.

If a residue occurs multiply within a molecule, then this residue can have respectively different meanings for various substituents: if, for example, both $R^2$ and $R^3$ denote $C_{1-6}$-alkyl. then $C_{1-6}$-alkyl can e.g. represent ethyl for $R^2$ and can represent methyl for $R^3$.

In connection with the terms "$C_{1-10}$-alkyl", "$C_{1-6}$-alkyl", "$C_{1-4}$-alky", "$C_{3-10}$-cycloalkyl". "$C_{3-6}$-cycloalkyl", "3 to 7 membered heterocycloalkyl", "3 to 6-membered heterocycloalkyl", "$C_{1-6}$-alkylene", "$C_{1-4}$-alkylene" and "$C_{1-2}$-alkylene", the term "substituted" refers in the sense of the present invention, with respect to the corresponding residues or groups, to the single substitution (monosubstitution) or multiple substitution (polysubstitution), e.g. disubstitution or trisubstitution; more preferably to monosubstitution or disubstitution; of one or more hydrogen atoms each independently of one another by at least one substituent. In case of a multiple substitution, i.e. in case of polysubstituted residues, such as di- or trisubstituted residues, these residues may be polysubstituted either on different or on the same atoms, for example trisubstituted on the same carbon atom, as in the case of $CF_3$, $CH_2CF_3$ or disubstituted as in the case of 1,1-difluorocyclohexyl, or at various points, as in the case of CH(OH)—CH=CH—$CHCl_2$ or 1-chloro-3-fluorocyclohexyl. The multiple substitution can be carried out using the same or using different substituents.

In relation to the terms "aryl", "phenyl", "heteroaryl" and "5- to 6-membered heteroaryl", the term "substituted" refers in the sense of this invention to the single substitution (monosubstitution) or multiple substitution (polysubstitution), e.g. disubstitution or trisubstitution, of one or more hydrogen atoms each independently of one another by at least one substituent. The multiple substitution can be carried out using the same or using different substituents.

According to the present invention, preferably $C_{1-10}$-alkyl, $C_{1-6}$-alkyl. $C_{1-4}$-alkyl, $C_{3-10}$-cycloalkyl, $C_{3-6}$-cycloalkyl, 3 to 7 membered heterocycloalkyl, 3 to 6-membered heterocycloalkyl, $C_{1-6}$-alkylene. $C_{1-4}$-alkylene and $C_{1-2}$-alkylene in each case independently from one another are unsubstituted or mono- or polysubstituted with one or more substituents selected from F; Cl; Br; I; CN; $C_{1-6}$-alkyl; $CF_3$; $CF_2H$; $CFH_2$; $CF_2Cl$; $CFCl_2$; C(O)—$C_{1-6}$-alkyl; C(O)—OH; C(O)—O$C_{1-6}$-alkyl; C(O)—$NH_2$; C(O)—N(H)($C_{1-6}$-alkyl); C(O)—N($C_{1-6}$-alkyl)$_2$; OH; =O; $OCF_3$; $OCF_2H$; $OCFH_2$; $OCF_2Cl$; $OCFCl_2$; O—$C_{1-6}$-alkyl; O—C(O)—$C_{1-6}$-alkyl; O—C(O)—O—$C_{1-6}$-alkyl; O—(CO)—N(H)($C_{1-6}$-alkyl); O—C(O)—N($C_{1-6}$-alkyl)$_2$; O—S(O)$_2$—$NH_2$; O—S(O)$_2$—N(H)($C_{1-6}$-alkyl); O—S(O)$_2$—N($C_{1-6}$-alkyl)$_2$; $NH_2$; N(H)($C_{1-6}$-alkyl); N($C_{1-6}$-alkyl)$_2$; N(H)—C(O)—$C_{1-6}$-alkyl; N(H)—C(O)—O—$C_{1-6}$-alkyl; N(H)—C(O)—$NH_2$; N(H)—C(O)—N(H)($C_{1-6}$-alkyl); N(H)—C(O)—N($C_{1-6}$-alkyl)$_2$; N($C_{1-6}$-alkyl)-C(O)—$C_{1-6}$-alkyl; N($C_{1-6}$-alkyl)-C(O)—O—$C_{1-6}$-alkyl; N($C_{1-6}$-alkyl)-C(O)—$NH_2$; N($C_{1-6}$-alkyl)-C(O)—N(H)($C_{1-6}$-alkyl); N($C_{1-6}$-alkyl)-C(O)—N($C_{1-6}$-alkyl)$_2$; N(H)—S(O)$_2$OH; N(H)—S(O)$_2$—$C_{1-6}$-alkyl; N(H)—S(O)$_2$—O—$C_{1-6}$-alkyl; N(H)—S(O)$_2$—$NH_2$; N(H)—S(O)$_2$—N(H)($C_{1-6}$-alkyl); N(H)—S(O)$_2$N($C_{1-6}$-alkyl)$_2$; N($C_{1-6}$-alkyl)-S(O)$_2$—OH; N($C_{1-6}$-alkyl)-S(O)$_2$—$C_{1-6}$-alkyl; N($C_{1-6}$-alkyl)-S(O)$_2$—O—$C_{1-6}$-alkyl; N($C_{1-6}$-alkyl)-S(O)$_2$—$NH_2$; N($C_{1-6}$-alkyl)-S(O)$_2$—N(H)($C_{1-6}$-alkyl); N($C_{1-6}$-alkyl)-S(O)$_2$—N($C_{1-6}$-alkyl)$_2$; $SCF_3$; $SCF_2H$; $SCFH_2$; S—$C_{1-6}$-alkyl; S(O)—$C_{1-6}$-alkyl; S(O)$_2$—$C_{1-6}$-alkyl; S(O)$_2$—OH; S(O)$_2$—O—$C_{1-6}$-alkyl; S(O)$_2$—$NH_2$; S(O)$_2$—N(H)($C_{1-6}$-alkyl); S(O)$_2$—N($C_{1-6}$-alkyl)$_2$; $C_{3-6}$-cycloalkyl; 3 to 6-membered heterocycloalkyl; phenyl; 5 or 6-membered heteroaryl; O—$C_{3-6}$-cycloalkyl; O-(3 to 6-membered heterocycloalkyl); O-phenyl; O-(5 or 6-membered heteroaryl); C(O)—$C_{3-6}$-cycloalkyl; C(O)-(3 to 6-membered heterocycloalkyl); C(O)-phenyl; C(O)-(5 or 6-membered heteroaryl); S(O)$_2$—($C_{3-6}$-cycloalkyl); S(O)$_2$-(3 to 6-membered heterocycloalkyl); S(O)$_2$-phenyl and S(O)$_2$-(5 or 6-membered heteroaryl).

Preferred substituents of $C_{1-10}$-alkyl. $C_{1-6}$-alkyl. $C_{1-4}$-alkyl, $C_{3-10}$-cycloalkyl, $C_{3-6}$-cycloalkyl, 3 to 7 membered heterocycloalkyl, 3 to 6-membered heterocycloalkyl, $C_{1-6}$-alkylene and $C_{1-4}$-alkylene are selected from the group consisting of F; Cl; Br; I; CN; $C_{1-6}$-alkyl; $CF_3$; $CF_2H$; $CFH_2$; C(O)—$NH_2$; C(O)—N(H)($C_{1-6}$-alkyl); C(O)—N($C_{1-6}$-alkyl)$_2$; OH; $OCF_3$; $OCF_2H$; $OCFH_2$; O—$C_{1-6}$-alkyl; $NH_2$; N(H)($C_{1-6}$-alkyl); N($C_{1-6}$-alkyl)$_2$; $SCF_3$; $SCF_2H$; $SCFH_2$; S—$C_{1-6}$-alkyl; S(O)—$C_{1-6}$-alkyl; S(O)$_2$—$C_{1-6}$-alkyl; $C_{3-6}$- cycloalkyl; 3 to 6-membered heterocycloalkyl; phenyl and 5 or 6-membered heteroaryl; and particularly preferably F, CN, CH₃, CH₂CH₃, CF₃; CF₂H; CFH₂; C(O)—NH₂; C(O)—N(H)(CH₃); C(O)—N(CH₃)₂; OH, NH₂, OCH₃, SCH₃, S(O)₂(CH₃), S(O)(CH₃), N(CH₃)₂, cyclopropyl and oxetanyl. According to this embodiment, $C_{1-10}$-alkyl. $C_{1-6}$-alkyl. $C_{1-4}$-alkyl, $C_{3-10}$-cycloalkyl, $C_{3-6}$-cycloalkyl, 3 to 7 membered heterocycloalkyl, 3 to 6-membered heterocycloalkyl are preferably each independently from one another unsubstituted, mono- di- or trisubstituted, more preferably unsubstituted or monosubstituted or disubstituted with a substituent selected from the group consisting of F; Cl; Br; I; CN; $C_{1-6}$-alkyl; CF₃; CF₂H; CFH₂; C(O)—NH₂; C(O)—N(H)($C_{1-6}$-alkyl); C(O)—N($C_{1-6}$-alkyl)₂; OH; OCF₃; OCF₂H; OCFH₂; O—$C_{1-6}$-alkyl; NH₂; N(H)($C_{1-6}$-alkyl); N($C_{1-6}$-alkyl)₂; SCF₃; SCF₂H; SCFH₂; S—$C_{1-6}$-alkyl; S(O)—$C_{1-6}$-alkyl; S(O)₂—$C_{1-6}$-alkyl; $C_{3-6}$-cycloalkyl; 3 to 6-membered heterocycloalkyl; phenyl and 5 or 6-membered heteroaryl. Preferably, $C_{1-6}$-alkylene groups and $C_{1-4}$-alkylene groups are unsubstituted.

According to the present invention, preferably aryl, phenyl and 5 or 6-membered heteroaryl in each case independently from one another are unsubstituted or mono- or polysubstituted with one or more substituents selected from F; Cl; Br; I; CN; $C_{1-6}$-alkyl; CF₃; CF₂H; CFH₂; CF₂Cl; CFCl₂; $C_{1-4}$-alkylene-CF₃; $C_{1-4}$-alkylene-CF₂H; $C_{1-4}$-alkylene-CFH₂; C(O)—$C_{1-6}$-alkyl; C(O)—OH; C(O)—O$C_{1-6}$-alkyl; C(O)—N(H)(OH); C(O)—NH₂; C(O)—N(H)($C_{1-6}$-alkyl); C(O)—N($C_{1-6}$-alkyl)₂; OH; OCF₃; OCF₂H; OCFH₂; OCF₂Cl; OCFCl₂; O—$C_{1-6}$-alkyl; O—$C_{3-6}$-cycloalkyl; O-(3 to 6-membered heterocycloalkyl); NH₂; N(H)($C_{1-6}$-alkyl); N($C_{1-6}$-alkyl)₂; N(H)—C(O)—$C_{1-6}$-alkyl; N($C_{1-6}$-alkyl)-C(O)—$C_{1-6}$-alkyl; N(H)—C(O)—NH₂; N(H)—C(O)—N(H)($C_{1-6}$-alkyl); N(H)—C(O)—N($C_{1-6}$-alkyl)₂; N($C_{1-6}$-alkyl)-C(O)—N(H)($C_{1-6}$-alkyl); N($C_{1-6}$-alkyl)-C(O)—N($C_{1-6}$-alkyl)₂; N(H)—S(O)₂—$C_{1-6}$-alkyl; SCF₃; S—$C_{1-6}$-alkyl; S(O)—$C_{1-6}$-alkyl; S(O)₂—$C_{1-6}$-alkyl; S(O)₂—NH₂; S(O)₂—N(H)($C_{1-6}$-alkyl); S(O)₂—N($C_{1-6}$-alkyl)₂; $C_{3-6}$-cycloalkyl; $C_{1-4}$-alkylene-$C_{3-6}$-cycloalkyl; 3 to 6-membered heterocycloalkyl; $C_{1-4}$-alkylene-(3 to 6-membered heterocycloalkyl); phenyl or 5 or 6-membered heteroaryl.

Preferred substituents of aryl, phenyl and 5 or 6-membered heteroaryl are selected from the group consisting of F; Cl; Br; I; CN; $C_{1-6}$-alkyl; CF₃; CF₂H; CFH₂; $C_{1-4}$-alkylene-CF₃; $C_{1-4}$-alkylene-CF₂H; $C_{1-4}$-alkylene-CFH₂; OH; OCF₃; OCF₂H; OCFH₂; O—$C_{1-6}$-alkyl; O—$C_{3-6}$-cycloalkyl and $C_{3-6}$-cycloalkyl; and particularly preferably of F; Cl; Br; CN; CH₃; CH₂CH₃; CF₃; CF₂H; CFH₂; CH₂—CF₃; OH; OCF₃; OCF₂H; OCFH₂; O—CH₃; O-cyclopropyl and cyclopropyl. According to this embodiment, aryl, phenyl and 5 or 6-membered heteroaryl are preferably each independently from one another unsubstituted, mono- di- or trisubstituted, more preferably unsubstituted or monosubstituted or disubstituted with a substituent selected from the group consisting of F; Cl; Br; I; CN; $C_{1-6}$-alkyl; CF₃; CF₂H; CFH₂; $C_{1-4}$-alkylene-CF₃; $C_{1-4}$-alkylene-CF₂H; $C_{1-4}$-alkylene-CFH₂; OH; OCF₃; OCF₂H; OCFH₂; O—$C_{1-6}$-alkyl; O—$C_{3-6}$-cycloalkyl and $C_{3-6}$-cycloalkyl.

In a preferred embodiment, the compound according to the present invention is according to general formula (II) or (III)

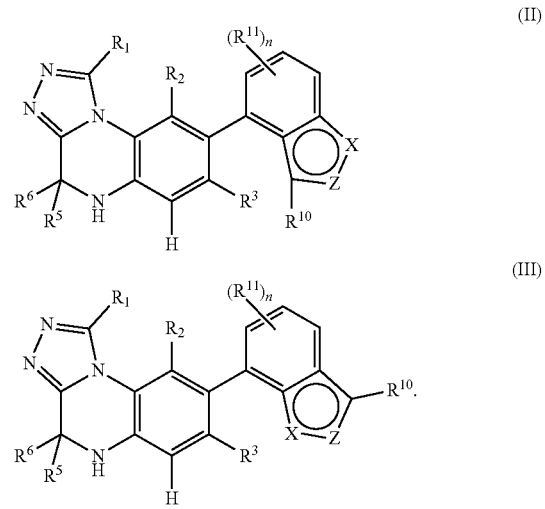

In a preferred embodiment, X represents NR⁷ and Z represents N or CR⁹. More preferably, X represents NR and Z represents CR⁹. In another preferred embodiment, X represents N and Z represents NR⁷.

More preferably, the compound according to the present invention is according to general formula (II) or (III), wherein X represents NR⁷ and Z represents N or CR⁹, more preferably CR⁹.

In a preferred embodiment, R¹ represents H; $C_{1-6}$-alkyl; $C_{3-6}$-cycloalkyl; 3 to 6-membered heterocycloalkyl; phenyl; or 5 or 6-membered heteroaryl; wherein $C_{3-6}$-cycloalkyl, 3 to 6-membered heterocycloalkyl, phenyl and 5 or 6-membered heteroaryl can optionally be bridged via $C_{1-4}$-alkylene. According to this embodiment, preferably $C_{1-6}$-alkyl; $C_{3-6}$-cycloalkyl; $C_{1-4}$-alkylene and 3 to 6-membered heterocycloalkyl in each case independently from one another are unsubstituted or mono-; di- or trisubstituted with one or more substituents selected from F; Cl; Br; I; CN; $C_{1-6}$-alkyl; CF₃; CF₂H; CFH₂; CF₂Cl; CFCl₂; C(O)—NH₂; C(O)—N(H)($C_{1-6}$-alkyl); C(O)—N($C_{1-6}$-alkyl)₂; OH; OCF₃; OCF₂H; OCFH₂; O—$C_{1-6}$-alkyl; O—C(O)—$C_{1-6}$-alkyl; NH₂; N(H)($C_{1-6}$-alkyl); N($C_{1-6}$-alkyl)₂; N(H)—C(O)—$C_{1-6}$-alkyl; N(H)—C(O)—O—$C_{1-6}$-alkyl; SCF₃; SCF₂H; SCFH₂; S—$C_{1-6}$-alkyl; S(O)—$C_{1-6}$-alkyl; S(O)₂—$C_{1-6}$-alkyl; S(O)₂—O—$C_{1-6}$-alkyl; S(O)₂—NH₂; S(O)₂—N(H)($C_{1-6}$-alkyl); S(O)₂—N($C_{1-6}$-alkyl)₂; $C_{3-6}$-cycloalkyl; 3 to 6-membered heterocycloalkyl; phenyl; 5 or 6-membered heteroaryl; O—$C_{3-6}$-cycloalkyl; O-(3 to 6-membered heterocycloalkyl); O-phenyl; O-(5 or 6-membered heteroaryl); C(O)—$C_{3-6}$-cycloalkyl; C(O)-(3 to 6-membered heterocycloalkyl); C(O)-phenyl; C(O)-(5 or 6-membered heteroaryl); S(O)₂—($C_{3-6}$-cycloalkyl); S(O)₂-(3 to 6-membered heterocycloalkyl); S(O)₂-phenyl or S(O)₂-(5 or 6-membered heteroaryl); more preferably F; Cl; Br; I; CN; $C_{1-6}$-alkyl; CF₃; CF₂H; CFH₂; C(O)—NH₂; C(O)—N(H)($C_{1-6}$-alkyl); C(O)—N($C_{1-6}$-alkyl)₂; OH; OCF₃; OCF₂H; OCFH₂; O—$C_{1-6}$-alkyl; NH₂; N(H)($C_{1-6}$-alkyl); N($C_{1-6}$-alkyl)₂; SCF₃; SCF₂H; SCFH₂; S—$C_{1-6}$-alkyl; S(O)—$C_{1-6}$-alkyl; S(O)₂—$C_{1-6}$-alkyl; $C_{3-6}$-cycloalkyl; 3 to 6-membered heterocycloalkyl; phenyl and 5 or 6-membered heteroaryl; and particularly preferably F, CN, CH₃, CH₂CH₃, CF₃; CF₂H; CFH₂; C(O)—NH₂; C(O)—N(H)(CH₃); C(O)—N(CH₃)₂; OH, NH₂, OCH₃, SCH₃, S(O)₂(CH₃), S(O)(CH₃), N(CH₃)₂, cyclopropyl and oxetanyl;

and preferably phenyl and 5 or 6-membered heteroaryl in each case independently from one another are unsubstituted or mono-; di- or trisubstituted with one or more substituents selected from F; Cl; Br; I; CN; $C_{1-6}$-alkyl; $CF_3$; $CF_2H$; $CFH_2$; $C_{1-4}$-alkylene-$CF_3$; $C_{1-4}$-alkylene-$CF_2H$; $C_{1-4}$-alkylene-$CFH_2$; C(O)—$C_{1-6}$-alkyl; C(O)—$OC_{1-6}$-alkyl; C(O)—; C(O)—$NH_2$; C(O)—N(H)($C_{1-6}$-alkyl); C(O)—N($C_{1-6}$-alkyl)$_2$; OH; $OCF_3$; $OCF_2H$; $OCFH_2$; O—$C_{1-6}$-alkyl; O—$C_{3-6}$-cycloalkyl; O-(3 to 6-membered heterocycloalkyl); $NH_2$; N(H)($C_{1-6}$-alkyl); N($C_{1-6}$-alkyl)$_2$; $SCF_3$; S—$C_{1-6}$-alkyl; S(O)—$C_{1-6}$-alkyl; S(O)$_2$—$C_{1-6}$-alkyl; $C_{3-6}$-cycloalkyl; $C_{1-4}$-alkylene-$C_{3-6}$-cycloalkyl; 3 to 6-membered heterocycloalkyl; $C_{1-4}$-alkylene-(3 to 6-membered heterocycloalkyl); phenyl or 5 or 6-membered heteroaryl; more preferably F; Cl; Br; I; CN; $C_{1-6}$-alkyl; $CF_3$; $CF_2H$; $CFH_2$; $C_{1-4}$-alkylene-$CF_3$; $C_{1-4}$-alkylene-$CF_2H$; $C_{1-4}$-alkylene-$CFH_2$; OH; $OCF_3$; $OCF_2H$; $OCFH_2$; O—$C_{1-6}$-alkyl; O—$C_{3-6}$-cycloalkyl and $C_{3-6}$-cycloalkyl; and particularly preferably F; Cl; Br; CN; $CH_3$; $CH_2CH_3$; $CF_3$; $CF_2H$; $CFH_2$; $CH_2$—$CF_3$; OH; $OCF_3$; $OCF_2H$; $OCFH_2$; O—$CH_3$; O-cyclopropyl and cyclopropyl.

In another preferred embodiment, $R^1$ represents H; $C_{1-4}$-alkyl; $C_{3-6}$-cycloalkyl, optionally bridged via $C_{1-2}$-alkylene; 3 to 6-membered heterocycloalkyl, optionally bridged via $C_{1-2}$-alkylene; phenyl, optionally bridged via $C_{1-2}$-alkylene; or 5 or 6-membered heteroaryl, optionally bridged via $C_{1-2}$-alkylene;
preferably wherein
$C_{1-4}$-alkyl, $C_{3-6}$-cycloalkyl and 3 to 6-membered heterocycloalkyl in each case independently from one another is unsubstituted, mono-, di- or trisubstituted with one or more substituents selected from the group consisting of F, CN, $CH_3$, $CH_2CH_3$, $CF_3$; $CF_2H$; $CFH_2$; C(O)—$NH_2$; C(O)—N(H)($CH_3$); C(O)—N($CH_3$)$_2$; OH, $NH_2$, $OCH_3$, $SCH_3$, S(O)$_2$($CH_3$), S(O)($CH_3$), N($CH_3$)$_2$, cyclopropyl and oxetanyl; and $C_{1-2}$-alkylene is unsubstituted; and
phenyl and 5 or 6-membered heteroaryl in each case independently from one another is unsubstituted, mono-, di- or trisubstituted with one or more substituents selected from the group consisting of F; Cl; Br; CN; $CH_3$; $CH_2CH_3$; $CF_3$; $CF_2H$; $CFH_2$; $CH_2$—$CF_3$; OH; $OCF_3$; $OCF_2H$; $OCFH_2$; O—$CH_3$; O-cyclopropyl and cyclopropyl.

In still another preferred embodiment, $R^1$ represents H; $CH_3$, $CF_3$, $CF_2H$; $CFH_2$; ethyl, n-propyl, 2-propyl, 1-propynyl, 2-propynyl, propenyl (—$CH_2CH$=$CH_2$, —CH=CH—$CH_3$, —C(=$CH_2$)—$CH_3$), n-butyl, 1-butynyl, 2-butynyl, 1-butenyl, 2-butenyl, isobutyl, sec-butyl; tert-butyl; $(CH_2)_{1-2}OCH_3$; $(CH_2)_{1-2}OH$; $(CH_2)_{0-2}$C(H)(OH)—$(CH_2)_{0-2}$—$CH_3$; $(CH_2)_{1-2}SCH_3$; $(CH_2)_{1-2}$N($CH_3$)$_2$; $(CH_2)_{1-2}$S(O)$CH_3$; $(CH_2)_{1-2}$S(O)$_2$$CH_3$; $(CH_2)_{1-2}$CN; $(CH_2)_{0-2}$C(H)(CN)—$(CH_2)_{0-2}$—$CH_3$; $(CH_2)_{0-2}$-cyclopropyl, $(CH_2)_{0-2}$-cyclobutyl, $(CH_2)_{0-2}$-cyclopentyl and $(CH_2)_{0-2}$-cyclohexyl; $(CH_2)_{0-2}$-tetrahydropyranyl, $(CH_2)_{0-2}$-oxetanyl, $(CH_2)_{0-2}$-oxiranyl, $(CH_2)_{0-2}$-tetrahydrofuranyl; $(CH_2)_{0-2}$-phenyl; $(CH_2)_{0-2}$-pyridyl, $(CH_2)_{0-2}$-pyrimidinyl, $(CH_2)_{0-2}$-pyridazinyl, $(CH_2)_{0-2}$-thienyl, $(CH_2)_{0-2}$-oxazolyl or $(CH_2)_{0-2}$-thiazolyl.

Preferably, $R^2$ represents H; F; Cl; Br; CN; $C_{1-6}$-alkyl; $C_{3-6}$-cycloalkyl; O—$C_{1-6}$-alkyl; N(H)($C_{1-6}$-alkyl), N($C_{1-6}$-alkyl)$_2$; C(O)—$C_{1-6}$-alkyl; C(O)—O—$C_{1-6}$-alkyl; C(O)—$NH_2$; C(O)—N(H)($C_{1-6}$-alkyl); C(O)—N($C_{1-6}$-alkyl)$_2$; O—$C_{3-6}$-cycloalkyl; N(H)($C_{3-6}$-cycloalkyl), N($C_{1-6}$-alkyl)($C_{3-6}$-cycloalkyl); C(O)—$C_{3-6}$-cycloalkyl; C(O)—O—$C_{3-6}$-cycloalkyl; C(O)—N(H)($C_{3-6}$-cycloalkyl) or C(O)—N($C_{1-6}$-alkyl)($C_{3-6}$-cycloalkyl); wherein $C_{3-6}$-cycloalkyl can optionally be bridged via $C_{1-4}$-alkylene.

In a preferred embodiment, $R^2$ represents H; F; Cl; Br; CN; $C_{1-6}$-alkyl; $C_{3-6}$-cycloalkyl; O—$C_{1-6}$-alkyl; C(O)—$NH_2$; C(O)—N(H)($C_{1-6}$-alkyl); C(O)—N($C_{1-6}$-alkyl)$_2$; C(O)—N(H)($C_{3-6}$-cycloalkyl) or C(O)—N($C_{1-6}$-alkyl)($C_{3-6}$-cycloalkyl);
wherein $C_{3-6}$-cycloalkyl can optionally be bridged via $C_{1-4}$-alkylene;
preferably wherein
$C_{1-6}$-alkyl and $C_{3-6}$-cycloalkyl in each case independently from one another is unsubstituted, mono-, di- or trisubstituted with one or more substituents selected from the group consisting of F, CN, $CH_3$, $CH_2CH_3$, $CF_3$; $CF_2H$; $CFH_2$; C(O)—$NH_2$; C(O)—N(H)($CH_3$); C(O)—N($CH_3$)$_2$; OH, $NH_2$, $OCH_3$, $SCH_3$, S(O)$_2$($CH_3$), S(O)($CH_3$), N($CH_3$)$_2$, cyclopropyl and oxetanyl; and $C_{1-4}$-alkylene is unsubstituted.

In a particularly preferred embodiment, $R^2$ represents H; F; Cl; Br; CN; methyl; ethyl; ethenyl (vinyl); n-propyl; 2-propyl; 1-propynyl; 2-propynyl; propenyl (—$CH_2CH$=$CH_2$; —CH=CH—$CH_3$; —C(=$CH_2$)—$CH_3$); n-butyl; isobutyl; sec-butyl; tert-butyl; $CF_3$; $CH_2CF_3$; $CHF_2$; $CH_2CHF_2$; $CH_2F$; $CH_2CH_2F$; $OCH_3$; $OCH_2CH_3$; OC(H)($CH_3$)$_2$; $OCH_2CH_2CH_3$; O—C($CH_3$)$_3$; $OCF_3$; $OCH_2CF_3$; $OCHF_2$; $OCH_2CHF_2$; $OCH_2F$; $OCH_2CH_2F$; $CH_2OH$; $CH_2CH_2OH$; $CH_2C(H)(OH)CH_3$; $CH_2CH_2CH_2OH$; $CH_2CH_2CH_2CH_2OH$; $C(CH_3)_2CH_2OH$; C(O)—$CH_3$; C(O)—$CH_2CH_3$; C(O)—C(H)($CH_3$)$_2$ C(O)—$CH_2CH_2CH_3$; C(O)—C($CH_3$)$_3$; cyclopropyl; cyclobutyl; cycopentyl; cyclohexyl; $CH_2$-cyclopropyl; $CH_2$-cyclobutyl; $CH_2$-cycopentyl; $CH_2$-cyclohexyl; O-cyclopropyl; O-cyclobutyl; O-cycopentyl; O-cyclohexyl; C(O)-cyclopropyl; C(O)-cyclobutyl; C(O)-cycopentyl; C(O)-cyclohexyl or C(O)—$NH_2$.

Preferably, $R^3$ represents H; F; Cl; Br; CN; $C_{1-6}$-alkyl; $C_{3-6}$-cycloalkyl; O—$C_{1-6}$-alkyl; N(H)($C_{1-6}$-alkyl), N($C_{1-6}$-alkyl)$_2$; C(O)—$C_{1-6}$-alkyl; C(O)—O—$C_{1-6}$-alkyl; C(O)—$NH_2$; C(O)—N(H)($C_{1-6}$-alkyl); C(O)—N($C_{1-6}$-alkyl)$_2$; O—$C_{3-6}$-cycloalkyl; N(H)($C_{3-6}$-cycloalkyl), N($C_{1-6}$-alkyl)($C_{3-6}$-cycloalkyl); C(O)—$C_{3-6}$-cycloalkyl; C(O)—O—$C_{3-6}$-cycloalkyl; C(O)—N(H)($C_{3-6}$-cycloalkyl) or C(O)—N($C_{1-6}$-alkyl)($C_{3-6}$-cycloalkyl); wherein $C_{3-6}$-cycloalkyl can optionally be bridged via $C_{1-4}$-alkylene.

In a preferred embodiment, $R^3$ represents H; F; Cl; Br; CN; $C_{1-6}$-alkyl; $C_{3-6}$-cycloalkyl; O—$C_{1-6}$-alkyl; C(O)—$NH_2$; C(O)—N(H)($C_{1-6}$-alkyl); C(O)—N($C_{1-6}$-alkyl)$_2$; C(O)—N(H)($C_{3-6}$-cycloalkyl) or C(O)—N($C_{1-6}$-alkyl)($C_{3-6}$-cycloalkyl);
wherein $C_{3-6}$-cycloalkyl can optionally be bridged via $C_{1-4}$-alkylene:
preferably wherein
$C_{1-6}$-alkyl and $C_{3-6}$-cycloalkyl in each case independently from one another is unsubstituted, mono-, di- or trisubstituted with one or more substituents selected from the group consisting of F, CN, $CH_3$, $CH_2CH_3$, $CF_3$; $CF_2H$; $CFH_2$; C(O)—$NH_2$; C(O)—N(H)($CH_3$); C(O)—N($CH_3$)$_2$; OH, $NH_2$, $OCH_3$, $SCH_3$, S(O)$_2$($CH_3$), S(O)($CH_3$), N($CH_3$)$_2$, cyclopropyl and oxetanyl; and $C_{1-4}$-alkylene is unsubstituted.

In a particularly preferred embodiment, $R^3$ represents H; F; Cl; Br; CN; methyl; ethyl; ethenyl (vinyl); n-propyl; 2-propyl; 1-propynyl; 2-propynyl; propenyl (—$CH_2CH$=$CH_2$; —CH=CH—$CH_3$; —C(=$CH_2$)—$CH_3$); n-butyl; isobutyl; sec-butyl; tert-butyl; $CF_3$; $CH_2CF_3$; $CHF_2$; $CH_2CHF_2$; $CH_2F$; $CH_2CH_2F$; $OCH_3$; $OCH_2CH_3$; OC(H)($CH_3$)$_2$; $OCH_2CH_2CH_3$; O—C($CH_3$)$_3$; $OCF_3$; $OCH_2CF_3$; $OCHF_2$; $OCH_2CHF_2$; $OCH_2F$; $OCH_2CH_2F$; $CH_2OH$; $CH_2CH_2OH$; $CH_2C(H)(OH)CH_3$;

CH$_2$CH$_2$CH$_2$OH; CH$_2$CH$_2$CH$_2$CH$_2$OH; C(CH$_3$)$_2$CH$_2$OH; C(O)—CH$_3$; C(O)—CH$_2$CH$_3$; C(O)—C(H)(CH$_3$)$_2$ C(O)—CH$_2$CH$_2$CH$_3$; C(O)—C(CH$_3$)$_3$; cyclopropyl; cyclobutyl; cycopentyl; cyclohexyl; CH$_2$-cyclopropyl; CH$_2$-cyclobutyl; CH$_2$-cycopentyl; CH$_2$-cyclohexyl; O-cyclopropyl; O-cyclobutyl; O-cycopentyl; O-cyclohexyl; C(O)-cyclopropyl; C(O)-cyclobutyl; C(O)-cycopentyl; C(O)-cyclohexyl; C(O)—NH$_2$.

In a preferred embodiment,

R$^2$ represents H; F; Cl; Br; CN; C$_{1-6}$-alkyl; C$_{3-6}$-cycloalkyl; O—C$_{1-6}$-alkyl; C(O)—NH$_2$; C(O)—N(H)(C$_{1-6}$-alkyl); C(O)—N(C$_{1-6}$-alkyl)$_2$; C(O)—N(H)(C$_{3-6}$-cycloalkyl) or C(O)—N(C$_{1-6}$-alkyl)(C$_{3-6}$-cycloalkyl);
wherein C$_{3-6}$-cycloalkyl can optionally be bridged via C$_{1-4}$-alkylene; and/or R$^3$ represents H; F; Cl; Br; CN; C$_{1-6}$-alkyl; C$_{3-6}$-cycloalkyl; O—C$_{1-6}$-alkyl; C(O)—NH$_2$; C(O)—N(H)(C$_{1-6}$-alkyl); C(O)—N(C$_{1-6}$-alkyl)$_2$; C(O)—N(H)(C$_{3-6}$-cycloalkyl) or C(O)—N(C$_{1-6}$-alkyl)(C$_{3-6}$-cycloalkyl);
wherein C$_{3-6}$-cycloalkyl can optionally be bridged via C$_{1-4}$-alkylene.

According to the present invention, R$^5$ and R$^6$ represent independently from one another H or unsubstituted C$_{1-4}$-alkyl. Preferably, R$^5$ and R$^6$ represent independently from one another H, CH$_3$, CH$_2$CH$_3$; CH$_2$CH$_2$CH$_3$, CH(CH$_3$)$_2$ or CH$_2$CH$_2$CH$_2$CH$_3$, more preferably H, CH$_3$, CH$_2$CH$_3$ or CH$_2$CH$_2$CH$_3$; still more preferably H, CH$_3$ or CH$_2$CH$_3$; most preferably H or CH$_3$. In a particularly preferred embodiment, R$^5$ and R$^6$ both represent CH$_3$.

In a particularly preferred embodiment, the compound according to the present invention is according to general formula (II) or (III), wherein X represents NR$^7$ and Z represents N or CR$^9$, more preferably CR$^9$, and wherein R$^5$ and R$^6$ both represent CH$_3$.

In a preferred embodiment, at least one of R$^1$, R$^2$, R$^3$, R$^5$ and R$^6$ is not H. More preferably, both R$^5$ and R$^6$ are not H and at least one of R$^1$, R$^2$ and R$^3$ is not H. In a preferred embodiment, both R$^5$ and R$^6$ are not H and one of R$^1$, R$^2$ and R$^3$ is not H. In another preferred embodiment, both R$^5$ and R$^6$ are not H and two of R$^1$, R$^2$ and R$^3$ are not H. In yet another preferred embodiment, R$^1$, R$^2$, R$^3$, R$^5$ and R$^6$ are not H.

In a particularly preferred embodiment,
the compound according to the present invention is according to general formula (II) or (III); and/or
X represents NR$^7$ and Z represents N or CR$^9$; and/or
R$^5$ and R$^6$ both represent methyl; and/or
at least one of R$^1$, R$^2$ and R$^3$ is not H.

According to the present invention, R$^7$ represents H or L-R$^8$.

In a preferred embodiment, R$^7$ represents H. According to this embodiment, preferably X represents NH and Z represents N or CR$^9$; or X represents N and Z represents NH. More preferably, X represents NH and Z represents CR$^9$.

Still further according to this embodiment, preferably the compound according to the present invention is according to general formula (II) or (III), wherein X represents NH and Z represents N or CR$^9$, more preferably CR$^9$.

In another preferred embodiment, R$^7$ is not H. According to this preferred embodiment, R$^7$ represents L-R$^8$.

In a preferred embodiment, L represents bond; S(O); S(O)$_2$; C$_{1-4}$-alkylene; C(O); C$_{1-4}$-alkylene-C(O); C(O)—O; C$_{1-4}$-alkylene-C(O)—O; C$_{1-4}$-alkylene-N(H)—C(O); C$_{1-4}$-alkylene-N(C$_{1-6}$-alkyl)-C(O); C$_{1-4}$-alkylene-N(H)—C(O)-0 or C$_{1-4}$-alkylene-N(C$_{1-6}$-alkyl)-C(O)—O. According to this embodiment, C$_{1-4}$-alkylene and C$_{1-6}$-alkyl are preferably unsubstituted.

More preferably, L represents bond; S(O); S(O)$_2$; C$_{1-4}$-alkylene; C(O); C$_{1-4}$-alkylene-C(O); C(O)—O; C$_{1-4}$-alkylene-C(O)—O; C$_{1-4}$-alkylene-N(H)—C(O) or C$_{1-4}$-alkylene-N(H)—C(O)—O; still more preferably bond; S(O); S(O)$_2$; CH$_2$; CH$_2$CH$_2$; C(CH$_3$)$_2$; CH$_2$CH$_2$CH$_2$; C(O); CH$_2$—C(O); CH$_2$CH$_2$—C(O); CH$_2$CH$_2$CH$_2$—C(O); C(CH$_3$)$_2$—C(O); C(O)—O; CH$_2$—C(O)—O; CH$_2$CH$_2$—C(O)—O; CH$_2$CH$_2$CH$_2$—C(O)—O; C(CH$_3$)$_2$—C(O)—O; CH$_2$—N(H)—C(O); CH$_2$CH$_2$—N(H)—C(O); C(CH$_3$)$_2$—N(H)—C(O); CH$_2$CH$_2$CH$_2$—N(H)—C(O); CH$_2$—N(H)—C(O)—O; CH$_2$CH$_2$—N(H)—C(O)—O; C(CH$_3$)$_2$—N(H)—C(O)—O or CH$_2$CH$_2$CH$_2$—N(H)—C(O)—O; most preferably bond; S(O)$_2$; CH$_2$; C(O); C(O)—O; CH$_2$—C(O)—O; CH$_2$CH$_2$—C(O)—O; CH$_2$CH$_2$—N(H)—C(O) or CH$_2$CH$_2$—N(H)—C(O)—O.

In a preferred embodiment, R$^8$ represents C$_{1-6}$-alkyl; C$_{3-6}$-cycloalkyl or 3 to 6-membered heterocycloalkyl;
wherein C$_{3-6}$-cycloalkyl and 3 to 6-membered heterocycloalkyl can optionally be bridged via C$_{1-4}$-alkylene; and preferably wherein C$_{1-6}$-alkyl; C$_{3-6}$-cycloalkyl and 3 to 6-membered heterocycloalkyl in each case independently from one another are unsubstituted or mono- or polysubstituted with one or more substituents selected from the group consisting of F; Cl; Br; I; CN; C$_{1-6}$-alkyl; CF$_3$; CF$_2$H; CFH$_2$; C(O)—NH$_2$; C(O)—N(H)(C$_{1-6}$-alkyl); C(O)—N(C$_{1-6}$-alkyl)$_2$; OH; OCF$_3$; OCF$_2$H; OCFH$_2$; O—C$_{1-6}$-alkyl; NH$_2$; N(H)(C$_{1-6}$-alkyl); N(C$_{1-6}$-alkyl)$_2$; SCF$_3$; SCF$_2$H; SCFH$_2$; S—C$_{1-6}$-alkyl; S(O)—C$_{1-6}$-alkyl; S(O)$_2$—C$_{1-6}$-alkyl; C$_{3-6}$-cycloalkyl; 3 to 6-membered heterocycloalkyl; phenyl and 5 or 6-membered heteroaryl.

More preferably R$^8$ represents

C$_{1-6}$-alkyl, which is selected from the group consisting of methyl, ethyl, ethenyl (vinyl), n-propyl, 2-propyl, n-butyl, isobutyl, sec-butyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; preferably methyl, ethyl, ethenyl (vinyl), n-propyl, 2-propyl, 1-propynyl, 2-propynyl, propenyl (—CH$_2$CH=CH$_2$, —CH=CH—CH$_3$, —C(=CH$_2$)—CH$_3$), n-butyl, 1-butynyl, 2-butynyl, 1-butenyl, 2-butenyl, isobutyl, sec-butyl and tert-butyl;

C$_{3-6}$-cycloalkyl, which is selected from the group consisting of cyclopropyl, cyclobutyl, cyclopentyl, cyclohexyl, cyclopentenyl and cyclohexenyl; preferably cyclopropyl, cyclobutyl, cyclopentyl and cyclohexyl; or 3 to 6-membered heterocycloalkyl, which is selected from the group consisting of tetrahydropyranyl, oxetanyl, oxiranyl, tetrahydrofuranyl, thiazolidinyl, tetrahydrothiophenyl, tetrahydropyridinyl, thiomorpholinyl, morpholinyl, pyrrolidinyl, 4-methylpiperazinyl, morpholinonyl, azetidinyl, aziridinyl, dithiolanyl, dihydropyrrolyl, dioxanyl, dioxolanyl, dihydropyridinyl, dihydrofuranyl, dihydroisoxazolyl, dihydrooxazolyl, imidazolidinyl, isoxazolidinyl, oxazolidinyl, piperazinyl, piperidinyl, pyrazolidinyl, pyranyl, tetrahydropyrrolyl, dihydroindolinyl, dihydroisoindolyl and tetrahydroindolinyl; preferably tetrahydropyranyl, oxetanyl, oxiranyl and tetrahydrofuranyl;

wherein C$_{3-6}$-cycloalkyl and 3 to 6-membered heterocycloalkyl can optionally be bridged via C$_{1-4}$-alkylene; and wherein C$_{1-6}$-alkyl. C$_{3-6}$-cycloalkyl and 3 to 6-membered heterocycloalkyl in each case independently from one another are unsubstituted or mono- or polysubstituted with one or more substituents selected from the group consisting of F, CN, $CH_3$, $CH_2CH_3$, $CF_3$; $CF_2H$; $CFH_2$; $C(O)-NH_2$; $C(O)-N(H)(CH_3)$; $C(O)-N(CH_3)_2$; OH, $NH_2$, $OCH_3$, $SCH_3$, $S(O)_2(CH_3)$, $S(O)(CH_3)$, $N(CH_3)_2$, cyclopropyl and oxetanyl.

Most preferably $R^8$ represents methyl, ethyl, n-propyl, 2-propyl, n-butyl, isobutyl, sec-butyl, tert-butyl, $CF_3$, $CHF_2$, $CH_2F$, $CH_2CF_3$, $CH_2CHF_2$, $CH_2CH_2F$, $CHFCH_3$, $CHFCH_2F$, $CHFCHF_2$, $CHFCF_3$, $CF_2CH_3$, $CF_2CH_2F$, $CF_2CHF_2$, $CF_2CF_3$, $CH_2CH_2CF_3$, $CH_2CH_2CHF_2$, $CH_2CH_2CH_2F$, $CH_2CHFCH_3$, $CH_2CHFCH_2F$, $CH_2CHFCHF_2$, $CH_2CHFCF_3$, $CH_2CF_2CH_3$, $CH_2CF_2CH_2F$, $CH_2CF_2CHF_2$, $CH_2CF_2CF_3$, $CH_2OH$, $CH_2CH_2OH$, $C(H)(OH)CH_3$, $CH_2CH_2CH_2OH$, $C(CH_3)_2OH$, $C(H)(OH)CH_2CH_3$, $C(H)(CH_3)-CH_2OH$, $CH_2C(H)(OH)-CH_3$, $CH_2CH_2CH_2CH_2OH$, $CH_2CH_2C(H)(OH)CH_3$, $CH_2C(H)(OH)CH_2CH_3$, $C(H)(OH)CH_2CH_2CH_3$, $CH_2-C(CH_3)_2-OH$, $C(CH_3)_2CH_2OH$, $C(H)(OH)CH_2CF_3$, $C(H)(OH)CH_2CHF_2$, $C(H)(OH)CH_2CH_2F$, $CH_2C(H)(OH)-CF_3$, $CH_2C(H)(OH)-CHF_2$, $CH_2C(H)(OH)-CH_2F$, $CH_2OCH_3$, $CH_2CH_2OCH_3$, $C(H)(CH_3)-OCH_3$, $CH_2CH_2CH_2OCH_3$, $C(CH_3)_2OCH_3$, $C(H)(OCH_3)CH_2CH_3$, $C(H)(CH_3)-CH_2OCH_3$, $CH_2C(H)(OCH_3)-CH_3$, $CH_2CH_2CH_2OCH_3$, $CH_2CH_2C(H)(OCH_3)CH_3$, $CH_2C(H)(OCH_3)CH_2CH_3$, $C(H)(OCH_3)CH_2CH_2CH_3$, $CH_2-C(CH_3)_2-OCH_3$, $C(CH_3)_2CH_2OCH_3$, $CH_2NH_2$, $CH_2CH_2NH_2$, $CH_2CH_2CH_2NH_2$, $C(CH_3)_2NH_2$, $C(H)(NH_2)CH_2CH_3$, $C(H)(CH_3)-CH_2NH_2$, $CH_2C(H)(NH_2)-CH_3$, $CH_2CH_2CH_2CH_2NH_2$, $CH_2CH_2C(H)(NH_2)CH_3$, $CH_2C(H)(NH_2)CH_2CH_3$, $C(H)(NH_2)CH_2CH_2CH_3$, $CH_2-C(CH_3)_2-NH_2$, $C(CH_3)_2CH_2NH_2$, $CH_2N(CH_3)_2$, $CH_2CH_2N(CH_3)_2$, $CH_2CH_2CH_2N(CH_3)_2$, $C(CH_3)_2N(CH_3)_2$, $C(H)(N(CH_3)_2)CH_2CH_3$, $C(H)(CH_3)-CH_2N(CH_3)_2$, $CH_2C(H)(N(CH_3)_2)-CH_3$, $CH_2CH_2CH_2CH_2N(CH_3)_2$, $CH_2CH_2C(H)(N(CH_3)_2)CH_3$, $CH_2C(H)(N(CH_3)_2)CH_2CH_3$, $C(H)(N(CH_3)_2)CH_2CH_2CH_3$, $CH_2-C(CH_3)_2-N(CH_3)_2$, $C(CH_3)_2CH_2N(CH_3)_2$, $CH_2-C(O)N(CH_3)_2$, $CH_2CH_2-C(O)N(CH_3)_2$, $CH_2CH_2CH_2-C(O)N(CH_3)_2$, $C(CH_3)_2-C(O)N(CH_3)_2$, $C(H)(C(O)N(CH_3)_2)CH_2CH_3$, $C(H)(CH_3)-CH_2-C(O)N(CH_3)_2$, $CH_2C(H)(C(O)N(CH_3)_2)-CH_3$, $CH_2CH_2CH_2-C(O)N(CH_3)_2$, $CH_2CH_2C(H)(C(O)N(CH_3)_2)CH_3$, $CH_2C(H)(C(O)N(CH_3)_2)CH_2CH_3$, $C(H)(C(O)N(CH_3)_2)CH_2CH_2CH_3$, $CH_2-C(CH_3)_2-C(O)N(CH_3)_2$, $C(CH_3)_2CH_2-C(O)N(CH_3)_2$, $(CH_2)_{0-2}$-cyclopropyl, $(CH_2)_{0-2}$-cyclobutyl, $(CH_2)_{0-2}$-cyclopentyl, $(CH_2)_{0-2}$-cyclohexyl, $(CH_2)_{0-2}$-tetrahydropyranyl, $(CH_2)_{0-2}$-oxetanyl, $(CH_2)_{0-2}$-oxiranyl or $(CH_2)_{0-2}$-tetrahydrofuranyl.

Preferred embodiments (E1 to E45) encompass those wherein L and $R^8$ have the meaning as given in the table below:

| | L | $R^8$ |
|---|---|---|
| E1 | bond | $(CH_2)_{0-6}$-$C_{1-10}$-alkyl |
| E2 | bond | $(CH_2)_{0-6}$-$C_{3-10}$-cycloalkyl |
| E3 | bond | $(CH_2)_{0-6}$-3 to 7 membered heterocycloalkyl |
| E4 | S(O) | $(CH_2)_{0-6}$-$C_{1-10}$-alkyl |
| E5 | S(O) | $(CH_2)_{0-6}$-$C_{3-10}$-cycloalkyl |
| E6 | S(O) | $(CH_2)_{0-6}$-3 to 7 membered heterocycloalkyl |
| E7 | $S(O)_2$ | $(CH_2)_{0-6}$-$C_{1-10}$-alkyl |
| E8 | $S(O)_2$ | $(CH_2)_{0-6}$-$C_{3-10}$-cycloalkyl |
| E9 | $S(O)_2$ | $(CH_2)_{0-6}$-3 to 7 membered heterocycloalkyl |
| E10 | $C_{1-6}$-alkylene | $(CH_2)_{0-6}$-$C_{1-10}$-alkyl |
| E11 | $C_{1-6}$-alkylene | $(CH_2)_{0-6}$-$C_{3-10}$-cycloalkyl |
| E12 | $C_{1-6}$-alkylene | $(CH_2)_{0-6}$-3 to 7 membered heterocycloalkyl |
| E13 | C(O) | $(CH_2)_{0-6}$-$C_{1-10}$-alkyl |
| E14 | C(O) | $(CH_2)_{0-6}$-$C_{3-10}$-cycloalkyl |
| E15 | C(O) | $(CH_2)_{0-6}$-3 to 7 membered heterocycloalkyl |
| E16 | $C_{1-6}$-alkylene-C(O) | $(CH_2)_{0-6}$-$C_{1-10}$-alkyl |
| E17 | $C_{1-6}$-alkylene-C(O) | $(CH_2)_{0-6}$-$C_{3-10}$-cycloalkyl |
| E18 | $C_{1-6}$-alkylene-C(O) | $(CH_2)_{0-6}$-3 to 7 membered heterocycloalkyl |
| E19 | C(O)—O | $(CH_2)_{0-6}$-$C_{1-10}$-alkyl |
| E20 | C(O)—O | $(CH_2)_{0-6}$-$C_{3-10}$-cycloalkyl |
| E21 | C(O)—O | $(CH_2)_{0-6}$-3 to 7 membered heterocycloalkyl |
| E22 | $C_{1-6}$-alkylene-C(O)—O | $(CH_2)_{0-6}$-$C_{1-10}$-alkyl |
| E23 | $C_{1-6}$-alkylene-C(O)—O | $(CH_2)_{0-6}$-$C_{3-10}$-cycloalkyl |
| E24 | $C_{1-6}$-alkylene-C(O)—O | $(CH_2)_{0-6}$-3 to 7 membered heterocycloalkyl |
| E25 | $C_{1-6}$-alkylene-N(H)—C(O) | $(CH_2)_{0-6}$-$C_{1-10}$-alkyl |
| E26 | $C_{1-6}$-alkylene-N(H)—C(O) | $(CH_2)_{0-6}$-$C_{3-10}$-cycloalkyl |
| E27 | $C_{1-6}$-alkylene-N(H)—C(O) | $(CH_2)_{0-6}$-3 to 7 membered heterocycloalkyl |
| E28 | $C_{1-6}$-alkylene-N($C_{1-10}$-alkyl)—C(O) | $(CH_2)_{0-6}$-$C_{1-10}$-alkyl |
| E29 | $C_{1-6}$-alkylene-N($C_{1-10}$-alkyl)—C(O) | $(CH_2)_{0-6}$-$C_{3-10}$-cycloalkyl |
| E30 | $C_{1-6}$-alkylene-N($C_{1-10}$-alkyl)—C(O) | $(CH_2)_{0-6}$-3 to 7 membered heterocycloalkyl |
| E31 | $C_{1-6}$-alkylene-N(H)—C(O)—O | $(CH_2)_{0-6}$-$C_{1-10}$-alkyl |
| E32 | $C_{1-6}$-alkylene-N(H)—C(O)—O | $(CH_2)_{0-6}$-$C_{3-10}$-cycloalkyl |
| E33 | $C_{1-6}$-alkylene-N(H)—C(O)—O | $(CH_2)_{0-6}$-3 to 7 membered heterocycloalkyl |
| E34 | $C_{1-6}$-alkylene-N($C_{1-10}$-alkyl)—C(O)—O | $(CH_2)_{0-6}$-$C_{1-10}$-alkyl |
| E35 | $C_{1-6}$-alkylene-N($C_{1-10}$-alkyl)—C(O)—O | $(CH_2)_{0-6}$-$C_{3-10}$-cycloalkyl |
| E36 | $C_{1-6}$-alkylene-N($C_{1-10}$-alkyl)—C(O)—O | $(CH_2)_{0-6}$-3 to 7 membered heterocycloalkyl |
| E37 | O | $(CH_2)_{0-6}$-$C_{1-10}$-alkyl |
| E38 | O | $(CH_2)_{0-6}$-$C_{3-10}$-cycloalkyl |
| E39 | O | $(CH_2)_{0-6}$-3 to 7 membered heterocycloalkyl |
| E40 | NH | $(CH_2)_{0-6}$-$C_{1-10}$-alkyl |
| E41 | NH | $(CH_2)_{0-6}$-$C_{3-10}$-cycloalkyl |
| E42 | NH | $(CH_2)_{0-6}$-3 to 7 membered heterocycloalkyl |
| E43 | N($C_{1-10}$-alkyl) | $(CH_2)_{0-6}$-$C_{1-10}$-alkyl |
| E44 | N($C_{1-10}$-alkyl) | $(CH_2)_{0-6}$-$C_{3-10}$-cycloalkyl |
| E45 | N($C_{1-10}$-alkyl) | $(CH_2)_{0-6}$-3 to 7 membered heterocycloalkyl |

Preferably,

L represents bond; S(O); $S(O)_2$; $C_{1-4}$-alkylene; C(O); $C_{1-4}$-alkylene-C(O); C(O)—O; $C_{1-4}$-alkylene-C(O)—O; $C_{1-4}$-alkylene-N(H)—C(O); $C_{1-4}$-alkylene-N($C_{1-6}$-alkyl)-C(O); $C_{1-4}$-alkylene-N(H)—C(O)-O or $C_{1-4}$-alkylene-N($C_{1-6}$-alkyl)-C(O)—O; and $R^8$ represents $C_{1-6}$-alkyl; $C_{3-6}$-cycloalkyl or 3 to 6-membered heterocycloalkyl; wherein $C_{3-6}$-cycloalkyl and 3 to 6-membered heterocycloalkyl can optionally be bridged via $C_{1-4}$-alkylene.

In a particularly preferred embodiment,

L represents bond; S(O); S(O)$_2$; C$_{1-4}$-alkylene; C(O); C$_{1-4}$-alkylene-C(O); C(O)—O; C$_{1-4}$-alkylene-C(O)—O; C$_{1-4}$-alkylene-N(H)—C(O) or C$_{1-4}$-alkylene-N(H)—C(O)—O;

R$^8$ represents C$_{1-6}$-alkyl; C$_{3-6}$-cycloalkyl or 3 to 6-membered heterocycloalkyl; wherein C$_{3-6}$-cycloalkyl and 3 to 6-membered heterocycloalkyl can optionally be bridged via C$_{1-4}$-alkylene.

More preferably,

L represents bond; S(O); S(O)$_2$; C$_{1-4}$-alkylene; C(O); C$_{1-4}$-alkylene-C(O); C(O)—O; C$_{1-4}$-alkylene-C(O)—O; C$_{1-4}$-alkylene-N(H)—C(O) or C$_{1-4}$-alkylene-N(H)—C(O)—O; still more preferably bond; S(O); S(O)$_2$; CH$_2$; CH$_2$CH$_2$; C(CH$_3$)$_2$; CH$_2$CH$_2$CH$_2$; C(O); CH$_2$—C(O); CH$_2$CH$_2$—C(O); CH$_2$CH$_2$CH$_2$—C(O); C(CH$_3$)$_2$—C(O); C(O)—O; CH$_2$—C(O)—O; CH$_2$CH$_2$—C(O)—O; CH$_2$CH$_2$CH$_2$—C(O)—O; C(CH$_3$)$_2$—C(O)—O; CH$_2$—N(H)—C(O); CH$_2$CH$_2$—N(H)—C(O); C(CH$_3$)$_2$—N(H)—C(O); CH$_2$CH$_2$CH$_2$—N(H)—C(O); CH$_2$—N(H)—C(O)—O; CH$_2$CH$_2$—N(H)—C(O)—O; C(CH$_3$)$_2$—N(H)—C(O)—O or CH$_2$CH$_2$CH$_2$—N(H)—C(O)—O; most preferably bond; S(O)$_2$; CH$_2$; C(O); C(O)—O; CH$_2$—C(O)—O; CH$_2$CH$_2$—C(O)—O; CH$_2$CH$_2$—N(H)—C(O) or CH$_2$CH$_2$—N(H)—C(O)—O; and R$^8$ represents C$_{1-6}$-alkyl; C$_{3-6}$-cycloalkyl or 3 to 6-membered heterocycloalkyl; wherein C$_{3-6}$-cycloalkyl and 3 to 6-membered heterocycloalkyl can optionally be bridged via C$_{1-4}$-alkylene; and preferably wherein C$_{1-6}$-alkyl; C$_{3-6}$-cycloalkyl and 3 to 6-membered heterocycloalkyl in each case independently from one another are unsubstituted or mono- or poly substituted with one or more substituents selected from the group consisting of F; Cl; Br; I; CN; C$_{1-6}$-alkyl; CF$_3$; CF$_2$H; CFH$_2$; C(O)—NH$_2$; C(O)—N(H)(C$_{1-6}$-alkyl); C(O)—N(C$_{1-6}$-alkyl)$_2$; OH; OCF$_3$; OCF$_2$H; OCFH$_2$; O—C$_{1-6}$-alkyl; NH$_2$; N(H)(C$_{1-6}$-alkyl); N(C$_{1-6}$-alkyl)$_2$; SCF$_3$; SCF$_2$H; SCFH$_2$; S—C$_{1-6}$-alkyl; S(O)—C$_{1-6}$-alkyl; S(O)$_2$—C$_{1-6}$-alkyl; C$_{3-6}$-cycloalkyl; 3 to 6-membered heterocycloalkyl; phenyl and 5 or 6-membered heteroaryl.

Preferably, R$^9$ represents H; F; Cl; Br; I; CN; C$_{1-6}$-alkyl; C$_{3-6}$-cycloalkyl, 3 to 6-membered heterocycloalkyl; S(O)—(C$_{1-6}$-alkyl); S(O)—(C$_{3-6}$-cycloalkyl); S(O)-(3 to 6-membered heterocycloalkyl); S(O)$_2$—(C$_{1-6}$-alkyl); S(O)$_2$—(C$_{3-6}$-cycloalkyl); S(O)$_2$-(3 to 6-membered heterocycloalkyl); P(O)—(C$_{1-6}$-alkyl)$_2$; P(O)(C$_{1-6}$-alkyl)(C$_{3-6}$-cycloalkyl); P(O)(C$_{1-6}$-alkyl)(3 to 6-membered heterocycloalkyl); P(O)—(O—C$_{1-6}$-alkyl)$_2$; P(O)(O—C$_{1-6}$-alkyl)(O—C$_{3-6}$-cycloalkyl); P(O)(O—C$_{1-6}$-alkyl)(O-(3 to 6-membered heterocycloalkyl)); O—C$_{1-6}$-alkyl; S—C$_{1-6}$-alkyl; N(H)(C$_{1-6}$-alkyl), N(C$_{1-6}$-alkyl)$_2$; C(O)—C$_{1-6}$-alkyl; C(O)—O—C$_{1-6}$-alkyl; C(O)—NH$_2$; C(O)—N(H)(C$_{1-6}$-alkyl); C(O)—N(C$_{1-6}$-alkyl)$_2$; O—C$_{3-6}$-cycloalkyl; N(H)(C$_{3-6}$-cycloalkyl), N(C$_{1-6}$-alkyl)(C$_{3-6}$-cycloalkyl); C(O)—C$_{3-6}$-cycloalkyl; C(O)—O—C$_{3-6}$-cycloalkyl; C(O)—N(H)(C$_{3-6}$-cycloalkyl); C(O)—N(C$_{1-6}$-alkyl)(C$_{3-6}$-cycloalkyl); O-(3 to 6-membered heterocycloalkyl); N(H)(3 to 6-membered heterocycloalkyl), N(C$_{1-6}$-alkyl) (3 to 6-membered heterocycloalkyl); C(O)-3 to 6-membered heterocycloalkyl); C(O)—O-(3 to 6-membered heterocycloalkyl); C(O)—N(H)(3 to 6-membered heterocycloalkyl) or C(O)—N(C$_{1-6}$-alkyl)(3 to 6-membered heterocycloalkyl);

wherein C$_{3-6}$-cycloalkyl and 3 to 6-membered heterocycloalkyl can optionally be bridged via C$_{1-4}$-alkylene;

preferably wherein C$_{1-6}$-alkyl. C$_{3-6}$-cycloalkyl and 3 to 6-membered heterocycloalkyl is in each case unsubstituted.

More preferably, R$^9$ represents H; F; Cl; Br; I; CN; methyl, ethyl, n-propyl, 2-propyl, n-butyl, isobutyl, sec-butyl, tert-butyl, CF$_3$, CHF$_2$, CH$_2$F, CH$_2$CF$_3$, CH$_2$CHF$_2$, CH$_2$CH$_2$F, cyclopropyl, cyclobutyl, tetrahydropyranyl, oxetanyl, oxiranyl, tetrahydrofuranyl, S(O)—(CH$_3$); S(O)—(CH$_2$CH$_3$); S(O)—((CH$_2$)$_{0-2}$-cyclopropyl); S(O)—((CH$_2$)$_{0-2}$-cyclobutyl); S(O)—((CH$_2$)$_{0-2}$-cyclopentyl); S(O)—((CH$_2$)$_{0-2}$-cyclohexyl); S(O)—((CH$_2$)$_{0-2}$-tetrahydropyranyl), S(O)—((CH$_2$)$_{0-2}$-oxetanyl), S(O)—((CH$_2$)$_{0-2}$-oxiranyl), S(O)—((CH$_2$)$_{0-2}$-tetrahydrofuranyl), S(O)$_2$—(CH$_3$); S(O)$_2$—(CH$_2$CH$_3$); S(O)$_2$—((CH$_2$)$_{0-2}$-cyclopropyl); S(O)$_2$—((CH$_2$)$_{0-2}$-cyclobutyl); S(O)$_2$—((CH$_2$)$_{0-2}$-cyclopentyl); S(O)$_2$—((CH$_2$)$_{0-2}$-cyclohexyl); S(O)$_2$—((CH$_2$)$_{0-2}$-tetrahydropyranyl), S(O)$_2$—((CH$_2$)$_{0-2}$-oxetanyl), S(O)$_2$—((CH$_2$)$_{0-2}$-oxiranyl), S(O)$_2$—((CH$_2$)$_{0-2}$-tetrahydrofuranyl), O—CH$_3$, O—CH$_2$CH$_3$, O—CH$_2$CH$_2$CH$_3$, O—C(H)(CH$_3$)$_2$, N(H)(CH$_3$), N(H)(CH$_2$CH$_3$), N(CH$_3$)$_2$ or N(CH$_3$)(CH$_2$CH$_3$).

In a particularly preferred embodiment, R$^9$ represents H; F; CN; methyl; ethyl; n-propyl; 2-propyl; CF$_3$; CH$_2$CF$_3$; CHF$_2$; CH$_2$CHF$_2$; CH$_2$F; CH$_2$CH$_2$F; S(O)—CH$_3$; S(O)—CH$_2$CH$_3$; S(O)—CH$_2$CH$_2$CH$_3$; S(O)—CH(CH$_3$)$_2$; S(O)$_2$—CH$_3$; S(O)$_2$—CH$_2$CH$_3$; S(O)$_2$—CH$_2$CH$_2$CH$_3$ or S(O)$_2$—CH(CH$_3$)$_2$.

Preferably, R$^{10}$ represents H; F; Cl; Br; I; CN; C$_{1-6}$-alkyl; C$_{3-6}$-cycloalkyl, 3 to 6-membered heterocycloalkyl; S(O)—(C$_{1-6}$-alkyl); S(O)—(C$_{3-6}$-cycloalkyl); S(O)-(3 to 6-membered heterocycloalkyl); S(O)$_2$—(C$_{1-6}$-alkyl); S(O)$_2$—(C$_{3-6}$-cycloalkyl); S(O)$_2$-(3 to 6-membered heterocycloalkyl); P(O)—(C$_{1-6}$-alkyl)$_2$; P(O)(C$_{1-6}$-alkyl)(C$_{3-6}$-cycloalkyl); P(O)(C$_{1-6}$-alkyl)(3 to 6-membered heterocycloalkyl); P(O)—(O—C$_{1-6}$-alkyl)$_2$; P(O)(O—C$_{1-6}$-alkyl)(O—C$_{3-6}$-cycloalkyl); P(O)(O—C$_{1-6}$-alkyl)(O-(3 to 6-membered heterocycloalkyl)); O—C$_{1-6}$-alkyl; S—C$_{1-6}$-alkyl; N(H)(C$_{1-6}$-alkyl), N(C$_{1-6}$-alkyl)$_2$; C(O)—C$_{1-6}$-alkyl; C(O)—O—C$_{1-6}$-alkyl; C(O)—NH$_2$; C(O)—N(H)(C$_{1-6}$-alkyl); C(O)—N(C$_{1-6}$-alkyl)$_2$; O—C$_{3-6}$-cycloalkyl; N(H)(C$_{3-6}$-cycloalkyl), N(C$_{1-6}$-alkyl)(C$_{3-6}$-cycloalkyl); C(O)—C$_{3-6}$-cycloalkyl; C(O)—O—C$_{3-6}$-cycloalkyl; C(O)—N(H)(C$_{3-6}$-cycloalkyl); C(O)—N(C$_{1-6}$-alkyl)(C$_{3-6}$-cycloalkyl); O-(3 to 6-membered heterocycloalkyl); N(H)(3 to 6-membered heterocycloalkyl), N(C$_{1-6}$-alkyl) (3 to 6-membered heterocycloalkyl); C(O)-3 to 6-membered heterocycloalkyl); C(O)—O-(3 to 6-membered heterocycloalkyl); C(O)—N(H)(3 to 6-membered heterocycloalkyl) or C(O)—N(C$_{1-6}$-alkyl)(3 to 6-membered heterocycloalkyl);

wherein C$_{3-6}$-cycloalkyl and 3 to 6-membered heterocycloalkyl can optionally be bridged via C$_{1-4}$-alkylene; and preferably wherein C$_{1-6}$-alkyl; C$_{3-6}$-cycloalkyl and 3 to 6-membered heterocycloalkyl in each case independently from one another are unsubstituted or mono- or polysubstituted with one or more substituents selected from the group consisting of F; Cl; Br; I; CN; C$_{1-6}$-alkyl; CF$_3$; CF$_2$H; CFH$_2$; C(O)—NH$_2$; C(O)—N(H)(C$_{1-6}$-alkyl); C(O)—N(C$_{1-6}$-alkyl)$_2$; OH; OCF$_3$; OCF$_2$H; OCFH$_2$; O—C$_{1-6}$-alkyl; NH$_2$; N(H)(C$_{1-6}$-alkyl); N(C$_{1-6}$-alkyl)$_2$; SCF$_3$; SCF$_2$H; SCFH$_2$; S—C$_{1-6}$-alkyl; S(O)—C$_{1-6}$-alkyl; S(O)$_2$—C$_{1-6}$-alkyl; C$_{3-6}$-cycloalkyl; 3 to 6-membered heterocycloalkyl; phenyl and 5 or 6-membered heteroaryl.

In another preferred embodiment, R$^{10}$ represents H; F; Cl; Br; CN; C$_{1-6}$-alkyl; C$_{3-6}$-cycloalkyl; 3 to 6-membered heterocycloalkyl; P(O)—(C$_{1-6}$-alkyl)$_2$; P(O)(C$_{1-6}$-alkyl)(C$_{3-6}$- cycloalkyl); P(O)(C$_{1-6}$-alkyl)(3 to 6-membered heterocycloalkyl) P(O)—(O—C$_{1-6}$-alkyl)$_2$; P(O)(O—C$_{1-6}$-alkyl)(O—C$_{3-6}$-cycloalkyl); P(O)(O—C$_{1-6}$-alkyl)(O-(3 to 6-membered heterocycloalkyl));

preferably wherein C$_{1-6}$-alkyl; C$_{3-6}$-cycloalkyl and 3 to 6-membered heterocycloalkyl in each case independently from one another are unsubstituted or mono- or polysubstituted with one or more substituents selected from the group consisting of F; Cl; Br; I; CN; C$_{1-4}$-alkyl; CF$_3$; CF$_2$H; CFH$_2$; OH; OCF$_3$; OCF$_2$H; OCFH$_2$; O—C$_{1-4}$-alkyl; NH$_2$; N(H)(C$_{1-4}$-alkyl); N(C$_{1-4}$-alkyl)$_2$; S—C$_{1-4}$-alkyl; S(O)—C$_{1-4}$-alkyl and S(O)$_2$—C$_{1-4}$-alkyl; more preferably F, Cl, Br, CF$_3$, OCH$_3$, OCF$_3$, OCHF$_2$, OCH$_2$F, OH and NH$_2$.

More preferably, R$^{10}$ represents H; F; Cl; Br; I; CN; methyl, ethyl, n-propyl, 2-propyl, 1-propynyl, 2-propynyl, propenyl (—CH$_2$CH=CH$_2$, —CH=CH—CH$_3$, —C(=CH$_2$)—CH$_3$), n-butyl, 1-butynyl, 2-butynyl, 1-butenyl, 2-butenyl, 3-methyl-1-butynyl, n-butyl, isobutyl, sec-butyl, tert-butyl, CF$_3$, CHF$_2$, CH$_2$F, CH$_2$CF$_3$, CH$_2$CHF$_2$, CH$_2$CH$_2$F, CH$_2$CHFCH$_3$, CH$_2$CHFCH$_2$F, CH$_2$CHFCHF$_2$, CH$_2$CHFCF$_3$, CH$_2$CF$_2$CH$_3$, CH$_2$CF$_2$CH$_2$F, CH$_2$CF$_2$CHF$_2$, CH$_2$CF$_2$CF$_3$, CH$_2$OH, CH$_2$CH$_2$OH, C(H)(OH)CH$_3$, CH$_2$CH$_2$CH$_2$OH, C(CH$_3$)$_2$OH, C(H)(OH)CH$_2$CH$_3$, C(H)(CH$_3$)—CH$_2$OH, CH$_2$C(H)(OH)—CH$_3$, CH$_2$CH$_2$CH$_2$CH$_2$OH, CH$_2$CH$_2$C(H)(OH)CH$_3$, CH$_2$C(H)(OH)CH$_2$CH$_3$, C(H)(OH)CH$_2$CH$_2$CH$_3$, CH$_2$—C(CH$_3$)$_2$—OH, C(CH$_3$)$_2$CH$_2$OH, C≡C—C(H)(OH)CH$_3$, C(H)(OH)—C≡C—CH$_3$, C≡C—C(CH$_3$)(OH)CH$_3$, C(CH$_3$)(OH)—C≡C—CH$_3$, C(H)(OH)CH$_2$CF$_3$, C(H)(OH)CH$_2$CHF$_2$, C(H)(OH)CH$_2$CH$_2$F, CH$_2$C(H)(OH)—CF$_3$, CH$_2$C(H)(OH)—CHF$_2$, CH$_2$C(H)(OH)—CH$_2$F, CH$_2$OCH$_3$, CH$_2$CH$_2$OCH$_3$, C(H)(CH$_3$)—OCH$_3$, CH$_2$CH$_2$CH$_2$OCH$_3$, C(CH$_3$)$_2$OCH$_3$, C(H)(OCH$_3$)CH$_2$CH$_3$, C(H)(CH$_3$)—CH$_2$OCH$_3$, CH$_2$C(H)(OCH$_3$)—CH$_3$, CH$_2$CH$_2$CH$_2$CH$_2$OCH$_3$, CH$_2$CH$_2$C(H)(OCH$_3$)CH$_3$, CH$_2$C(H)(OCH$_3$)CH$_2$CH$_3$, C(H)(OCH$_3$)CH$_2$CH$_2$CH$_3$, CH$_2$—C(CH$_3$)$_2$—OCH$_3$, C(CH$_3$)$_2$CH$_2$OCH$_3$, CH$_2$NH$_2$, CH$_2$CH$_2$NH$_2$, CH$_2$CH$_2$CH$_2$NH$_2$, C(CH$_3$)$_2$NH$_2$, C(H)(NH$_2$)CH$_2$CH$_3$, C(H)(CH$_3$)—CH$_2$NH$_2$, CH$_2$C(H)(NH$_2$)—CH$_3$, CH$_2$CH$_2$CH$_2$CH$_2$NH$_2$, CH$_2$CH$_2$C(H)(NH$_2$)CH$_3$, CH$_2$C(H)(NH$_2$)CH$_2$CH$_3$, C(H)(NH$_2$)CH$_2$CH$_2$CH$_3$, CH$_2$—C(CH$_3$)$_2$—NH$_2$, C(CH$_3$)$_2$CH$_2$NH$_2$, C≡C—C(H)(NH$_2$)CH$_3$, C(H)(NH$_2$)—C≡C—CH$_3$, C≡C—C(CH$_3$)(NH$_2$)CH$_3$, C(CH$_3$)(NH$_2$)—C≡C—CH$_3$, CH$_2$N(CH$_3$)$_2$, CH$_2$CH$_2$N(CH$_3$)$_2$, CH$_2$CH$_2$CH$_2$N(CH$_3$)$_2$, C(CH$_3$)$_2$N(CH$_3$)$_2$, C(H)(N(CH$_3$)$_2$)CH$_2$CH$_3$, C(H)(CH$_3$)—CH$_2$N(CH$_3$)$_2$, CH$_2$C(H)(N(CH$_3$)$_2$)—CH$_3$, CH$_2$CH$_2$CH$_2$CH$_2$N(CH$_3$)$_2$, CH$_2$CH$_2$C(H)(N(CH$_3$)$_2$)CH$_3$, CH$_2$C(H)(N(CH$_3$)$_2$)CH$_2$CH$_3$, C(H)(N(CH$_3$)$_2$)CH$_2$CH$_2$CH$_3$, CH$_2$—C(CH$_3$)$_2$—N(CH$_3$)$_2$, C(CH$_3$)$_2$CH$_2$N(CH$_3$)$_2$, S(O)—CH$_3$, S(O)—CH$_2$CH$_3$, S(O)—((CH$_2$)$_{0-2}$-cyclopropyl), S(O)—((CH$_2$)$_{0-2}$-cyclobutyl), S(O)—((CH$_2$)$_{0-2}$-cyclopentyl), S(O)—((CH$_2$)$_{0-2}$-cyclohexyl), S(O)$_2$—CH$_3$, S(O)$_2$—CH$_2$CH$_3$, S(O)$_2$—((CH$_2$)$_{0-2}$-cyclopropyl), S(O)$_2$—((CH$_2$)$_{0-2}$-cyclobutyl), S(O)$_2$—((CH$_2$)$_{0-2}$-cyclopentyl), S(O)$_2$—((CH$_2$)$_{0-2}$-cyclohexyl), P(O)—(CH$_3$)$_2$, P(O)—(CH$_3$)(CH$_2$CH$_3$), P(O)—(CH$_3$)((CH$_2$)$_{0-2}$-cyclopropyl), P(O)—(CH$_3$)((CH$_2$)$_{0-2}$-cyclobutyl), P(O)—(CH$_3$)((CH$_2$)$_{0-2}$-cyclopentyl), P(O)—(CH$_3$)((CH$_2$)$_{0-2}$-cyclohexyl), (CH$_2$)$_{0-2}$-cyclopropyl, (CH$_2$)$_{0-2}$-cyclobutyl, (CH$_2$)$_{0-2}$-tetrahydropyranyl, (CH$_2$)$_{0-2}$-oxetanyl, (CH$_2$)$_{0-2}$-oxiranyl, (CH$_2$)$_{0-2}$-tetrahydrofuranyl, O—CH$_3$, O—CH$_2$CH$_3$, O—CH$_2$CH$_2$CH$_3$, O—C(H)(CH$_3$)$_2$, N(H)(CH$_3$), N(H)(CH$_2$CH$_3$), N(CH$_3$)$_2$ or N(CH$_3$)(CH$_2$CH$_3$).

In a preferred embodiment, at least one of R$^9$ and R$^{10}$ is H.

According to the present invention, n represents 0, 1, 2 or 3. In a preferred embodiment, n represents 0. In another preferred embodiment, n represents 1. In yet another preferred embodiment, n represents 2. In still another preferred embodiment, n represents 3. More preferably, n represents 1 or 2, most preferably 1.

Preferably, R$^{11}$ represents F; Cl; Br; I; CN; C$_{1-6}$-alkyl; O—C$_{1-6}$-alkyl; NO$_2$; OH, NH$_2$; C$_{3-6}$-cycloalkyl; 3 to 6-membered heterocycloalkyl; S(O)—(C$_{1-6}$-alkyl); S(O)$_2$—(C$_{1-6}$-alkyl); P(O)—(C$_{1-6}$-alkyl)$_2$; O—C$_{1-6}$-alkyl; N(H)(C$_{1-6}$-alkyl), N(C$_{1-6}$-alkyl)$_2$;

preferably wherein C$_{1-6}$-alkyl; C$_{3-6}$-cycloalkyl and 3 to 6-membered heterocycloalkyl in each case independently from one another are unsubstituted or mono- or polysubstituted with one or more substituents selected from the group consisting of F; Cl; Br; I; CN; C$_{1-4}$-alkyl; CF$_3$; CF$_2$H; CFH$_2$; OH; OCF$_3$; OCF$_2$H; OCFH$_2$; O—C$_{1-4}$-alkyl; NH$_2$; N(H)(C$_{1-4}$-alkyl); N(C$_{1-4}$-alkyl)$_2$; S—C$_{1-4}$-alkyl; S(O)—C$_{1-4}$-alkyl and S(O)$_2$—C$_{1-4}$-alkyl; more preferably F, Cl, Br, CF$_3$, OCH$_3$, OCF$_3$, OCHF$_2$, OCH$_2$F, OH and NH$_2$.

In a particularly preferred embodiment, R$^{11}$ represents F; Cl; Br; I; CN; C$_{1-6}$-alkyl or O— C$_{1-6}$-alkyl; preferably wherein C$_{1-6}$-alkyl in each case independently from one another is unsubstituted or mono- or polysubstituted with one or more substituents selected from the group consisting of F and CF$_3$.

More preferably, R$^{11}$ represents F; Cl; Br; I; CN; CH$_3$, CH$_2$CH$_3$, O—CH$_3$ or O—CH$_2$CH$_3$.

In a particularly preferred embodiment, R$^{11}$ represents F; Cl; Br; I; CN; C$_{1-6}$-alkyl or O— C$_{1-6}$-alkyl; and/or n represents 0, 1 or 2.

In a preferred embodiment, the compound according to the present invention is selected from the 35 group consisting of 1 7,9-Difluoro-8-(6-fluoro-1H-indol-4-yl)-1,4,4-trimethyl-5H-[1,2,4]triazolo[4,3-a]quinoxaline
2 8-(1-Cyclopropyl-6-fluoro-1H-indol-4-yl)-7,9-difluoro-1,4,4-trimethyl-5H-[1,2,4]triazolo[4,3-a]quinoxaline
3 7,9-Difluoro-8-(6-fluoro-1-methylsulfonyl-1H-indol-4-yl)-1,4,4-trimethyl-5H-[1,2,4]triazolo[4,3-a]quinoxaline
4 1-[4-(7,9-Difluoro-1,4,4-trimethyl-5H-[1,2,4]triazolo[4,3-a]quinoxalin-8-yl)-6-fluoro-1H-indol-1-yl]-ethanone
5 7,9-Difluoro-8-(6-fluoro-2-methyl-1H-indol-4-yl)-1,4,4-trimethyl-5H-[1,2,4]triazolo[4,3-a]quinoxaline
6 4-(7,9-Difluoro-1,4,4-trimethyl-5H-[1,2,4]triazolo[4,3-a]quinoxalin-8-yl)-6-fluoro-1H-indole-2-carbonitrile
9 7,9-Difluoro-8-(1H-indol-7-yl)-1,4,4-trimethyl-5H-[1,2,4]triazolo[4,3-a]quinoxaline
10 7,9-Difluoro-1,4,4-trimethyl-8-[3-(trifluoromethyl)-1H-indol-7-yl]-5H-[1,2,4]triazolo[4,3-a]quinoxaline
11 1-Ethyl-7,9-difluoro-8-(1H-indol-7-yl)-4,4-dimethyl-5H-[1,2,4]triazolo[4,3-a]quinoxaline
12 7-(1-Ethyl-7,9-difluoro-4,4-dimethyl-5H-[1,2,4]triazolo[4,3-a]quinoxalin-8-yl)-1H-indole-3-carbonitrile
13 1-Ethyl-7,9-difluoro-4,4-dimethyl-8-(3-prop-1-ynyl-1H-indol-7-yl)-5H-[1,2,4]triazolo[4,3-a]quinoxaline
14 1-Ethyl-7,9-difluoro-8-(5-fluoro-1H-indol-7-yl)-4,4-dimethyl-5H-[1,2,4]triazolo[4,3-a]quinoxaline
15 7-(1-Ethyl-7,9-difluoro-4,4-dimethyl-5H-[1,2,4]triazolo[4,3-a]quinoxalin-8-yl)-5-fluoro-1H-indole-3-carbonitrile
16 1-Ethyl-7,9-difluoro-8-(5-fluoro-3-prop-1-ynyl-1H-indol-7-yl)-4,4-dimethyl-5H-[1,2,4]triazolo[4,3-a]quinoxaline
17 7-(1-Ethyl-7,9-difluoro-4,4-dimethyl-5H-[1,2,4]triazolo[4,3-a]quinoxalin-8-yl)-5-methyl-1H-indole-3-carbonitrile
18 8-[1-(Ethylsulfonyl)-6-fluoro-1H-indol-4-yl]-7,9-difluoro-1,4,4-trimethyl-5H-[1,2,4]triazolo[4,3-a]quinoxaline 19 8-[1-(Cyclopropylsulfonyl)-6-fluoro-1H-indol-4-yl]-7,9-difluoro-1,4,4-trimethyl-5H-[1,2,4]triazolo[4,3-a]quinoxaline 20 1-[4-(7,9-Difluoro-1,4,4-trimethyl-5H-[1,2,4]triazolo[4,3-a]quinoxalin-8-yl)-1H-indol-1-yl]-ethanone 21 7,9-Difluoro-8-[6-fluoro-1-(2,2,2-trifluoro-ethyl)-1H-indol-4-yl]-1,4,4-trimethyl-5H-[1,2,4]triazolo[4,3-a]quinoxaline 22 7,9-Difluoro-1,4,4-trimethyl-8-(1-methylsulfonyl-1H-indol-4-yl)-5H-[1,2,4]triazolo[4,3-a]quinoxaline 23 7-Fluoro-8-[5-fluoro-3-(2,2,2-trifluoro-ethyl)-1H-indol-7-yl]-1,4,4,9-tetramethyl-5H-[1,2,4]triazolo[4,3-a]quinoxaline 24 7-Fluoro-1,4,4,9-tetramethyl-8-[3-(2,2,2-trifluoro-ethyl)-1H-indol-7-yl]-5H-[1,2,4]triazolo[4,3-a]quinoxaline 25 7-Fluoro-8-(1H-indol-7-yl)-1,4,4,9-tetramethyl-5H-[1,2,4]triazolo[4,3-a]quinoxaline 26 7-Fluoro-8-(1H-indol-4-yl)-1,4,4,9-tetramethyl-5H-[1,2,4]triazolo[4,3-a]quinoxaline 27 8-(1-Cyclopropyl-1H-indol-4-yl)-7-fluoro-1,4,4,9-tetramethyl-5H-[1,2,4]triazolo[4,3-a]quinoxaline 28 7-Fluoro-1,4,4,9-tetramethyl-8-(3-prop-1-ynyl-1H-indol-7-yl)-5H-[1,2,4]triazolo[4,3-a]quinoxaline 29 7-Fluoro-1,4,4-trimethyl-8-(3-methyl-1H-indol-7-yl)-9-(trifluoromethyl)-5H-[1,2,4]triazolo[4,3-a]quinoxaline 30 9-Chloro-7-fluoro-8-(5-fluoro-3-methyl-1H-indol-7-yl)-1,4,4-trimethyl-5H-[1,2,4]triazolo[4,3-a]quinoxaline 31 7-Fluoro-8-(5-fluoro-3-methyl-1H-indol-7-yl)-1,4,4,9-tetramethyl-5H-[1,2,4]triazolo[4,3-a]quinoxaline 32 7-Fluoro-8-(5-fluoro-1H-indol-7-yl)-1,4,4,9-tetramethyl-5H-[1,2,4]triazolo[4,3-a]quinoxaline 33 8-(3-Cyclopropyl-5-fluoro-1H-indol-7-yl)-7-fluoro-1,4,4,9-tetramethyl-5H-[1,2,4]triazolo[4,3-a]quinoxaline 34 1-Ethyl-7-fluoro-8-(6-fluoro-1H-indol-4-yl)-4,4,9-trimethyl-5H-[1,2,4]triazolo[4,3-a]quinoxaline 35 8-[1-(Cyclopropyl-methyl)-6-fluoro-1H-indol-4-yl]-1-ethyl-7-fluoro-4,4,9-trimethyl-5H-[1,2,4]triazolo[4,3-a]quinoxaline 36 1-Ethyl-7-fluoro-8-[6-fluoro-1-(2-methoxy-ethyl)-1H-indol-4-yl]-4,4,9-trimethyl-5H-[1,2,4]triazolo[4,3-a]quinoxaline 37 7-Fluoro-8-(6-fluoro-1-methylsulfonyl-1H-indol-4-yl)-1,4,4-trimethyl-9-(trifluoromethyl)-5H-[1,2,4]triazolo[4,3-a]quinoxaline 39 4-[7-(7-Fluoro-1,4,4,9-tetramethyl-5H-[1,2,4]triazolo[4,3-a]quinoxalin-8-yl)-1H-indol-3-yl]-2-methyl-but-3-yn-2-ol 40 [3-[7-(7-Fluoro-1,4,4,9-tetramethyl-5H-[1,2,4]triazolo[4,3-a]quinoxalin-8-yl)-1H-indol-3-yl]-1,1-dimethyl-prop-2-ynyl]-amine 41 9-Chloro-8-(3-cyclobutyl-1H-indol-7-yl)-7-fluoro-1,4,4-trimethyl-5H-[1,2,4]triazolo[4,3-a]quinoxaline 42 7-Fluoro-1,4,4,9-tetramethyl-8-(3-tetrahydro-furan-3-yl-1H-indol-7-yl)-5H-[1,2,4]triazolo[4,3-a]quinoxaline 43 8-(3-Ethyl-5-fluoro-1H-indol-7-yl)-7,9-difluoro-1,4,4-trimethyl-5H-[1,2,4]triazolo[4,3-a]quinoxaline 44 2-[4-(9-Ethyl-7-fluoro-1,4,4-trimethyl-5H-[1,2,4]triazolo[4,3-a]quinoxalin-8-yl)-6-fluoro-1H-indol-1-yl]-ethanol 45 2-[4-(9-Ethyl-7-fluoro-1,4,4-trimethyl-5H-[1,2,4]triazolo[4,3-a]quinoxalin-8-yl)-6-fluoro-1H-indazol-1-yl]-ethanol 46 9-Ethyl-7-fluoro-8-(6-fluoro-1-methylsulfonyl-1H-indol-4-yl)-1,4,4-trimethyl-5H-[1,2,4]triazolo[4,3-a]quinoxaline 47 9-Ethyl-7-fluoro-8-(5-fluoro-3-methyl-1H-indol-7-yl)-1,4,4-trimethyl-5H-[1,2,4]triazolo[4,3-a]quinoxaline 50 9-Ethyl-7-fluoro-1,4,4-trimethyl-8-(1-methylsulfonyl-1H-indol-4-yl)-5H-[1,2,4]triazolo[4,3-a]quinoxaline 51 9-Ethyl-7-fluoro-1,4,4-trimethyl-8-(1-methylsulfonyl-1H-indazol-4-yl)-5H-[1,2,4]triazolo[4,3-a]quinoxaline 52 9-Ethyl-7-fluoro-8-(6-fluoro-1-methylsulfonyl-1H-indazol-4-yl)-1,4,4-trimethyl-5H-[1,2,4]triazolo[4,3-a]quinoxaline 67 1-Benzyl-7,9-difluoro-8-(5-fluoro-3-methyl-1H-indol-7-yl)-4,4-dimethyl-5H-[1,2,4]triazolo[4,3-a]quinoxaline 68 1-Benzyl-7,9-difluoro-4,4-dimethyl-8-(3-methyl-1H-indol-7-yl)-5H-[1,2,4]triazolo[4,3-a]quinoxaline 69 1-But-2-ynyl-7,9-difluoro-8-(5-fluoro-3-methyl-1H-indol-7-yl)-4,4-dimethyl-5H-[1,2,4]triazolo[4,3-a]quinoxaline 70 1-But-2-ynyl-7,9-difluoro-4,4-dimethyl-8-(3-methyl-1H-indol-7-yl)-5H-[1,2,4]triazolo[4,3-a]quinoxaline 71 7,9-Difluoro-8-(5-fluoro-3-methyl-1H-indol-7-yl)-4,4-dimethyl-1-(pyridin-4-yl-methyl)-5H-[1,2,4]triazolo[4,3-a]quinoxaline 72 7,9-Difluoro-4,4-dimethyl-8-(3-methyl-1H-indol-7-yl)-1-(pyridin-4-yl-methyl)-5H-[1,2,4]triazolo[4,3-a]quinoxaline 73 7,9-Difluoro-8-(5-fluoro-3-methyl-1H-indol-7-yl)-4,4-dimethyl-1-(pyridin-3-yl-methyl)-5H-[1,2,4]triazolo[4,3-a]quinoxaline 74 7,9-Difluoro-8-(5-fluoro-3-methyl-1H-indol-7-yl)-4,4-dimethyl-1-(pyridin-2-yl-methyl)-5H-[1,2,4]triazolo[4,3-a]quinoxaline 75 7,9-Difluoro-4,4-dimethyl-8-(3-methyl-1H-indol-7-yl)-1-(pyridin-2-yl-methyl)-5H-[1,2,4]triazolo[4,3-a]quinoxaline 76 7-Fluoro-8-(5-fluoro-3-prop-1-ynyl-1H-indol-7-yl)-1-(methoxymethyl)-4,4,9-trimethyl-5H-[1,2,4]triazolo[4,3-a]quinoxaline 77 [7-Fluoro-8-(5-fluoro-3-prop-1-ynyl-1H-indol-7-yl)-4,4,9-trimethyl-5H-[1,2,4]triazolo[4,3-a]quinoxalin-1-yl]-MeOH 78 1-[7-Fluoro-8-(5-fluoro-3-prop-1-ynyl-1H-indol-7-yl)-4,4,9-trimethyl-5H-[1,2,4]triazolo[4,3-a]quinoxalin-1-yl]-ethanol 79 7-Fluoro-8-(5-fluoro-3-prop-1-ynyl-1H-indol-7-yl)-1-(2-methoxy-ethyl)-4,4,9-trimethyl-5H-[1,2,4]triazolo[4,3-a]quinoxaline 80 1-(Cyclopropyl-methyl)-7,9-difluoro-8-(1H-indol-7-yl)-4,4-dimethyl-5H-[1,2,4]triazolo[4,3-a]quinoxaline 81 1-Cyclopropyl-7,9-difluoro-8-(1H-indol-7-yl)-4,4-dimethyl-5H-[1,2,4]triazolo[4,3-a]quinoxaline 82 8-(3-Cyclopropyl-1H-indol-7-yl)-1,4,4,9-tetramethyl-7-(trifluoromethyl)-5H-[1,2,4]triazolo[4,3-a]quinoxaline 83 8-(6-Fluoro-1-methylsulfonyl-1H-indol-4-yl)-1,4,4,9-tetramethyl-7-(trifluoromethyl)-5H-[1,2,4]triazolo[4,3-a]quinoxaline 84 1,4,4,9-Tetramethyl-8-(1-methylsulfonyl-1H-indol-4-yl)-7-(trifluoromethyl)-5H-[1,2,4]triazolo[4,3-a]quinoxaline 85 9-Chloro-8-(3-cyclopropyl-1H-indol-7-yl)-7-fluoro-1,4,4-trimethyl-5H-[1,2,4]triazolo[4,3-a]quinoxaline 86 7-Fluoro-8-(1H-indol-7-yl)-1,4,4-trimethyl-9-(trifluoromethyl)-5H-[1,2,4]triazolo[4,3-a]quinoxaline 87 8-(3-Cyclopropyl-5-fluoro-1H-indol-7-yl)-7-fluoro-1,4,4-trimethyl-9-(trifluoromethyl)-5H-[1,2,4]triazolo[4,3-a]quinoxaline 88 8-(1-Cyclopropyl-6-fluoro-1H-indol-4-yl)-7-fluoro-1,4,4-trimethyl-9-(trifluoromethyl)-5H-[1,2,4]triazolo[4,3-a]quinoxaline 89 7-[7-Fluoro-1,4,4-trimethyl-9-(trifluoromethyl)-5H-[1,2,4]triazolo[4,3-a]quinoxalin-8-yl]-1H-indole-3-carbonitrile 200 7,9-Difluoro-8-[1-(isopropylsulfonyl)-1H-indol-4-yl]-1,4,4-trimethyl-5H-[1,2,4]triazolo[4,3-a]quinoxaline 201 8-[1-(Cyclopentylsulfonyl)-1H-indol-4-yl]-7,9-difluoro-1,4,4-trimethyl-5H-[1,2,4]triazolo[4,3-a]quinoxaline 202 8-[1-(Cyclopropyl-methyl)-1H-indol-4-yl]-7,9-difluoro-1,4,4-trimethyl-5H-[1,2,4]triazolo[4,3-a]quinoxaline 203 7,9-Difluoro-1,4,4-trimethyl-8-[1-(tetrahydro-pyran-4-ylsulfonyl)-1H-indol-4-yl]-5H-[1,2,4]triazolo[4,3-a]quinoxaline 204 7,9-Difluoro-8-[1-(2-methoxy-ethyl)-1H-indol-4-yl]-1,4,4-trimethyl-5H-[1,2,4]triazolo[4,3-a]quinoxaline 205 8-[1-(Cyclopropylsulfonyl)-1H-indol-4-yl]-7,9-difluoro-1,4,4-trimethyl-5H-[1,2,4]triazolo[4,3-a]quinoxaline 207 7,9-Difluoro-1,4,4-trimethyl-8-[6-(trifluoromethyl)-1H-indol-4-yl]-5H-[1,2,4]triazolo[4,3-a]quinoxaline 208 7,9-Difluoro-8-(6-fluoro-1H-indol-4-yl)-1,4,4-trimethyl-5H-[1,2,4]triazolo[4,3-a]quinoxaline 210 8-[1-(Cyclopropyl-methylsulfonyl)-1H-indol-4-yl]-7,9-difluoro-1,4,4-trimethyl-5H-[1,2,4]triazolo[4,3-a]quinoxaline 212 2-[4-(7,9-Difluoro-1,4,4-trimethyl-5H-[1,2,4]triazolo[4,3-a]quinoxalin-8-yl)-1H-indol-1-yl]-N,N-dimethyl-acetamide 213 1-[4-(7,9-Difluoro-1,4,4-trimethyl-5H-[1,2,4]triazolo[4,3-a]quinoxalin-8-yl)-1H-indol-1-yl]-2-methoxy-ethanone 214 7,9-Difluoro-8-(5-fluoro-1H-indol-4-yl)-1,4,4-trimethyl-5H-[1,2,4]triazolo[4,3-a]quinoxaline 219 3-[4-(7,9-Difluoro-1,4,4-trimethyl-5H-[1,2,4]triazolo[4,3-a]quinoxalin-8-yl)-1H-indol-1-yl]-propionic acid methyl ester 221 7,9-Difluoro-1,4,4-trimethyl-8-(1-methyl-1H-indazol-4-yl)-5H-[1,2,4]triazolo[4,3-a]quinoxaline 222 7,9-Difluoro-1,4,4-trimethyl-8-(2-methyl-2H-indazol-4-yl)-5H-[1,2,4]triazolo[4,3-a]quinoxaline 223 1-[4-(7,9-Difluoro-1,4,4-trimethyl-5H-[1,2,4]triazolo[4,3-a]quinoxalin-8-yl)-1H-indol-1-yl]-2-dimethylamino-ethanone 224 7,9-Difluoro-8-(5-fluoro-1-methylsulfonyl-1H-indol-4-yl)-1,4,4-trimethyl-5H-[1,2,4]triazolo[4,3-a]quinoxaline 225 7,9-Difluoro-1,4,4-trimethyl-8-[2-(trifluoromethyl)-1H-indol-4-yl]-5H-[1,2,4]triazolo[4,3-a]quinoxaline 228 N-[2-[4-(7,9-Difluoro-1,4,4-trimethyl-5H-[1,2,4]triazolo[4,3-a]quinoxalin-8-yl)-1H-indol-1-yl]-ethyl]-carbamic acid tert-butyl ester 229 N-[2-[4-(7,9-Difluoro-1,4,4-trimethyl-5H-[1,2,4]triazolo[4,3-a]quinoxalin-8-yl)-1H-indol-1-yl]-ethyl]-2,2-difluoro-propionamide 230 2-[4-(7,9-Difluoro-1,4,4-trimethyl-5H-[1,2,4]triazolo[4,3-a]quinoxalin-8-yl)-1H-indol-1-yl]-ethyl-amine 232 7,9-Difluoro-8-(1H-indazol-4-yl)-1,4,4-trimethyl-5H-[1,2,4]triazolo[4,3-a]quinoxaline 233 7,9-Difluoro-8-[1-(2-methoxy-ethyl)-1H-indazol-4-yl]-1,4,4-trimethyl-5H-[1,2,4]triazolo[4,3-a]quinoxaline 234 8-[1-(Cyclopropylsulfonyl)-1H-indazol-4-yl]-7,9-difluoro-1,4,4-trimethyl-5H-[1,2,4]triazolo[4,3-a]quinoxaline 235 8-[1-(Cyclopropyl-methyl)-1H-indazol-4-yl]-7,9-difluoro-1,4,4-trimethyl-5H-[1,2,4]triazolo[4,3-a]quinoxaline 236 8-(1-Ethyl-1H-indazol-4-yl)-7,9-difluoro-1,4,4-trimethyl-5H-[1,2,4]triazolo[4,3-a]quinoxaline 237 8-(2-Ethyl-2H-indazol-4-yl)-7,9-difluoro-1,4,4-trimethyl-5H-[1,2,4]triazolo[4,3-a]quinoxaline 238 4-(7,9-Difluoro-1,4,4-trimethyl-5H-[1,2,4]triazolo[4,3-a]quinoxalin-8-yl)-1H-indazole-1-carboxylic acid tert-butyl ester 239 8-[1-(Cyclopropyl-methylsulfonyl)-1H-indazol-4-yl]-7,9-difluoro-1,4,4-trimethyl-5H-[1,2,4]triazolo[4,3-a]quinoxaline 240 1-Ethyl-7-fluoro-4,4,9-trimethyl-8-(1-methyl-1H-indazol-4-yl)-5H-[1,2,4]triazolo[4,3-a]quinoxaline 241 1-Ethyl-7-fluoro-4,4,9-trimethyl-8-(1-methylsulfonyl-1H-indazol-4-yl)-5H-[1,2,4]triazolo[4,3-a]quinoxaline 242 8-(1-Cyclopropyl-1H-indazol-4-yl)-1-ethyl-7-fluoro-4,4,9-trimethyl-5H-[1,2,4]triazolo[4,3-a]quinoxaline 243 8-(1-Cyclopropyl-1H-indazol-4-yl)-7,9-difluoro-1,4,4-trimethyl-5H-[1,2,4]triazolo[4,3-a]quinoxaline 244 1-Ethyl-7-fluoro-8-(5-fluoro-1H-indol-4-yl)-4,4,9-trimethyl-5H-[1,2,4]triazolo[4,3-a]quinoxaline 247 1-Ethyl-7-fluoro-4,4,9-trimethyl-8-(1-methylsulfonyl-1H-indol-4-yl)-5H-[1,2,4]triazolo[4,3-a]quinoxaline 248 7-Fluoro-9-methoxy-1,4,4-trimethyl-8-(1-methylsulfonyl-1H-indol-4-yl)-5H-[1,2,4]triazolo[4,3-a]quinoxaline 249 7-Fluoro-8-(5-fluoro-3-methyl-1H-indol-7-yl)-9-methoxy-1,4,4-trimethyl-5H-[1,2,4]triazolo[4,3-a]quinoxaline 250 7-Fluoro-8-(6-fluoro-1-methylsulfonyl-1H-indol-4-yl)-9-methoxy-1,4,4-trimethyl-5H-[1,2,4]triazolo[4,3-a]quinoxaline 251 9-Fluoro-8-(5-fluoro-3-methyl-1H-indol-7-yl)-7-methoxy-1,4,4-trimethyl-5H-[1,2,4]triazolo[4,3-a]quinoxaline 252 7-(Difluoro-methoxy)-9-fluoro-1,4,4-trimethyl-8-[2-(trifluoromethyl)-1H-indol-4-yl]-5H-[1,2,4]triazolo[4,3-a]quinoxaline 253 8-[1-(2,2-Difluoro-ethyl)-1H-indol-4-yl]-7,9-difluoro-1,4,4-trimethyl-5H-[1,2,4]triazolo[4,3-a]quinoxaline 254 7-Chloro-9-fluoro-1,4,4-trimethyl-8-[2-(trifluoromethyl)-1H-indol-4-yl]-5H-[1,2,4]triazolo[4,3-a]quinoxaline 255 9-Fluoro-8-(6-fluoro-1-methylsulfonyl-1H-indol-4-yl)-7-methoxy-1,4,4-trimethyl-5H-[1,2,4]triazolo[4,3-a]quinoxaline 256 9-Fluoro-8-(1H-indol-4-yl)-7-methoxy-1,4,4-trimethyl-5H-[1,2,4]triazolo[4,3-a]quinoxaline 257 9-Fluoro-7-methoxy-1,4,4-trimethyl-8-[2-(trifluoromethyl)-1H-indol-4-yl]-5H-[1,2,4]triazolo[4,3-a]quinoxaline 258 2-[4-(7,9-Difluoro-1,4,4-trimethyl-5H-[1,2,4]triazolo[4,3-a]quinoxalin-8-yl)-1H-indazol-1-yl]-ethanol 259 7-(Difluoro-methoxy)-9-fluoro-8-[1-(2-methoxy-ethyl)-2-(trifluoromethyl)-1H-indol-4-yl]-1,4,4-trimethyl-5H-[1,2,4]triazolo[4,3-a]quinoxaline 260 4-(7-Fluoro-9-methoxy-1,4,4-trimethyl-5H-[1,2,4]triazolo[4,3-a]quinoxalin-8-yl)-1H-indole-1-carboxylic acid tert-butyl ester 263 9-Fluoro-7-methoxy-1,4,4-trimethyl-8-(1-methylsulfonyl-1H-indol-4-yl)-5H-[1,2,4]triazolo[4,3-a]quinoxaline 264 7-Fluoro-9-methoxy-1,4,4-trimethyl-8-(1-methyl-1H-indazol-4-yl)-5H-[1,2,4]triazolo[4,3-a]quinoxaline 266 9-Fluoro-7-methoxy-1,4,4-trimethyl-8-(3-methyl-1H-indol-7-yl)-5H-[1,2,4]triazolo[4,3-a]quinoxaline 267 7-(Difluoro-methoxy)-9-fluoro-8-(5-fluoro-3-methyl-1H-indol-7-yl)-1,4,4-trimethyl-5H-[1,2,4]triazolo[4,3-a]quinoxaline 268 7-(Difluoro-methoxy)-9-fluoro-8-(6-fluoro-1-methyl-sulfonyl-1H-indol-4-yl)-1,4,4-trimethyl-5H-[1,2,4]triazolo[4,3-a]quinoxaline 269 9-Fluoro-7-methoxy-1,4,4-trimethyl-8-(1-methyl-1H-indazol-4-yl)-5H-[1,2,4]triazolo[4,3-a]quinoxaline 270 7-Fluoro-9-methoxy-1,4,4-trimethyl-8-(3-methyl-1H-indol-7-yl)-5H-[1,2,4]triazolo[4,3-a]quinoxaline 271 7,9-Difluoro-1,4,4-trimethyl-8-[1-methylsulfonyl-2-(trifluoromethyl)-1H-indol-4-yl]-5H-[1,2,4]triazolo[4,3-a]quinoxaline 272 7-Chloro-9-fluoro-1,4,4-trimethyl-8-(3-methyl-1H-indol-7-yl)-5H-[1,2,4]triazolo[4,3-a]quinoxaline 273 7-(Difluoro-methoxy)-9-fluoro-1,4,4-trimethyl-8-(1-methyl-1H-indazol-4-yl)-5H-[1,2,4]triazolo[4,3-a]quinoxaline 275 7-(Difluoro-methoxy)-9-fluoro-1,4,4-trimethyl-8-(1-methylsulfonyl-1H-indol-4-yl)-5H-[1,2,4]triazolo[4,3-a]quinoxaline 276 7,9-Difluoro-8-(6-fluoro-1-methylsulfonyl-1H-indazol-4-yl)-1,4,4-trimethyl-5H-[1,2,4]triazolo[4,3-a]quinoxaline 277 7-Chloro-9-fluoro-8-(6-fluoro-1-methylsulfonyl-1H-indol-4-yl)-1,4,4-trimethyl-5H-[1,2,4]triazolo[4,3-a]quinoxaline 278 7-Fluoro-8-[1-(2-methoxy-ethyl)-1H-indol-4-yl]-1,4,4,9-tetramethyl-5H-[1,2,4]triazolo[4,3-a]quinoxaline 279 7-Fluoro-8-(6-fluoro-1-methylsulfonyl-1H-indazol-4-yl)-1,4,4,9-tetramethyl-5H-[1,2,4]triazolo[4,3-a]quinoxaline 280 7-Chloro-9-fluoro-8-[1-(2-methoxy-ethyl)-1H-indol-4-yl]-1,4,4-trimethyl-5H-[1,2,4]triazolo[4,3-a]quinoxaline 281 7-Fluoro-9-methoxy-8-[1-(2-methoxy-ethyl)-1H-indol-4-yl]-1,4,4-trimethyl-5H-[1,2,4]triazolo[4,3-a]quinoxaline 282 7-(Difluoro-methoxy)-9-fluoro-1,4,4-trimethyl-8-(3-methyl-1H-indol-7-yl)-5H-[1,2,4]triazolo[4,3-a]quinoxaline 283 9-Fluoro-8-(5-fluoro-3-methyl-1H-indol-7-yl)-1,4,4-trimethyl-5H-[1,2,4]triazolo[4,3-a]quinoxaline 284 7-Chloro-9-fluoro-1,4,4-trimethyl-8-(1-methylsulfonyl-1H-indol-4-yl)-5H-[1,2,4]triazolo[4,3-a]quinoxaline 285 7-Chloro-9-fluoro-1,4,4-trimethyl-8-(1-methyl-1H-indazol-4-yl)-5H-[1,2,4]triazolo[4,3-a]quinoxaline 286 7-Fluoro-8-(1H-indol-4-yl)-9-methoxy-1,4,4-trimethyl-5H-[1,2,4]triazolo[4,3-a]quinoxaline 287 7-(Difluoro-methoxy)-9-fluoro-8-[1-(2-methoxy-ethyl)-1H-indol-4-yl]-1,4,4-trimethyl-5H-[1,2,4]triazolo[4,3-a]quinoxaline 288 9-Fluoro-7-methoxy-8-[1-(2-methoxy-ethyl)-1H-indol-4-yl]-1,4,4-trimethyl-5H-[1,2,4]triazolo[4,3-a]quinoxaline 289 7,9-Difluoro-8-[1-(2-methoxy-ethyl)-2-(trifluoromethyl)-1H-indol-4-yl]-1,4,4-trimethyl-5H-[1,2,4]triazolo[4,3-a]quinoxaline 290 7-Chloro-9-fluoro-8-(5-fluoro-3-methyl-1H-indol-7-yl)-1,4,4-trimethyl-5H-[1,2,4]triazolo[4,3-a]quinoxaline 292 9-(Difluoro-methyl)-7-fluoro-8-[1-(2-methoxy-ethyl)-1H-indol-4-yl]-1,4,4-trimethyl-5H-[1,2,4]triazolo[4,3-a]quinoxaline 293 7-Chloro-9-fluoro-8-(1H-indol-4-yl)-1,4,4-trimethyl-5H-[1,2,4]triazolo[4,3-a]quinoxaline 294 9-(Difluoro-methyl)-7-fluoro-8-(1-methyl-1H-indazol-4-yl)-1,4,4-trimethyl-5H-[1,2,4]triazolo[4,3-a]quinoxaline 295 7-(Difluoro-methyl)-9-fluoro-8-[1-(2-methoxy-ethyl)-1H-indol-4-yl]-1,4,4-trimethyl-5H-[1,2,4]triazolo[4,3-a]quinoxaline 296 7-(Difluoro-methyl)-9-fluoro-8-(5-fluoro-3-methyl-1H-indol-7-yl)-1,4,4-trimethyl-5H-[1,2,4]triazolo[4,3-a]quinoxaline 297 7-(Difluoro-methoxy)-9-fluoro-8-(1H-indol-4-yl)-1,4,4-trimethyl-5H-[1,2,4]triazolo[4,3-a]quinoxaline 298 7-(Difluoro-methyl)-9-fluoro-8-(6-fluoro-1-methylsulfonyl-1H-indol-4-yl)-1,4,4-trimethyl-5H-[1,2,4]triazolo[4,3-a]quinoxaline 299 1-Ethyl-7-fluoro-8-[1-(2-methoxy-ethyl)-1H-indol-4-yl]-4,4,9-trimethyl-5H-[1,2,4]triazolo[4,3-a]quinoxaline 302 9-(Difluoro-methyl)-7-fluoro-8-(5-fluoro-3-methyl-1H-indol-7-yl)-1,4,4-trimethyl-5H-[1,2,4]triazolo[4,3-a]quinoxaline 306 7-(Difluoro-methyl)-9-fluoro-1,4,4-trimethyl-8-(3-methyl-1H-indol-7-yl)-5H-[1,2,4]triazolo[4,3-a]quinoxaline 309 1,4,4,7,9-Pentamethyl-8-(1-methylsulfonyl-1H-indol-4-yl)-5H-[1,2,4]triazolo[4,3-a]quinoxaline 310 7-Methoxy-1,4,4-trimethyl-8-(1-methylsulfonyl-1H-indol-4-yl)-9-(trifluoromethyl)-5H-[1,2,4]triazolo[4,3-a]quinoxaline 312 8-[1-Cyclopropyl-2-(trifluoromethyl)-1H-indol-4-yl]-7,9-difluoro-1,4,4-trimethyl-5H-[1,2,4]triazolo[4,3-a]quinoxaline 313 7-Chloro-8-[1-(2,2-difluoro-ethyl)-1H-indol-4-yl]-9-fluoro-1,4,4-trimethyl-5H-[1,2,4]triazolo[4,3-a]quinoxaline 314 8-[1-(2,2-Difluoro-ethyl)-1H-indol-4-yl]-9-fluoro-7-methoxy-1,4,4-trimethyl-5H-[1,2,4]triazolo[4,3-a]quinoxaline 315 9-(Difluoro-methyl)-7-fluoro-1,4,4-trimethyl-8-(1-methylsulfonyl-1H-indol-4-yl)-5H-[1,2,4]triazolo[4,3-a]quinoxaline 317 7-Chloro-1,4,4,9-tetramethyl-8-(1-methylsulfonyl-1H-indol-4-yl)-5H-[1,2,4]triazolo[4,3-a]quinoxaline 318 7-(Difluoro-methoxy)-1,4,4,9-tetramethyl-8-(1-methylsulfonyl-1H-indol-4-yl)-5H-[1,2,4]triazolo[4,3-a]quinoxaline 319 9-(Difluoro-methyl)-7-fluoro-8-(1H-indol-4-yl)-1,4,4-trimethyl-5H-[1,2,4]triazolo[4,3-a]quinoxaline 320 9-(Difluoro-methyl)-7-fluoro-1,4,4-trimethyl-8-(3-methyl-1H-indol-7-yl)-5H-[1,2,4]triazolo[4,3-a]quinoxaline 321 9-Fluoro-1,4,4,7-tetramethyl-8-(1-methylsulfonyl-1H-indol-4-yl)-5H-[1,2,4]triazolo[4,3-a]quinoxaline 324 8-[1-(2,2-Difluoro-ethyl)-1H-indol-4-yl]-1,4,4,7,9-pentamethyl-5H-[1,2,4]triazolo[4,3-a]quinoxaline 325 7-(Difluoro-methyl)-9-fluoro-1,4,4-trimethyl-8-(1-methyl-1H-indazol-4-yl)-5H-[1,2,4]triazolo[4,3-a]quinoxaline 327 7-Chloro-8-[1-(2,2-difluoro-ethyl)-1H-indol-4-yl]-1,4,4,9-tetramethyl-5H-[1,2,4]triazolo[4,3-a]quinoxaline 328 8-(6-Fluoro-1-methylsulfonyl-1H-indol-4-yl)-1,4,4,7,9-pentamethyl-5H-[1,2,4]triazolo[4,3-a]quinoxaline 329 8-(6-Fluoro-1-methylsulfonyl-1H-indol-4-yl)-7-methoxy-1,4,4-trimethyl-9-(trifluoromethyl)-5H-[1,2,4]triazolo[4,3-a]quinoxaline 330 8-[1-(2,2-Difluoro-ethyl)-1H-indol-4-yl]-7-fluoro-1,4,4,9-tetramethyl-5H-[1,2,4]triazolo[4,3-a]quinoxaline 331 8-[1-(2-Methoxy-ethyl)-1H-indol-4-yl]-1,4,4,7,9-pentamethyl-5H-[1,2,4]triazolo[4,3-a]quinoxaline 332 9-Fluoro-8-(6-fluoro-1-methylsulfonyl-1H-indol-4-yl)-1,4,4,7-tetramethyl-5H-[1,2,4]triazolo[4,3-a]quinoxaline 333 7-Chloro-8-(6-fluoro-1-methylsulfonyl-1H-indol-4-yl)-1,4,4,9-tetramethyl-5H-[1,2,4]triazolo[4,3-a]quinoxaline 334 7-Methoxy-8-[1-(2-methoxy-ethyl)-1H-indol-4-yl]-1,4,4-trimethyl-9-(trifluoromethyl)-5H-[1,2,4]triazolo[4,3-a]quinoxaline 335 7-(Difluoro-methoxy)-8-(6-fluoro-1-methylsulfonyl-1H-indol-4-yl)-1,4,4,9-tetramethyl-5H-[1,2,4]triazolo[4,3-a]quinoxaline 336 7-(Difluoro-methoxy)-8-[1-(2-methoxy-ethyl)-1H-indol-4-yl]-1,4,4,9-tetramethyl-5H-[1,2,4]triazolo[4,3-a]quinoxaline 337 9-Fluoro-8-[1-(2-methoxy-ethyl)-1H-indol-4-yl]-1,4,4,7-tetramethyl-5H-[1,2,4]triazolo[4,3-a]quinoxaline 338 7-Chloro-8-[1-(2-methoxy-ethyl)-1H-indol-4-yl]-1,4,4,9-tetramethyl-5H-[1,2,4]triazolo[4,3-a]quinoxaline 339 7-Fluoro-8-(6-fluoro-1-methylsulfonyl-1H-indazol-4-yl)-9-methoxy-1,4,4-trimethyl-5H-[1,2,4]triazolo[4,3-a]quinoxaline 341 8-(5-Fluoro-3-methyl-1H-indol-7-yl)-1,4,4,7,9-pentamethyl-5H-[1,2,4]triazolo[4,3-a]quinoxaline 342 7-Fluoro-9-methoxy-1,4,4-trimethyl-8-(1-methylsulfonyl-1H-indazol-4-yl)-5H-[1,2,4]triazolo[4,3-a]quinoxaline 343 7-(Difluoro-methyl)-9-fluoro-8-(1H-indol-4-yl)-1,4,4-trimethyl-5H-[1,2,4]triazolo[4,3-a]quinoxaline 344 7-Methoxy-8-[1-(2-methoxy-ethyl)-1H-indol-4-yl]-1,4,4,9-tetramethyl-5H-[1,2,4]triazolo[4,3-a]quinoxaline 345 8-(5-Fluoro-3-methyl-1H-indol-7-yl)-7-methoxy-1,4,4,9-tetramethyl-5H-[1,2,4]triazolo[4,3-a]quinoxaline 346 9-(Difluoro-methyl)-7-fluoro-8-(6-fluoro-1-methylsulfonyl-1H-indazol-4-yl)-1,4,4-trimethyl-5H-[1,2,4]triazolo[4,3-a]quinoxaline 347 7-Chloro-8-(6-fluoro-1-methylsulfonyl-1H-indazol-4-yl)-1,4,4,9-tetramethyl-5H-[1,2,4]triazolo[4,3-a]quinoxaline 348 1-Ethyl-7-fluoro-8-(6-fluoro-1-methylsulfonyl-1H-indazol-4-yl)-4,4,9-trimethyl-5H-[1,2,4]triazolo[4,3-a]quinoxaline 351 7-Fluoro-8-[6-fluoro-1-(2-methoxy-ethyl)-1H-indol-4-yl]-9-methoxy-1,4,4-trimethyl-5H-[1,2,4]triazolo[4,3-a]quinoxaline 353 9-Fluoro-8-[6-fluoro-1-(2-methoxy-ethyl)-1H-indol-4-yl]-7-methoxy-1,4,4-trimethyl-5H-[1,2,4]triazolo[4,3-a]quinoxaline 354 7,9-Difluoro-1,4,4-trimethyl-8-(3-methyl-1H-indazol-7-yl)-5H-[1,2,4]triazolo[4,3-a]quinoxaline 356 1,4,4,7,9-Pentamethyl-8-(3-methyl-1H-indol-7-yl)-5H-[1,2,4]triazolo[4,3-a]quinoxaline 357 7-Methoxy-1,4,4-trimethyl-8-(3-methyl-1H-indol-7-yl)-9-(trifluoromethyl)-5H-[1,2,4]triazolo[4,3-a]quinoxaline 358 7-Chloro-1,4,4,9-tetramethyl-8-(3-methyl-1H-indol-7-yl)-5H-[1,2,4]triazolo[4,3-a]quinoxaline 359 9-Fluoro-1,4,4,7-tetramethyl-8-(3-methyl-1H-indol-7-yl)-5H-[1,2,4]triazolo[4,3-a]quinoxaline 360 7-(Difluoro-methoxy)-1,4,4,9-tetramethyl-8-(3-methyl-1H-indol-7-yl)-5H-[1,2,4]triazolo[4,3-a]quinoxaline 361 7-Fluoro-1,4,4,9-tetramethyl-8-(3-methyl-1H-indazol-7-yl)-5H-[1,2,4]triazolo[4,3-a]quinoxaline 362 8-[1-(Ethylsulfonyl)-6-fluoro-1H-indol-4-yl]-7-fluoro-9-methoxy-1,4,4-trimethyl-5H-[1,2,4]triazolo[4,3-a]quinoxaline 363 7-Chloro-8-(5-fluoro-3-methyl-1H-indol-7-yl)-1,4,4,9-tetramethyl-5H-[1,2,4]triazolo[4,3-a]quinoxaline 364 9-Fluoro-8-(5-fluoro-3-methyl-1H-indol-7-yl)-1,4,4,7-tetramethyl-5H-[1,2,4]triazolo[4,3-a]quinoxaline 365 7-(Difluoro-methoxy)-8-(5-fluoro-3-methyl-1H-indol-7-yl)-1,4,4,9-tetramethyl-5H-[1,2,4]triazolo[4,3-a]quinoxaline 367 9-(Difluoro-methyl)-7-fluoro-1,4,4-trimethyl-8-(3-methyl-1H-indazol-7-yl)-5H-[1,2,4]triazolo[4,3-a]quinoxaline 368 7-Chloro-1,4,4,9-tetramethyl-8-(3-methyl-1H-indazol-7-yl)-5H-[1,2,4]triazolo[4,3-a]quinoxaline 369 8-[1-(Ethylsulfonyl)-6-fluoro-1H-indol-4-yl]-7-methoxy-1,4,4-trimethyl-9-(trifluoromethyl)-5H-[1,2,4]triazolo[4,3-a]quinoxaline 370 8-[1-(Ethylsulfonyl)-6-fluoro-1H-indol-4-yl]-7-fluoro-1,4,4,9-tetramethyl-5H-[1,2,4]triazolo[4,3-a]quinoxaline 371 8-[1-(Ethylsulfonyl)-1H-indol-4-yl]-7-methoxy-1,4,4-trimethyl-9-(trifluoromethyl)-5H-[1,2,4]triazolo[4,3-a]quinoxaline 372 8-[1-(Ethylsulfonyl)-1H-indol-4-yl]-7-fluoro-1,4,4,9-tetramethyl-5H-[1,2,4]triazolo[4,3-a]quinoxaline 373 8-(6-Fluoro-1-methylsulfonyl-1H-indazol-4-yl)-1,4,4,7,9-pentamethyl-5H-[1,2,4]triazolo[4,3-a]quinoxaline 376 8-(6-Fluoro-1-methylsulfonyl-1H-indazol-4-yl)-7-methoxy-1,4,4-trimethyl-9-(trifluoromethyl)-5H-[1,2,4]triazolo[4,3-a]quinoxaline 377 7-Fluoro-1,4,4,9-tetramethyl-8-(1-methylsulfonyl-1H-indazol-4-yl)-5H-[1,2,4]triazolo[4,3-a]quinoxaline 379 2-[6-Fluoro-4-(9-fluoro-7-methoxy-1,4,4-trimethyl-5H-[1,2,4]triazolo[4,3-a]quinoxalin-8-yl)-1H-indol-1-yl]-ethanol 380 2-[6-Fluoro-4-(7-fluoro-9-methoxy-1,4,4-trimethyl-5H-[1,2,4]triazolo[4,3-a]quinoxalin-8-yl)-1H-indol-1-yl]-ethanol 381 7-Fluoro-9-methoxy-1,4,4-trimethyl-8-(3-methyl-1H-indazol-7-yl)-5H-[1,2,4]triazolo[4,3-a]quinoxaline 382 9-(Difluoro-methyl)-7-fluoro-1,4,4-trimethyl-8-(1-methylsulfonyl-1H-indazol-4-yl)-5H-[1,2,4]triazolo[4,3-a]quinoxaline 383 [2-[4-(7,9-Difluoro-1,4,4-trimethyl-5H-[1,2,4]triazolo[4,3-a]quinoxalin-8-yl)-1H-indol-1-yl]-ethyl]-dimethyl-amine 384 8-[1-(2,2-Difluoro-ethyl)-1H-indol-4-yl]-7-(difluoromethoxy)-1,4,4,9-tetramethyl-5H-[1,2,4]triazolo[4,3-a]quinoxaline 385 2-[4-[7-(Difluoro-methyl)-9-fluoro-1,4,4-trimethyl-5H-[1,2,4]triazolo[4,3-a]quinoxalin-8-yl]-6-fluoro-1H-indol-1-yl]-ethanol 386 7-Chloro-1,4,4,9-tetramethyl-8-(1-methylsulfonyl-1H-indazol-4-yl)-5H-[1,2,4]triazolo[4,3-a]quinoxaline 387 7-Methoxy-1,4,4-trimethyl-8-(1-methylsulfonyl-1H-indazol-4-yl)-9-(trifluoromethyl)-5H-[1,2,4]triazolo[4,3-a]quinoxaline 388 1,4,4,7,9-Pentamethyl-8-(1-methylsulfonyl-1H-indazol-4-yl)-5H-[1,2,4]triazolo[4,3-a]quinoxaline 390 9-(Difluoro-methyl)-7-fluoro-8-(6-fluoro-1-methylsulfonyl-1H-indol-4-yl)-1,4,4-trimethyl-5H-[1,2,4]triazolo[4,3-a]quinoxaline 392 8-[1-(2,2-Difluoro-ethyl)-1H-indol-4-yl]-9-fluoro-1,4,4,7-tetramethyl-5H-[1,2,4]triazolo[4,3-a]quinoxaline 393 8-[1-(2,2-Difluoro-ethyl)-1H-indol-4-yl]-7-(difluoromethoxy)-9-fluoro-1,4,4-trimethyl-5H-[1,2,4]triazolo[4,3-a]quinoxaline 394 7-(Difluoro-methoxy)-9-fluoro-8-[6-fluoro-1-(2-methoxy-ethyl)-1H-indol-4-yl]-1,4,4-trimethyl-5H-[1,2,4]triazolo[4,3-a]quinoxaline 395 2-[4-[7-(Difluoro-methoxy)-9-fluoro-1,4,4-trimethyl-5H-[1,2,4]triazolo[4,3-a]quinoxalin-8-yl]-6-fluoro-1H-indol-1-yl]-ethanol 396 7-(Difluoro-methyl)-9-fluoro-8-[6-fluoro-1-(2-methoxy-ethyl)-1H-indol-4-yl]-1,4,4-trimethyl-5H-[1,2,4]triazolo[4,3-a]quinoxaline 397 8-[1-(2,2-Difluoro-ethyl)-1H-indol-4-yl]-7-fluoro-9-methoxy-1,4,4-trimethyl-5H-[1,2,4]triazolo[4,3-a]quinoxaline
398 8-[1-(2,2-Difluoro-ethyl)-1H-indol-4-yl]-9-(difluoro-methyl)-7-fluoro-1,4,4-trimethyl-5H-[1,2,4]triazolo[4,3-a]quinoxaline
399 7-Fluoro-8-(1H-indol-4-yl)-1,4,4,9-tetramethyl-5H-[1,2,4]triazolo[4,3-a]quinoxaline
400 9-(Difluoro-methyl)-7-fluoro-8-[1-(isopropylsulfonyl)-1H-indol-4-yl]-1,4,4-trimethyl-5H-[1,2,4]triazolo[4,3-a]quinoxaline
401 8-[1-(Cyclopropylsulfonyl)-1H-indol-4-yl]-9-(difluoro-methyl)-7-fluoro-1,4,4-trimethyl-5H-[1,2,4]triazolo[4,3-a]quinoxaline
402 9-(Difluoro-methyl)-7-fluoro-8-[6-fluoro-1-(2-methoxy-ethyl)-1H-indol-4-yl]-1,4,4-trimethyl-5H-[1,2,4]triazolo[4,3-a]quinoxaline
403 8-(6-Fluoro-1-methylsulfonyl-1H-indol-4-yl)-1,4,4,9-tetramethyl-7-(trifluoromethyloxy)-5H-[1,2,4]triazolo[4,3-a]quinoxaline
404 7-Chloro-9-fluoro-8-[6-fluoro-1-(2-methoxy-ethyl)-1H-indol-4-yl]-1,4,4-trimethyl-5H-[1,2,4]triazolo[4,3-a]quinoxaline
405 1,4,4,9-Tetramethyl-8-(3-methyl-1H-indol-7-yl)-7-(trifluoromethyloxy)-5H-[1,2,4]triazolo[4,3-a]quinoxaline
406 8-(5-Fluoro-3-methyl-1H-indol-7-yl)-1,4,4,9-tetramethyl-7-(trifluoromethyloxy)-5H-[1,2,4]triazolo[4,3-a]quinoxaline
407 8-(5-Fluoro-3-methyl-1H-indol-7-yl)-7-methoxy-1,4,4-trimethyl-9-(trifluoromethyl)-5H-[1,2,4]triazolo[4,3-a]quinoxaline
445 7,9-Difluoro-8-(1H-indol-4-yl)-1,4,4-trimethyl-5H-[1,2,4]triazolo[4,3-a]quinoxaline
446 7-Fluoro-1,4,4-trimethyl-8-(1-methylsulfonyl-1H-indazol-4-yl)-9-(trifluoromethyl)-5H-[1,2,4]triazolo[4,3-a]quinoxaline
447 2-[6-Fluoro-4-[7-fluoro-1,4,4-trimethyl-9-(trifluoromethyl)-5H-[1,2,4]triazolo[4,3-a]quinoxalin-8-yl]-1H-indol-1-yl]-ethanol
448 8-[1-(Ethylsulfonyl)-6-fluoro-1H-indazol-4-yl]-7-fluoro-1,4,4-trimethyl-9-(trifluoromethyl)-5H-[1,2,4]triazolo[4,3-a]quinoxaline
449 2-[6-Fluoro-4-[7-fluoro-1,4,4-trimethyl-9-(trifluoromethyl)-5H-[1,2,4]triazolo[4,3-a]quinoxalin-8-yl]-1H-indazol-1-yl]-ethanol
450 1,4,4,9-Tetramethyl-8-(1-methylsulfonyl-1H-indol-4-yl)-5H-[1,2,4]triazolo[4,3-a]quinoxaline
451 2-[6-Fluoro-4-(1,4,4,9-tetramethyl-5H-[1,2,4]triazolo[4,3-a]quinoxalin-8-yl)-1H-indol-1-yl]-ethanol
452 8-(5-Fluoro-3-methyl-1H-indol-7-yl)-1,4,4,9-tetramethyl-5H-[1,2,4]triazolo[4,3-a]quinoxaline
453 8-(6-Fluoro-1-methylsulfonyl-1H-indol-4-yl)-1,4,4,9-tetramethyl-5H-[1,2,4]triazolo[4,3-a]quinoxaline
454 7-Fluoro-8-(6-fluoro-1-methylsulfonyl-1H-indazol-4-yl)-1,4,4-trimethyl-9-(trifluoromethyl)-5H-[1,2,4]triazolo[4,3-a]quinoxaline
455 8-[1-(Ethylsulfonyl)-1H-indol-4-yl]-7-fluoro-1,4,4-trimethyl-9-(trifluoromethyl)-5H-[1,2,4]triazolo[4,3-a]quinoxaline
456 2-[4-[7-Fluoro-1,4,4-trimethyl-9-(trifluoromethyl)-5H-[1,2,4]triazolo[4,3-a]quinoxalin-8-yl]-1H-indol-1-yl]-ethanol
457 1,4,4,9-Tetramethyl-8-(1-methylsulfonyl-1H-indazol-4-yl)-5H-[1,2,4]triazolo[4,3-a]quinoxaline
458 8-(5-Fluoro-3-methyl-1H-indol-7-yl)-1,4,4,9-tetramethyl-7-(trifluoromethyloxy)-5H-[1,2,4]triazolo[4,3-a]quinoxaline
459 8-(5-Fluoro-3-methyl-1H-indol-7-yl)-7-methoxy-1,4,4-trimethyl-9-(trifluoromethyl)-5H-[1,2,4]triazolo[4,3-a]quinoxaline
460 8-[1-(2-Methoxy-ethyl)-1H-indol-4-yl]-1,4,4,9-tetramethyl-7-(trifluoromethyloxy)-5H-[1,2,4]triazolo[4,3-a]quinoxaline
461 9-(Difluoro-methyl)-8-[1-(ethylsulfonyl)-1H-indol-4-yl]-7-fluoro-1,4,4-trimethyl-5H-[1,2,4]triazolo[4,3-a]quinoxaline
462 9-Cyclopropyl-7-fluoro-1,4,4-trimethyl-8-(1-methylsulfonyl-1H-indol-4-yl)-5H-[1,2,4]triazolo[4,3-a]quinoxaline
463 9-Cyclopropyl-7-fluoro-1,4,4-trimethyl-8-(3-methyl-1H-indol-7-yl)-5H-[1,2,4]triazolo[4,3-a]quinoxaline
464 7-Fluoro-8-(6-fluoro-1H-indol-4-yl)-1,4,4-trimethyl-9-(trifluoromethyl)-5H-[1,2,4]triazolo[4,3-a]quinoxaline
465 1,4,4,9-Tetramethyl-8-(1-methylsulfonyl-1H-indol-4-yl)-7-(trifluoromethyloxy)-5H-[1,2,4]triazolo[4,3-a]quinoxaline
466 9-(Difluoro-methyl)-7-fluoro-8-(6-fluoro-1H-indol-4-yl)-1,4,4-trimethyl-5H-[1,2,4]triazolo[4,3-a]quinoxaline
467 7-Fluoro-8-(1H-indol-4-yl)-1,4,4-trimethyl-9-(trifluoromethyl)-5H-[1,2,4]triazolo[4,3-a]quinoxaline
468 7-Fluoro-8-(6-fluoro-1H-indol-4-yl)-9-methoxy-1,4,4-trimethyl-5H-[1,2,4]triazolo[4,3-a]quinoxaline
469 8-[1-(2,2-Difluoro-ethyl)-6-fluoro-1H-indazol-4-yl]-1,4,4,9-tetramethyl-7-(trifluoromethyloxy)-5H-[1,2,4]triazolo[4,3-a]quinoxaline
470 7-Fluoro-1,4,4,9-tetramethyl-8-[6-(trifluoromethyl)-1H-indol-4-yl]-5H-[1,2,4]triazolo[4,3-a]quinoxaline
471 2-[6-Fluoro-4-[1,4,4,9-tetramethyl-7-(trifluoromethyloxy)-5H-[1,2,4]triazolo[4,3-a]quinoxalin-8-yl]-1H-indol-1-yl]-ethanol
472 8-[1-(2,2-Difluoro-ethyl)-6-fluoro-1H-indazol-4-yl]-9-(difluoro-methyl)-7-fluoro-1,4,4-trimethyl-5H-[1,2,4]triazolo[4,3-a]quinoxaline
473 7-Fluoro-1,4,4-trimethyl-9-(trifluoromethyl)-8-[6-(trifluoromethyl)-1H-indol-4-yl]-5H-[1,2,4]triazolo[4,3-a]quinoxaline
474 7-Fluoro-9-methoxy-1,4,4-trimethyl-8-[6-(trifluoromethyl)-1H-indol-4-yl]-5H-[1,2,4]triazolo[4,3-a]quinoxaline
475 7-Chloro-1,4,4,9-tetramethyl-8-[6-(trifluoromethyl)-1H-indol-4-yl]-5H-[1,2,4]triazolo[4,3-a]quinoxaline
476 7-Fluoro-1,4,4-trimethyl-8-(6-methyl-1-methylsulfonyl-1H-indol-4-yl)-9-(trifluoromethyl)-5H-[1,2,4]triazolo[4,3-a]quinoxaline
477 7-Fluoro-9-methoxy-1,4,4-trimethyl-8-(6-methyl-1-methylsulfonyl-1H-indol-4-yl)-5H-[1,2,4]triazolo[4,3-a]quinoxaline
478 9-(Difluoro-methyl)-7-fluoro-1,4,4-trimethyl-8-(6-methyl-1-methylsulfonyl-1H-indol-4-yl)-5H-[1,2,4]triazolo[4,3-a]quinoxaline
479 4-[7-Fluoro-1,4,4-trimethyl-9-(trifluoromethyl)-5H-[1,2,4]triazolo[4,3-a]quinoxalin-8-yl]-1H-indole-6-carbonitrile
480 8-[6-Fluoro-1-(2-methoxy-ethyl)-1H-indazol-4-yl]-1,4,4,9-tetramethyl-7-(trifluoromethyloxy)-5H-[1,2,4]triazolo[4,3-a]quinoxaline
481 9-(Difluoro-methyl)-7-fluoro-1,4,4-trimethyl-8-(1-methyl-1H-indol-4-yl)-5H-[1,2,4]triazolo[4,3-a]quinoxaline
482 8-(3-Cyclopropyl-5-fluoro-1H-indol-7-yl)-7-methoxy-1,4,4-trimethyl-9-(trifluoromethyl)-5H-[1,2,4]triazolo[4,3-a]quinoxaline 483 8-(3-Cyclopropyl-5-fluoro-1H-indol-7-yl)-7-fluoro-9-methoxy-1,4,4-trimethyl-5H-[1,2,4]triazolo[4,3-a]quinoxaline
484 7-Fluoro-8-(7-fluoro-1-methylsulfonyl-1H-indol-4-yl)-1,4,4-trimethyl-9-(trifluoromethyl)-5H-[1,2,4]triazolo[4,3-a]quinoxaline
485 7-Chloro-8-(3-cyclopropyl-5-fluoro-1H-indol-7-yl)-1,4,4,9-tetramethyl-5H-[1,2,4]triazolo[4,3-a]quinoxaline
486 7-Fluoro-1,4,4,9-tetramethyl-8-(1-methyl-1H-indol-4-yl)-5H-[1,2,4]triazolo[4,3-a]quinoxaline
487 7-Fluoro-9-methoxy-1,4,4-trimethyl-8-(1-methyl-1H-indol-4-yl)-5H-[1,2,4]triazolo[4,3-a]quinoxaline
488 7-Chloro-1,4,4,9-tetramethyl-8-(1-methyl-1H-indol-4-yl)-5H-[1,2,4]triazolo[4,3-a]quinoxaline
489 8-[1-(2,2-Difluoro-ethyl)-6-fluoro-1H-indazol-4-yl]-7,9-difluoro-1,4,4-trimethyl-5H-[1,2,4]triazolo[4,3-a]quinoxaline
490 7-Fluoro-8-(1H-indazol-4-yl)-9-methoxy-1,4,4-trimethyl-5H-[1,2,4]triazolo[4,3-a]quinoxaline
491 7-Chloro-1,4,4,9-tetramethyl-8-(6-methyl-1-methylsulfonyl-1H-indol-4-yl)-5H-[1,2,4]triazolo[4,3-a]quinoxaline
492 7,9-Difluoro-1,4,4-trimethyl-8-(6-methyl-1-methylsulfonyl-1H-indol-4-yl)-5H-[1,2,4]triazolo[4,3-a]quinoxaline
493 7-Fluoro-1,4,4,9-tetramethyl-8-(6-methyl-1-methylsulfonyl-1H-indol-4-yl)-5H-[1,2,4]triazolo[4,3-a]quinoxaline
494 4-(7-Fluoro-1,4,4,9-tetramethyl-5H-[1,2,4]triazolo[4,3-a]quinoxalin-8-yl)-1H-indole-6-carbonitrile
495 8-[1-(Cyclopropyl-methylsulfonyl)-1H-indol-4-yl]-7-fluoro-1,4,4,9-tetramethyl-5H-[1,2,4]triazolo[4,3-a]quinoxaline
496 9-(Difluoro-methyl)-7-fluoro-8-(7-fluoro-1H-indol-4-yl)-1,4,4-trimethyl-5H-[1,2,4]triazolo[4,3-a]quinoxaline
497 7,9-Difluoro-8-(7-fluoro-1H-indol-4-yl)-1,4,4-trimethyl-5H-[1,2,4]triazolo[4,3-a]quinoxaline
498 1,4,4-Trimethyl-8-(1-methylsulfonyl-1H-indol-4-yl)-9-(trifluoromethyl)-5H-[1,2,4]triazolo[4,3-a]quinoxaline
499 8-(6-Fluoro-1-methylsulfonyl-1H-indol-4-yl)-1,4,4-trimethyl-9-(trifluoromethyl)-5H-[1,2,4]triazolo[4,3-a]quinoxaline
500 8-[1-(2,2-Difluoro-ethyl)-1H-indol-4-yl]-7-methoxy-1,4,4-trimethyl-9-(trifluoromethyl)-5H-[1,2,4]triazolo[4,3-a]quinoxaline
501 7,9-Difluoro-8-(7-fluoro-1H-indazol-4-yl)-1,4,4-trimethyl-5H-[1,2,4]triazolo[4,3-a]quinoxaline
502 8-[1-(Cyclopropyl-methylsulfonyl)-1H-indol-4-yl]-9-(difluoro-methyl)-7-fluoro-1,4,4-trimethyl-5H-[1,2,4]triazolo[4,3-a]quinoxaline
503 1,4,4-Trimethyl-8-(3-methyl-1H-indol-7-yl)-9-(trifluoromethyl)-5H-[1,2,4]triazolo[4,3-a]quinoxaline
504 7-Fluoro-8-(7-fluoro-1H-indol-4-yl)-1,4,4,9-tetramethyl-5H-[1,2,4]triazolo[4,3-a]quinoxaline
505 7-Fluoro-8-(7-fluoro-1H-indol-4-yl)-1,4,4-trimethyl-9-(trifluoromethyl)-5H-[1,2,4]triazolo[4,3-a]quinoxaline
506 7-Chloro-8-(7-fluoro-1H-indol-4-yl)-1,4,4,9-tetramethyl-5H-[1,2,4]triazolo[4,3-a]quinoxaline
507 8-(5-Fluoro-3-methyl-1H-indol-7-yl)-1,4,4-trimethyl-9-(trifluoromethyl)-5H-[1,2,4]triazolo[4,3-a]quinoxaline
508 7-Chloro-8-[1-(2,2-difluoro-ethyl)-6-fluoro-1H-indazol-4-yl]-9-fluoro-1,4,4-trimethyl-5H-[1,2,4]triazolo[4,3-a]quinoxaline
509 7-Methoxy-1,4,4-trimethyl-8-(1-methyl-1H-indol-4-yl)-9-(trifluoromethyl)-5H-[1,2,4]triazolo[4,3-a]quinoxaline
510 7-Fluoro-8-(1H-indazol-4-yl)-1,4,4,9-tetramethyl-5H-[1,2,4]triazolo[4,3-a]quinoxaline
511 8-(6-Chloro-1H-indol-4-yl)-7,9-difluoro-1,4,4-trimethyl-5H-[1,2,4]triazolo[4,3-a]quinoxaline
512 9-(Difluoro-methyl)-7-fluoro-1,4,4-trimethyl-8-(7-methyl-1-methylsulfonyl-1H-indol-4-yl)-5H-[1,2,4]triazolo[4,3-a]quinoxaline
513 8-(6-Chloro-1H-indol-4-yl)-7-fluoro-1,4,4,9-tetramethyl-5H-[1,2,4]triazolo[4,3-a]quinoxaline
514 8-(1-Cyclopropyl-1H-indol-4-yl)-9-(difluoro-methyl)-7-fluoro-1,4,4-trimethyl-5H-[1,2,4]triazolo[4,3-a]quinoxaline
515 9-(Difluoro-methyl)-7-fluoro-8-(5-fluoro-1H-indol-7-yl)-1,4,4-trimethyl-5H-[1,2,4]triazolo[4,3-a]quinoxaline
516 7-Fluoro-8-(5-fluoro-1H-indol-7-yl)-1,4,4-trimethyl-9-(trifluoromethyl)-5H-[1,2,4]triazolo[4,3-a]quinoxaline
517 8-(6-Fluoro-1-methyl-1H-indol-4-yl)-7-methoxy-1,4,4-trimethyl-9-(trifluoromethyl)-5H-[1,2,4]triazolo[4,3-a]quinoxaline
518 7-Fluoro-8-(6-fluoro-1-methyl-1H-indol-4-yl)-1,4,4,9-tetramethyl-5H-[1,2,4]triazolo[4,3-a]quinoxaline
519 7-Chloro-8-(6-fluoro-1-methyl-1H-indol-4-yl)-1,4,4,9-tetramethyl-5H-[1,2,4]triazolo[4,3-a]quinoxaline
520 9-Fluoro-8-(6-fluoro-1-methyl-1H-indol-4-yl)-1,4,4,7-tetramethyl-5H-[1,2,4]triazolo[4,3-a]quinoxaline
521 9-(Difluoro-methyl)-7-fluoro-8-(6-fluoro-1-methyl-1H-indol-4-yl)-1,4,4-trimethyl-5H-[1,2,4]triazolo[4,3-a]quinoxaline
522 8-(6-Fluoro-1-methyl-1H-indol-4-yl)-1,4,4-trimethyl-9-(trifluoromethyl)-5H-[1,2,4]triazolo[4,3-a]quinoxaline
523 8-(1-Cyclopropyl-1H-indol-4-yl)-7-methoxy-1,4,4-trimethyl-9-(trifluoromethyl)-5H-[1,2,4]triazolo[4,3-a]quinoxaline
524 7-Fluoro-8-(7-fluoro-1H-indazol-4-yl)-1,4,4,9-tetramethyl-5H-[1,2,4]triazolo[4,3-a]quinoxaline
525 8-(7-Chloro-1-methylsulfonyl-1H-indol-4-yl)-7-fluoro-1,4,4,9-tetramethyl-5H-[1,2,4]triazolo[4,3-a]quinoxaline
526 9-(Difluoro-methyl)-8-(6-fluoro-1-methylsulfonyl-1H-indol-4-yl)-1,4,4-trimethyl-5H-[1,2,4]triazolo[4,3-a]quinoxaline
527 9-(Difluoro-methyl)-8-(5-fluoro-3-methyl-1H-indol-7-yl)-1,4,4-trimethyl-5H-[1,2,4]triazolo[4,3-a]quinoxaline
528 9-(Difluoro-methyl)-1,4,4-trimethyl-8-(1-methylsulfonyl-1H-indol-4-yl)-5H-[1,2,4]triazolo[4,3-a]quinoxaline
529 8-(7-Chloro-1H-indol-4-yl)-7,9-difluoro-1,4,4-trimethyl-5H-[1,2,4]triazolo[4,3-a]quinoxaline
530 8-(7-Chloro-1H-indol-4-yl)-7-fluoro-1,4,4-trimethyl-9-(trifluoromethyl)-5H-[1,2,4]triazolo[4,3-a]quinoxaline
531 4-[7-Fluoro-1,4,4-trimethyl-9-(trifluoromethyl)-5H-[1,2,4]triazolo[4,3-a]quinoxalin-8-yl]-1H-indole-7-carbonitrile
532 7-Fluoro-8-(6-fluoro-1-methyl-1H-indol-4-yl)-1,4,4-trimethyl-9-(trifluoromethyl)-5H-[1,2,4]triazolo[4,3-a]quinoxaline
533 7-Chloro-8-(1-cyclopropyl-1H-indol-4-yl)-1,4,4,9-tetramethyl-5H-[1,2,4]triazolo[4,3-a]quinoxaline
534 4-(7-Fluoro-1,4,4,9-tetramethyl-5H-[1,2,4]triazolo[4,3-a]quinoxalin-8-yl)-1H-indole-7-carbonitrile
535 7-Fluoro-8-(7-fluoro-1H-indazol-4-yl)-1,4,4-trimethyl-9-(trifluoromethyl)-5H-[1,2,4]triazolo[4,3-a]quinoxaline
536 7-Fluoro-8-(6-methoxy-1-methylsulfonyl-1H-indol-4-yl)-1,4,4-trimethyl-9-(trifluoromethyl)-5H-[1,2,4]triazolo[4,3-a]quinoxaline
537 7-Fluoro-8-(6-methoxy-1-methylsulfonyl-1H-indol-4-yl)-1,4,4,9-tetramethyl-5H-[1,2,4]triazolo[4,3-a]quinoxaline in the form of the free compound or a physiologically acceptable salt thereof.

The compounds according to the present invention can be synthesized by standard reactions in the field of organic chemistry known to the person skilled in the art or in a manner as described herein 5 (cf. Reaction Scheme 1 below) or analogously. The reaction conditions in the synthesis routes described herein are known to the skilled person and are for some cases also exemplified in the Examples described herein.

ben-Weyl, 2007). If desired, compound of formula (II) can be brominated to compound (V) which can undergo a metal catalyzed cross-coupling reaction to give compound (VI). Triazole formation leads to an alternate route to compounds of general formula (VII). Copper mediated quinoxaline cyclization of compound (I) to compound (II) is known in the art (cf. *Adv. Synth. Catal.*, 2010, 352, 2531-2537). Compounds of formula (I) are commercially available or can be prepared according to methods known in the art.

Reaction Scheme 1

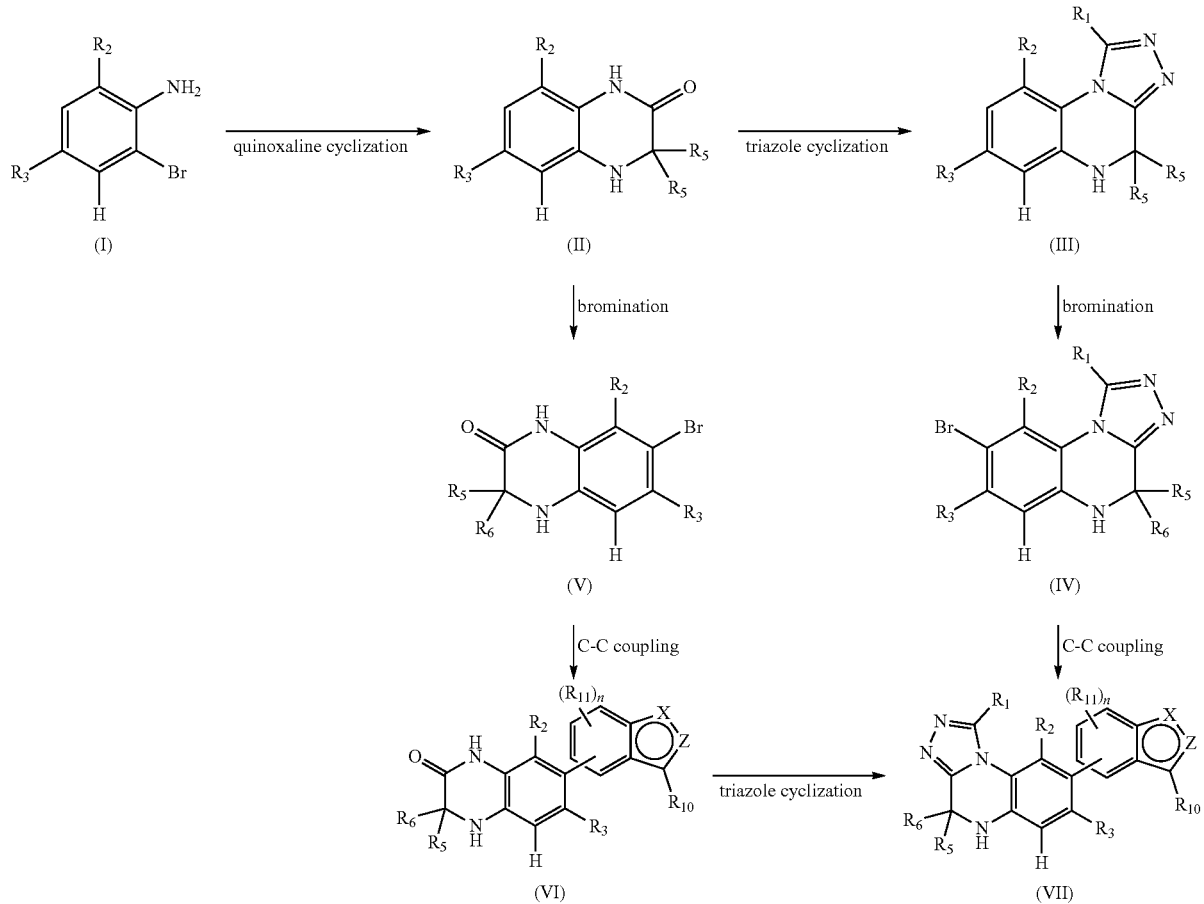

Substituted indole/indazole moiety in compounds of formula (VII) can be introduced by subjecting a compound of formula (IV) in a metal catalyzed C—C coupling reaction. Metal catalyzed C—C coupling reactions are known in the art (cf. *Metal Catalyzed Cross-Coupling Reactions and More*, 3 Volume Set Wiley, 2014; *Angew. Chem. Int. Ed.*, 2012, 51, 5062-5085). Favorable C—C coupling reactions are palladium catalyzed cross coupling reactions (cf. *Angew. Chem.*, 2005, 117, 4516-4563). Triazole cyclization of compound (II) gives access to compounds of general formula (III). Triazole formation on quinoxalines is known in the art (cf. Heterocycles, 1992, 34, 771-780; *Biological and Pharmaceutical Bulletin*, 2005, 28, 1216-1220). Electrophilic aromatic bromination of compound (III) gives compound (IV). Bromination reactions of aromatic compounds are generally known (cf. *Science of Synthesis*, Compounds with One Saturated Carbon-Heteroatom Bond, Volume 35, Hou- The compounds according to the present invention can be produced in the manner described here or in an analogous manner.

In a preferred embodiment, the compounds according to the present invention are modulators of the glucocorticoid receptor. In the sense of the present invention, the term "selective modulator of the glucocorticoid receptor (glucocorticoid receptor modulator)" preferably means that the respective compound exhibits in a cellular target engagement assay for agonistic or antagonistic potency on the glucocorticoid receptor an EC50 or IC50 value on the glucocorticoid receptor of at most 15 µM ($10^{-6}$ mol/L) or at most 10 µM; more preferably at most 1 µM; still more preferably at most 500 nM ($10^{-9}$ mol/L); yet more preferably at most 300 nM; even more preferably at most 100 nM; most preferably at most 10 nM; and in particular at most 1 nM.

The person skilled in the art knows how to test compounds for modulation (agonistic or antagonistic) of the activity of the glucocorticoid receptor. Preferred target engagement assays for testing compounds for their agonistic or antagonistic potency (EC50, IC50) on the glucocorticoid receptor are described herein below:

Glucocorticoid Receptor Cell-Based Assays

Potential selective glucocorticoid receptor modulators of this intervention can be tested for modulation of the activity of the glucocorticoid receptor using cell-based assays. These assays involve a Chinese hamster ovary (CHO) cell line which contains fragments of the glucocorticoid receptor as well as fusion proteins. The glucocorticoid receptor fragments used are capable of binding the ligand (e.g. beclomethasone) to identify molecules that compete for binding with glucocorticoid receptor ligands. In more detail, the glucocorticoid receptor ligand binding domain is 25 fused to the DNA binding domain (DBD) of the transcriptionfactor GAL4 (GAL4 DBD-GR) and is stably integrated into a CHO cell line containing a GAL4-UAS-Luciferase reporter construct. To identify selective glucocorticoid receptor modulators, the reporter cell line is incubated with the molecules using an 8-point half-log compound dilution curve for several hours. After cell lysis the luminescence that is produced by luciferase after addition of the substrate is detected and EC50 or IC50 values can be calculated. Engagement of molecules which induce gene expression via glucocortocoid receptor binding to the DNA leads to expression of the luciferase gene under the control of the fusion protein GAL4 DBD-GR and therefore to a dose-dependent increase of the luminescence signal. Binding of molecules which repress beclomethasone-induced gene expression of the luciferase gene under the control of the fusion protein GAL4 DBD-GR leads to a dose-dependent reduction of the luminescence signal.

In a preferred embodiment, the compound according to the present invention exhibits in a cellular target engagement assay for agonistic or antagonistic potency on the glucocorticoid receptor an EC50 or IC50 value on the glucocorticoid receptor of at most 1 µM ($10^{-6}$ mol/L); still more preferably at most 500 nM ($10^{-9}$ mol/L); yet more preferably at most 300 nM; even more preferably at most 100 nM; most preferably at most 50 nM; and in particular at most 10 nM or at most 1 nM.

In a preferred embodiment, the compound according to the present invention exhibits in a cellular target engagement assay for agonistic or antagonistic potency on the glucocorticoid receptor an EC50 or IC50 value on the glucocorticoid receptor in the range of from 0.1 nM ($10^{-9}$ mol/L) to 1000 nM; still more preferably 1 nM to 800 nM; yet more preferably 1 nM to 500 nM; even more preferably 1 nM to 300 nM; most preferably 1 nM to 100 nM; and in particular 1 nM to 80 nM.

Preferably, the compounds according to the present invention are useful as selective modulators of the glucocorticoid receptor.

Therefore, the compounds according to the present invention are preferably useful for the in vivo treatment or prevention of diseases in which participation of the glucocorticoid receptor is implicated.

The present invention therefore further relates to a compound according to the present invention for use in the modulation of glucocorticoid receptor activity.

Therefore, another aspect of the present invention relates to a compound according to the present invention for use in the treatment and/or prophylaxis of a disorder which is mediated at least in part by the glucocorticoid receptor. Still another aspect of the present invention relates to a method of treatment of a disorder which is mediated at least in part by the glucocorticoid receptor comprising the administration of a therapeutically effective amount of a compound according to the present invention to a subject in need thereof, preferably a human.

A further aspect of the invention relates to the use of a compound according to the present invention as medicament.

Another aspect of the present invention relates to a pharmaceutical dosage form comprising a compound according to the present invention. Preferably, the pharmaceutical dosage form comprises a compound according to the present invention and one or more pharmaceutical excipients such as physiologically acceptable carriers, additives and/or auxiliary substances; and optionally one or more further pharmacologically active ingredient. Examples of suitable physiologically acceptable carriers, additives and/or auxiliary substances are fillers, solvents, diluents, colorings and/or binders. These substances are known to the person skilled in the art (see H. P. Fiedler, Lexikon der Hilfsstoffe fur Pharmazie, Kosmetik und angrenzende Gebiete, Editio Cantor Aulendoff).

The pharmaceutical dosage form according to the present invention is preferably for systemic, topical or local administration, preferably for oral administration. Therefore, the pharmaceutical dosage form can be in form of a liquid, semisolid or solid, e.g. in the form of injection solutions, drops, juices, syrups, sprays, suspensions, tablets, patches, films, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and can also be administered as such.

The pharmaceutical dosage form according to the present invention is preferably prepared with the aid of conventional means, devices, methods and processes known in the art. The amount of the compound according to the present invention to be administered to the patient may vary and is e.g. dependent on the patient's weight or age and also on the type of administration, the indication and the severity of the disorder. Preferably 0.001 to 100 mg/kg, more preferably 0.05 to 75 mg/kg, most preferably 0.05 to 50 mg of a compound according to the present invention are administered per kg of the patient's body weight.

The glucocorticoid receptor is believed to have potential to modify a variety of diseases or disorders in mammals such as humans. These include in particular inflammatory diseases.

Another aspect of the present invention relates to a compound according to the present invention for use in the treatment and/or prophylaxis of pain and/or inflammation; more preferably inflammatory pain.

A further aspect of the present invention relates to a method of treatment of pain and/or inflammation; more preferably inflammatory pain.

EXAMPLES

The following abbreviations are used in the descriptions of the experiments:

AcOH=acetic acid; Ac=acetyl group; Attaphos=bis(di-tert-butyl(4 dimethylaminophenyl)phosphine)dichloropalladium(II); Ar=argon; BISPIN (or Bis-Pin)=bis(pinacolato) diborane; dba=dibenzylideneacetone; DCM=dichloromethane; DIPEA=N,N-35 diisopropylethylamine; DMADMF=N,N-dimethylformamide dimethylacetal; DMAP=4-(dimethylamino)-pyridine; DMF=N,N-dimethylformamid; DMSO=dimethylsulfoxid; dppf=1,1'; bis (diphenylphosphanyl)ferrocene; EtOAc=ethyl acetate; EtOH=ethanol; h=hour; LDA=lithiumdiisopropylamide; LiHMDS=lithium bis(trimethylsilyl)amide; MeOH=methanol; min=minute; n-BuLi=n-butyllithium; RT=room temperature; Rt=retention time; tert=tertiary; TEA=triethylamine; THF=tetrahydrofuran; p-TSA=para-toluene sulfonic acid; TMSCl=trimethylsilyl chloride; X-Phos=2-dicyclohexylphosphino-2',4',6'-triisopropylbiphenyl.

Synthesis of 6-fluoro-4-(4,4,5,5-tetramethyl-1,3,2-dioxaborolan-2-yl)-1H-indole (Intermediate A-1)

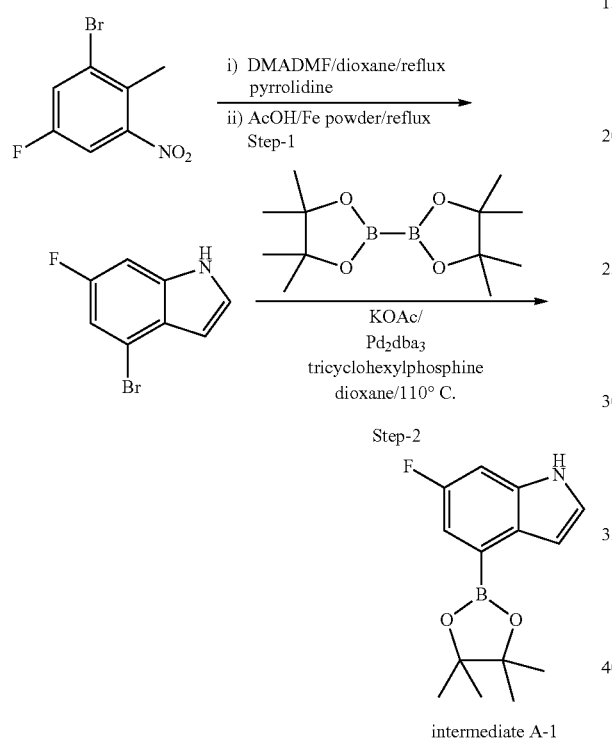

intermediate A-1

Step1: To a stirring solution of 2-bromo-4-fluoro-6-nitrotoluene (4.69 g, 20 mmol, 1 eq) in 1,4-dioxane (25 ml) was slowly added N,N-dimethylformamide dimethylacetal (13.3 mL, 100 mmol, 5 eq) and pyrrolidine (1.47 mL, 20 mmol, 1 eq). The reaction mixture was then stirred for 18 h at 100° C. The reaction mixture was concentrated to a dark residue. To this residue were added AcOH (30 mL) and iron powder (11 g, 200 mmol, 10 eq) and then the reaction mixture was refluxed for 1 h. The reaction mixture was then cooled to RT and then filtered through a celite bed. The filtrate was neutralised by 50% sodium hydroxide solution and then extracted with EtOAc (2×100 mL). Combined organic layers was washed with water (100 mL), brine (100 mL), dried over anhydrous Na$_2$SO$_4$ and evaporated to get the crude which was purified by column chromatography to afford 4-bromo-6-fluoro-1H-indole (1.3 g, 30%) as brown liquid.

Step2: To a stirring suspension of 4-bromo-6-fluoro-1H-indole (1.1 g, 5.1 mmol, 1 eq), bis(pinacolato)diborane (2.6 g, 10.2 mmol, 2 eq) and potassium acetate (2.0 g, 20.4 mmol, 4 eq) in 1,4-dioxan (20 mL) was deoxygenated by Ar for 10 min. Pd$_2$(dba)$_3$ (0.07 g, 0.07 mmol. 0.015 eq) and tricyclohexylphosphine (0.102 g, 0.36 mmol, 0.07 eq) was then added to the reaction mixture and again deoxygenated by Ar for 10 min. The reaction mixture was then stirred for 14 h at 110° C. The reaction mixture then cooled to RT and then filtered through celite bed. Filtrate was concentrated under reduced pressure to get the crude material which was purified by column chromatography to afford 6-fluoro-4-(4,4,5,5-tetramethyl-1,3,2-dioxaborolan-2-yl)-1H-indole (1.1 g, 82%) as light yellow solid.

Synthesis of 6-fluoro-1-(methylsulfonyl)-4-(4,4,5,5-tetramethyl-1,3,2-dioxaborolan-2-yl)-1H-indole (Intermediate A-2)

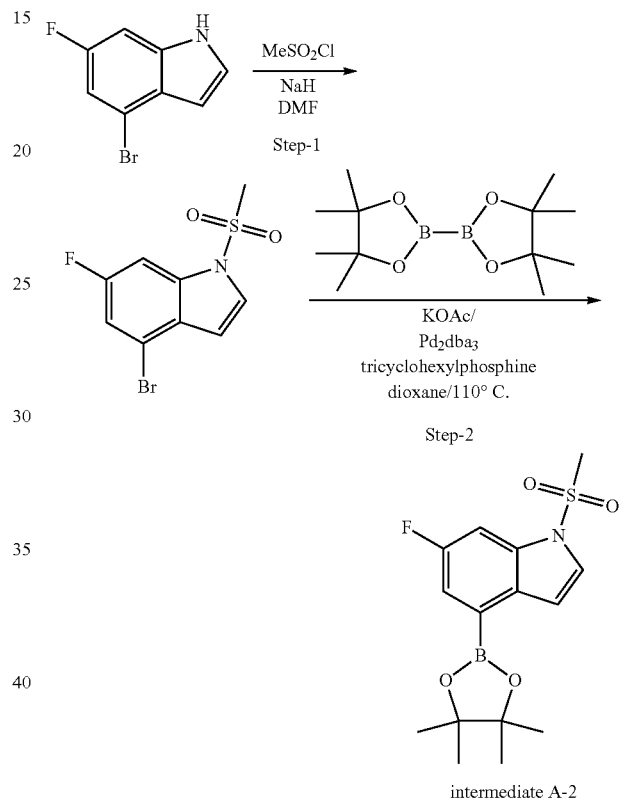

intermediate A-2

Step1: To a stirring solution of 4-bromo-6-fluoro-1H-indole (0.18 g, 0.841 mmol, 1 eq) in DMF (5 mL) was portion wise added sodium hydride (60%, 0.07 g, 1.68 mmol, 2 eq) at 0° C. The reaction mixture was then stirred for 30 min at RT. Methanesulfonylchloride (0.114 ml, 1.26 mmol, 1.5 eq) was then added to the reaction mixture at 0° C. The reaction mixture was stirred for 2 h at RT. Reaction mixture was diluted with EtOAc (50 mL). Combined organic layers were washed with water (5×10 mL), brine (10 mL), dried over anhydrous Na$_2$SO$_4$ and the solvent was evaporated under reduced pressure. Crude product was purified by column chromatography to afford 4-bromo-6-fluoro-1-(methylsulfonyl)-1H-indole (0.1 g, 41%) as off-white solid.

Step2: To a stirring suspension of 4-bromo-6-fluoro-1-(methylsulfonyl)-1H-indole (1.2 g, 3.53 mmol, 1 eq) in 1,4-dioxan (20 mL), bis-pinacolatodiborane (1.79 g, 7.06 mmol, 2 eq) and potassium acetate (1.39 g, 10.62 mmol, 4 eq) were added and the mixture was deoxygenated by Ar for 10 min. Pd$_2$(dba)$_3$ (0.048 g, 0.052 mmol. 0.015 eq) and triclyclohexylphosphine (0.071 g, 0.25 mmol, 0.07 eq) was then added to the reaction mixture and again deoxygenated by Ar for 10 min. The reaction mixture was stirred for 14 h at 110° C. The reaction mixture was cooled to RT and then filtered through celite bed. Filtrate was concentrated under reduced pressure to get the crude product which was purified by column chromatography to afford 6-fluoro-1-(methylsulfonyl)-4-(4,4,5,5-tetramethyl-1,3,2-dioxaborolan-2-yl)-1H-indole (1.0 g, 80%) as light yellow solid.

Synthesis of 6-fluoro-2-methyl-4-(4,4,5,5-tetramethyl-1,3,2-dioxaborolan-2-yl)-1H-indole (Intermediate A-3)

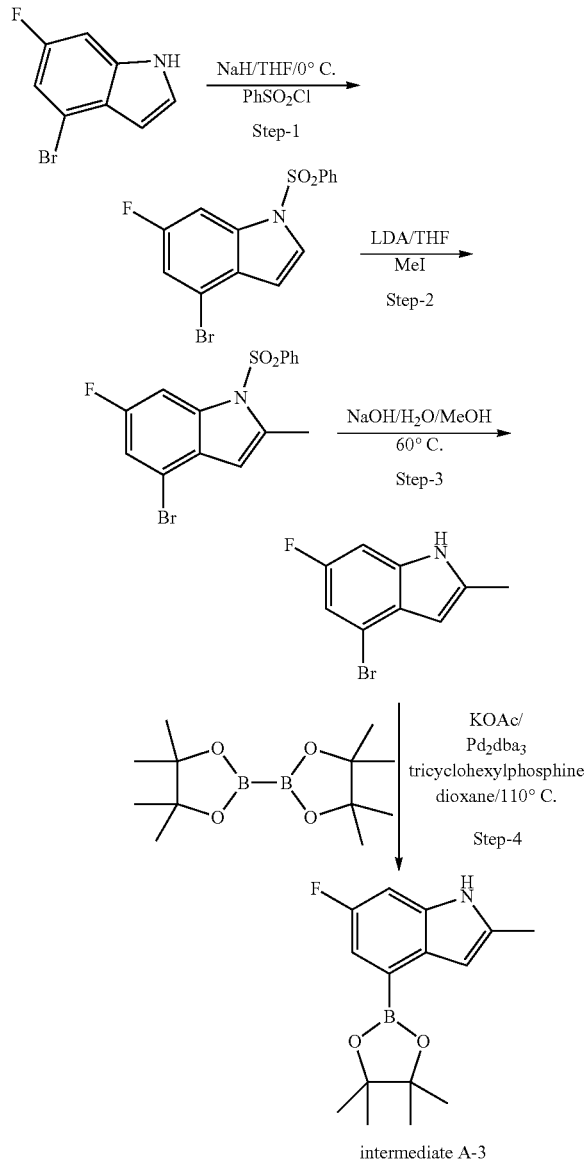

intermediate A-3

Step1: To a stirring solution of 4-bromo-6-fluoroindole (3.4 g, 15.88 mmol, 1 eq) in THF (80 mL) was portion wise added sodium hydride (60% suspension) (0.95 g, 23.8 mmol, 1.5 eq) at 0° C. The reaction mixture was stirred for 30 min at RT. p-Toluenesulfonylchloride (3.36 g, 19.06 mmol, 1.2 eq) was then added to the reaction mixture at 0° C. The reaction mixture was stirred for 2 h at RT. The reaction mixture was quenched by ice (20 g). The organic layer was separated and the aqueous layer was extracted by EtOAc (2×30 mL). The combined organic layer was washed by brine (50 mL), dried over $Na_2SO_4$, concentrated under reduced pressure to get the crude product which was purified by column chromatography to afford 4-bromo-6-fluoro-1-(phenylsulfonyl)-1H-indole (2.1 g, 38%) as white solid.

Step2: To a stirring solution of 4-bromo-6-fluoro-1-(phenylsulfonyl)-1H-indole (2.0 g, 5.43 mmol, 1 eq) in THF (26 mL) was drop wise added LDA (11.96 ml, 11.96 mmol, 2.2 eq) at 0° C. The reaction mixture then stirred for 20 min at 0° C. Methyl iodide (1.96 g, 11.96 mmol, 2.2 eq) was then added to the reaction mixture and stirred for 16 h at RT. The reaction mixture was quenched with addition of saturated solution of ammonium chloride (30 mL). The organic layer was separated and the aqueous layer was extracted with EtOAc (2×50 mL). The combined organic layer was washed with brine (50 mL), dried over $Na_2SO_4$, concentrated under reduced pressure to get the crude product which was purified by column chromatography to afford 4-bromo-6-fluoro-2-methyl-1-(phenylsulfonyl)-1H-indole (1.8 g, 90%) as white solid.

Step3: To a stirred solution of 4-bromo-6-fluoro-2-methyl-1-(phenylsulfonyl)-1H-indole (0.2 g, 0.53 mmol, 1 eq) in a mixture of THF, MeOH and water (2 mL, 1 mL, 0.5 mL) was added sodium hydroxide (0.08 g, 2.11 mmol, 4 eq). The reaction mixture then stirred for 4 h at RT. Solvents were evaporated and water was added to the residue and a precipitate was formed which was collected by filtration and dried under vacuum to get the 4-bromo-6-fluoro-2-methyl-1H-indole (0.1 g, 83%) as white solid.

Step4: To a stirring suspension of 4-bromo-6-fluoro-2-methyl-1H-indole (0.5 g, 2.19 mmol, 1 eq), bis(pinacolato)diborane (0.67 g, 4.39 mmol, 2 eq) and potassium acetate (0.86 g, 8.8 mmol, 4 eq) in 1,4-dioxan (20 mL) was deoxygenated by Ar for 10 min. $Pd_2(dba)_3$ (0.11 g, 1.09 mmol. 0.05 eq) and tricyclohexylphosphine (0.05 g, 0.17 mmol, 0.08 eq) was then added to the reaction mixture and again deoxygenated by Ar for 10 min. The reaction mixture was then stirred for 14 h at 110° C. The reaction mixture then cooled to RT and then filtered through celite bed. Filtrate was concentrated under reduced pressure to get the crude product which was purified by column chromatography to afford 6-fluoro-2-methyl-4-(4,4,5,5-tetramethyl-1,3,2-dioxaborolan-2-yl)-1H-indole (0.4 g, 66%) as light yellow solid.

Synthesis of 6-fluoro-4-(4,4,5,5-tetramethyl-1,3,2-dioxaborolan-2-yl)-1H-indole-2-carbonitrile (Intermediate A-4)

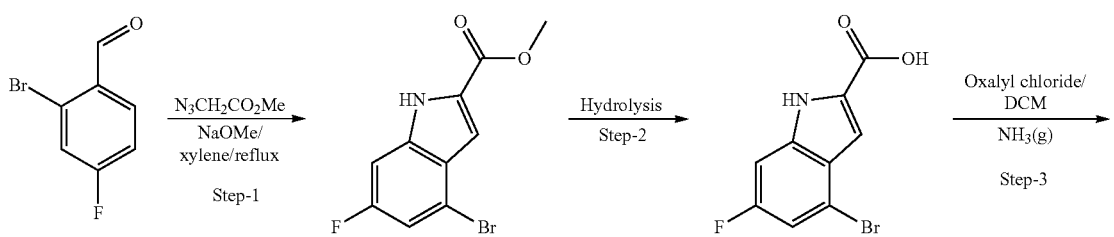

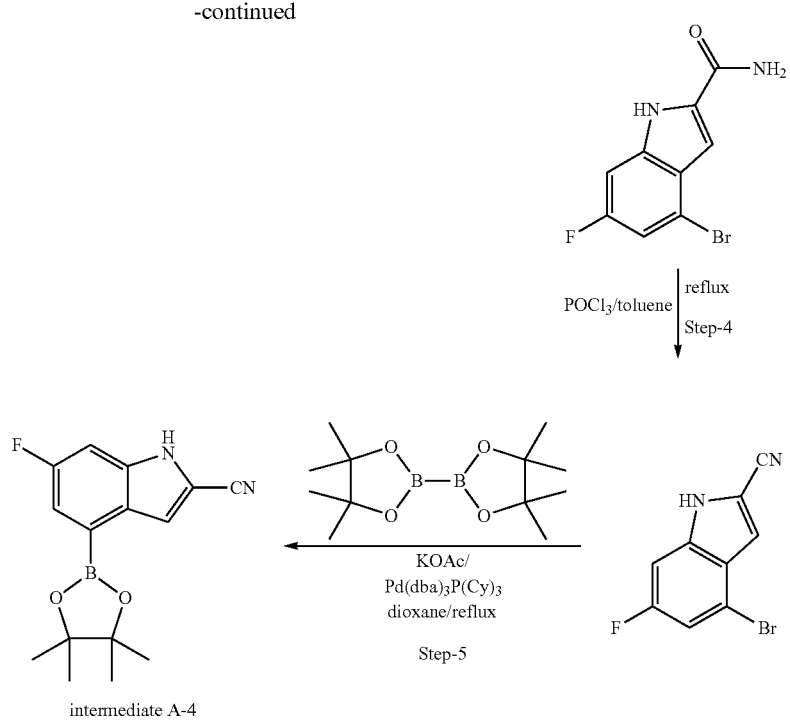

intermediate A-4

Step1: To a stirred solution of 2-bromo-4-fluoro-benzaldehyde (0.6 g, 2.95 mmol, 1 eq) in MeOH (5 mL) was added methylazidoacetate (1.35 g, 11.22 mmol, 4 eq) and cooled to −15° C. Then 25% NaOMe (2.7 ml, 11.82 mmol, 4 eq) was added and the mixture was stirred for 4 h at the same temperature. Then the reaction mixture was poured into ice, the resulting solid was filtered and dried. To this solid was added xylene and heated to reflux for 16 h. Then the reaction mass was evaporated and the crude product was taken into EtOAc (20 mL), washed with brine (10 mL), dried over $Na_2SO_4$ and concentrated. The crude product was purified by column chromatography to afford methyl 4-bromo-6-fluoro-1H-indole-2-carboxylate (0.35 g, 41%) as white solid.

Step2: To a stirred solution of methyl 4-bromo-6-fluoro-1H-indole-2-carboxylate (3 g, 11.03 mmol, 1 eq) was added THF (8 mL), MeOH (4 mL), $H_2O$ (4 mL) followed by LiOH (1.3 g, 33.08 mmol, 3 eq) and stirred for 16 h at RT. Then the reaction mass was evaporated and the crude was taken into $H_2O$ and acidified with 2N HCl and extracted with EtOAc (2×50 mL), washed with $H_2O$ (20 mL), brine (20 mL), dried over $Na_2SO_4$ and concentrated to afford 4-bromo-6-fluoro-1H-indole-2-carboxylic acid (1.2 g, 43%) as an off white solid.

Step3: To a stirred solution of 4-bromo-6-fluoro-1H-indole-2-carboxylic acid (1 g, 3.87 mmol, 1 eq) in DCM (20 mL) was added oxaylchloride (0.6 mL, 7.75 mmol, 2 eq) at 0° C. and stirred for 2 h. Then the solvent was evaporated under $N_2$, the crude was cooled to 0° C. and then aq $NH_3$ solution was added and the mixture was stirred for 20 min. Then the reaction mass was extracted with EtOAc (2×30 mL), washed with brine (20 mL), dried over $Na_2SO_4$ and concentrated. The crude product was purified by column chromatography to afford 4-bromo-6-fluoro-1H-indole-2-carboxamide (0.5 g, 50%) as white solid.

Step4: To a stirred solution of 4-bromo-6-fluoro-1H-indole-2-carboxamide (0.15 g, 0.58 mmol, 1 eq) in toluene (10 mL) was added $POCl_3$ (0.27 mL, 2.91 mmol, 5 eq) and heated to reflux for 3 h. Then the solvent was evaporated and the crude product was cooled and basified with sat $NaHCO_3$ solution and extracted with EtOAc (2×15 mL), washed with $H_2O$ (10 mL), brine (10 mL), dried over $Na_2SO_4$ and concentrated. The crude product was purified by column chromatography to afford 4-bromo-6-fluoro-1H-indole-2-carbonitrile (0.08 g, 58%) as sticky mass.

Step5: To a stirred solution of 4-bromo-6-fluoro-1H-indole-2-carbonitrile (0.08 g, 0.33 mmol, 1 eq.) in 1,4-dioxane was added KOAc (0.07 g, 0.67 mmol, 2 eq) and Bispincolatediborane (0.17 g, 0.67 mmol, 2 eq) and degassed with Ar for 10 min. Then was added $Pd_2(dba)_3$ (0.03 g, 0.03 mmol, 0.1 eq), $P(Cy)_3$ (0.01 g, 0.03 mmol, 0.1 eq) and the mixture was heated to reflux for 16 h. Then the reaction mass was filtered on celite bed, washed with EtOAc, the filtrate was washed with $H_2O$ (10 mL), brine (10 mL), dried over $Na_2SO_4$ and concentrated to afford crude 6-fluoro-4-(4,4,5,5-tetramethyl-1,3,2-dioxaborolan-2-yl)-1H-indole-2-carbonitrile (0.08 g) which was used for next step without further purification.

Synthesis of 5-methyl-7-(4,4,5,5-tetramethyl-1,3,2-dioxaborolan-2-yl)-1H-indole (Intermediate A-7)

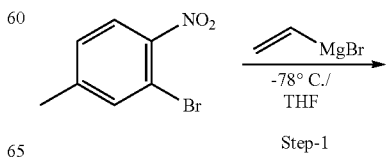

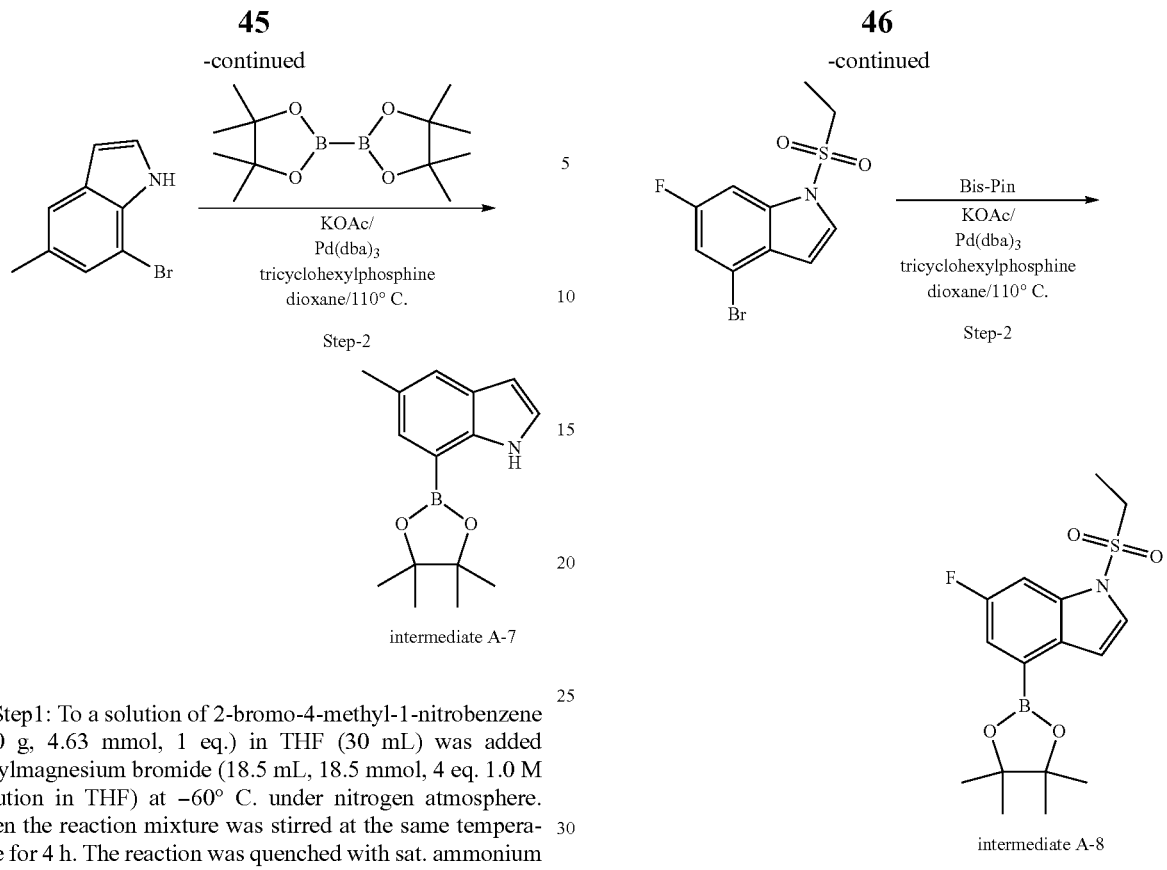

intermediate A-7

Step1: To a solution of 2-bromo-4-methyl-1-nitrobenzene (1.0 g, 4.63 mmol, 1 eq.) in THF (30 mL) was added vinylmagnesium bromide (18.5 mL, 18.5 mmol, 4 eq. 1.0 M solution in THF) at −60° C. under nitrogen atmosphere. Then the reaction mixture was stirred at the same temperature for 4 h. The reaction was quenched with sat. ammonium chloride solution at −60° C. Then the resulting mixture was extracted with EtOAc (2×50 mL), washed with brine solution and concentrated under reduced pressure to give the crude product which was purified by flash column chromatography to afford 7-bromo-5-methyl-1H-indole (0.5 g, 52%) as dense yellow liquid.

Step2: To a solution of 7-bromo-5-methyl-1H-indole (0.5 g, 2.38 mmol, 1 eq.) in 1,4-dioxane (10 mL) were added KOAc (0.932 g, 9.52 mmol, 4 eq.), bis-pinacolatodiborane (1.2 g, 4.76 mmol, 2 eq.) and the reaction mixture was deoxygenated with Ar for 15 min. Then Pd$_2$dba$_3$ (0.032 g, 0.0375 mmol, 0.015 eq.) and tricyclohexylphosphine (0.48 g, 0.171 mmol, 0.072 eq.) were added and the mixture was deoxygenated with Ar for 10 min. The reaction mixture is refluxed for 16 h. Then the reaction mixture is cooled to RT and filtered through celite and concentrated under reduced pressure. The concentrated mass was purified by flash column chromatography to afford 5-methyl-7-(4,4,5,5-tetramethyl-1,3,2-dioxaborolan-2-yl)-1H-indole (0.5 g, 81.7%) yellow solid.

Synthesis of 1-(ethylsulfonyl)-6-fluoro-4-(4,4,5,5-tetramethyl-1,3,2-dioxaborolan-2-yl)-1H-indole (Intermediate A-8)

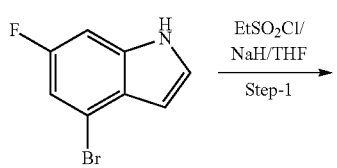

intermediate A-8

Step1: To a stirring solution of 4-bromo-6-fluoro-1H-indole (1.0 g, 4.67 mmol, 1 eq) in DMF (24 mL) was portion wise added sodium hydride (60%, 0.224 g, 9.34 mmol, 2 eq) at 0° C. The reaction mixture was then stirred for 30 min at RT. Ethanesulfonylchloride (0.604 mL, 7 mmol, 1.5 eq) then added to the reaction mixture at 0° C. The reaction mixture then stirred for 2 h at RT. Reaction mixture was diluted with EtOAc (200 mL). Combined organic layers was washed with water (5×30 mL), brine (30 mL), dried over anhydrous Na$_2$SO$_4$ and evaporated under reduced pressure. Crude product was purified by column chromatography to afford 4-bromo-1-(ethylsulfonyl)-6-fluoro-1H-indole (0.513 g, 36%) as off white solid.

Step2: To a stirring suspension of 4-bromo-1-(ethylsulfonyl)-6-fluoro-1H-indole (0.51 g, 1.6 mmol, 1 eq), bis(pinacolato)diborane (0.843 g, 3.2 mmol, 2 eq) and potassium acetate (0.653 g, 6.4 mmol, 4 eq) in 1,4-dioxan (15 mL) was deoxygenated by Ar for 10 min. Pd$_2$(dba)$_3$ (0.023 g, 0.025 mmol. 0.015 eq) and tricyclohexylphosphine (0.036 g, 0.12 mmol, 0.072 eq) was then added to the reaction mixture and again deoxygenated by Ar for 10 min. The reaction mixture was then stirred for 14 h at 110° C. The reaction mixture cooled to RT and then filtered through celite bed. Filtrate was concentrated under reduced pressure to get the crude material which was purified by column chromatography to afford 1-(ethylsulfonyl)-6-fluoro-4-(4,4,5,5-tetramethyl-1,3,2-dioxaborolan-2-yl)-1H-indole (0.212 g, 38%) as off white solid.

Synthesis of 1-(cyclopropylsulfonyl)-6-fluoro-4-(4,
4,5,5-tetramethyl-1,3,2-dioxaborolan-2-yl)-1H-indole (Intermediate A-9)

Synthesis of 1-(4-(4,4,5,5-tetramethyl-1,3,2-dioxaborolan-2-yl)-1H-indol-1-yl)ethanone (Intermediate A-10)

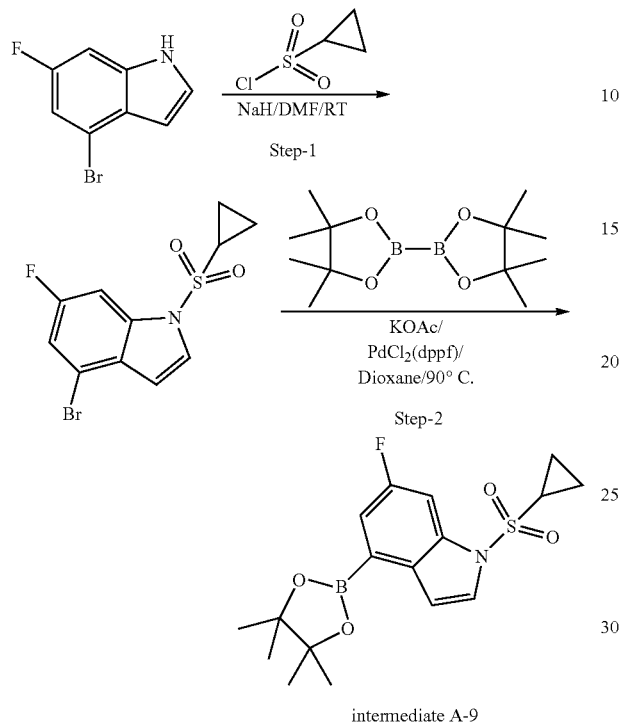

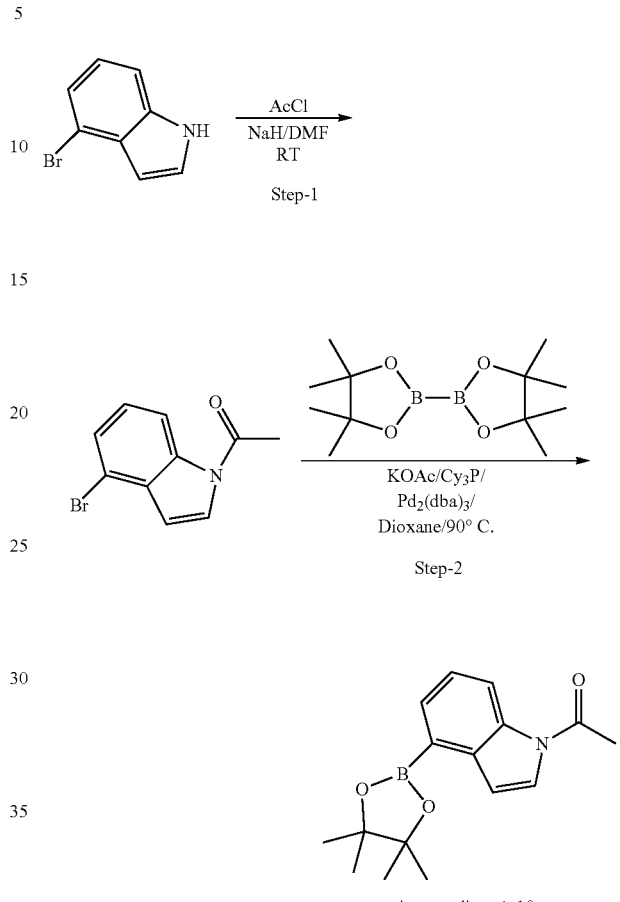

Step1: To a stirred solution of 4-bromo-6-fluoro-1H-indole (1.0 g, 4.67 mmol, 1 eq) in DMF (24 mL) was added sodium hydride (60%) (0.467 g, 11.68 mmol, 2.5 eq) at 0° C. and the mixture was stirred at RT for 30 min. Cyclopropanesulfonyl chloride (1.3 g, 9.34 mmol, 2.0 eq) was then added to the reaction mixture and again stirred for another 2 h. After completion of reaction, reaction mixture was quenched with water and extracted with EtOAc (2×100 mL). Combined organic layers were washed with water (100 mL), brine (100 mL), dried over anhydrous $Na_2SO_4$ and the solvent was evaporated to get the crude product which was purified by column chromatography to afford 4-bromo-1-(cyclopropylsulfonyl)-6-fluoro-1H-indole (0.6 g, 40%) as white solid.

Step2: To a stirred solution of 4-bromo-1-(cyclopropylsulfonyl)-6-fluoro-1H-indole (0.5 g, 1.57 mmol, 1 eq), bis(pinacolato)diborane (0.790 g, 3.14 mmol, 2 eq) and potassium acetate (0.46 g, 4.71 mmol, 3 eq) in 1,4-dioxan (20 mL) was added and the mixture was deoxygenated by Ar for 10 min. $PdCl_2$(dppf).DCM (0.128 g, 0.157 mmol. 0.1 eq) was then added and the mixture was stirred at 90° C. for another 16 h. After completion of reaction, reaction mixture was filtered through celite bed. Filtrate was concentrated under reduced pressure to get the crude material which was purified by column chromatography to afford 1-(eyelopropylsulfonyl)-6-fluoro-4-(4,4,5,5-tetramethyl-1,3,2-dioxaborolan-2-yl)-1H-indole (0.600 g, 76%) as light yellow solid.

Step1: To a stirred solution of 4-bromo-1H-indole (0.5 g, 2.55 mmol, 1 eq) in THF (25 mL) was added sodium hydride (60%) (0.122 g, 3.06 mmol, 1.2 eq) at 0° C. and continued stirred at RT for 30 min. Acetyl chloride (0.02 mL, 3.06 mmol, 1.2 eq) was then added to the reaction mixture and again stirred for another 2 h. The reaction mixture was quenched with water and extracted with EtOAc (2×100 mL). Combined organic layers were washed with water (100 mL), brine (100 mL), dried over anhydrous $Na_2SO_4$ and the solvent was evaporated to get the crude product which was purified by column chromatography to afford 1-(4-bromo-1H-indol-1-yl)ethanone (0.55 g, 91%) as brown liquid.

Step2: To a stirred solution of 1-(4-bromo-1H-indol-1-yl) ethanone (0.55 g, 2.31 mmol, 1 eq), bis(pinacolato)diborane (0.707 g, 4.62 mmol, 2 eq) and potassium acetate (0.680 g, 6.93 mmol, 3 eq) in 1,4-dioxan (20 mL) was deoxygenated by Ar for 10 min. $Pd_2(dba)_3$ (0.106 g, 0.1155 mmol, 0.08 eq) and $Cy_3P$ (0.052 g, 0.1848 mmol. 0.08 eq) was then added to the reaction mixture and reflux at 90° C. for another 16 h. The reaction mixture was cooled to RT and filtered through celite bed. Filtrate was concentrated under reduced pressure to get the crude material which was purified by column chromatography to afford 1-(4-(4,4,5,5-tetramethyl-1,3,2-dioxaborolan-2-yl)-1H-indol-1-yl)ethanone (0.600 g, 92%) as brown liquid.

49

Synthesis of 6-fluoro-4-(4,4,5,5-tetramethyl-1,3,2-dioxaborolan-2-yl)-1-(2,2,2-trifluoroethyl)-1H-indole (Intermediate A-11)

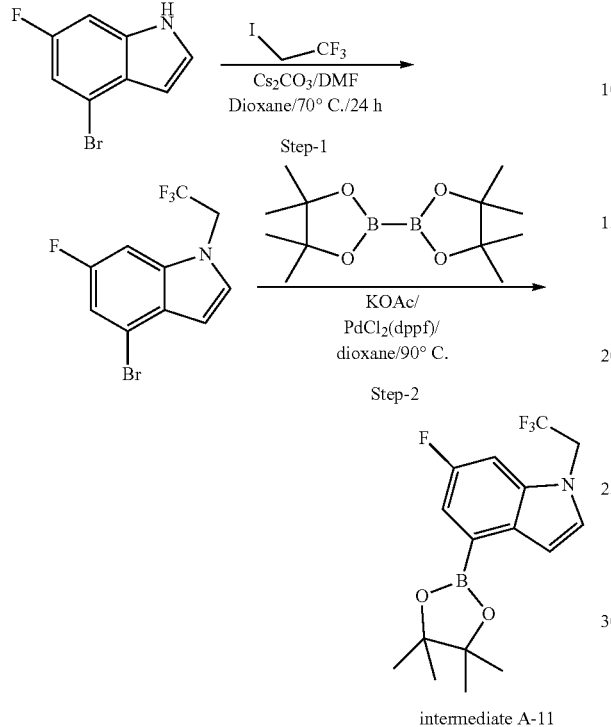

intermediate A-11

Step1: To a solution of 4-bromo-6-fluoro-1H-indole (2.0 g, 9.345 mmol, 1 eq.) in DMF (25 mL) was added Cs$_2$CO$_3$ (15.18 g, 46.72 mmol, 5 eq.) and 1,1,1-trifluoro-2-iodoethane (5.8 g, 28.037 mmol, 3.0 eq) in a sealed tube. The reaction mixture was refluxed at 50° C. for 24 h. The reaction mixture was filtered through sintered and the filtrate was diluted with EtOAc (100 mL). Organic layer was washed with cold water (3×50 mL), brine (25 mL), dried over anhydrous Na$_2$SO$_4$ and the solvent was evaporated to get the crude product, which was purified by flash column chromatography to afford mixture which further purified by Prep HPLC to afford 4-bromo-6-fluoro-1-(2,2,2-trifluoroethyl)-1H-indole (0.400 g, 14%) as off white solid.

Step2: To a stirred solution of 4-bromo-6-fluoro-1-(2,2,2-trifluoroethyl)-1H-indole (0.450 g, 1.52 mmol, 1 eq), bis(pinacolato)diborane (0.461 g, 1.824 mmol, 1.2 eq) and potassium acetate (0.446 g, 4.56 mmol, 3 eq) in 1,4-dioxan (20 mL) was deoxygenated by Ar for 10 min. PdCl$_2$(dppf).DCM (0.124 g, 0.152 mmol. 0.1 eq) was then added to the reaction mixture and stirred at 90° C. for another 16 h. The reaction mixture was filtered through celite bed. Filtrate was concentrated under reduced pressure to get crude 6-fluoro-4-(4,4,5,5-tetramethyl-1,3,2-dioxaborolan-2-yl)-1-(2,2,2-trifluoroethyl)-1H-indole which was used in next step without further purification.

50

Synthesis of 1-(methylsulfonyl)-4-(4,4,5,5-tetramethyl-1,3,2-dioxaborolan-2-yl)-1H-indole (Intermediate A-12)

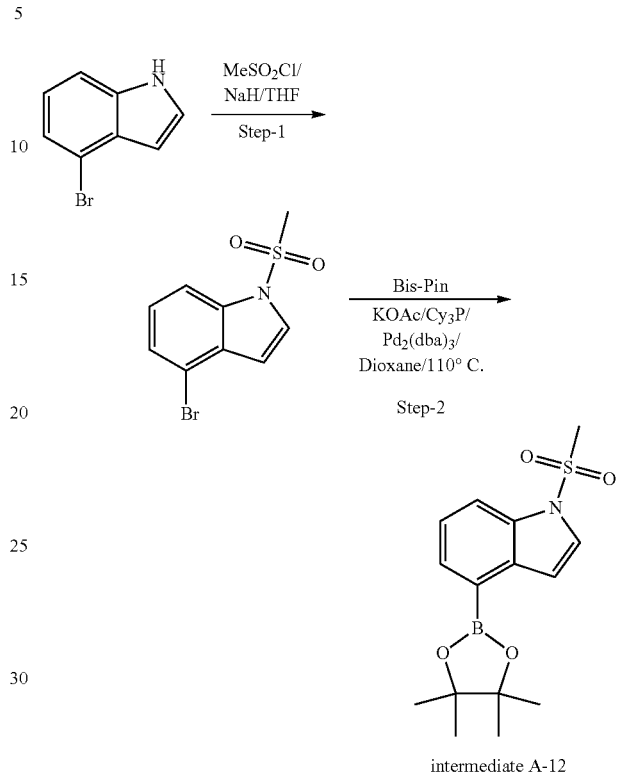

intermediate A-12

Step1: To a stirring solution of 4-bromo-1H-indole (1.0 g, 5.1 mmol, 1 eq) in DMF (20 ml) was portion wise added sodium hydride (60%, 0.245 g, 10.2 mmol, 2 eq) at 0° C. The reaction mixture was then stirred for 30 min at RT. Methanesulfonylchloride (0.584 ml, 7.6 mmol, 1.5 eq) then added to the reaction mixture at 0° C. The reaction mixture was stirred for 2 h at RT. Reaction mixture was diluted with EtOAc (100 mL). Combined organic layers was washed with water (5×20 mL), brine (20 mL), dried over anhydrous Na$_2$SO$_4$ and the solvent was evaporated under reduced pressure. The crude product was purified by column chromatography to afford 4-bromo-1-(methylsulfonyl)-1H-indole (0.532 g, 38%) as off white solid.

Step2: To a stirring suspension of 4-bromo-1-(methylsulfonyl)-1H-indole (0.36 g, 1.31 mmol, 1 eq), bis(pinacolato)diborane (0.66 g, 2.62 mmol, 2 eq) and potassium acetate (0.57 g, 5.25 mmol, 4 eq) in 1,4-dioxan (10 LI) was deoxygenated by Ar for 10 min. Pd$_2$(dba)$_3$ (0.018 g, 0.019 mmol. 0.015 eq) and tricyclohexylphosphine (0.027 g, 0.094 mmol, 0.072 eq) was then added to the reaction mixture and again deoxygenated by Ar for 10 min. The reaction mixture was then stirred for 14 h at 110° C. The reaction mixture then cooled to RT and then filtered through celite bed. Filtrate was concentrated under reduced pressure to get the crude material which was purified by column chromatography to afford 1-(methylsulfonyl)-4-(4,4,5,5-tetramethyl-1,3,2-dioxaborolan-2-yl)-1H-indole (0.31 g, 73%) as off white solid.

Synthesis of 5-fluoro-7-(4,4,5,5-tetramethyl-1,3,2-dioxaborolan-2-yl)-3-(2,2,2-trifluoroethyl)-1H-indole (Intermediate A-13)

Synthesis of 7-(4,4,5,5-tetramethyl-1,3,2-dioxaborolan-2-yl)-3-(2,2,2-trifluoroethyl)-1H-indole (Intermediate A-14)

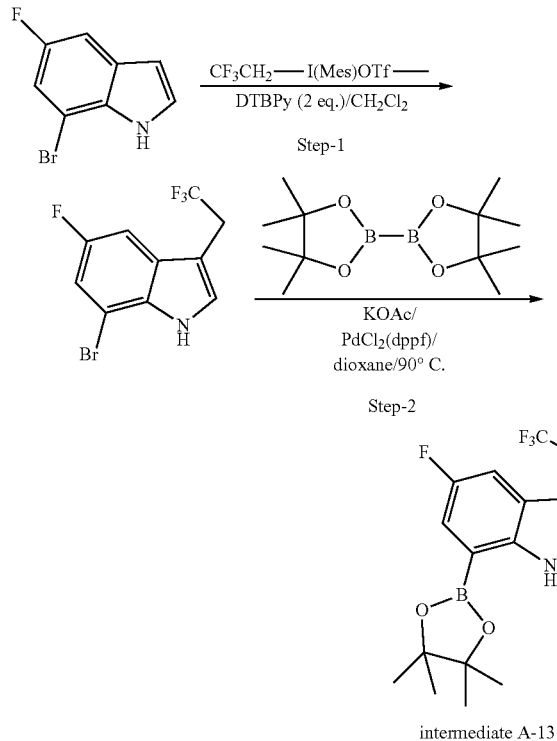

intermediate A-13

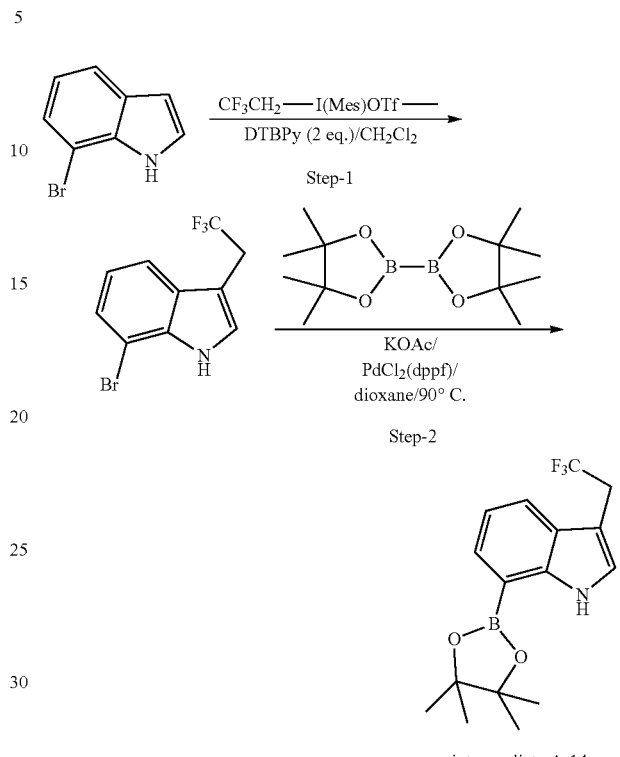

intermediate A-14

Step1: To a solution of 7-bromo-5-fluoro-1H-indole (0.5 g, 2.336 mmol, 1 eq.) in DCM (25 mL) was added 2,6-di-tert-butylpyridine (0.893 g, 4.672 mmol, 2 eq.) and the mixture was stirred for 10 min at RT. 2,2,2-trifluoroethyl(2,4,6-trimethylphenyl)iodonium trifluoromethanesulfonate (1.45 g, 3.063 mmol, 1.3 eq) was added and the mixture was stirred for 2 h at RT. The solvent was evaporated to get the crude product, which was purified by flash column chromatography to afford 7-bromo-5-fluoro-3-(2,2,2-trifluoroethyl)-1H-indole (0.300 g, 43%) as off white solid.

Step2: To a stirred solution of 7-bromo-5-fluoro-3-(2,2,2-trifluoroethyl)-1H-indole (0.9 g, 3.04 mmol, 1 eq), bis(pinacolato)diborane (1.53 g, 6.081 mmol, 2 eq) and potassium acetate (0.893 g, 9.121 mmol, 3 eq) in 1,4-dioxan (20 mL) was deoxygenated by Ar for 10 min. PdCl$_2$(dppf).DCM (0.215 g, 0.304 mmol. 0.1 eq) was then added to the reaction mixture and the mixture was stirred at 90° C. for another 16 h. The reaction mixture was filtered through celite bed. Filtrate was concentrated under reduced pressure to get the crude product, which was purified by flash column chromatography to 5-fluoro-7-(4,4,5,5-tetramethyl-1,3,2-dioxaborolan-2-yl)-3-(2,2,2-trifluoroethyl)-1H-indole (0.600 g, 58%) as gummy liquid.

Step1: To a solution of 7-bromo-1H-indole (0.264 g, 1.346 mmol, 1 eq.) in DCM (25 mL) was added 2,6-di-tert-butylpyridine (0.515 g, 2.694 mmol, 2 eq.) and the mixture was stirred for 10 min at RT. 2,2,2-trifluoroethyl(2,4,6-trimethylphenyl)iodonium trifluoromethanesulfonate (1.4 g, 1.7509 mmol, 1.3 eq) was added and stirring was continued for 2 h at RT. The solvent was evaporated to get the crude product, which was purified by flash column chromatography to afford 7-bromo-3-(2,2,2-trifluoroethyl)-1H-indole (0.300 g, 81%) as off white solid.

Step2: To a stirred solution of 7-bromo-3-(2,2,2-trifluoroethyl)-1H-indole (0.15 g, 0.539 mmol, 1 eq), bis(pinacolato)diborane (273 g, 1.079 mmol, 2 eq) and potassium acetate (0.158 g, 1.617 mmol, 3 eq) in 1,4-dioxan (20 ml) was deoxygenated by Ar for 10 min. PdCl$_2$(dppf).DCM (0.044 g, 0.054 mmol. 0.1 eq) was then added to the reaction mixture and stirred at 90° C. for another 16 h. The reaction mixture was filtered through celite bed. The filtrate was concentrated under reduced pressure to get the crude product, which was purified by flash column chromatography to afford 7-(4,4,5,5-tetramethyl-1,3,2-dioxaborolan-2-yl)-3-(2,2,2-trifluoroethyl)-1H-indole (0.100 g, 57%) as gummy liquid.

Synthesis of 5-fluoro-3-methyl-7-(4,4,5,5-tetramethyl-1,3,2-dioxaborolan-2-yl)-1H-indole (Intermediate A-15)

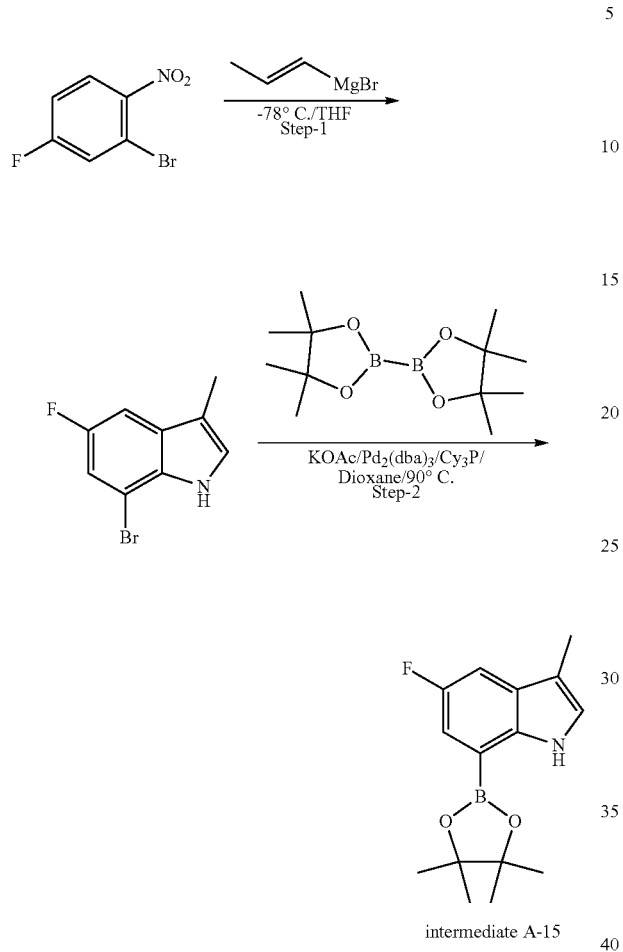

intermediate A-15

Step1: To a solution of 2-bromo-4-fluoro-1-nitrobenzene (0.5 g, 2.27 mmol, 1 eq.) in THF (20 mL) was added (E)-prop-1-en-1-ylmagnesium bromide (0.5 M in THF) (13.6 mL, 6.818 mmol, 3 eq) at −60° C. under nitrogen atmosphere. Then the reaction mixture was stirred at the same temperature for 4 h. The reaction was quenched with saturated ammonium chloride solution at −60° C. Then the resulting mixture was extracted with EtOAc (2×100 mL), washed with brine solution and concentrated under reduced pressure to give the crude product which was purified by flash column chromatography to afford 7-bromo-5-fluoro-3-methyl-1H-indole (0.3 g, 58%) as dense yellow liquid.

Step2: To a solution of 7-bromo-5-fluoro-3-methyl-1H-indole (0.8 g, 3.669 mmol, 1 eq) in 1,4-dioxane (15.0 mL) were added KOAC (1.43 g, 14.67 mmol, 4 eq) and bispincolatediborane (1.12 g, 7.33 mmol, 2 eq). The solution was degassed with Ar for 20 min followed by addition of Pd$_2$(dba)$_3$ (0.16 g, 0.183 mmol, 0.05 eq) and Cy$_3$P (0.082 g, 0.293 mmol, 0.08 eq). The reaction mixture was refluxed for 16 h. After completion of reaction (monitored by TLC), solvent was evaporated under reduced pressure to get the crude product which was purified by column chromatography to afford 5-fluoro-3-methyl-7-(4,4,5,5-tetramethyl-1,3,2-dioxaborolan-2-yl)-1H-indole (0.7 g, 70%), as brown solid.

Synthesis of 3-cyclopropyl-5-fluoro-7-(4,4,5,5-tetramethyl-1,3,2-dioxaborolan-2-yl)-1H-indole (Intermediate A-16)

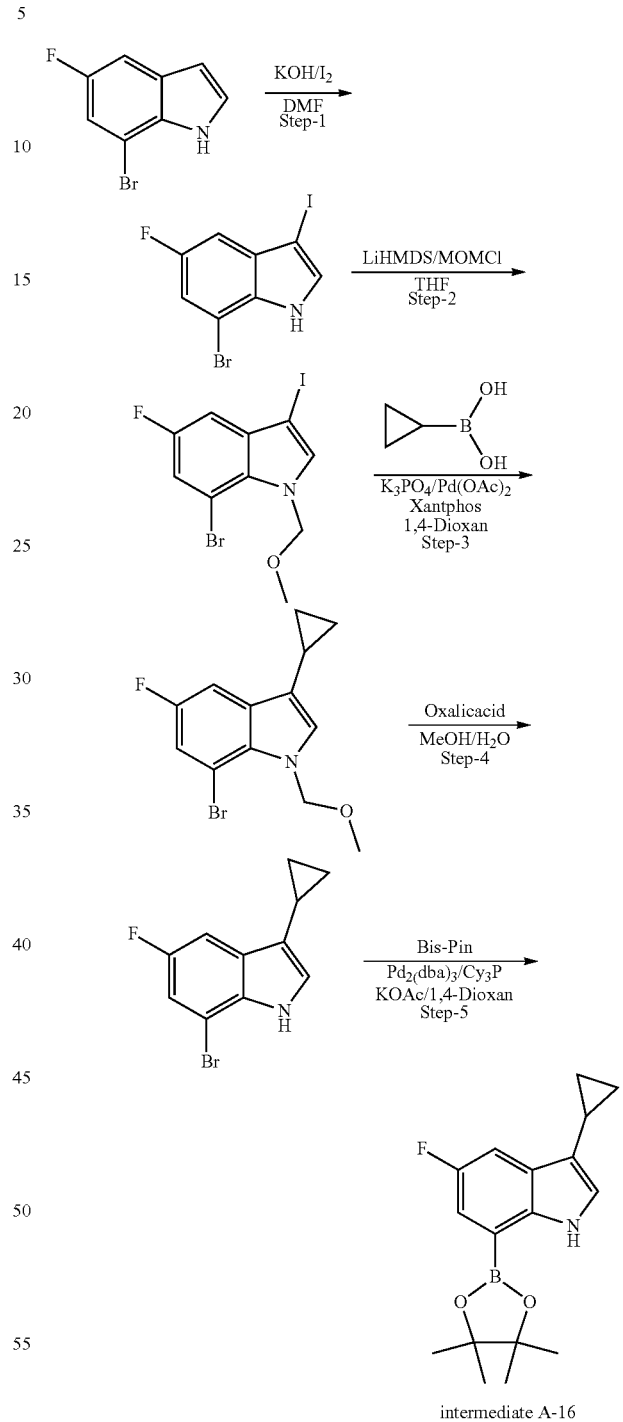

intermediate A-16

Step1: To a stirring solution of 7-bromo-5-fluoroindole (7.0 g, 32.7 mmol, 1 eq) in DMF (175 mL) was added powdered potassium hydroxide (4.56 g, 81.77 mmol, 2.5 eq). The reaction mixture was then stirred for 30 min at RT. Iodine (12.46 g, 49.06 mmol, 1.5 eq) was then added to the reaction mixture and finally stirred for 2 h at RT. The reaction mixture was diluted with EtOAc (1000 mL) and washed with water (5×100 mL) followed brine (100 mL).

The organic layer was dried over anhydrous Na₂SO₄ and the solvent was evaporated to get the crude product, which was purified by column chromatography to afford 7-bromo-5-fluoro-3-iodo-1H-indole (6.2, 56%) as brown solid.

Step2: To a stirring solution of 7-bromo-5-fluoro-3-iodo-1H-indole (6.2 g, 18.23 mmol, 1 eq) in THF (109 mL) was added drop wise LiHMDS (1M) (91.15 mL, 91.15 mmol, 5 eq) at −78° C. under inert atmosphere. The reaction mixture was stirred for 30 min at same condition. MOMCl (5.83 g, 72.94 mmol, 4 eq) was then added to the reaction mixture at −78° C. The reaction mixture was allowed to warm up to RT and then stirred for 16 h. The reaction mixture was quenched by addition of saturated solution of ammonium chloride (100 mL). Organic layer was separated and the aqueous layer was extracted with EtOAc (100 mL). The combined organic layers were washed with brine (100 mL). The organic layer was dried over anhydrous Na₂SO₄ and the solvent was evaporated to get the crude product, which was purified by column chromatography to afford 7-bromo-5-fluoro-3-iodo-1-(methoxymethyl)-1H-indole (5.4 g, 57%) as off white solid.

Step3: To a stirred suspension of 7-bromo-5-fluoro-3-iodo-1-(methoxymethyl)-1H-indole (2.7 g, 7.03 mmol, 1 eq), cyclopropylbronic acid (1.84 g, 2.03 mmol, 3 eq) and K₃PO₄ (4.5 g, 21.05 mmol, 3 eq) in 1,4-dioxan (45 mL) was deoxygenated by Ar for 10 min. Pd(OAc)₂ (0.08 g, 0.3525 mmol, 0.05 eq) and xantphos (0.407 g, 0.713 mmol, 0.1 eq) were then added to the reaction mixture and again deoxygenated for 10 min. Finally the reaction mixture was stirred at 100° C. for 16 h. The reaction mixture was cooled to RT and then filtered through celit bed. The filtrate was concentrated under reduced pressure to get the crude material which was purified by column chromatography to afford 7-bromo-3-cyclopropyl-5-fluoro-1-(methoxymethyl)-1H-indole (0.65 g, 31%) as off white solid.

Step4: To a stirring solution of 7-bromo-3-cyclopropyl-5-fluoro-1-(methoxymethyl)-1H-indole (1.25 g, 4.19 mmol, 1 eq) in mixture of MeOH and water (3:1) (66 mL) was added oxalic acid (1.13 g, 12.58 mmol, 3 eq). The reaction mixture was then stirred at 90° C. for 18 h. The reaction mixture was cooled to RT and concentrated under reduced pressure to get the residue. The residue was diluted with EtOAc (100 mL) and washed with water (2×40 mL) and brine (40 mL). The organic layer was dried over anhydrous Na₂SO₄ and the solvent was evaporated to get the crude product, which was purified by column chromatography to afford 7-bromo-3-cyclopropyl-5-fluoro-1H-indole (0.57 g, 54%) as color less liquid.

Step5: To a stirring suspension of 7-bromo-3-cyclopropyl-5-fluoro-1H-indole (0.57 g, 2.24 mmol, 1 eq), bis-pinacolatodiborane (1.7 g, 6.73 mmol, 3 eq) and potassium acetate (0.66 g, 6.73 mmol, 3 eq) in 1,4-dioxan (20 mL) was deoxygenated by Ar for 10 min. Pd₂(dba)₃ (0.031 g, 0.033 mmol. 0.015 eq) and triclyclohexylphosphine (0.047 g, 0.168 mmol, 0.075 eq) was then added to the reaction mixture and again deoxygenated by Ar for 10 min. The reaction mixture was then stirred for 14 h at 110° C. The reaction mixture was then cooled to RT and then filtered through celite bed. Filtrate was concentrated under reduced pressure to get the crude material which was purified by column chromatography to afford 3-cyclopropyl-5-fluoro-7-(4,4,5,5-tetramethyl-1,3,2-dioxaborolan-2-yl)-1H-indole (0.35 g, 52%) as off white solid.

Synthesis of 3-cyclobutyl-7-(4,4,5,5-tetramethyl-1,3,2-dioxaborolan-2-yl)-1H-indole (Intermediate A-17)

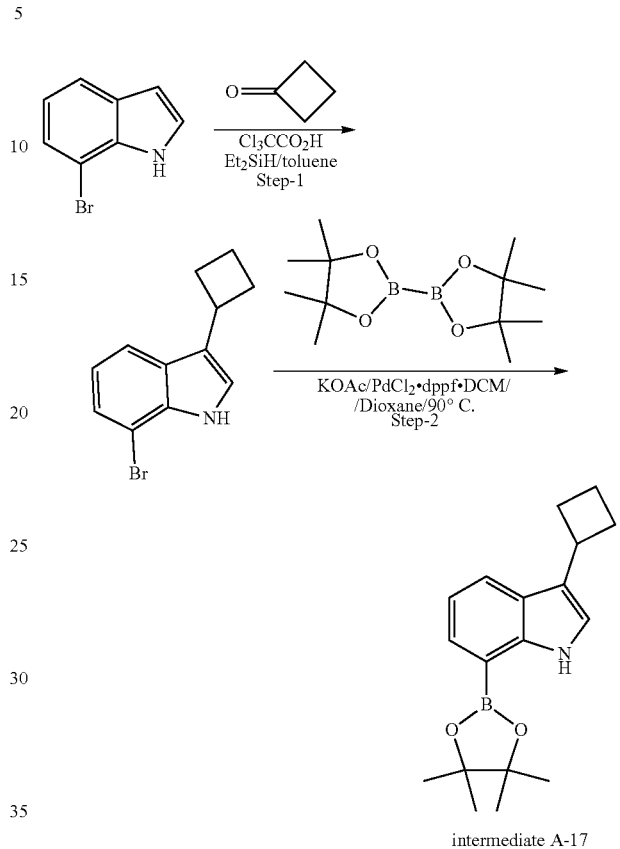

intermediate A-17

Step1: To a stirring solution of 2,2,2-trichloroacetic acid (9.97 g, 61.22 mmol, 1.5 eq) and triethylsilane (19.7 mL, 122.4 mmol, 3.0 eq) in toluene (20 mL) were added 7-bromo-1H-indole (8.0 g, 40.81 mmol) and cyclobutanone (3.37 ml, 44.89 mmol, 1.1 eq) in toluene (20 mL) and the mixture was stirred at 70° C. for 16 h. After completion of reaction (monitored by TLC), the reaction mixture was cooled to 10° C., quenched with sat. aqueous NaHCO₃ solution, extracted with EtOAc (2×300 mL), organic layer was washed with brine (50 mL), dried over anhydrous Na₂SO₄, filtered and the solvent was evaporated under reduced pressure to get crude product which was purified by combiflash column to afford 7-bromo-3-cyclobutyl-1H-indole (5.0 g, 49%) as white solid.

Step2: To a solution of 7-bromo-3-cyclobutyl-1H-indole (1.0 g, 4.0 mmol, 1 eq) in 1,4-dioxane (30 mL) were added KOAC (1.17 g, 12.0 mmol, 3.0 eq) and bis-pincolate diborane (2.03 g, 8.0 mmol, 2 eq) The solution was degassed with Ar for 20 min followed by addition of PdCl₂.dppf.DCM (0.16 g, 0.2 mmol, 0.05 eq). The reaction mixture was stirred at 90° C. for 16 h. After completion of reaction (monitored by TLC), reaction mixture was evaporated under reduced pressure to get the crude product which was purified by column chromatography to afford 3-cyclobutyl-7-(4,4,5,5-tetramethyl-1,3,2-dioxaborolan-2-yl)-1H-indole (1.1 g, 93%), as off white solid.

Synthesis of 3-(tetrahydrofuran-3-yl)-7-(4,4,5,5-tetramethyl-1,3,2-dioxaborolan-2-yl)-1H-indole (Intermediate A-18)

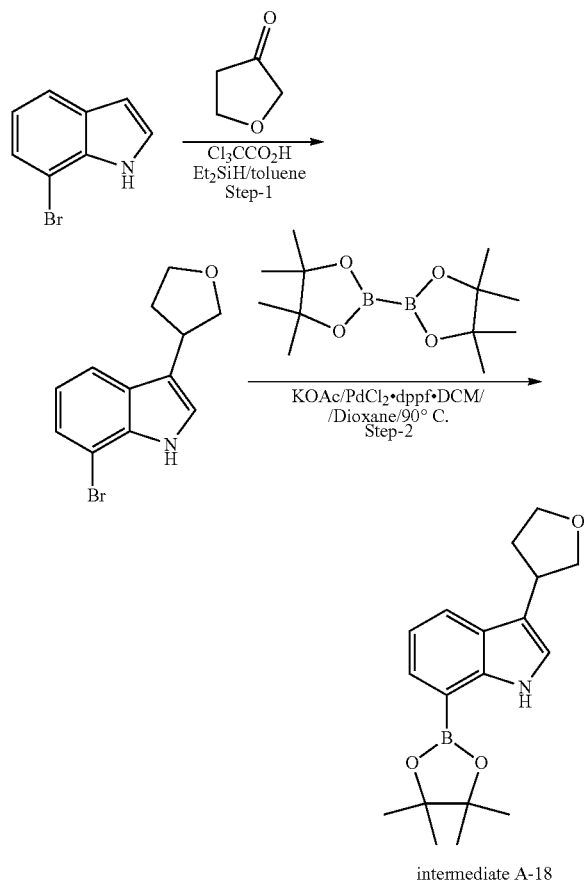

intermediate A-18

Step 1: To a stirring solution of 2,2,2-trichloroacetic acid (7.48 g, 45.91 mmol, 1.5 eq) and triethylsilane (14.8 ml, 91.83 mmol, 3.0 eq) in toluene (15 mL) were added 7-bromoindole (6.0 g, 30.611 mmol) and dihydro-furan-3-one (2.58 mL, 33.67 mmol, 1.1 eq) in toluene (15 mL) at 70° C. and stirred for 24 h. After completion of reaction (monitored by TLC), the reaction mixture cooled to 10° C., quenched with sat. aq NaHCO₃ solution, extracted with EtOAc (2×300 mL), organic layer was washed with brine (50 mL), dried over anhydrous Na₂SO₄, filtered and evaporated under reduced pressure to get crude product which was purified by combiflash column to afford 7-bromo-3-(tetrahydrofuran-3-yl)-1H-indole (1.1 g, 14%) as sticky solid.

Step 2: To a solution of 7-bromo-3-(tetrahydrofuran-3-yl)-1H-indole (1.0 g, 3.75 mmol, 1 eq) in 1,4-dioxane (30 mL) were added KOAC (1.1 g, 11.27 mmol, 3.0 eq) and bis-pincolatediborane (1.9 g, 7.51 mmol, 2 eq). The solution was degassed with Ar for 20 min followed by addition of PdCl₂.dppf.DCM (0.15 g, 0.18 mmol, 0.05 eq). The reaction mixture was stirred at 90° C. for 16 h. After completion of reaction (monitored by TLC), solvent was evaporated under reduced pressure to get the crude product which was purified by column chromatography to afford 3-(tetrahydrofuran-3-yl)-7-(4,4,5,5-tetramethyl-1,3,2-dioxaborolan-2-yl)-1H-indole (1.0 g, 85%), as off white solid.

Synthesis of 3-ethyl-5-fluoro-7-(4,4,5,5-tetramethyl-1,3,2-dioxaborolan-2-yl)-1H-indole (Intermediate A-19)

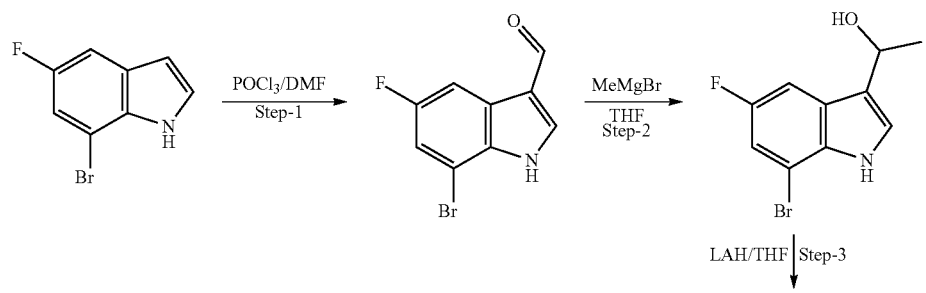

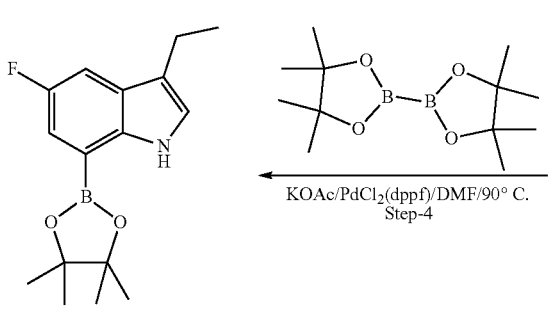

intermediate A-119

Step1: To the DMF (10 mL) POCl₃ (0.22 mL, 2.412 mmol, 1.1 eq) was added at 0° C. To this solution 7-bromo-5-fluoro-1H-indole (0.5 g, 2.192 mmol, 1 eq) was added drop wise and the mixture was stirred at 0° C. for 1 h. After completion of reaction (monitored by TLC) reaction mixture was basified with NaOH and again acidified with HCl. A solid was precipitated out which was filtered, washed with water and dried under reduced pressure to afford 7-bromo-5-fluoro-1H-indole-3-carbaldehyde (0.23 g, 43%) as white solid.

Step2: To a solution of 7-bromo-5-fluoro-1H-indole-3-carbaldehyde (0.23 g, 0.95 mmol, 1 eq.) in THF (10 mL) was added methylmagnesium bromide (3.0 M in THF) (1.1 mL, 3.33 mmol, 3.5 eq) at −78° C. under nitrogen atmosphere. Then the reaction mixture was stirred at the same temperature for 4 h. The reaction was quenched with saturated ammonium chloride solution at −78° C. Then the resulting mixture was extracted with EtOAc (2×20 mL), washed with brine solution and concentrated under reduced pressure to afford the crude 1-(7-bromo-5-fluoro-1H-indol-3-yl)ethanol (0.12 g, 50%) as dense yellow liquid, which was used for the next step without further purification.

Step3: To a solution of 1-(7-bromo-5-fluoro-1H-indol-3-yl)ethanol (0.12 g, 0.465 mmol, 1 eq.) in THF (5 mL) was added LAH (0.045 g, 1.162 mmol, 2.5 eq) at 0° C. under nitrogen atmosphere. The reaction mixture was stirred at RT for 1 h. After completion of reaction (monitored by TLC) reaction was quenched with Fisher work up technique. Then the resulting mixture was filtered through cintered and filtrate was evaporated under reduced pressure to afford the crude product which was purified by column chromatography to afford 7-bromo-3-ethyl-5-fluoro-1H-indole (0.07 g, 63%) as brown gum.

Step4: To a stirring suspension of 7-bromo-3-ethyl-5-fluoro-1H-indole (0.4 g, 1.652 mmol, 1 eq), bis(pinacolato)diborane (0.46 g, 1.818 mmol, 1.1 eq) and potassium acetate (0.485 g, 4.956 mmol, 3 eq) in 1,4-dioxan (25 ml) was deoxygenated by Ar for 10 min. PdCl₂(dppf).DCM (0.13 g, 0.165 mmol. 0.1 eq) was then added to the reaction mixture and again deoxygenated by Ar for 10 min. The reaction mixture was then stirred for 16 h at 110° C. The reaction mixture was cooled to RT and then filtered through celite bed. Filtrate was concentrated under reduced pressure to get the crude material which was purified by column chromatography to afford 3-ethyl-5-fluoro-7-(4,4,5,5-tetramethyl-1,3,2-dioxaborolan-2-yl)-1H-indole (0.36 g, 75%) as light yellow gum.

Synthesis of 2-(6-fluoro-4-(4,4,5,5-tetramethyl-1,3,2-dioxaborolan-2-yl)-1H-indol-1-yl)ethanol (Intermediate A-20)

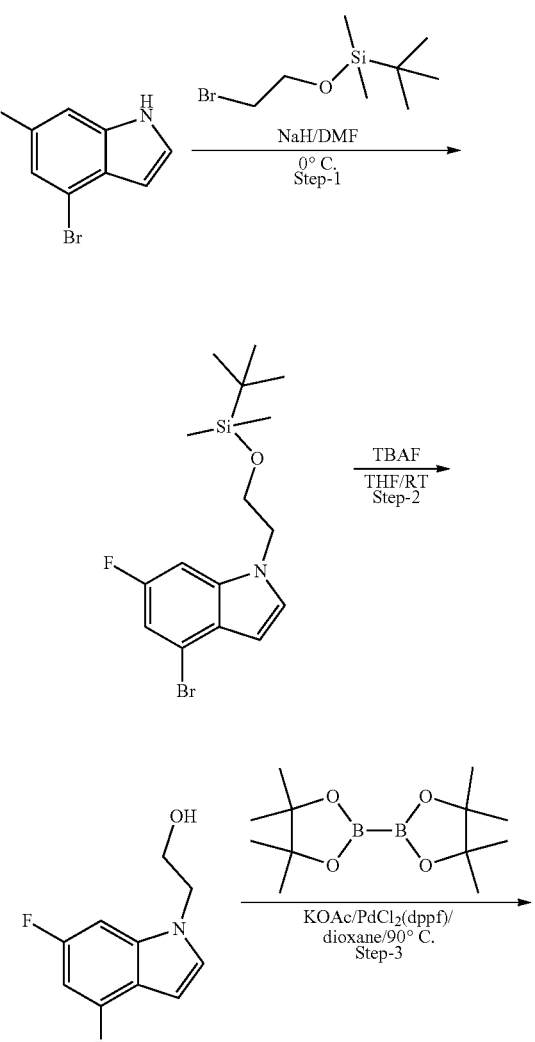

-continued

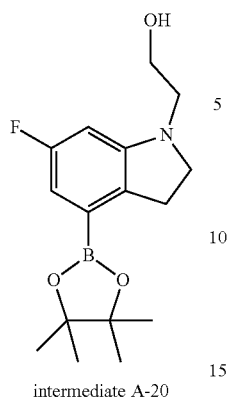

intermediate A-20

Step1: To a solution of 4-bromo-6-fluoro-1H-indole (0.5 g, 2.34 mmol, 1 eq.) in DMF (5 mL) was added sodium hydride (0.130 g, 2.80 mmol, 1.2 eq) at 0° C. The solution was stirred at RT for 30 min followed by addition of (2-bromoethoxy)(tert-butyl)dimethylsilane (1.17 g, 4.67 mmol, 2.0 eq) and reaction mixture was stirred at RT for 2 h. After completion of reaction (monitored by LCMS), reaction mixture was diluted with EtOAc (20 mL) and organic layer was washed with cold water (5×10 mL), brine (10 mL), dried over anhydrous Na₂SO₄ and the solvent was evaporated under reduced pressure. Crude product was purified by column chromatography to afford 4-bromo-1-(2-((tert-butyldimethylsilyl)oxy)ethyl)-6-fluoro-1H-indole (0.85 g, 98%) as brown liquid having (2-bromoethoxy)(tert-butyl)dimethylsilane as impurity.

Step2: To a stirred solution of 4-bromo-1-(2-((tert-butyldimethylsilyl)oxy)ethyl)-6-fluoro-1H-indole (1.3 g, 3.49 mmol, 1 eq.) in THF (15 mL) was added TBAF (3.49 mL) (1M) at RT and the mixture was stirred for 16 h. After completion of reaction (monitored by LCMS & TLC), reaction mixture was diluted with EtOAc (20 mL) and organic layer was washed with cold water (5×10 mL), brine (10 mL), dried over anhydrous Na₂SO₄ and the solvent was evaporated under reduced pressure. Crude product was purified by column chromatography to afford 2-(4-bromo-6-fluoro-1H-indol-1-yl)ethanol (0.55 g, 61%) as brown liquid.

Step3: To a stirred solution of 2-(4-bromo-6-fluoro-1H-indol-1-yl)ethanol (0.55 g, 2.13 mmol, 1 eq), bis(pinacolato)diborane (0.647 g, 2.55 mmol, 1.2 eq) and potassium acetate (0.626 g, 6.393 mmol, 3 eq) in 1,4-dioxan (20 mL) was deoxygenated by Ar for 10 min. PdCl₂(dppf).DCM (0.173 g, 0.213 mmol. 0.1 eq) was then added to the reaction mixture and the mixture was stirred at 90° C. for 16 h.

After completion of reaction (monitored by TLC), reaction mixture was filtered through celite bed. Filtrate was concentrated under reduced pressure to get the crude product which was used in next step without further purification.

Synthesis of 2-(6-fluoro-4-(4,4,5,5-tetramethyl-1,3,2-dioxaborolan-2-yl)-1H-indazol-1-yl)ethanol (Intermediate A-21)

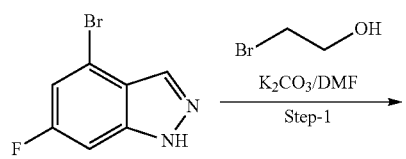

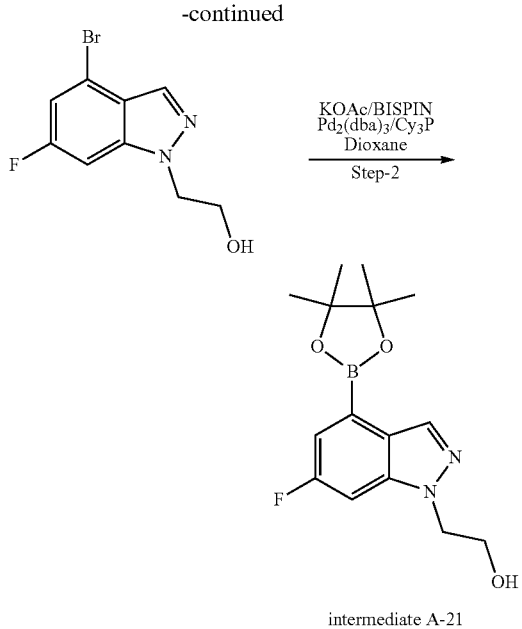

intermediate A-21

Step1: To a stirred solution of 4-bromo-6-fluoro-1H-indazole (0.2 g, 0.93 mmol, 1 eq) in DMF (5 mL) was added K₂CO₃ (0.38 g, 2.79 mmol, 3.0 eq) at RT and the mixture was stirred for 20 min. Then 2-bromo-ethanol (0.07 mL, 0.93 mmol, 1 eq) was added and the mixture was stirred for 16 h at 50° C. After completion of the reaction (monitored by TLC), the reaction mass quenched with ice cold water and extracted with EtOAc (3×20 mL), washed with FLO (3×20 mL), brine (25 mL), dried over Na₂SO₄ and concentrated. The crude product was purified by column chromatography to afford 2-(4-bromo-6-fluoro-1H-indazol-1-yl)ethanol (0.12 g, 50%) as white solid.

Step2: To a solution of 2-(4-bromo-6-fluoro-1H-indazol-1-yl)ethanol (0.9 g, 3.473 mmol, 1 eq) in 1,4-dioxane (60.0 mL) were added KOAc (1.02 g, 10.419 mmol, 3 eq) and bispincolatediborane (1.76 g, 6.947 mmol, 2.0 eq). The solution was degassed with Ar for 20 min followed by addition of Pd₂(dba)₃ (0.17 g, 0.173 mmol, 0.05 eq) and Cy₃P (0.077 g, 0.277 mmol, 0.08 eq). The reaction mixture was refluxed for 16 h. After completion of reaction (monitored by TLC), solvent was evaporated under reduced pressure to get the crude product which was purified by column chromatography to afford -(6-fluoro-4-(4,4,5,5-tetramethyl-1,3,2-dioxaborolan-2-yl)-1H-indol-1-yl)ethanol (0.95 g, 89%) as brown solid.

Synthesis of 1-(methylsulfonyl)-4-(4,4,5,5-tetramethyl-1,3,2-dioxaborolan-2-yl)-1H-indazole (Intermediate A-22)

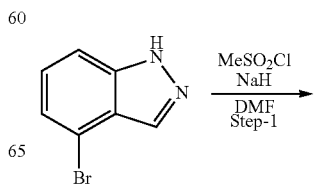

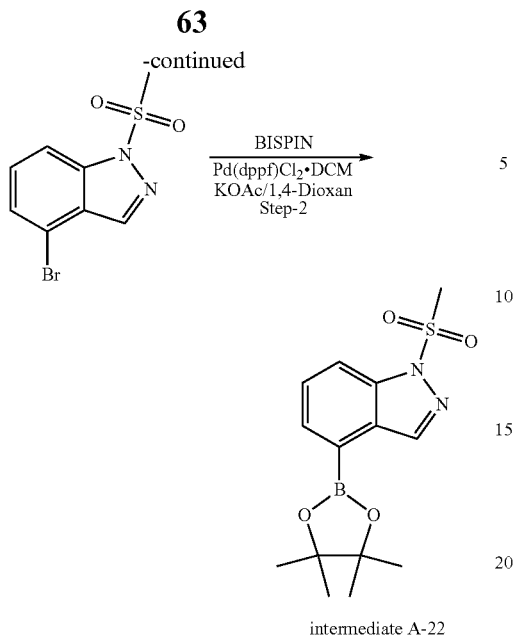

intermediate A-22

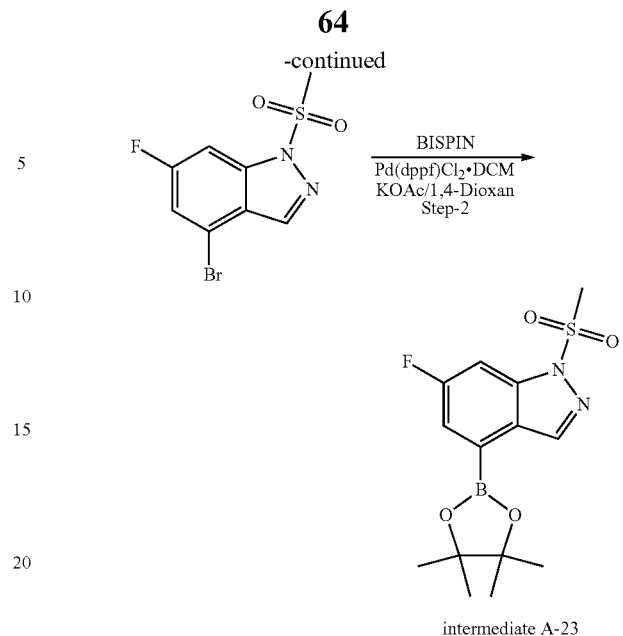

intermediate A-23

Step 1: To a stirring solution of 4-bromo-1H-indazole (1.0 g, 5.07 mmol, 1 eq) in DMF (25 ml) was portion wise added sodium hydride (60%, 0.406 g, 10.152 mmol, 2 eq) at 0° C. The reaction mixture was stirred for 30 min at RT. Methanesulfonylchloride (0.59 mL, 7.6 mmol, 1.5 eq) was added to the reaction mixture at 0° C. The reaction mixture was stirred for 2 h at RT. Reaction mixture was diluted with EtOAc (150 mL). Combined organic layers were washed with water (5×30 mL), brine (30 mL), dried over anhydrous $Na_2SO_4$ and the solvent was evaporated under reduced pressure. Crude product was purified by column chromatography (230-400 mesh silica gel 10% EtOAc/hexane; $R_f$-value-0.5) to afford 4-bromo-1-(methylsulfonyl)-1H-indazole (0.95 g, 69%) as light yellow solid.

Step 2: To a stirring suspension of 4-bromo-1-(methylsulfonyl)-1H-indazole (0.95, 3.45 mmol, 1 eq), bis(pinacolato)diborane (1.75 g, 6.91 mmol, 2 eq) and potassium acetate (1.01 g, 10.36 mmol, 3 eq) in 1,4-dioxane (35 mL) was deoxygenated by Ar for 10 min. Pd(dppf)C$_{1-2}$DCM (0.141 g, 0.1727 mmol. 0.05 eq) was added to the reaction mixture and again deoxygenated by Ar for 10 min. The reaction mixture was stirred for 14 h at 110° C. The reaction mixture was cooled to RT and then filtered through celite bed. Filtrate was concentrated under reduced pressure to get the crude material which was purified by column chromatography (230-400 mesh silica gel, 10% EtOAc/hexane; $R_f$-value-0.45) to afford 1-(methylsulfonyl)-4-(4,4,5,5-tetramethyl-1,3,2-dioxaborolan-2-yl)-1H-indazole (0.9 g, 85.4%) as off white solid.

Step 1: To a stirring solution of 4-bromo-6-fluoro-1H-indazole (1.2 g, 5.58 mmol, 1 eq) in DMF (30 mL) was portion wise added sodium hydride (60%, 0.446 g, 11.16 mmol, 2 eq) at 0° C. The reaction mixture was then stirred for 30 min at RT. Methanesulfonylchloride (0.65 ml, 8.37 mmol, 1.5 eq) was added to the reaction mixture at 0° C. The reaction mixture was stirred for 2 h at RT. Reaction mixture was diluted with EtOAc (150 mL). Combined organic layers were washed with water (5×30 mL), brine (30 mL), dried over anhydrous $Na_2SO_4$ and evaporated under reduced pressure. Crude product was purified by column chromatography (230-400 mesh silica gel 10% EtOAc/hexane; $R_f$-value-0.5) to afford 4-bromo-6-fluoro-1-(methylsulfonyl)-1H-indazole (1.3 g, 80%) as light yellow solid.

Step 2: To a stirring suspension of 4-bromo-6-fluoro-1-(methylsulfonyl)-1H-indazole (1.3, 4.43 mmol, 1 eq), bis(pinacolato)diborane (2.25 g, 8.87 mmol, 2 eq) and potassium acetate (1.3 g, 13.3 mmol, 3 eq) in 1,4-dioxane (45 mL) was deoxygenated by Ar for 10 min. Pd(dppf)C$_{1-2}$DCM (0.18 g, 0.22 mmol. 0.05 eq) and was then added to the reaction mixture and again deoxygenated by Ar for 10 min. The reaction mixture was stirred for 14 h at 110° C. The reaction mixture was cooled to RT and then filtered through celite bed. Filtrate was concentrated under reduced pressure to get the crude material which was purified by column chromatography (230-400 mesh silica gel, 10% EtOAc/hexane; $R_f$-value-0.45) to afford 6-fluoro-1-(methylsulfonyl)-4-(4,4,5,5-tetramethyl-1,3,2-dioxaborolan-2-yl)-1H-indazole (1.1 g, 73%) as off white solid.

Synthesis of 6-fluoro-1-(methylsulfonyl)-4-(4,4,5,5-tetramethyl-1,3,2-dioxaborolan-2-yl)-1H-indazole (Intermediate A-23)

Synthesis of 6-fluoro-1-(2-methoxyethyl)-4-(4,4,5,5-tetramethyl-1,3,2-dioxaborolan-2-yl)-1H-indole (Intermediate A-24)

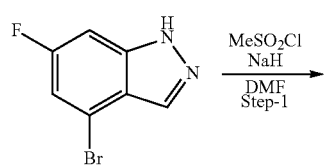

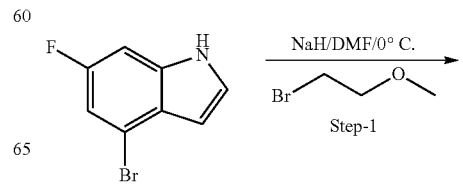

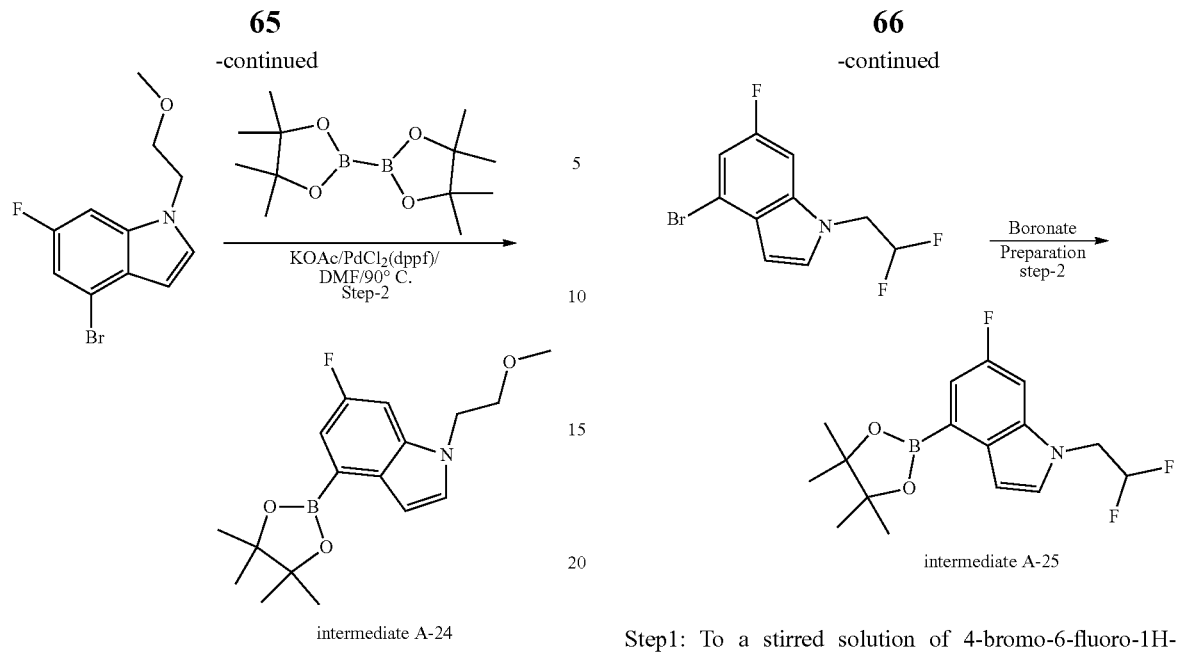

intermediate A-24 intermediate A-25

Step1: To a stirring solution of 4-bromo-6-fluoro-1H-indole (0.5 g, 2.34 mmol, 1 eq) in DMF (5 mL) was portion wise added sodium hydride (0.112 g, 2.8 mmol, 1.2 eq.) at 0° C. The reaction mixture was then stirred for 30 min at RT. 1-Bromo-2-methoxyethane (0.812 mL, 5.84 mmol, 2.5 eq) was then added to the reaction mixture at 0° C. The reaction mixture was stirred for 2 h at RT. Reaction mixture was diluted with EtOAc (50 mL). Combined organic layers were washed with water (5×10 mL), brine (10 mL), dried over anhydrous $Na_2SO_4$ and the solvent was evaporated under reduced pressure. Crude product was purified by column chromatography (230-400 mesh silica gel 20% EtOAc/hexane; $R_f$-value-0.6) to afford 4-bromo-6-fluoro-1-(2-methoxyethyl)-1H-indole (0.63 g, 99%) as brown gum.

Step2: To a stirring suspension of 4-bromo-6-fluoro-1-(2-methoxyethyl)-1H-indole (0.8 g, 2.94 mmol, 1 eq), bis-pinacolatodiborane (1.2 g, 4.4 mmol, 1.5 eq.) and potassium acetate (0.865 g, 8.823 mmol, 3 eq.) in 1,4-dioxan (20 mL) was deoxygenated by Ar for 10 min. $PdCl_2(dppf).DCM$ (0.239 g, 0.29 mmol. 0.01 eq.) q) was then added and the reaction mixture was stirred for 14 h at 90° C. The reaction mixture was cooled to RT and then filtered through celite bed. Filtrate was concentrated under reduced pressure to get the crude product which was purified by column chromatography (230-400 mesh silica gel 5% EtOAc/hexane; $R_f$-value-0.6) to afford 6-fluoro-1-(2-methoxyethyl)-4-(4,4,5,5-tetramethyl-1,3,2-dioxaborolan-2-yl)-1H-indole (0.93 g, 99%) as light brown gummy solid.

Synthesis of 1-(2,2-difluoroethyl)-6-fluoro-4-(4,4,5, 5-tetramethyl-1,3,2-dioxaborolan-2-yl)-1H-indole (Intermediate A-25)

Step1: To a stirred solution of 4-bromo-6-fluoro-1H-indole (0.1 g, 0.469 mmol, 1 eq) in DMF (25 ml) was added $Cs_2CO_3$ (0.457 g, 1.407 mmol, 3 eq) followed by LiBr (86.84 g, 0.469 mmol, 1 eq) and the mixture was stirred at RT for 10 minutes. Then 2,2-difluoroethyl 4-methylbenzenesulfonate (0.133 g, 0.563 mmol, 1.2 eq) was added to the reaction mixture and heated at 80° C. for 3 h (TLC). Reaction mixture was then diluted with water (10 mL) and EtOAc (15 mL). The organic layer was washed with cold water (3×10 mL) brine (10 mL), dried over anhydrous $Na_2SO_4$ and concentrated under reduced pressure to get crude product which was purified by column chromatography (100-200 mesh silica gel; TLC system: EtOAc/Hexane (3:7); $R_f$-value-0.5) to afford 4-bromo-1-(2,2-difluoroethyl)-6-fluoro-1H-indole (0.75 g, 58%).

Step2: A suspension of 4-bromo-1-(2,2-difluoroethyl)-6-fluoro-1H-indole (0.2 g, 0.722 mmol, 1 eq), bis(pinacolato)diboron (0.275 g, 1.083 mmol, 1.5 eq) and potassium acetate (0.212 g, 2.166 mmol, 3 eq) in 1,4-dioxane (10 mL) was deoxygenated well by Ar for 10 min. 1,1'-Bis(diphenylphosphino)ferrocene palladium(II)dichloride DCM complex (0.03 g, 0.0361 mmol, 0.05 eq) was then added to the reaction mixture and the reaction mixture heated at 100° C. for 16 h (LCMS). The reaction mixture was then cooled to RT, filtered through celite pad and the filtrate was concentrated under reduced pressure to get the crude 1-(2,2-difluoroethyl)-6-fluoro-4-(4,4,5,5-tetramethyl-1,3,2-dioxaborolan-2-yl)-1H-indole which was used in the next step without further purification (Yield 49% in LCMS).

Synthesis of 3-cyclopropyl-7-(4,4,5,5-tetramethyl-1, 3,2-dioxaborolan-2-yl)-1H-indole (Intermediate A-26)

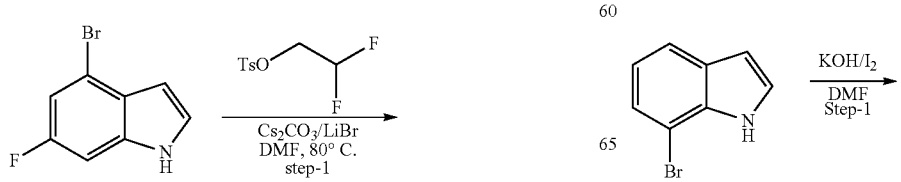

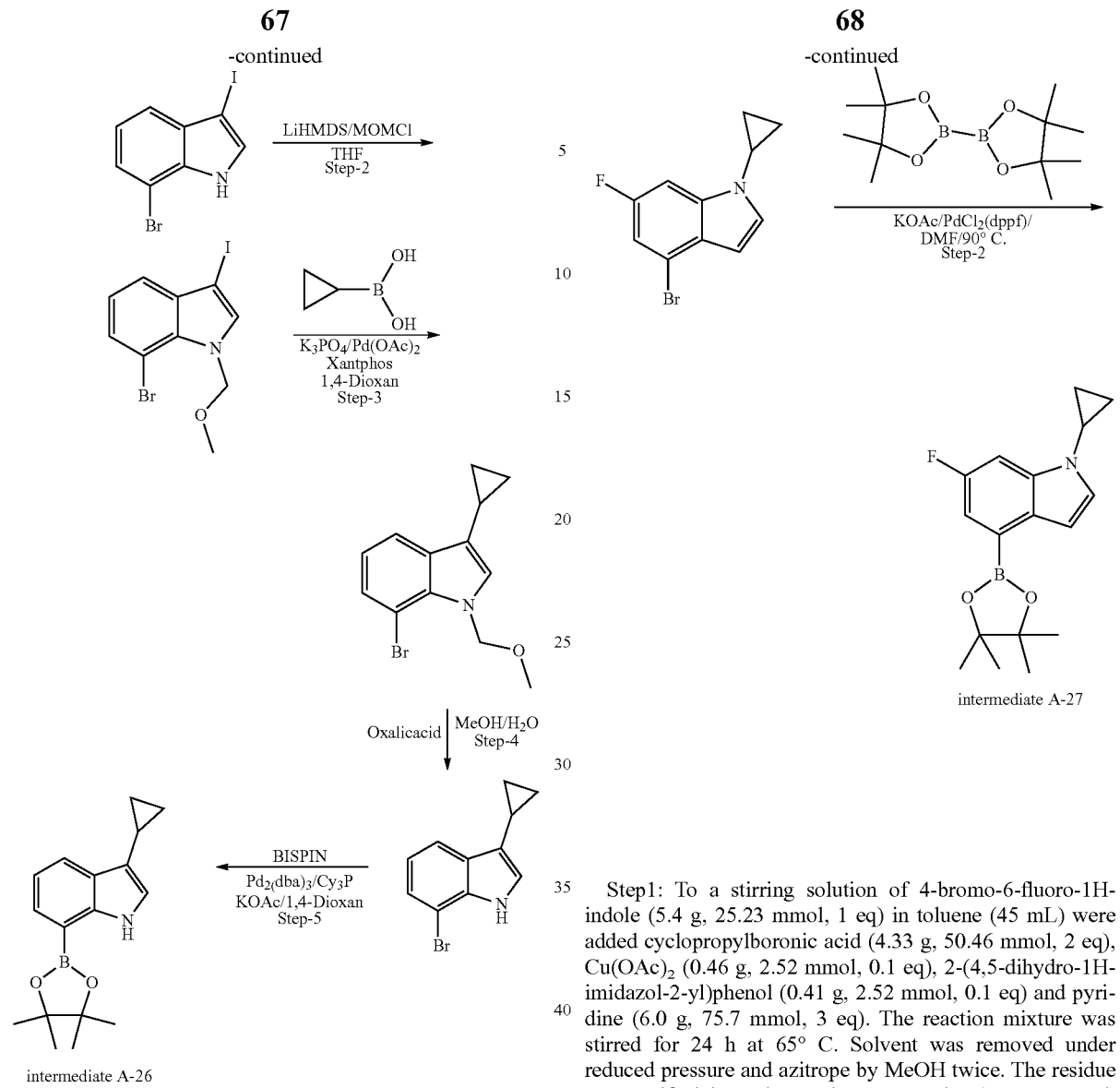

intermediate A-26

Starting from 7-bromo-1H-indole intermediate A-26 was synthesized in analogy to synthesis described for intermediate A-16.

Synthesis of 1-cyclopropyl-6-fluoro-4-(4,4,5,5-tetramethyl-1,3,2-dioxaborolan-2-yl)-1H-indole (Intermediate A-27)

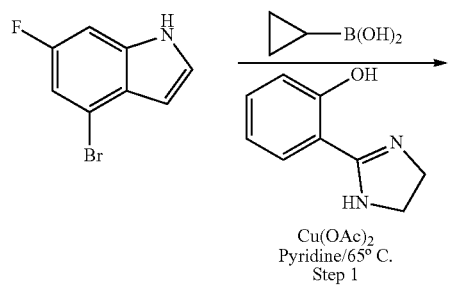

Cu(OAc)$_2$
Pyridine/65° C.
Step 1

Step1: To a stirring solution of 4-bromo-6-fluoro-1H-indole (5.4 g, 25.23 mmol, 1 eq) in toluene (45 mL) were added cyclopropylboronic acid (4.33 g, 50.46 mmol, 2 eq), Cu(OAc)$_2$ (0.46 g, 2.52 mmol, 0.1 eq), 2-(4,5-dihydro-1H-imidazol-2-yl)phenol (0.41 g, 2.52 mmol, 0.1 eq) and pyridine (6.0 g, 75.7 mmol, 3 eq). The reaction mixture was stirred for 24 h at 65° C. Solvent was removed under reduced pressure and azitrope by MeOH twice. The residue was purified by column chromatography (230-400 mesh silica gel; 10% EtOAc/hexane; R$_f$-value-0.6) to afford 4-bromo-1-cyclopropyl-6-fluoro-1H-indole (0.85 g, 13%) as brown liquid.

Step2: To a stirring suspension of 4-bromo-1-cyclopropyl-6-fluoro-1H-indole (0.85 g, 3.35 mmol, 1 eq), bis(pinacolato)diborane (1.7 g, 6.7 mmol, 2 eq) and potassium acetate (1.31 g, 13.38 mmol, 4 eq) in 1,4-dioxan (20 mL) was deoxygenated by Ar for 10 min. Pd$_2$(dba)$_3$ (0.046 g, 0.05 mmol. 0.015 eq) and Ttricyclohexylphosphine (0.067 g, 0.24 mmol, 0.072 eq) was then added to the reaction mixture and again deoxygenated by Ar for 10 min. The reaction mixture was stirred for 14 h at 110° C. The reaction mixture was cooled to RT and then filtered through celite bed. Filtrate was concentrated under reduced pressure to get the crude material which was purified by column chromatography (230-400 mesh silica gel, 20% EtOAc/hexane; R$_f$-value-0.6) to afford 1-cyclopropyl-6-fluoro-4-(4,4,5,5-tetramethyl-1,3,2-dioxaborolan-2-yl)-1H-indole (0.61 g, 61%) as light yellow solid.

1H-NMR (400 MHz; DMSO-D$_6$, 20° C.): δ 7.45 (dd, 1H), 7.35 (d, 1H), 7.15 (dd, 1H), 6.67 (d, 1H), 3.41 (m, 1H), 1.32 (12H), 1.03-1.08 (2H), 0.82-0.92 (2H).

Synthesis of 5-fluoro-7-(4,4,5,5-tetramethyl-1,3,2-dioxaborolan-2-yl)-1H-indole (Intermediate A-71)

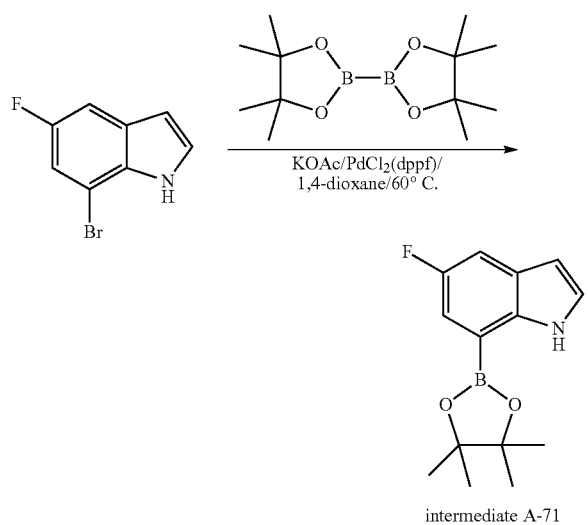

intermediate A-71

A mixture of 7-bromo-5-fluoro-1H-indole (1 g, 4.7 mmol, 1 eq), bis(pinacolato)diborane (2.02 g, 7.9 mmol, 1.7 eq), potassium acetate (917 mg, 9.4 mmol, 2 eq), 1,1'-Bis(diphenylphospino)ferrocene palladium(II)dichloride DCM complex (382 mg, 0.467 mmol, 0.1 eq) in 1,4-dioxane (13 mL) was degassed with nitrogen, and the reaction mixture was stirred at 60° C. After completion of the reaction (monitored by LCMS), a sat. sodiumbicarbonate solution was added to the reaction mixture, which was then extracted with EtOAc (2×). The combined organic layers were washed with brine, dried over anhydrous MgSO$_4$ and evaporated under reduced pressure. The crude product was purified by column chromatography (silica gel; EtOAc/cyclo-Hexane as eluent) to afford 5-fluoro-7-(4,4,5,5-tetramethyl-1,3,2-dioxaborolan-2-yl)-1H-indole (940 mg, 77%).

The intermediates in Table 1 were synthesized in analogy to Intermediate A-1 to Intermediate A-27.

| Intermediate | Synthesized in analogy to | Structure |
|---|---|---|
| Int-A-30 | Int-A-2 | 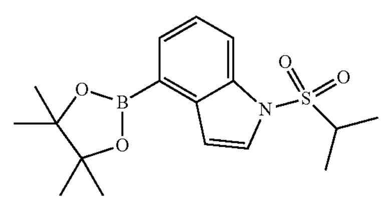 [SMILES: CC(C)S(=O)(=O)n1ccc2c(B3OC(C)(C)C(C)(C)O3)cccc21] |
| Int-A-31 | Int-A-2 | 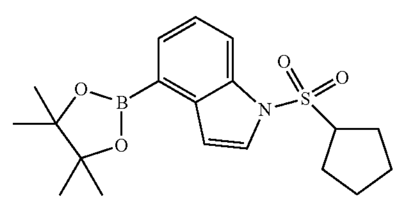 [SMILES: CC1(C)OB(c2cccc3c2ccn3S(=O)(=O)C2CCCC2)OC1(C)C] |
| Int-A-32 | Int-A-11 | 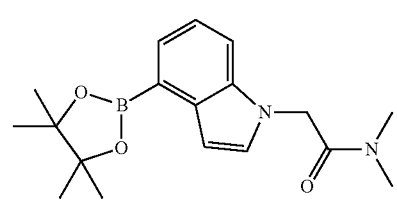 |
| Int-A-33 | Int-A-10 | 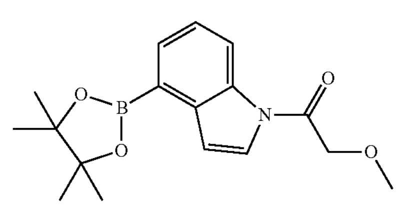 |

-continued

| Intermediate | Synthesized in analogy to | Structure |
|---|---|---|
| Int-A-34 | Int-A-11 | (4-(4,4,5,5-tetramethyl-1,3,2-dioxaborolan-2-yl)-1H-indol-1-yl)ethyl tert-butyl carbamate |
| Int-A-35 | Int-A-2 | 1-(cyclopropylsulfonyl)-4-(4,4,5,5-tetramethyl-1,3,2-dioxaborolan-2-yl)-1H-indazole |
| Int-A-36 | Int-A-11 | 1-(2-methoxyethyl)-4-(4,4,5,5-tetramethyl-1,3,2-dioxaborolan-2-yl)-1H-indazole |
| Int-A-37 | Int-A-11 | 1-(cyclopropylmethyl)-4-(4,4,5,5-tetramethyl-1,3,2-dioxaborolan-2-yl)-1H-indazole |
| Int-A-38 | Int-A-11 | 1-ethyl-4-(4,4,5,5-tetramethyl-1,3,2-dioxaborolan-2-yl)-1H-indazole |
| Int-A-39 | Int-A-11 | 2-ethyl-4-(4,4,5,5-tetramethyl-1,3,2-dioxaborolan-2-yl)-2H-indazole |
| Int-A-40 | Int-A-2 | 1-((cyclopropylmethyl)sulfonyl)-4-(4,4,5,5-tetramethyl-1,3,2-dioxaborolan-2-yl)-1H-indazole |

-continued
| Intermediate | Synthesized in analogy to | Structure |
|---|---|---|
| Int-A-41 | Int-A-27 | 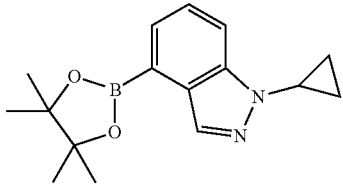 [SMILES: CC1(C)OB(c2cccc3c2cnn3C2CC2)OC1(C)C] |
| Int-A-42 | Int-A-11 | 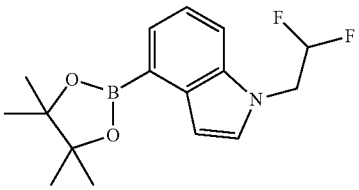 [SMILES: CC1(C)OB(c2cccc3c2ccn3CC(F)F)OC1(C)C] |
| Int-A-43 | Int-A-11 | 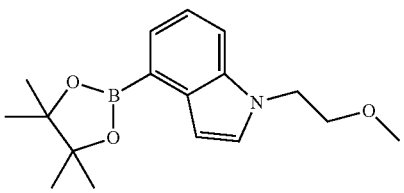 |
| Int-A-44 | Int-A-27 | 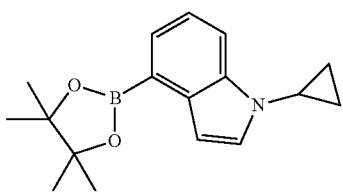 [SMILES: CC1(C)OB(c2cccc3c2ccn3C2CC2)OC1(C)C] |
| Int-A-45 | Int-A-2 | 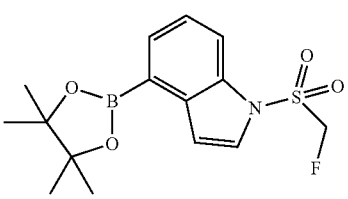 |
| Int-A-46 | Int-A-11 | 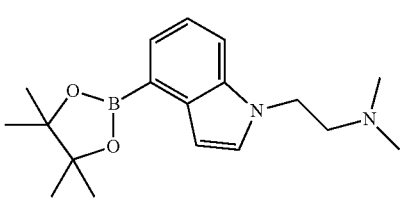 |
| Int-A-47 | Int-A-2 | 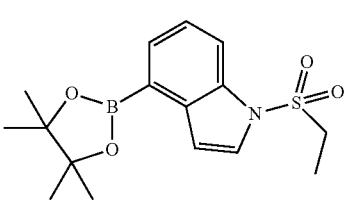 [SMILES: CCS(=O)(=O)n1ccc2c(B3OC(C)(C)C(C)(C)O3)cccc21] |

-continued
| Intermediate | Synthesized in analogy to | Structure |
|---|---|---|
| Int-A-48 | Int-A-2 | 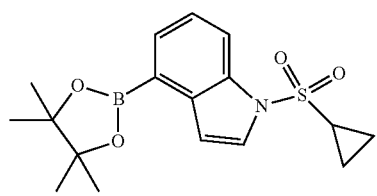 [SMILES: CC1(C)OB(c2cccc3c2ccn3S(=O)(=O)C2CC2)OC1(C)C] |
| Int-A-49 | Int-A-11 | 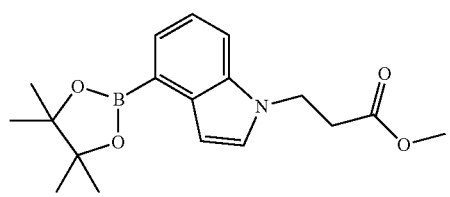 |
| Int-A-50 | Int-A-22 | 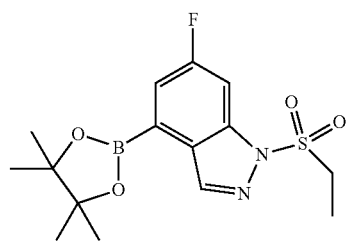 [SMILES: CCS(=O)(=O)n1ncc2c(B3OC(C)(C)C(C)(C)O3)cc(F)cc21] |
| Int-A-51 | Int-A-20 | 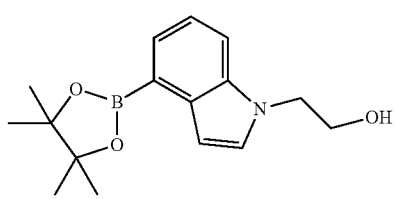 [SMILES: CC1(C)OB(c2cccc3c2ccn3CCO)OC1(C)C] |
| Int-A-54 | Int-A-22 | 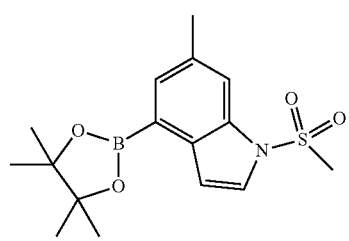 [SMILES: Cc1cc(B2OC(C)(C)C(C)(C)O2)c2ccn(S(C)(=O)=O)c2c1] |
| Int-A-56 | Int-A-11 | 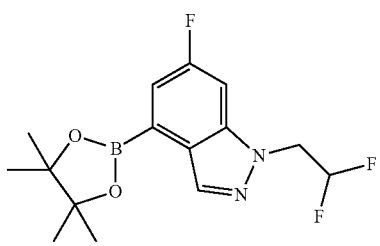 [SMILES: CC1(C)OB(c2cc(F)cc3c2cnn3CC(F)F)OC1(C)C] |

-continued
| Intermediate | Synthesized in analogy to | Structure |
|---|---|---|
| Int-A-57 | Int-A-22 | 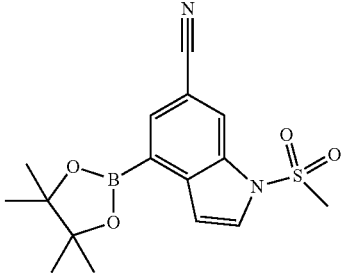 [SMILES: CC1(C)OB(c2cc(C#N)cc3c2ccn3S(C)(=O)=O)OC1(C)C] |
| Int-A-58 | Int-A-22 | 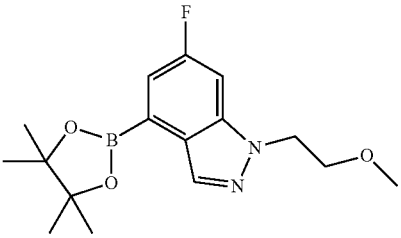 |
| Int-A-59 | Int-A-21 | 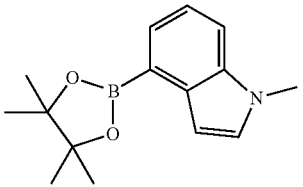 |
| Int-A-60 | Int-A-22 | 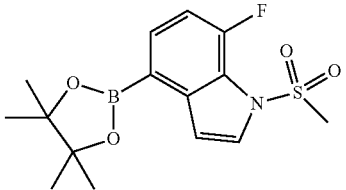 [SMILES: CC1(C)OB(c2ccc(F)c3c2ccn3S(C)(=O)=O)OC1(C)C] |
| Int-A-63 | Int-A-22 | 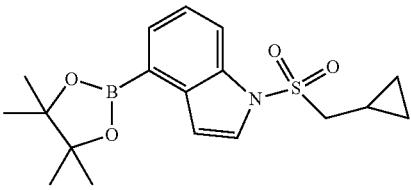 [SMILES: CC1(C)OB(c2cccc3c2ccn3S(=O)(=O)CC2CC2)OC1(C)C] |
| Int-A-66 | Int-A-22 | 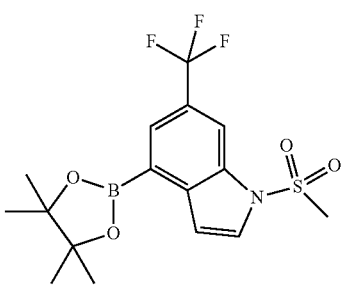 [SMILES: CC1(C)OB(c2cc(C(F)(F)F)cc3c2ccn3S(C)(=O)=O)OC1(C)C] |

-continued
| Intermediate | Synthesized in analogy to | Structure |
|---|---|---|
| Int-A-68 | Int-A-22 | 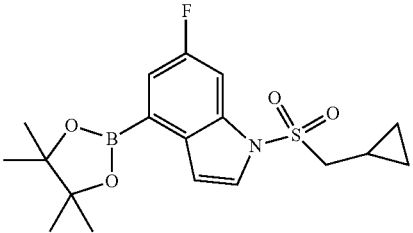 [SMILES: CC1(C)OB(c2cc(F)cc3c2ccn3S(=O)(=O)CC2CC2)OC1(C)C] |
| Int-A-72 | Int-A-22 | 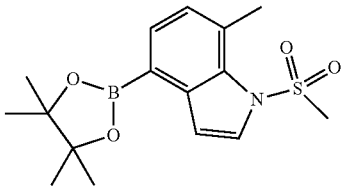 [SMILES: Cc1ccc(B2OC(C)(C)C(C)(C)O2)c2ccn(S(C)(=O)=O)c12] |
| Int-A-73 | Int-A-21 | 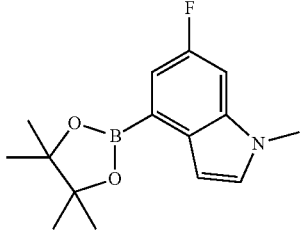 |
| Int-A-75 | Int-A-71 | 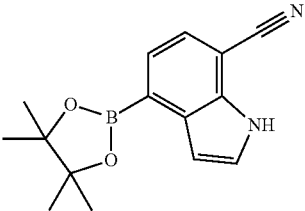 [SMILES: CC1(C)OB(c2ccc(C#N)c3[nH]ccc23)OC1(C)C] |
| Int-A-76 | Int-A-22 | 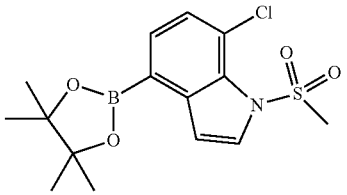 |
| Int-A-77 | Int-A-22 | 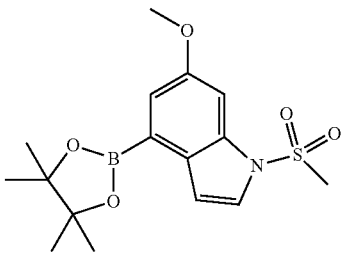 [SMILES: COc1cc(B2OC(C)(C)C(C)(C)O2)c2ccn(S(C)(=O)=O)c2c1] |

The Intermediates in Table 2 are commercially available:

| Name | Structure |
| --- | --- |
| 4-(tetramethyl-1,3,2-dioxaborolan-2-yl)-6-(trifluoromethyl)-1H-indole | 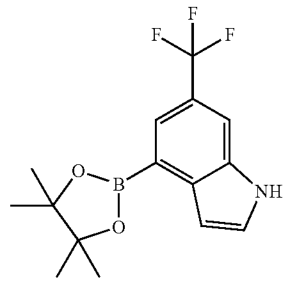 [SMILES: CC1(C)OB(c2cc(C(F)(F)F)cc3[nH]ccc23)OC1(C)C] |
| 5-fluoro-1H-indole-4-boronic acid pinacol ester | 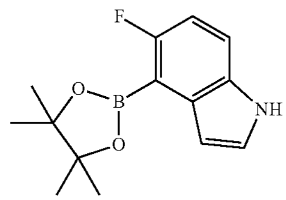 [SMILES: CC1(C)OB(c2c(F)ccc3[nH]ccc23)OC1(C)C] |
| 2-methyl-4-(4,4,5,5-tetramethyl-1,3,2-dioxaborolan-2-yl)-2H-indazole | 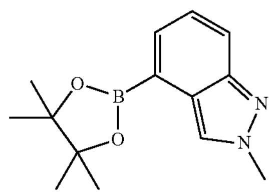 |
| 1-methyl-4-(4,4,5,5-tetramethyl-[1,3,2]dioxaborolan-2-yl)-1H-indazole | 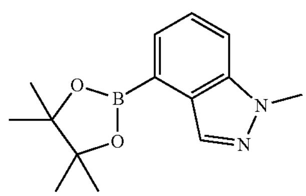 |
| 4-(tetramethyl-1,3,2-dioxaborolan-2-yl)-2-(trifluoromethyl)-1H-indole | 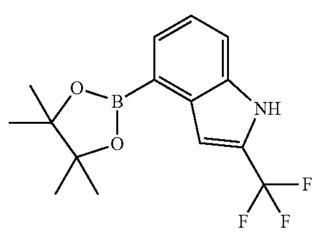 [SMILES: CC1(C)OB(c2cccc3[nH]c(C(F)(F)F)cc23)OC1(C)C] |
| 4-(4,4,5,5-tetramethyl-1,3,2-dioxaborolan-2-yl)-1H-indazole | 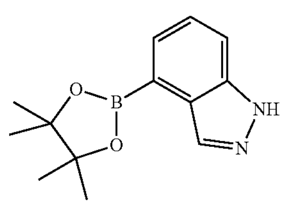 [SMILES: CC1(C)OB(c2cccc3[nH]ncc23)OC1(C)C] |
| tert-butyl 4-(4,4,5,5-tetramethyl-1,3,2-dioxaborolan-2-yl)-1H-indazole-1-carboxylate | 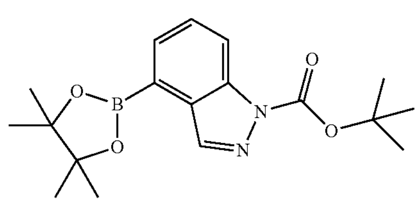 [SMILES: CC(C)(C)OC(=O)n1ncc2c(B3OC(C)(C)C(C)(C)O3)cccc21] |

-continued

| Name | Structure |
|---|---|
| indole-4-boronic acid | 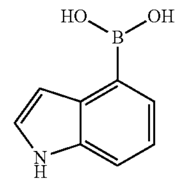 [SMILES: OB(O)c1cccc2[nH]ccc12] |
| 1,1-dimethylethyl 4-(4,4,5,5-tetramethyl-1,3,2-dioxaborolan-2-yl)-1H-indole-1-carboxylate | 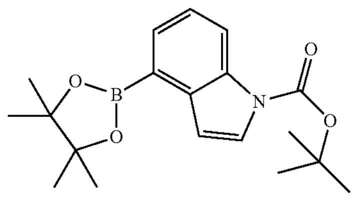 [SMILES: CC(C)(C)OC(=O)n1ccc2c(B3OC(C)(C)C(C)(C)O3)cccc21] |
| 3-methyl-7-(4,4,5,5-tetramethyl-1,3,2-dioxaborolan-2-yl)-1H-indole | |
| (7-chloro-1H-indazol-4-yl)boronic acid | 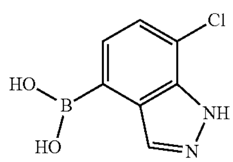 [SMILES: OB(O)c1ccc(Cl)c2[nH]ncc12] |
| 7-fluoro-4-(4,4,5,5-tetramethyl-1,3,2-dioxaborolan-2-yl)-1H-indazole | 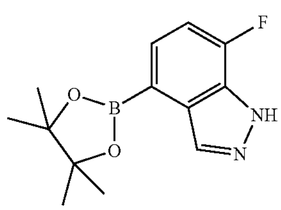 [SMILES: CC1(C)OB(c2ccc(F)c3[nH]ncc23)OC1(C)C] |
| 7-methoxy-4-(4,4,5,5-tetramethyl-1,3,2-dioxaborolan-2-yl)-1H-indazole | 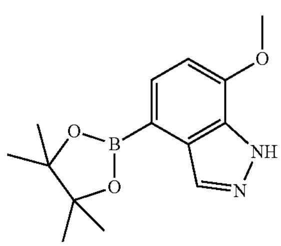 |
| 4-(4,4,5,5-tetramethyl-1,3,2-dioxaborolan-2-yl)-7-(trifluoromethyl)-1H-indazole | 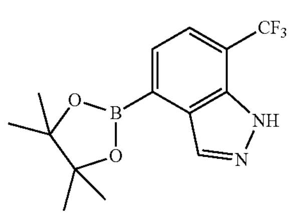 [SMILES: CC1(C)OB(c2ccc(C(F)(F)F)c3[nH]ncc23)OC1(C)C] |

-continued

| Name | Structure |
|---|---|
| (6-(trifluoromethyl)-1H-indazol-4-yl)boronic acid | 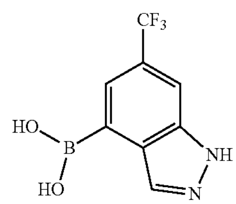 [SMILES: OB(O)c1cc(C(F)(F)F)cc2[nH]ncc12] |
| (6-fluoro-1H-indazol-4-yl)boronic acid | 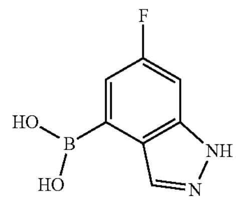 [SMILES: OB(O)c1cc(F)cc2[nH]ncc12] |
| 7-chloro-6-fluoro-4-(4,4,5,5-tetramethyl-1,3,2-dioxaborolan-2-yl)-1H-indazole | 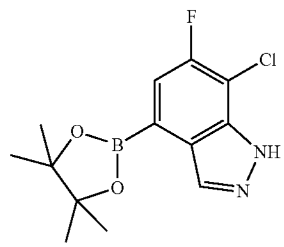 [SMILES: CC1(C)OB(c2cc(F)c(Cl)c3[nH]ncc23)OC1(C)C] |
| 7-fluoro-4-(4,4,5,5-tetramethyl-[1,3,2]dioxaborolan-2-yl)-1H-indole | 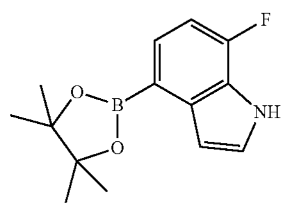 [SMILES: CC1(C)OB(c2ccc(F)c3[nH]ccc23)OC1(C)C] |
| 7-methyl-4-(4,4,5,5-tetramethyl-[1,3,2]dioxaborolan-2-yl)-1H-indole | 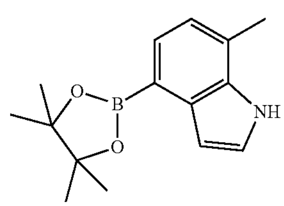 |
| 6-methoxy-4-(4,4,5,5-tetramethyl-[1,3,2]dioxaborolan-2-yl)-1H-indole | 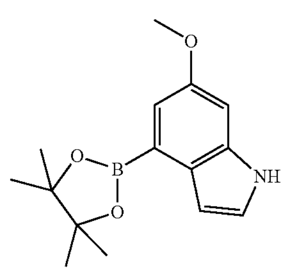 [SMILES: COc1cc(B2OC(C)(C)C(C)(C)O2)c2cc[nH]c2c1] |
| (1H-indol-7-yl)boronic acid | 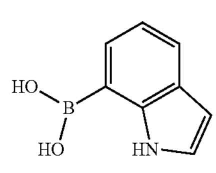 [SMILES: OB(O)c1cccc2cc[nH]c12] |

-continued

| Name | Structure |
|---|---|
| 3-Methyl-1H-indazole-7-boronic acid | 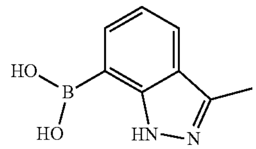 |
| 4-(4,4,5,5-Tetramethyl-1,3,2-dioxaborolan-2-yl)-1H-indole-6-carbonitrile | 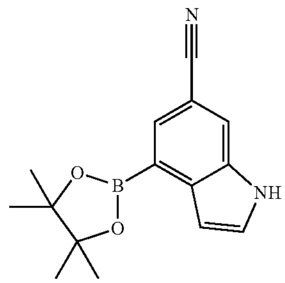 [SMILES: CC1(C)OB(c2cc(C#N)cc3[nH]ccc23)OC1(C)C] |
| 7-fluoro-4-(4,4,5,5-tetramethyl-1,3,2-dioxaborolan-2-yl)-1H-indazole | 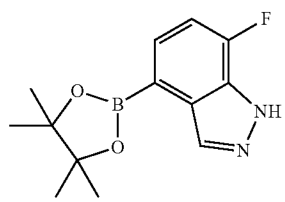 [SMILES: CC1(C)OB(c2ccc(F)c3[nH]ncc23)OC1(C)C] |
| 7-fluoro-4-(tetramethyl-1,3,2-dioxaborolan-2-yl)-1H-indole | 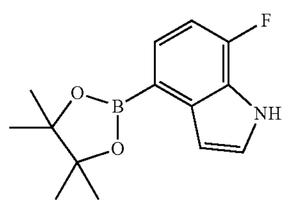 [SMILES: CC1(C)OB(c2ccc(F)c3[nH]ccc23)OC1(C)C] |
| 6-fluoro-4-(4,4,5,5-tetramethyl-1,3,2-dioxaborolan-2-yl)-1H-indazole | 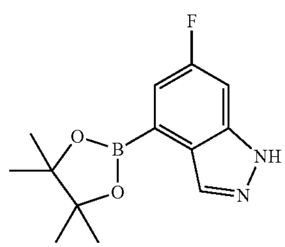 [SMILES: CC1(C)OB(c2cc(F)cc3[nH]ncc23)OC1(C)C] |
| 6-chloro-4-(4,4,5,5-tetramethyl-1,3,2-dioxaborolan-2-yl)-1H-indole | 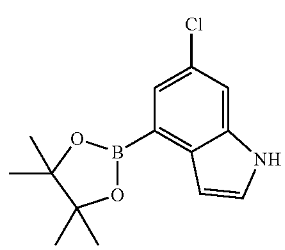 [SMILES: CC1(C)OB(c2cc(Cl)cc3[nH]ccc23)OC1(C)C] |
| 7-chloro-4-(4,4,5,5-tetramethyl-1,3,2-dioxaborolan-2-yl)-1H-indole | 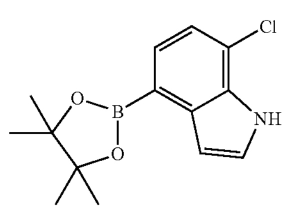 [SMILES: CC1(C)OB(c2ccc(Cl)c3[nH]ccc23)OC1(C)C] |

Synthesis of 8-bromo-7,9-difluoro-1,4,4-trimethyl-4,
5-dihydro-[1,2,4]triazolo[4,3-a]quinoxaline (Intermediate B-1)

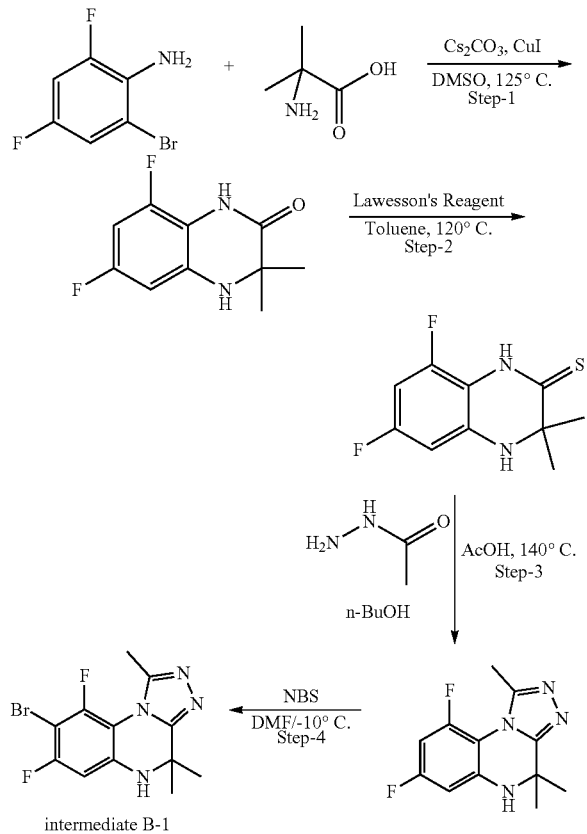

intermediate B-1

Step1: A suspension of 2-bromo-4,6-difluoroaniline (25 g, 120.19 mmol, 1 eq.), 2-amino-2-methylpropanoic acid (24.75 g, 240.38 mmol, 2 eq.), $K_3PO_4$ (50.96 g, 240.38 mmol, 2 eq.) and CuI (2.29 g, 12.02 mmol, 0.1 eq.) in dry DMSO (375 mL) in a sealed tube were deoxygenated with Ar for 20 min. Reaction mixture was then stirred at 125° C. for 16 h. After completion of the reaction, it was filtered through celite bed and washed by EtOAc (100 mL). The filtrate was diluted with EtOAc (500 mL) and washed with water (3×150 mL), brine (200 mL), dried over anhydrous $Na_2SO_4$ and evaporated under reduced pressure. Crude product was purified by column chromatography to afford 6,8-difluoro-3,3-dimethyl-3,4-dihydroquinoxalin-2(1H)-one (34.0 g, 67%) as brown solid.

Step2: To a solution of 6,8-difluoro-3,3-dimethyl-3,4-dihydroquinoxalin-2(1H)-one (34.0 g, 160 mmol, 1 eq.) in toluene (650 mL) was added Lawesson's reagent (97.3 g, 240 mmol, 1.5 eq.) at RT and the reaction mixture was refluxed at 120° C. for 40 min. After completion of reaction, the reaction mixture was quenched with sat. $NaHCO_3$ solution (250 mL) followed by extraction with EtOAc (3×150 mL). Combined organic layers was washed with water (300 mL), brine (200 mL), dried over anhydrous $Na_2SO_4$ and evaporated to get the crude product which was purified by column chromatography to afford 6,8-difluoro-3,3-dimethyl-3,4-dihydroquinoxaline-2(1H)-thione (26 g, 66%) as yellow solid.

Step3: To a solution of 6,8-difluoro-3,3-dimethyl-3,4-dihydroquinoxaline-2(1H)-thione (5.0 g, 21.9 mmol, 1 eq.) in n-BuOH (60 mL) is added acetohydrazide (5.35 g, 72.3 mmol, 3.3 eq) followed by addition of AcOH (6 mL) and then the reaction mixture is stirred at 140° C. for 16 h. After completion of reaction, reaction mixture is concentrated and the residue was diluted with EtOAc (150 mL). Combined organic layers washed with water (100 mL), brine (100 mL), dried over anhydrous $Na_2SO_4$ and evaporated to get the crude product which was purified by column chromatography to afford 7,9-difluoro-1,4,4-trimethyl-4,5-dihydro-[1,2,4]triazolo[4,3-a]quinoxaline (4.5 g, 82%) as off white solid.

Step4: To the stirred solution of 7,9-difluoro-1,4,4-trimethyl-4,5-dihydro-[1,2,4]triazolo[4,3-a]quinoxaline (4.5 g, 18 mmol, 1 eq.) in DMF (40 mL) was added N-bromosuccinimide (3.5 g, 19.8 mmol, 1.1 eq) portion wise. Reaction mixture was allowed to warm to RT and stirred for 2 h. Reaction mixture was diluted with EtOAc (300 mL). Combined organic layers was washed with water (5×50 mL), brine (50 mL), dried over anhydrous $Na_2SO_4$ and evaporated under reduced pressure. Crude product was purified by column chromatography to afford 8-bromo-7,9-difluoro-1,4,4-trimethyl-4,5-dihydro-[1,2,4]triazolo[4,3-a]quinoxaline (4.0 g, 61%) as brown solid.

Synthesis of 8-bromo-1-ethyl-7,9-difluoro-4,4-dimethyl-4,5-dihydro-[1,2,4]triazolo[4,3-a]quinoxaline
(Intermediate B-2)

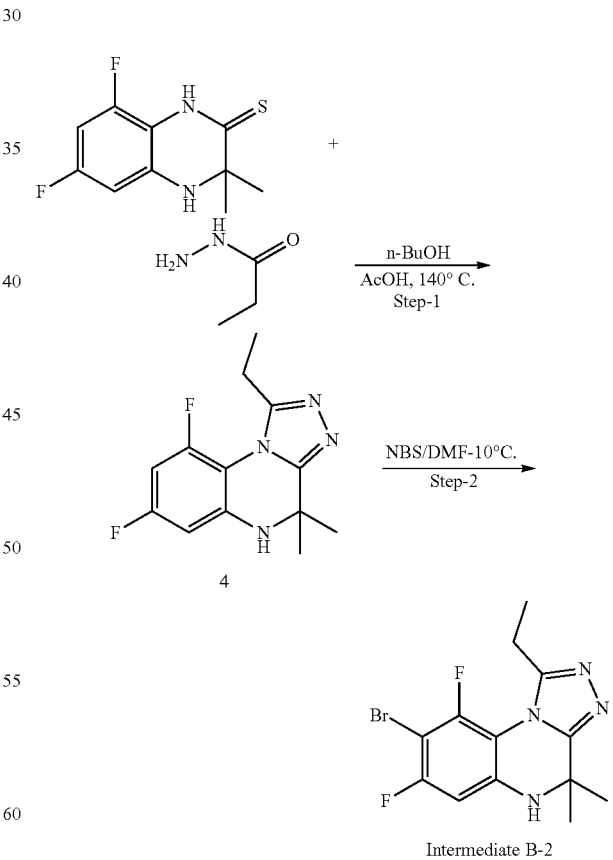

Intermediate B-2

Step1: To a solution of 6,8-difluoro-3,3-dimethyl-3,4-dihydroquinoxaline-2(1H)-thione (7.0 g, 30.7 mmol, 1 eq.) in n-BuOH (84 mL) was added propionohydrazide (8.92 g, 101.3 mmol, 3.3 eq) followed by addition of acetic acid (8.4 mL) and then the reaction mixture was stirred at 140° C. for 16 h. After completion of reaction, reaction mixture was concentrated and the residue was diluted with EtOAc (150 mL). Combined organic layers was washed with water (100 mL), brine (100 mL), dried over anhydrous Na₂SO₄ and evaporated to get the crude product which was purified by column chromatography to afford 1-ethyl-7,9-difluoro-4,4-dimethyl-4,5-dihydro-[1,2,4]triazolo[4,3-a]quinoxaline (6.0 g, 74%) as off white solid.

Step2: A stirred solution of 1-ethyl-7,9-difluoro-4,4-dimethyl-4,5-dihydro-[1,2,4]triazolo[4,3-a]quinoxaline (5.5 g, 20.8 mmol, 1 eq) in DMF (50 mL) at −10° C. was treated portion wise over 10 min with solid N-bromosuccinimide (3.89 g, 21.8 mmol, 1.05 eq). Reaction mixture was allowed to warm to RT and stirred for 1.5 h. After completion of reaction, reaction mixture was diluted with EtOAc (300 mL) and organic layers was washed with water (5×50 mL), brine (50 mL), dried over anhydrous Na₂SO₄ and solvent was evaporated under reduced pressure. Crude product was purified by column chromatography to afford 8-bromo-1-ethyl-7,9-difluoro-4,4-dimethyl-4,5-dihydro-[1,2,4]triazolo[4,3-a]quinoxaline (4.4 g, 62%) as off white solid.

Synthesis of 8-bromo-7-fluoro-1,4,4,9-tetramethyl-4,5-dihydro-[1,2,4]triazolo[4,3-a]quinoxaline (Intermediate B-3)

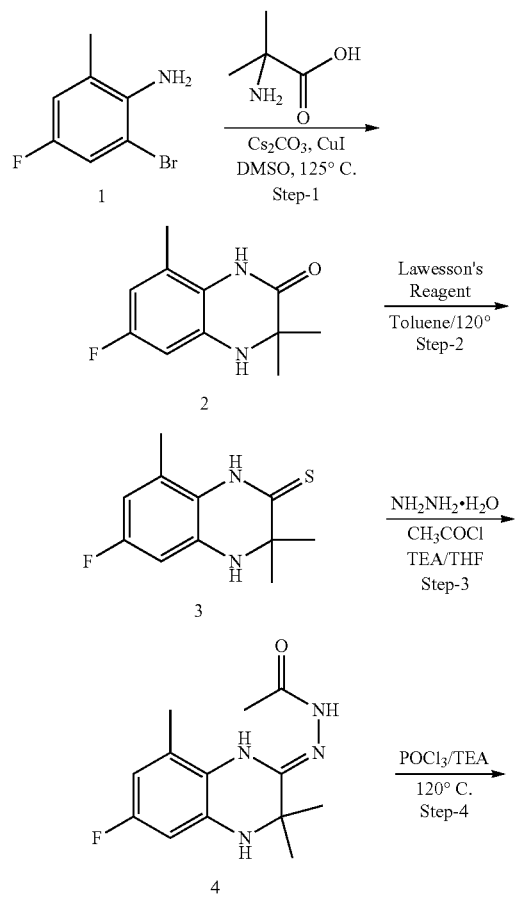

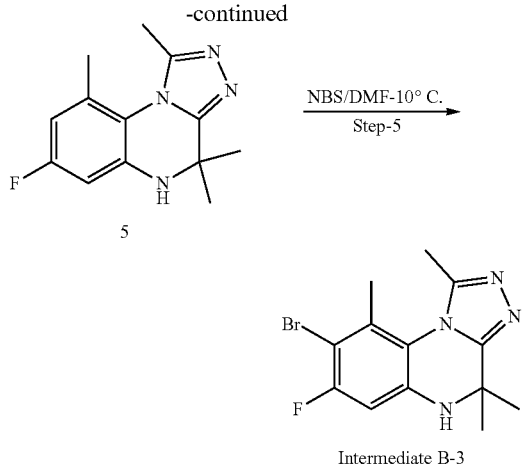

Step1: A suspension of 2-bromo-4-fluoro-6-methyl aniline (5 g, 24.5 mmol, 1 eq.), 2-aminoisobutaric acid (5.05 g, 49 mmol, 2 eq.), Cs₂CO₃ (15.92 g, 49 mmol, 2 eq.) and cuprous iodide (0.466 g, 2.45 mmol, 0.1 eq.) in dry DMSO (75 mL) in a sealed tube were deoxygenated with Ar for 20 min. Reaction mixture was then stirred at 125° C. for 16 h. The reaction mixture was filtered through celite bed and washed with EtOAc (100 mL). The filtrate was diluted with EtOAc (200 mL) and washed with water (3×100 mL), brine (100 mL), dried over anhydrous Na₂SO₄ and evaporated under reduced pressure to get the crude product which was purified by column chromatography to afford 6-fluoro-3,3,8-trimethyl-3,4-dihydroquinoxalin-2(1H)-one (3.0 g, 59%) as brown solid.

Step2: To a solution of 6-fluoro-3,3,8-trimethyl-3,4-dihydroquinoxalin-2(1H)-one (3.66 g, 17.6 mmol, 1 eq.) in toluene (75 mL) was added Lawesson's reagent (10.67 g, 26.2 mmol, 1.5 eq.) at RT and the reaction mixture was stirred at 120° C. for 40 min. The reaction mixture was quenched with sat. NaHCO₃ solution (100 mL) followed by extraction with EtOAc (2×100 mL). Combined organic layers were washed with water (100 mL), brine (100 mL), dried over anhydrous Na₂SO₄ and the solvent was evaporated to get the crude product which was purified by column chromatography to afford 6-fluoro-3,3,8-trimethyl-3,4-dihydroquinoxaline-2(1H)-thione (2.8 g, 71%) as yellow solid.

Step3: To a stirring solution of 6-fluoro-3,3,8-trimethyl-3,4-dihydroquinoxaline-2(1H)-thione (5.50 g, 24.55 mmol, 1 eq) in THF (30 mL) was drop wise added hydrazine hydrate (5.17 mL, 122.76 mmol, 5 eq) at 0° C. The reaction mixture was then stirred for 16 h at RT. TEA (16.7 ml, 122.76 mmol, 5 eq) was added to the reaction mixture and stirred for another 10 min. Acetyl chloride (5.78 g, 73.65 mmol, 3 eq) was added to the reaction mixture very slowly at 0° C. and then stirred for 2 h at RT. The reaction mixture was diluted with water (50 mL) and extracted with DCM (5×100 mL). The combine organic layers were washes with brine (100 mL). The organic layer was dried over Na₂SO₄, concentrated under reduced pressure to get the crude material which was washed with diethyl ether to afford N'-(6-fluoro-3,3,8-trimethyl-3,4-dihydroquinoxalin-2(1H)-ylidene)acetohydrazide (5.5 g, 85%) as a white solid.

Step4: N'-(6-fluoro-3,3,8-trimethyl-3,4-dihydroquinoxalin-2(1H)-ylidene)acetohydrazide (5.5 g, 20.8 mmol, 1 eq) was taken in round bottom flax (50 mL) and then cooled to −10° C. Phosphorus oxychloride (18.4 ml, 197.6 mmol, 9.5 eq) was then added drop wise to the compound followed by drop wise addition of TEA (2.9 ml, 20.8 mmol, 1 eq). After that the reaction mixture was stirred at −10° C. for 10 min and then 10 min at RT and finally heated to reflux for 4 h. The reaction mixture was cooled to 0° C. and then crushed ice was drop wise added with constant stirring. To this aqueous part was then slowly added cold ammonium solution (100 mL). The aqueous layer was extracted with DCM (2×100 mL). The combined organic layers were washed with brine (100 mL). The organic layer was dried over anhydrous $Na_2SO_4$, concentrated under reduced pressure to get the crude material. Crude product was purified by column chromatography to afford 7-fluoro-1,4,4,9-tetramethyl-4,5-dihydro-[1,2,4]triazolo[4,3-a]quinoxaline (3.0 g, 59%) as yellow solid.

Step5: A stirred solution of 7-fluoro-1,4,4,9-tetramethyl-4,5-dihydro-[1,2,4]triazolo[4,3-a]quinoxaline (4.0 g, 16.2 mmol, 1 eq) in DMF (40 mL) at −10° C. is treated portion wise over 10 min with solid N-bromosuccinimide (3.1 g, 17.1 mmol, 1.05 eq). The reaction mixture was allowed to warm to RT and stirred for 1.5 h. The reaction mixture was diluted with EtOAc (300 mL) and the organic layers were washed with water (5×50 mL), brine (50 mL), dried over anhydrous $Na_2SO_4$ and the solvent was evaporated under reduced pressure. The crude product was purified by column chromatography to afford 8-bromo-7-fluoro-1,4,4,9-tetramethyl-4,5-dihydro-[1,2,4]triazolo[4,3-a]quinoxaline (3.3 g, 63%) as off white solid.

Synthesis of 8-bromo-7-fluoro-1,4,4-trimethyl-9-(trifluoromethyl)-4,5-dihydro-[1,2,4]triazolo[4,3-a]quinoxaline (Intermediate B-4)

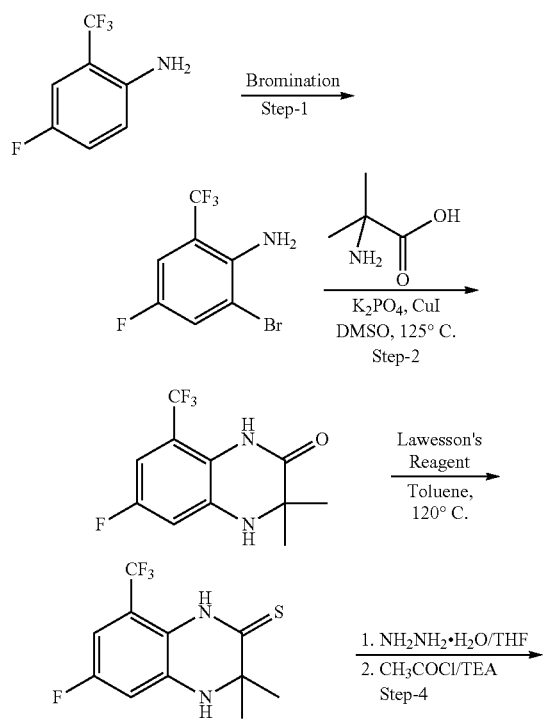

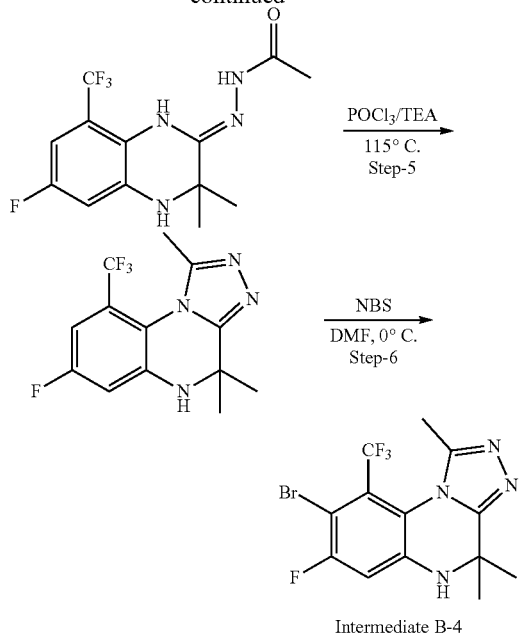

Intermediate B-4

Step1: To a solution of 4-fluoro-2-trifluoromethyl-phenylamine (50 g, 0.279 mol) in DCM (550 mL) was added solution of $Br_2$ (15.1 ml, 0.29 mol) in DCM (100 mL) drop-wise at 0° C. and the resulting reaction mixture was stirred at 0° C. for 2 h. The reaction mixture was diluted with water (1000 mL) and extracted with EtOAc (2×500 mL). Combined organic layers were washed with water (2×500 mL) followed by brine (250 mL), dried over anhydrous $Na_2SO_4$ and concentrated to afford crude product, which was purified by column chromatography to afford 2-bromo-4-fluoro-6-trifluoromethyl-phenylamine (50 g, 69.4%) as brown liquid.

Step2: To the stirred suspension of 2-bromo-4-fluoro-6-trifluoromethyl-phenylamine (25 g, 0.097 mol) in dry DMSO (375 mL) was added 2-amino-2-methyl-propionic acid (20 g, 0.194 mol) followed by $K_3PO_4$ (41.1 g, 0.194 mol) at RT. Resulting reaction mixture was degassed with nitrogen for 30 min, then CuCl (0.96 g, 0.0097 mol) was added and the reaction mixture was stirred at 140° C. for 16 h. The reaction mixture was cooled to RT and filtered through celite. Celite bed was washed with EtOAc (500 mL). Resulting filtrate was poured into ice cold water (1000 mL). Resulting aqueous layer was extracted with EtOAc (2×250 mL). Total organic part was washed with water (2×500 mL), brine (250 mL), dried over anhydrous $Na_2SO_4$ and the solvent was evaporated under reduced pressure to afford crude product which was purified by column chromatography to afford 6-fluoro-3,3-dimethyl-8-trifluoromethyl-3,4-dihydro-1H-quinoxalin-2-one (16 g, 63%) as brown solid.

Step3: To a solution of 6-fluoro-3,3-dimethyl-8-trifluoromethyl-3,4-dihydro-1H-quinoxalin-2-one (26 g, 0.0992 mol) in toluene (390 mL) was added Lawesson's reagent (60.14 g, 0.1488 mol) at RT and the reaction mixture was refluxed at 120° C. for 2 h. The reaction mixture was concentrated. Obtained solid residue was quenched with sat. $NaHCO_3$ solution (1500 mL) and resulting aqueous layer was extracted with EtOAc (3×500 mL). Combined organic layers were washed with water (1000 mL), brine (1000 mL), dried over anhydrous $Na_2SO_4$ and the solvent was evaporated to get the crude product. Obtained crude product was purified by column chromatography to afford 6-fluoro-3,3-dimethyl-8-trifluoromethyl-3,4-dihydro-1H-quinoxaline-2-thione (26 g, 94.3%) as yellow solid.

Step 4: To a stirring solution of 6-fluoro-3,3-dimethyl-8-trifluoromethyl-3,4-dihydro-1H-quinoxaline-2-thione (29.5 g, 0.106 mol) in THF (750 mL) was drop wise added hydrazine hydrate (15.91 g, 0.318 mol) at 0° C. The reaction mixture was stirred at RT for 16 h. TEA (101.19 mL, 0.742 mol) and acetyl chloride (30.14 ml, 0.424 mol) were added subsequently to the reaction mixture drop-wise at 0° C. and the mixture was stirred for 2 h at RT. The reaction mixture was diluted with water (500 mL) and extracted with 10% MeOH-DCM (5×500 mL). The total organic part was washed with brine (250 mL), dried over Na$_2$SO$_4$ and concentrated under reduced pressure to afford acetic acid (6-fluoro-3,3-dimethyl-8-trifluoromethyl-3,4-dihydro-1H-quinoxalin-2-ylidene)-hydrazide (30 g, 88.9%) as an off white solid.

Step 5: Acetic acid (6-fluoro-3,3-dimethyl-8-trifluoromethyl-3,4-dihydro-1H-quinoxalin-2-ylidene)-hydrazide (17 g, 0.053 mol) was taken in a round bottom flask and then cooled to −10° C. Phosphorus oxalylchloride (24.7 mL, 0.265 mol) was then added drop wise to the compound followed by drop wise addition of TEA (7.36 ml, 0.053 mol). After that the reaction mixture was stirred at −10° C. for 10 min and then for 10 min at RT and finally the mixture was heated to reflux for 4 h. The reaction mixture was cooled to 0° C. and quenched with crushed ice water (250 mL). The aqueous part was then basified using cold ammonium solution (250 mL) drop-wise. Resulting basic aqueous layer was then extracted with EtOAc (3 Xx 500 mL). Total organic part was washed with brine (250 mL), dried over anhydrous Na$_2$SO$_4$ and concentrated under reduced pressure to afford crude product. Obtained crude product was purified by trituration using MTBE to afford 7-fluoro-1,4,4-trimethyl-9-trifluoromethyl-4,5-dihydro-[1,2,4]triazolo[4,3-a]quinoxaline (8.5 g, 53%) as yellow solid.

Step 6: To a solution of 7-fluoro-1,4,4-trimethyl-9-trifluoromethyl-4,5-dihydro-[1,2,4]triazolo[4,3-a]quinoxaline (5.9 g, 19.64 mmol) in DMF (177 mL) was added NBS (3.84 g, 21.61 mol) portion wise at −10° C. Resulting reaction mixture was stirred at RT for 16 h. The reaction mixture was diluted with water (500 mL) and extracted with EtOAc (2×750 mL). Combined organic layers were washed with water (750 mL) followed by brine (400 mL), dried over anhydrous Na$_2$SO$_4$ and concentrated to afford crude product. Obtained crude product was purified by column chromatography to afford 8-bromo-7-fluoro-1,4,4-trimethyl-9-trifluoromethyl-4,5-dihydro-[1,2,4]triazolo[4,3-a]quinoxaline (3 g, 40%) as off white solid.

Synthesis of 8-bromo-9-chloro-7-fluoro-1,4,4-trimethyl-4,5-dihydro-[1,2,4]triazolo[4,3-a]quinoxaline (Intermediate B-5)

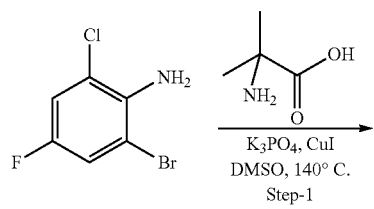

Step 1: To the stirred suspension of 2-bromo-6-chloro-4-fluoro-phenylamine (75 g, 0.334 mol) in dry DMSO (1125 mL) was added 2-amino-2-methyl-propionic acid (68.8 g, 0.668 mol) followed by K$_3$PO$_4$ (141.8 g, 0.668 mol) at RT. Resulting reaction mixture was degassed with nitrogen for 30 min, then CuCl (6.36 g, 0.0334 mol) was added and reaction mixture was heated at 140° C. for 6 h. The reaction mixture was cooled to RT and filtered through celite. Celite bed was washed with EtOAc (1500 mL). Resulting filtrate was poured into ice cold water (2000 mL). Resulting aqueous phase was extracted with EtOAc (2×750 mL). Total organic part was washed with water (2×1500 mL), followed by brine (750 mL), dried over anhydrous Na$_2$SO$_4$ and evaporated under reduced pressure to afford crude product. Crude product was purified by column chromatography to afford 8-chloro-6-fluoro-3,3-dimethyl-3,4-dihydro-1H-quinoxalin-2-one (40 g, 52.4%) as brown solid.

Step 2: To a solution of 8-chloro-6-fluoro-3,3-dimethyl-3,4-dihydro-1H-quinoxalin-2-one (25 g, 0.109 mol) in toluene (375 mL) was added Lawesson's reagent (66.26 g, 0.1639 mol) at RT and the reaction mixture was refluxed at 120° C. for 2 h. The reaction mixture was concentrated. Obtained solid residue was quenched with sat. NaHCO$_3$ solution (1500 mL) and resulting aqueous layer was extracted with EtOAc (3×500 mL). Combined organic layers were washed with water (750 mL), brine (750 mL), dried over anhydrous Na$_2$SO$_4$ and evaporated to get the crude product. Obtained crude product was purified by column chromatography to afford 8-chloro-6-fluoro-3,3-dimethyl-3,4-dihydro-1H-quinoxaline-2-thione (24 g, 89.7%) as yellow solid.

Step3: To a stirred solution of 8-chloro-6-fluoro-3,3-dimethyl-3,4-dihydro-1H-quinoxaline-2-thione (28.8 g, 0.118 mol) in THF (750 mL) was drop wise added hydrazine hydrate (17.7 g, 0.354 mol) at 0° C. The reaction mixture was stirred at RT for 16 h. TEA (82.4 mL, 0.59 mol) followed acetyl chloride (25.16 mL, 0.354 mol) were added to the reaction mixture drop-wise at 0° C. and stirred for 2 h at RT. After completion of starting material (monitored by LCMS) reaction mixture diluted with water (500 mL) and extracted by 10% MeOH-DCM (5×500 mL). The total organic part was washed by brine (250 mL), dried over $Na_2SO_4$ and concentrated under reduced pressure to afford acetic acid (8-chloro-6-fluoro-3,3-dimethyl-3,4-dihydro-1H-quinoxalin-2-ylidene)-hydrazide (30 g, 90%) as white solid.

Step4: Acetic acid (8-chloro-6-fluoro-3,3-dimethyl-3,4-dihydro-1H-quinoxalin-2-ylidene)-hydrazide (15 g, 0.052 mol) was taken in round bottom flax (500 mL) and then cooled to −10° C. Phosphorus oxalylchloride (24.23 ml, 0.26 mol) was then added drop wise to the compound followed by drop wise addition of TEA (7.22 mL, 0.052 mol). After that the reaction mixture was stirred at −10° C. for 10 min and then 10 min at RT and finally at reflux condition for 1.5 h. After completion of starting material (monitored by LCMS) reaction mixture was cooled to 0° C. and quenched with crushed ice water (250 mL). The aqueous part was then basified using cold ammonium solution (250 mL) drop-wise. Resulting basic aqueous layer was then extracted with EtOAc (3×500 mL). Total organic part was washed with brine (250 mL), dried over anhydrous $Na_2SO_4$ and concentrated under reduced pressure to afford crude compound. Obtained crude product was purified by trituration using MTBE to afford 9-chloro-7-fluoro-1,4,4-trimethyl-4,5-dihydro-[1,2,4]triazolo[4,3-a]quinoxaline (8.6 g, 61%) as off white solid.

Step5: To a solution of 9-chloro-7-fluoro-1,4,4-trimethyl-4,5-dihydro-[1,2,4]triazolo[4,3-a]quinoxaline (15 g, 0.056 mol) in DMF (450 mL) was added NBS (10.9 g, 0.0616 mol) portion wise at −10° C. Resulting reaction mixture was stirred at RT for 16 h. After completion of starting material (monitored by LCMS), reaction mixture was diluted with water (800 mL) and extracted with EtOAc (2×750 mL). Combined organic layers were washed with water (2×750 mL) followed by brine (400 mL), dried over anhydrous $Na_2SO_4$ and concentrated to afford crude compound. Obtained crude product was purified by column chromatography to afford 8-bromo-9-chloro-7-fluoro-1,4,4-trimethyl-4,5-dihydro-[1,2,4]triazolo[4,3-a]quinoxaline (12.1 g, 62%) as off white solid.

Synthesis of 8-bromo-1-ethyl-7-fluoro-4,4,9-trimethyl-4,5-dihydro-[1,2,4]triazolo[4,3-a]quinoxaline (Intermediate B-6)

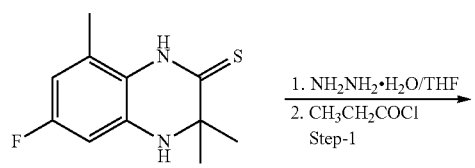

1. $NH_2NH_2 \cdot H_2O$/THF
2. $CH_3CH_2COCl$
Step-1

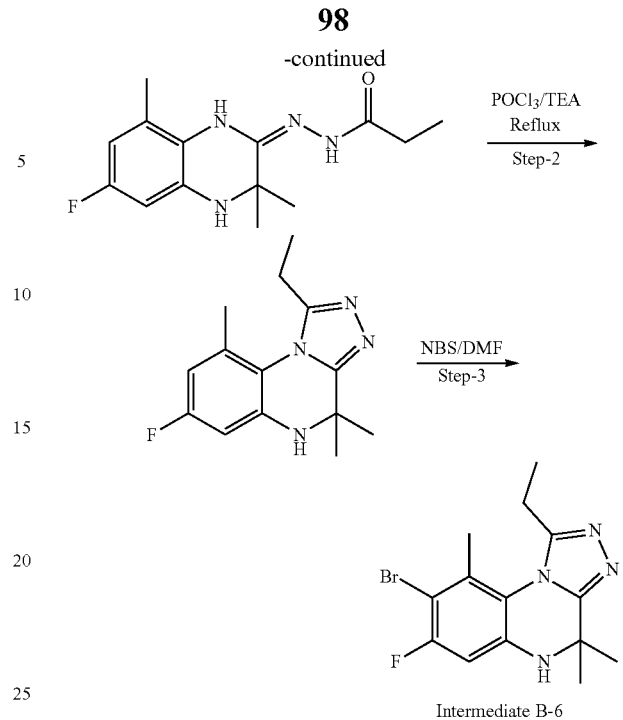

POCl₃/TEA
Reflux
Step-2

NBS/DMF
Step-3

Intermediate B-6

Step1: To a stirring solution of 6-fluoro-3,3,8-trimethyl-3,4-dihydro-1H-quinoxaline-2-thione (10 g, 0.0445 mol) in THF (250 mL) was drop wise added hydrazine hydrate (6.69 g, 0.1337 mol) at 0° C. The reaction mixture was stirred at RT for 16 h. TEA (30.98 mL, 0.2229 mol) was added followed by drop wise addition of propionyl chloride (11.67 mL, 0.1337 mol) at 0° C. and the mixture was stirred for 2 h at RT. After completion of starting material (monitored by LCMS) reaction mixture was diluted with water (250 mL) and extracted by 10% MeOH-DCM (5×250 mL). The total organic part was washed by brine (250 mL), dried over $Na_2SO_4$ and concentrated under reduced pressure to afford propionic acid (6-fluoro-3,3,8-trimethyl-3,4-dihydro-1H-quinoxalin-2-ylidene)-hydrazide (12 g, 96.7%) as an off white solid.

Step2: Propionic acid (6-fluoro-3,3,8-trimethyl-3,4-dihydro-1H-quinoxalin-2-ylidene)-hydrazide (12 g, 0.0431 mol) was taken in a round bottom flax and then cooled to −10° C. Phosphorus oxalylchloride (20.1 mL, 0.2158 mol) was then added drop wise to the compound followed by drop wise addition of TEA (6 mL, 0.0431 mol). After that the reaction mixture was stirred at −10° C. for 10 min and then 10 min at RT and finally at reflux condition for 4 h. After completion of starting material (monitored by LCMS) reaction mixture was cooled to 0° C. and quenched with crushed ice water (250 mL). The aqueous part was then basified using cold ammonium solution (250 mL) drop-wise. Resulting basic aqueous layer was then extracted with EtOAc (3×500 mL). Total organic part was washed with brine (250 mL), dried over anhydrous $Na_2SO_4$ and concentrated under reduced pressure to afford crude compound. Obtained crude product was purified by trituration using MTBE to afford 1-ethyl-7-fluoro-4,4,9-trimethyl-4,5-dihydro-[1,2,4]triazolo[4,3-a]quinoxaline (6.5 g, 58%) as off white solid.

Step3: To a solution of 1-ethyl-7-fluoro-4,4,9-trimethyl-4,5-dihydro-[1,2,4]triazolo[4,3-a]quinoxaline (7.5 g, 0.0288 mol) in DMF (180 mL) was added NBS (5.3 g, 0.0302 mol) portion wise at −10° C. Resulting reaction mixture was stirred at RT for 4 h. After completion of starting material (monitored by LCMS), reaction mixture was diluted with water (500 mL) and extracted with EtOAc (2×250 mL). Combined organic layers were washed with water (500 mL) followed by brine (400 mL), dried over anhydrous Na$_2$SO$_4$ and concentrated to afford crude compound. Obtained crude product was purified by column chromatography to afford 8-bromo-1-ethyl-7-fluoro-4,4,9-trimethyl-4,5-dihydro-[1,2,4]triazolo[4,3-a]quinoxaline (3.8 g, 38%) as off white solid.

Synthesis of 8-bromo-9-ethyl-7-fluoro-1,4,4-trimethyl-4,5-dihydro-[1,2,4]triazolo[4,3-a]quinoxaline (Intermediate B-8)

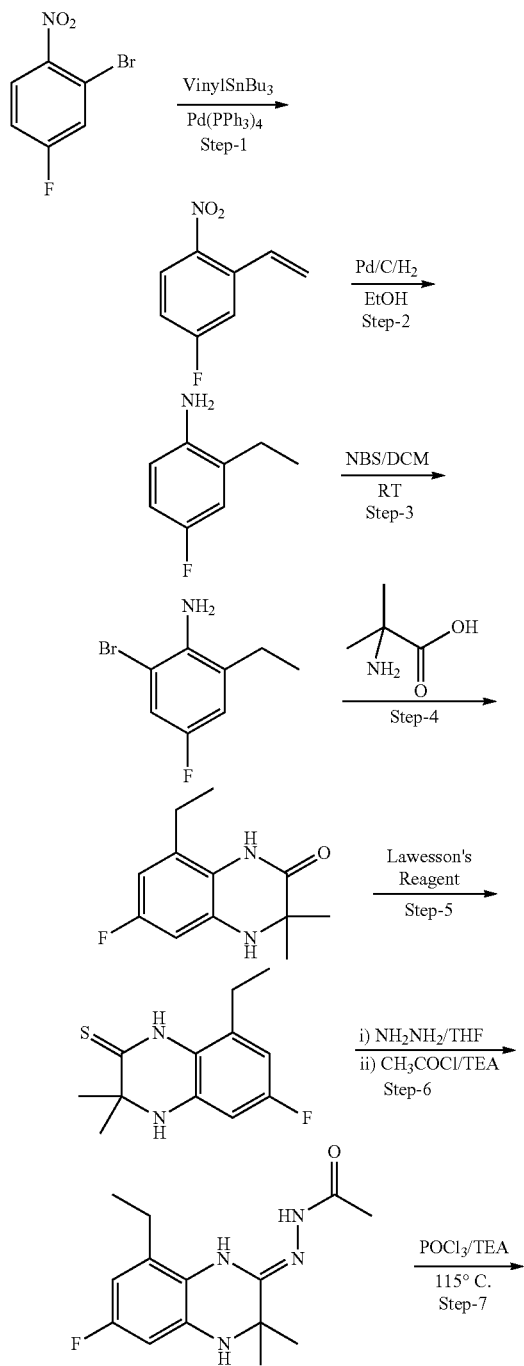

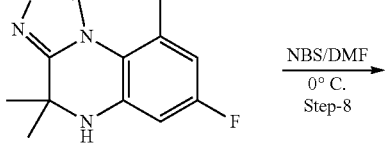

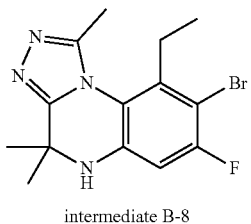 [SMILES: CCc1c(Br)c(F)cc2c1-n1c(C)nnc1C(C)(C)N2]

intermediate B-8

Step1: Stirred solution of 2-bromo-4-fluoro-1-nitrobenzene (5.0 g, 22.52 mmol, 1 eq) in toluene (110 mL) was degassed with Ar for 20 min. To the above solution tertiary butyl vinyl tin (7.8 g, 24.77 mmol, 1.1 eq) and Pd(PPh$_3$)$_4$ (0.832 ml, 0.72 mmol, 0.05 eq) was added, then stirred for 48 h at 90° C. and 2 4 h at RT. The solvent was evaporated and residue was dissolved in EtOAc (500 mL). Organic layer was washed with water and then with brine (100 mL). The organic layer was dried over Na$_2$SO$_4$, concentrated under reduced pressure to get the crude material which purified by column chromatography (230-400 mesh silica gel; 5% EtOAc/hexane; R$_f$-value-0.4) to afford 4-fluoro-1-nitro-2-vinylbenzene (3.5 g, 93%) as brown solid which still includes some tine reagents and starting material (were not removed completely).

Step2: Stirred solution of 4-fluoro-1-nitro-2-vinylbenzene (6.0 g) in EtOH (400 mL) was degassed with Ar for 20 min. To the above solution Pd/C (50% moist) (1.0 g, 20%) was added, purged with hydrogen in Parr shaker at 60 psi for 1 h. The solvent was evaporated and residue was dissolved in EtOAc (500 mL). Organic layer was washed with water many times and then with brine (100 mL). The organic layer was dried over Na$_2$SO$_4$, concentrated under reduced pressure to get the crude material which purified by column chromatography (230-400 mesh silica gel; 10% EtOAc/hexane; R$_f$-value-0.4) to afford 2-ethyl-4-fluoroaniline (2.0 g, 99%) as light brown solid which still includes some starting material.

Step3: A stirred solution of 2-ethyl-4-fluoroaniline (0.6 g, 4.314 mmol, 1 eq) in DCM (40 mL) at −10° C. was treated portion wise with solid N-bromosuccinimide (0.844 g, 4.745 mmol, 1.1 eq). Reaction mixture was allowed to warm to RT and stirred for 1.5 h. The reaction mixture was diluted with DCM (100 mL) and organic layer was washed with water (2×50 mL), brine (50 mL), dried over anhydrous Na$_2$SO$_4$ and the solvent was evaporated under reduced pressure. Crude product was purified by silica gel (230-400) column chromatography (5% EtOAc/hexane; R$_f$-value-0.4)) to afford 2-bromo-6-ethyl-4-fluoroaniline (0.875 g, 93%) as red color liquid.

Step4: A suspension of 2-bromo-6-ethyl-4-fluoroaniline (0.2 g, 0.917 mmol, 1 eq.), 2-amino-2-methylpropanoic acid (0.19 g, 1.834 mmol, 2 eq.), K$_3$PO$_4$ (0.39 g, 1.834 mmol, 2 eq.) and cuprous chloride (0.01 g, 0.092 mmol, 0.1 eq.) in dry DMSO (10 mL) in a sealed tube were deoxygenated with Ar for 20 min. Reaction mixture was then stirred at 100° C. for 16 h. The reaction mixture was filtered through celite bed and washed with EtOAc (50 mL). The filtrate was diluted with EtOAc (50 mL) and washed with water (3×50 mL), brine (100 mL), dried over anhydrous Na$_2$SO$_4$ and evaporated under reduced pressure to get the crude product which was purified by column chromatography (230-400 mesh silica gel; 20% EtOAc/hexane; R$_f$-value-0.4) to afford 8-ethyl-6-fluoro-3,3-dimethyl-3,4-dihydroquinoxalin-2(1H)-one (0.1 g, 49%) as brown solid.

Step5: To a solution of compound 8-ethyl-6-fluoro-3,3-dimethyl-3,4-dihydroquinoxalin-2(1H)-one (1.5 g, 6.76 mmol, 1 eq.) in toluene (25 mL) was added Lawesson's reagent (2.7 g, 6.76 mmol, 1.0 eq.) at RT and the reaction mixture was refluxed at 120° C. for 40 min. The reaction mixture was quenched with sat. NaHCO$_3$ solution (100 mL) followed by extraction with EtOAc (2×100 mL). Combined organic layer was washed with water (100 mL), brine (100 mL), dried over anhydrous Na$_2$SO$_4$ and evaporated to get the crude product which was purified by column chromatography (230-400 mesh silica gel; 20% EtOAc/hexane; R$_f$-value-0.4) to afford 8-ethyl-6-fluoro-3,3-dimethyl-3,4-dihydroquinoxaline-2(1H)-thione (1.5 g, 93%) as yellow solid.

Step6: To a stirring solution of 8-ethyl-6-fluoro-3,3-dimethyl-3,4-dihydroquinoxaline-2(1H)-thione (0.5 g, 2.1 mmol, 1 eq) in THF (30 mL) was drop wise added hydrazine hydrate (1 mL, 31.2 mmol, 14 eq) at 0° C. The reaction mixture then stirred for 16 h at RT. TEA (1.5 mL, 10.50 mmol, 5 eq) then added to the reaction mixture and stirred for another 10 min. Acetyl chloride (0.85 mL, 10.50 mmol, 5 eq) then added to the reaction mixture very slowly at 0° C. and then stirred for 2 h at RT. The reaction mixture was diluted with water (50 mL) and extracted with DCM (5×100 mL). The combine organic layer was washed with brine (100 mL). The organic layer dried over Na$_2$SO$_4$, concentrated under reduced pressure to get the crude material which purified by washing with diethyl ether to afford N'-(8-ethyl-6-fluoro-3,3-dimethyl-3,4-dihydroquinoxalin-2(1H)-ylidene)acetohydrazide (1.55 g, 89%) as a white solid.

Step7: To N'-(8-ethyl-6-fluoro-3,3-dimethyl-3,4-dihydroquinoxalin-2(1H)-ylidene)acetohydrazide (2.05 g, 7.37 mmol, 1 eq.) was added POCl$_3$ (7.1 mL) at 0° C. To the mixture was added TEA (1.0 mL) and it was stirred for 5 min at 0° C. The reaction mixture was gradually brought to RT and then it was refluxed overnight. After completion of the reaction the reaction mixture was cooled to 0° C. and portion wise added to cooled (0° C.) aqueous ammonia solution with vigorous stirring. After neutralization it was extracted with DCM (3×100 mL). Combined organic layer was washed with water (2×25 mL), brine (25 mL), dried over anhydrous Na$_2$SO$_4$ and the solvent was evaporated under reduced pressure. Crude product was purified by column chromatography (100-200 mesh silica gel; EtOAc; R$_f$-value-0.4) to afford 9-ethyl-7-fluoro-1,4,4-trimethyl-4,5-dihydro-[1,2,4]triazolo[4,3-a]quinoxaline (1 g, 52%) as yellow solid.

Step8: A stirred solution of 9-ethyl-7-fluoro-1,4,4-trimethyl-4,5-dihydro-[1,2,4]triazolo[4,3-a]quinoxaline (0.1 g, 3.84 mmol, 1 eq.) in DMF (20 mL) at −10° C. was treated portion wise over 10 min with solid N-bromosuccinimide (0.684 g, 0.47 mmol, 1 eq). Reaction mixture was allowed to warm to RT and stirred for 1 h. After completion of reaction (monitored by TLC), reaction mixture was diluted with EtOAc (50 mL) and organic layer was washed with water (5×10 mL), brine (20 mL), dried over anhydrous Na$_2$SO$_4$ and evaporated under reduced pressure. Crude product was purified by column chromatography (230-400 mesh silica gel; 5% MeOH/DCM; R$_f$-value-0.3) to afford 8-bromo-9-ethyl-7-fluoro-1,4,4-trimethyl-4,5-dihydro-[1,2,4]triazolo[4,3-a]quinoxaline (1.2 g, 93%) as off white solid.

1H-NMR (400 MHz; DMSO-D$_6$, 20° C.): δ 6.93 (s, 1H), 6.78-6.81 (1H), 2.80-2.93 (2H), 2.38 (s, 3H), 1.43 (bs, 6H), 0.95-0.98 (3H).

Synthesis of 1-benzyl-8-bromo-7,9-difluoro-4,4-dimethyl-4,5-dihydro-[1,2,4]triazolo[4,3-a]quinoxaline (Intermediate B-13)

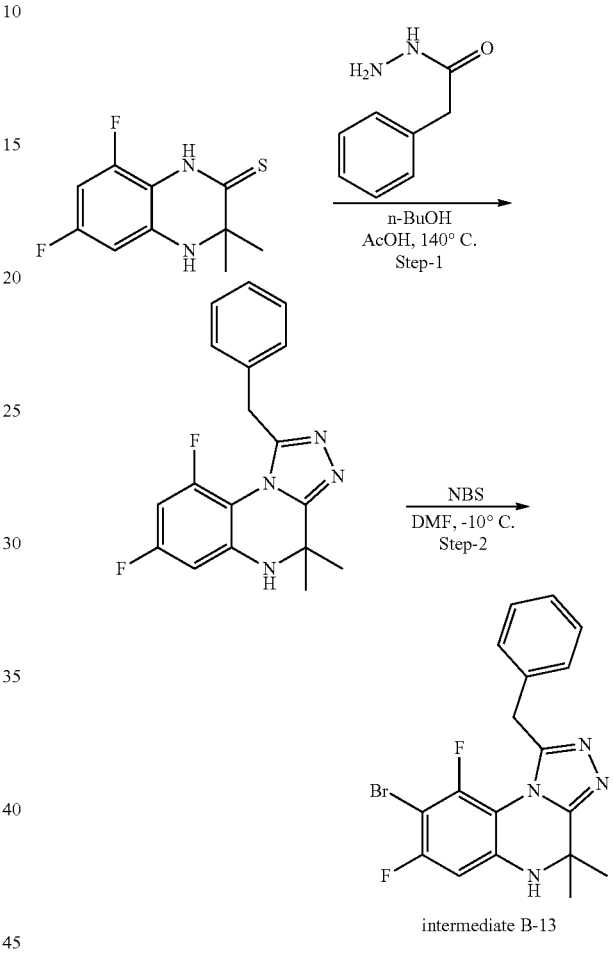

intermediate B-13

Step1: To a solution of 6,8-difluoro-3,3-dimethyl-3,4-dihydroquinoxaline-2(1H)-thione (1.5 g, 6.571 mmol, 1 eq) in n-BuOH (25 mL) was added 2-phenylacetohydrazide (3.25 g, 21.685 mmol, 3.3 eq) followed by addition of acetic acid (2.5 mL) and then the reaction mixture was stirred at 140° C. for 16 h. After completion of reaction (monitored by TLC), reaction mixture was diluted with water (50 mL) and extracted with EtOAc (2×50 mL). Combined organic layers were washed with water (50 mL), brine (50 mL), dried over anhydrous Na$_2$SO$_4$ and the solvent was evaporated to get the crude product which was purified by combiflash column chromatography (7% MeOHl/DCM; R$_f$-value-0.3) to afford 1-benzyl-7,9-difluoro-4,4-dimethyl-4,5-dihydro-[1,2,4]triazolo[4,3-a]quinoxaline (1 g, 47%) as off white solid.

Step2: A stirred solution of 1-benzyl-7,9-difluoro-4,4-dimethyl-4,5-dihydro-[1,2,4]triazolo[4,3-a]quinoxaline (1.0 g, 3.067 mmol, 1 eq) in DMF (8 mL) at −10° C. was treated portion wise over 10 min with solid N-bromosuccinimide (0.573 g, 3.22 mmol, 1.05 eq). Reaction mixture was allowed to warm to RT and stirred for 1.5 h. After completion of reaction (monitored by TLC), reaction mixture was diluted with EtOAc (100 mL) and organic layers were washed with water (5×20 mL), brine (20 mL), dried over anhydrous Na$_2$SO$_4$ and the solvent was evaporated under reduced pressure. Crude product was purified by combiflash column chromatography (5% MeOH/DCM; R$_f$-value-0.3) to afford 1-benzyl-8-bromo-7,9-difluoro-4,4-dimethyl-4,5-dihydro-[1,2,4]triazolo[4,3-a]quinoxaline (0.8 g, 64.5%) as off white solid.

1H-NMR (400 MHz; DMSO-D$_6$, 20° C.): δ 7.15-7.26 (4H), 7.03-7.06 (2H), 6.72 (d, 1H), 4.36 (d, 2H), 1.48 (s, 6H).

Synthesis of 8-bromo-7,9-difluoro-4,4-dimethyl-1-(pyridin-4-ylmethyl)-4,5-dihydro-[1,2,4]triazolo[4,3-a]quinoxaline (Intermediate B-14)

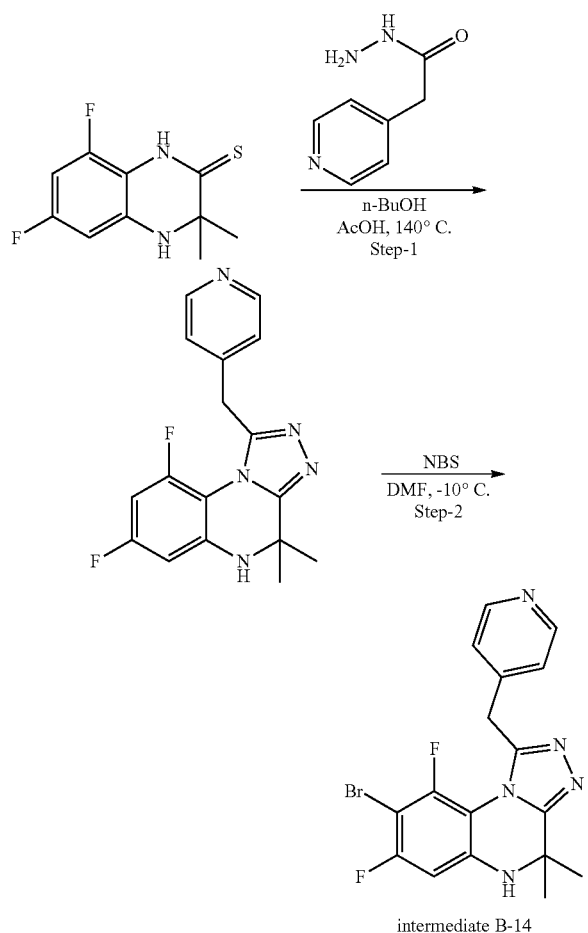

intermediate B-14

Step1: To a solution of 6,8-difluoro-3,3-dimethyl-3,4-dihydroquinoxaline-2(1H)-thione (1.5 g, 6.5 mmol, 1 eq.) in n-BuOH (50 mL) was added pyridin-4-yl-acetic acid hydrazide (3.27 g, 21 mmol, 3.3 eq) followed by addition of acetic acid (5 mL) and then the reaction mixture was stirred at 140° C. for 16 h. After completion of reaction (monitored by TLC), reaction mixture was diluted with water (100 mL) and extracted with EtOAc (2×100 mL), the combined organic layers were washed with water (100 mL), brine (100 mL), dried over anhydrous Na$_2$SO$_4$ and the solvent was evaporated to get the crude product which was purified by column chromatography (100-200 mesh silica gel; 10% MeOH/DCM; R$_f$-value-0.5) to afford 7,9-difluoro-4,4-dimethyl-1-(pyridin-4-ylmethyl)-4,5-dihydro-[1,2,4]triazolo[4,3-a]quinoxaline (1 g, 47%) as off white solid.

Step2: A stirred solution of 7,9-difluoro-4,4-dimethyl-1-(pyridin-4-ylmethyl)-4,5-dihydro-[1,2,4]triazolo[4,3-a]quinoxaline (1 g, 3.05 mmol, 1 eq.) in DMF (30 mL) at −10° C. was treated portion wise over 10 min with solid N-bromosuccinimide (0.598 g, 3.36 mmol, 1.1 eq.). Reaction mixture was allowed to warm to RT and stirred for 16 h. After completion of the reaction (monitored by TLC), the reaction mixture was diluted with water (100 mL) and extracted with EtOAc (3×50 mL). Combined organic layers were washed with water (50 mL), brine (50 mL), dried over anhydrous Na$_2$SO$_4$ and the solvent was evaporated under reduced pressure. The crude product was purified by column chromatography (100-200 mesh silica gel; 10% MeOH/DCM; R$_f$-value-0.4) to afford 8-bromo-7,9-difluoro-4,4-dimethyl-1-(pyridin-4-ylmethyl)-4,5-dihydro-[1,2,4]triazolo[4,3-a]quinoxaline (0.48 g, 39%) as brown solid.

1H-NMR (400 MHz; DMSO-D$_6$, 20° C.): δ 8.38-8.41 (2H), 7.55 (d, 1H), 7.55 (d, 1H), 7.29 (dd, 1H), 7.24 (s, 1H), 6.77 (d, 1H), 4.34-4.36 (2H), 1.49 (s, 6H).

Synthesis of 8-bromo-7,9-difluoro-4,4-dimethyl-1-(pyridin-3-ylmethyl)-4,5-dihydro-[1,2,4]triazolo[4,3-a]quinoxaline (Intermediate B-15)

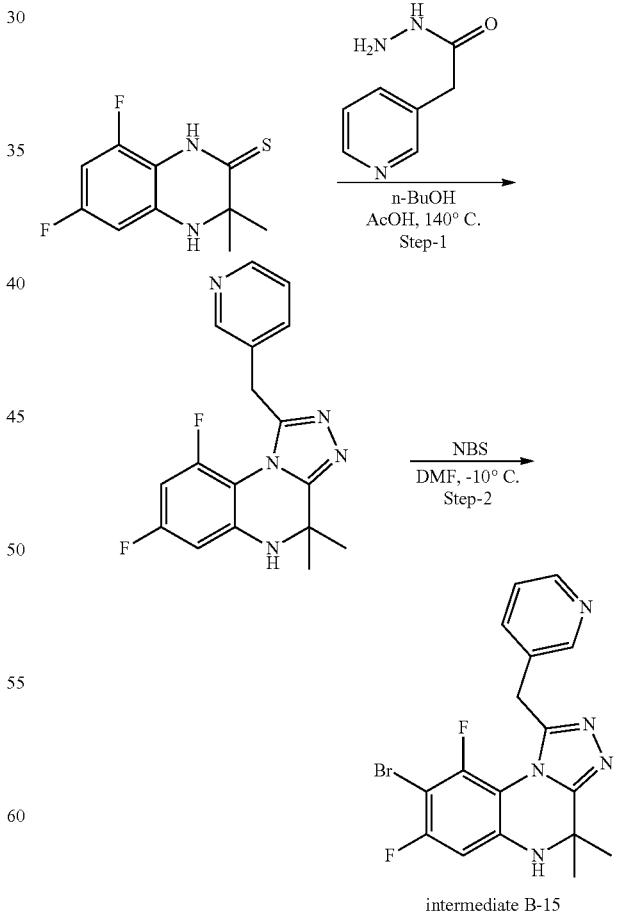

intermediate B-15

Step1: To a solution of 6,8-difluoro-3,3-dimethyl-3,4-dihydroquinoxaline-2(1H)-thione (1.5 g, 6.5 mmol, 1 eq.) in n-BuOH (50 mL) was added compound pyridin-3-yl-acetic acid hydrazide (3.27 g, 21 mmol, 3.3 eq) followed by addition of acetic acid (5 mL) and then the reaction mixture was stirred at 140° C. for 16 h. After completion of reaction (monitored by TLC), reaction mixture was diluted with water (100 mL) and extracted with EtOAc (2×100 mL), the combined organic layer was washed with water (100 mL), brine (100 mL), dried over anhydrous $Na_2SO_4$ and evaporated to get the crude product which was purified by column chromatography (100-200 mesh silica gel; 10% MeOH/DCM; $R_f$-value-0.5) to afford 7,9-difluoro-4,4-dimethyl-1-(pyridin-3-ylmethyl)-4,5-dihydro-[1,2,4]triazolo[4,3-a]quinoxaline (0.3 g, 47%) as off white solid.

Step2: A stirred solution of 7,9-difluoro-4,4-dimethyl-1-(pyridin-3-ylmethyl)-4,5-dihydro-[1,2,4]triazolo[4,3-a]quinoxaline (1 g, 3.05 mmol, 1 eq.) in DMF (30 mL) at −10° C. was treated portion wise over 10 min with solid N-bromosuccinimide (0.598 g, 3.36 mmol, 1.1 eq.). Reaction mixture was allowed to warm to RT and stirred for 16 h. After completion of the reaction (monitored by TLC), the reaction mixture was diluted with water (100 mL) and extracted with EtOAc (3×50 mL). Combined organic layers was washed with water (50 mL), brine (50 mL), dried over anhydrous $Na_2SO_4$ and evaporated under reduced pressure. The crude product was purified by column chromatography (100-200 mesh silica gel; 10% MeOH/DCM; $R_f$-value-0.4) to afford 8-bromo-7,9-difluoro-4,4-dimethyl-1-(pyridin-3-ylmethyl)-4,5-dihydro-[1,2,4]triazolo[4,3-a]quinoxaline (0.8 g, 65%) as brown solid.

1H-NMR (400 MHz; DMSO-$D_6$, 20° C.): δ 8.44 (d, 1H), 7.25 (s, 1H), 7.14 (d, 2H), 6.76 (d, 1H), 4.37-4.39 (2H), 1.49 (s, 6H), 1.123 (s, 3H).

Synthesis of 8-bromo-7,9-difluoro-4,4-dimethyl-1-(pyridin-2-ylmethyl)-4,5-dihydro-[1,2,4]triazolo[4,3-a]quinoxaline (Intermediate B-16)

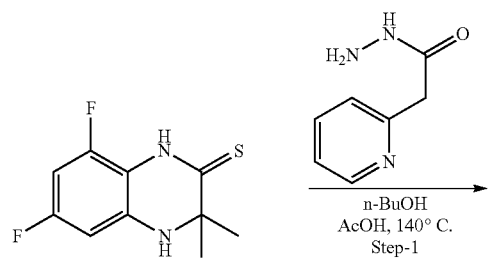

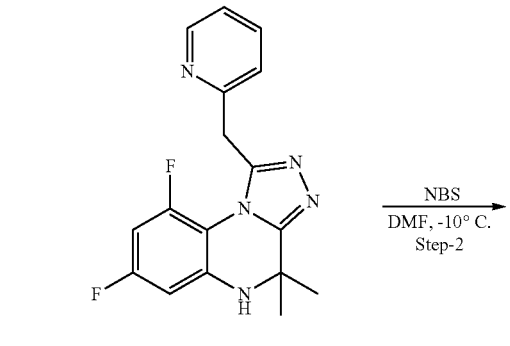

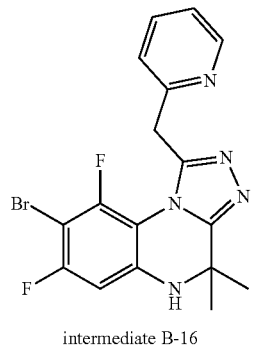

intermediate B-16

Step1: To a solution of 6,8-difluoro-3,3-dimethyl-3,4-dihydroquinoxaline-2(1H)-thione (1.5 g, 6.5 mmol, 1 eq.) in n-BuOH (50 mL) was added compound pyridin-2-yl-acetic acid hydrazide (3.27 g, 21 mmol, 3.3 eq) followed by addition of acetic acid (5 mL) and then the reaction mixture was stirred at 140° C. for 16 h. After completion of reaction (monitored by TLC), reaction mixture was diluted with water (100 mL) and extracted with EtOAc (2×100 mL), the combined organic layer was washed with water (100 mL), brine (100 mL), dried over anhydrous $Na_2SO_4$ and the solvent was evaporated to get the crude product which was purified by cColumn chromatography (100-200 mesh silica gel; 10% MeOH/DCM; $R_f$-value-0.5) to afford 7,9-difluoro-4,4-dimethyl-1-(pyridin-2-ylmethyl)-4,5-dihydro-[1,2,4]triazolo[4,3-a]quinoxaline (0.3 g, 14%) as off white solid.

Step2: A stirred solution of 7,9-difluoro-4,4-dimethyl-1-(pyridin-2-ylmethyl)-4,5-dihydro-[1,2,4]triazolo[4,3-a]quinoxaline (1 g, 3.05 mmol, 1 eq.) in DMF (30 mL) at −10° C. was treated portion wise over 10 min with solid N-bromosuccinimide (0.598 g, 3.36 mmol, 1.1 eq.). Reaction mixture was allowed to warm to RT and stirred for 16 h. After completion of the reaction (monitored by TLC), the reaction mixture was diluted with water (100 mL) and extracted with EtOAc (3×50 mL). Combined organic layers were washed with water (50 mL), brine (50 mL), dried over anhydrous $Na_2SO_4$ and the solvent was evaporated under reduced pressure. The crude product was purified by column chromatography (100-200 mesh silica gel; 10% MeOH/DCM; $R_f$-value-0.4) to afford 8-bromo-7,9-difluoro-4,4-dimethyl-1-(pyridin-2-ylmethyl)-4,5-dihydro-[1,2,4]triazolo[4,3-a]quinoxaline (0.3 g, 56%) as brown solid.

Synthesis of 8-bromo-7-fluoro-1-(methoxymethyl)-4,4,9-trimethyl-4,5-dihydro-[1,2,4]triazolo[4,3-a]quinoxaline (Intermediate B-17)

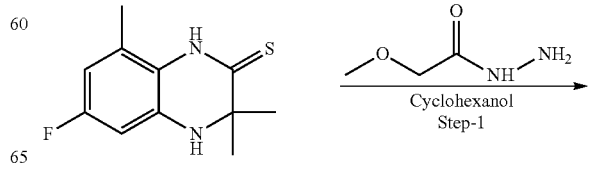

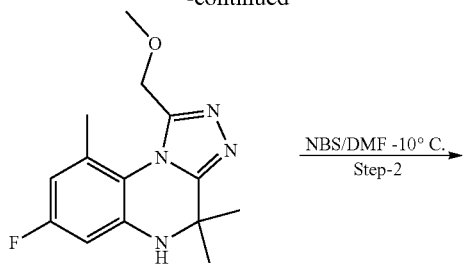

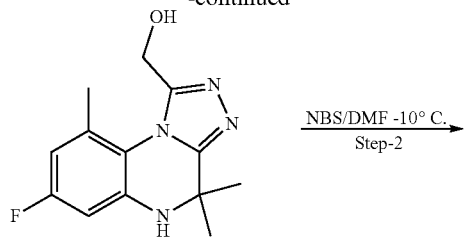

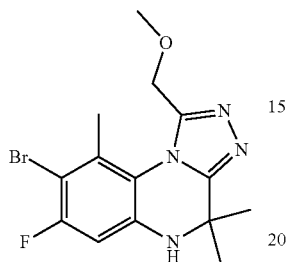

intermediate B-17

Step1: To a stirring solution of 6-fluoro-3,3,8-trimethyl-3,4-dihydroquinoxaline-2(1H)-thione (4.5 g, 20.09 mmol, 1 eq) in cyclohexanol (20 mL) was added 2-methoxyacetohydrazide (2.5 g, 24.10 mmol, 1.2 eq). The reaction mixture then stirred at 160° C. for 6 h. The reaction mixture was cooled to RT, diluted with EtOAc (100 mL) and washed with water (2×50 mL) followed by brine (50 mL). The organic layer was dried over $Na_2SO_4$, concentrated under reduced pressure to get the crude material which was purified by silica gel (230-400) column chromatography (5% MeOH/DCM; $R_f$-value-0.4) to afford 7-fluoro-1-(methoxymethyl)-4,4,9-trimethyl-4,5-dihydro-[1,2,4]triazolo[4,3-a]quinoxaline (1.1 g, 20%) as off white solid.

Step2: A stirred solution of 7-fluoro-1-(methoxymethyl)-4,4,9-trimethyl-4,5-dihydro-[1,2,4]triazolo[4,3-a]quinoxaline (1.1 g, 3.96 mmol, 1 eq) in DMF (12 mL) at −10° C. was treated portion wise over 10 min with solid N-bromosuccinimide (0.744 g, 4.18 mmol, 1.05 eq). Reaction mixture was allowed to warm to RT and stirred for 1.5 h. After completion of reaction (monitored by LCMS), reaction mixture was diluted with EtOAc (100 mL) and organic layers were washed with water (5×30 mL), brine (30 mL), dried over anhydrous $Na_2SO_4$ and the solvent was evaporated under reduced pressure. Crude product was purified by silica gel (230-400) column chromatography (5% MeOH/DCM; $R_f$-value-0.3) to afford 8-bromo-7-fluoro-1-(methoxymethyl)-4,4,9-trimethyl-4,5-dihydro-[1,2,4]triazolo[4,3-a]quinoxaline (1.0 g, 71%) as off white solid.

Synthesis of (8-bromo-7-fluoro-4,4,9-trimethyl-4,5-dihydro-[1,2,4]triazolo[4,3-a]quinoxalin-1-yl)MeOH (Intermediate B-18)

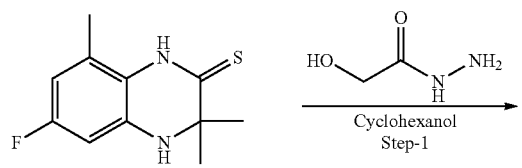

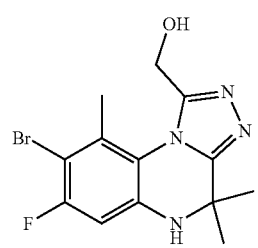

intermediate B-18

Step1: To a stirring solution of 6-fluoro-3,3,8-trimethyl-3,4-dihydroquinoxaline-2(1H)-thione (see example 69 for synthesis) (7.7 g, 34.37 mmol, 1 eq) in cyclohexanol (34.4 mL) was added 2-hydroxyacetohydrazide (3.77 g, 42.25 mmol, 1.2 eq). The reaction mixture was stirred at 160° C. for 6 h. The reaction mixture was cooled to RT, diluted with EtOAc (34.4 mL) and washed with water (2×50 mL) followed by brine (50 mL). The organic layer was dried over $Na_2SO_4$, concentrated under reduced pressure to get the crude material which was purified by silica gel (230-400) column chromatography (5% MeOH/DCM; $R_f$-value-0.3) to afford (7-fluoro-4,4,9-trimethyl-4,5-dihydro-[1,2,4]triazolo[4,3-a]quinoxalin-1-yl)MeOH (0.95 g, 11%) as off white solid.

Step2: A stirred solution of (7-fluoro-4,4,9-trimethyl-4,5-dihydro-[1,2,4]triazolo[4,3-a]quinoxalin-1-yl)MeOH (1.745 g, 6.66 mmol, 1 eq) in DMF (25 mL) at −10° C. was treated portion wise over 10 min with solid N-bromosuccinimide (1.24 g, 6.99 mmol, 1.05 eq). Reaction mixture was allowed to warm to RT and stirred for 1.5 h. After completion of reaction (monitored by LCMS), reaction mixture was diluted with EtOAc (150 mL) and organic layers were washed with water (5×30 mL), brine (30 mL), dried over anhydrous $Na_2SO_4$ and the solvent was evaporated under reduced pressure. Crude product was purified by silica gel (230-400) column chromatography (5% MeOH/DCM; $R_f$-value-0.3) to afford (8-bromo-7-fluoro-4,4,9-trimethyl-4,5-dihydro-[1,2,4]triazolo[4,3-a]quinoxalin-1-yl)MeOH (1.45 g, 63.8%) as off white solid.

Synthesis of 1-(8-bromo-7-fluoro-4,4,9-trimethyl-4, 5-dihydro-[1,2,4]triazolo[4,3-a]quinoxalin-1-yl)ethanol (Intermediate B-19)

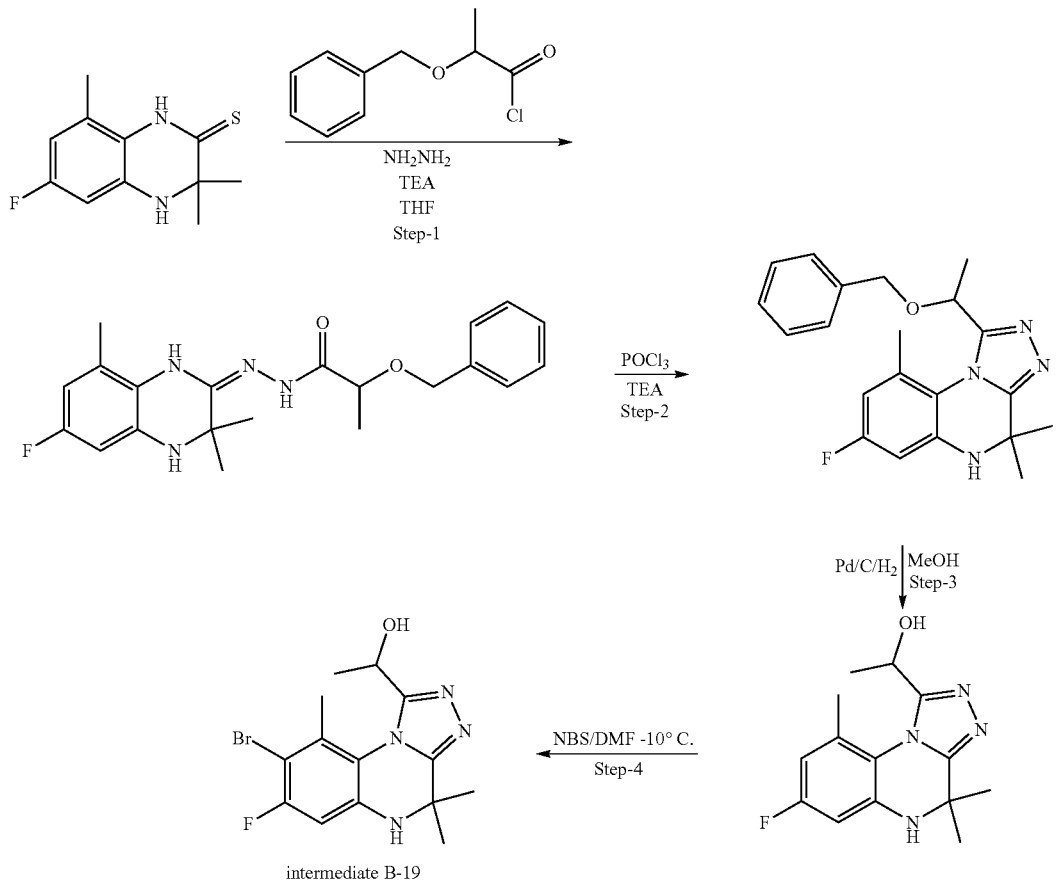

intermediate B-19

Step1: To a stirring solution of 6-fluoro-3,3,8-trimethyl-3,4-dihydroquinoxaline-2(1H)-thione (6.5 g, 29 mmol, 1 eq) in THF (36 mL) was drop wise added hydrazine hydrate (7.25 mL, 145 mmol, 5 eq) at 0° C. The reaction mixture was stirred for 16 h at RT. TEA (19.73 mL, 145 mmol, 5 eq) was added to the reaction mixture and stirred for another 10 min. 2-(Benzyloxy)propanoyl chloride (7.5 mL, 72.5 mmol, 2.5 eq) was added to the reaction mixture very slowly at 0° C. and then stirred for 2 h at RT. The reaction mixture diluted with water (50 mL) and extracted with DCM (3×100 mL). The combined organic layers were washed with brine (100 mL). The organic layer was dried over $Na_2SO_4$, concentrated under reduced pressure to get the crude material which purified by washed with diethyl ether to afford 2-(benzyloxy)-N'-(6-fluoro-3,3,8-trimethyl-3,4-dihydroquinoxalin-2(1H)-ylidene)propanehydrazide (7.5 g, 67%) as a off white solid.

Step2: 2-(benzyloxy)-N'-(6-fluoro-3,3,8-trimethyl-3,4-dihydroquinoxalin-2(1H)-ylidene)propanehydrazide (2.5 g, 6.51 mmol, 1 eq) was taken in round bottom flax (50 mL) and then cooled to −10° C. Phosphorus oxychloride (6.23 mL, 65.1 mmol, 10 eq) was then added drop wise to the compound followed by drop wise addition of TEA (0.903 mL, 6.51 mmol, 1 eq). After that the reaction mixture was stirred at −10° C. for 10 min and then 10 min at RT and finally at reflux condition for 4 h. The reaction mixture was cooled to 0° C. and then it was drop wise added into crushed ice with constant stirring. To this aqueous part was slowly added cold ammonium solution (100 mL). The aqueous part was extracted with DCM (2×100 mL). The combined organic layers were washed with brine (100 mL). The organic layer was dried over anhydrous $Na_2SO_4$, concentrated under reduced pressure to get the crude material which was purified by column chromatography (230-400 mesh silica gel; 5% MeOH/DCM; $R_f$-value-0.4) to afford 1-(1-(benzyloxy)ethyl)-7-fluoro-4,4,9-trimethyl-4,5-dihydro-[1,2,4]triazolo[4,3-a]quinoxaline (1.0 g, 42%) as yellow solid.

Step3: A stirring solution of 1-(1-(benzyloxy)ethyl)-7-fluoro-4,4,9-trimethyl-4,5-dihydro-[1,2,4]triazolo[4,3-a] quinoxaline (2.5 g, 6.83 mmol, 1 eq) in MeOH (250 mL) was deoxygenated well by Ar for 10 min. Pd/C (0.5 g) was added to the reaction mixture and the mixture was again deoxygenated for 10 min. Finally the reaction mixture was set in par apparatus. The reaction mixture was shaked at RT for 24 h under hydrogen atmosphere at 50 psi. The reaction mixture was filtered through celite bed and washed with MeOH (100 mL), the filtrate was concentrated under reduced pressure to get the pure 1-(7-fluoro-4,4,9-trimethyl-4,5-dihydro-[1,2,4]triazolo[4,3-a]quinoxalin-1-yl)ethanol (1.0 g, 53%) as white sold.

Step4: A stirred solution of 1-(7-fluoro-4,4,9-trimethyl-4,5-dihydro-[1,2,4]triazolo[4,3-a]quinoxalin-1-yl)ethanol (1.0 g, 3.8 mmol, 1 eq) in DMF (15 mL) at −10° C. was treated portion wise over 10 min with solid N-bromosuccinimide (0.71 g, 3.99 mmol, 1.05 eq). Reaction mixture was allowed to warm to RT and stirred for 1.5 h. After completion of reaction (monitored by LCMS), reaction mixture was diluted with EtOAc (100 mL) and organic layers were washed with water (5×30 mL), brine (30 mL), dried over anhydrous Na$_2$SO$_4$ and the solvent was evaporated under reduced pressure. Crude product was purified by silica gel (230-400) column chromatography (5% MeOH/DCM; R$_f$-value-0.3) to afford 1-(8-bromo-7-fluoro-4,4,9-trimethyl-4,5-dihydro-[1,2,4]triazolo[4,3-a]quinoxalin-1-yl)ethanol (0.95 g, 70%) as off white solid.

Synthesis of 8-bromo-7-fluoro-1-(2-methoxyethyl)-4,4,9-trimethyl-4,5-dihydro-[1,2,4]triazolo[4,3-a]quinoxaline (Intermediate B-20)

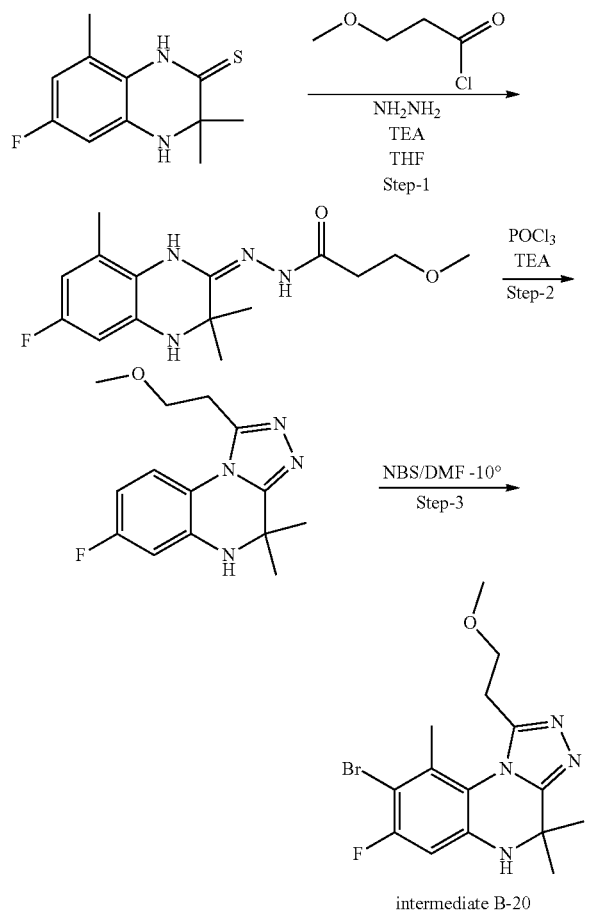

intermediate B-20

Step1: To a stirring solution of 6-fluoro-3,3,8-trimethyl-3,4-dihydroquinoxaline-2(1H)-thione (3.0 g, 13.5 mmol, 1 eq) in THF (18 mL) was drop wise added hydrazine hydrate (3 mL, 67.56 mmol, 5 eq) at 0° C. The reaction mixture then stirred for 16 h at RT. TEA (15 mL, 94.57 mmol, 7 eq) was added to the reaction mixture and stirred for another 10 min. 3-methoxypropanoyl chloride (4.9 g, 40.5 mmol, 3 eq) was added very slowly at 0° C. and then stirred for 2 h at RT. The reaction mixture was diluted with water (50 mL) and extracted with DCM (3×100 mL). The combined organic layers were washed with brine (100 mL). The organic layer was dried over Na$_2$SO$_4$, concentrated under reduced pressure to get the crude material which purified by washing with diethyl ether to afford N'-(6-fluoro-3,3,8-trimethyl-3,4-dihydroquinoxalin-2(1H)-ylidene)-3-methoxypropanehydrazide (2.5 g, 60%) as a off white solid.

Step2 and Step3: N'-(6-fluoro-3,3,8-trimethyl-3,4-dihydroquinoxalin-2(1H)-ylidene)-3-methoxypropanehydrazide—was converted to intermediate B-20 following general synthetic route described for intermediate B-12 (step2 and step3). 1H-NMR (400 MHz; DMSO-D$_6$, 20° C.): δ 6.81-6.87 (2H), 3.60 (m, 2H), 3.15 (s, 3H), 2.37 (s, 3H), 1.20-1.65 (8H).

Synthesis of 8-bromo-1-(cyclopropylmethyl)-7,9-difluoro-4,4-dimethyl-4,5-dihydro-[1,2,4]triazolo[4,3-a]quinoxaline (Intermediate B-21)

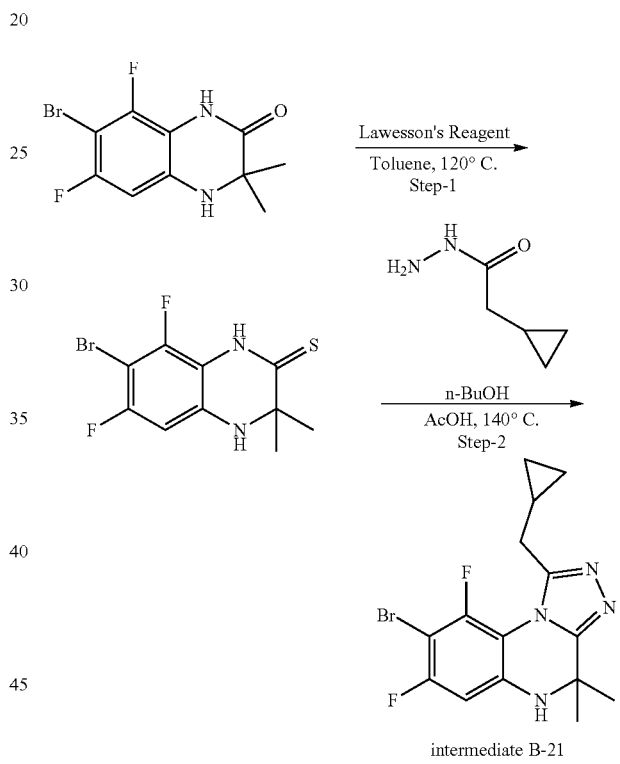

intermediate B-21

Step1: To a solution of 7-bromo-6,8-difluoro-3,3-dimethyl-3,4-dihydroquinoxalin-2(1H)-one (4 g, 13.79 mmol, 1 eq.) in toluene (50 mL) was added Lawesson's reagent (8.36 g, 20.69 mmol, 1.5 eq.) at RT and the reaction mixture was refluxed at 120° C. for 40 min. After completion of reaction (monitored by TLC), the reaction mixture was quenched with sat. NaHCO$_3$ solution (50 mL) followed by extraction with EtOAc (3×75 mL). Combined organic layers were washed with water (100 mL), brine (100 mL), dried over anhydrous Na$_2$SO$_4$ and the solvent was evaporated to get the crude product which was purified by column chromatography (100-200 mesh silica gel; 15% EtOAc/hexane; R$_f$-value-0.3) to afford 7-bromo-6,8-difluoro-3,3-dimethyl-3,4-dihydroquinoxaline-2(1H)-thione (3.1 g, 73%) as yellow solid.

Step2: To a solution of 7-bromo-6,8-difluoro-3,3-dimethyl-3,4-dihydroquinoxaline-2(1H)-thione (0.5 g, 1.63 mmol, 1 eq.) in n-BuOH (10 mL) was added 2-cyclopropylacetohydrazide (0.614 g, 5.39 mmol, 3.3 eq) followed by addition of acetic acid (1 mL) and then the reaction mixture was stirred at 140° C. for 16 h. After completion of reaction (monitored by TLC), reaction mixture was diluted with water (20 mL) and extracted with EtOAc (3×30 mL). Combined organic layers were washed with water (30 mL), brine (30 mL), dried over anhydrous Na$_2$SO$_4$ and the solvent was evaporated to get the crude product which was purified by column chromatography (100-200 mesh silica gel; EtOAc; R$_f$-value-0.2) to afford 8-bromo-1-(cyclopropyhn-ethyl)-7,9-difluoro-4,4-dimethyl-4,5-dihydro-[1,2,4]triazolo[4,3-a]quinoxaline (0.35 g, 79%) as white solid.

Synthesis of 8-bromo-1-cyclopropyl-7,9-difluoro-4,4-dimethyl-4,5-dihydro-[1,2,4]triazolo[4,3-a]quinoxaline (Intermediate B-22)

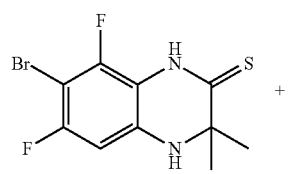

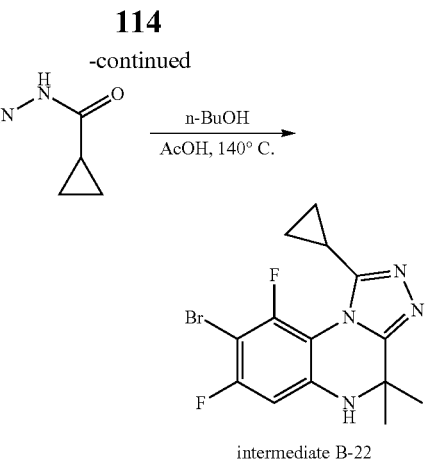

intermediate B-22

Starting from 7-bromo-6,8-difluoro-3,3-dimethyl-3,4-dihydroquinoxaline-2(1H)-thione and cyclopropanecarbohydrazide Intermediate B-22 was synthesized in analogy to synthesis described for intermediate B-21 (step2).

Synthesis of 8-bromo-1,4,4,9-tetramethyl-7-(trifluoromethyl)-4,5-dihydro-[1,2,4]triazolo[4,3-a]quinoxaline (Intermediate B-23)

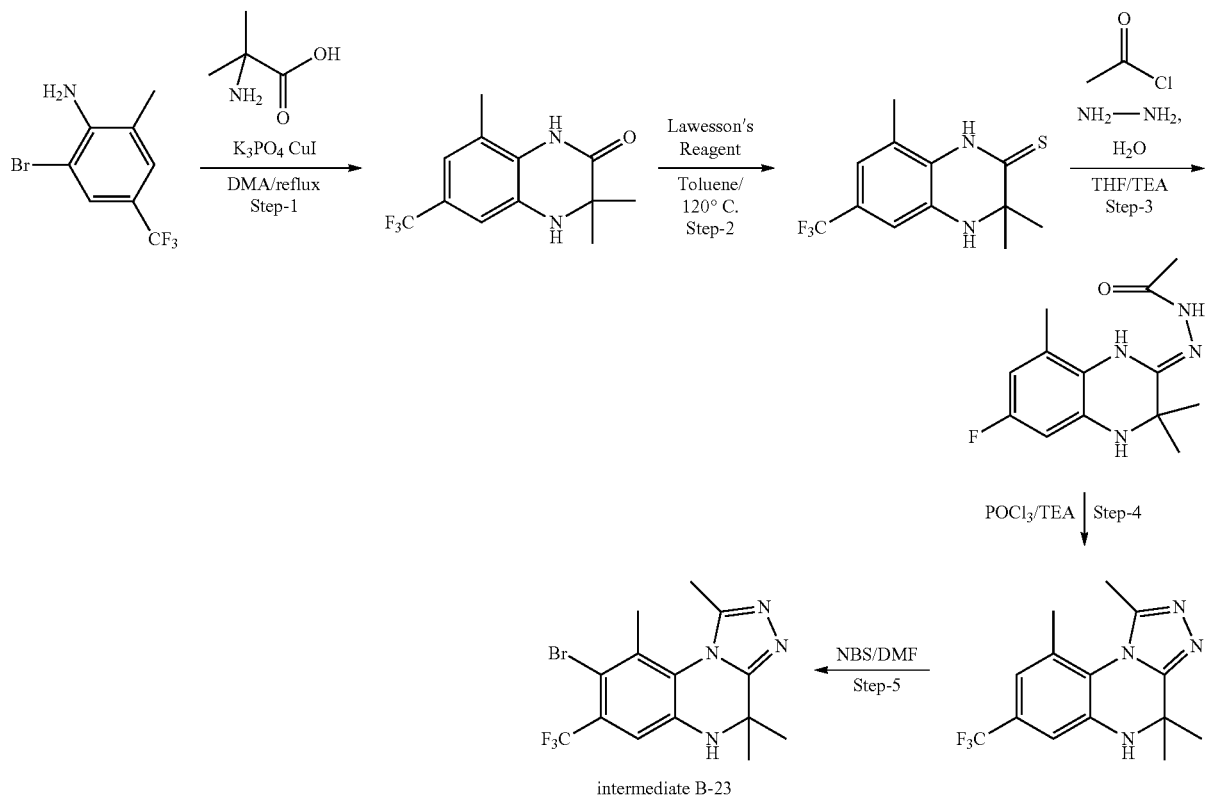

intermediate B-23

Starting from 2-bromo-6-methyl-4-(trifluoromethyl)aniline intermediate B-23 was synthesized in analogy to synthesis described for intermediate B-4 (step2 to step6).

The intermediates in Table 3 were synthesized in analogy to the synthesis depicted in Reaction Scheme 1:

| Intermediate | Structure | NMR |
|---|---|---|
| Int-B-24 | 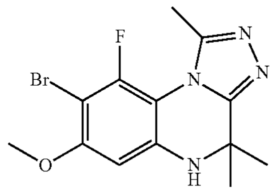 | $^1$H NMR (DMSO-d$_6$) δ: 6.94 (d, 1H), 6.58 (d, 1H), 3.85 (s, 3H), 2.49 (d, 3H), 1.47 (s, 6H) |
| Int-B-25 | 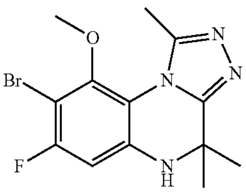 [SMILES: COc1c(Br)c(F)cc2c1-n1c(C)nnc1C(C)(C)N2] | $^1$H NMR (DMSO-d$_6$) δ: 7.00 (s, 1H), 6.77 (d, 1H), 3.61 (s, 3H), 2.47 (s, 3H), 1.47 (s, 6H) |
| Int-B-26 | 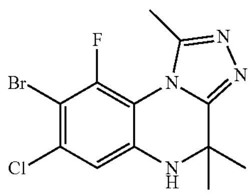 [SMILES: Cc1nnc2n1-c1c(cc(Cl)c(Br)c1F)NC2(C)C] | $^1$H NMR (DMSO-d$_6$) δ: 7.15 (s, 1H), 7.04 (s, 1H), 2.52 (s, 3H), 1.48 (s, 6H). |
| Int-B-27 | 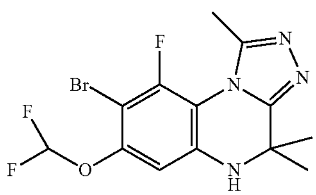 [SMILES: Cc1nnc2n1-c1c(cc(OC(F)F)c(Br)c1F)NC2(C)C] | $^1$H NMR (DMSO-d$_6$) δ: 7.29 (t, 1H), 7.19 (d, 1H), 6.81 (s, 1H), 2.52 (d, 3H), 1.48 (s, 6H) |
| Int-B-29 | 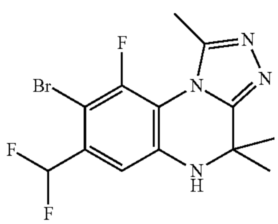 [SMILES: Cc1nnc2n1-c1c(cc(C(F)F)c(Br)c1F)NC2(C)C] | $^1$H NMR (DMSO-d$_6$) δ: 7.24 (d, 1H), 7.14 (d, 1H), 7.12 (t, 1H), 2.54 (d, 3H), 1.49 (s, 6H) |
| Int-B-31 | 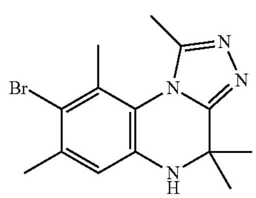 [SMILES: Cc1cc2c(c(C)c1Br)-n1c(C)nnc1C(C)(C)N2] | $^1$H NMR (DMSO-d$_6$) δ: 6.85 (s, 1H), 6.48 (s, 1H), 2.39 (s, 3H), 2.35 (s, 3H), 2.33 (s, 3H), 1.42 (s, 6H) |
| Int-B-32 | 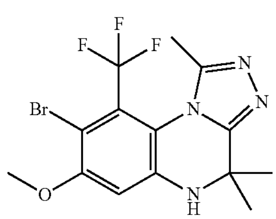 | $^1$H NMR (DMSO-d$_6$) δ: 7.24 (s, 1H), 6.94 (s, 1H), 3.87 (s, 3H), 2.32 (s, 3H), 1.69 (s, 3H), 1.23 (s, 3H). |

-continued
| Intermediate | Structure | NMR |
|---|---|---|
| Int-B-33 | 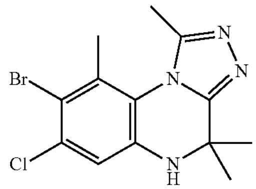 [SMILES: Cc1c(Br)c(Cl)cc2c1-n1c(C)nnc1C(C)(C)N2] | $^1$H NMR (DMSO-d$_6$) δ: 7.07 (s, 1H), 6.82 (s, 1H), 2.39 (s, 6H), 1.43 (bs, 6H). |
| Int-B-34 | 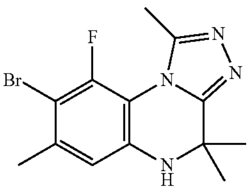 [SMILES: Cc1cc2c(c(F)c1Br)-n1c(C)nnc1C(C)(C)N2] | $^1$H NMR (CDCl$_3$) δ: 6.60 (s, 1H), 4.06 (bs, 1H), 2.62 (d, 3H), 2.37 (s, 3H), 1.59 (s, 6H). |
| Int-B-35 | 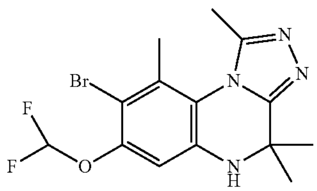 [SMILES: Cc1c(Br)c(OC(F)F)cc2c1-n1c(C)nnc1C(C)(C)N2] | $^1$H NMR (DMSO-d$_6$) δ: 7.22 (t, 1H), 6.84 (s, 1H), 6.83 (s, 1H), 2.40 (s, 3H), 2.39 (s, 3H), 1.44 (s, 6H) |
| Int-B-36 | 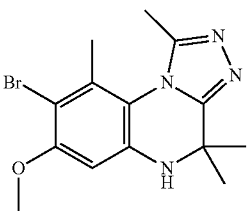 [SMILES: COc1cc2c(c(C)c1Br)-n1c(C)nnc1C(C)(C)N2] | $^1$H NMR (DMSO-d$_6$) δ: 6.61 (s, 1H), 6.59 (s, 1H), 3.81 (s, 3H), 2.33 (s, 3H), 2.32 (s, 3H), 1.41 (bs, 6H). |
| Int-B-37 | 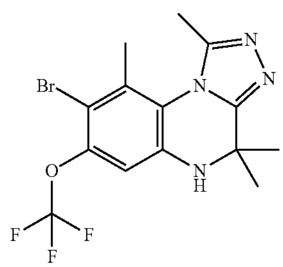 [SMILES: Cc1c(Br)c(OC(F)(F)F)cc2c1-n1c(C)nnc1C(C)(C)N2] | $^1$H NMR (DMSO-d$_6$) δ: 7.01 (s, 1H), 6.95 (s, 1H), 2.40 (s, 6H), 1.43 (bs, 6H). |
Synthesis of 8-bromo-9-(difluoromethyl)-7-fluoro-1,4,4-trimethyl-4,5-dihydro-[1,2,4]triazolo[4,3-a]quinoxaline (Intermediate B-28)
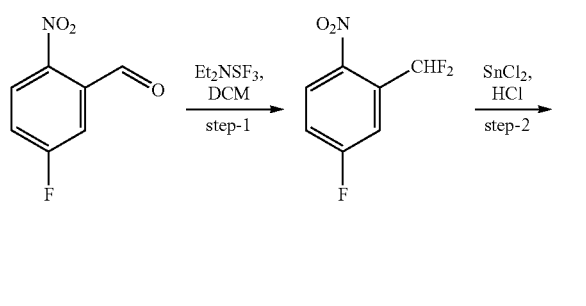
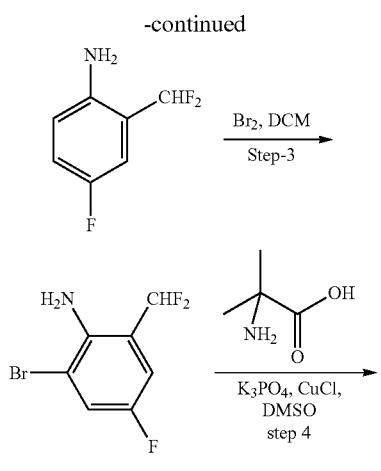

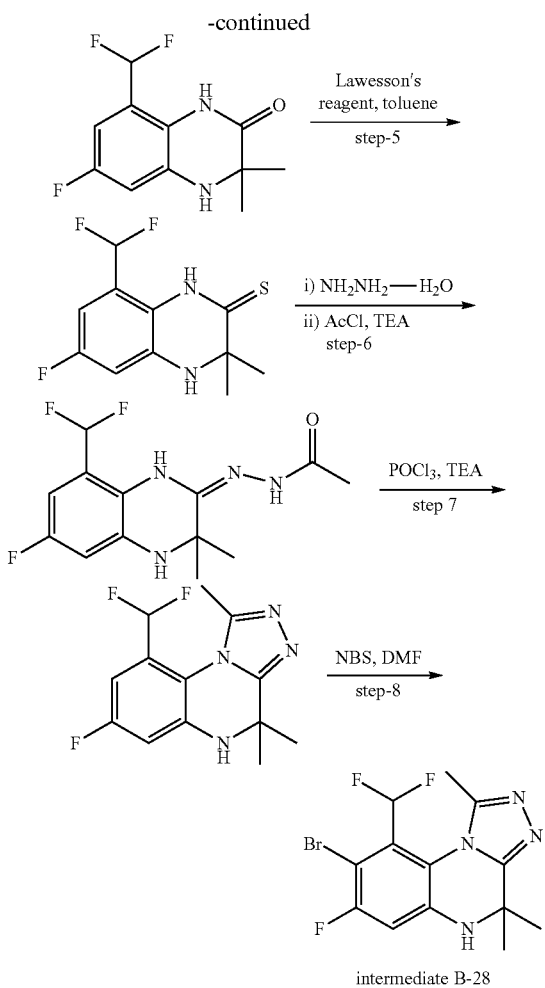

intermediate B-28

Step 1: To a stirred solution of 5-fluoro-2-nitro-benzaldehyde (20.0 g, 118.27 mmol) in DCM (600 mL) was added DAST (23.3 ml, 177.51 mmol) at 0° C. The reaction mixture was stirred at ambient temperature for 4 h. After completion of the reaction, the reaction mixture was quenched with sat. NaHCO$_3$ solution and was extracted with DCM (2×500 mL). The combined organic layers were washed with water (500 mL) followed by brine (500 mL), were then dried over anhydrous Na$_2$SO$_4$ and concentrated. The crude material was purified by column chromatography using 2-3% EtOAc/hexane to afford 2-difluoromethyl-4-fluoro-1-nitro-benzene (22.0 g, 88%) as a yellow liquid.

Step 2: To a stirred solution of 2-difluoromethyl-4-fluoro-1-nitro-benzene (22.0 g, 115.16 mmol) in ethanol (372 mL) was added SnCl$_2$.2H$_2$O (103.7 g, 460.46 mmol) followed by con. HCl (76 mL) at 0° C. The reaction mixture was stirred at ambient temperature for 2 h. After completion of the reaction the reaction mixture was concentrated, the residue was basified with 5N NaOH solution and was extracted with MTBE (2×500 mL). The combined organic layers were washed with water (500 mL) followed by brine (500 mL), were dried over anhydrous Na$_2$SO$_4$ and concentrated. The crude material was purified by column chromatography using 2-3% EtOAc/hexane to afford 2-difluoromethyl-4-fluoro-phenylamine (12.5 g, 41%) as a yellow gummy liquid.

Step 3: To a solution of 2-difluoromethyl-4-fluoro-phenylamine (8.0 g, 49.64 mmol) in DCM (150 mL) was added a solution of bromine (3.84 mL, 74.47 mmol) in DCM (100 ml) dropwise at 0° C. The resulting reaction mixture was stirred at ambient temperature for 16 h. After completion of the reaction (monitored by TLC in 10% EA-Hexane, R$_f$=0.7), the reaction mixture was quenched with saturated NaHCO$_3$ solution. The two layers were separated, the aqueous layer was then extracted with DCM (2×200 mL). The combined organic layers were washed with water (2×500 ml) and brine (250 ml) and were then dried over anhydrous Na$_2$SO$_4$ and concentrated under reduced pressure. Three batches of this reaction were performed in parallel, which were afterwards combined to give the crude compound. This combined crude material was purified by column chromatography (1 GO-200 mesh silica gel and 5% EtOAc/hexane as eluent) to afford to afford 2-bromo-6-difluoromethyl-4-fluoro-phenylamine (18.0 g, 51%) as a white solid.

Step 4: To the stirred suspension of 2-bromo-6-difluoromethyl-4-fluoro-phenylamine (18.0 g, 73.77 mmol) in dry DMSO (270 mL) was added 2-amino-2-methyl-propionic acid (15.2 g, 147.54 mmol) followed by K$_3$PO$_4$ (31.31 g, 147.54 mmol) at ambient temperature. The resulting reaction mixture was degassed with nitrogen for 30 minutes, then cuprous chloride (730 mg, 7.37 mmol) was added and reaction mixture was heated at 125° C. for 16 h. After completion of the reaction (monitored by TLC, 20% EA-Hexane, Rf 0.4), the reaction mixture was cooled to ambient temperature and was filtered through celite. The celite bed was washed with EtOAc (2×200 mL). The resulting filtrate was poured into ice cold water (500 mL). The resulting aqueous layer was extracted with EtOAc (2×250 mL). The combined organic layers were washed with water (3×200 mL) and brine (400 ml), were dried over anhydrous Na$_2$SO$_4$ and the solvent was evaporated under reduced pressure to afford the crude mixture. The crude mixture was purified by column chromatography (100-200 mesh silica gel and 15% EtOAc/hexane as eluent) to afford 8-difluoromethyl-6-fluoro-3,3-dimethyl-3,4-dihydro-1H-quinoxalin-2-one (9.0 g, 50%) as a brown solid.

Step 5: To a stirred solution of 8-difluoromethyl-6-fluoro-3,3-dimethyl-3,4-dihydro-1H-quinoxalin-2-one (9.0 g, 36.88 mmol) in toluene (300 ml) was added Lawesson's reagent (22.39 g, 55.32 mmol) at ambient temperature and the reaction mixture was then heated to 120° C. for 3 h. After completion of the reaction (monitored by TLC in 20% EA-Hexane, Rf 0.6) the reaction mixture was cooled to ambient temperature and was then concentrated under reduced pressure. The obtained residue was quenched with sat. NaHCO$_3$ solution (500 ml) and the resulting aqueous layer was extracted with EtOAc (3×250 ml). The combined organic layers were washed with water (500 ml) and brine (250 ml), were dried over anhydrous Na$_2$SO$_4$ and then evaporated to dryness under reduced pressure. The crude material was purified by column chromatography (100-200 mesh silica gel and 20% EtOAc/hexane as eluent) to afford 8-difluoromethyl-6-fluoro-3,3-dimethyl-3,4-dihydro-1H-quinoxaline-2-thione (9.0 g, 94%) as a yellow solid.

Step 6: To a stirred solution of 8-difluoromethyl-6-fluoro-3,3-dimethyl-3,4-dihydro-1H-quinoxaline-2-thione (9.0 g, 34.57 mmol) in THF (60 ml) was added dropwise hydrazine hydrate (5.19 g, 103.73 mmol) at 0° C. The reaction mixture was stirred at ambient temperature for 16 h. TEA (24.2 ml, 172.89 mmol) followed acetyl chloride (7.4 ml, 103.73 mmol) were added to the reaction mixture dropwise at 0° C. and the resulting reaction mixture was then stirred for 2 h at ambient temperature. After completion of the reaction (monitored by LCMS) the reaction mixture was diluted with water and extracted with 10% MeOH-DCM (5×100 ml). The combined organic layers were washed by brine, dried over Na₂SO₄ and concentrated under reduced pressure to afford acetic acid (8-difluoromethyl-6-fluoro-3,3-dimethyl-3,4-dihydro-1H-quinoxalin-2-ylidene)-hydrazide (9.0 g, 87%, crude) as pale yellow solid.

Step 7: Acetic acid (8-difluoromethyl-6-fluoro-3,3-dimethyl-3,4-dihydro-1H-quinoxalin-2-ylidene)-hydrazide (9.0 g, 30 mmol) in a round bottom flask was cooled to −10° C. Phosphorus oxalylchloride (13.98 ml, 150 mmol) was added dropwise, followed by the dropwise addition of triethyl amine (4.2 ml, 30 mmol). The reaction mixture was stirred at −10° C. for 10 minutes and then 10 minutes at RT and finally under reflux for 2 h. After completion of the reaction (monitored by LCMS) the reaction mixture was cooled to 0° C. and was quenched with crushed ice in water (200 ml). The aqueous part was then basified by adding cold aqueous ammonia solution (500 ml) dropwise. The resulting basic aqueous layer was then extracted with EtOAc (3×250 ml). The combined organic layers were washed with brine, dried over anhydrous Na₂SO₄ and were concentrated under reduced pressure to afford the crude compound. The obtained crude was co-distilled with MTBE twice, then triturated with hexane and dried to afford 9-difluoromethyl-7-fluoro-1,4,4-trimethyl-4,5-dihydro-[1,2,4]triazolo[4,3-a]quinoxaline (4.5 g, 53%) as a pale yellow solid.

Step 8: To a solution of 9-difluoromethyl-7-fluoro-1,4,4-trimethyl-4,5-dihydro-[1,2,4]triazolo[4,3-a]quinoxaline (11.0 g, 39.0 mmol) in DMF (180 mL) was added NBS (7.2 g, 40.2 mmol) portion wise at 0° C. The resulting reaction mixture was stirred at 0° C. for 1 h. After completion of the reaction (monitored by LCMS) the reaction mixture was diluted with water (400 mL) and was extracted with EtOAc (2×400 mL). The combined organic layers were washed with water (2×200 mL) and brine, dried over anhydrous Na₂SO₄ and concentrated under reduced pressure. The crude was purified via column chromatography (100-200 mesh silica gel and 5% MeOH/DCM as eluent) to afford 8-bromo-9-difluoromethyl-7-fluoro-1,4,4-trimethyl-4,5-dihydro-[1,2,4]triazolo[4,3-a]quinoxaline (7.2 g, 65%) as an off white solid.

¹H-NMR (400 MHz, DMSO-d₆): δ=6.91-6.64 (m, 2H), 4.58 (s, 1H), 2.56 (s, 3H), 1.58 (brs, 3H), 1.24 (brs, 3H).

Synthesis of 8-bromo-1,4,4,9-tetramethyl-4,5-dihydro-[1,2,4]triazolo[4,3-a]quinoxaline (Intermediate B-40)

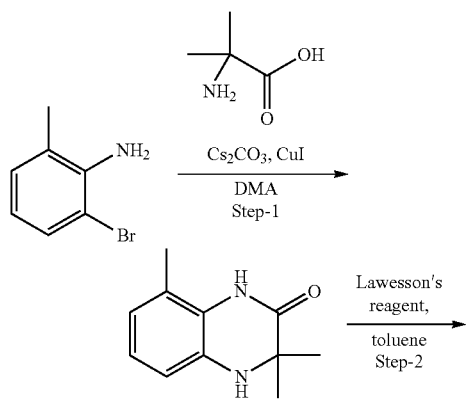

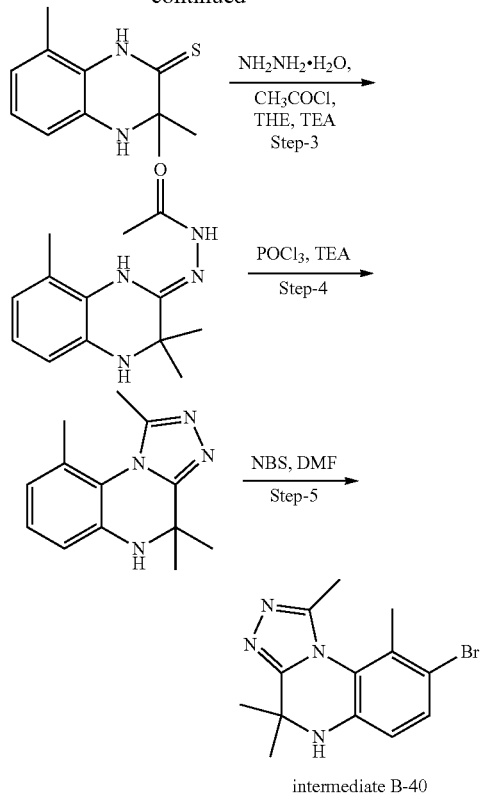

intermediate B-40

Step 1: A suspension of 2-bromo-6-methylaniline (1.0 g, 54.0 mmol, 1.0 eq) and 2-aminobutyric acid (1.1 g, 10.8 mmol, 2.0 eq) in DMSO (10 ml) in a sealed tube was deoxygenated with Ar for 20 minutes. K₃PO₄ (2.3 g, 10.8 mmol, 2.0 eq) and CuCl (53.0 mg, 5.4 mmol, 0.1 eq) were then added. The reaction mixture was then stirred at 140° C. for 16 h. After completion of the reaction, the reaction mixture was filtered through a celite bed and the celite bed was washed with EtOAc (100 ml). The filtrate was diluted with EtOAc (100 ml) and was washed with water (3×150 ml) and brine (200 ml), dried over anhydrous Na₂SO4 and was then evaporated under reduced pressure to obtain the crude compound, which was purified by column chromatography (100-200 mesh silica gel; 30% EtOAc/hexane; $R_f$-value-0.4) to afford 3,3,8-trimethyl-3,4-dihydroquinoxalin-2(1H)-one (0.6 g, 60%).

Step 2: To a solution of 3,3,8-trimethyl-3,4-dihydroquinoxalin-2(1H)-one (7.0 g, 36.0 mmol, 1.0 eq) in toluene (75 ml) was added Lawesson's reagent (22.0 g, 55 mmol, 1.5 eq.) at ambient temperature and the reaction mixture was then refluxed at 120° C. for 40 minutes. After completion of the reaction (monitored by TLC), the reaction mixture was quenched with sat. NaHCO₃ solution (100 ml) followed by extraction with EtOAc (2×100 ml). The combined organic layers were washed with water (100 ml) and brine (100 ml), were dried over anhydrous Na₂SO₄ and evaporated under reduced pressure to obtain the crude compound which was purified by column chromatography (230-400 mesh silica gel; 20% EtOAc/hexane; $R_f$-value-0.4) to afford 3,3,8-trimethyl-3,4-dihydroquinoxaline-2(1H)-thione (5.0 g, 66%) as a yellow solid.

Step 3: To a stirring solution of compound 3,3,8-trimethyl-3,4-dihydroquinoxaline-2(1H)-thione (5.0 g, 62.4 mmol, 1 eq) in THF (30 ml) was added dropwise hydrazine hydrate (6.0 ml, 121.0 mmol, 5 eq) at 0° C. The reaction mixture was then stirred for 16 h at ambient temperature. TEA (16.5 ml, 122.7 mmol, 5 eq) was then added to the reaction mixture and the reaction mixture was stirred for another 10 minutes. Acetyl chloride (5.65 g, 73.65 mmol, 3 eq) was then added to the reaction mixture very slowly at 0° C. and the resulting reaction mixture was then stirred for 2 h at ambient temperature. The reaction mixture was then diluted with water (50 ml) and extracted with DCM (5×100 ml). The combined organic layers were washed with brine (100 ml), dried over Na$_2$SO$_4$ and concentrated under reduced pressure to obtain the crude material which was purified by washing with diethyl ether to afford N'-(3,3,8-trimethyl-3,4-dihydroquinoxalin-2(1H)-ylidene)acetohydrazide (2.0 g, 34%) as a white solid.

Step 4: N'-(3,3,8-trimethyl-3,4-dihydroquinoxalin-2(1H)-ylidene)acetohydrazide (6.0 g, 24 mmol, 1 eq) was taken up in a round bottom flask (50 ml) and was then cooled to −10° C. Phosphorus oxychloride (23.0 ml, 243 mmol, 10 eq) was then added dropwise to the compound followed by drop wise addition of TEA (3.5 ml, 24 mmol, 1 eq). After that the reaction mixture was stirred at −10° C. for 10 minutes and then 10 minutes at ambient temperature and finally at reflux for 4 h. The reaction mixture was then cooled to 0° C. and was then added dropwise into crushed ice in water under constant stirring. To this was then slowly added cold ammonia solution (100 ml). The aqueous part was then extract with DCM (2×100 mL). The combined organic layers were washed with brine (100 ml), dried over anhydrous Na$_2$SO$_4$ and concentrated under reduced pressure to obtain the crude compound, which was purified by column chromatography (230-400 mesh silica gel; 5% MeOH/DCM; R$_f$-value-0.4) to afford 1,4,4,9-tetramethyl-4,5-dihydro-[1,2,4]triazolo[4,3-a]quinoxaline (3.2 g, 58.6%) as a yellow solid.

Step 5: A stirred solution of 1,4,4,9-tetramethyl-4,5-dihydro-[1,2,4]triazolo[4,3-a]quinoxaline (3.2 g, 14 mmol, 1.00 eq) in DMF (40 ml) at −10° C. is treated with solid N-bromosuccinimide (2.7 g, 15 mmol, 1.05 eq) portionwise over 10 minutes. The reaction mixture was allowed to warm to ambient temperature and was then stirred for 1.5 h. After completion of the reaction (monitored by LCMS) the reaction mixture was diluted with EtOAc (300 ml) and was washed with water (5×50 ml) and brine (50 ml), dried over anhydrous Na$_2$SO$_4$ and evaporated under reduced pressure to obtain the crude compound, which was purified by silica gel (230-400) column chromatography (5% MeOH/DCM; R$_f$-value-0.3) to afford 8-bromo-1,4,4,9-tetramethyl-4,5-dihydro-[1,2,4]triazolo[4,3-a]quinoxaline (2.0 g, 48%) as an off white solid.

Synthesis of 8-bromo-9-cyclopropyl-7-fluoro-1,4,4-trimethyl-4,5-dihydro-[1,2,4]triazolo[4,3-a]quinoxaline (Intermediate B-44)

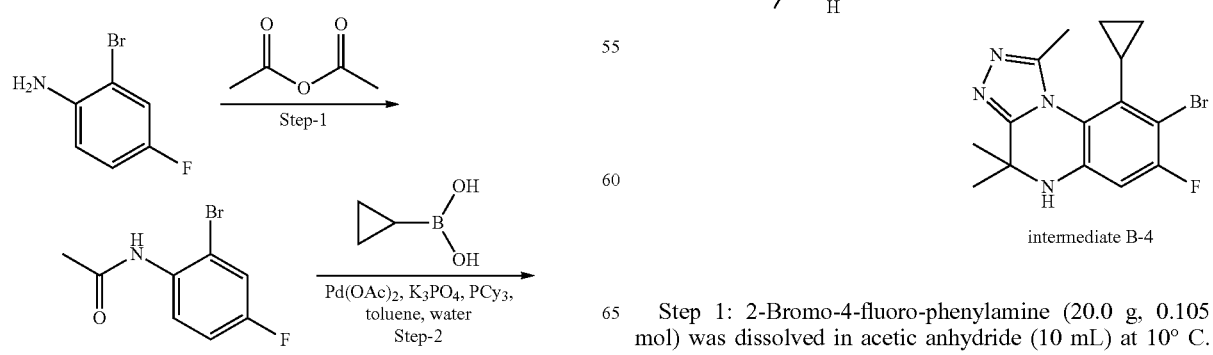

Step 1: 2-Bromo-4-fluoro-phenylamine (20.0 g, 0.105 mol) was dissolved in acetic anhydride (10 mL) at 10° C. and was stirred at ambient temperature for 3 h. After completion of the reaction (monitored by TLC, 10% ethylacetate/hexane) the thick reaction mass was diluted with n-hexane and was filtered. The solid material was washed with n-hexane and was then dried under vacuum to afford N-(2-bromo-4-fluoro-phenyl)-acetamide (20.0 g, 82%) as an off white solid.

Step 2: To a stirred solution of N-(2-bromo-4-fluoro-phenyl)-acetamide (65.0 g, 0.28 mol) in a mixture of toluene-water (1:1, 1.3 L) was added tricyclohexyl phosphine (7.85 g, 0.03 mol) followed by the addition of $K_3PO_4$ (208.2 g, 0.98 mol) at ambient temperature. This mixture was then degassed with Ar for 30 minutes. Cyclopropyl boronic acid (31.2 g, 0.37 mol) followed by $Pd(OAc)_2$ (3.2 g, 0.01 mol) was added and the reaction mixture was heated to 100° C. for 16 h. After consumption of the starting material (monitored by TLC, 20% EA-Hexane, Rf 0.4) the reaction mixture was cooled to ambient temperature, diluted with EtOAc (1 L), washed with water (2×500 ml) followed by brine (500 ml) and was then dried over anhydrous $Na_2SO_4$ and concentrated under reduced pressure to afford the crude compound. The obtained crude compound was purified by column chromatography (100-200 mesh silica gel and 15-20% EtOAc/hexane as eluent) to afford N-(2-cyclopropyl-4-fluoro-phenyl)-acetamide (51.5 g, 95%) as a brownish solid.

Step 3: A stirred suspension of N-(2-cyclopropyl-4-fluoro-phenyl)-acetamide (4) (52.0 g, 0.269 mol) in HCl (2.1 L, 2M) was heated to 90° C. for 16 h. After completion of reaction (monitored by TLC, 20% EA-Hexane, Rf 0.6), it was cooled to ambient temperature and was basified to pH ~13-14 with NaOH solution (2M). The mixture was extracted with EtOAc (1 L). The organic layer was then washed with water (2×500 ml) and brine (500 ml), dried over anhydrous $Na_2SO_4$ and was concentrated under reduced pressure to afford 2-cyclopropyl-4-fluoro-phenylamine (40.0 g, crude) as a dark brown liquid.

Step 4: To a stirred solution of 2-cyclopropyl-4-fluoro-phenylamine (20.0 g, 0.132 mol) in DMF (350 ml) was added NBS (85.0 g, 0.477 mol) portion wise at −10° C. The resulting reaction mixture was stirred at 0° C. for 1 h. After completion of reaction (monitored by TLC, 20% EtOAc/hex) the reaction mixture was diluted with water (1 L) and was extracted with MTBE (2×750 ml). The combined organic layers were washed with cold brine (3×500 ml), dried over anhydrous $Na_2SO_4$ and concentrated under reduced pressure. The obtained crude material was purified by column chromatography (100-200 mesh silica gel and 5-10% EtOAc/hexane as eluent) to afford 2-bromo-6-cyclopropyl-4-fluoro-phenylamine (20.2 g, 65% over two steps) as a brownish liquid.

Step 5: To a stirred suspension of 2-bromo-6-cyclopropyl-4-fluoro-phenylamine (20.0 g, 86.88 mmol) in dry DMSO (300 mL) was added 2-amino-2-methyl-propionic acid (17.9 g, 173.94 mmol) followed by $K_3PO_4$ (36.9 g, 173.94 mmol) at ambient temperature. The resulting reaction mixture was degassed with Ar for 30 minutes. Then, CuCl (860 mg, 8.69 mmol) was added and the reaction mixture was heated to 140° C. for 16 h. After consumption of the starting material (monitored by TLC, 30% EA-Hexane, Rf 0.4) the reaction mixture was cooled to ambient temperature and was filtered through a celite bed. The celite bed was washed with EtOAc (500 ml). The organic layers were washed with water (2×750 ml) and brine (500 ml), were dried over anhydrous $Na_2SO_4$ and the solvent was evaporated under reduced pressure to afford the crude material. The obtained crude material was purified by column chromatography using 15-20% EtOAc-hexane to afford 8-cyclopropyl-6-fluoro-3,3-dimethyl-3,4-dihydro-1H-quinoxalin-2-one (10.1 g, 50%) as a brown solid.

Step 6: To a solution of 8-cyclopropyl-6-fluoro-3,3-dimethyl-3,4-dihydro-1H-quinoxalin-2-one (10.0 g, 42.7 mmol) in toluene (200 ml) was added Lawesson's reagent (25.9 g, 64.1 mmol) at ambient temperature and the reaction mixture was refluxed at 120° C. for 1 h. After completion of the reaction (monitored by TLC in 20% EA-Hexane, Rf 0.7) the reaction mass was cooled to ambient temperature and was quenched with saturated $NaHCO_3$ solution (35 ml). The resulting aqueous layer was extracted with EtOAc (3×500 ml). The combined organic layers were washed with water (500 ml) followed by brine (500 ml), dried over anhydrous $Na_2SO_4$ and concentrated to afford the crude material. The obtained crude material was purified via column chromatography (using silica 100-200 mesh and 5-10% EtOAc/hexane) to afford 8-cyclopropyl-6-fluoro-3,3-dimethyl-3,4-dihydro-1H-quinoxaline-2-thione (9.5 g, 89%) as a yellow solid.

Step 7: To a stirred solution of 8-cyclopropyl-6-fluoro-3,3-dimethyl-3,4-dihydro-1H-quinoxaline-2-thione (9.0 g, 36.0 mmol) in THF (216 ml) was hydrazine hydrate (5.3 ml, 108 mmol) added dropwise at 0° C. The reaction mixture was then stirred at ambient temperature for 16 h. TEA (30.2 ml, 216.0 mmol) followed by acetyl chloride (10.3 ml, 144.0 mmol) were then added to the reaction mixture dropwise at 0° C. and the reaction mixture was stirred for 2 h at ambient temperature. After completion of the reaction (monitored by LCMS) the reaction mixture was diluted with water (300 ml) and extracted with EtOAc (2×500 ml). The combined organic layers were washed with brine (300 ml), dried over $Na_2SO_4$ and concentrated under reduced pressure to afford acetic acid [8-cyclopropyl-6-fluoro-3,3-dimethyl-3,4-dihydro-1H-quinoxalin-(2E)-ylidene]-hydrazide (9.0 g, crude) as a pale yellow solid.

Step 8: Acetic acid [8-cyclopropyl-6-fluoro-3,3-dimethyl-3,4-dihydro-1H-quinoxalin-(2E)-ylidene]-hydrazide (6.0 g, 20.66 mmol) was taken up in a round bottom flask and was cooled to −10° C. Phosphorus oxalylchloride (9.7 ml, 103.32 mmol) was added to it and the mixture was stirred at −10° C. for 15 min. TEA (2.9 ml, 20.66 mmol) was slowly added to the reaction mixture at −10° C. and the mixture was stirred for 15 min. The reaction mixture was then stirred at ambient temperature for 15 minutes, followed by heating to 120° C. for 1.5 h. After completion of the reaction (monitored by LCMS) the reaction mixture was cooled to ambient temperature, poured into crushed ice in water and basified (pH8-9) using aqueous ammonia solution. The resulting basic aqueous layer was extracted with EtOAc (2×500 mL). The combined organic layers were washed with water (500 ml) followed by brine (500 ml), dried over anhydrous $Na_2SO_4$ and concentrated under reduced pressure. The residue was triturated with 50% MTBE-Hexane (50 mL×2) to afford 9-cyclopropyl-7-fluoro-1,4,4-trimethyl-4,5-dihydro-[1,2,4]triazolo[4,3-a]quinoxaline (5.0 g, crude) as a pale yellow solid.

Step 9: To a stirred solution of 9-cyclopropyl-7-fluoro-1,4,4-trimethyl-4,5-dihydro-[1,2,4]triazolo[4,3-a]quinoxaline (5.0 g, 18.36 mmol) in DMF (80 mL) was added NBS (3.4 g, 18.91 mol) portionwise at −10° C. The resulting reaction mixture was stirred at 0° C. for 1 h. After completion of the reaction (monitored by LCMS) the reaction mixture was diluted with water (250 ml) and extracted with EtOAc (2×250 ml). The combined organic layers were washed with cold brine (3×250 ml), dried over anhydrous $Na_2SO_4$ and were concentrated under reduced pressure. The obtained crude material was purified by column chromatography (100-200 mesh silica gel and 30-35% acetone/hexane as eluent) to afford 8-bromo-9-cyclopropyl-7-fluoro-1,4,4-trimethyl-4,5-dihydro-[1,2,4]triazolo[4,3-a]quinoxaline (1.2 g, 17% over three steps) as an off white solid.

$^1$H-NMR (400 MHz, DMSO-$d_6$): δ=6.89 (s, 1H), 6.81-6.79 (t, 1H), 2.50-2.47 (d, 3H), 2.08 (t, 1H), 1.67 (s, 3H), 1.37 (bs, 1H), 1.10 (s, 3H), 0.92 (b, 1H) 0.82 (bs, 1H), 0.01 (bs, 1H).

Synthesis of 8-bromo-1,4,4-trimethyl-9-(trifluoromethyl)-4,5-dihydro-[1,2,4]triazolo[4,3-a]quinoxaline (Intermediate B-48)

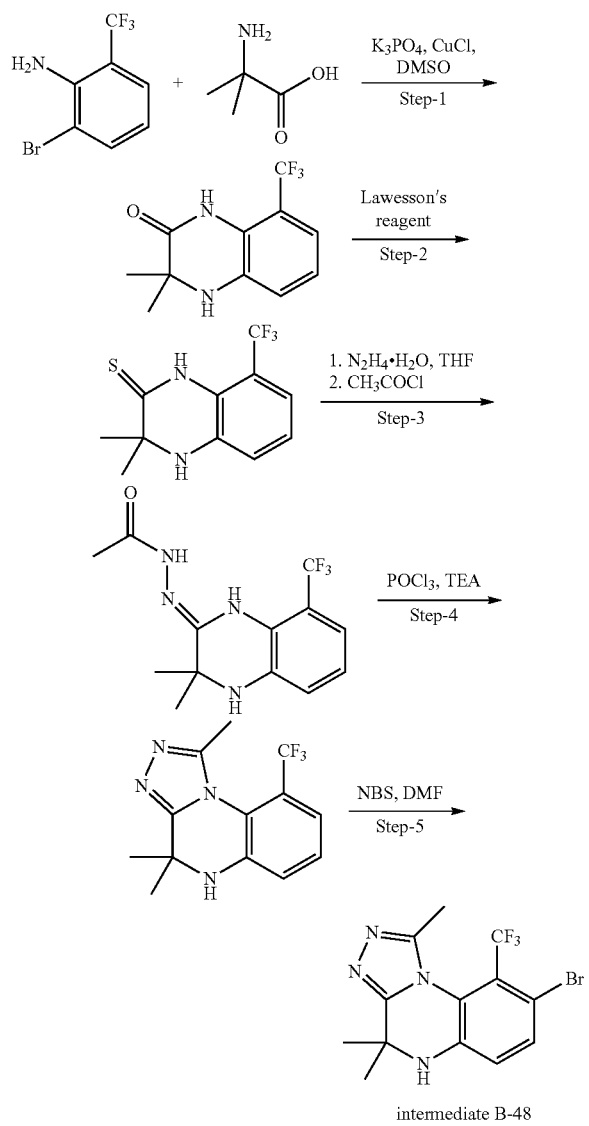

intermediate B-48

Step 1: To a stirred suspension of 2-bromo-6-trifluoromethyl-phenylamine (25.0 g, 0.104 mol) in dry DMSO (375 ml) was added 2-amino-2-methyl-propionic acid (21.5 g, 0.208 mol) followed by $K_3PO_4$ (44.2 g, 0.208 mol) at ambient temperature. The resulting reaction mixture was degassed with nitrogen for 30 minutes, then cuprous chloride (1.03 g, 0.010 mol) was added and reaction mixture was heated to 140° C. for 6 h. After completion of the starting material (monitored by TLC, 20% EA-Hexane, Rf 0.4) the reaction mixture was cooled to ambient temperature and was filtered through celite. The celite bed was washed with EtOAc (2×250 ml). The resulting filtrate was poured into ice cold water (800 ml). The resulting aqueous layer was extracted with EtOAc (2×500 ml). The combined organic layers were washed with water (2×650 ml) and brine (650 ml), were dried over anhydrous $Na_2SO_4$ and the solvent was evaporated under reduced pressure to afford the crude material. The obtained crude material was triturated with MTBE-Hexane to afford 3,3-dimethyl-8-trifluoromethyl-3,4-dihydro-1H-quinoxalin-2-one (17.0 g, 66%) as a brown solid.

Step 2: To a solution of 3,3-dimethyl-8-trifluoromethyl-3,4-dihydro-1H-quinoxalin-2-one (17.0 g, 0.07 mol) in toluene (300 ml) was added Lawesson's reagent (42.6 g, 0.105 mol) at ambient temperature and the reaction mixture was then refluxed at 120° C. for 2 h. After completion of the reaction (monitored by TLC in 20% EA-Hexane, Rf 0.6) the reaction mixture was quenched with sat. $NaHCO_3$ solution (450 ml) and the resulting aqueous layer was extracted with EtOAc (2×300 ml). The combined organic layers were washed with water (400 ml) and brine (200 ml), were dried over anhydrous $Na_2SO_4$ and the solvent was evaporated to obtain the crude compound. The obtained crude was purified by column chromatography (100-200 mesh silica gel and 10% EtOAc/hexane as eluent) to afford 3,3-dimethyl-8-trifluoromethyl-3,4-dihydro-1H-quinoxaline-2-thione (17.0 g, 94%) as a yellow solid.

Step 3: To a stirred solution of 3,3-dimethyl-8-trifluoromethyl-3,4-dihydro-1H-quinoxaline-2-thione (17.0 g, 0.065 mol) in THF (500 ml) was added hydrazine hydrate (9.8 g, 0.195 mol) dropwise at 0° C. The reaction mixture was then stirred at ambient temperature for 4 h. TEA (63.7 ml, 0.455 mol) followed by acetyl chloride (20.4 g, 0.260 mol) were then added to the reaction mixture dropwise at 0° C. and the resulting mixture was stirred for 16 h at ambient temperature. After completion of the reaction (monitored by LCMS) the reaction mixture was diluted with water (300 ml) and extracted with 10% MeOH-DCM (2×300 ml). The combined organic layers were washed by brine (350 ml), dried over $Na_2SO_4$ and concentrated under reduced pressure to afford acetic acid (3,3-dimethyl-8-trifluoromethyl-3,4-dihydro-1H-quinoxalin-2-ylidene)-hydrazide (16.0 g, crude) as an off white solid.

Step 4: Acetic acid (3,3-dimethyl-8-trifluoromethyl-3,4-dihydro-1H-quinoxalin-2-ylidene)-hydrazide (16.0 g, 0.053 mol) was taken up in a round bottom flask and was then cooled to –10° C. Phosphorus oxalylchloride (24.7 ml, 0.265 mol) was then added dropwise followed by the dropwise addition of triethyl amine (7.34 ml, 0.053 mol). After that the reaction mixture was stirred at –10° C. for 10 minutes, was then allowed to stir at ambient temperature for 10 minutes and was then heated to reflux for 4 h. After completion of the reaction (monitored by LCMS) the reaction mixture was cooled to 0° C. and was then quenched with crushed ice in water (300 ml). The aqueous part was then basified by adding cold ammonium solution (150 ml) dropwise. The resulting basic aqueous layer was then extracted with EtOAc (3×150 ml). The combined organic layers were washed with brine (250 ml), dried over anhydrous $Na_2SO_4$ and concentrated under reduced pressure to afford the crude compound. The obtained crude was purified by column chromatography (230-400 mesh silica gel and 5% MeOH/DCM as eluent) to afford 1,4,4-trimethyl-9-trifluoromethyl-4,5-dihydro-[1,2,4]triazolo[4,3-a]quinoxaline (5.0 g, 27% over two steps) as an off white solid.

Step 5: To a solution of 1,4,4-trimethyl-9-trifluoromethyl-4,5-dihydro-[1,2,4]triazolo[4,3-a]quinoxaline (4.8 g, 0.017 mol) in DMF (120 ml) was added NBS (3.3 g, 0.019 mol) portionwise at 0° C. The resulting reaction mixture was stirred at ambient temperature for 16 h. After completion of the reaction (monitored by LCMS) the reaction mixture was diluted with water (250 ml) and extracted with EtOAc (2×150 ml). The combined organic layers were washed with water (2×180 ml) and brine (200 ml), dried over anhydrous $Na_2SO_4$ and concentrated under reduced pressure to afford the crude compound. The obtained crude compound was combined with another batch of the same reaction (using 5.0 g of 1,4,4-trimethyl-9-trifluoromethyl-4,5-dihydro-[1,2,4]triazolo[4,3-a]quinoxaline) and was then purified by column chromatography (230-400 mesh silica gel and 5% MeOH/DCM as eluent) to afford 8-bromo-1,4,4-trimethyl-9-trifluoromethyl-4,5-dihydro-[1,2,4]triazolo[4,3-a]quinoxaline (5.3 g, 42% overall yield) as an off white solid.

$^1$H-NMR (400 MHz, DMSO-$d_6$): δ=7.66-7.64 (d, 1H), 7.31 (s, 1H), 7.14-7.12 (d, 1H), 2.34 (s, 3H), 1.70 (s, 3H), 1.21 (s, 3H).

Synthesis of 8-bromo-9-(difluoromethyl)-1,4,4-trimethyl-4,5-dihydro-[1,2,4]triazolo[4,3-a]quinoxaline (Intermediate B-52)

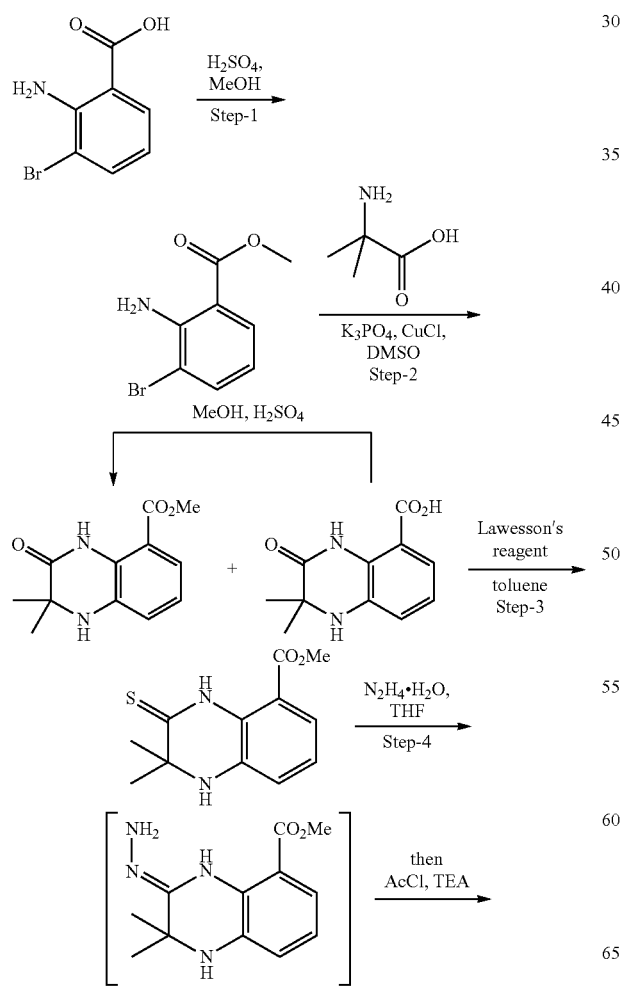

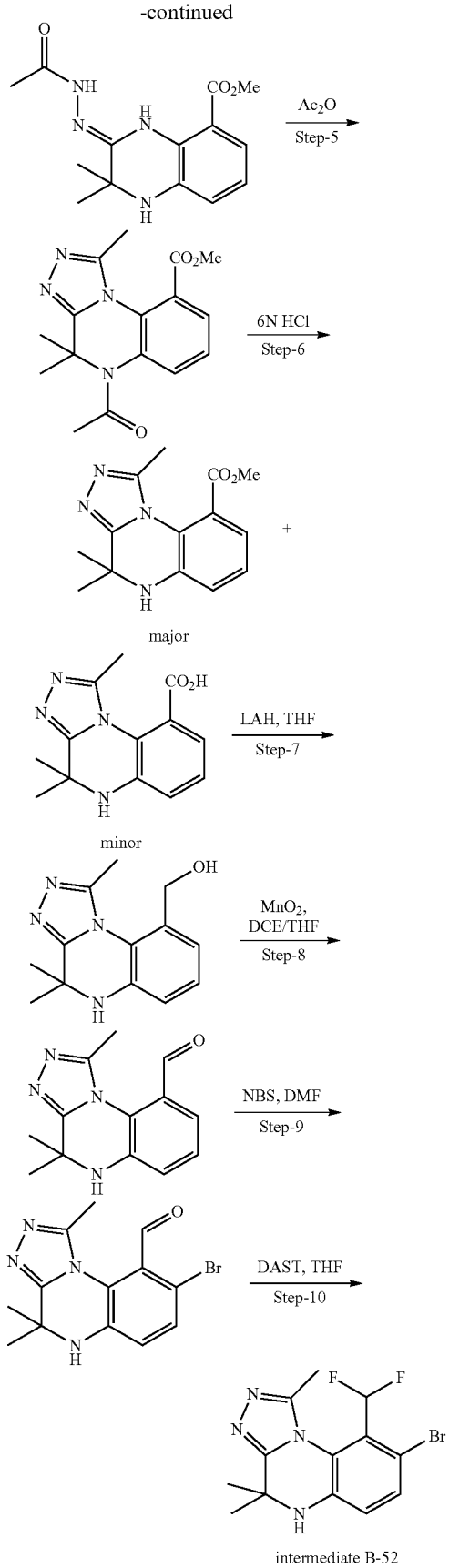

intermediate B-52

Step 1: To a stirring solution of 2-amino-3-bromo-benzoic acid (100.0 g, 0.465 mol) in MeOH (1 L) was added con. $H_2SO_4$ (100 ml) at 0° C. and the mixture was heated to 80° C. for 48 h. After completion of the reaction (monitored by TLC, 5% EA-Hexane, Rf 0.4) the reaction mixture was cooled to ambient temperature. The reaction mixture was then concentrated under reduced pressure, the obtained residue was basified with sat. $NaHCO_3$ solution (to pH8-9) and was then extracted with EtOAc (2×500 ml). The combined organic layers were washed with water (250 ml) and brine (250 ml), were then dried over anhydrous $Na_2SO_4$ and concentrated under reduced pressure to afford 2-amino-3-bromo-benzoic acid methyl ester (80.0 g, 75%) as a brownish solid.

Step 2: To a stirring suspension of 2-amino-3-bromo-benzoic acid methyl ester (30.0 g, 0.131 mol) in dry DMSO (450 ml) was added 2-amino-2-methyl-propionic acid (27.1 g, 0.262 mol) followed by $K_3PO_4$ (55.6 g, 0.262 mol) at ambient temperature. The resulting reaction mixture was degassed with nitrogen for 30 minutes, then cuprous chloride (1.29 g, 0.01 mol) was added and the reaction mixture was heated to 140° C. for 4-5 h. After completion of the reaction (monitored by TLC, 20% EA-Hexane, Rf 0.4) the reaction mixture was cooled to ambient temperature and filtered through celite. The celite bed was washed with EtOAc (2×250 ml). The resulting filtrate was poured into ice cold water (800 ml). The aqueous layer was extracted with EtOAc (2×500 ml). The combined organic layers were washed with water (2×650 ml) and brine (650 ml), dried over anhydrous $Na_2SO_4$ and concentrated under reduced pressure to afford methyl 2,2-dimethyl-3-oxo-1,2,3,4-tetrahydroquinoxaline-5-carboxylate (3.0 g, crude). The aqueous layer was acidified with conc. HCl (pH2-3) and was then extracted with EtOAc (2×500 ml). The combined organic layers were washed with brine (500 ml), dried over anhydrous $Na_2SO_4$ and were evaporated under reduced pressure to yield 2,2-dimethyl-3-oxo-1,2,3,4-tetrahydroquinoxaline-5-carboxylic acid (15.0 g). This material was dissolved in MeOH (150 ml), followed by the slow addition of conc. $H_2SO_4$ (15 ml) at 0° C. The resulting reaction mixture was then stirred at 90° C. for 50 h. The reaction mixture was concentrated and the obtained residue was basified with sat. $NaHCO_3$ solution (pH8-9) and was then extracted with EtOAc (2×250 ml). The combined organic layers were washed with water (150 ml) and brine (150 ml), dried over anhydrous $Na_2SO_4$ and evaporated under reduced pressure to obtain methyl 2,2-dimethyl-3-oxo-1,2,3,4-tetrahydroquinoxaline-5-carboxylate (13 g, crude). The combined batches of methyl 2,2-dimethyl-3-oxo-1,2,3,4-tetrahydroquinoxaline-5-carboxylate were triturated with hexane to afford 2,2-dimethyl-3-oxo-1,2,3,4-tetrahydro-quinoxaline-5-carboxylic acid methyl ester (13.1 g, 43%) as a brownish solid.

Step 3: To a stirring solution of 2,2-dimethyl-3-oxo-1,2,3,4-tetrahydro-quinoxaline-5-carboxylic acid methyl ester (20.0 g, 85.47 mmol) in toluene (430 ml) was added Lawesson's reagent (51.9 g, 128.21 mmol) at ambient temperature and the reaction mixture was then heated to 120° C. for 2 h. After completion of the reaction (monitored by TLC in 20% EA-Hexane, Rf 0.6) the reaction mixture was quenched with sat. $NaHCO_3$ solution (500 ml) and the resulting aqueous layer was extracted with EtOAc (2×400 ml). The combined organic layers were washed with water (500 ml) and brine (300 ml), dried over anhydrous $Na_2SO_4$ and concentrated under reduced pressure to obtain the crude compound. The obtained crude was purified by column chromatography (100-200 mesh silica gel, 7-8% EtOAc in hexane as eluent) to afford 2,2-dimethyl-3-thioxo-1,2,3,4-tetrahydro-quinoxaline-5-carboxylic acid methyl ester (16.0 g, 75%) as a yellow solid.

Step 4: To a stirring solution of 2,2-dimethyl-3-thioxo-1,2,3,4-tetrahydro-quinoxaline-5-carboxylic acid methyl ester (30.0 g, 0.12 mol) in THF (800 ml) was added hydrazine hydrate (10.6 ml, 0.22 mol) dropwise at 0° C. and the mixture was then stirred at ambient temperature for 10 h. To the reaction mixture was then added TEA (60.3 ml, 0.43 mol) dropwise at 0° C. followed by acetyl chloride (23.1 ml, 0.32 mol), and the resulting mixture was stirred for 4 h at ambient temperature. After completion of the reaction (monitored by LCMS) the reaction mixture was diluted with water (500 ml) and extracted with 10% MeOH-DCM (2×300 ml). The combined organic layers were then washed with brine (350 ml), dried over $Na_2SO_4$ and concentrated under reduced pressure. The obtained compound was then purified by column chromatography (100-200 mesh silica gel and 1.5-2% MeOH in DCM as eluent) to afford 3-(acetyl-hydrazono)-2,2-dimethyl-1,2,3,4-tetrahydro-quinoxaline-5-carboxylic acid methyl ester (20.1 g, 58%) as an off white solid.

Step 5: To 3-(acetyl-hydrazono)-2,2-dimethyl-1,2,3,4-tetrahydro-quinoxaline-5-carboxylic acid methyl ester (12.0 g, 41.35 mmol) was added acetic anhydride (200 ml) and the resulting mixture was heated to 140° C. for 8 h. After completion of the reaction (monitored by LCMS) the reaction mixture was concentrated under reduced pressure. The residue was diluted with EtOAc, washed with saturated $NaHCO_3$ solution, dried over $Na_2SO_4$ and concentrated under reduced pressure. The obtained crude material was purified by column chromatography (100-200 mesh silica gel and 1.5-2% MeOH in DCM as eluent) to afford 5-acetyl-1,4,4-trimethyl-4,5-dihydro-[1,2,4]triazolo[4,3-a]quinoxaline-9-carboxylic acid methyl ester (5.5 g, 42%) as an off white solid.

Step 6: A stirring solution of 5-acetyl-1,4,4-trimethyl-4,5-dihydro-[1,2,4]triazolo[4,3-a]quinoxaline-9-carboxylic acid methyl ester (5.4 g, 0.12 mol) in 6N HCl (200 ml) was heated to 80° C. for 6 h. After completion of the reaction (monitored by LCMS) the reaction mixture was concentrated, the residue was azeotroped with toluene (four times) followed by trituration with ether-pentane to afforded the di-hydrochloride salt of 1,4,4-Trimethyl-4,5-dihydro-[1,2,4]triazolo[4,3-a]quinoxaline-9-carboxylic acid methyl ester (5.2 g, crude) as a greenish solid.

Step 7: To a stirring solution of the di-hydrochloride salt of 1,4,4-trimethyl-4,5-dihydro-[1,2,4]triazolo[4,3-a]quinoxaline-9-carboxylic acid methyl ester (2.5 g, 7.25 mmol) in THF (70 ml) was slowly added lithium aluminium hydride (18.12 ml, 18.12 mmol, 2M in THF) at 0° C. and the resulting reaction mixture was stirred at ambient temperature for 16 h. After completion of the reaction (monitored by LCMS) the reaction mixture was quenched with saturated $Na_2SO_4$ and was then filtered through a celite bed. The celite bed was then washed with hot THF (3×50 ml). The combined filtrates were concentrated under reduced pressure and were then azeotropted with toluene (3×50 ml) to afford (1,4,4-trimethyl-4,5-dihydro-[1,2,4]triazolo[4,3-a]quinoxalin-9-yl)methanol (1.9 g, crude) as a brownish solid.

Step 8: (1,4,4-trimethyl-4,5-dihydro-[1,2,4]triazolo[4,3-a]quinoxalin-9-yl)methanol (2.2 g, 9.01 mmol) was dissolved in THF-DCE (1:1, 65 ml). Manganese dioxide was added (4.7 g, 54.06 mmol) and the resulting reaction mixture was stirred at 80-90° C. for 48 h. After completion of the reaction (monitored by LCMS) the reaction mixture was filtered through a celite bed and the celite bed was washed with THF-DCE (1:1, 25 ml). The combined filtrate was concentrated under reduced pressure and the obtained crude material was purified by column chromatography (Silica gel 100-200 mesh, 2-2.5% MeOH-DCM as eluent) to afford 1,4,4-trimethyl-4,5-dihydro-[1,2,4]triazolo[4,3-a]quinoxaline-9-carbaldehyde (1.74 g, 80%) as an off white solid.

Step 9: To a stirring solution of 1,4,4-Trimethyl-4,5-dihydro-[1,2,4]triazolo[4,3-a]quinoxaline-9-carbaldehyde (2.0 g, 8.25 mmol) in DMF (30 ml) was added NBS (1.5 g, 8.50 mmol) portionwise at 0° C. and the resulting reaction mixture was then stirred at this temperature for 1 h. After completion of the reaction (monitored by LCMS) the reaction mixture was diluted with water (250 ml) and was extracted with EtOAc (2×150 ml). The combined organic layers were washed with water (2×180 ml), dried over anhydrous $Na_2SO_4$ and were then concentrated under reduced pressure. The obtained crude material was purified by column chromatography (230-400 mesh silica gel, 2-3% MeOH in DCM as eluent) to afford 8-bromo-1,4,4-trimethyl-4,5-dihydro-[1,2,4]triazolo[4,3-a]quinoxaline-9-carbaldehyde (1.1 g, 42%) as a brownish solid.

Step 10: 8-Bromo-1,4,4-trimethyl-4,5-dihydro-[1,2,4]triazolo[4,3-a]quinoxaline-9-carbaldehyde (1.0 g, 3.12 mmol) was dissolved in DCM (10 ml) and was cooled to 0° C. DAST (0.61 ml, 1.5 eq) was added and the reaction mixture was stirred at 10-15° C. for 6 h. The reaction mixture was then kept at −20° C. for 16 h. The reaction mixture was then warmed to 0° C. DAST (0.61 ml, 1.5 eq) was added and the reaction mixture was stirred for three hours. Then, DAST (0.61 ml, 1.5 eq) was added and the reaction mixture was stirred for another three hours. The reaction mixture was then quenched with sat. $NaHCO_3$ solution (pH8-9) at 0° C. and was extracted with DCM (50 mL×2). The combined organic layers were washed with cold water (30 ml), and brine (30 ml), dried over sodium sulphate and were then concentrated under reduced pressure to obtain the crude compound. The described reaction was conducted in four batches in parallel, each using 1.0 g (3.12 mmol) of 8-bromo-1,4,4-trimethyl-4,5-dihydro-[1,2,4]triazolo[4,3-a]quinoxaline-9-carbaldehyde. The combined batches of the crude compounds were purified by column chromatography (Silica gel 230-400 mesh, 30-35% acetone in hexane as eluent) to afford 8-bromo-9-difluoromethyl-1,4,4-trimethyl-4,5-dihydro-[1,2,4]triazolo[4,3-a]quinoxaline (1.4 g, 33%) as an off white solid.

$^1$H-NMR (400 MHz, DMSO-$d_6$): δ=7.57-7.54 (d, 1H), 7.27-7.06 (t, 1H), 7.04-7.03 (m, 2H), 2.41 (s, 3H), 1.68 (brs, 3H), 1.19 (brs, 3H).

Any of intermediates-A can be coupled to any of intermediates-B in standard chemical reactions which are known to the person skilled in the art, e.g. those as described herein below.

Example 1: 7,9-difluoro-8-(6-fluoro-1H-indol-4-yl)-1,4,4-trimethyl-4,5-dihydro-[1,2,4]triazolo[4,3-a]quinoxaline

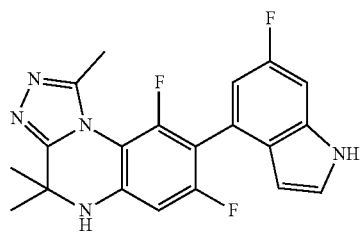 [SMILES: Cc1nnc2n1-c1c(cc(F)c(-c3cc(F)cc4[nH]ccc34)c1F)NC2(C)C]

To a solution of 8-bromo-7,9-difluoro-1,4,4-trimethyl-4,5-dihydro-[1,2,4]triazolo[4,3-a]quinoxaline (intermediate B-1) (0.5 g, 1.52 mmol, 1 eq.) in toluene:EtOH (2:1) (9 mL) were added 10% $Na_2CO_3$ (1.5 mL) solution and 6-fluoro-4-(4,4,5,5-tetramethyl-1,3,2-dioxaborolan-2-yl)-1H-indole (intermediate A-1) (0.40 g, 1.52 mmol, 1 eq) in sealed tube. The solution was degassed with Ar for 20 min followed by addition of $Pd(PPh_3)_4$ (0.09 g, 0.08 mmol, 0.05 eq.) The reaction mixture was refluxed at 130° C. for 16 h. After completion of reaction, reaction mixture was evaporated to dryness and the residue was diluted with EtOAc (50 mL) and washed with water (2×25 mL), brine (25 mL), dried over anhydrous $Na_2SO_4$ and evaporated to get the crude product, which was purified by flash column chromatography to afford 7,9-difluoro-8-(6-fluoro-1H-indol-4-yl)-1,4,4-trimethyl-4,5-dihydro-[1,2,4]triazolo[4,3-a]quinoxaline (0.35 g, 60%) as light yellow solid.

1H-NMR (400 MHz; DMSO-De, 20° C.): δ 11.3 (s, 1H), 7.39-7.41 (1H), 7.25-7.29 (1H), 7.18 (s, 1H), 6.96-7.00 (1H), 6.78-6.81 (1H), 5.75 (s, 1H), 2.48 (s, 3H), 1.16-1.57 (6H).

LC MS: found [M+H]$^+$: 384.

Example 2: 8-(1-cyclopropyl-6-fluoro-1H-indol-4-yl)-7,9-difluoro-1,4,4-trimethyl-4,5-dihydro-[1,2,4]triazolo[4,3-a]quinoxaline

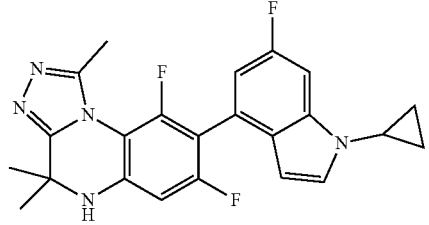 [SMILES: Cc1nnc2n1-c1c(cc(F)c(-c3cc(F)cc4c3ccn4C3CC3)c1F)NC2(C)C]

A stirring solution of 7,9-difluoro-8-(6-fluoro-1H-indol-4-yl)-1,4,4-trimethyl-4,5-dihydro-[1,2,4]triazolo[4,3-a]quinoxaline (example 1) (0.2 g, 0.52 mmol, 1 eq), cyclopropylboronic acid (0.09 g, 1.05 mmol, 2 eq) and $Na_2CO_3$ (0.11 g, 1.04 mmol, 2 eq) in DCM (4 mL) was deoxygenated well by Ar. A hot suspension of Cu(OAc) (0.95 g, 0.52 mml, 1 eq) and bipyridine (0.71 g, 0.522 mmol, 1 eq) in DCM (4 mL) was added to the reaction mixture. The reaction mixture then stirred for 16 h at 70° C. The reaction mixture was filtered through celite bed and washed with DCM (30 mL). The organic layer washed with water (2×25 mL), brine (25 mL), dried over anhydrous $Na_2SO_4$ and evaporated to get the crude product which was purified by flash column chromatography to afford compound 8-(1-cyclopropyl-6-fluoro-1H-indol-4-yl)-7,9-difluoro-1,4,4-trimethyl-4,5-dihydro-[1,2,4]triazolo[4,3-a]quinoxaline (0.045 g, 20%) as off white solid.

1H-NMR (400 MHz, DMSO-D$_6$, 20° C.): δ 7.43 (d, 1H, J=9.2 Hz), 7.38 (d, 1H, J=2.8 Hz), 7.19 (s, 1H), 7.04 (d, 1H, J=9.6 Hz), 6.78 (d, 1H, J=10.8 Hz), 6.25 (s, 1H), 3.45 (m, 1H), 2.5 (s, 3H), 1.56 (s, 3H), 1.48 (s, 3H), 1.05-0.98 (m, 4H).

LC MS: found [M+H]$^+$: 424.

Example 3: 7,9-difluoro-8-(6-fluoro-1-(methylsulfonyl)-1H-indol-4-yl)-1,4,4-trimethyl-4,5-dihydro-[1,2,4]triazolo[4,3-a]quinoxaline

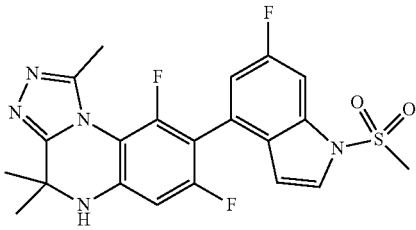 [SMILES: Cc1nnc2n1-c1c(cc(F)c(-c3cc(F)cc4c3ccn4S(C)(=O)=O)c1F)NC2(C)C]

To a solution of 8-bromo-7,9-difluoro-1,4,4-trimethyl-4,5-dihydro-[1,2,4]triazolo[4,3-a]quinoxaline (intermediate B-1) (0.8 g, 2.43 mmol, 1 eq.) in toluene:EtOH (2:1) (15 mL) were added 10% $Na_2CO_3$ (2 mL) solution and 6-fluoro-1-(methylsulfonyl)-4-(4,4,5,5-tetramethyl-1,3,2-dioxaborolan-2-yl)-1H-indole (intermediate A-2) (0.99 g, 2.92 mmol, 1.2 eq) in sealed tube. The solution was degassed with Ar for 20 min followed by addition of $Pd(PPh_3)_4$ (0.14 g, 0.12 mmol, 0.05 eq.) The reaction mixture was refluxed at 130° C. for 16 h. After completion of reaction, solvent was removed under reduced pressure and the residue was diluted with EtOAc (50 mL) and washed with water (2×25 mL), brine (25 mL), dried over anhydrous $Na_2SO_4$ and the solvent was evaporated to get the crude product which was purified by flash column chromatography to afford compound 7,9-difluoro-8-(6-fluoro-1-(methylsulfonyl)-1H-indol-4-yl)-1,4,4-trimethyl-4,5-dihydro-[1,2,4]triazolo[4,3-a]quinoxaline (0.12 g, 12%) as white solid.

1H-NMR (400 MHz; DMSO-$D_6$, 20° C.): δ 7.71 (d, 1H, J=9.2 Hz), 7.66 (d, 1H, J=3.2 Hz), 7.35 (d, 1H, J=9.6 Hz), 7.27 (s, 1H), 6.81 (d, 1H, J=10.8 Hz), 6.72 (s, 1H), 3.58 (s, 3H), 2.74 (s, 3H), 1.56 (s, 3H), 1.50 (s, 3H).

LC MS: found $[M+H]^+$: 461.8.

Example 4: 1-(4-(7,9-difluoro-1,4,4-trimethyl-4,5-dihydro-[1,2,4]triazolo[4,3-a]quinoxalin-8-yl)-6-fluoro-1H-indol-1-yl)ethanone

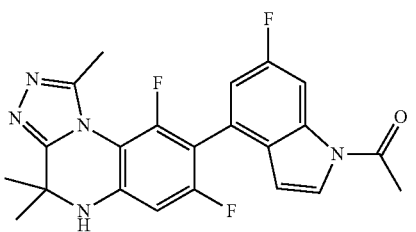 [SMILES: CC(=O)n1ccc2c(-c3c(F)cc4c(c3F)-n3c(C)nnc3C(C)(C)N4)cc(F)cc21]

To a stirring solution of 7,9-difluoro-8-(6-fluoro-1H-indol-4-yl)-1,4,4-trimethyl-4,5-dihydro-[1,2,4]triazolo[4,3-a]quinoxaline (example 1) (0.4 g, 1.044 mmol, 1 eq) were added powder sodium hydroxide (0.105 g, 2.61 mmol, 2.5 eq) and tetrabutylammonium hydrogen sulfate (0.071 g, 0.21 mmol, 0.02 eq) in DCM (8 mL). A solution of acetyl chloride (0.123 g, 1.55 mmol, 1.5 eq) in DCM (4 mL) was added to the reaction mixture. The reaction mixture was then stirred for 4 h at RT. The reaction mixture diluted with DCM (50 mL) and washed with water (2×20 mL), brine (20 mL), dried over anhydrous $Na_2SO_4$ and evaporated to get the crude, which was purified by flash column chromatography to afford 1-(4-(7,9-difluoro-1,4,4-trimethyl-4,5-dihydro-[1,2,4]triazolo[4,3-a]quinoxalin-8-yl)-6-fluoro-1H-indol-1-yl)ethanone (0.065 g, 15%) as white solid.

1H-NMR (400 MHz; DMSO-De, 20° C.): δ 8.17 (d, 1H, J=8.4 Hz), 7.94 (d, 1H, J=3.6 Hz), 7.30 (d, 1H, J=9.6 Hz), 7.26 (s, 1H), 6.81 (d, 1H, J=10.4 Hz), 6.64 (s, 1H), 2.67 (s, 3H), 2.5 (s, 3H), 1.57 (s, 3H), 1.49 (s, 3H).

LC MS: found $[M+H]^+$: 426.1.

Example 5: 7,9-difluoro-8-(6-fluoro-2-methyl-1H-indol-4-yl)-1,4,4-trimethyl-4,5-dihydro-[1,2,4]triazolo[4,3-a]quinoxaline

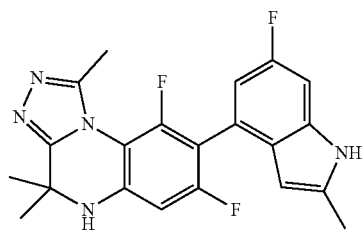

Example 5 was synthesized in analogy to procedure described for example 1 using 6-fluoro-2-methyl-4-(4,4,5,5-tetramethyl-1,3,2-dioxaborolan-2-yl)-1H-indole (intermediate A-3) and intermediate B-1.

1H-NMR (400 MHz; DMSO-$D_6$, 20° C.): δ 11.17 (s, 1H), 7.16-7.12 (m, 2H), 6.89 (d, 1H, J=9.92 Hz), 6.78 (d, 1H, J=10.56 Hz), 5.95 (s, 1H), 2.50 (s, 3H), 2.34 (s, 3H), 1.52 (s, 6H).

Example 6: 4-(7,9-difluoro-1,4,4-trimethyl-4,5-dihydro-[1,2,4]triazolo[4,3-a]quinoxalin-8-yl)-6-fluoro-1H-indole-2-carbonitrile

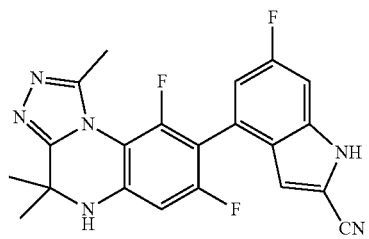 [SMILES: Cc1nnc2n1-c1c(cc(F)c(-c3cc(F)cc4[nH]c(C#N)cc34)c1F)NC2(C)C]

Example 6 was synthesized in analogy to the procedure described for example 1 using 6-fluoro-4-(4,4,5,5-tetramethyl-1,3,2-dioxaborolan-2-yl)-1H-indole-2-carbonitrile (intermediate A-4) and intermediate B-1.

$^1$H NMR (400 MHz, DMSO-d6): δ 12.66 (s, 1H), 7.39 (dd, J=8.16 Hz, 1H), 7.32 (s, 1H), 7.25 (s, 1H), 7.22 (dd, J=10.56 Hz, 1H), 6.81 (dd, J=10.64 Hz, 1H), 2.49 (s. 3H), 1.54 (s, 6H).

LCMS: found $[M+H]^+$: 409.1

Example 9: 7,9-difluoro-8-(1H-indol-7-yl)-1,4,4-trimethyl-4,5-dihydro-[1,2,4]triazolo[4,3-a]quinoxaline

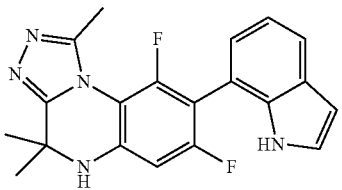 [SMILES: Cc1nnc2n1-c1c(cc(F)c(-c3cccc4cc[nH]c34)c1F)NC2(C)C]

Example 9 was synthesized in analogy to the procedure described for example 5 using 7-(4,4,5,5-tetramethyl-1,3,2-dioxaborolan-2-yl)-1H-indole and intermediate B-1.

$^1$H NMR (400 MHz, DMSO-d$_6$): δ 11.01 (s, 1H), 7.60-7.64 (1H), 7.34 (s, 1H), 7.06-7.14 (3H), 6.79-6.82 (1H), 6.51 (s, 1H), 2.43 (s, 3H), 1.54-1.56 (6H).

Example 10: 7,9-difluoro-1,4,4-trimethyl-8-(3-(trifluoromethyl)-1H-indol-7-yl)-4,5-dihydro-[1,2,4]triazolo[4,3-a]quinoxaline

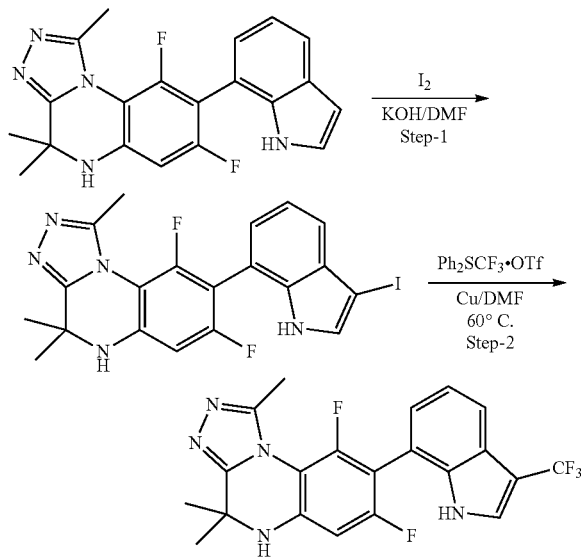

Step1: To a stirred solution of 7,9-difluoro-8-(1H-indol-7-yl)-1,4,4-trimethyl-4,5-dihydro-[1,2,4]triazolo[4,3-a]quinoxaline (example 9) (1.4 g, 3.83 mmol, 1 eq) in DMF (4 mL) was added potassium hydroxide powder (0.537 g, 9.5 mmol, 2.5 eq). The reaction mixture then stirred for 30 min at RT. Iodine (0.487 g, 3.83 mmol, 1 eq) was then added and the reaction mixture was stirred for 4 h. The reaction mixture then poured into ice cold water and precipitate was formed. Precipitate was then collected by filtration and dried to afford 7,9-difluoro-8-(3-iodo-1H-indol-7-yl)-1,4,4-trimethyl-4,5-dihydro-[1,2,4]triazolo[4,3-a]quinoxaline (0.5 g, 27%) as brown solid.

Step2: To a suspension of 7,9-difluoro-8-(3-iodo-1H-indol-7-yl)-1,4,4-trimethyl-4,5-dihydro-[1,2,4]triazolo[4,3-a]quinoxaline (1.0 g, 2.04 mmol, 1 eq) and diphenyl(trifluoromethyl)sulfonium trifluoromethanesulfonate (1.645 g, 4.07 mmol, 2 eq) in DMF (20 mL) was deoxygenated by Ar for 10 min. Cupper powder (0.388 mg, 6.11 mmol, 3 eq) then added to the reaction mixture. The reaction mixture then stirred at 100° C. for 24 h. The reaction mixture was filtered through celite bed and the filtrate was diluted with EtOAc (150 mL). The organic layer then washed with water (5×30 mL) and brine (30 mL), dried over anhydrous Na$_2$SO$_4$ and evaporated to get the crude product, which was purified by flash column chromatography to afford 7,9-difluoro-1,4,4-trimethyl-8-(3-(trifluoromethyl)-1H-indol-7-yl)-4,5-dihydro-[1,2,4]triazolo[4,3-a]quinoxaline (0.12 g, 14%) as white solid.

1H-NMR (400 MHz; DMSO-D$_6$, 20° C.): δ 11.86 (s, 1H), 7.99 (s, 1H), 7.68 (m, 1H), 7.3 (d, 2H, J=4.04 Hz), 7.2 (s, 1H), 6.81 (d, 1H, J=10.28 Hz), 2.5 (s, 3H), 1.55 (d, 6H, J=4.72 Hz).

LC MS: found [M+H]$^+$: 434.2.

Example 11: 1-ethyl-7,9-difluoro-8-(1H-indol-7-yl)-4,4-dimethyl-4,5-dihydro-[1,2,4]triazolo[4,3-a]quinoxaline

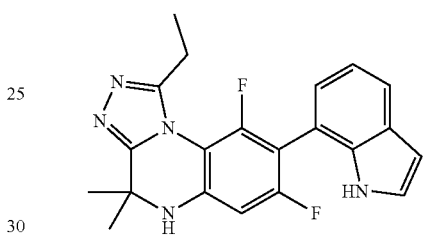

To a solution of 8-bromo-1-ethyl-7,9-difluoro-4,4-dimethyl-4,5-dihydro-[1,2,4]triazolo[4,3-a]quinoxaline (intermediate B-2) (1.0 g, 2.91 mmol, 1 eq) in toluene:EtOH (2:1) (10 mL) were added 10% Na$_2$CO$_3$ (2 mL) solution and (1H-indol-7-yl)boronic acid (1.06 g, 4.37 mmol, 1.5 eq) in sealed tube. The solution was degassed with Ar for 20 min followed by addition of Pd(PPh$_3$)$_4$ (0.168 g, 0.145 mmol, 0.05 eq) The reaction mixture was refluxed at 110° C. for 16 h. After completion of reaction, solvent was evaporated and the residue was diluted with EtOAc (150 mL). The organic layer was washed with water (2×50 mL), brine (30 mL), dried over anhydrous Na$_2$SO$_4$ and evaporated to get the crude product, which was purified by column chromatography to afford 1-ethyl-7,9-difluoro-8-(1H-indol-7-yl)-4,4-dimethyl-4,5-dihydro-[1,2,4]triazolo[4,3-a]quinoxaline (0.93 g, 84%) as off white solid.

1H-NMR (400 MHz; DMSO-De, 20° C.): δ 10.99 (s, 1H), 7.61-7.63 (1H), 7.35 (s, 1H), 7.08-7.12 (3H), 6.79-6.82 (1H, 6.52 (s, 1H), 2.80-2.92 (2H), 1.55 (s, 6H), 1.17-1.23 (3H).

LC MS: found [M+H]$^+$: 380.2.

Example 12: 7-(T-ethyl-7,9-difluoro-4,4-dimethyl-4,5-dihydro-[1,2,4]triazolo[4,3-a]quinoxalin-8-yl)-1H-indole-3-carbonitrile

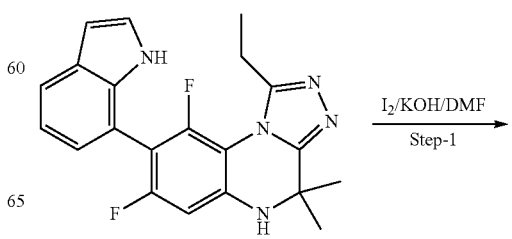

-continued

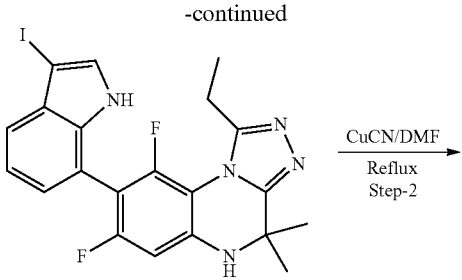

CuCN/DMF
Reflux
Step-2

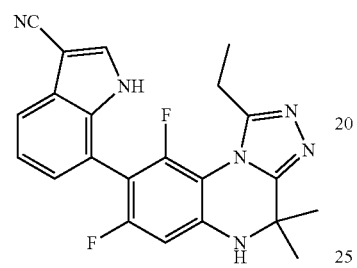

Step1: To a stirred solution of 1-ethyl-7,9-difluoro-8-(1H-indol-7-yl)-4,4-dimethyl-4,5-dihydro-[1,2,4]triazolo[4,3-a]quinoxaline (example 11) (0.50 g, 1.32 mmol, 1 eq) in DMF (10 mL) was added potassium hydroxide powder (0.185 g, 3.3 mmol, 2.5 eq). The reaction mixture then stirred for 30 min at RT. Iodine (0.402 g, 1.58 mmol, 1.2 eq) was then added to the reaction mixture and stirred for 4 h. The reaction mixture then diluted with EtOAc (80 mL) and washed with water (5×20 mL) and brine (30 mL). The organic layer dried over anhydrous $Na_2SO_4$, concentrated under reduced pressure to get the crude material, which was purified by column chromatography to afford 1-ethyl-7,9-difluoro-8-(3-iodo-1H-indol-7-yl)-4,4-dimethyl-4,5-dihydro-[1,2,4]triazolo[4,3-a]quinoxaline (0.25 g, 38%) as light brown solid.

Step2: A stirring suspension of 1-ethyl-7,9-difluoro-8-(3-iodo-1H-indol-7-yl)-4,4-dimethyl-4,5-dihydro-[1,2,4]triazolo[4,3-a]quinoxaline (0.25 g, 0.495 mmol, 1 eq), CuCN (0.088 g, 0.99 mmol, 2 eq) and tetraethylammoniumcyanide (0.038 g, 0.247 mmol, 0.5 eq) in DMF and THF (1:1) (8 mL) was deoxygenated well by Ar for 10 min. $Pd_2dba_3$ (0.022 g, 0.0247 mmol, 0.05 eq) and dppf (0.041 g, 0.0742 mmol, 0.15 eq) then added to the reaction mixture and again deoxygenated by Ar for 10 min. Finally the reaction mixture stirred for 18 h at 110° C. The reaction mixture was filtered through celite bed and the filtrate was diluted with EtOAc (30 mL). The organic layer washed by water (5×20 mL) and brine (20 mL). The organic layer dried over anhydrous $Na_2SO_4$, concentrated under reduced pressure to get the crude material, which was purified by column chromatography to afford 7-(7,9-difluoro-1,4,4-trimethyl-4,5-dihydro-[1,2,4]triazolo[4,3-a]quinoxalin-8-yl)-1H-indole-3-carbonitrile (0.08 g, 40%) as off white solid.

Example 13: 1-ethyl-7,9-difluoro-4,4-dimethyl-8-(3-(prop-1-yn-1-yl)-1H-indol-7-yl)-4,5-dihydro-[1,2,4]triazolo[4,3-a]quinoxaline

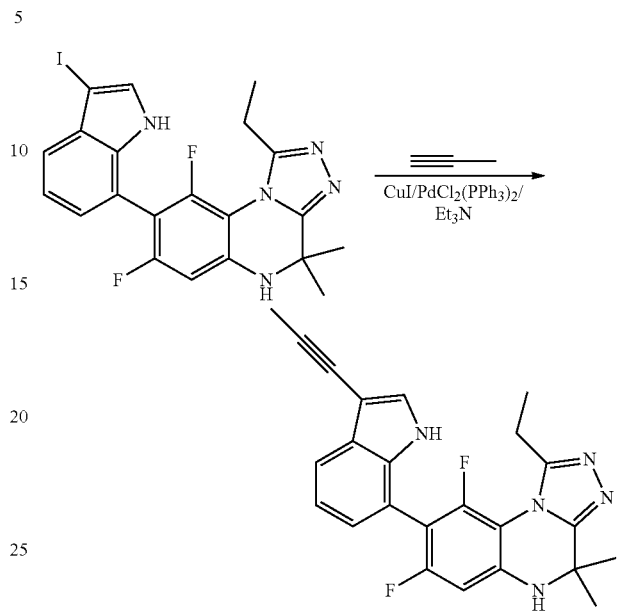

A solution of 1-ethyl-7,9-difluoro-8-(3-iodo-1H-indol-7-yl)-4,4-dimethyl-4,5-dihydro-[1,2,4]triazolo[4,3-a]quinoxaline (0.5 g, 0.99 mmol, 1 eq) in THF and TEA (1:1) (8 mL) was deoxygenated by Ar for 10 min in sealed tube. $Pd(PPh_3)_2Cl_{1-2}$ (0.035 g, 0.0455 mmol, 0.05 eq) and CuI (0.038 g, 0.198 mmol, 0.2 eq) then added to the reaction mixture and again deoxygenated by Ar for 10 min at −78° C. In test tube prop-1-yne gas was condensed in TEA (4 mL) at −78° C. The volume raised to 5 mL. The condensed prop-1-yne gas then instantly poured to the reaction mixture at −78° C. The reaction mixture then stirred for 2 h at −78° C. and 14 h at RT. The reaction mixture was diluted by DCM (50 mL). The organic layer washed with water (2×20 mL) and brine (20 mL). The organic layer dried over anhydrous $Na_2SO_4$, concentrated under reduced pressure to get the crude material, which was purified by column chromatography to afford 1-ethyl-7,9-difluoro-4,4-dimethyl-8-(3-(prop-1-yn-1-yl)-1H-indol-7-yl)-4,5-dihydro-[1,2,4]triazolo[4,3-a]quinoxaline (0.09 g, 22%) as off white solid.

$^1$H NMR (400 MHz, DMSO-$d_6$): δ 11.27 (s, 1H), 7.62-7.60 (m, 1H), 7.56 (d, J=2.48 Hz, 1H), 7.20-7.13 (m, 3H), 6.80 (d, J=10.24 Hz, 1H), 2.90-2.81 (m, 2H), 2.10 (s, 3H), 1.56 (s, 3H), 1.53 (s, 3H), 1.21 (t, J=7.44 Hz, 3H).

Example 14: 1-ethyl-7,9-difluoro-8-(5-fluoro-1H-indol-7-yn-4,4-dimethyl-4,5-dihydro-[1,2,4]triazolo[4,3-a]quinoxaline

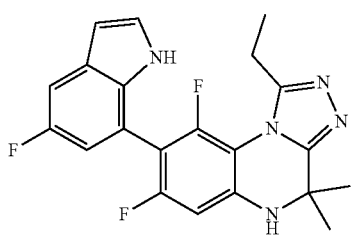 [SMILES: CCc1nnc2n1-c1c(cc(F)c(-c3cc(F)cc4cc[nH]c34)c1F)NC2(C)C]

Example 14 was synthesized in analogy to the procedure described for example 11 using 5-fluoro-7-(4,4,5,5-tetramethyl-1,3,2-dioxaborolan-2-yl)-1H-indole and intermediate B-2.

$^1$H NMR (400 MHz, DMSO-$d_6$): δ 11.2 (s, 1H), 7.40-7.44 (2H), 7.19 (s, 1H), 7.00-7.03 (1H), 6.80-6.83 (1H), 6.51 (s, 1H), 2.85-2.90 (2H), 1.55 (s, 6H), 1.20-1.24 (3H).

Example 15: 7-(1-ethyl-7,9-difluoro-4,4-dimethyl-4,5-dihydro-[1,2,4]triazolo[4,3-a]quinoxalin-8-yl)-5-fluoro-1H-indole-3-carbonitrile

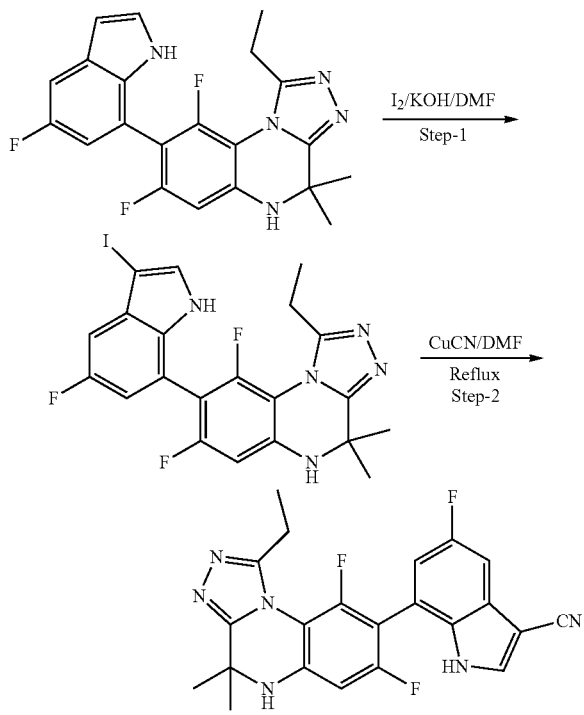

Step1: To a stirred solution of 1-ethyl-7,9-difluoro-8-(1H-indol-7-yl)-4,4-dimethyl-4,5-dihydro-[1,2,4]triazolo[4,3-a]quinoxaline (example 14) (1.2 g, 3.0 mmol, 1 eq) in DMF (25 mL) was added potassium hydroxide powder (0.425 g, 7.5 mmol, 2.5 eq). The reaction mixture then stirred for 30 min at RT. Iodine (1.14 g, 4.5 mmol, 1.5 eq) was then added to the reaction mixture and stirred for 4 h. The reaction mixture then diluted with EtOAc (200 mL) and washed with water (5×20 mL) and brine (30 mL). The organic layer dried over anhydrous $Na_2SO_4$, concentrated under reduced pressure to get the crude material, which was purified by column chromatography to afford 1-ethyl-7,9-difluoro-8-(5-fluoro-3-iodo-1H-indol-7-yl)-4,4-dimethyl-4,5-dihydro-[1,2,4]triazolo[4,3-a]quinoxaline (1.0 g, 64%) as light brown solid.

Step2: A stirring suspension of 1-ethyl-7,9-difluoro-8-(5-fluoro-3-iodo-1H-indol-7-yl)-4,4-dimethyl-4,5-dihydro-[1,2,4]triazolo[4,3-a]quinoxaline (0.4 g, 0.764 mmol, 1 eq), CuCN (0.137 g, 1.53 mmol, 2 eq) and tetraethylammoniumcyanide (0.06 g, 0.382 mmol, 0.5 eq) in DMF and THF (1:1) (14 mL) was deoxygenated well by Ar for 10 min. $Pd_2dba_3$ (0.035 g, 0.038 mmol, 0.05 eq) and dppf (0.063 g, 0.114 mmol, 0.15 eq) then added to the reaction mixture and again deoxygenated by Ar for 10 min.

Finally the reaction mixture stirred for 18 h at 110° C. The reaction mixture was filtered through celite bed and the filtrate was diluted with EtOAc (30 mL). The organic layer washed by water (5×20 mL) and brine (20 mL). The organic layer dried over anhydrous $Na_2SO_4$, concentrated under reduced pressure to get the crude material, which was purified by column chromatography to afford 7-(1-ethyl-7,9-difluoro-4,4-dimethyl-4,5-dihydro-[1,2,4]triazolo[4,3-a]quinoxalin-8-yl)-5-fluoro-1H-indole-3-carbonitrile (0.110 g, 34%) as off white solid.

$^1$H NMR (400 MHz, DMSO-$d_6$): δ 12.28 (s, 1H), 8.37 (s, 1H), 7.56-7.53 (m, 1H), 7.30-7.26 (m, 2H), 6.82 (d, J=10.36 Hz, 1H), 2.89-2.82 (m, 2H), 1.57 (s, 3H), 1.53 (s, 3H), 1.22 (t, J=7.32 Hz, 3H).

Example 16: 1-ethyl-7,9-difluoro-8-(5-fluoro-3-(prop-1-yn-1-yl)-1H-indol-7-yl)-4,4-dimethyl-4,5-dihydro-[1,2,4]triazolo[4,3-a]quinoxaline

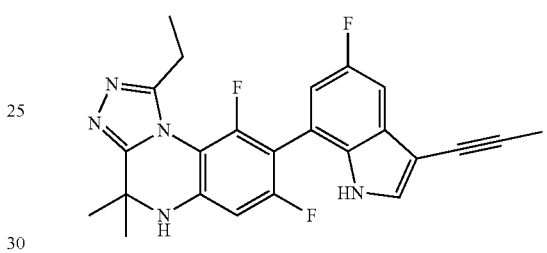

Example 16 was synthesized in analogy to procedure described for Example 13 starting from 1-ethyl-7,9-difluoro-8-(5-fluoro-3-iodo-1H-indol-7-yl)-4,4-dimethyl-4,5-dihydro-[1,2,4]triazolo[4,3-a]quinoxaline.

$^1$H NMR (400 MHz, DMSO-$d_6$): δ 11.37 (s, 1H), 7.65 (d, J=1.96 Hz, 1H), 7.33 (t, J=1.68 Hz, 1H), 7.20 (s, 1H), 7.10 (d, J=8.76 Hz, 1H), 6.80 (d, J=10.4 Hz, 1H), 2.88-2.84 (m, 2H), 2.09 (s, 3H), 1.56 (s, 3H), 1.53 (s, 3H), 1.21 (t, J=7.28 Hz, 3H).

Example 17: 7-(1-ethyl-7,9-difluoro-4,4-dimethyl-4,5-dihydro-[1,2,4]triazolo[4,3-a]quinoxalin-8-yl)-5-methyl-1H-indole-3-carbonitrile

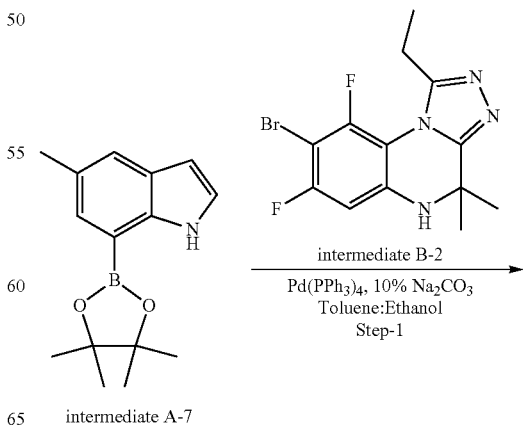

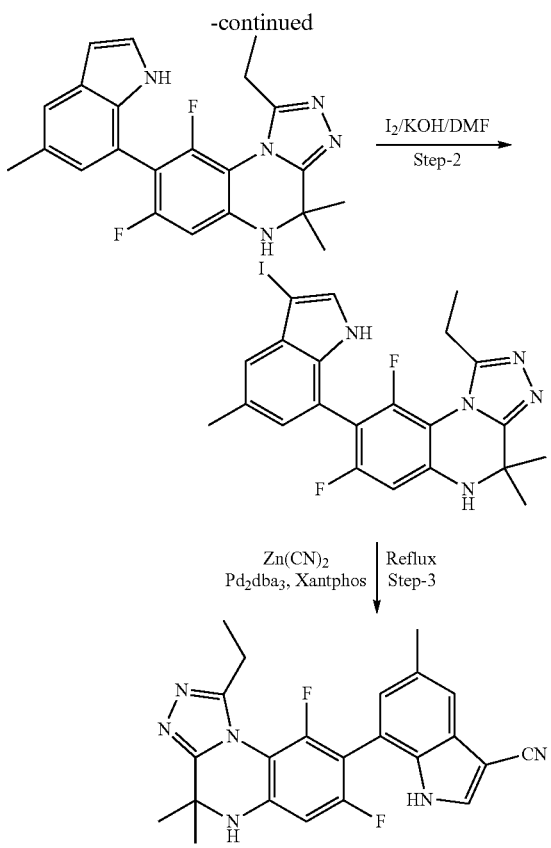

Step1: To a solution of intermediate B-2 (0.65 g, 1.77 mmol, 1 eq) in toluene:EtOH (2:1) (9 mL) were added 10% Na$_2$CO$_3$ (1.0 mL) solution and intermediate A-7 (0.548 g, 2.13 mmol, 1.2 eq) in a sealed tube. The solution was degassed with Ar for 20 min followed by addition of Pd(PPh$_3$)$_4$ (0.102 g, 0.0885 mmol, 0.05 eq) The reaction mixture was refluxed at 110° C. for 16 h. After completion of reaction, reaction mixture was evaporated to dryness and the residue was diluted with EtOAc (50 mL). The organic layer was washed with water (2×30 mL), brine (30 mL), dried over anhydrous Na$_2$SO$_4$ and evaporated to get the crude product, which was purified by column chromatography to afford 1-ethyl-7,9-difluoro-4,4-dimethyl-8-(5-methyl-1H-indol-7-yl)-4,5-dihydro-[1,2,4]triazolo[4,3-a]quinoxaline (0.61 g, 88%) as off white solid.

Step2: To a stirred solution of 1-ethyl-7,9-difluoro-4,4-dimethyl-8-(5-methyl-1H-indol-7-yl)-4,5-dihydro-[1,2,4]triazolo[4,3-a]quinoxaline (0.6 g, 1.52 mmol, 1 eq) in DMF (10 mL) was added potassium hydroxide powder (0.213 g, 3.816 mmol, 2.5 eq). The reaction mixture then stirred for 30 min at RT. Iodine (0.387 g, 3.052 mmol, 2 eq) was then added to the reaction mixture and stirred for 4 h. The reaction mixture was then diluted with EtOAc (100 mL) and washed with water (5×20 mL) and brine (30 mL). The organic layer was dried over anhydrous Na$_2$SO$_4$, concentrated under reduced pressure to get the crude material, which was purified by column chromatography to afford 1-ethyl-7,9-difluoro-8-(3-iodo-5-methyl-1H-indol-7-yl)-4,4-dimethyl-4,5-dihydro-[1,2,4]triazolo[4,3-a]quinoxaline (0.35 g, 44%) as light brown solid.

Step3: A stirring suspension of 1-ethyl-7,9-difluoro-8-(3-iodo-5-methyl-1H-indol-7-yl)-4,4-dimethyl-4,5-dihydro-[1,2,4]triazolo[4,3-a]quinoxaline (0.15 g, 0.308 mmol, 1 eq), Zn(CN)$_2$ (0.036 g, 0.308 mmol, 1 eq) and TMEDA (0.014 mL, 0.0929 mmol, 0.3 eq) in DMA (3 mL) was deoxygenated well by Ar for 10 min. Pd$_2$dba$_3$ (0.028 g, 0.0308 mmol, 0.1 eq) and xantphos (0.018 g, 0.0308 mmol, 0.1 eq) was then added to the reaction mixture and again deoxygenated by Ar for 10 min. Finally the reaction mixture was stirred for 14 h at 90° C. The reaction mixture was filtered through celite bed and the filtrate was diluted with EtOAc (30 mL). The organic layer was washed with water (5×20 mL) and brine (20 mL). The organic layer was dried over anhydrous Na$_2$SO$_4$, concentrated under reduced pressure to get the crude material, which was purified by column chromatography to afford 7-(1-ethyl-7,9-difluoro-4,4-dimethyl-4,5-dihydro-[1,2,4]triazolo[4,3-a]quinoxalin-8-yl)-5-methyl-1H-indole-3-carbonitrile (0.08 g, 63.%) as off white solid.

$^1$H NMR (400 MHz, DMSO-d$_6$): δ 12.04 (s, 1H), 8.22 (s, 1H), 7.51 (s, 1H), 7.22 (s, 1H), 7.14 (s, 1H), 6.82 (d, J=9.48 Hz, 1H), 2.94-2.82 (m, 2H), 2.47 (s, 3H), 1.56 (s, 3H), 1.53 (s, 3H), 1.21 (t, J=7.4 Hz, 3H).

Example 18: 8-(1-(ethylsulfonyl)-6-fluoro-1H-indol-4-yl)-7,9-difluoro-1,4,4-trimethyl-4,5-dihydro-[1,2,4]triazolo[4,3-a]quinoxaline

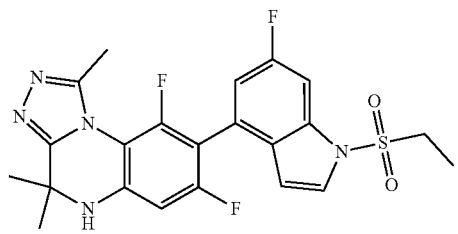 [SMILES: CCS(=O)(=O)n1ccc2c(-c3c(F)cc4c(c3F)-n3c(C)nnc3C(C)(C)N4)cc(F)cc21]

Example 18 was synthesized in analogy to procedure described for example 3 using 1-(ethylsulfonyl)-6-fluoro-4-(4,4,5,5-tetramethyl-1,3,2-dioxaborolan-2-yl)-1H-indole (intermediate A-8) and intermediate B-1.

$^1$H NMR (400 MHz, DMSO-d$_6$): δ 7.72-7.67 (m, 2H), 7.36 (d, J=9.92 Hz, 1H), 7.27 (s, 1H), 6.81 (d, J=10.64 Hz, 1H), 6.72 (s, 1H), 3.74 (q, J=7.28 Hz, 2H), 2.25 (s, 3H), 1.56 (s, 3H), 1.5 (s, 3H), 1.12 (t, J=7.28 Hz, 3H).

Example 19: 8-(1-(cyclopropylsulfonyl)-6-fluoro-1H-indol-4-yl)-7,9-difluoro-1,4,4-trimethyl-4,5-dihydro-[1,2,4]triazolo[4,3-a]quinoxaline

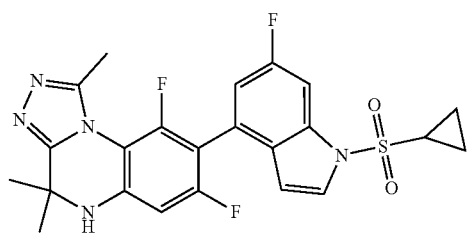 [SMILES: Cc1nnc2n1-c1c(cc(F)c(-c3cc(F)cc4c3ccn4S(=O)(=O)C3CC3)c1F)NC2(C)C]

Example 19 was synthesized in analogy to procedure described for example 3 using 1-(cyclopropylsulfonyl)-6-fluoro-4-(4,4,5,5-tetramethyl-1,3,2-dioxaborolan-2-yl)-1H-indole (intermediate A-9) and intermediate B-1.

$^1$H NMR (400 MHz, DMSO-d$_6$): δ 7.75 (d, J=9.2 Hz, 1H), 7.69 (s, 1H), 7.36 (d, J=8.4 Hz, 1H), 7.28 (s, 1H), 6.81 (d, J=10.0 Hz, 1H), 3.33 (s, 3H), 1.50-1.57 (m, 6H), 1.31 (s, 2H), 1.13 (s, 2H).

Example 20: 1-(4-(7,9-difluoro-1,4,4-trimethyl-4,5-dihydro-[1,2,4]triazolo[4,3-a]quinoxalin-8-yl)-1H-indol-1-yl)ethanone

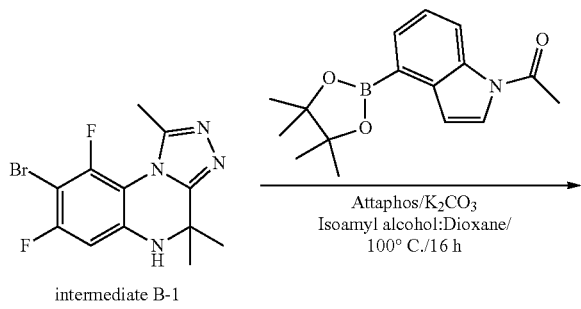

To a solution of 8-bromo-7,9-difluoro-1,4,4-trimethyl-4,5-dihydro-[1,2,4]triazolo[4,3-a]quinoxaline (intermediate B-1) (0.5 g, 1.57 mmol, 1 eq.) in dioxane:isoamylacohol (2:1) (9 mL) were added K$_2$CO$_3$ (0.725 g, 5.25 mmol, 3 eq.) solution and 1-(4-(4,4,5,5-tetramethyl-1,3,2-dioxaborolan-2-yl)-1H-indol-1-yl)ethanone (intermediate A-10) (0.634 g, 1.929 mmol, 1.1 eq). The solution was degassed with Ar for 20 min followed by addition of Attaphos (0.061 g, 0.087 mmol, 0.05 eq.) The reaction mixture was refluxed at 100° C. for 16 h. The solvent was evaporated to dryness and the residue was diluted with EtOAc (50 mL) and washed with water (2×25 mL), brine (25 mL), dried over anhydrous Na$_2$SO$_4$ and the solvent was evaporated to get the crude product, which was purified by prep HPLC to afford 1-(4-(7,9-difluoro-1,4,4-trimethyl-4,5-dihydro-[1,2,4]triazolo[4,3-a]quinoxalin-8-yl)-1H-indol-1-yl)ethanone (0.160 g, 22%) as white solid.

$^1$H NMR (400 MHz, DMSO-d$_6$): δ 8.41 (d, J=8 Hz, 1H), 7.92 (d, J=3.6 Hz, 1H), 7.43 (t, J=8.0 Hz, 1H), 7.33 (d, J=7.6 Hz, 1H), 7.19 (s, 1H), 6.81 (d, J=10.4 Hz, 1H), 6.62 (bs, 1H), 2.67 (s, 3H), 1.57 (s, 3H), 1.49 (s, 3H).

Example 21: 7,9-difluoro-8-(6-fluoro-1-(2,2,2-trifluoroethyl)-1H-indol-4-yl)-1,4,4-trimethyl-4,5-dihydro-[1,2,4]triazolo[4,3-a]quinoxaline

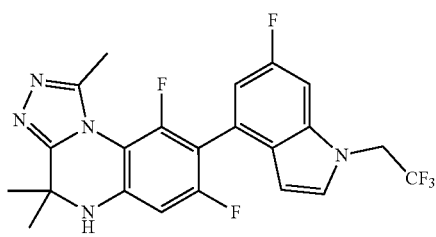 [SMILES: Cc1nnc2n1-c1c(cc(F)c(-c3cc(F)cc4c3ccn4CC(F)(F)F)c1F)NC2(C)C]

To a solution of 6-fluoro-4-(4,4,5,5-tetramethyl-1,3,2-dioxaborolan-2-yl)-1-(2,2,2-trifluoroethyl)-1H-indole (intermediate A-11) (0.4 g, 1.166 mmol, 1 eq.) in toluene:EtOH (2:1) (9 mL) were added 10% Na$_2$CO$_3$ (0.4 mL) solution and intermediate B-1 (0.307 g, 0.932 mmol, 0.8 eq) in a sealed tube. The solution was degassed with Ar for 20 min followed by addition of Pd(PPh$_3$)$_4$ (0.067 g, 0.058 mmol, 0.05 eq.) The reaction mixture was refluxed at 90° C. for 16 h. The reaction mixture was filtered through celite bed. Filtrate was concentrated under reduced pressure to get the crude product which was purified by prep HPLC to afford compound 7,9-difluoro-8-(6-fluoro-1-(2,2,2-trifluoroethyl)-1H-indol-4-yl)-1,4,4-trimethyl-4,5-dihydro-[1,2,4]triazolo[4,3-a]quinoxaline (0.055 g, 10%) as off white solid.

$^1$H NMR (400 MHz, DMSO-d$_6$): δ 7.65 (d, J=10 Hz, 1H), 7.46 (d, J=3.2 Hz, 1H), 7.21 (s, 1H), 7.09 (d, J=9.6 Hz, 1H), 6.80 (d, J=10.4 Hz, 1H), 6.43 (s, 1H), 6.81 (d, J=10.0 Hz, 1H), 5.24 (q, J 5=8.8 Hz, 2H), 5.86 (bs, 6H).

Example 22: 7,9-difluoro-1,4,4-trimethyl-8-(1-(methylsulfonyl)-1H-indol-4-yl)-4,5-dihydro-[1,2,4]triazolo[4,3-a]quinoxaline

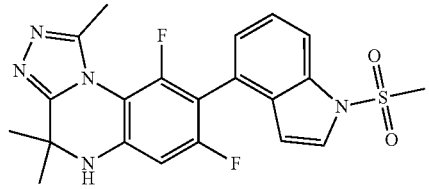

Example 22 was synthesized in analogy to procedure described for example 3 using 1-(methylsulfonyl)-4-(4,4,5,5-tetramethyl-1,3,2-dioxaborolan-2-yl)-1H-indole (intermediate A-12) and intermediate B-1.

$^1$H NMR (400 MHz, DMSO-d$_6$): 7.93 (d, J=8.28 Hz, 1H), 7.64 (d, J=3.64 Hz, 1H), 7.49 (t, J=7.68 Hz, 1H), 7.38 (d, J=7.24 Hz, 1H), 7.21 (s, 1H), 6.81 (d, J=10.16 Hz, 1H), 6.71 (s, 1H), 3.52 (s, 3H), 1.57 (s, 3H), 1.5 (s, 3H).

Example 23: 7-fluoro-8-(5-fluoro-3-(2,2,2-trifluoroethyl)-1H-indol-7-yl)-1,4,4,9-tetramethyl-4,5-dihydro-[1,2,4]triazolo[4,3-a]quinoxaline

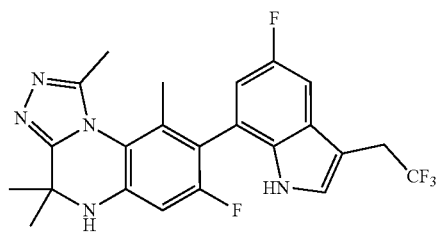 [SMILES: Cc1c(-c2cc(F)cc3c(CC(F)(F)F)c[nH]c23)c(F)cc2c1-n1c(C)nnc1C(C)(C)N2]

To a solution of 5-fluoro-7-(4,4,5,5-tetramethyl-1,3,2-dioxaborolan-2-yl)-3-(2,2,2-trifluoroethyl)-1H-indole (intermediate A-13) (0.600 g, 1.749 mmol, 1.0 eq.) in dioxane:isoamyl alcohol (2:1) (25 mL) were added K$_2$CO$_3$ (0.724 g, 5.247 mmol, 3 eq.) solution and 8-bromo-7-fluoro-1,4,4,9-tetramethyl-4,5-dihydro-[1,2,4]triazolo[4,3-a]quinoxaline (intermediate B-3) (0.284 g, 0.874 mmol, 0.5 eq). The solution was degassed with Ar for 20 min followed by addition of Attaphos (0.062 g, 0.087 mmol, 0.05 eq.) The reaction mixture was stirred at 100° C. for 16 h. The solvent was evaporated to get the crude product, which was purified by flash column chromatography and by prep HPLC to afford 7-fluoro-8-(5-fluoro-3-(2,2,2-trifluoroethyl)-1H-indol-7-yl)-1,4,4,9-tetramethyl-4,5-dihydro-[1,2,4]triazolo[4,3-a]quinoxaline (0.200 g, 25%) as white solid.

$^1$H NMR (400 MHz, DMSO-d$_6$): δ 11.10 (s, 1H), 7.45-7.40 (m, 2H), 6.97 (d, J=8.8, 1H), 6.80 (s, 2H), 3.76 (q, J=10.8 Hz, 2H), 2.50 (s, 3H), 1.96 (s, 3H), 1.53 (s, 3H), 1.44 (s, 3H).

Example 24: 7-fluoro-1,4,4,9-tetramethyl-8-(3-(2,2,2-trifluoroethyl)-1H-indol-7-yl)-4,5-dihydro-[1,2,4]triazolo[4,3-a]quinoxaline

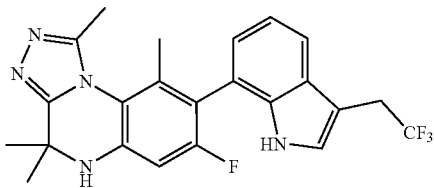 [SMILES: Cc1c(-c2cccc3c(CC(F)(F)F)c[nH]c23)c(F)cc2c1-n1c(C)nnc1C(C)(C)N2]

Example 24 was synthesized in analogy to procedure described for example 3 using 7-(4,4,5,5-tetramethyl-1,3,2-dioxaborolan-2-yl)-3-(2,2,2-trifluoroethyl)-1H-indole (intermediate A-14) and intermediate C.

$^1$H NMR (400 MHz, DMSO-d$_6$): δ 10.97 (s, 1H), 7.64 (d, J=7.2 Hz, 1H), 7.32 (s, 1H), 7.13 (d, J=6.8, 1H), 7.04 (d, J=6.4, 1H), 6.80 (d, J=10, 1H), 6.74 (s, 1H), 3.76 (q, J=12 Hz, 2H), 2.49 (s, 3H), 1.93 (s, 3H), 1.55 (s, 3H), 1.43 (s, 3H).

Example 25: 7-fluoro-8-(1H-indol-7-yl)-1,4,4,9-tetramethyl-4,5-dihydro-[1,2,4]triazolo[4,3-a]quinoxaline

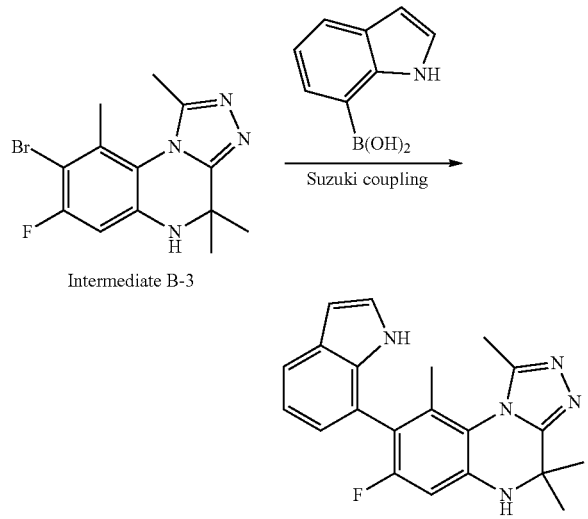

Intermediate B-3

To a solution of intermediate B-3 (1.2 g, 3.69 mmol, 1 eq) in toluene:EtOH (2:1) (15 mL) were added 10% Na$_2$CO$_3$ (2 mL) solution and (1H-indol-7-yl)boronic acid (1.07 g, 4.43 mmol, 1.2 eq) in a sealed tube. The solution was degassed with Ar for 20 min followed by addition of Pd(PPh$_3$)$_4$ (0.213 g, 0.1845 mmol, 0.05 eq). The reaction mixture was stirred at 110° C. for 16 h. The solvent was evaporated to dryness and the residue was diluted with EtOAc (150 mL). The organic layer was washed with water (2×50 mL), brine (30 mL), dried over anhydrous Na$_2$SO$_4$ and the solvent was evaporated to get the crude product, which was purified by column chromatography to afford 7-fluoro-8-(1H-indol-7-yl)-1,4,4,9-tetramethyl-4,5-dihydro-[1,2,4]triazolo[4,3-a]quinoxaline (0.85 g, 64%) as off white solid.

$^1$H NMR (400 MHz, DMSO-d$_6$): δ 10.88 (s, 1H), 7.58-7.60 (1H), 7.30 (s, 1H), 7.06-7.11 (1H), 6.98-7.00 (1H), 6.78-6.81 (1H), 6.73 (s, 1H), 6.50 (s, 1H), 2.47 (s, 3H), 1.94 (s, 3H), 1.56 (s, 3H), 1.43 (s, 3H).

Example 26: 7-fluoro-8-(1H-indol-4-yl)-1,4,4,9-tetramethyl-4,5-dihydro-[1,2,4]triazolo[4,3-a]quinoxaline

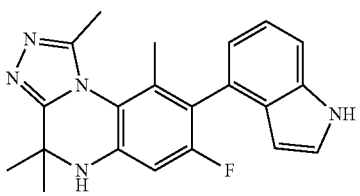 [SMILES: Cc1c(-c2cccc3[nH]ccc23)c(F)cc2c1-n1c(C)nnc1C(C)(C)N2]

Example 26 was synthesized in analogy to procedure described for example 1 using 4-(4,4,5,5-tetramethyl-1,3,2-dioxaborolan-2-yl)-1H-indole and intermediate B-3.

$^1$H NMR (400 MHz, DMSO-d$_6$): δ 11.21 (s, 1H), 7.44-7.46 (1H), 7.37 (s, 1H), 7.17-7.20 (1H), 6.96-6.98 (1H), 6.77-6.79 (1H), 6.69 (s, 1H), 6.09 (s, 1H), 2.44 (s, 3H), 1.98 (s, 3H), 1.54 (s, 3H), 1.44 (s, 3H).

Example 27: 8-(1-cyclopropyl-1H-indol-4-yl)-7-fluoro-1,4,4,9-tetramethyl-4,5-dihydro-[1,2,4]triazolo[4,3-a]quinoxaline

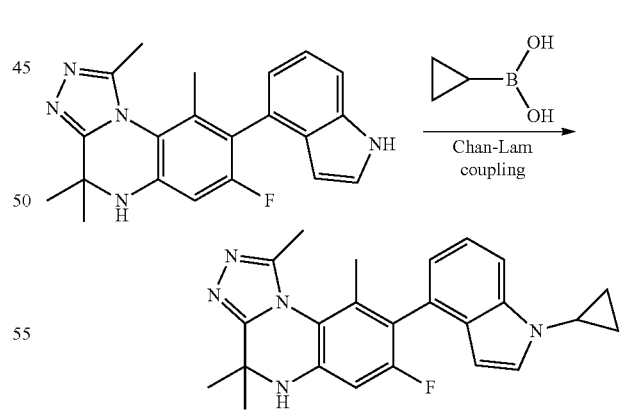

A stirring solution of 7-fluoro-8-(1H-indol-4-yl)-1,4,4,9-tetramethyl-4,5-dihydro-[1,2,4]triazolo[4,3-a]quinoxaline (example 26) (0.2 g, 0.554 mmol, 1 eq), cyclopropylboronic acid (0.095 g, 1.1 mmol, 2 eq) and Na$_2$CO$_3$ (0.12 g, 1.1 mmol, 2 eq) in DCM (4 mL) was deoxygenated by Ar. A hot suspension of Cu(OAc) (0.1 g, 0.554 mml, 1 eq) and bipyridine (0.86 g, 0.554 mmol, 1 eq) in DCM (4 mL) was added to the reaction mixture. The reaction mixture then stirred for 16 h at 70° C. The reaction mixture was filtered through celite bed and washed with DCM (30 mL). The organic layer was washed with water (2×25 mL), brine (25 mL), dried over anhydrous $Na_2SO_4$ and the solvent was evaporated to get the crude product, which was purified by flash column chromatography to afford 8-(1-cyclopropyl-1H-indol-4-yl)-7-fluoro-1,4,4,9-tetramethyl-4,5-dihydro-[1,2,4]triazolo[4,3-a]quinoxaline (0.07 g, 32%) as off white solid.

$^1$H NMR (400 MHz, DMSO-$d_6$): δ 7.60 (d, J=8.16 Hz, 1H), 7.35 (d, J=2.96 Hz, 1H), 7.26 (t, J=7.56 Hz, 1H), 7.02 (d, J=7.08 Hz, 1H), 6.76 (d, J=10.12 Hz, 1H), 6.71 (s, 1H), 6.05 (s, 1H), 3.49-3.48 (m, 1H), 2.42 (s, 3H), 1.98 (s, 3H), 1.52 (s, 3H), 1.42 (s, 3H), 1.08-0.99 (m, 4H).

Example 28: 7-fluoro-1,4,4,9-tetramethyl-8-(3-(prop-1-yn-1-yl)-1H-indol-7-yl)-4,5-dihydro-[1,2,4]triazolo[4,3-a]quinoxaline

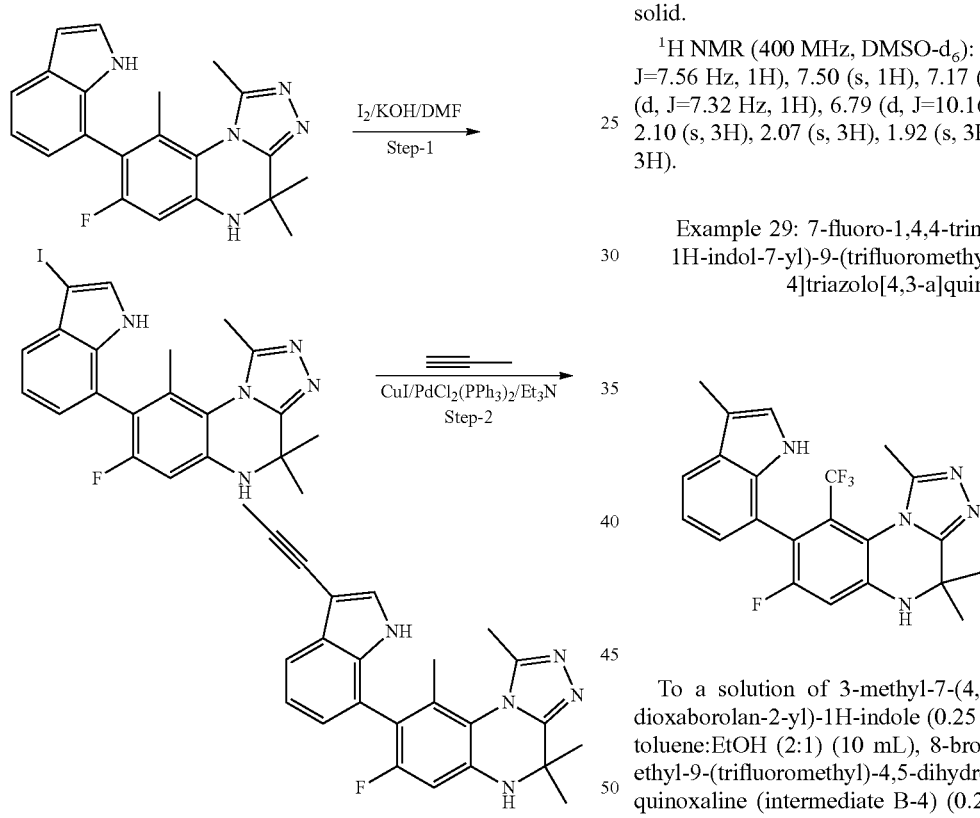

Step1: To a stirred solution of 7-fluoro-8-(1H-indol-7-yl)-1,4,4,9-tetramethyl-4,5-dihydro-[1,2,4]triazolo[4,3-a]quinoxaline (example 25) (0.85 g, 2.35 mmol, 1 eq) in DMF (20 mL) was added potassium hydroxide powder (0.329 g, 5.87 mmol, 2.5 eq). The reaction mixture was then stirred for 30 min at RT. Iodine (0.897 g, 3.53 mmol, 1.5 eq) was then added to the reaction mixture and stirred for 4 h. The reaction mixture then diluted with EtOAc (100 mL) and washed with water (5×20 mL) and brine (30 mL). The organic layer was dried over anhydrous $Na_2SO_4$, concentrated under reduced pressure to get the crude material, which was purified by column chromatography to afford 7-fluoro-8-(3-iodo-1H-indol-7-yl)-1,4,4,9-tetramethyl-4,5-dihydro-[1,2,4]triazolo[4,3-a]quinoxaline (0.27 g, 24%) as light brown solid.

Step2: A solution of 7-fluoro-8-(3-iodo-1H-indol-7-yl)-1,4,4,9-tetramethyl-4,5-dihydro-[1,2,4]triazolo[4,3-a]quinoxaline (0.48 g, 0.98 mmol, 1 eq) in THF and TEA (1:1) (8 mL) was deoxygenated by Ar for 10 min in a sealed tube. Pd(PPh$_3$)$_2$Cl$_2$ (0.035 g, 0.049 mmol, 0.05 eq) and CuI (0.038 g, 0.197 mmol, 0.2 eq) were then added to the reaction mixture and again deoxygenated by Ar for 10 min at −78° C. In test tube prop-1-yne gas was condensed in TEA (3 mL) at −78° C. The volume rose to 5 mL. The condensed prop-1-yne gas was instantly poured to the reaction mixture at −78° C. The reaction mixture was then stirred for 2 h at −78° C. and for 14 h at RT. The reaction mixture was diluted with DCM (50 mL). The organic layer was washed with water (2×20 mL) and brine (20 mL). The organic layer was dried over anhydrous $Na_2SO_4$, concentrated under reduced pressure to get the crude material, which was purified by column chromatography to afford 7-fluoro-1,4,4,9-tetramethyl-8-(3-(prop-1-yn-1-yl)-1H-indol-7-yl)-4,5-dihydro-[1,2,4]triazolo[4,3-a]quinoxaline (0.08 g, 20%) as off white solid.

$^1$H NMR (400 MHz, DMSO-$d_6$): δ 11.12 (s, 1H), 7.58 (d, J=7.56 Hz, 1H), 7.50 (s, 1H), 7.17 (t, J=7.56 Hz, 1H), 7.07 (d, J=7.32 Hz, 1H), 6.79 (d, J=10.16 Hz, 1H), 6.74 (s, 1H), 2.10 (s, 3H), 2.07 (s, 3H), 1.92 (s, 3H), 1.53 (s, 3H), 1.43 (s, 3H).

Example 29: 7-fluoro-1,4,4-trimethyl-8-(3-methyl-1H-indol-7-yl)-9-(trifluoromethyl)-4,5-dihydro-[1,2,4]triazolo[4,3-a]quinoxaline

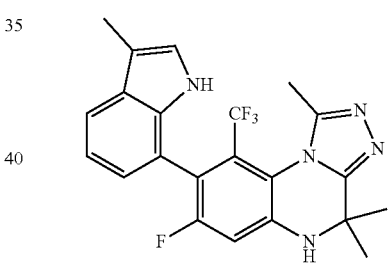

To a solution of 3-methyl-7-(4,4,5,5-tetramethyl-1,3,2-dioxaborolan-2-yl)-1H-indole (0.25 g, 0.579 mmol, 1 eq) in toluene:EtOH (2:1) (10 mL), 8-bromo-7-fluoro-1,4,4-trimethyl-9-(trifluoromethyl)-4,5-dihydro-[1,2,4]triazolo[4,3-a]quinoxaline (intermediate B-4) (0.223 g, 0.254 mmol, 1.5 eq) and 10% $Na_2CO_3$ (0.5 mL) was added at RT. After degassing the reaction mixture Pd(PPh$_3$)$_4$ (0.038 g, 0.028 mmol, 0.05 eq) was added at RT and the reaction mixture was stirred at 90° C. for another 16 h. The reaction mixture was filtered through cintered and diluted with water (20 mL). The aqueous layer was extracted with EtOAc (3×50 mL). Combined organic layers were washed with water (50 mL), brine (50 mL), dried over anhydrous $Na_2SO_4$ and the solvent was evaporated to get the crude product which was purified by column chromatography to afford 7-fluoro-1,4,4-trimethyl-8-(3-methyl-1H-indol-7-yl)-9-(trifluoromethyl)-4,5-dihydro-[1,2,4]triazolo[4,3-a]quinoxaline (0.042 g, 17%) as white solid.

$^1$H NMR (400 MHz, DMSO-$d_6$, T=100° C.): δ 10.29 (s, 1H), 7.55 (d, J=8.0 Hz, 1H), 7.13-7.04 (m, 4H), 2.45 (s, 3H), 2.28 (s, 3H), 1.75 (s, 3H), 1.31 (bs, 3H).

Example 30: 9-chloro-7-fluoro-8-(5-fluoro-3-methyl-1H-indol-7-yn-1,4,4-trimethyl-4,5-dihydro-[1,2,4]triazolo[4,3-a]quinoxaline

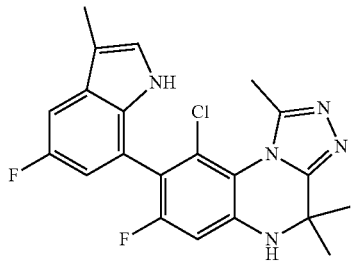 [SMILES: Cc1c[nH]c2c(-c3c(F)cc4c(c3Cl)-n3c(C)nnc3C(C)(C)N4)cc(F)cc12]

Example 30 was synthesized in analogy to procedure described for example 29 using 5-fluoro-3-methyl-7-(4,4,5,5-tetramethyl-1,3,2-dioxaborolan-2-yl)-1H-indole (intermediate A-15) and intermediate B-5.

$^1$H NMR (400 MHz, DMSO-d$_6$): δ 10.71 (s, 1H), 7.29 (d, J=9.6 Hz, 1H), 7.15 (s, 1H), 7.1 (s, 1H), 6.90 (d, J=10.0 Hz, 2H), 2.54 (s, 3H), 2.23 (s, 3H), 1.52 (s, 3H), 1.45 (s, 3H).

Example 31: 7-fluoro-8-(5-fluoro-3-methyl-1H-indol-7-yl)-1,4,4,9-tetramethyl-4,5-dihydro-[1,2,4]triazolo[4,3-a]quinoxaline

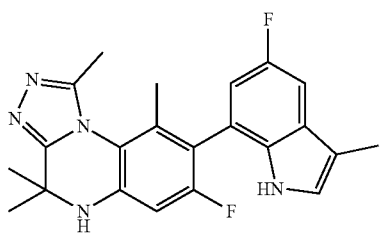

Example 31 was synthesized in analogy to procedure described for example 29 using 5-fluoro-3-methyl-7-(4,4,5,5-tetramethyl-1,3,2-dioxaborolan-2-yl)-1H-indole (intermediate A-15) and intermediate B-3.

$^1$H NMR (400 MHz, DMSO-d$_6$): δ 10.65 (s, 1H), 7.28 (d, J=10.0 Hz, 1H), 7.15 (s, 1H), 6.90 (d, J=8.2 Hz, 1H), 6.77-6.80 (m, 2H), 2.46 (s, 3H), 2.25 (s, 3H), 1.95 (s, 3H), 1.53 (s, 3H), 1.43 (s, 3H).

Example 32: 7-fluoro-8-(5-fluoro-1H-indol-7-yl)-1,4,4,9-tetramethyl-4,5-dihydro-[1,2,4]triazolo[4,3-a]quinoxaline

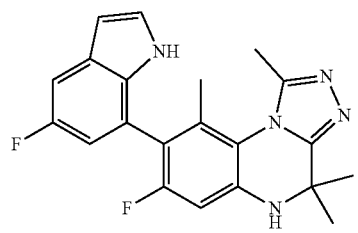 [SMILES: Cc1c(-c2cc(F)cc3cc[nH]c23)c(F)cc2c1-n1c(C)nnc1C(C)(C)N2]

Example 32 was synthesized in analogy to procedure described for example 29 using 5-fluoro-7-(4,4,5,5-tetramethyl-1,3,2-dioxaborolan-2-yl)-1H-indole and intermediate B-3.

$^1$H NMR (400 MHz, DMSO-d$_6$): δ 11.0 (s, 1H), 7.35-7.38 (2H), 6.91-6.93 (1H), 6.77-6.81 (2H), 6.50 (s, 1H), 2.47 (s, 3H), 1.96 (s, 3H), 1.54 (s, 3H), 1.44 (s, 3H).

Example 33: 8-(3-cyclopropyl-5-fluoro-1H-indol-7-yl)-7-fluoro-1,4,4,9-tetramethyl-4,5-dihydro-[1,2,4]triazolo[4,3-a]quinoxaline

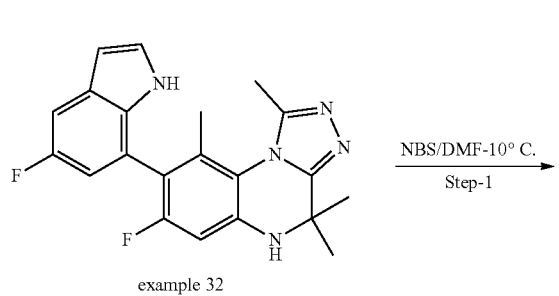

example 32

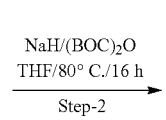

NBS/DMF-10° C.
Step-1

NaH/(BOC)$_2$O
THF/80° C./16 h
Step-2

-continued

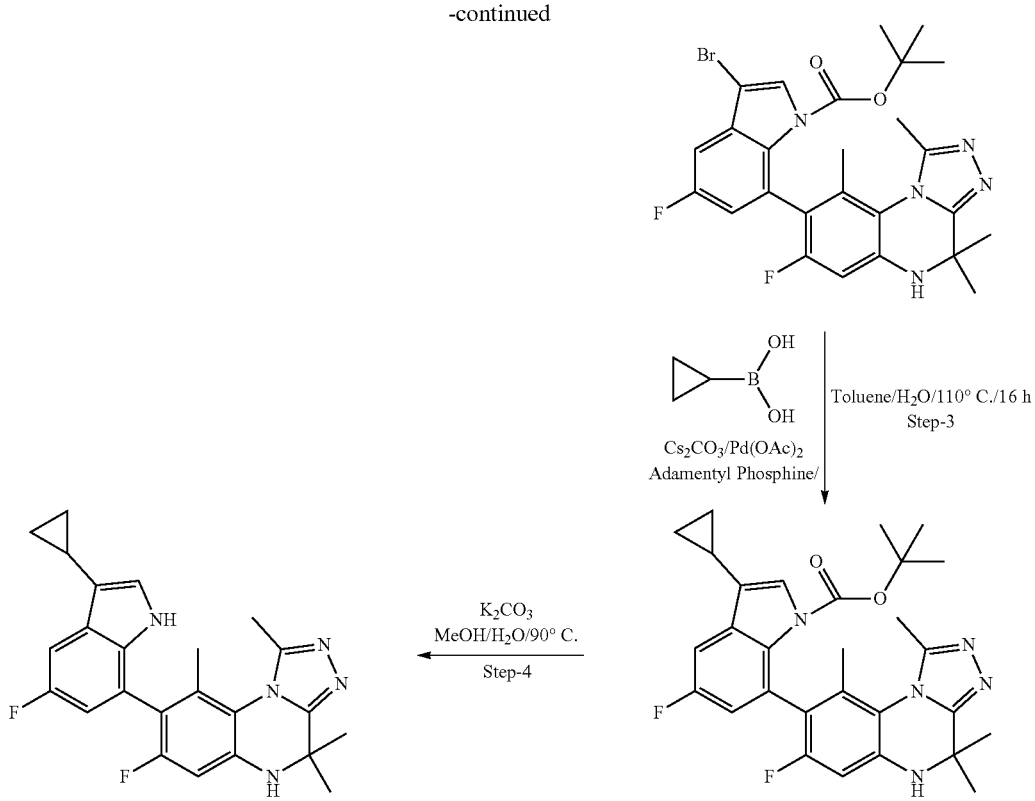

Step1: A stirred solution of 7-fluoro-8-(5-fluoro-1H-indol-7-yl)-1,4,4,9-tetramethyl-4,5-dihydro-[1,2,4]triazolo[4,3-a]quinoxaline (example 32) (0.7 g, 1.846 mmol, 1 eq) in DMF (6 mL) at −10° C. was added portion wise over 10 min solid N-bromosuccinimide (0.338 g, 1.902 mmol, 1.03 eq). Reaction mixture was allowed to warm to RT and stirred for 1.5 h. After completion of reaction (monitored by LCMS), reaction mixture was diluted with EtOAc (30 mL) and organic layers were washed with water (5×25 mL), brine (25 mL), dried over anhydrous $Na_2SO_4$ and the solvent was evaporated under reduced pressure to get crude product which was purified by Eether wash to afford 8-(3-bromo-5-fluoro-1H-indol-7-yl)-7-fluoro-1,4,4,9-tetramethyl-4,5-dihydro-[1,2,4]triazolo[4,3-a]quinoxaline (0.8 g, 95%) as off white solid.

Step2: To a solution of 8-(3-bromo-5-fluoro-1H-indol-7-yl)-7-fluoro-1,4,4,9-tetramethyl-4,5-dihydro-[1,2,4]triazolo[4,3-a]quinoxaline (22.0 g, 48.034 mmol, 1 eq) in THF (400 mL), NaH (6.72 g, 168.11 mmol, 3.5 eq) was added at RT. After 15 min of stirring $(BOC)_2O$ (15.4 mL, 75.052 mmol, 1.5 eq) was added at RT. The reaction was then refluxed for 16 h. After completion of reaction (monitored by TLC), reaction mixture was quenched with ice and extracted with EtOAc. The organic layer was washed with water, brine, dried over Na2SO4, filtered and the solvent was evaporated under reduced pressure to get the crude product. Crude product was purified by column chromatography to afford tert-butyl 3-bromo-5-fluoro-7-(7-fluoro-1,4,4,9-tetramethyl-4,5-dihydro-[1,2,4]triazolo[4,3-a]quinoxalin-8-yl)-1H-indole-1-carboxylate (17.0 g, 63%) as brown solid.

Step3: To a solution of tert-butyl 3-bromo-5-fluoro-7-(7-fluoro-1,4,4,9-tetramethyl-4,5-dihydro-[1,2,4]triazolo[4,3-a]quinoxalin-8-yl)-1H-indole-1-carboxylate (0.35 g, 0.627 mmol, 1 eq) in toluene: EtOH (2:1) (10.0 ml), $Cs_2CO_3$ (0.611 g, 1.881 mmol, 3 eq) and Cyclopropylboronic acid (0.108 g, 1.254 mmol, 2 eq) was added at RT. The solution was degassed with Ar for 20 min followed by addition of $Pd(OAc)_2$ (0.014 g, 0.062 mmol, 0.1 eq) and Adamentyl Phosphine (0.019 g, 0.062 mmol, 0.1 eq) at RT and the reaction mixture was stirred at 110° C. for 16 h. After completion of reaction (monitored by LCMS), solvent was evaporated and the residue was diluted with EtOAc (150 mL). The organic layer was washed with water (2×50 mL), brine (30 mL), dried over anhydrous $Na_2SO_4$ and evaporated to get the crude tert-butyl 3-cyclopropyl-5-fluoro-7-(7-fluoro-1,4,4,9-tetramethyl-4,5-dihydro-[1,2,4]triazolo[4,3-a]quinoxalin-8-yl)-1H-indole-1-carboxylate (0.15 g, 46%), as brown gum, which was used for the next step without further purification.

Step4: To a solution of tert-butyl 3-cyclopropyl-5-fluoro-7-(7-fluoro-1,4,4,9-tetramethyl-4,5-dihydro-[1,2,4]triazolo[4,3-a]quinoxalin-8-yl)-1H-indole-1-carboxylate (0.5 g, 0.96 mmol, 1 eq) in MeOH (12.0 mL) and $H_2O$ (4.0 mL), $K_2CO_3$ (0.4 g, 2.884 mmol, 3 eq) was added at RT. The reaction mixture was then heated at 90° C. for 24 h. After completion of reaction (monitored by TLC), reaction mixture was filtered through cintered and the solvent was evaporated under reduced pressure. The crude product was purified by prep HPLC to afford 8-(3-cyclopropyl-5-fluoro-1H-indol-7-yl)-7-fluoro-1,4,4,9-tetramethyl-4,5-dihydro-[1,2,4]triazolo[4,3-a]quinoxaline (0.18 g, 45%) as white solid.

$^1$H NMR (400 MHz, DMSO-$d_6$): δ 10.67 (s, 1H), 7.37 (d, J=9.2 Hz, 1H), 7.06 (s, 1H), 6.90 (d, J=9.6 Hz, 1H), 6.76-6.79 (m, 2H), 1.95 (s, 4H), 1.43-1.53 (m, 6H), 0.85 (d, J=8.8 Hz, 2H), 0.61 (s, 2H); ($CH_3$— omitted by DMSO).

Example 34: 1-ethyl-7-fluoro-8-(6-fluoro-1H-indol-4-yl)-4,4,9-trimethyl-4,5-dihydro-[1,2,4]triazolo[4,3-a]quinoxaline

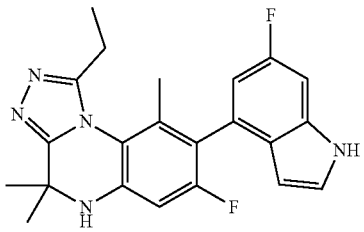 [SMILES: CCc1nnc2n1-c1c(cc(F)c(-c3cc(F)cc4[nH]ccc34)c1C)NC2(C)C]

Example 34 was synthesized in analogy to procedure described for example 29 using 6-fluoro-4-(4,4,5,5-tetramethyl-1,3,2-dioxaborolan-2-yl)-1H-indole and intermediate B-6. LC MS: found [M+H]$^+$: 394.

Example 35: 8-(1-(cyclopropylmethyl)-6-fluoro-1H-indol-4-yl)-1-ethyl-7-fluoro-4,4,9-trimethyl-4,5-dihydro-[1,2,4]triazolo[4,3-a]quinoxaline

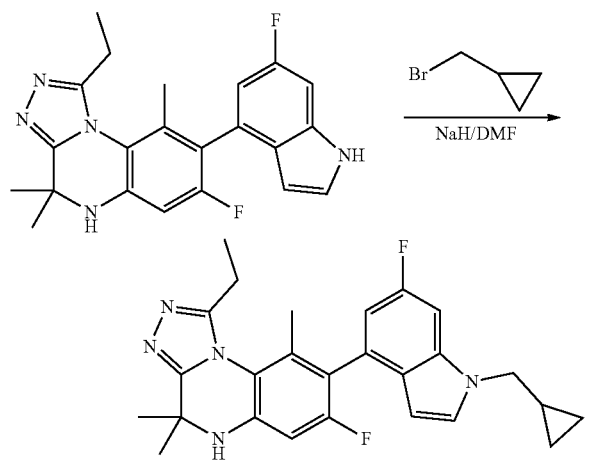

To a solution of 1-ethyl-7-fluoro-8-(6-fluoro-1H-indol-4-yl)-4,4,9-trimethyl-4,5-dihydro-[1,2,4]triazolo[4,3-a]quinoxaline (example 34) (0.1 g, 0.254 mmol, 1 eq.) in DMF (5 mL) was added sodium hydride (0.022 g, 0.508 mmol, 2 eq) at 0° C. The solution was stirred at RT for 30 min followed by addition of bromomethyl-cyclopropane (0.02 g, 0.152 mmol, 0.6 eq) and reaction mixture was stirred at RT for 2 h. After completion of reaction (monitored by LCMS), reaction mixture is diluted with EtOAc (20 mL) and organic layer was washed with cold water (5×10 mL), brine (10 mL), dried over anhydrous Na$_2$SO$_4$ and evaporated under reduced pressure. Crude product was purified by prep HPLC to afford 8-(1-(cyclopropylmethyl)-6-fluoro-1H-indol-4-yl)-1-ethyl-7-fluoro-4,4,9-trimethyl-4,5-dihydro-[1,2,4]triazolo[4,3-a]quinoxaline (0.03 g, 27%) as off white solid.

$^1$H NMR (400 MHz, DMSO-d$_6$): δ 7.47 (d, J=9.2 Hz, 2H), 6.89 (s, 1H), 6.77 (t, J=10.1 Hz, J=8.4 Hz, 1H), 6.06 (s, 1H), 4.04 (s, 2H), 2.78 (bs, 2H), 1.99 (s, 3H), 1.47 (bs, 6H), 1.25 (t, J=7.08 Hz, 3H), 0.53 (d, J=7.08 Hz, 2H), 0.42 (s, 2H).

Example 36: 1-ethyl-7-fluoro-8-(6-fluoro-1-(2-methoxyethyl)-1H-indol-4-yl)-4,4,9-trimethyl-4,5-dihydro-[1,2,4]triazolo[4,3-a]quinoxaline

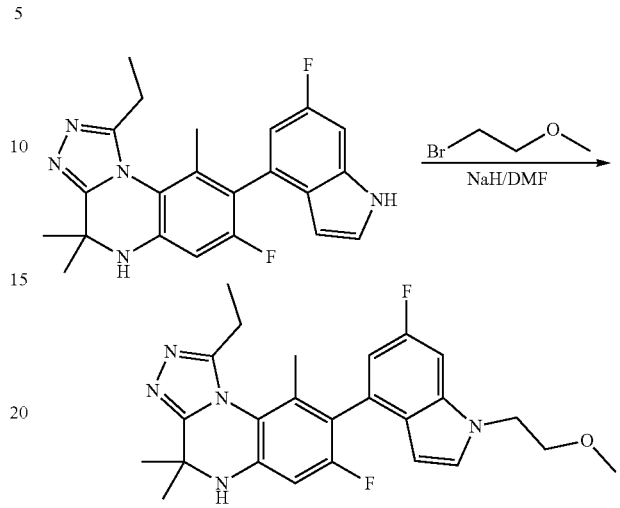

To a solution of 1-ethyl-7-fluoro-8-(6-fluoro-1H-indol-4-yl)-4,4,9-trimethyl-4,5-dihydro-[1,2,4]triazolo[4,3-a]quinoxaline (example 34) (0.1 g, 0.254 mmol, 1 eq.) in DMF (5 mL) was added sodium hydride (0.022 g, 0.508 mmol, 2 eq) at 0° C. The solution was stirred at RT for 30 min followed by addition of 1-bromo-2-methoxy-ethane (0.022 g, 0.152 mmol, 0.6 eq) and reaction mixture was stirred at RT for 2 h. After completion of reaction (monitored by LCMS), reaction mixture was diluted with EtOAc (20 mL) and organic layer was washed with cold water (5×10 mL), brine (10 mL), dried over anhydrous Na$_2$SO$_4$ and the solvent was evaporated under reduced pressure. Crude product was purified by prep HPLC to afford 1-ethyl-7-fluoro-8-(6-fluoro-1-(2-methoxyethyl)-1H-indol-4-yl)-4,4,9-trimethyl-4,5-dihydro-[1,2,4]triazolo[4,3-a]quinoxaline (0.08 g, 70%) as off white solid.

$^1$H NMR (400 MHz, DMSO-d$_6$): δ 7.48 (d, J=9.4 Hz, 1H), 7.39 (s, 1H), 6.9 (bs, 1H), 6.79 (d, J=8.4 Hz, 1H), 6.05 (s, 1H), 4.34 (s, 2H), 3.68 (s, 2H), 3.24 (s, 3H), 2.67 (bs, 2H), 1.98 (s, 3H), 1.46 (bs, 6H), 1.24 (t, J=7.2 Hz, 3H).

Example 37: 7-fluoro-8-(6-fluoro-1-(methylsulfonyl)-1H-indol-4-yl)-1,4,4-trimethyl-9-(trifluoromethyl)-4,5-dihydro-[1,2,4]triazolo[4,3-a]quinoxaline

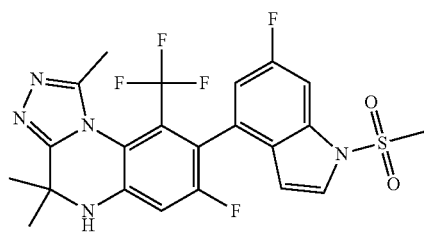

A suspension of 8-bromo-7-fluoro-1,4,4-trimethyl-9-(trifluoromethyl)-4,5-dihydro-[1,2,4]triazolo[4,3-a]quinoxaline (intermediate B-4) (0.5 g, 1.32 mmol, 1 eq), 6-fluoro-1-(methylsulfonyl)-4-(4,4,5,5-tetramethyl-1,3,2-dioxaborolan-2-yl)-1H-indole (intermediate A-2) (0.536 g, 1.58 mmol, 1.2 eq) and K$_2$CO$_3$ (0.55 g, 3.96 mmol, 3 eq) in isoamyl alcohol and water (2:1) (15 mL) was degassed with Ar for 20 min followed by addition of Attaphos (0.047 g, 0.066 mmol, 0.05 eq) The reaction mixture was stirred at 110° C. for 16 h in a sealed tube. After completion of reaction (monitored by LCMS), reaction mixture is evaporated to dryness and the residue was diluted with EtOAc (50 mL). The organic layer was washed with water (2×30 mL), brine (30 mL), dried over anhydrous Na$_2$SO$_4$ and evaporated to get the crude product, which was purified by column chromatography to afford 7-fluoro-8-(6-fluoro-1-(methylsulfonyl)-1H-indol-4-yl)-1,4,4-trimethyl-9-(trifluoromethyl)-4,5-dihydro-[1,2,4]triazolo[4,3-a]quinoxaline (0.055 g, 8%) as off white solid.

$^1$H NMR (400 MHz, DMSO-d$_6$, T=100° C.): δ 7.73 (d, J=9.44 Hz, 1H), 7.60 (d, J=3.64 Hz, 1H), 7.24 (bs, 2H), 7.17 (d, J=10 Hz, 1H), 6.51 (bs, 1H), 3.49 (s, 3H), 2.46 (s, 3H), 1.75 (bs, 3H), 1.38 (bs, 3H).

Example 38: 8-(3-cyclopropyl-5-fluoro-1H-indol-7-yl)-6-fluoro-1,4,4,9-tetramethyl-4,5-dihydro-[1,2,4]triazolo[4,3-a]quinoxaline

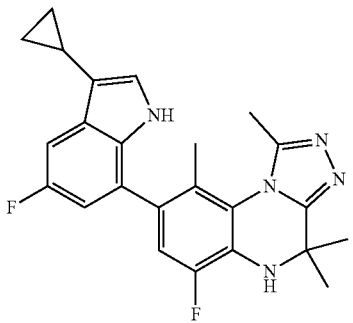 [SMILES: Cc1c(-c2cc(F)cc3c(C4CC4)c[nH]c23)cc(F)c2c1-n1c(C)nnc1C(C)(C)N2]

Example 38 was synthesized in analogy to procedure described for example 29 using 3-cyclopropyl-5-fluoro-7-(4,4,5,5-tetramethyl-1,3,2-dioxaborolan-2-yl)-1H-indole (intermediate A-16) and intermediate B-7.

$^1$H NMR (400 MHz, DMSO-d$_6$): δ 10.64 (s, 1H), 7.36 (d, J=7.76 Hz, 1H), 7.17 (d, J=10.64 Hz, 1H), 7.08 (s, 1H), 6.9 (d, J=9.8 Hz, 1H), 6.49 (s, 1H), 2.5 (s, 3H), 1.98 (s, 3H), 1.93-1.9 (m, 1H), 1.53-1.48 (m, 6H), 0.85 (d, J=8.08 Hz, 2H), 0.60 (d, J=3.32 Hz, 2H).

Example 39: 4-(7-(7-fluoro-1,4,4,9-tetramethyl-4,5-dihydro-[1,2,4]triazolo[4,3-a]quinoxalin-8-yn-1H-indol-3-yl)-2-methylbut-3-yn-2-ol

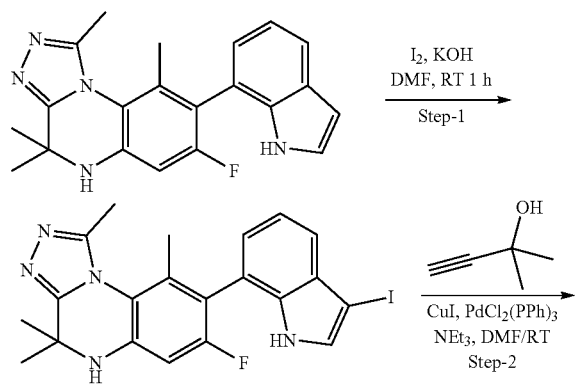

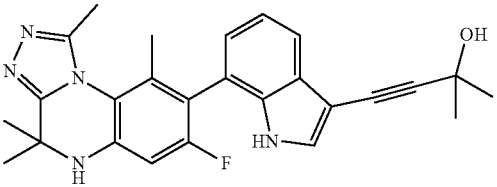

Step 1: To a stirred solution of 7-fluoro-8-(1H-indol-7-yl)-1,4,4,9-tetramethyl-4,5-dihydro-[1,2,4]triazolo[4,3-a]quinoxaline (example 25) (3.7 g, 10.24 mmol, 1 eq) in DMF (25 mL), KOH (1.43 g, 25.62 mmol, 2.5 eq) and iodine (2.6 g, 10.24 mmol, 1.0 eq) in DMF (20 mL) were added at 0° C. and the resulting reaction mixture was stirred for 1 h at 0° C. The reaction mixture was diluted with EtOAc (800 mL), washed with aqueous sodium metabisulfite (2×300 mL), water (4×300 mL), brine solution (300 mL), dried (Na$_2$SO$_4$), filtered and concentrated under reduced pressure to afforded 7-fluoro-8-(3-iodo-1H-indol-7-yl)-1,4,4,9-tetramethyl-4,5-dihydro-[1,2,4]triazolo[4,3-a]quinoxaline (3.0 g, 61%).

Step 2: A solution of 7-fluoro-8-(3-iodo-1H-indol-7-yl)-1,4,4,9-tetramethyl-4,5-dihydro-[1,2,4]triazolo[4,3-a]quinoxaline (0.3 g, 0.61 mmol, 1.0 eq.) in DMF (5 mL) and TEA (5 mL) was degassed with Ar for 20 min followed by addition of CuI (2.9 mg, 0.015 mmol, 0.025 eq.), PdCl$_2$(PPh$_3$) (21.5 g, 0.03 mmol, 0.05 eq.) and 2-methylbut-3-yn-2-ol (0.077 g, 0.92 mmol, 1.5 eq). The reaction mixture was stirred at RT for 16 h. After completion of reaction (monitored by TLC), reaction mixture was filtered through celite bed and filterate was concentrated to get the crude product, which was purified by prep-HPLC to afford 4-(7-(7-fluoro-1,4,4,9-tetramethyl-4,5-dihydro-[1,2,4]triazolo[4,3-a]quinoxalin-8-yl)-1H-indol-3-yl)-2-methylbut-3-yn-2-ol (0.08 g, 30%) as white solid.

$^1$H NMR (400 MHz, DMSO-d$_6$): δ 11.2 (s, 1H), 7.59 (d, J=8.0 Hz, 1H), 7.54 (s, 1H), 7.20 (t, J=7.6 Hz, 1H), 7.09 (d, J=6.8 Hz, 1H), 6.79 (d, J=10 HZ, 1H), 6.75 (s, 1H), 5.37 (s, 1H), 2.46 (s, 3H), 1.92 (s, 3H) 1.44-1.51 (m, 12H).

Example 40: 4-(7-(7-fluoro-1,4,4,9-tetramethyl-4,5-dihydro-[1,2,4]triazolo[4,3-a]quinoxalin-8-yn-1H-indol-3-yl)-2-methylbut-3-yn-2-amine

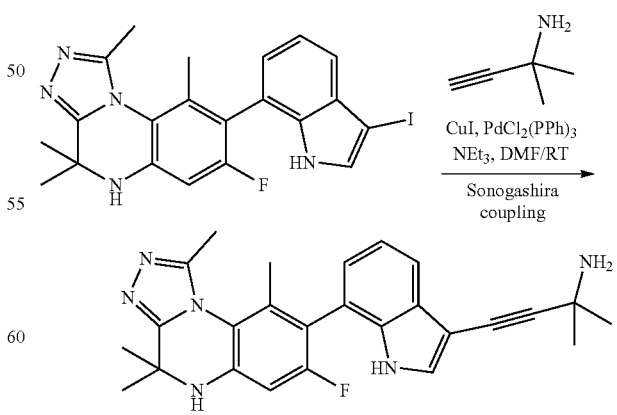

A solution of 7-fluoro-8-(3-iodo-1H-indol-7-yl)-1,4,4,9-tetramethyl-4,5-dihydro-[1,2,4]triazolo[4,3-a]quinoxaline (0.3 g, 0.61 mmol, 1.0 eq) in DMF (1.8 mL) and TEA (0.17 mL, 1.23 mmol, 2.0 eq) was degassed with Ar for 20 min followed by addition of CuI (2.9 mg, 0.015 mmol, 0.025 eq.), PdCl$_2$(PPh)$_3$ (21.5 g, 0.03 mmol, 0.05 eq.) and 2-methylbut-3-yn-2-amine (0.103 g, 1.23 mmol, 2.0 eq). The reaction mixture was stirred at RT for 2 h. After completion of reaction (monitored by TLC), reaction mixture was filtered through celite bed and filtrate was concentrated to get the crude product, which was purified by prep-HPLC to afford 4-(7-(7-fluoro-1,4,4,9-tetramethyl-4,5-dihydro-[1,2,4]triazolo[4,3-a]quinoxalin-8-yl)-1H-indol-3-yl)-2-methylbut-3-yn-2-amine (0.15 g, 55%) as off-white solid.

$^1$H NMR (400 MHz, DMSO-d$_6$): δ 11.15 (s, 1H), 7.59 (d, J=7.8 Hz, 1H), 7.48 (s, 1H), 7.19 (t, J=7.4 Hz, 1H), 7.07 (d, J=6.8 Hz, 1H), 6.79 (d, J=10 HZ, 1H), 6.74 (s, 1H), 2.46 (s, 3H), 2.05 (s, 1H), 1.92 (s, 3H) 1.42-1.53 (m, 12H).

Example 41: 9-chloro-8-(3-cyclobutyl-1H-indol-7-yl)-7-fluoro-1,4,4-trimethyl-4,5-dihydro-[1,2,4]triazolo[4,3-a]quinoxaline

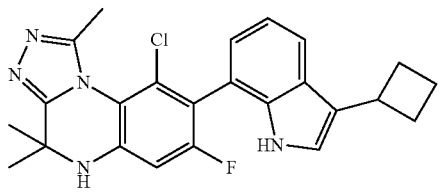 [SMILES: Cc1nnc2n1-c1c(cc(F)c(-c3cccc4c(C5CCC5)c[nH]c34)c1Cl)NC2(C)C]

Example 41 was synthesized in analogy to procedure described for example 37 using 3-cyclobutyl-7-(4,4,5,5-tetramethyl-1,3,2-dioxaborolan-2-yl)-1H-indole (intermediate A-17) and intermediate B-5.

$^1$H NMR (400 MHz, DMSO-d$_6$): δ 10.67 (s, 1H), 7.57 (d, J=7.6 Hz, 1H), 7.13 (s, 1H), 7.00-7.08 (m, 3H), 6.93 (d, J=10 Hz, 1H), 3.69-3.74 (m, 1H), 2.57 (s, 3H), 2.32-2.42 (m, 2H), 2.20-2.23 (m, 2H), 2.00-2.07 (m, 1H), 1.89-1.91 (m, 1H), 1.57 (s, 3H), 1.47 (s, 3H).

Example 42: 7-fluoro-1,4,4,9-tetramethyl-8-(3-(tetrahydrofuran-3-yl)-1H-indol-7-yl)-4,5-dihydro-[1,2,4]triazolo[4,3-a]quinoxaline

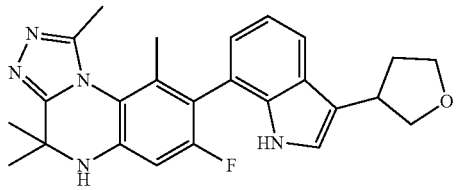 [SMILES: Cc1c(-c2cccc3c(C4CCOC4)c[nH]c23)c(F)cc2c1-n1c(C)nnc1C(C)(C)N2]

Example 42 was synthesized in analogy to procedure described for example 37 using 3-(tetrahydrofuran-3-yl)-7-(4,4,5,5-tetramethyl-1,3,2-dioxaborolan-2-yl)-1H-indole (intermediate A-18) and intermediate B-3.

$^1$H NMR (400 MHz, DMSO-d$_6$): δ 10.67 (s, 1H), 7.61 (d, J=8.0 Hz, 1H), 7.15 (s, 1H), 7.08 (t, J=7.6 Hz, 1H), 6.99 (d, J=7.2 Hz, 1H), 6.78 (d, J=10 Hz, 1H), 6.72 (s, 1H), 4.12-4.15 (m, 1H), 3.92-3.97 (m, 1H), 3.84 (q, J=7.6 Hz, J=15.6 Hz, 1H), 3.59-3.69 (m, 2H), 2.46 (s, 3H), 2.33-2.37 (m, 1H), 2.04-2.10 (m, 1H), 1.93 (s, 3H), 1.55 (s, 3H), 1.42 (s, 3H).

Example 43: 8-(3-ethyl-5-fluoro-1H-indol-7-yl)-7,9-difluoro-1,4,4-trimethyl-4,5-dihydro-[1,2,4]triazolo[4,3-a]quinoxaline

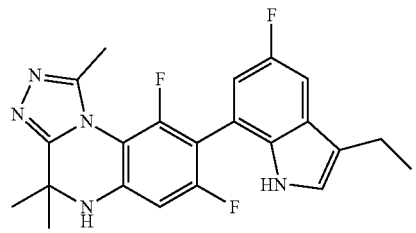 [SMILES: CCc1c[nH]c2c(-c3c(F)cc4c(c3F)-n3c(C)nnc3C(C)(C)N4)cc(F)cc12]

Example 43 was synthesized in analogy to procedure described for example 1 using 3-ethyl-5-fluoro-7-(4,4,5,5-tetramethyl-1,3,2-dioxaborolan-2-yl)-1H-indole (intermediate A-19) and intermediate B-1.

$^1$H NMR (400 MHz, DMSO-d$_6$): δ 10.81 (bs, 1H), 7.36 (d, J=8.8 Hz, 1H), 7.20 (s, 2H), 6.99 (d, J=7.2 Hz, 1H), 6.80 (d, J=9.6 Hz, 1H), 2.69-2.71 (m, 2H), 1.54 (bs, 6H), 1.27 (bs, 3H); (CHs-omitted by DMSO).

Example 44: 2-(4-(9-ethyl-7-fluoro-1,4,4-trimethyl-4,5-dihydro-[1,2,4]triazolo[4,3-a]quinoxalin-8-yl)-6-fluoro-1H-indol-1-yl)ethanol

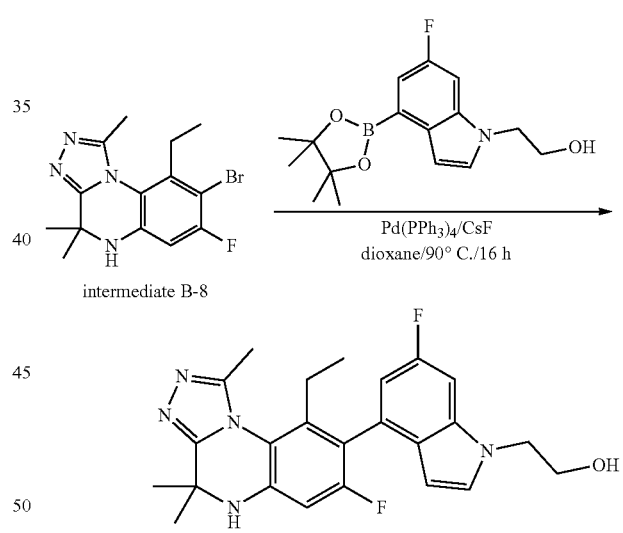

To a stirred solution of intermediate B-8 (0.14 g, 0.413 mmol, 1 eq.) in 1,4-dioxane (10 mL) were added CsF (0.19 g, 1.24 mmol, 3 eq.) and compound intermediate A-20 (0.138 g, 0.45 mmol, 1.1 eq) in sealed tube. The solution was degassed with Ar for 20 min followed by addition of Pd(PPh$_3$)$_4$ (0.023 g, 0.021 mmol, 0.05 eq.) The reaction mixture was refluxed at 90° C. for 16 h. After completion of reaction (monitored by TLC), reaction mixture was filtered through celite bed. Filtrate was concentrated under reduced pressure to get the crude product which was purified by column chromatography (5% MeOH/DCM, R$_f$-0.3) followed by prep HPLC to afford 2-(4-(9-ethyl-7-fluoro-1,4,4-trimethyl-4,5-dihydro-[1,2,4]triazolo[4,3-a]quinoxalin-8-yl)-6-fluoro-1H-indol-1-yl)ethanol (0.1 g, 56%) as off white solid.

¹H NMR (400 MHz, DMSO-d₆): δ 7.45-7.39 (m, 2H), 6.95 (d, J=10 Hz, 1H), 6.83 (s, 1H), 6.75 (d, J=10.1 Hz, 1H), 6.13 (s, 1H), 4.92 (s, 1H), 4.22 (d, J=5.6 Hz, 2H), 3.75 (d, J=4.8 Hz, 2H), 2.68-2.62 (m, 1H), 1.54-1.18 (m, 6H), 0.51 (s, 3H).

Example 69: 1-(but-2-yn-1-yl)-7,9-difluoro-8-(5-fluoro-3-methyl-1H-indol-7-yl)-4,4-dimethyl-4,5-dihydro-[1,2,4]triazolo[4,3-a]quinoxaline

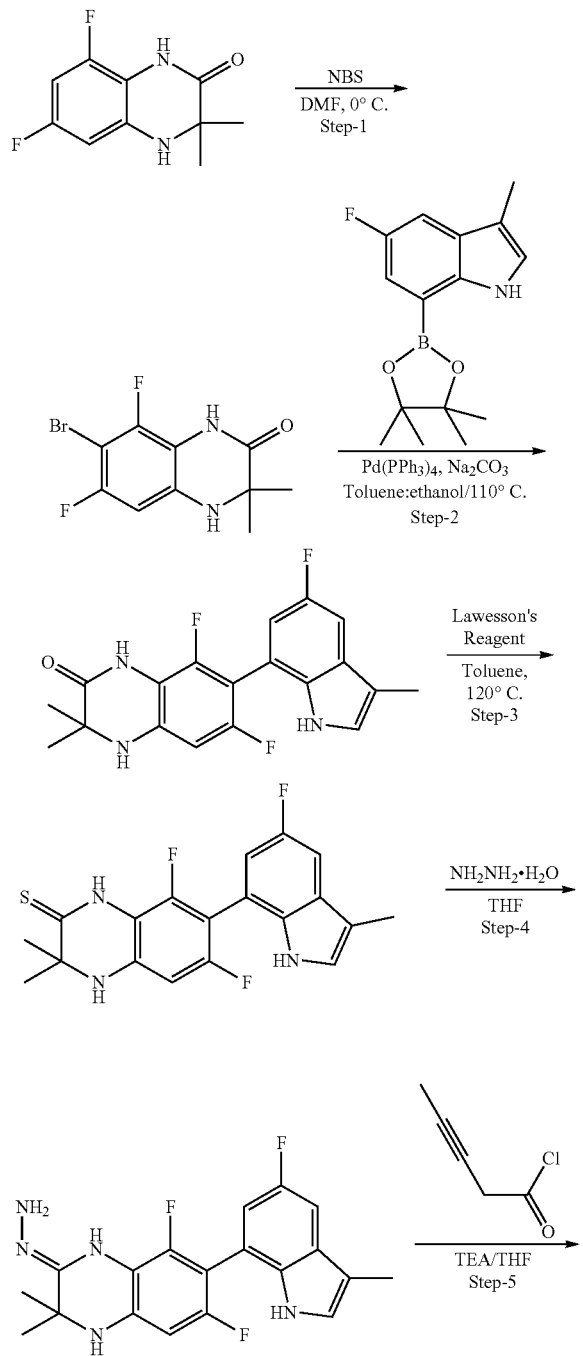

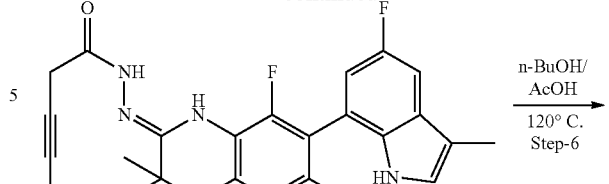

-continued

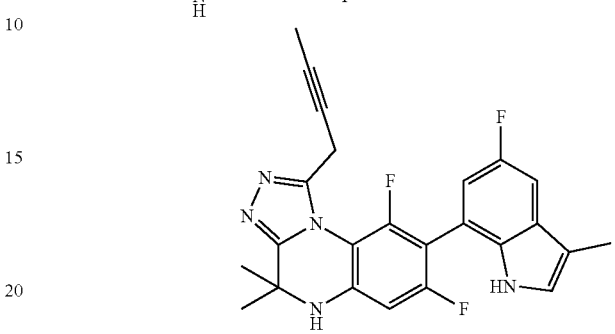

Step 1: A stirred solution of 6,8-difluoro-3,3-dimethyl-3,4-dihydroquinoxalin-2(1H)-one (3.43 g, 16.18 mmol, 1 eq.) in DMF (30 mL) at 0° C. was treated portion wise over 10 min with N-bromosuccinimide (3.02 g, 16.99 mmol, 1.05 eq.). Reaction mixture was stirred at 0° C. for 1 h and at RT for 30 min. After completion of reaction (monitored by TLC), reaction mixture is diluted with water (100 mL) and extracted with EtOAc (3×100 mL). Combined organic layer was washed with water (4×50 mL), brine (50 mL), dried over anhydrous Na₂SO₄ and evaporated under reduced pressure. Crude product was purified by column chromatography (100-200 mesh silica gel; 30% EtOAc/hexane; R$_f$-value-0.5) to afford 7-bromo-6,8-difluoro-3,3-dimethyl-3,4-dihydroquinoxalin-2(1H)-one (4.0 g, 85%) as brown solid.

Step 2: To a solution of 7-bromo-6,8-difluoro-3,3-dimethyl-3,4-dihydroquinoxalin-2(1H)-one (1.0 g, 3.44 mmol, 1 eq.) in toluene:EtOH (2:1) (20 mL) were added 10% aqueous Na₂CO₃ solution (5.5 mL) and intermediate A-15 (1.42 g, 5.16 mmol, 1.5 eq). The solution was degassed with Ar for 20 min followed by addition of Pd(PPh₃)₄ (0.199 g, 0.17 mmol, 0.05 eq.). Degassing was continued for another 10 min and the reaction mixture was heated at 110° C. for 16 h in a sealed tube. After completion of reaction (monitored by TLC), reaction mixture was evaporated, the residue was diluted with water (25 mL) and extracted with EtOAc (3×100 mL). Combined organic layers were washed with water (25 mL), brine (25 mL), dried over anhydrous Na₂SO₄ and evaporated to get the crude product, which was purified by flash column chromatography (100-200 mesh silica gel; 50% EtOAc/hexane; R$_f$-value-0.3) to afford 6,8-difluoro-7-(5-fluoro-3-methyl-1H-indol-7-yl)-3,3-dimethyl-3,4-dihydroquinoxalin-2(1H)-one (0.510 g, 41%) as brown solid.

Step 3: To a solution of 6,8-difluoro-7-(5-fluoro-3-methyl-1H-indol-7-yl)-3,3-dimethyl-3,4-dihydroquinoxalin-2(1H)-one (0.500 g, 1.4 mmol, 1 eq.) in toluene (10 mL) was added Lawesson's reagent (0.848 g, 2.1 mmol, 1.5 eq.) at RT and the reaction mixture was refluxed at 120° C. for 30 min. After completion of reaction (monitored by TLC), the reaction mixture was cooled, quenched with sat. NaHCO₃ solution (50 mL) followed by extraction with EtOAc (3×100 mL). Combined organic layers were washed with water (25 mL), brine (25 mL), dried over anhydrous Na₂SO₄ and the solvent was evaporated to get the crude product which was purified by column chromatography (100-200 mesh silica gel; 10% EtOAc/hexane; R$_f$-value-0.6) to afford 6,8-difluoro-7-(5-fluoro-3-methyl-1H-indol-7-yl)-3,3-dimethyl-3,4-dihydroquinoxaline-2(1H)-thione (0.480 g, 91%) as yellow solid.

Step4: To a solution of 6,8-difluoro-7-(5-fluoro-3-methyl-1H-indol-7-yl)-3,3-dimethyl-3,4-dihydroquinoxaline-2(1H)-thione (0.240 g, 0.64 mmol, 1 eq) in THF (6 mL) was added hydrazine hydrate (0.11 mL, 2.32 mmol, 3 eq) and the mixture was stirred overnight at RT. The completion of formation of 5,7-difluoro-6-(5-fluoro-3-methyl-1H-indol-7-yl)-3-hydrazono-2,2-dimethyl-1,2,3,4-tetrahydroquinoxaline was monitored by TLC and LCMS, (EtOAc; R$_f$-value-0.1). This reaction mixture was used for the next step without work up and purification.

Step5: To a solution of pent-3-ynoic acid (0.376 g, 3.84 mmol, 6 eq) in benzene (8 mL) was added oxalylchloride (0.8 mL) at 0° C. and the mixture was heated at 50° C. for 1 h under nitrogen atmosphere. The reaction mixture was concentrated under reduced pressure under nitrogen atmosphere at 25° C. The residue was dissolved in THF (5 mL) and the resulting solution was drop wise added to the 5,7-difluoro-6-(5-fluoro-3-methyl-1H-indol-7-yl)-3-hydrazono-2,2-dimethyl-1,2,3,4-tetrahydroquinoxaline solution already prepared (mentioned above) at 0° C. TEA (0.6 mL, 3.84 mmol, 6 eq) was added to the mixture and it was stirred for 1.5 h at RT. After completion of reaction (monitored by TLC), the reaction mixture was quenched with water (5 mL) and extracted with EtOAc (3×20 ml). Combined organic layers were washed with brine (10 mL), dried over anhydrous Na$_2$SO$_4$ and the solvent was evaporated to get the crude N'-(6,8-difluoro-7-(5-fluoro-3-methyl-1H-indol-7-yl)-3,3-dimethyl-3,4-dihydroquinoxalin-2(1H)-ylidene)pent-3-ynehydrazide (0.285 g) (50% EtOAc-hexane; R$_f$-value-0.5) which was used for the next step without further purification.

Step6: To a solution of N'-(6,8-difluoro-7-(5-fluoro-3-methyl-1H-indol-7-yl)-3,3-dimethyl-3,4-dihydroquinoxalin-2(1H)-ylidene)pent-3-ynehydrazide (0.280, 0.62 mmol) in n-butanol (8 mL) was added glacial acetic acid (catalytic amount, 2 drops with capillary tube) and the mixture was heated at 140° C. for 3 h. After completion of reaction (monitored by TLC), the reaction mixture was concentrated under reduced pressure. The residue was diluted with water (25 mL) and extracted with EtOAc (3×50 mL). The combined organic part was washed with brine (10 mL), dried (anhydrous Na$_2$SO$_4$) and concentrated reduced pressure to a sticky mass which was purified prep-HPLC (5% MeOH-DCM; R$_f$-value-0.35) to get 1-(but-2-yn-1-yl)-7,9-difluoro-8-(5-fluoro-3-methyl-1H-indol-7-yl)-4,4-dimethyl-4,5-dihydro-[1,2,4]triazolo[4,3-a]quinoxaline (57 mg, 10% over three steps) as off-white solid [another 240 mg scale reaction starting from 6,8-difluoro-7-(5-fluoro-3-methyl-1H-indol-7-yl)-3,3-dimethyl-3,4-dihydroquinoxaline-2(1H)-thione had been done and the yield mentioned here is combined yield].

$^1$H NMR (400 MHz, DMSO-d$_6$): δ 10.74 (s, 1H), 7.34 (dd, 1H), 7.21 (s, 2H), 6.94 (dd, 1H), 6.78 (d, 1H), 3.91 (s, 2H), 2.26 (s, 3H), 1.60 (s, 6H), 1.51 (bs, 3H).

Example 70: 1-(but-2-yn-1-yl)-7,9-difluoro-4,4-dimethyl-8-(3-methyl-1H-indol-7-yl)-4,5-dihydro-[1,2,4]triazolo[4,3-a]quinoxaline

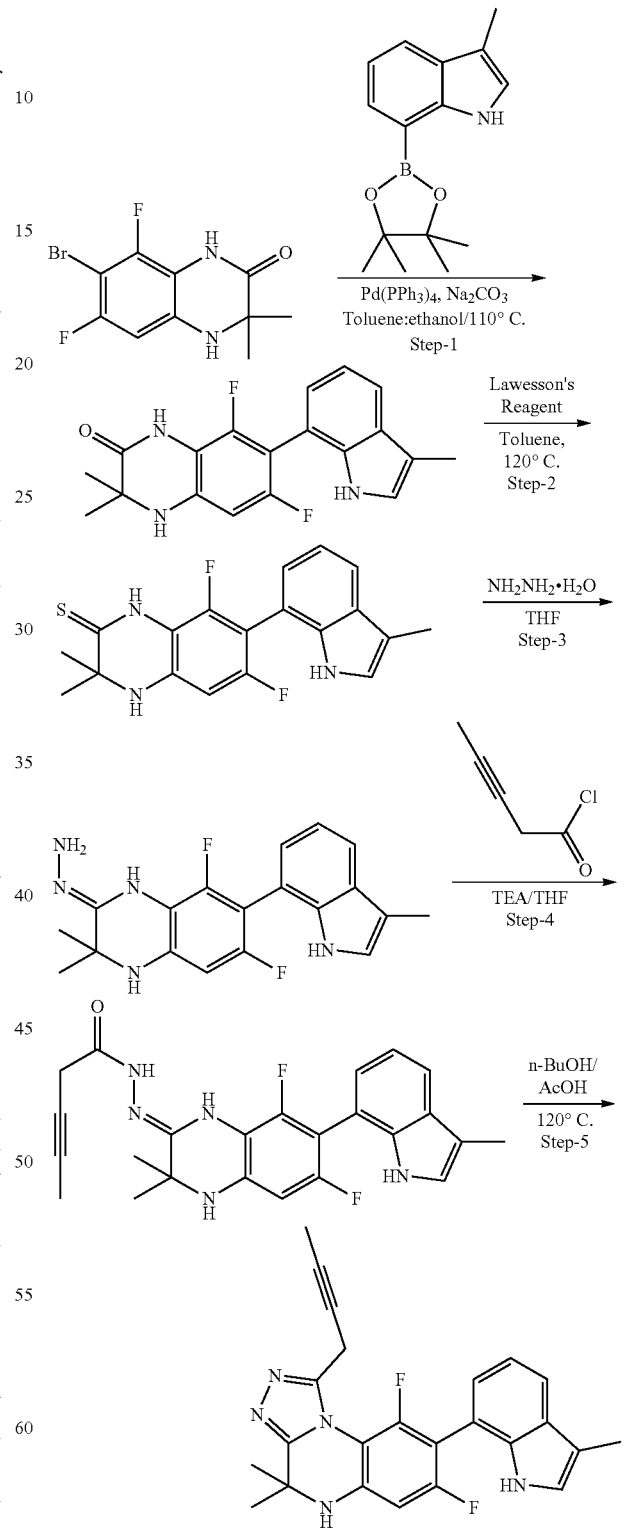

Step1: To a solution of 7-bromo-6,8-difluoro-3,3-dimethyl-3,4-dihydroquinoxalin-2(1H)-one (1.32 g, 4.53 mmol, 1 eq.) in toluene:EtOH (2:1) (15 mL) were added 10% aqueous $Na_2CO_3$ solution (7.3 mL) and 3-methyl-7-(4,4,5,5-tetramethyl-1,3,2-dioxaborolan-2-yl)-1H-indole (1.75 g, 6.8 mmol, 1.5 eq). The solution was degassed with Ar for 20 min followed by addition of $Pd(PPh_3)_4$ (0.262 g, 0.23 mmol, 0.05 eq.). Degassing was continued for another 10 min and the reaction mixture was heated at 110° C. for 16 h in a sealed tube. After completion of reaction (monitored by TLC), solvent was evaporated, the residue was diluted with water (25 mL) and extracted with EtOAc (3×100 mL). Combined organic layers were washed with water (25 mL), brine (25 mL), dried over anhydrous $Na_2SO_4$ and the solvent was evaporated to get the crude product, which was purified by flash column chromatography (100-200 mesh silica gel; 50% EtOAc/hexane; $R_f$-value-0.3) to afford 6,8-difluoro-3,3-dimethyl-7-(3-methyl-1H-indol-7-yl)-3,4-dihydroquinoxalin-2(1H)-one (0.55 g, 35%) as brown solid.

Step2: To a solution of 6,8-difluoro-3,3-dimethyl-7-(3-methyl-1H-indol-7-yl)-3,4-dihydroquinoxalin-2(1H)-one (0.55 g, 1.61 mmol, 1 eq.) in toluene (10 mL) was added Lawesson's reagent (0.975 g, 2.41 mmol, 1.5 eq.) at RT and the reaction mixture was refluxed at 120° C. for 30 min. After completion of reaction (monitored by TLC), the reaction mixture was cooled, quenched with sat. $NaHCO_3$ solution (50 mL) followed by extraction with EtOAc (3×100 mL). Combined organic layers were washed with water (25 mL), brine (25 mL), dried over anhydrous $Na_2SO_4$ and the solvent was evaporated to get the crude product which was purified by column chromatography (100-200 mesh silica gel; 10% EtOAc/hexane; $R_f$-value-0.7) to afford 6,8-difluoro-3,3-dimethyl-7-(3-methyl-1H-indol-7-yl)-3,4-dihydroquinoxaline-2(1H)-thione (0.503 g, 87%) as yellow solid.

Step3: To a solution of 6,8-difluoro-3,3-dimethyl-7-(3-methyl-1H-indol-7-yl)-3,4-dihydroquinoxaline-2(1H)-thione (0.400 g, 1.12 mmol, 1 eq) in THF (8 mL) was added hydrazine hydrate (0.16 mL, 3.36 mmol, 3 eq) and the mixture was stirred overnight at RT. The completion of formation of 5,7-difluoro-3-hydrazono-2,2-dimethyl-6-(3-methyl-1H-indol-7-yl)-1,2,3,4-tetrahydroquinoxaline was monitored by TLC and LCMS, (EtOAc; $R_f$-value-0.1). This reaction mixture was used for the next step without work up and purification.

Step4: To a solution of pent-3-ynoic acid (0.658 g, 6.72 mmol, 6 eq) in benzene (10 mL) was added oxalylchloride (1.4 mL) at 0° C. and the mixture was heated at 50° C. for 1 h under nitrogen atmosphere. The reaction mixture was concentrated under reduced pressure under nitrogen atmosphere at 25° C. The residue was dissolved in THF (5 mL) and the resulting solution was drop wise added to the 5,7-difluoro-3-hydrazono-2,2-dimethyl-6-(3-methyl-1H-indol-7-yl)-1,2,3,4-tetrahydroquinoxaline solution already prepared (mentioned above) at 0° C. TEA (1 mL, 6.72 mmol, 6 eq) was added to the mixture and it was stirred for 1.5 h at RT. After completion of reaction (monitored by TLC), the reaction mixture was quenched with water (5 mL) and extracted with EtOAc (3×20 mL). Combined organic layers were washed with brine (10 mL), dried over anhydrous $Na_2SO_4$ and the solvent was evaporated to get the crude N'-(6,8-difluoro-3,3-dimethyl-7-(3-methyl-1H-indol-7-yl)-3,4-dihydroquinoxalin-2(1H)-ylidene)pent-3-ynehydrazide (0.450 g) (50% EtOAc-hexane; $R_f$-value-0.5) which was used for the next step without further purification.

Step5: To a solution of N'-(6,8-difluoro-3,3-dimethyl-7-(3-methyl-1H-indol-7-yl)-3,4-dihydroquinoxalin-2(1H)-ylidene)pent-3-ynehydrazide (0.450 g, 1.03 mmol) in n-butanol (8 mL) was added glacial acetic acid (catalytic amount, 2 drops with capillary tube) and the mixture was heated at 140° C. for 3 h. After completion of reaction (monitored by TLC), the reaction mixture was concentrated under reduced pressure. The residue was diluted with water (25 mL) and extracted with EtOAc (3×50 mL). The combined organic part was washed with brine (10 mL), dried (anhydrous $Na_2SO_4$) and concentrated reduced pressure to a sticky mass which was purified prep-HPLC (5% MeOH-DCM; $R_f$-value-0.35) to get 1-(but-2-yn-1-yl)-7,9-difluoro-4,4-dimethyl-8-(3-methyl-1H-indol-7-yl)-4,5-dihydro-[1,2,4]triazolo[4,3-a]quinoxaline (76 mg, 11% over three steps) as off-white solid [another 200 mg scale reaction starting from 6,8-difluoro-3,3-dimethyl-7-(3-methyl-1H-indol-7-yl)-3,4-dihydroquinoxaline-2(1H)-thione had been done and the yield mentioned here is combined yield].

$^1$H NMR (400 MHz, DMSO-$d_6$): δ 10.60 (s, 1H), 7.56 (d, 1H), 7.06-7.15 (4H), 6.77 (d, 1H), 3.90 (s, 2H), 2.29 (s, 3H), 1.60 (s, 6H), 1.51 (s, 3H).

Example 76: 7-fluoro-8-(5-fluoro-3-(prop-1-yn-1-yl)-1H-indol-7-yl)-1-(methoxymethyl)-4,4,9-trimethyl-4,5-dihydro-[1,2,4]triazolo[4,3-a]quinoxaline

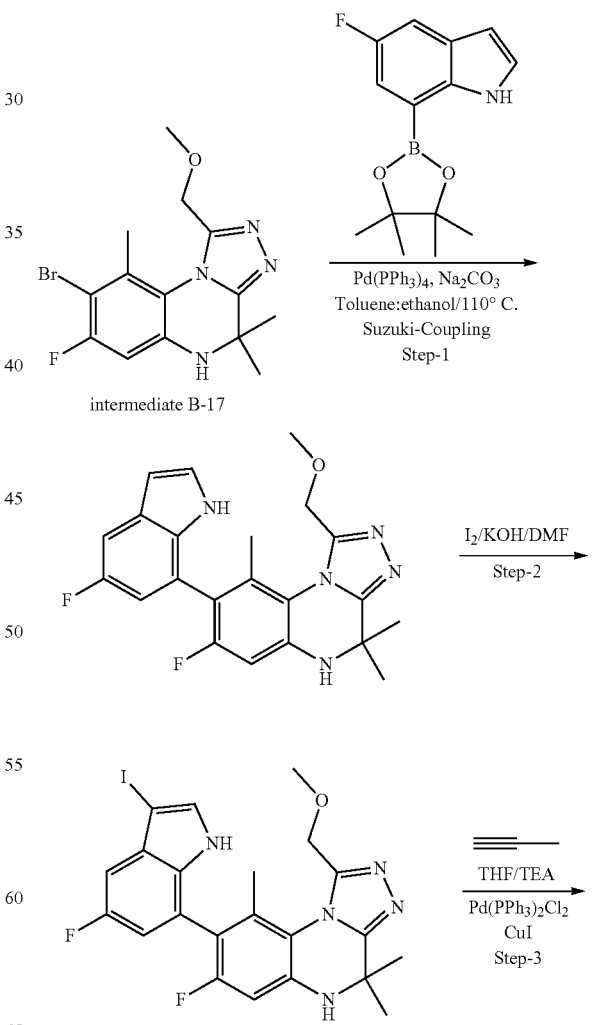

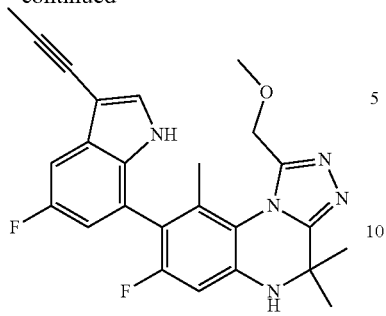

Step1: To a solution of intermediate B-17 (1.0, 2.82 mmol, 1 eq) in toluene:ethanol (2:1) (15 mL) was added 10% Na₂CO₃ (2 mL) solution and 5-fluoro-7-(tetramethyl-1,3,2-dioxaborolan-2-yl)-1H-indole (1.1 g, 4.22 mmol, 1.5 eq) in sealed tube. The solution was degassed with Ar for 20 min followed by addition of Pd(PPh₃)₄ (0.162 g, 0.14 mmol, 0.05 eq). The reaction mixture was refluxed at 110° C. for 16 h. After completion of reaction (monitored by LCMS), reaction mixture is evaporated to dryness and the residue was diluted with EtOAc (100 mL). The organic layer was washed with water (2×30 mL), brine (30 mL), dried over anhydrous Na₂SO₄ and the solvent was evaporated to get the crude product, which was purified by combiflash column chromatography (5% MeOH/DCM; R$_f$-value-0.4) to afford 7-fluoro-8-(5-fluoro-1H-indol-7-yl)-1-(methoxymethyl)-4,4,9-trimethyl-4,5-dihydro-[1,2,4]triazolo[4,3-a]quinoxaline (1.1 g, 96%) as off white solid.

Step2: To a stirred solution of 7-fluoro-8-(5-fluoro-1H-indol-7-yl)-1-(methoxymethyl)-4,4,9-trimethyl-4,5-dihydro-[1,2,4]triazolo[4,3-a]quinoxaline (1.1 g, 2.68 mmol, 1 eq) in DMF (20 mL) was added potassium hydroxide powder (0.39 g, 6.95 mmol, 2.5 eq). The reaction mixture was stirred for 30 min at RT. Iodine (1.06 g, 4.18 mmol, 1.5 eq) was then added to the reaction mixture and stirred for 4 h. The reaction mixture was diluted with EtOAc (150 mL) and washed with water (5×30 mL) and brine (30 mL). The organic layer was dried over anhydrous Na₂SO₄, concentrated under reduced pressure to get the crude material, which was purified by silica gel (230-400) column chromatography (5% MeOH/DCM; R$_f$-value-0.4) to afford 7-fluoro-8-(5-fluoro-3-iodo-1H-indol-7-yl)-1-(methoxymethyl)-4,4,9-trimethyl-4,5-dihydro-[1,2,4]triazolo[4,3-a]quinoxaline (0.26 g, 18%) as light brown solid.

Step3: A solution of 7-fluoro-8-(5-fluoro-3-iodo-1H-indol-7-yl)-1-(methoxymethyl)-4,4,9-trimethyl-4,5-dihydro-[1,2,4]triazolo[4,3-a]quinoxaline (0.26 g, 0.49 mmol, 1 eq) in THF and TEA (1:1) (6 mL) was deoxygenated by Ar for 10 min in sealed tube. Pd(PPh₃)₂C$_{1-2}$ (0.017 g, 0.024 mmol, 0.05 eq) and CuI (0.019 g, 0.097 mmol, 0.1 eq) was added to the reaction mixture and again deoxygenated by Ar for 10 min at −78° C. In test tube propyne gas was condensed in TEA (3 mL) at −78° C. The volume rose to 5 mL. The condensed propyne gas was instantly poured to the reaction mixture at −78° C. The reaction mixture was stirred for 2 h at −78° C. and 14 h at RT. The reaction mixture was diluted with DCM (50 mL). The organic layer was washed with water (2×20 mL) and brine (20 mL). The organic layer was dried over anhydrous Na₂SO₄, concentrated under reduced pressure to get the crude material, which was purified by silica gel (230-400) column chromatography (5% MeOH/DCM; R$_f$-value-0.4) to afford 7-fluoro-8-(5-fluoro-3-(prop-1-yn-1-yl)-1H-indol-7-yl)-1-(methoxymethyl)-4,4,9-trimethyl-4,5-dihydro-[1,2,4]triazolo[4,3-a]quinoxaline (0.055 g, 25%) as off white solid.

¹H NMR (400 MHz, DMSO-d₆): δ 11.21 (s, 1H), 7.59 (d, J=2.28 Hz, 1H), 7.28 (dd, J=1.96 Hz, J=6.96 Hz, 1H), 6.96 (dd, J=2.24 Hz, J=7.56 Hz, 1H), 6.83 (s, 1H), 6.78 (d, J=10.08 Hz, 1H), 4.69 (d, J=13.32 Hz, 1H), 4.61 (d, J=13.32 Hz, 1H), 3.25 (s, 3H), 2.09 (s, 3H), 1.98 (s, 3H), 1.52 (s, 3H), 1.5 (s, 3H).

Example 77: (7-fluoro-8-(5-fluoro-3-(prop-1-yn-1-yl)-1H-indol-7-yl)-4,4,9-trimethyl-4,5-dihydro-[1,2,4]triazolo[4,3-a]quinoxalin-1-yl)methanol

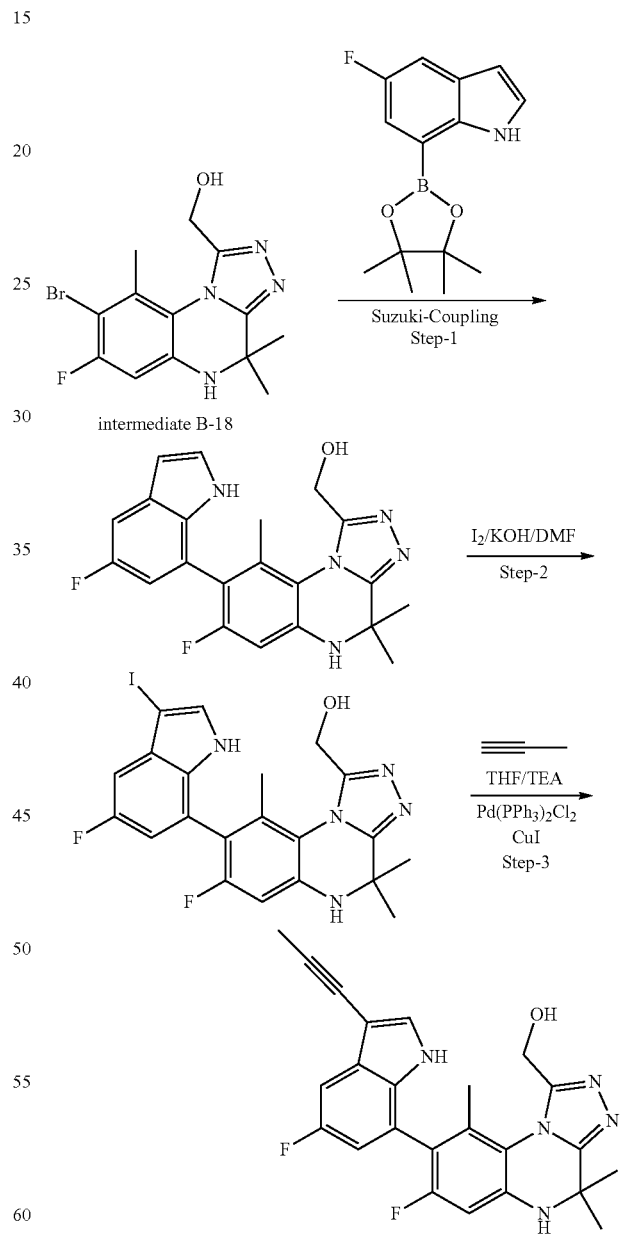

Example 77 was synthesized starting from intermediate B-18 following similar synthetic route as described for Example 76.

¹H NMR (400 MHz, DMSO-d₆): δ 11.14 (s, 1H), 7.59 (s, 1H), 7.28 (d, J=7.28 Hz 1H), 6.98 (d, J=9.6 Hz, 1H), 6.78 (t,

J=6.96 Hz, 2H), 5.53 (d, J=5.48 Hz, 1H), 4.73 (d, J=5.4 Hz, 2H), 2.08 (d, J=9.28 Hz, 3H), 2.03 (s, 3H), 1.53 (s, 3H), 1.48 (s, 3H).

Example 78: 1-(7-fluoro-8-(5-fluoro-3-(prop-1-yn-1-yl)-1H-indol-7-yn-4,4,9-trimethyl-4,5-dihydro-[1,2,4]triazolo[4,3-a]quinoxalin-1-yl)ethanol

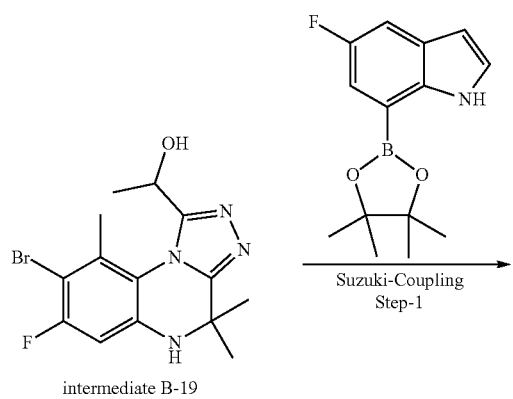

intermediate B-19

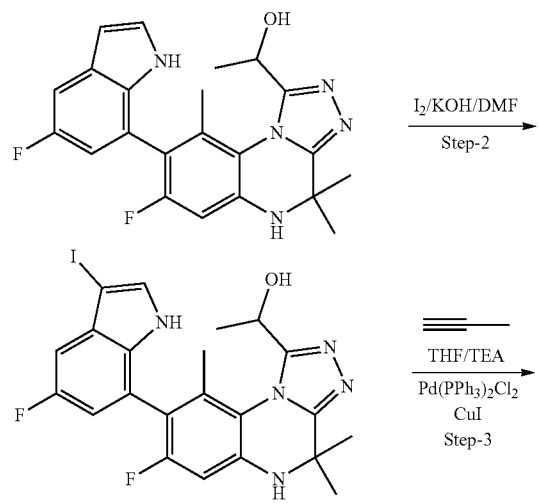

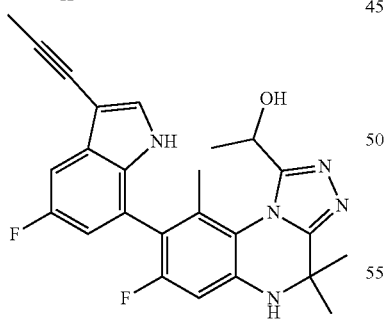

Example 79: 7-fluoro-8-(5-fluoro-3-(prop-1-yn-1-yl)-1H-indol-7-yl)-1-(2-methoxyethyl)-4,4,9-trimethyl-4,5-dihydro-[1,2,4]triazolo[4,3-a]quinoxaline

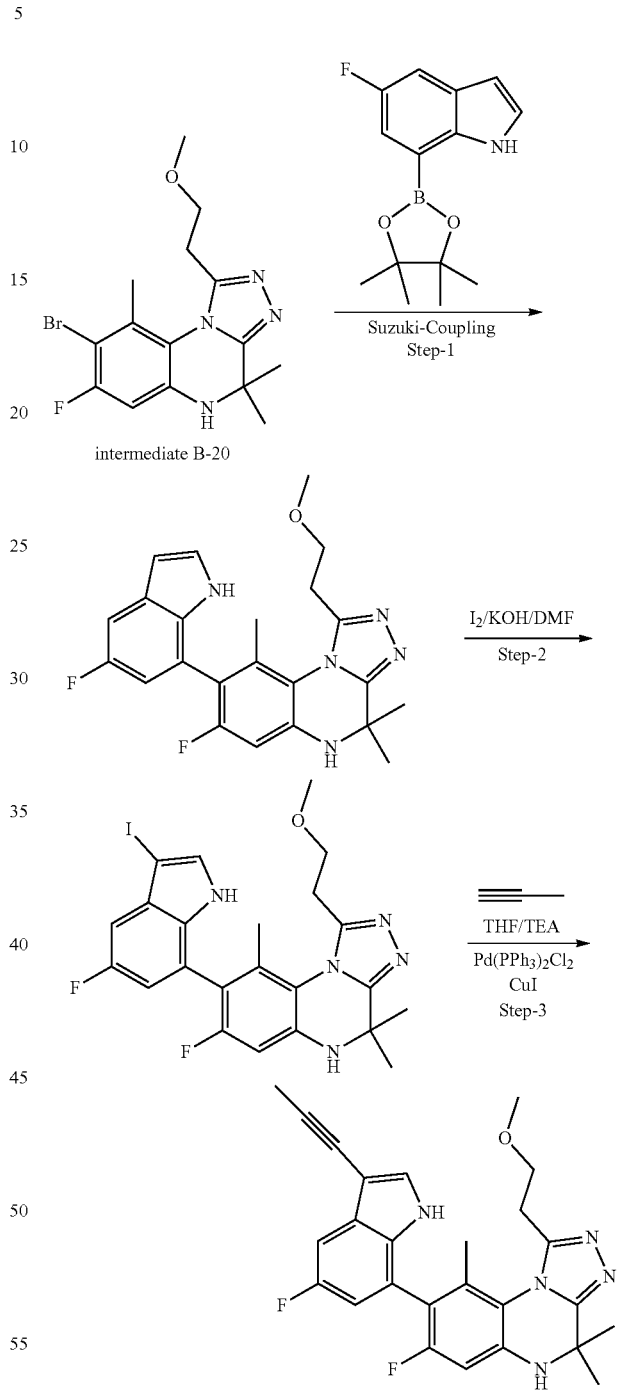

Example 78 was synthesized starting from intermediate B-19 following similar synthetic route as described for Example 76.

¹H NMR (400 MHz, DMSO-d₆): δ 11.25 (s, 1H), 10.9 (bs, 2H), 7.59 (t, J=2.56 Hz, 2H), 7.28 (d, J=9.04 Hz, 2H), 7.06 (d, J=9.72 Hz, 1H), 6.96 (dd, J=2.32 Hz, J=7.6 Hz, 2H), 6.77-6.71 (m, 4H), 5.5 (d, J=7.04 Hz, 1H), 5.36 (bs, 1H), 5.03-4.95 (m, 2H), 2.08 (t, J=6.6 Hz, 10H), 1.55 (bs, 17H).

Example 79 was synthesized starting from intermediate B-20 following similar synthetic route as described for Example 76.

¹H NMR (400 MHz, DMSO-d₆): δ 11.29 (s, 1H), 7.59 (d, J=2.52 Hz, 1H), 7.28 (dd, J=1.6 Hz, J=6.8 Hz 1H), 7.01 (bs, 1H), 6.81 (s, 1H), 6.79 (s, 1H), 3.74 (t, J=6.56 Hz, 2H), 3.2 (s, 3H), 3.07 (bs, 1H), 2.97 (bs, 1H), 2.08 (d, J=9.48 Hz, 3H), 1.95 (s, 3H), 1.48 (bs, 6H).

Example 87: 8-(3-cyclopropyl-1H-indol-7-yl)-7-fluoro-1,4,4-trimethyl-9-(trifluoromethyl)-4,5-dihydro-[1,2,4]triazolo[4,3-a]quinoxaline

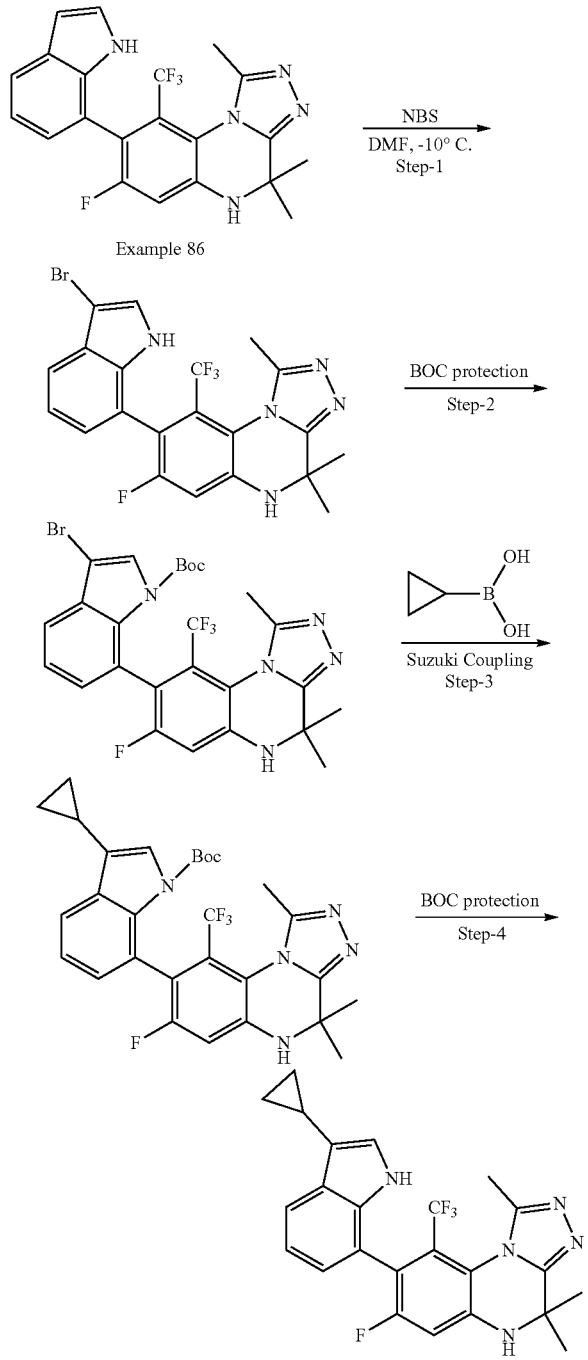

Starting from 7-fluoro-8-(1H-indol-7-yl)-1,4,4-trimethyl-9-(trifluoromethyl)-4,5-dihydro-[1,2,4]triazolo[4,3-a]quinoxaline (=Example 86) example 87 was synthesized in analogy to synthesis described for example 33.

$^1$H NMR (400 MHz, DMSO-d$_6$): δ 10.58-10.6 (1H), 7.66 (d, J=8.0 Hz, 1H), 7.36-7.40 (1H), 7.15-6.99 (m, 4H), 2.44 (s, 3H), 1.94 (m, 1H), 1.75 (s, 3H), 1.31-1.34 (3H), 0.85 (d, J=7.96 Hz, 2H), 0.63 (m, 2H).

Example 89: 7-(7-fluoro-1,4,4-trimethyl-9-(trifluoromethyl)-4,5-dihydro-[1,2,4]triazolo[4,3-a]quinoxalin-8-yl)-1H-indole-3-carbonitrile

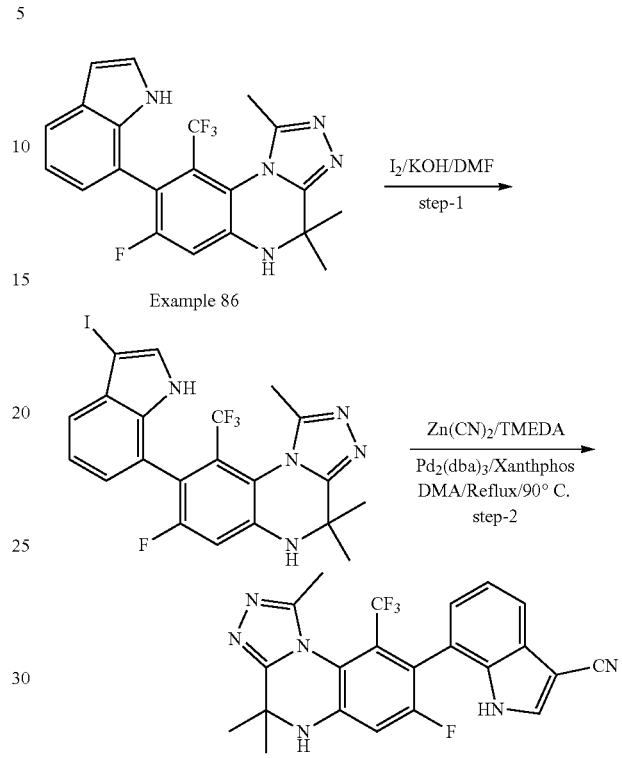

Step1: To a stirred solution of 7-fluoro-8-(1H-indol-7-yl)-1,4,4-trimethyl-9-(trifluoromethyl)-4,5-dihydro-[1,2,4]triazolo[4,3-a]quinoxaline (=Example 86) (0.4 g, 1.04 mmol, 1 eq) in DMF (12 mL) was added KOH powder (0.147 g, 2.62 mmol, 2.5 eq). The reaction mixture was stirred for 30 min at RT. Iodine (0.264 g, 2.08 mmol, 2 eq) was then added to the reaction mixture and stirred for 4 h. The reaction mixture was diluted with EtOAc (80 mL) and washed with water (5×20 mL) and brine (30 mL). The organic layer was dried over anhydrous Na$_2$SO$_4$, concentrated under reduced pressure to get the crude material, which was purified by silica gel (230-400) column chromatography (5% MeOH/DCM; R$_f$-value-0.4) to afford 7-fluoro-8-(3-iodo-1H-indol-7-yl)-1,4,4-trimethyl-9-(trifluoromethyl)-4,5-dihydro-[1,2,4]triazolo[4,3-a]quinoxaline (0.400 g, 66%) as light brown solid.

Step2: A stirring suspension of 7-fluoro-8-(3-iodo-1H-indol-7-yl)-1,4,4-trimethyl-9-(trifluoromethyl)-4,5-dihydro-[1,2,4]triazolo[4,3-a]quinoxaline (0.2 g, 0.369 mmol, 1 eq), Zn(CN)$_2$ (0.043 g, 0.369 mmol, 1 eq) and TMEDA (0.016 mL, 0.110 mmoL, 0.3 eq) in DMA (3 mL) was deoxygenated well with Ar for 10 min. Pd$_2$dba$_3$ (0.033 g, 0.0369 mmol, 0.1 eq) and Xantphos (0.021 g, 0.0369 mmol, 0.1 eq) were added to the reaction mixture and again deoxygenated with Ar for 10 min. Finally the reaction mixture was stirred for 14 h at 90° C. The reaction mixture was filtered through celite bed and the filtrate was diluted by EtOAc (30 mL). The organic layer was washed with water (5×20 mL) and brine (20 mL). The organic layer was dried over anhydrous Na$_2$SO$_4$, concentrated under reduced pressure to get the crude material, which was purified by silica gel (230-400) column chromatography (5% MeOH/DCM; R$_f$-value-0.4) to afford 7-(7-fluoro-1,4,4-trimethyl-9-(trifluoromethyl)-4,5- dihydro-[1,2,4]triazolo[4,3-a]quinoxalin-8-yl)-1H-indole-3-carbonitrile (0.072 g, 44%) as off white solid.

$^1$H NMR (400 MHz, DMSO-d$_6$): δ 12.10-12.19 (1H), 8.28 (d, J=2.7 Hz, 1H), 7.72 (d, J=6.8 Hz, 1H), 7.46-7.51 (1H), 7.34-7.25 (m, 2H), 7.19-7.12 (m, 1H), 2.45 (s, 3H), 1.76 (s, 3H), 1.32-1.36 (3H).

Example 446: 7-fluoro-1,4,4-trimethyl-8-(1-(methylsulfonyl)-1H-indazol-4-yl)-9-(trifluoromethyl)-4,5-dihydro-[1,2,4]triazolo[4,3-a]quinoxaline

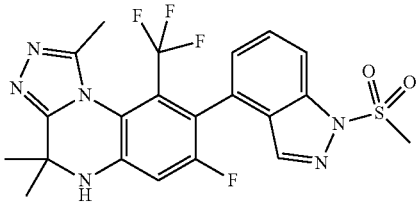 [SMILES: Cc1nnc2n1-c1c(cc(F)c(-c3cccc4c3cnn4S(C)(=O)=O)c1C(F)(F)F)NC2(C)C]

To a solution of 8-bromo-7-fluoro-1,4,4-trimethyl-9-(trifluoromethyl)-4,5-dihydro-[1,2,4]triazolo[4,3-a]quinoxaline (intermediate B-4) (0.3 g, 0.7912 mmol, 1 eq.) in t-amyl alcohol:dioxane (2:1) (15.0-7.0 ml) was added 2M K$_2$CO$_3$ (1.0 ml) solution and 1-(methylsulfonyl)-4-(4,4,5,5-tetramethyl-1,3,2-dioxaborolan-2-yl)-1H-indazole (intermediate A-22) (0.48 g, 1.5824 mmol, 2.0 eq). The solution was degassed with Ar for 20 min followed by addition of Attaphos (0.028 g, 0.0395 mmol, 0.05 eq.) The reaction mixture was heated at 90° C. for 16 h. After completion of reaction (monitored by TLC), reaction mixture was filtered through celite pad and washed with EtOAc. Combined organic layer was evaporated to get the crude product which was purified by prep-HPLC (R$_f$-value-0.3:5% MeOH/DCM) to afford 7-fluoro-1,4,4-trimethyl-8-(1-(methylsulfonyl)-1H-indazol-4-yl)-9-(trifluoromethyl)-4,5-dihydro-[1,2,4]triazolo[4,3-a]quinoxaline (0.065 g, 17%) as white solid.

$^1$H NMR (400 MHz, DMSO-d$_6$): δ 8.34 (s, 1H), 8.09 (d, 1H), 7.73 (t, 1H), 7.45 (bs, 1H), 7.27 (s, 1H), 7.19 (d, 1H), 3.50 (s, 3H), 2.49 (s, 3H), 1.66-1.78 (bs, 3H), 1.23-1.52 (bs, 3H).

Example 450: 1,4,4,9-tetramethyl-8-(1-(methylsulfonyl)-1H-indol-4-yl)-4,5-dihydro-[1,2,4]triazolo[4,3-a]quinoxaline

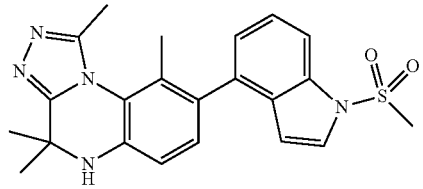 [SMILES: Cc1c(-c2cccc3c2ccn3S(C)(=O)=O)ccc2c1-n1c(C)nnc1C(C)(C)N2]

To a solution of 8-bromo-1,4,4,9-tetramethyl-4,5-dihydro-[1,2,4]triazolo[4,3-a]quinoxaline (intermediate B-40) (0.15 g, 0.488 mmol, 1 eq) in dioxane:water (10:1) (22 ml) was added CsF (0.222 g, 1.464 mmol, 3 eq) and 1-(methylsulfonyl)-4-(4,4,5,5-tetramethyl-1,3,2-dioxaborolan-2-yl)-1H-indole (intermediate A-12) (0.313 g, 0.977 mmol, 2 eq). The solution was degassed with Ar for 20 min followed by addition of Pd(PPh$_3$)$_4$ (0.028 g, 0.024 mmol, 0.05 eq) The reaction mixture was heated at 90° C. for 16 h. After completion of reaction (monitored by TLC), reaction mixture was filtered through celite pad and washed with EtOAc. Combined organic layer was evaporated to get the crude product which was purified by prep-HPLC to afford 1,4,4,9-tetramethyl-8-(1-(methylsulfonyl)-1H-indol-4-yl)-4,5-dihydro-[1,2,4]triazolo[4,3-a]quinoxaline (0.085 g, 41%) as white solid.

1H NMR (400 MHz, dmso-d6): δ 7.88-7.85 (m, 1H), 7.62 (d, 1H), 7.48 (t, 1H), 7.28 (d, 1H), 7.13-7.11 (m, 1H), 6.97-6.95 (m, 1H), 6.53 (s, 2H), 3.49 (s, 3H), 2.03 (s, 3H), 1.46 (bs, 6H).

In the following Tables 4, 5, 6 and 7 it is summarized how the remaining examples have been obtained.

TABLE 4

| Ex. # | Intermediates | Synthesis in analogy to | yield (mol-%) | $^1$H-NMR |
|---|---|---|---|---|
| 45 | Int-A-21 + Int-B-8 | Ex. 44 | 67% | $^1$H NMR (400 MHz, DMSO-d$_6$, T = 100° C.): δ 7.83 (s, 1H), 7.59 (d, 1H), 7.14 (d, 1H), 6.93 (s, 1H), 4.92-4.89 (m, 1H), 4.44 (s, 1H), 3.83 (bs, 2H), 2.68-2.78 (m, 1H), 1.48 (bs, 6H), 0.51 (bs, 3H). |
| 46 | Int-A-2 + Int-B-8 | Ex. 44 | 48% | $^1$H NMR (400 MHz, DMSO-d$_6$, T = 100° C.): δ 7.71-7.65 (m, 2H), 7.35 (d, 1H), 6.92 (s, 1H), 6.78 (d, 1H), 6.52 (s, 1H), 3.59 (s, 3H), 2.67 (s, 1H), 1.49 (bs, 6H), 0.50 (s, 3H). |
| 47 | Int-A-15 + Int-B-8 | Ex. 44 | 24% | $^1$H NMR (400 MHz, DMSO-d$_6$, T = 100° C.): δ 10.6 (s, 1H), 7.28 (dd, 1H), 7.15 (s, 1H), 6.95 (d1H), 6.83 (s, 1H), 6.76 (d, 1H), 2.67 (q, J = 7.2 Hz, 1H), 2.25 (s, 3H), 1.50 (bs, 6H), 0.5 (bs, 3H). |
| 50 | Int-A-12 + Int-B-8 | Ex. 44 | 46% | 1H NMR (400 MHz, dmso-d$_6$, at 100° C.): 7.93 (d, 1H), 7.6 (d, 1H,), 7.48 (t, 1H,), 7.32 (d, 1H,), 6.8 (d, 1H, J = 10.32 Hz), 6.55 (s, 1H), 6.5 (d, 1H,), 3.44 (s, 3H), 2.76-2.67(m, 1H), 2.57-2.53 (m, 3H), 2.49 (s, 3H), 1.55 (s, 3H), 1.51 (s, 3H), 0.53 (t, 3H). |
| 51 | Int-A-22 + Int-B-8 | Ex. 44 | 15% | 1H NMR (400 MHz, DMSO-d$_6$, at 100° C.): 8.27 (s, 1H), 8.06 (d, 1H, J = 8.52 Hz), 7.73 (t, 1H, J = 7.6 Hz), 7.45 (d, 1H, J = 7.2 Hz), 6.83 (d, 1H, J = 10.48 Hz), 6.65 (s, 1H), 3.50 (s, 3H), 2.79-2.74(m, 1H), 2.57-2.53 (m, 3H), 2.51 (s, 3H), 1.55 (s, 3H), 1.53 (s, 3H), 0.54 (t, 3H). |

TABLE 4-continued

| Ex. # | Intermediates | Synthesis in analogy to | yield (mol-%) | $^1$H-NMR |
|---|---|---|---|---|
| 52 | Int-A-23 + Int-B-8 | Ex. 44 | 23% | 1H NMR (400 MHz, DMSO-d$_6$, at 100° C.): 8.28 (s, 1H), 7.76 (d, 1H, J = 9.2 Hz), 7.41 (d, 1H, J = 9.8 Hz), 6.83 (d, 1H, J = 10.52 Hz), 6.72 (s, 1H), 3.54 (s, 3H), 2.83-2.76(m, 1H), 2.60-2.54 (m, 3H), 2.52 (s, 3H), 1.55 (s, 3H), 1.53 (s, 3H), 0.57 (t, 3H). |
| 67 | Int-A-15 + Int-B-13 | Ex. 3 | 56% | $^1$H NMR (400 MHz, DMSO-d$_6$): δ 10.73 (s, 1H), 7.32 (d, 1H), 7.16-7.25 (5H), 7.02 (d, 2H), 6.74 (t, 2H), 4.27-4.39 (2H), 2.48 (s, 3H), 1.62 (bs, 3H), 1.47 (bs, 3H). |
| 68 | 3-methyl-7-(4,4,5,5-tetramethyl-1,3,2-dioxaborolan-2-yl)-1H-indole + Int-B-13 | Ex. 3 | 60% | $^1$H NMR (400 MHz, DMSO-d$_6$): δ 10.59 (s, 1H), 7.54 (d, 1H), 7.14-7.26 (3H), 7.06-7.12 (3H), 7.01-7.03 (2H), 6.90 (d, 1H), 6.72 (d, 1H), 4.24-4.38 (2H), 2.28 (s, 3H), 1.62 (s, 3H), 1.48 (s, 3H). |
| 71 | Int-A-15 + Int-B-14 | Ex. 3 | 40% | $^1$H NMR (400 MHz, DMSO-d$_6$) δ 10.76 (s, 1H), 8.42 (d, 2H), 7.32 (dd, 1H), 7.21 (d, 2H), 7.12 (d, 2H), 6.76-6.83 (2H), 4.34-4.36 (2H), 2.25 (s, 3H), 1.48-1.60 (6H). |
| 72 | 3-methyl-7-(4,4,5,5-tetramethyl-1,3,2-dioxaborolan-2-yl)-1H-indole + Int-B-14 | Ex. 3 | 38% | $^1$H NMR (400 MHz, DMSO-d$_6$) δ: 6 10.62 (s, 1H), 8.42 (d, 2H), 7.54 (d, 1H), 7.06-7.15 (5H), 6.92-6.94 (1H), 6.77 (d, 1H), 4.33-4.38 (2H), 2.28 (s, 3H), 1.60 (s, 3H), 1.53 (s, 3H). |
| 73 | Int-A-15 + Int-B-15 | Ex. 3 | 58% | $^1$H NMR (400 MHz, DMSO-d$_6$): δ 10.77 (s, 1H), 8.40 (d, 1H), 8.35 (s, 1H), 7.53 (d, 1H), 7.26-7.35 (2H), 7.20 (s, 1H), 6.89 (d, 1H), 6.78 (d, 1H), 4.32.4.36 (2H), 2.52 (s, 3H), 1.47-1.60 (6H). |
| 74 | Int-A-15 + Int-B-16 | Ex. 3 | 58% | $^1$H NMR (400 MHz, DMSO-d$_6$): δ 10.82 (s, 1H), 8.30 (s, 1H), 7.67 (t, 1H), 7.30 (d, 1H), 7.16-7.25 (4H), 6.72 (d, 1H), 6.67 (d, 1H), 4.51 (bs, 2H), 2.24 (s, 3H), 1.60 (s, 3H), 1.51 (s, 3H). |
| 75 | 3-methyl-7-(4,4,5,5-tetramethyl-1,3,2-dioxaborolan-2-yl)-1H-indole + Int-B-16 | Ex. 3 | 33% | $^1$H NMR (400 MHz, DMSO-d$_6$): δ 10.70 (s, 1H), 8.30 (d, 1H), 7.68 (t, 1H), 7.52 (d, 1H), 7.17-7.22 (2H), 7.09 (s, 2H), 7.04 (t, 1H), 6.81 (d, 1H), 6.72 (d, 1H), 4.97-4.54 (2H), 2.27 (s, 3H), 1.60 (s, 3H), 1.51 (s, 3H). |
| 80 | (1H-indol-7-yl)boronic acid + Int-B-21 | Ex. 3 | 29% | $^1$H NMR (400 MHz, DMSO-d$_6$): δ 10.97 (1H), 7.63 (dd, 1H), 7.34 (m, 1H), 7.08-7.2 (3H), 6.80 (d, 1H), 6.51 (m, 1H), 2.78 (m, 2H), 1.57 (s, 3H), 1.54 (s, 3H), 1.59 (m, 1H), 0.42 (m, 2H), 0.12 (m, 2H). |
| 81 | (1H-indol-7-yl)boronic acid + Int-B-22 | Ex. 3 | 20% | $^1$H NMR (400 MHz, DMSO-d$_6$): δ 10.98 (s, 1H), 7.62 (dd, 1H), 7.43 (m, 1H), 7.08-7.11 (3H), 6.80 (d, 1H), 6.50 (m, 1H), 2.09 (m, 1H), 1.60 (s, 3H), 1.52 (s, 3H), 0.88-0.95 (4H). |
| 82 | Int-A-26 + Int-B-23 | Ex. 37 | 19% | 1H NMR (400 MHz, dmso-d$_6$): 10.48 (s, 1H), 7.63 (d, 1H, J = 7.76 Hz), 7.32 (s, 1H), 7.06 (t, 1H, J = 7.44 Hz), 6.95 (d, 1H, J = 1.76 Hz), 6.9 (s, 1H), 6.87 (d, 1H, J = 7.16 Hz), 2.4 (s, 3H), 1.97-1.93 (m, 1H), 1.78 (s, 3H), 1.61 (s, 3H), 1.39 (s, 3H), 0.88-083 (m, 1H), 0.65-0.62 (m, 1H). |
| 83 | Int-A-2 +Int-B-23 | Ex. 37 | 14% | 1H NMR (400 MHz, dmso-d$_6$): 7.69 (d, 1H, J = 10.24 Hz), 7.6 (d, 1H, J = 3.68 Hz), 7.33 (s, 1H), 7.15 (d, 1H, J = 9.12 Hz), 7.03 (s, 1H), 6.41 (s, 1H), 3.59 (s, 3H), 2.39 (s, 3H), 1.86 (s, 3H), 1.56 (s, 3H), 1.43 (s, 3H). |
| 84 | Int-A-12 + Int-B-23 | Ex. 37 | 13% | 1H NMR (400 MHz, dmso-d$_6$): 7.9 (d, 1H, J = 8.44 Hz), 7.59 (d, 1H, J = 3.44 Hz), 7.46 (t, 1H, J = 7.84 Hz), 7.33 (s, 1H), 7.17 (d, 1H, J = 7.04 Hz), 6.99 (s, 1H), 6.41 (s, 1H), 3.53 (s, 3H), 2.38 (s, 3H), 1.82 (s, 3H), 1.58 (s, 3H), 1.41 (s, 3H). |
| 85 | Int-A-26 + Int-B-5 | Ex. 3 | 12% | $^1$H NMR (400 MHz, DMSO-d$_6$): δ 10.62 (s, 1H), 7.66 (d, J = 8.0 Hz, 1H), 7.08 (t, J = 9.6 Hz, 2H), 7.00-7.02 (m, 2H), 6.92 (d, J = 10.0 Hz, 1H), 2.56 (s, 3H), 1.94 (d, J = 4.8 Hz, 1H), 1.56 (s, 3H), 1.46 (s, 3H), 0.83-0.88 (m, 2H), 0.61-0.64 (m, 2H). |
| 86 | (1H-indol-7-yl)boronic acid + Int-B-4 | Ex. 3 | 20% | $^1$H NMR (400 MHz, DMSO-d$_6$): δ 10.95-10.98 (1H), 7.59-7.63 (1H), 7.36-7.41 (1H), 7.31 (m, 1H), 7.02-7.16 (3H), 6.48 (s, 1H), 2.45-2.48 (3H), 1.76 (s, 3H), 1.32-1.36 (3H). |

TABLE 4-continued

| Ex. # | Intermediates | Synthesis in analogy to | yield (mol-%) | $^1$H-NMR |
|---|---|---|---|---|
| 88 | Int-A-27 + Int-B-5 | Ex. 37 | 12% | $^1$H NMR (400 MHz, DMSO-d$_6$, T = 100° C.): δ 7.41 (d, J = 9.88 Hz, 1H), 7.28 (d, J = 3.28 Hz, 1H), 7.14 (d, J = 10 Hz, 1H), 6.96 (bs, 1H), 6.07 (s, 1H), 3.49-3.46 (m, 1H), 2.45 (s, 3H), 1.75 (bs, 3H), 1.36(bs, 3H), 1.10-1.00 (m, 4H). |

The examples in Table 5 were synthesized in analogy to Example 1.

| Ex. # | Intermediates | Catalyst Solvent | Yield (%) | LC-MS ([M + H]$^+$) | $^1$H NMR |
|---|---|---|---|---|---|
| 200 | Int-B-1 + Int-A-30 | Bis(tri-tert-butylphosphine palladium(0) THF | 58% | | $^1$H NMR (DMSO-d$_6$) δ: 7.94 (d, 1H), 7.65 (d, 1H), 7.48 (t, 1H), 7.38 (d, 1H), 7.20 (d, 1H), 6.82 (d, 1H), 6.71 (d, 1H), 3.86 (hept, 1H), 2.51 (d, 3H), 1.57 (s, 3H), 1.52 (s, 3H), 1.24 (t, 6H) |
| 201 | Int-B-1 + Int-A-31 | Bis(tri-tert-butylphosphine palladium(0) THF | 44% | | $^1$H NMR (DMSO-d$_6$) δ: 7.96 (d, 1H), 7.68 (d, 1H), 7.48 (t, 1H), 7.38 (d, 1H), 7.22-7.18 (m, 1H), 6.85-6.80 (m, 1H), 6.70 (d, 1H), 4.16-4.07 (m, 1H), 2.51 (d, 3H), 1.94 (dt, 2H), 1.84 (dq, 2H), 1.71-1.61 (m, 2H), 1.57 (s, 5H), 1.52 (s, 3H) |
| 207 | Int-B-1 + 4-(tetramethyl-1,3,2-dioxaborolan-(trifluoromethyl)-1H-indole | Bis(tri-tert-butylphosphine palladium(0) THF | 81% | | $^1$H NMR (DMSO-d$_6$) δ: 7.84 (s, 1H), 7.67 (t, 1H), 7.36 (s, 1H), 7.19 (s, 1H), 6.86-6.80 (m, 1H), 6.44 (s, 1H), 2.51 (d, 3H), 1.59 (s, 3H), 1.51 (s, 3H) |
| 208 | Int-B-1 + Int-A-1 | Bis(tri-tert-butylphosphine palladium(0) THF | 48% | | $^1$H NMR (DMSO-d$_6$) δ: 11.31 (s, 1H), 7.40 (t, 1H), 7.28 (dd, 1H), 7.17 (d, 1H), 6.98 (dd, 1H), 6.86-6.71 (m, 1H), 6.28 (s, 1H), 2.51 (d, 3H), 1.57 (s, 3H), 1.51 (s, 3H) |
| 212 | Int-B-1 + Int-A-32 | Bis(tri-tert-butylphosphine palladium(0) THF | 48% | | $^1$H NMR (DMSO-d$_6$) δ: 7.44 (d, 1H), 7.30 (d, 1H), 7.21 (dd, 1H), 7.12 (d, 1H), 7.08 (d, 1H), 6.81 (dd, 1H), 6.30-6.25 (m, 1H), 5.19 (s, 2H), 3.14 (s, 3H), 2.88 (s, 3H), 2.51-2.49 (m, 3H), 1.59 (s, 3H), 1.50 (s, 3H) |
| 213 | Int-B-1 + Int-A-33 | Bis(tri-tert-butylphosphine palladium(0) THF | 38% | | $^1$H NMR (DMSO-d$_6$) δ: 8.44 (d, 1H), 7.84 (d, 1H), 7.47 (t, 1H), 7.35 (s, 1H), 7.19 (d, 1H), 6.82 (dd, 1H), 6.65 (d, 1H), 4.79 (s, 2H), 3.45 (s, 3H), 2.53-2.48 (m, 3H), 1.59 (s, 3H), 1.51 (s, 3H) |
| 214 | Int-B-1 + 5-fluoro-1H-indole-4-boronic acid pinacol ester | Bis(tri-tert-butylphosphine palladium(0) THF | 64% | | $^1$H NMR (DMSO-d$_6$) δ: 11.45-11.25 (m, 1H), 7.51 (ddd, 1H), 7.47 (t, 1H), 7.23-7.18 (m, 1H), 7.08 (dd, 1H), 6.82 (dd, 1H), 6.29 (p, 1H), 2.49 (d, 3H), 1.58 (s, 3H), 1.51 (s, 3H) |
| 219 | Int-B-1 + Int-A-49 | Bis(tri-tert-butylphosphine palladium(0) THF | 44% | | $^1$H NMR (DMSO-d$_6$) δ: 7.58 (d, 1H), 7.40 (d, 1H), 7.25 (dd, 1H), 7.14-7.07 (m, 2H), 6.80 (dd, 1H), 6.30-6.25 (m, 1H), 4.48 (t, 2H), 3.60 (s, 3H), 2.90 (t, 2H), 2.49 (d, 3H), 1.58 (s, 3H), 1.51 (d, 3H) |
| 221 | Int-B-1 + 1-methyl-4-(4,4,5,5-tetramethyl-[1,3,2]dioxaborolan-2-yl)-1H-indazole | Bis(tri-tert-butylphosphine palladium(0) THF | 62% | | $^1$H NMR (DMSO-d$_6$) δ: 7.96 (s, 1H), 7.72 (d, 1H), 7.51 (dd, 1H), 7.23 (d, 1H), 7.21 (d, 1H), 6.86-6.80 (m, 1H), 4.10 (s, 3H), 2.51 (q, 3H), 1.55 (s, 6H) |
| 222 | Int-B-1 + 2-methyl-4-(4,4,5,5-tetramethyl-1,3,2- | Bis(tri-tert-butylphosphine palladium(0) THF | 52% | | $^1$H NMR (DMSO-d$_6$) δ: 8.28 (s, 1H), 7.67 (d, 1H), 7.35 (dd, 1H), 7.19 (d, 1H), 7.12 (d, 1H), 6.82 (dd, 1H), 4.16 (s, 3H), 2.53-2.51 (m, 3H), 1.55 (s, 6H) |

-continued

| Ex. # | Intermediates | Catalyst Solvent | Yield (%) | LC-MS ([M + H]+) | 1H NMR |
|---|---|---|---|---|---|
| | dioxaborolan-2-yl)-2H-indazole | | | | |
| 225 | Int-B-1 + 4-(tetramethyl-1,3,2-dioxaborolan-2-yl)-2-(trifluoromethyl)-1H-indole | Bis(tri-tert-butylphosphine palladium(0) THF | 76% | | 1H NMR (DMSO-$d_6$) δ: 7.58 (d, 1H), 7.41 (t, 1H), 7.22 (d, 1H), 7.16 (d, 1H), 6.89 (s, 1H), 6.81 (d, 1H), 2.49 (s, 3H), 1.57 (s, 3H), 1.53 (s, 3H) |
| 228 | Int-B-1 + Int-A-34 | Bis(tri-tert-butylphosphine palladium(0) THF | 72% | | 1H NMR (DMSO-$d_6$) δ: 7.54 (d, 1H), 7.37 (d, 1H), 7.24 (t, 1H), 6.98 (t, 1H), 6.79 (dd, 1H), 6.27 (t, 1H), 4.26 (t, 2H), 2.49 (d, 3H), 1.58 (s, 3H), 1.49 (s, 3H), 1.36 (s, 9H), 1.13 (s, 2H) |
| 232 | Int-B-1 + 4-(4,4,5,5-tetramethyl-1,3,2-dioxaborolan-2-yl)-1H-indazole | Tetrakis-(triphenylphosphin)-palladium (0) Toluol/Ethanol | 31% | | 1H NMR (DMSO-$d_6$) δ: 7.98 (s, 1H), 7.62 (d, 1H), 7.46 (dd, 1H), 7.20 (dd, 2H), 6.86-6.79 (m, 1H), 2.53 (d, 3H), 1.55 (s, 6H) |
| 233 | Int-B-1 + Int-A-36 | Tetrakis-(triphenylphosphin)-palladium (0) Toluol/Ethanol | 80% | | 1H NMR (DMSO-$d_6$) δ: 7.98 (d, 1H), 7.78-7.73 (m, 1H), 7.49 (dd, 1H), 7.24-7.19 (m, 2H), 6.83 (dd, 1H), 4.61 (t, 2H), 3.80 (t, 2H), 3.23 (s, 3H), 2.53 (s, 3H), 1.55 (s, 6H) |
| 234 | Int-B-1 + Int-A-35 | Tetrakis-(triphenylphosphin)-palladium (0) Toluol/Ethanol | 29% | | 1H NMR (DMSO-$d_6$) δ: 8.57 (d, 1H), 8.10-8.04 (m, 1H), 7.76 (dd, 1H), 7.60-7.50 (m, 1H), 7.30 (t, 1H), 6.85 (dd, 1H), 3.17 (tt, 1H), 2.54 (d, 3H), 1.56 (s, 6H), 1.36-1.24 (m, 2H), 1.22-1.11 (m, 2H) |
| 235 | Int-B-1 + Int-A-37 | Tetrakis-(triphenylphosphin)-palladium (0) Toluol/Ethanol | 57% | | 1H NMR (DMSO-$d_6$) δ: 7.97 (s, 1H), 7.79 (dd, 1H), 7.49 (dd, 1H), 7.24-7.19 (m, 2H), 6.83 (dd, 1H), 4.35 (d, 2H), 2.52 (d, 3H), 1.55 (s, 6H), 1.38-1.27 (m, 1H), 0.56-0.48 (m, 2H), 0.49-0.41 (m, 2H) |
| 236 | Int-B-1 + Int-A-38 | Tetrakis-(triphenylphosphin)-palladium (0) Toluol/Ethanol | 72% | | 1H NMR (DMSO-$d_6$) δ: 7.97 (s, 1H), 7.76 (d, 1H), 7.50 (dd, 1H), 7.22 (d, 2H), 6.86-6.80 (m, 1H), 4.49 (q, 2H), 2.53 (s, 3H), 1.55 (s, 6H), 1.44 (t, 3H) |
| 237 | Int-B-1 + Int-A-39 | Tetrakis-(triphenylphosphin)-palladium (0) Toluol/Ethanol | 99% | | 1H NMR (DMSO-$d_6$) δ: 8.33 (s, 1H), 7.68 (d, 1H), 7.35 (dd, 1H), 7.18 (d, 1H), 7.12 (d, 1H), 6.82 (dd, 1H), 4.45 (q, 2H), 2.53 (s, 3H), 1.55 (s, 6H), 1.51 (t, 3H) |
| 238 | Int-B-1 + tert-butyl 4-(4,4,5,5-tetramethyl-1,3,2-dioxaborolan-2-yl)-1H-indazole-1-carboxylate | Tetrakis-(triphenylphosphin)-palladium (0) Toluol/Ethanol | 41% | | 1H NMR (DMSO-$d_6$) δ: 8.38 (s, 1H), 8.18 (d, 1H), 7.73 (dd, 1H), 7.48 (d, 1H), 7.29 (s, 1H), 6.85 (d, 1H), 2.53 (d, 3H), 1.68 (s, 9H), 1.56 (s, 6H) |
| 239 | Int-B-1 + Int-A-40 | Tetrakis-(triphenylphosphin)-palladium (0) Toluol/Ethanol | 66% | | 1H NMR (DMSO-$d_6$) δ: 8.57 (s, 1H), 8.08 (dd, 1H), 7.75 (dd, 1H), 7.52 (d, 1H), 7.30 (d, 1H), 6.85 (dd, 1H), 3.66 (d, 2H), 2.54 (d, 3H), 1.56 (s, 6H), 0.81 (tt, 1H), 0.31-0.25 (m, 2H), −0.02 (d, 2H) |
| 240 | Int-B-6 + 1-methyl-4-(4,4,5,5-tetramethyl-[1,3,2]dioxaborolan-2-yl)-1H-indazole | Tetrakis-(triphenylphosphin)-palladium (0) Toluol/Ethanol | 64% | | 1H NMR (DMSO-$d_6$) δ: 7.74 (s, 1H), 7.70 (d, 1H), 7.51 (ddd, 1H), 7.13 (d, 1H), 6.82 (d, 1H), 6.77 (s, 1H), 4.10 (s, 3H), 2.79 (s, 2H), 1.99 (s, 3H), 1.49 (s, 6H), 1.26 (t, 3H) |
| 241 | Int-B-6 + Int-A-22 | Tetrakis-(triphenylphosphin)-palladium (0) Toluol/Ethanol | 60% | | 1H NMR (DMSO-$d_6$) δ: 8.35 (s, 1H), 8.05 (dt, 1H), 7.75 (dd, 1H), 7.45 (d, 1H), 6.85 (d, 2H), 3.55 (s, 3H), 2.81 (s, 2H), 2.02 (s, 3H), 1.50 (s, 6H), 1.28 (t, 3H) |

-continued

| Ex. # | Intermediates | Catalyst Solvent | Yield (%) | LC-MS ([M + H]⁺) | ¹H NMR |
|---|---|---|---|---|---|
| 242 | Int-B-6 + Int-A-41 | Tetrakis-(triphenylphosphin)-palladium (0) Toluol/Ethanol | 18% | | ¹H NMR (DMSO-d₆) δ: 7.76 (d, 1H), 7.71 (s, 1H), 7.53 (dd, 1H), 7.15 (d, 1H), 6.81 (d, 1H), 6.77 (s, 1H), 3.84-3.77 (m, 1H), 2.79 (s, 2H), 1.99 (s, 3H), 1.52 (s, 6H), 1.26 (t, 3H), 1.18-1.14 (m, 4H) |
| 243 | Int-B-1 + Int-A-41 | Tetrakis-(triphenylphosphin)-palladium (0) Toluol/Ethanol | 34% | | ¹H NMR (DMSO-d₆) δ: 7.93 (s, 1H), 7.78 (d, 1H), 7.55-7.51 (m, 1H), 7.24 (d, 1H), 7.22 (d, 1H), 6.82 (dd, 1H), 3.79 (tt, 1H), 2.53-2.49 (m, 3H), 1.54 (s, 6H), 1.20-1.12 (m, 4H) |
| 244 | Int-B-6 + 5-fluoro-1H-indole-4-boronic acid pinacol ester | Bis(tri-tert-butylphosphine palladium(0) THF | 55% | | ¹H NMR (DMSO-d₆) δ: 11.32 (s, 1H), 7.49-7.44 (m, 2H), 7.06 (d, 1H), 6.80 (d, 1H), 6.77 (s, 1H), 6.08 (s, 1H), 2.77 (s, 2H), 2.00 (s, 3H), 1.64-1.36 (m, 6H), 1.24 (t, 3H) |
| 247 | Int-B-6 + Int-A-12 | Bis(tri-tert-butylphosphine palladium(0) THF | 47% | | ¹H NMR (DMSO-d₆) δ: 7.92 (d, 1H), 7.63 (d, 1H), 7.49 (t, 1H), 7.30 (d, 1H), 6.82 (d, 1H), 6.77 (s, 1H), 6.45 (s, 1H), 3.52 (s, 3H), 2.79 (s, 2H), 1.98 (s, 3H), 1.71-1.34 (m, 6H), 1.26 (t, 3H) |
| 248 | Int-B-25 + Int-A-12 | Bis(tri-tert-butylphosphine palladium(0) THF | 90% | | ¹H NMR (DMSO-d₆) δ: 7.91 (d, 1H), 7.61 (d, 1H), 7.48 (dd, 1H), 7.35 (d, 1H), 6.96 (s, 1H), 6.74 (d, 1H), 6.59 (d, 1H), 3.52 (s, 3H), 3.20 (s, 3H), 1.59 (s, 3H), 1.46 (s, 3H), 1.29 (d, 3H) |
| 249 | Int-B-25 + Int-A-15 | Bis(tri-tert-butylphosphine palladium(0) THF | 92% | | ¹H NMR (DMSO-d₆) δ: 10.67-10.59 (m, 1H), 7.29 (dd, 1H), 7.15 (d, 1H), 6.97-6.91 (m, 2H), 6.72 (d, 1H), 3.22 (s, 3H), 2.52-2.50 (m, 3H), 2.28-2.25 (m, 3H), 1.57 (s, 3H), 1.49 (s, 3H) |
| 250 | Int-B-25 + Int-A-2 | Bis(tri-tert-butylphosphine palladium(0) THF | 64% | | ¹H NMR (DMSO-d₆) δ: 7.69 (dd, 1H), 7.63 (d, 1H), 7.29 (dd, 1H), 7.03 (s, 1H), 6.74 (d, 1H), 6.61-6.57 (m, 1H), 3.59-3.56 (m, 3H), 3.24 (s, 3H), 2.50 (d, 3H), 1.59 (s, 3H), 1.46 (s, 3H) |
| 251 | Int-B-24 + Int-A-15 | Tetrakis-(triphenylphosphin)-palladium (0) Toluol/Ethanol | 73% | | ¹H NMR (DMSO-d₆) δ: 10.54 (d, 1H), 7.24 (dd, 1H), 7.15-7.11 (m, 1H), 6.88 (dd, 1H), 6.61 (s, 1H), 3.70 (s, 3H), 2.47 (d, 3H), 2.27-2.23 (m, 3H), 1.55 (s, 3H), 1.53 (s, 3H) |
| 252 | Int-B-27 + 4-(tetramethyl-1,3,2-dioxaborolan-2-yl-)-2-(trifluoromethyl)-1H-indole | Bis(tri-tert-butylphosphine palladium(0) THF | 86% | | ¹H NMR (DMSO-d₆) δ: 12.39 (d, 1H), 7.55 (d, 1H), 7.40 (dd, 1H), 7.27-6.94 (m, 3H), 6.85 (s, 1H), 6.82 (s, 1H), 2.47 (d, 3H), 1.57 (s, 3H), 1.53 (s, 3H) |
| 253 | Int-B-1 + Int-A-42 | Tetrakis-(triphenylphosphin)-palladium (0) Toluol/Ethanol | 53% | | ¹H NMR (DMSO-d₆) δ: 7.66 (d, 1H), 7.44 (d, 1H), 7.29 (t, 1H), 7.18-7.10 (m, 2H), 6.82 (d, 1H), 6.53-6.30 (m, 2H), 4.75 (td, 2H), 2.52 (d, 3H), 1.60 (s, 3H), 1.55-1.47 (m, 3H) |
| 254 | Int-B-26 + 4-(tetramethyl-1,3,2-dioxaborolan-2-yl-)-2-(trifluoromethyl)-1H-indole | Bis(tri-tert-butylphosphine) palladium(0) THF | 41% | | ¹H NMR (DMSO-d₆) δ: 12.45-12.42 (m, 1H), 7.60-7.54 (m, 1H), 7.42 (dd, 1H), 7.17 (dd, 1H), 7.10 (d, 1H), 7.06 (d, 1H), 6.86-6.82 (m, 1H), 2.46 (d, 3H), 1.57 (s, 3H), 1.53 (s, 3H) |
| 255 | Int-B-24 + Int-A-2 | Tetrakis-(triphenylphosphin)-palladium (0) Toluol/Ethanol | 72% | | ¹H NMR (DMSO-d₆) δ: 7.65 (ddd, 1H), 7.60 (d, 1H), 7.22 (dd, 1H), 6.99 (d, 1H), 6.63 (d, 1H), 6.59 (dd, 1H), 3.72 (s, 3H), 3.56 (s, 3H), 2.47 (d, 3H), 1.56 (s, 3H), 1.50 (s, 3H) |

-continued

| Ex. # | Intermediates | Catalyst Solvent | Yield (%) | LC-MS ([M + H]$^+$) | $^1$H NMR |
|---|---|---|---|---|---|
| 256 | Int-B-24 + indole-4-boronic acid | Tetrakis-(triphenylphosphin)-palladium (0) Toluol/Ethanol | 47% | | $^1$H NMR (DMSO-d$_6$) δ: 11.10 (s, 1H), 7.40 (dt, 1H), 7.32 (t, 1H), 7.13 (dd, 1H), 6.96 (dd, 1H), 6.82 (d, 1H), 6.61 (d, 1H), 6.15 (dt, 1H), 3.68 (s, 3H), 2.45 (d, 3H), 1.56 (s, 3H), 1.48 (s, 3H) |
| 257 | Int-B-24 + 4-(tetramethyl-1,3,2-dioxaborolan-2-yl-)-2-(trifluoromethyl)-1H-indole | Bis(tri-tert-butylphosphine palladium(0) THF | 63% | | $^1$H NMR (DMSO-d$_6$) δ: 12.30 (d, 1H), 7.50 (dt, 1H), 7.36 (dd, 1H), 7.12 (dd, 1H), 6.88 (d, 1H), 6.74-6.70 (m, 1H), 6.62 (d, 1H), 3.69 (s, 3H), 2.45 (d, 3H), 1.55 (s, 3H), 1.51 (s, 3H) |
| 260 | Int-B-25 + 1,1-dimethylethyl 4-(4,4,5,5-tetramethyl-1,3,2-dioxaborolan-2-yl)-1H-indole-1-carboxylate | Bis(tri-tert-butylphosphine palladium(0) THF | 51% | | $^1$H NMR (DMSO-d$_6$) δ: 8.13 (d, 1H), 7.70 (d, 1H), 7.43 (dd, 1H), 7.29 (dt, 1H), 6.94 (s, 1H), 6.73 (d, 1H), 6.46 (dt, 1H), 3.16 (s, 3H), 2.50 (s, 3H), 1.66 (s, 9H), 1.57 (s, 3H), 1.47 (s, 3H) |
| 263 | Int-B-24 + Int-A-12 | Bis(tri-tert-butylphosphine palladium(0) THF | 30% | | $^1$H NMR (DMSO-d$_6$) δ: 7.89-7.84 (m, 1H), 7.58 (d, 1H), 7.44 (t, 1H), 7.29 (d, 1H), 6.92 (d, 1H), 6.63 (s, 1H), 6.56 (d, 1H), 3.70 (s, 3H), 3.49 (s, 3H), 2.46 (d, 3H), 1.56 (s, 3H), 1.50 (s, 3H) |
| 264 | Int-B-25 + 1-methyl-4-(4,4,5,5-tetramethyl-[1,3,2]dioxaborolan-2-yl)-1H-indazole | Bis(tri-tert-butylphosphine palladium(0) THF | 66% | | $^1$H NMR (DMSO-d$_6$) δ: 7.86-7.82 (m, 1H), 7.69-7.66 (m, 1H), 7.50 (s, 1H), 7.19 (d, 1H), 6.96 (s, 1H), 6.74 (d, 1H), 4.09 (s, 3H), 3.16 (s, 3H), 2.52 (s, 3H), 1.52 (d, 6H) |
| 266 | Int-B-24 + 3-methyl-7-(4,4,5,5-tetramethyl-1,3,2-dioxaborolan-2-yl)-1H-indole | Bis(tri-tert-butylphosphine palladium(0) THF | 70% | | $^1$H NMR (DMSO-d$_6$) δ: 10.39 (d, 1H), 7.48 (d, 1H), 7.06-7.02 (m, 2H), 7.01 (dd, 1H), 6.87-6.79 (m, 1H), 6.60 (s, 1H), 3.67 (s, 3H), 2.46 (d, 3H), 2.29 (s, 3H), 1.56 (s, 3H), 1.52 (s, 3H) |
| 267 | Int-B-27 + Int-A-15 | Tetrakis-(triphenylphosphin)-palladium (0) Toluol/Ethanol | 32% | | $^1$H NMR (DMSO-d$_6$) δ: 10.69 (d, 1H), 7.31 (dd, 1H), 7.22-7.07 (m, 3H), 6.98-6.92 (m, 1H), 6.81 (s, 1H), 2.51-2.46 (m, 3H), 2.35-2.17 (m, 3H), 1.57 (s, 3H), 1.54 (s, 3H) |
| 268 | Int-B-27 + Int-A-2 | Tetrakis-(triphenylphosphin)-palladium (0) Toluol/Ethanol | 34% | | $^1$H NMR (DMSO-d$_6$) δ: 7.73-7.68 (m, 1H), 7.64 (d, 1H), 7.30-7.23 (m, 2H), 7.09 (d, 1H), 6.83 (s, 1H), 6.67 (d, 1H), 3.57 (s, 3H), 2.49 (d, 3H), 1.58 (s, 3H), 1.51 (s, 3H) |
| 269 | Int-B-24 + 1-methyl-4-(4,4,5,5-tetramethyl-[1,3,2]dioxaborolan-2-yl)-1H-indazole | Bis(tri-tert-butylphosphine palladium(0) THF | 77% | | $^1$H NMR (DMSO-d$_6$) δ: 7.81 (s, 1H), 7.63 (d, 1H), 7.45 (dd, 1H), 7.13 (d, 1H), 6.93 (d, 1H), 6.65-6.61 (m, 1H), 4.07 (s, 3H), 3.70 (s, 3H), 2.47 (d, 3H), 1.57 (s, 3H), 1.50 (s, 3H) |
| 270 | Int-B-25 + 3-methyl-7-(4,4,5,5-tetramethyl-1,3,2-dioxaborolan-2-yl)-1H-indole | Bis(tri-tert-butylphosphine palladium(0) THF | 56% | | $^1$H NMR (DMSO-d$_6$) δ: 10.50 (d, 1H), 7.55-7.50 (m, 1H), 7.11-7.03 (m, 3H), 6.86 (s, 1H), 6.71 (d, 1H), 3.18 (s, 3H), 2.50 (s, 3H), 2.30 (d, 3H), 1.57 (s, 3H), 1.49 (s, 3H) |

| Ex. # | Intermediates | Catalyst Solvent | Yield (%) | LC-MS ([M + H]⁺) | ¹H NMR |
|---|---|---|---|---|---|
| 272 | Int-B-26 + 3-methyl-7-(4,4,5,5-tetramethyl-1,3,2-dioxaborolan-2-yl)-1H-indole | Bis(tri-tert-butylphosphine palladium(0) THF | 31% | | ¹H NMR (DMSO-d₆) δ: 10.60 (d, 1H), 7.58-7.53 (m, 1H), 7.12-7.08 (m, 2H), 7.08-7.03 (m, 3H), 2.46 (d, 3H), 2.30 (d, 3H), 1.58 (s, 3H), 1.54 (s, 3H) |
| 273 | Int-B-27 + 1-methyl-4-(4,4,5,5-tetramethyl-[1,3,2]dioxaborolan-2-yl)-1H-indazole | Bis(tri-tert-butylphosphine palladium(0) THF | 41% | | ¹H NMR (DMSO-d₆) δ: 7.91 (d, 1H), 7.69 (dd, 1H), 7.50 (dd, 1H), 7.27-7.00 (m, 3H), 6.83 (s, 1H), 4.09 (s, 3H), 2.49 (d, 3H), 1.59 (s, 3H), 1.51 (s, 3H) |
| 275 | Int-B-27 + Int-A-12 | Bis(tri-tert-butylphosphine palladium(0) THF | 58% | | ¹H NMR (DMSO-d₆) δ: 7.93-7.89 (m, 1H), 7.62 (d, 1H), 7.48 (dd, 1H), 7.32 (dd, 1H), 7.19 (s, 1H), 7.12 (t, 1H), 6.83 (s, 1H), 6.66 (d, 1H), 3.51 (s, 3H), 2.48 (d, 3H), 1.58 (s, 3H), 1.51 (s, 3H) |
| 276 | Int-B-1 + Int-A-23 | Bis(tri-tert-butylphosphine palladium(0) THF | 30% | | ¹H NMR (DMSO-d₆) δ: 8.59 (s, 1H), 7.78 (ddd, 1H), 7.52 (dd, 1H), 7.37 (d, 1H), 6.86 (dd, 1H), 3.59 (s, 3H), 2.55 (d, 3H), 1.56 (s, 6H) |
| 277 | Int-B-26 + Int-A-2 | Bis(tri-tert-butylphosphine palladium(0) THF | 29% | | ¹H NMR (DMSO-d₆) δ: 7.73 (ddd, 1H), 7.65 (dd, 1H), 7.31 (dd, 1H), 7.20 (d, 1H), 7.07 (d, 1H), 6.66 (dd, 1H), 3.60 (s, 3H), 2.48 (d, 3H), 1.58 (s, 3H), 1.52 (s, 3H) |
| 278 | Int-B-3 + Int-A-43 | Bis(tri-tert-butylphosphine palladium(0) THF | 57% | | ¹H NMR (DMSO-d₆) δ: 7.54 (dd, 1H), 7.38 (d, 1H), 7.23 (dd, 1H), 6.99 (d, 1H), 6.79 (d, 1H), 6.70 (s, 1H), 6.09 (d, 1H), 4.43-4.32 (m, 2H), 3.71 (t, 2H), 3.26 (s, 3H), 2.44 (s, 3H), 1.98 (s, 3H), 1.54 (s, 3H), 1.44 (s, 3H) |
| 279 | Int-B-3 + Int-A-23 | Bis(tri-tert-butylphosphine palladium(0) THF | 71% | | ¹H NMR (DMSO-d₆) δ: 8.39 (s, 1H), 7.75 (ddd, 1H), 7.49 (dd, 1H), 6.93 (s, 1H), 6.85 (d, 1H), 3.58 (s, 3H), 2.49 (s, 3H), 2.06 (s, 3H), 1.51 (s, 3H), 1.49 (s, 3H) |
| 280 | Int-B-26 + Int-A-43 | Bis(tri-tert-butylphosphine palladium(0) THF | 58% | | ¹H NMR (DMSO-d₆) δ: 7.57 (dt, 1H), 7.38 (d, 1H), 7.24 (dd, 1H), 7.07 (s, 1H), 7.06 (d, 1H), 7.03 (dd, 1H), 6.22-6.18 (m, 1H), 4.38 (tt, 2H), 3.71 (t, 2H), 3.26 (s, 3H), 2.45 (d, 3H), 1.58 (s, 3H), 1.50 (s, 3H) |
| 281 | Int-B-25 + Int-A-43 | Bis(tri-tert-butylphosphine palladium(0) THF | 31% | | ¹H NMR (DMSO-d₆) δ: 7.54 (dd, 1H), 7.36 (d, 1H), 7.22 (dd, 1H), 7.05 (d, 1H), 6.86 (s, 1H), 6.71 (d, 1H), 6.18 (d, 1H), 4.42-4.31 (m, 2H), 3.71 (t, 2H), 3.26 (d, 3H), 3.17 (s, 3H), 2.49 (s, 3H), 1.57 (s, 3H), 1.47 (s, 3H) |
| 282 | Int-B-27 + 3-methyl-7-(4,4,5,5-tetramethyl-1,3,2-dioxaborolan-2-yl)-1H-indole | Bis(tri-tert-butylphosphine palladium(0) THF | 71% | | ¹H NMR (DMSO-d₆) δ: 10.56 (d, 1H), 7.54 (dd, 1H), 7.18-6.93 (m, 5H), 6.81 (s, 1H), 2.47 (d, 3H), 2.29 (d, 3H), 1.58 (s, 3H), 1.53 (s, 3H) |
| 283 | Int-B-26 + Int-A-15 (dechlorination) | Bis(tri-tert-butylphosphine palladium(0) THF | 19% | | ¹H NMR (DMSO-d₆) δ: 10.81 (d, 1H), 7.29 (dd, 1H), 7.22 (dd, 1H), 7.12-7.05 (m, 2H), 7.01 (dd, 1H), 6.88 (d, 1H), 2.57 (d, 3H), 2.26 (d, 3H), 1.52 (s, 6H) |
| 284 | Int-B-26 + Int-A-12 | Bis(tri-tert-butylphosphine palladium(0) THF | 48% | | ¹H NMR (DMSO-d₆) δ: 7.94 (d, 1H), 7.63 (d, 1H), 7.50 (dd, 1H), 7.34 (d, 1H), 7.15 (d, 1H), 7.07 (d, 1H), 6.64 (d, 1H), 3.53 (s, 3H), 2.46 (d, 3H), 1.58 (s, 3H), 1.51 (s, 3H) |
| 285 | Int-B-26 + 1-methyl-4-(4,4,5,5-tetramethyl- | Bis(tri-tert-butylphosphine palladium(0) THF | 62% | | ¹H NMR (DMSO-d₆) δ: 7.90 (s, 1H), 7.72 (d, 1H), 7.52 (dd, 1H), 7.20-7.13 (m, 2H), 7.07 (d, 1H), 4.09 (s, 3H), 2.46 (d, 3H), 1.59 (s, 3H), 1.51 |

-continued

| Ex. # | Intermediates | Catalyst Solvent | Yield (%) | LC-MS ([M + H]+ | 1H NMR |
|---|---|---|---|---|---|
| | [1,3,2]dioxabo rolan-2-yl)- 1H-indazole | | | | (s, 3H) |
| 286 | Int-B-25 + 1H-indol-4- ylboronic acid | Bis(tri-tert- butylphosphine palladium(0) THF | 18% | | 1H NMR (DMSO-d6) δ: 11.16 (s, 1H), 7.45 (dd, 1H), 7.34 (t, 1H), 7.18 (dd, 1H), 7.02 (d, 1H), 6.84 (s, 1H), 6.70 (d, 1H), 6.18 (td, 1H), 3.15 (s, 3H), 2.49 (s, 3H), 1.56 (s, 3H), 1.47 (s, 3H) |
| 287 | Int-B-27 + Int- A-43 | Bis(tri-tert- butylphosphine palladium(0) THF | 43% | | 1H NMR (DMSO-d6) δ: 7.54 (dd, 1H), 7.37 (d, 1H), 7.22 (dd, 1H), 7.12-7.10 (m, 1H), 7.08 (t, 1H), 7.03 (dd, 1H), 6.81 (s, 1H), 6.22 (d, 1H), 4.37 (td, 2H), 3.71 (t, 2H), 3.25 (s, 3H), 2.46 (d, 3H), 1.58 (s, 3H), 1.49 (s, 3H) |
| 288 | Int-B-24 + Int- A-43 | Bis(tri-tert- butylphosphine palladium(0) THF | 69% | | 1H NMR (DMSO-d6) δ: 7.48 (dd, 1H), 7.32 (d, 1H), 7.18 (dd, 1H), 6.99 (dd, 1H), 6.83 (d, 1H), 6.61 (d, 1H), 6.14 (t, 1H), 4.35 (t, 2H), 3.70 (t, 2H), 3.67 (s, 3H), 3.26 (s, 3H), 2.44 (d, 3H), 1.56 (s, 3H), 1.48 (s, 3H) |
| 290 | Int-B-26 + Int- A-15 | Bis(tri-tert- butylphosphine palladium(0) THF | 9% | | 1H NMR (DMSO-d6) δ: 10.73 (d, 1H), 7.33 (dd, 1H), 7.18 (dd, 1H), 7.12 (d, 1H), 7.06 (d, 1H), 6.95 (dd, 1H), 2.47 (d, 3H), 2.26 (d, 3H), 1.58 (s, 3H), 1.54 (s, 3H) |
| 292 | Int-B-28 + Int- A-43 | Bis(tri-tert- butylphosphine palladium(0) THF | 45% | | 1H NMR (DMSO-d6) δ: 7.55 (d, 1H), 7.35 (d, 1H), 7.21 (dd, 1H), 7.13 (s, 1H), 7.06-7.01 (m, 2H), 6.87 (t, 1H), 6.08 (s, 1H), 4.43-4.31 (m, 2H), 3.71 (t, 2H), 3.26 (s, 3H), 2.47 (s, 3H), 1.85-1.12 (m, 6H) |
| 293 | Int-B-26 + 1H-indol-4- ylboromc acid | Tetrakis- (triphenylpho sphin)- palladium (0) Toluol/Ethanol | 91% | | 1H NMR (DMSO-d6) δ: 11.22 (s, 1H), 7.48 (dt, 1H), 7.36 (t, 1H), 7.19 (dd, 1H), 7.05 (d, 2H), 7.00 (dd, 1H), 6.20 (td, 1H), 2.45 (d, 3H), 1.58 (s, 3H), 1.49 (d, 3H) |
| 294 | Int-B-28 + 1- methyl-4- (4,4,5,5- tetramethyl- [1,3,2]dioxabo rolan-2-yl)- 1H-indazole | Bis(tri-tert- butylphosphine palladium(0) THF | 46% | | 1H NMR (DMSO-d6) δ: 7.74 (s, 1H), 7.69 (dt, 1H), 7.47 (dd, 1H), 7.21 (s, 1H), 7.17-7.12 (m, 1H), 7.06 (d, 1H), 6.94 (d, 1H), 4.09 (s, 3H), 2.48 (s, 3H), 1.89-1.19 (m, 6H) |
| 295 | Int-B-29 + Int- A-43 | Bis(tri-tert- butylphosphine palladium(0) THF | 39% | | 1H NMR (DMSO-d6) δ: 7.62 (dt, 1H), 7.41 (d, 1H), 7.26 (dd, 1H), 7.23 (s, 1H), 7.15 (d, 1H), 7.01 (d, 1H), 6.46 (t, 1H), 6.21 (d, 1H), 4.39 (q, 2H), 3.72 (t, 2H), 3.27 (s, 3H), 2.47 (d, 3H), 1.60 (s, 3H), 1.50 (s, 3H) |
| 296 | Int-B-29 + Int- A-15 | Tetrakis- (triphenylpho sphin)- palladium (0) Toluol/Ethanol | 39% | | 1H NMR (DMSO-d6) δ: 10.75 (d, 1H), 7.36 (dd, 1H), 7.26-7.17 (m, 3H), 6.92 (dd, 1H), 6.58 (t, 1H), 2.47 (s, 3H), 2.27 (d, 3H), 1.60 (s, 3H), 1.53 (s, 3H) |
| 297 | Int-B-27 + 1H-indol-4- ylboronic acid | Bis(tri-tert- butylphosphine palladium(0) THF | 12% | | 1H NMR (DMSO-d6) δ: 11.19 (s, 1H), 7.46 (dt, 1H), 7.36 (t, 1H), 7.17 (dd, 1H), 7.11-7.09 (m, 1H), 7.08- 6.94 (m, 2H), 6.81 (s, 1H), 6.22 (dt, 1H), 2.47 (d, 3H), 1.58 (s, 3H), 1.50 (s, 3H) |
| 298 | Int-B-29 + Int- A-2 | Tetrakis- (triphenylpho sphin)- palladium (0) Toluol/Ethanol | 30% | | 1H NMR (DMSO-d6) δ: 7.78-7.72 (m, 1H), 7.65 (d, 1H), 7.36-7.14 (m, 3H), 6.82-6.47 (m, 2H), 3.59 (d, 3H), 2.48 (d, 3H), 1.60 (s, 3H), 1.51 (s, 3H) |
| 299 | Int-B-6 + Int- A-43 | Bis(tri-tert- butylphosphine palladium(0) THF | 50% | | 1H NMR (DMSO-d6) δ: 7.54 (dd, 1H), 7.39 (d, 1H), 7.23 (dd, 1H), 6.98 (d, 1H), 6.79 (d, 1H), 6.68 (s, 1H), 6.07 (s, 1H), 4.43-4.32 (m, 2H), 3.71 (t, 2H), 3.26 (s, 3H), 2.78 (s, 2H), 1.98 (s, 3H), 1.65-1.31 (m, 6H), 1.25 (t, 3H) |

-continued

| Ex. # | Intermediates | Catalyst Solvent | Yield (%) | LC-MS ([M + H]+ | 1H NMR |
|---|---|---|---|---|---|
| 302 | Int-B-28 + Int-A-15 | Bis(tri-tert-butylphosphine palladium(0) THF | 13% | | 1H NMR (DMSO-d6) δ: 10.61 (d, 1H), 7.29 (dd, 1H), 7.19 (s, 1H), 7.14 (dd, 1H), 7.06-7.02 (m, 1H), 6.97-6.85 (m, 2H), 2.49 (s, 3H), 2.26 (d, 3H), 1.86-1.17 (m, 6H) |
| 306 | Int-B-29 + 3-methyl-7-(4,4,5,5-tetramethyl-1,3,2-dioxaborolan-2-yl)-1H-indole | Tetrakis-(triphenylphosphin)-palladium (0) Toluol/Ethanol | 63% | | 1H NMR (DMSO-d6) δ: 10.65 (d, 1H), 7.59 (d, 1H), 7.24 (s, 1H), 7.16-7.09 (m, 3H), 7.02 (d, 1H), 6.48 (t, 1H), 2.48 (d, 3H), 2.30 (s, 3H), 1.61 (s, 3H), 1.53 (s, 3H) |
| 309 | Int-B-31 + Int-A-12 | Bis(tri-tert-butylphosphine palladium(0) THF | 60% | | 1H NMR (DMSO-d6) δ: 7.88 (dt, 1H), 7.58 (d, 1H), 7.49 (dd, 1H), 7.20-7.15 (m, 1H), 6.84 (s, 1H), 6.38 (s, 1H), 6.34 (d, 1H), 3.51 (s, 3H), 2.39 (s, 3H), 1.89 (s, 3H), 1.86 (s, 3H), 1.50 (s, 3H), 1.44 (s, 3H) |
| 310 | Int-B-32 + Int-A-12 | Bis(tri-tert-butylphosphine palladium(0) THF | 30% | | 1H NMR (DMSO-d6) δ: 7.89-7.84 (1H), 7.56-7.53 (1H), 7.44-7.39 (1H), 7.29-7.13 (2H), 7.01-6.98 (1H), 6.54-6.30 (1H), 3.64-3.60 (3H), 3.53-3.48 (3H), 2.49-2.36 (3H), 1.80-1.27 (6H) |
| 313 | Int-B-26 Int-A-42 | Tetrakis-(triphenylphosphin)-palladium (0) Toluol/Ethanol | 65% | | 1H NMR (DMSO-d6) δ: 7.64 (d, 1H), 7.41 (d, 1H), 7.28 (dd, 1H), 7.09-7.07 (m, 2H), 7.06 (d, 1H), 6.42 (tt, 1H), 6.29 (d, 1H), 4.93-4.61 (m, 2H), 2.45 (d, 3H), 1.58 (s, 3H), 1.50 (s, 3H) |
| 314 | Int-B-24 + Int-A-42 | Tetrakis-(triphenylphosphin)-palladium (0) Toluol/Ethanol | 47% | | 1H NMR (DMSO-d6) δ: 7.55 (d, 1H), 7.35 (d, 1H), 7.23 (dd, 1H), 7.04 (dd, 1H), 6.85 (d, 1H), 6.61 (d, 1H), 6.40 (tt, 1H), 6.24 (d, 1H), 4.71 (td, 2H), 3.68 (s, 3H), 2.44 (s, 3H), 1.57 (s, 3H), 1.49 (s, 3H) |
| 315 | Int-B-28 + Int-A-12 | Bis(tri-tert-butylphosphine palladium(0) THF | 69% | | 1H NMR (DMSO-d6) δ: 7.91 (dt, 1H), 7.59 (d, 1H), 7.45 (dd, 1H), 7.38-7.28 (m, 1H), 7.22 (s, 1H), 7.06 (d, 1H), 6.92 (d, 1H), 6.48 (s, 1H), 3.51 (s, 3H), 2.47 (s, 3H), 1.90-1.17 (m, 6H) |
| 317 | Int-B-33 + Int-A-12 | Bis(tri-tert-butylphosphine palladium(0) THF | 62% | | 1H NMR (DMSO-d6) δ: 7.90 (dd, 1H), 7.61 (d, 1H), 7.50 (dd, 1H), 7.28-7.22 (m, 1H), 7.08 (s, 1H), 6.76 (s, 1H), 6.43 (d, 1H), 3.53 (s, 3H), 2.41 (s, 3H), 1.91 (s, 3H), 1.53 (s, 3H), 1.46 (s, 3H) |
| 318 | Int-B-35 + Int-A-12 | Bis(tri-tert-butylphosphine palladium(0) THF | 85% | | 1H NMR (DMSO-d6) δ: 7.89 (dt, 1H), 7.61 (d, 1H), 7.48 (dd, 1H), 7.26-7.22 (m, 1H), 7.12-6.78 (m, 3H), 6.45 (d, 1H), 3.51 (s, 3H), 2.43 (s, 3H), 1.92 (s, 3H), 1.53 (s, 3H), 1.45 (s, 3H) |
| 319 | Int-B-28 + 1H-indol-4-ylboronic acid | Bis(tri-tert-butylphosphine palladium(0) THF | 39% | | 1H NMR (DMSO-d6) δ: 11.18 (s, 1H), 7.45 (d, 1H), 7.33 (t, 1H), 7.16 (t, 1H), 7.11 (s, 1H), 7.04 (d, 1H), 7.00 (d, 1H), 6.86 (t, 1H), 6.08 (s, 1H), 2.47 (s, 3H), 1.85-1.10 (m, 6H) |
| 320 | Int-B-28 + 3-methyl-7-(4,4,5,5-tetramethyl-1,3,2-dioxaborolan-2-yl)-1H-indole | Bis(tri-tert-butylphosphine palladium(0) THF | 12% | | 1H NMR (DMSO-d6) δ: 10.56-10.40 (m, 1H), 7.62-7.43 (m, 1H), 7.13 (s, 1H), 7.08-6.99 (m, 4H), 6.87 (t, 1H), 2.49 (s, 3H), 2.30 (d, 3H), 1.88-1.04 (m, 6H) |
| 321 | Int-B-34 + Int-A-12 | Bis(tri-tert-butylphosphine palladium(0) THF | 22% | | 1H NMR (DMSO-d6) δ: 7.91 (dt, 1H), 7.60 (d, 1H), 7.49 (dd, 1H), 7.28 (dd, 1H), 6.82 (s, 1H), 6.80 (d, 1H), 6.53 (d, 1H), 3.52 (s, 3H), 2.44 (d, 3H), 2.02 (s, 3H), 1.56 (s, 3H), 1.49 (s, 3H) |
| 324 | Int-B-31 + Int-A-42 | Tetrakis-(triphenylpho | 13% | | 1H NMR (DMSO-d6) δ: 7.56 (d, 1H), 7.36 (d, 1H), 7.27 (dd, 1H), 6.92 (dd, |

-continued

| Ex. # | Intermediates | Catalyst Solvent | Yield (%) | LC-MS ([M + H]+ | 1H NMR |
|---|---|---|---|---|---|
| | | sphin)-palladium (0) Toluol/Ethanol | | | 1H), 6.82 (s, 1H), 6.52-6.32 (m, 1H), 6.31 (s, 1H), 6.04 (d, 1H), 4.72 (td, 2H), 2.38 (s, 3H), 1.89 (s, 3H), 1.86 (s, 3H), 1.52-1.47 (m, 3H), 1.43 (s, 3H) |
| 325 | Int-B-29 + 1-methyl-4-(4,4,5,5-tetramethyl-[1,3,2]dioxaborolan-2-yl)-1H-indazole | Bis(tri-tert-butylphosphine palladium(0) THF | 64% | | 1H NMR (DMSO-d6) δ: 7.92 (d, 1H), 7.75 (dt, 1H), 7.52 (dd, 1H), 7.26-7.20 (m, 2H), 7.12 (d, 1H), 6.57 (t, 1H), 4.10 (s, 3H), 2.48 (d, 3H), 1.61 (s, 3H), 1.50 (s, 3H) |
| 327 | Int-B-33 + Int-A-42 | Tetrakis-(triphenylphosphin)-palladium (0) Toluol/Ethanol | 30% | | 1H NMR (DMSO-d6) δ: 7.59 (d, 1H), 7.38 (d, 1H), 7.28 (dd, 1H), 7.06 (s, 1H), 6.97 (d, 1H), 6.69 (s, 1H), 6.42 (tt, 1H), 6.12 (d, 1H), 4.72 (td, 2H), 2.40 (s, 3H), 1.90 (s, 3H), 1.53 (s, 3H), 1.44 (s, 3H) |
| 328 | Int-B-31 + Int-A-2 | Bis(tri-tert-butylphosphine palladium(0) THF | 80% | | 1H NMR (DMSO-d6) δ: 7.68-7.63 (m, 1H), 7.60 (d, 1H), 7.14 (dd, 1H), 6.84 (s, 1H), 6.43 (s, 1H), 6.32 (d, 1H), 3.56 (s, 3H), 2.40 (s, 3H), 1.91 (s, 3H), 1.88 (s, 3H), 1.49 (s, 3H), 1.45 (s, 3H) |
| 329 | Int-B-32 + Int-A-2 | Bis(tri-tert-butylphosphine palladium(0) THF | 55% | | 1H NMR (DMSO-d6) δ: 7.69-7.63 (1H), 7.60-7.53 (1H), 7.29-7.05 (2H), 7.04-6.96 (1H), 6.56-6.29 (1H), 3.68-3.62 (3H), 3.61-3.54 (3H), 2.48-2.35 (3H), 1.78-1.28 (6H) |
| 330 | Int-B-3 + Int-A-42 | Tetrakis-(triphenylphosphin)-palladium (0) Toluol/Ethanol | 54% | | 1H NMR (DMSO-d6) δ: 7.61 (d, 1H), 7.41 (d, 1H), 7.28 (dd, 1H), 7.04 (d, 1H), 6.79 (d, 1H), 6.71 (s, 1H), 6.41 (tt, 1H), 6.18 (d, 1H), 4.73 (tdd, 2H), 2.44 (s, 3H), 1.98 (s, 3H), 1.53 (s, 3H), 1.44 (s, 3H) |
| 331 | Int-B-31 + Int-A-43 | Bis(tri-tert-butylphosphine palladium(0) THF | 47% | | 1H NMR (DMSO-d6) δ: 7.49 (dt, 1H), 7.34 (d, 1H), 7.23 (dd, 1H), 6.87 (dd, 1H), 6.82 (s, 1H), 6.29 (s, 1H), 5.97 (d, 1H), 4.36 (t, 2H), 3.73 (t, 2H), 3.26 (s, 3H), 2.38 (s, 3H), 1.90 (s, 3H), 1.86 (s, 3H), 1.50 (s, 3H), 1.43 (s, 3H) |
| 332 | Int-B-34 + Int-A-2 | Bis(tri-tert-butylphosphine palladium(0) THF | 89% | | 1H NMR (DMSO-d6) δ: 7.69 (ddd, 1H), 7.62 (d, 1H), 7.25 (dd, 1H), 6.85 (d, 1H), 6.82 (s, 1H), 6.55 (d, 1H), 3.59 (s, 3H), 2.46 (d, 3H), 2.05 (s, 3H), 1.56 (s, 3H), 1.49 (s, 3H) |
| 333 | Int-B-33 + Int-A-2 | Bis(tri-tert-butylphosphine palladium(0) THF | 72% | | 1H NMR (DMSO-d6) δ: 7.69 (ddd, 1H), 7.63 (d, 1H), 7.22 (dd, 1H), 7.08 (s, 1H), 6.81 (s, 1H), 6.43 (d, 1H), 3.59 (s, 3H), 2.43 (s, 3H), 1.95 (s, 3H), 1.52 (s, 3H), 1.47 (s, 3H) |
| 334 | Int-B-32 + Int-A-43 | Bis(tri-tert-butylphosphine palladium(0) THF | 15% | | 1H NMR (DMSO-d6) δ: 7.55-7.45 (1H), 7.32-7.24 (1H), 7.18-7.11 (1H), 7.10-7.01 (1H), 6.98-6.85 (2H), 6.09-5.93 (1H), 4.38-4.31 (2H), 3.74-3.69 (2H), 3.62-3.57 (3H), 3.27-3.22 (3H), 2.48-2.34 (3H), 1.79-1.27 (6H) |
| 335 | Int-B-35 + Int-A-2 | Bis(tri-tert-butylphosphine palladium(0) THF | 72% | | 1H NMR (DMSO-d6) δ: 7.67 (ddd, 1H), 7.62 (d, 1H), 7.20 (dd, 1H), 7.01 (t, 1H), 6.85 (d, 2H), 6.44 (d, 1H), 3.57 (s, 3H), 2.44 (s, 3H), 1.95 (s, 3H), 1.52 (s, 3H), 1.46 (s, 3H) |
| 336 | Int-B-35 + Int-A-43 | Bis(tri-tert-butylphosphine palladium(0) THF | 65% | | 1H NMR (DMSO-d6) δ: 7.51 (dt, 1H), 7.36 (d, 1H), 7.22 (dd, 1H), 7.06-6.77 (m, 3H), 6.72 (s, 1H), 6.05 (d, 1H), 4.40-4.33 (m, 2H), 3.72 (t, 2H), 3.26 (s, 3H), 2.41 (s, 3H), 1.91 (s, 3H), 1.54 (s, 3H), 1.43 (s, 3H) |
| 337 | Int-B-34 + Int-A-43 | Bis(tri-tert-butylphosphine palladium(0) THF | 58% | | 1H NMR (DMSO-d6) δ: 7.53 (dd, 1H), 7.35 (d, 1H), 7.22 (dd, 1H), 6.96 (dd, 1H), 6.80 (s, 1H), 6.71 (d, 1H), 6.16-6.04 (m, 1H), 4.37 (q, |

-continued

| Ex. # | Intermediates | Catalyst Solvent | Yield (%) | LC-MS ([M + H]+ | 1H NMR |
|---|---|---|---|---|---|
| | | | | | 2H), 3.71 (t, 2H), 3.26 (d, 3H), 2.43 (d, 3H), 2.01 (s, 3H), 1.55 (s, 3H), 1.48 (s, 3H) |
| 338 | Int-B-33 + Int-A-43 | Bis(tri-tert-butylphosphine palladium(0) THF | 40% | | 1H NMR (DMSO-d6) δ: 7.53 (dt, 1H), 7.36 (d, 1H), 7.24 (dd, 1H), 7.05 (s, 1H), 6.93 (dd, 1H), 6.68 (s, 1H), 6.03 (d, 1H), 4.37 (td, 2H), 3.72 (t, 2H), 3.26 (s, 3H), 2.40 (s, 3H), 1.91 (s, 3H), 1.54 (s, 3H), 1.44 (s, 3H) |
| 339 | Int-B-25 + Int-A-23 | Bis(tri-tert-butylphosphine palladium(0) THF | 30% | | 1H NMR (DMSO-d6) δ: 8.45 (s, 1H), 7.76-7.72 (m, 1H), 7.46 (dd, 1H), 7.14 (s, 1H), 6.78 (d, 1H), 3.59 (d, 3H), 3.25 (d, 3H), 2.55 (d, 3H), 1.62 (s, 3H), 1.45 (s, 3H) |
| 341 | Int-B-31 + Int-A-15 | Bis(tri-tert-butylphosphine palladium(0) THF | 42% | | 1H NMR (DMSO-d6) δ: 10.46-10.42 (m, 1H), 7.23 (dd, 1H), 7.10 (dd, 1H), 6.84 (s, 1H), 6.76 (dd, 1H), 6.36 (s, 1H), 2.42 (s, 3H), 2.26 (d, 3H), 1.91 (s, 3H), 1.86 (s, 3H), 1.54 (d, 6H), 1.42 (s, 3H) |
| 342 | Int-B-25 + Int-A-22 | Bis(tri-tert-butylphosphine palladium(0) THF | 67% | | 1H NMR (DMSO-d6) δ: 8.43 (d, 1H), 8.03 (dd, 1H), 7.74 (dd, 1H), 7.49 (d, 1H), 7.07 (s, 1H), 6.78 (d, 1H), 3.55 (s, 3H), 3.20 (d, 3H), 2.55 (d, 3H), 1.62 (s, 3H), 1.45 (s, 3H) |
| 343 | Int-B-29 + 1H-indol-4-ylboronic acid | Tetrakis-(triphenylphosphin)-palladium (0) Toluol/Ethanol | 73% | | 1H NMR (DMSO-d6) δ: 11.33-11.29 (m, 1H), 7.52 (dt, 1H), 7.39 (t, 1H), 7.25-7.19 (m, 2H), 7.14 (d, 1H), 6.98 (d, 1H), 6.45 (t, 1H), 6.20 (tt, 1H), 2.47 (d, 3H), 1.59 (s, 3H), 1.51 (s, 3H) |
| 344 | Int-B-36 + Int-A-43 | Bis(tri-tert-butylphosphine palladium(0) THF | 36% | | 1H NMR (DMSO-d6) δ: 7.45 (d, 1H), 7.31 (d, 1H), 7.18 (t, 1H), 6.88 (d, 1H), 6.65 (s, 1H), 6.42 (s, 1H), 6.00 (d, 1H), 4.35 (dt, 2H), 3.71 (t, 2H), 3.59 (s, 3H), 3.26 (s, 3H), 2.39 (s, 3H), 1.86 (s, 3H), 1.52 (s, 3H), 1.43 (s, 3H) |
| 345 | Int-B-36 + Int-A-15 | Bis(tri-tert-butylphosphine palladium(0) THF | 33% | | 1H NMR (DMSO-d6) δ: 10.39 (s, 1H), 7.19 (dd, 1H), 7.08 (dd, 1H), 6.76 (dd, 1H), 6.66 (s, 1H), 6.48 (s, 1H), 3.61 (s, 3H), 2.44 (s, 3H), 2.25 (d, 3H), 1.87 (s, 3H), 1.54 (s, 3H), 1.44 (s, 3H) |
| 346 | Int-B-28 + Int-A-23 | Bis(tri-tert-butylphosphine palladium(0) THF | 24% | | 1H NMR (DMSO-d6) δ: 8.42 (s, 1H), 7.76 (dd, 1H), 7.45 (d, 1H), 7.35 (s, 1H), 7.21-7.00 (m, 2H), 3.60 (d, 3H), 2.51 (d, 3H), 1.83-1.24 (m, 6H) |
| 347 | Int-B-33 + Int-A-23 | Bis(tri-tert-butylphosphine palladium(0) THF | 31% | | 1H NMR (DMSO-d6) δ: 8.34 (s, 1H), 7.75 (ddd, 1H), 7.41 (dd, 1H), 7.10 (s, 1H), 6.89 (s, 1H), 3.60 (s, 3H), 2.45 (s, 3H), 1.98 (s, 3H), 1.53 (s, 3H), 1.48 (s, 3H) |
| 348 | Int-B-6 + Int-A-23 | Bis(tri-tert-butylphosphine palladium(0) THF | 36% | | 1H NMR (DMSO-d6) δ: 8.36 (s, 1H), 7.79-7.73 (m, 1H), 7.49 (s, 1H), 6.91 (s, 1H), 6.85 (d, 1H), 3.59 (s, 3H), 2.81 (s, 2H), 2.05 (s, 3H), 1.62-1.37 (m, 6H), 1.28 (t, 3H) |
| 351 | Int-B-25 + Int-A-24 | Bis(tri-tert-butylphosphine palladium(0) THF | 57% | | 1H NMR (DMSO-d6) δ: 7.43 (ddd, 1H), 7.36 (d, 1H), 6.97-6.89 (m, 2H), 6.71 (d, 1H), 6.18 (dt, 1H), 4.34 (q, 2H), 3.69 (t, 2H), 3.25 (d, 3H), 3.20 (d, 3H), 2.49 (d, 3H), 1.57 (s, 3H), 1.47 (s, 3H) |
| 353 | Int-B-24 + Int-A-24 | Bis(tri-tert-butylphosphine palladium(0) THF | 59% | | 1H NMR (DMSO-d6) δ: 7.37 (ddd, 1H), 7.33 (d, 1H), 6.90-6.88 (m, 1H), 6.87 (dd, 1H), 6.61 (d, 1H), 6.16 (d, 1H), 4.32 (t, 2H), 3.69 (t, 2H), 3.68 (t, 2H), 3.25 (d, 3H), 2.45 (d, 3H), 1.56 (s, 3H), 1.48 (s, 3H) |
| 354 | Int-B-1 + 3-Methyl-1H-indazole-7-boronic acid | Bis(tri-tert-butylphosphine palladium(0) THF | 20% | | 1H NMR (DMSO-d6) δ: 12.65 (s, 1H), 7.79 (dd, 1H), 7.37 (d, 1H), 7.24-7.15 (m, 2H), 6.82 (dd, 1H), 2.53 (s, 3H), 1.56 (s, 6H) |

| Ex. # | Intermediates | Catalyst Solvent | Yield (%) | LC-MS ([M + H]+) | 1H NMR |
|---|---|---|---|---|---|
| 356 | Int-B-31 + 3-methyl-7-(4,4,5,5-tetramethyl-1,3,2-dioxaborolan-2-yl)-1H-indole | Bis(tri-tert-butylphosphine palladium(0) THF | 42% | | 1H NMR (DMSO-$d_6$) δ: 10.31 (s, 1H), 7.52-7.44 (m, 1H), 7.09 (dd, 1H), 7.02 (dd, 1H), 6.87 (dd, 1H), 6.83 (s, 1H), 6.31 (s, 1H), 2.42 (s, 3H), 2.30 (d, 3H), 1.89 (s, 3H), 1.84 (s, 3H), 1.55 (s, 3H), 1.41 (s, 3H) |
| 357 | Int-B-32 + 3-methyl-7-(4,4,5,5-tetramethyl-1,3,2-dioxaborolan-2-yl)-1H-indole | Bis(tri-tert-butylphosphine palladium(0) THF | 26% | | 1H NMR (DMSO-$d_6$) δ: 10.41-10.27 (1H), 7.51-7.44 (1H), 7.09-7.03 (1H), 7.03-6.86 (4H), 3.63-3.50 (3H), 2.44-2.42 (3H), 2.36-2.23 (3H), 1.81-1.31 (6H) |
| 358 | Int-B-33 + 3-methyl-7-(4,4,5,5-tetramethyl-1,3,2-dioxaborolan-2-yl)-1H-indole | Bis(tri-tert-butylphosphine palladium(0) THF | 84% | | 1H NMR (DMSO-$d_6$) δ: 10.47 (s, 1H), 7.51 (d, 1H), 7.15-7.03 (m, 3H), 6.92 (dd, 1H), 6.74-6.65 (m, 1H), 2.43 (s, 3H), 2.30 (d, 3H), 1.88 (s, 3H), 1.57 (s, 3H), 1.44 (s, 3H) |
| 359 | Int-B-34 + 3-methyl-7-(4,4,5,5-tetramethyl-1,3,2-dioxaborolan-2-yl)-1H-indole | Bis(tri-tert-butylphosphine palladium(0) THF | 22% | | 1H NMR (DMSO-$d_6$) δ: 10.47 (d, 1H), 7.52 (dd, 1H), 7.17-7.01 (m, 2H), 6.99 (dd, 1H), 6.81 (s, 1H), 6.71 (s, 1H), 2.45 (d, 3H), 2.30 (d, 3H), 2.00 (s, 3H), 1.57 (s, 3H), 1.50 (s, 3H) |
| 360 | Int-B-35 + 3-methyl-7-(4,4,5,5-tetramethyl-1,3,2-dioxaborolan-2-yl)-1H-indole | Bis(tri-tert-butylphosphine palladium(0) THF | 34% | | 1H NMR (DMSO-$d_6$) δ: 10.42 (s, 1H), 7.50 (d, 1H), 7.10-7.04 (m, 2H), 6.94 (dd, 1H), 6.90 (t, 1H), 6.85 (s, 1H), 6.72 (s, 1H), 2.45 (s, 3H), 2.30 (t, 3H), 1.88 (s, 3H), 1.57 (s, 3H), 1.44 (s, 3H) |
| 361 | Int-B-3 + 3-Methyl-1H-indazole-7-boronic acid | Tetrakis-(triphenylphosphin)-palladium (0) Toluol/Ethanol | 22% | | 1H NMR (DMSO-$d_6$) δ: 12.57 (s, 1H), 7.79-7.72 (m, 1H), 7.25 (d, 1H), 7.21-7.16 (m, 1H), 6.81 (d, 1H), 6.76 (s, 1H), 2.53 (s, 3H), 2.49 (s, 3H), 1.96 (s, 3H), 1.56 (s, 3H), 1.45 (s, 3H) |
| 362 | Int-B-25 + Int-A-8 | Bis(tri-tert-butylphosphine palladium(0) THF | 53% | | 1H NMR (DMSO-$d_6$) δ: 7.68 (ddd, 1H), 7.64 (d, 1H), 7.29 (dd, 1H), 7.03 (s, 1H), 6.75 (d, 1H), 6.62-6.57 (m, 1H), 3.73 (qd, 2H), 3.23 (s, 3H), 2.51 (s, 3H), 1.58 (s, 3H), 1.47 (s, 3H), 1.12 (t, 3H). |
| 363 | Int-B-33 + Int-A-15 | Bis(tri-tert-butylphosphine palladium(0) THF | 92% | | 1H NMR (DMSO-$d_6$) δ: 10.60 (d, 1H), 7.28 (dd, 1H), 7.14 (dd, 1H), 7.07 (s, 1H), 6.83 (dd, 1H), 6.73 (s, 1H), 2.44 (s, 3H), 2.26 (d, 3H), 1.91 (s, 3H), 1.50 (d, 6H) |
| 364 | Int-B-34 + Int-A-15 | Bis(tri-tert-butylphosphine palladium(0) THF | 78% | | 1H NMR (DMSO-$d_6$) δ: 10.62-10.58 (m, 1H), 7.28 (dd, 1H), 7.14 (dd, 1H), 6.89 (dd, 1H), 6.81 (s, 1H), 6.76 (d, 1H), 2.46 (d, 3H), 2.26 (d, 3H), 2.02 (s, 3H), 1.56 (s, 3H), 1.51 (s, 3H) |
| 365 | Int-B-35 + Int-A-15 | Bis(tri-tert-butylphosphine palladium(0) THF | 39% | | 1H NMR (DMSO-$d_6$) δ: 10.54 (d, 1H), 7.26 (dd, 1H), 7.13 (dd, 1H), 6.93 (s, 1H), 6.84 (d, 2H), 6.77 (s, 1H), 2.45 (d, 3H), 2.26 (d, 3H), 1.91 (s, 3H), 1.56 (s, 3H), 1.45 (s, 3H) |
| 367 | Int-B-28 + 3-Methyl-1H-indazole-7-boronic acid | Bis(tri-tert-butylphosphine palladium(0) THF | 27% | | 1H NMR (DMSO-$d_6$) δ: 12.51 (s, 1H), 7.74 (d, 1H), 7.31-7.24 (m, 1H), 7.18 (s, 1H), 7.14 (dd, 1H), 7.07-6.84 (m, 2H), 2.52 (s, 3H), 2.50 (s, 3H), 1.91-1.15 (m, 6H) |
| 368 | Int-B-33 + 3-Methyl-1H-indazole-7-boronic acid | Bis(tri-tert-butylphosphine palladium(0) THF | 28% | | 1H NMR (DMSO-$d_6$) δ: 12.53 (s, 1H), 7.76-7.72 (m, 1H), 7.21-7.16 (m, 2H), 7.08 (s, 1H), 6.74 (s, 1H), 2.53 (s, 3H), 2.45 (s, 3H), 1.89 (s, 3H), 1.56 (s, 3H), 1.45 (s, 3H) |

-continued

| Ex. # | Intermediates | Catalyst Solvent | Yield (%) | LC-MS ([M + H]+) | 1H NMR |
|---|---|---|---|---|---|
| 369 | Int-B-32 + Int-A-8 | Bis(tri-tert-butylphosphine palladium(0) THF | 29% | | 1H NMR (DMSO-d6) δ: 7.68-7.62 (1H), 7.59-7.55 (1H), 7.31-7.08 (2H), 7.03-6.96 (1H), 6.58-6.30 (1H), 3.76-3.70 (2H), 3.66-3.63 (3H), 2.47-2.36 (3H), 1.78-1.28 (6H), 1.12-1.03 (3H) |
| 370 | Int-B-3 + Int-A-8 | Bis(tri-tert-butylphosphine palladium(0) THF | 74% | | 1H NMR (DMSO-d6) δ: 7.71-7.61 (m, 2H), 7.34-7.22 (m, 1H), 6.88-6.78 (m, 2H), 6.49 (d, 1H), 3.73 (q, 2H), 2.45 (s, 3H), 2.01 (s, 3H), 1.50 (s, 3H), 1.47 (s, 3H), 1.12 (t, 3H) |
| 371 | Int-B-32 + Int-A-47 | Bis(tri-tert-butylphosphine palladium(0) THF | 16% | | 1H NMR (DMSO-d6) δ: 7.91-7.78 (1H), 7.56-7.53 (1H), 7.43-7.38 (1H), 7.30-7.13 (2H), 7.01-6.98 (1H), 6.57-6.28 (1H), 3.70-3.63 (2H), 3.64-3.60 (3H), 2.47-2.36 (3H), 1.77-1.28(6H), 1.10-1.00 (3H) |
| 372 | Int-B-3 + Int-A-47 | Bis(tri-tert-butylphosphine palladium(0) THF | 42% | | 1H NMR (DMSO-d6) δ: 7.91 (d, 1H), 7.64 (d, 1H), 7.49 (dd, 1H), 7.31 (d, 1H), 6.86-6.76 (m, 2H), 6.49 (d, 1H), 3.72-3.64 (m, 2H), 2.45 (s, 3H), 1.98 (s, 3H), 1.52 (s, 3H), 1.46 (s, 3H), 1.10 (t, 3H) |
| 373 | Int-B-31 + Int-A-23 | Bis(tri-tert-butylphosphine palladium(0) THF | 66% | | 1H NMR (DMSO-d6) δ: 8.24 (s, 1H), 7.74-7.69 (m, 1H), 7.34-7.28 (m, 1H), 6.86 (s, 1H), 6.50 (s, 1H), 3.59 (s, 3H), 2.43 (s, 3H), 1.93 (s, 3H), 1.91 (s, 3H), 1.53 (s, 3H), 1.43 (s, 3H) |
| 376 | Int-B-32 + Int-A-23 | Bis(tri-tert-butylphosphine palladium(0) THF | 11% | | 1H NMR (DMSO-d6) δ: 8.52-8.22 (1H), 7.77-7.70 (1H), 7.47-7.26 (2H), 7.07-7.00 (1H), 3.69-3.65 (3H), 3.62-3.56 (3H), 2.49-2.42 (3H), 1.77-1.30 (6H) |
| 377 | Int-B-3 + Int-A-22 | Bis(tri-tert-butylphosphine palladium(0) THF | 54% | | 1H NMR (DMSO-d6) δ: 8.39 (s, 1H), 8.04 (d, 1H), 7.75 (t, 1H), 7.46 (d, 1H), 6.92-6.78 (m, 2H), 3.60-3.50 (m, 3H), 2.48 (s, 3H), 2.02 (s, 3H), 1.53 (s, 3H), 1.48 (s, 3H) |
| 379 | Int-B-24 + Int-A-20 | Bis(tri-tert-butylphosphine palladium(0) THF | 35% | | 1H NMR (DMSO-d6) δ: 7.36 (dd, 1H), 7.35-7.33 (m, 1H), 6.89 (d, 1H), 6.87 (dd, 1H), 6.61 (s, 1H), 6.16 (d, 1H), 4.21 (t, 2H), 3.75 (q, 2H), 3.70 (s, 3H), 2.45 (d, 3H), 1.57 (s, 3H), 1.48 (s, 3H) |
| 380 | Int-B-25 + Int-A-20 | Bis(tri-tert-butylphosphine palladium(0) THF | 62% | | 1H NMR (DMSO-d6) δ: 7.41 (dd, 1H), 7.37 (d, 1H), 6.96-6.91 (m, 2H), 6.71 (d, 1H), 6.18 (d, 1H), 4.98-4.92 (m, 1H), 4.22 (q, 2H), 3.76 (q, 2H), 3.21 (s, 3H), 2.49 (s, 3H), 1.57 (s, 3H), 1.47 (s, 3H) |
| 381 | Int-B-25 + 3-Methyl-1H-indazole-7-boronic acid | Bis(tri-tert-butylphosphine palladium(0) THF | 37% | | 1H NMR (DMSO-d6) δ: 12.53 (s, 1H), 7.75 (d, 1H), 7.30 (d, 1H), 7.17 (t, 1H), 6.93 (s, 1H), 6.73 (d, 1H), 3.19 (s, 3H), 2.53 (s, 3H), 2.51 (d, 3H), 1.57 (s, 3H), 1.49 (s, 3H) |
| 382 | Int-B-28 + Int-A-22 | Bis(tri-tert-butylphosphine palladium(0) THF | 27% | | 1H NMR (DMSO-d6) δ: 8.39 (s, 1H), 8.05 (d, 1H), 7.72 (dd, 1H), 7.48-7.42 (m, 1H), 7.30 (s, 1H), 7.15-6.91 (m, 2H), 3.55 (s, 3H), 2.50 (d, 3H), 1.81-1.21 (m, 6H) |
| 383 | Int-B-1 + Int-A-46 | Bis(tri-tert-butylphosphine palladium(0) THF | 9% | | 1H NMR (DMSO-d6) δ: 7.70-7.54 (1H), 7.51-7.41 (1H), 7.31-7.20 (1H), 7.15-6.77 (3H), 6.36-6.23 (1H), 4.84-4.25 (2H), 3.77-3.16 (2H), 2.50-2.48 (3H), 2.27-2.18 (6H), 1.63-1.55 (3H), 1.53-1.47 (3H) |
| 384 | Int-B-35 + Int-A-42 | Tetrakis-(triphenylphosphin)-palladium (0) Toluol/Ethanol | 11% | | 1H NMR (DMSO-d6) δ: 7.58 (d, 1H), 7.38 (d, 1H), 7.26 (dd, 1H), 7.07-6.71 (m, 4H), 6.42 (tt, 1H), 6.14 (d, 1H), 4.72 (td, 2H), 2.41 (s, 3H), 1.91 (s, 3H), 1.54 (s, 3H), 1.43 (s, 3H) |
| 385 | Int-B-29 + Int-A-20 | Bis(tri-tert-butylphosphine | 22% | | 1H NMR (DMSO-d6) δ: 7.49 (dd, 1H), 7.41 (d, 1H), 7.21 (d, 2H), 6.92 |

-continued

| Ex. # | Intermediates | Catalyst Solvent | Yield (%) | LC-MS ([M + H]+) | 1H NMR |
|---|---|---|---|---|---|
| | | palladium(0) THF | | | (dd, 1H), 6.54 (t, 1H), 6.20 (d, 1H), 4.94 (td, 1H), 4.23 (q, 2H), 3.76 (q, 2H), 2.47 (d, 3H), 1.59 (s, 3H), 1.50 (s, 3H) |
| 386 | Int-B-33 + Int-A-22 | Bis(tri-tert-butylphosphine palladium(0) THF | 50% | | 1H NMR (DMSO-d6) δ: 8.34 (s, 1H), 8.04 (d, 1H), 7.78-7.71 (m, 1H), 7.38 (d, 1H), 7.11 (s, 1H), 6.84 (s, 1H), 3.56 (s, 3H), 2.45 (s, 3H), 1.94 (s, 3H), 1.54 (s, 3H), 1.47 (s, 3H) |
| 387 | Int-B-32 + Int-A-22 | Bis(tri-tert-butylphosphine palladium(0) THF | 21% | | 1H NMR (DMSO-d6) δ: 8.48-8.20 (1H), 8.05-7.98 (1H), 7.70-7.65 (1H), 7.45-7.20 (2H), 7.04-6.99 (1H), 3.67-3.63 (3H), 3.57-3.53 (3H), 2.48-2.41 (3H), 1.80-1.29 (6H) |
| 388 | Int-B-31 + Int-A-22 | Bis(tri-tert-butylphosphine palladium(0) THF | 43% | | 1H NMR (DMSO-d6) δ: 8.23 (s, 1H), 8.05-7.91 (m, 1H), 7.74 (ddd, 1H), 7.33-7.28 (m, 1H), 6.86 (s, 1H), 6.46 (d, 1H), 3.55 (d, 3H), 2.42 (d, 3H), 1.90 (s, 3H), 1.87 (s, 3H), 1.54 (s, 3H), 1.42 (s, 3H) |
| 390 | Int-B-28 + Int-A-2 | Bis(tri-tert-butylphosphine palladium(0) THF | 33% | | 1H NMR (DMSO-d6) δ: 7.69 (dd, 1H), 7.62 (d, 1H), 7.60 (d, 1H), 7.27 (d, 1H), 7.18 (d, 1H), 7.03 (t, 1H), 6.48 (s, 1H), 3.57 (s, 3H), 2.47 (s, 3H), 1.97-1.05 (m, 6H) |
| 392 | Int-B-34 + Int-A-42 | Tetrakis-(triphenylphosphine)-palladium (0) Toluol/Ethanol | 51% | | 1H NMR (DMSO-d6) δ: 7.60 (d, 1H), 7.38 (d, 1H), 7.27 (ddd, 1H), 7.01 (dd, 1H), 6.80 (s, 1H), 6.72 (d, 1H), 6.41 (tt, 1H), 6.22-6.18 (m, 1H), 4.73 (tt, 2H), 2.43 (d, 3H), 2.01 (s, 3H), 1.55 (s, 3H), 1.48 (s, 3H) |
| 393 | Int-B-27 + Int-A-42 | Tetrakis-(triphenylphosphin) (0) Toluol/Ethanol | 55% | | 1H NMR (DMSO-d6) δ: 7.61 (d, 1H), 7.40 (d, 1H), 7.29-6.96 (m, 4H), 6.82 (s, 1H), 6.54-6.28 (m, 2H), 4.73 (tt, 2H), 2.47 (d, 3H), 1.58 (s, 3H), 1.50 (s, 3H) |
| 394 | Int-B-27 + Int-A-24 | Bis(tri-tert-butylphosphine palladium(0) THF | 48% | | 1H NMR (DMSO-d6) δ: 7.48-7.42 (m, 1H), 7.38 (d, 1H), 7.26-6.99 (m, 2H), 6.94 (dd, 1H), 6.81 (s, 1H), 6.27-6.22 (m, 1H), 4.34 (td, 2H), 3.69 (t, 2H), 3.26 (d, 3H), 2.48 (d, 3H), 1.58 (s, 3H), 1.50 (s, 3H) |
| 395 | Int-B-27 + Int-A-20 | Bis(tri-tert-butylphosphine palladium(0) THF | 37% | | 1H NMR (DMSO-d6) δ: 7.43 (dd, 1H), 7.39 (d, 1H), 7.25-6.99 (m, 2H), 6.93 (dd, 1H), 6.81 (s, 1H), 6.24 (d, 1H), 4.92 (t, 1H), 4.22 (q, 2H), 3.75 (q, 2H), 2.47 (d, 3H), 1.58 (s, 3H), 1.49 (s, 3H) |
| 396 | Int-B-29 + Int-A-24 | Bis(tri-tert-butylphosphine palladium(0) THF | 28% | | 1H NMR (DMSO-d6) δ: 7.51 (dd, 1H), 7.40 (d, 1H), 7.22 (s, 1H), 7.19 (d, 1H), 6.93 (dd, 1H), 6.55 (t, 1H), 6.21 (d, 1H), 4.36 (q, 2H), 3.70 (t, 2H), 3.27 (s, 3H), 2.47 (d, 3H), 1.59 (s, 3H), 1.50 (s, 3H) |
| 397 | Int-B-25 + Int-A-42 | Bis(tri-tert-butylphosphine palladium(0) THF | 28% | | 1H NMR (DMSO-d6) δ: 7.61 (d, 1H), 7.39 (d, 1H), 7.27 (dd, 1H), 7.10 (d, 1H), 6.87 (s, 1H), 6.71 (d, 1H), 6.42 (tt, 1H), 6.27 (d, 1H), 4.73 (tdd, 2H), 3.16 (s, 3H), 2.49 (s, 3H), 1.57 (s, 3H), 1.47 (s, 3H) |
| 398 | Int-B-28 + Int-A-42 | Bis(tri-tert-butylphosphine palladium(0) THF | 55% | | 1H NMR (DMSO-d6) δ: 7.61 (d, 1H), 7.37 (d, 1H), 7.25 (dd, 1H), 7.14 (s, 1H), 7.06 (dd, 2H), 6.89 (t, 1H), 6.42 (tt, 1H), 6.16 (s, 1H), 4.72 (tdd, 2H), 2.47 (s, 3H), 1.83-1.14 (m, 6H) |
| 399 | Int-B-3 + 1H-indol-4-ylboronic acid | Tetrakis-(triphenylphosphin)-palladium (0) Toluol/Ethanol | 34% | | 1H NMR (DMSO-d6) δ: 11.21 (s, 1H), 7.45 (d, 1H), 7.37 (t, 1H), 7.19 (t, 1H), 6.96 (d, 1H), 6.78 (d, 1H), 6.69 (s, 1H), 6.09 (t, 1H), 2.44 (s, 3H), 1.98 (s, 3H), 1.54 (s, 3H), 1.44 (s, 3H) |
| 400 | Int-B-28 + Int-A-30 | Bis(tri-tert-butylphosphine palladium(0) THF | 42% | | 1H NMR (DMSO-d6) δ: 7.91 (d, 1H), 7.58 (dd, 1H), 7.47-7.41 (m, 1H), 7.31 (d, 1H), 7.21 (s, 1H), 7.10-6.84 (m, 2H), 6.48 (s, 1H), 3.85 (pd, |

| Ex. # | Intermediates | Catalyst Solvent | Yield (%) | LC-MS ([M + H]+) | 1H NMR |
|---|---|---|---|---|---|
| | | | | | 1H), 2.47 (s, 3H), 1.94-1.24 (m, 6H), 1.20 (dt, 6H) |
| 401 | Int-B-28 + Int-A-48 | Bis(tri-tert-butylphosphine palladium(0) THF | 40% | | 1H NMR (DMSO-d6) δ: 7.95 (d, 1H), 7.60 (dd, 1H), 7.47-7.41 (m, 1H), 7.31 (d, 1H), 7.22 (s, 1H), 7.11-6.83 (m, 2H), 6.47 (s, 1H), 3.17 (ddd, 1H), 2.48 (s, 3H), 1.90-1.33 (m, 6H), 1.29 (tt, 2H), 1.17-1.07 (m, 2H) |
| 402 | Int-B-28 + Int-A-24 | Bis(tri-tert-butylphosphine palladium(0) THF | 23% | | 1H NMR (DMSO-d6) δ: 7.44 (dd, 1H), 7.35 (d, 1H), 7.18 (s, 1H), 7.04 (d, 1H), 6.98-6.85 (m, 2H), 6.08 (s, 1H), 4.43-4.22 (m, 2H), 3.70 (t, 2H), 3.26 (s, 3H), 2.47 (s, 3H), 1.88-1.14 (m, 6H) |
| 403 | Int-B-37 + Int-A-2 | Bis(tri-tert-butylphosphine palladium(0) THF | 40% | | 1H NMR (DMSO-d6) δ: 7.70 (dd, 1H), 7.64 (d, 1H), 7.21 (d, 1H), 7.02 (s, 1H), 6.95 (s, 1H), 6.46 (d, 1H), 3.58 (d, 3H), 2.45 (d, 3H), 1.97 (d, 3H), 1.54 (s, 3H), 1.46 (s, 3H) |
| 404 | Int-B-26 + Int-A-24 | Bis(tri-tert-butylphosphine palladium(0) THF | 13% | | 1H NMR (DMSO-d6) δ: 7.50-7.44 (m, 1H), 7.38 (d, 1H), 7.12 (d, 1H), 7.05 (s, 1H), 6.95 (dd, 1H), 6.22 (s, 1H), 4.35 (t, 2H), 3.70 (t, 2H), 3.26 (d, 3H), 2.46 (d, 3H), 1.58 (s, 3H), 1.50 (s, 3H) |
| 405 | Int-B-37 + 3-methyl-7-(4,4,5,5-tetramethyl-1,3,2-dioxaborolan-2-yl)-1H-indole | Bis(tri-tert-butylphosphine palladium(0) THF | 31% | | 1H NMR (DMSO-d6) δ: 10.48 (d, 1H), 7.52 (d, 1H), 7.12-7.04 (m, 2H), 7.01 (d, 1H), 6.92 (d, 1H), 6.81 (s, 1H), 2.47 (s, 3H), 2.30 (d, 3H), 1.89 (s, 3H), 1.59 (s, 3H), 1.42 (s, 3H) |
| 406 | Int-B-37 + Int-A-15 | Tetrakis-(triphenylphosphin)-palladium (0) Toluol/Ethanol | 59% | | 1H NMR (DMSO-d6) δ: 10.60 (d, 1H), 7.29 (dd, 1H), 7.17-7.13 (m, 1H), 7.01 (d, 1H), 6.87 (s, 1H), 6.82 (dd, 1H), 2.48 (s, 3H), 2.26 (s, 3H), 1.92 (s, 3H), 1.58 (s, 3H), 1.43 (s, 3H) |
| 407 | Int-B-32 + Int-A-15 | Bis(tri-tert-butylphosphine palladium(0) THF | 19% | | 1H NMR (DMSO-d6) δ: 10.54-10.43 (1H), 7.26-7.20 (1H), 7.16-7.06 (2H), 7.02-6.95 (1H), 6.92-6.72 (1H), 3.66-3.59 (3H), 2.45-2.41 (3H), 2.30-2.21 (3H), 1.78-1.29 (6H) |
| 445 | Int-B-1 + indole-4-boronic acid | Bis(tri-tert-butylphosphine palladium(0) THF | 50% | | 1H NMR (DMSO-d6) δ: 11.23 (s, 1H), 7.48 (d, 1H), 7.39 (t, 1H), 7.19 (t, 1H), 7.10 (d, 1H), 7.06 (d, 1H), 6.80 (dd, 1H), 6.27 (s, 1H), 2.50 (d, 3H), 1.58 (s, 3H), 1.49 (d, 3H) |
| 458 | Int-B-37 + Int-A-15 | Tetrakis-(triphenylphosphin)-palladium (0) Toluol/Ethanol | 19% | | 1H NMR (DMSO-d6) δ: 10.60 (s, 1H), 7.31-7.26 (m, 1H), 7.17-7.13 (m, 1H), 7.01 (d, 1H), 6.87 (s, 1H), 6.84-6.79 (m, 1H), 2.48 (s, 3H), 2.26 (s, 3H), 1.92 (s, 3H), 1.58 (s, 3H), 1.43 (s, 3H). |
| 459 | Int-B-32 + Int-A-15 | Bis(tri-tert-butylphosphine palladium(0) THF | 19% | | 1H NMR (DMSO-d6) δ: 10.55-10.41 (1H), 7.26-7.20 (1H), 7.15-7.06 (2H), 7.00-6.95 (1H), 6.92-6.71 (1H), 3.65-3.58 (3H), 2.46-2.33 (3H), 2.28-2.22 (3H), 1.79-1.29 (6H) |
| 460 | Int-B-37 + Int-A-43 | Bis(tri-tert-butylphosphine palladium(0) THF | 42% | | 1H NMR (DMSO-d6) δ: 7.54 (d, 1H), 7.38 (d, 1H), 7.27-7.20 (m, 1H), 7.00 (d, 1H), 6.93 (d, 1H), 6.82 (s, 1H), 6.05 (d, 1H), 4.37 (t, 2H), 3.73 (t, 2H), 3.25 (s, 3H), 2.43 (s, 3H), 1.93 (s, 3H), 1.56 (s, 3H), 1.43 (s, 3H) |
| 461 | Int-B-28 + Int-A-47 | Bis(tri-tert-butylphosphine palladium(0) THF | 77% | | 1H NMR (DMSO-d6) δ: 7.91 (d, 1H), 7.59 (d, 1H), 7.45 (t, 1H), 7.32 (d, 1H), 7.22 (s, 1H), 7.11-6.81 (m, 2H), 6.48 (s, 1H), 3.67 (q, 2H), 2.47 (s, 3H), 1.90-1.17 (m, 6H), 1.07 (t, 3H) |

-continued

| Ex. # | Intermediates | Catalyst Solvent | Yield (%) | LC-MS ([M + H]+) | 1H NMR |
|---|---|---|---|---|---|
| 462 | Int-B-44 + Int-A-12 | Bis(tri-tert-butylphosphine palladium(0) THF | 39% | | 1H NMR (DMSO-$d_6$) δ: 7.93-7.87 (1H), 7.67-7.56 (1H), 7.52-7.24 (2H), 6.86-6.79 (2H), 6.68-6.40 (1H), 3.53-3.48 (3H), 2.61-2.54 (3H), 1.81-1.09 (6H), 0.71--0.42 (5H) |
| 463 | Int-B-44 + 3-methyl-7-(4,4,5,5-tetramethyl-1,3,2-dioxaborolan-2-yl)-1H-indole | Bis(tri-tert-butylphosphine palladium(0) THF | 54% | | 1H NMR (DMSO-$d_6$) δ: 10.66-10.37 (1H), 7.53-7.48 (1H), 7.17-6.96 (3H), 6.85-6.75 (1H), 6.74-6.71 (1H), 2.64-2.53 (3H), 2.33-2.27 (3H), 1.76-1.16 (6H), 0.62--0.24 (5H) |
| 464 | Int-B-4 + Int-A-1 | Bis(tri-tert-butylphosphine palladium(0) THF | 77% | | 1H NMR (DMSO-$d_6$) δ: 11.32-11.23 (1H), 7.46-7.38 (1H), 7.39-7.32 (1H), 7.32-7.11 (2H), 7.06-6.85 (1H), 6.24-6.03 (1H), 2.50-2.40 (3H), 1.86-1.24 (6H) |
| 465 | Int-B-37 + Int-A-12 | Tetrakis-(triphenylphosphin)-palladium (0) Toluol/Ethanol | 18% | | 1H NMR (DMSO-$d_6$) δ: 7.92 (d, 1H), 7.62 (d, 1H), 7.49 (t, 1H), 7.24 (d, 1H), 7.02 (s, 1H), 6.90 (s, 1H), 6.46 (d, 1H), 3.53 (d, 3H), 2.45 (s, 3H), 1.94 (s, 3H), 1.56 (s, 3H), 1.44 (s, 3H) |
| 466 | Int-B-28 + Int-A-1 | Bis(tri-tert-butylphosphine palladium(0) THF | 41% | | 1H NMR (DMSO-$d_6$) δ: 11.24 (s, 1H), 7.33 (m, 1H), 7.24 (d, 1H), 7.18-7.13 (m, 1H), 7.08-6.82 (m, 3H), 6.08 (s, 1H), 2.47 (s, 3H), 1.90-1.27 (m, 6H) |
| 467 | Int-B-4 + indole-4-boronic acid | Bis(tri-tert-butylphosphine palladium(0) THF | 54% | | 1H NMR (DMSO-$d_6$) δ: 11.29-11.13 (1H), 7.51-7.44 (1H), 7.39-7.32 (2H), 7.21-7.10 (2H), 7.08-6.94 (1H), 6.18-6.06 (1H), 2.49-2.39 (3H), 1.80-1.29 (6H) |
| 468 | Int-B-25 + Int-A-1 | Bis(tri-tert-butylphosphine palladium(0) THF | 86% | | 1H NMR (DMSO-$d_6$) δ: 11.23 (s, 1H), 7.35 (t, 1H), 7.24 (dd, 1H), 7.01-6.86 (m, 2H), 6.71 (d, 1H), 6.19 (t, 1H), 3.19 (s, 3H), 2.50 (s, 3H), 1.56 (s, 3H), 1.48 (s, 3H) |
| 469 | Int-B-37 + Int-A-56 | Bis(tri-tert-butylphosphine palladium(0) THF | 36% | | 1H NMR (DMSO-$d_6$) δ: 7.90 (s, 1H), 7.72 (d, 1H), 7.16-7.05 (m, 1H), 7.03 (s, 1H), 6.96 (d, 1H), 6.67-6.32 (m, 1H), 4.96 (tt, 2H), 2.47 (d, 3H), 1.98 (d, 3H), 1.55 (s, 3H), 1.46 (s, 3H). |
| 470 | Int-B-3 + 4-(tetramethyl-1,3,2-dioxaborolan-2-yl)-6-(trifluoromethyl)-1H-indole | Bis(tri-tert-butylphosphine palladium(0) THF | 77% | | 1H NMR (DMSO-$d_6$) δ: 11.64 (s, 1H), 7.78 (d, 1H), 7.64 (t, 1H), 7.36 (d, 1H), 7.28 (d, 1H), 6.67 (d, 1H), 6.47 (t, 1H), 3.15 (s, 3H), 2.57 (s, 3H), 1.57 (s, 6H) |
| 471 | Int-B-37 + Int-A-20 | Bis(tri-tert-butylphosphine palladium(0) THF | 33% | | 1H NMR (DMSO-$d_6$) δ: 7.42 (dd, 1H), 7.39 (d, 1H), 7.00 (s, 1H), 6.87 (s, 1H), 6.83 (dd, 1H), 6.05 (d, 1H), 4.92 (t, 1H), 4.23 (td, 2H), 3.77 (q, 2H), 2.43 (s, 3H), 1.96 (s, 3H), 1.55 (s, 3H), 1.44 (s, 3H) |
| 472 | Int-B-28 + Int-A-56 | Bis(tri-tert-butylphosphine palladium(0) THF | 46% | | 1H NMR (DMSO-$d_6$) δ: 7.91 (s, 1H), 7.80-7.62 (m, 1H), 7.28 (s, 1H), 7.20-6.96 (m, 3H), 6.48 (tt, 1H), 5.09-4.73 (m, 2H), 2.49 (s, 3H), 1.95-1.19 (m, 6H) |
| 473 | Int-B-4 + 4-(tetramethyl-1,3,2-dioxaborolan-(trifluoromethyl)-1H-indole | Bis(tri-tert-butylphosphine palladium(0) THF | 66% | | 1H NMR (DMSO-$d_6$) δ: 7.87-7.81 (1H), 7.65-7.59 (1H), 7.48-7.25 (2H), 7.21-7.12 (1H), 6.39-6.19 (1H), 2.50-2.41 (3H), 1.78-1.31 (6H) |
| 474 | Int-B-25 + 4-(tetramethyl-1,3,2-dioxaborolan-2-yl)-6-(trifluoromethyl)-1H-indole | Bis(tri-tert-butylphosphine palladium(0) THF | 82% | | 1H NMR (DMSO-$d_6$) δ: 11.63 (s, 1H), 7.80 (s, 1H), 7.62 (t, 1H), 7.31 (d, 1H), 6.94 (s, 1H), 6.73 (d, 1H), 6.33 (t, 1H), 3.19 (s, 3H), 2.50 (s, 3H), 1.58 (s, 3H), 1.47 (s, 3H) |

| Ex. # | Intermediates | Catalyst Solvent | Yield (%) | LC-MS ([M + H]+) | 1H NMR |
|---|---|---|---|---|---|
| 475 | Int-B-33 + 4-(tetramethyl-1,3,2-dioxaborolan-2-yl)-6-(trifluoromethyl)-1H-indole | Bis(tri-tert-butylphosphine palladium(0) THF | 2% | | 1H NMR (DMSO-$d_6$) δ: 7.82-7.78 (m, 1H), 7.62 (t, 1H), 7.21 (d, 1H), 7.08 (s, 1H), 6.74 (s, 1H), 6.20-6.16 (m, 1H), 2.42 (s, 3H), 1.92 (s, 3H), 1.54 (s, 3H), 1.46 (s, 3H) |
| 476 | Int-B-4 + Int-A-54 | Bis(tri-tert-butylphosphine palladium(0) THF | 58% | | 1H NMR (DMSO-$d_6$) δ: 7.78-7.74 (1H), 7.53-7.50 (1H), 7.47-7.41 (1H), 7.24-7.13 (2H), 6.61-6.41 (1H), 3.53-3.49 (3H), 2.53-2.42 (6H), 1.79-1.30 (6H) |
| 477 | Int-B-25 + Int-A-54 | Bis(tri-tert-butylphosphine palladium(0) THF | 55% | | 1H NMR (DMSO-$d_6$) δ: 7.72 (t, 1H), 7.51 (d, 1H), 7.18 (d, 1H), 6.94 (s, 1H), 6.72 (d, 1H), 6.52 (dd, 1H), 3.49 (s, 3H), 3.21 (s, 3H), 2.52 (s, 3H), 2.50 (s, 3H), 1.59 (s, 3H), 1.46 (s, 3H) |
| 478 | Int-B-28 + Int-A-54 | Bis(tri-tert-butylphosphine palladium(0) THF | 34% | | 1H NMR (DMSO-$d_6$) δ: 7.72 (dd, 1H), 7.49 (d, 1H), 7.19 (s, 1H), 7.16 (s, 1H), 7.07-6.82 (m, 2H), 6.41 (s, 1H), 3.49 (s, 3H), 2.51 (s, 3H), 2.47 (s, 3H), 2.05-1.10 (m, 6H) |
| 479 | Int-B-4 + Int-A-62 | Bis(tri-tert-butylphosphine palladium(0) THF | 44% | | 1H NMR (DMSO-$d_6$) δ: 8.02-7.97 (1H), 7.69-7.65 (1H), 7.51-7.34 (2H), 7.20-7.13 (1H), 6.39-6.24 (1H), 2.51-2.41 (3H), 1.79-1.31 (6H) |
| 480 | Int-B-37 + Int-A-58 | Bis(tri-tert-butylphosphine palladium(0) THF | 72% | | 1H NMR (DMSO-$d_6$) δ: 7.80 (s, 1H), 7.66-7.61 (m, 1H), 7.05-6.99 (m, 2H), 6.95 (s, 1H), 4.62-4.53 (m, 2H), 3.85-3.75 (m, 2H), 3.22 (s, 3H), 2.47 (s, 3H), 1.99 (s, 3H), 1.55 (s, 3H), 1.46 (s, 3H). |
| 481 | Int-B-28 + Int-A-59 | Bis(tri-tert-butylphosphine palladium(0) THF) | 24% | | 1H NMR (DMSO-$d_6$) δ: 7.49 (d, 1H), 7.32 (d, 1H), 7.23 (dd, 1H), 7.12 (s, 1H), 7.04 (d, 2H), 6.86 (t, 1H), 6.06 (s, 1H), 3.83 (s, 3H), 2.46 (s, 3H), 1.91-1.14 (m, 6H) |
| 482 | Int-B-32 + Int-A-16 | Bis(tri-tert-butylphosphine palladium(0) THF | 30% | | 1H NMR (DMSO-$d_6$) δ: 10.56-10.45 (1H), 7.36-7.30 (1H), 7.15-7.10 (1H), 7.02-6.95 (2H), 6.92-6.73 (1H), 3.65-3.59 (3H), 2.47-2.40 (3H), 1.96-1.87 (1H), 1.81-1.30 (6H), 0.96-0.55 (4H) |
| 483 | Int-B-25 + Int-A-16 | Bis(tri-tert-butylphosphine palladium(0) THF | 31% | | 1H NMR (DMSO-$d_6$) δ: 10.64 (d, 1H), 7.38 (dd, 1H), 7.06 (dd, 1H), 6.95 (dd, 1H), 6.92 (s, 1H), 6.71 (d, 1H), 3.22 (s, 3H), 2.50 (s, 3H), 1.97-1.88 (m, 1H), 1.57 (s, 3H), 1.48 (s, 3H), 0.86 (dd, 2H), 0.67-0.57 (m, 2H) |
| 484 | Int-B-4 + Int-A-60 | Bis(tri-tert-butylphosphine palladium(0) THF | 53% | | 1H NMR (DMSO-$d_6$) δ: 7.71-7.66 (1H), 7.51-7.45 (1H), 7.43-7.28 (2H), 7.19-7.14 (1H), 6.67-6.45 (1H), 3.76-3.72 (3H), 2.49-2.39 (3H), 1.80-1.29 (6H) |
| 485 | Int-B-33 + Int-A-16 | Bis(tri-tert-butylphosphine palladium(0) THF | 31% | | 1H NMR (DMSO-$d_6$) δ: 10.62 (d, 1H), 7.37 (dd, 1H), 7.09-7.03 (m, 2H), 6.84 (dd, 1H), 6.73 (s, 1H), 2.44 (s, 3H), 1.97-1.89 (m, 1H), 1.90 (s, 3H), 1.56 (s, 3H), 1.52-1.40 (m, 3H), 0.91-0.82 (m, 2H), 0.63 (td, 2H) |
| 486 | Int-B-3 + Int-A-59 | Bis(tri-tert-butylphosphine palladium(0) THF | 27% | | 1H NMR (DMSO-$d_6$) δ: 7.49 (dd, 1H), 7.35 (d, 1H), 7.26 (dd, 1H), 7.00 (d, 1H), 6.78 (d, 1H), 6.70 (s, 1H), 6.09 (d, 1H), 3.84 (s, 3H), 2.43 (s, 3H), 1.97 (s, 3H), 1.53 (s, 3H), 1.44 (s, 3H) |
| 487 | Int-B-25 + Int-A-59 | Bis(tri-tert-butylphosphine palladium(0) THF | 23% | | 1H NMR (DMSO-$d_6$) δ: 7.48 (dt, 1H), 7.33 (d, 1H), 7.25 (dd, 1H), 7.06 (d, 1H), 6.85 (s, 1H), 6.70 (d, 1H), 6.17 (d, 1H), 3.83 (s, 3H), 3.14 (s, 3H), 2.49 (s, 3H), 1.56 (s, 3H), 1.47 (s, 3H) |

-continued

| Ex. # | Intermediates | Catalyst Solvent | Yield (%) | LC-MS ([M + H]+) | 1H NMR |
|---|---|---|---|---|---|
| 488 | Int-B-33 + Int-A-59 | Bis(tri-tert-butylphosphine palladium(0) THF | 52% | | 1H NMR (DMSO-d6) δ: 7.47 (d, 1H), 7.32 (d, 1H), 7.26 (dd, 1H), 7.06 (s, 1H), 6.94 (dd, 1H), 6.68 (s, 1H), 6.02 (d, 1H), 3.84 (s, 3H), 2.39 (s, 3H), 1.90 (s, 3H), 1.53 (s, 3H), 1.45 (s, 3H) |
| 489 | Int-B-1 + Int-A-56 | Bis(tri-tert-butylphosphine palladium(0) THF | 51% | | 1H NMR (DMSO-d6) δ: 8.12 (s, 1H), 7.84-7.66 (m, 1H), 7.30 (d, 1H), 7.23 (dd, 1H), 6.84 (dd, 1H), 6.47 (tt, 1H), 4.96 (td, 2H), 2.53 (d, 3H), 1.55 (s, 6H) |
| 490 | Int-B-25 + 4-(4,4,5,5-tetramethyl-1,3,2-dioxaborolan-2-yl)-1H-indazole | Bis(tri-tert-butylphosphine palladium(0) THF | 19% | | 1H NMR (DMSO-d6) δ: 13.14 (s, 1H), 7.86 (d, 1H), 7.59 (dt, 1H), 7.45 (dd, 1H), 7.16 (d, 1H), 6.95 (s, 1H), 6.74 (d, 1H), 3.17 (s, 3H), 2.53 (s, 3H), 1.59 (s, 3H), 1.46 (s, 3H) |
| 491 | Int-B-33 + Int-A-54 | Bis(tri-tert-butylphosphine palladium(0) THF | 39% | | 1H NMR (DMSO-d6) δ: 7.71 (d, 1H), 7.51 (d, 1H), 7.08 (s, 1H), 7.07 (s, 1H), 6.74 (s, 1H), 6.36 (d, 1H), 3.50 (s, 3H), 2.52 (s, 3H), 2.41 (s, 3H), 1.92 (s, 3H), 1.52 (s, 3H), 1.46 (s, 3H) |
| 492 | Int-B-1 + Int-A-54 | Bis(tri-tert-butylphosphine palladium(0) THF | 50% | | 1H NMR (DMSO-d6) δ: 7.75 (d, 1H), 7.55 (d, 1H), 7.22 (s, 1H), 7.19 (d, 1H), 6.81 (dd, 1H), 6.63 (d, 1H), 3.49 (s, 3H), 2.51-2.48 (m, 6H), 1.58 (s, 3H), 1.50 (s, 3H) |
| 493 | Int-B-3 + Int-A-54 | Bis(tri-tert-butylphosphine palladium(0) THF | 42% | | 1H NMR (DMSO-d6) δ: 7.72 (d, 1H), 7.53 (d, 1H), 7.15 (s, 1H), 6.80 (d, 1H), 6.77 (s, 1H), 6.43 (d, 1H), 3.49 (s, 3H), 2.52 (s, 3H), 2.45 (s, 3H), 1.99 (s, 3H), 1.52 (s, 3H), 1.45 (s, 3H) |
| 494 | Int-B-3 + Int-A-62 | Bis(tri-tert-butylphosphine palladium(0) THF | 14% | | 1H NMR (DMSO-d6) δ: 7.96 (t, 1H), 7.69 (t, 1H), 7.38 (d, 1H), 6.81 (d, 1H), 6.78 (s, 1H), 6.25 (t, 1H), 2.46 (s, 3H), 1.99 (s, 3H), 1.55-1.45 (m, 6H) |
| 495 | Int-B-3 + Int-A-63 | Bis(tri-tert-butylphosphine palladium(0) THF | 59% | | 1H NMR (DMSO-d6) δ: 7.91 (d, 1H), 7.60 (d, 1H), 7.47 (dd, 1H), 7.29 (d, 1H), 6.81 (d, 1H), 6.79 (s, 1H), 6.50 (d, 1H), 3.61 (d, 2H), 2.45 (s, 3H), 1.98 (s, 3H), 1.52 (s, 3H), 1.46 (s, 3H), 0.89-0.78 (m, 1H), 0.39-0.27 (m, 2H), −0.04-−0.13 (m, 2H) |
| 496 | Int-B-28 + 7-fluoro-4-(4,4,5,5-tetramethyl-[1,3,2]dioxaborolan-2-yl)-1H-indole | Tetrakis-(triphenylphosphin)-palladium (0) Toluol/Ethanol | 61% | | 1H NMR (DMSO-d6) δ: 11.69 (t, 1H), 7.39 (t, 1H), 7.13 (s, 1H), 7.04 (d, 1H), 7.02-6.78 (m, 3H), 6.15 (s, 1H), 2.46 (s, 3H), 1.57 (s, 6H) |
| 497 | Int-B-1 + 7-fluoro-4-(4,4,5,5-tetramethyl-[1,3,2]dioxaborolan-2-yl)-1H-indole | Tetrakis-(triphenylphosphin)-palladium (0) Toluol/Ethanol | 38% | | 1H NMR (DMSO-d6) δ: 11.76 (s, 1H), 7.46 (t, 1H), 7.12 (d, 1H), 7.04 (d, 1H), 7.03 (s, 1H), 6.79 (dd, 1H), 6.36 (s, 1H), 2.49 (s, 3H), 1.58 (s, 3H), 1.50 (s, 3H) |
| 498 | Int-B-48 + Int-A-12 | Bis(tri-tert-butylphosphine palladium(0) THF | 80% | | 1H NMR (DMSO-d6) δ: 7.95-7.88 (1H), 7.63-7.57 (1H), 7.48-7.16 (5H), 6.63-6.45 (1H), 3.57-3.47 (3H), 2.50-2.46 (3H), 1.84-1.23 (6H) |
| 499 | Int-B-48 + Int-A-2 | Bis(tri-tert-butylphosphine palladium(0) THF | 89% | | 1H NMR (DMSO-d6) δ: 7.74-7.68-(1H), 7.65-7.58 (1H), 7.40-7.16 (4H), 6.63-6.45 (1H), 3.60-3.55 (3H), 2.53-2.46 (3H), 1.78-1.27 (6H) |

-continued

| Ex. # | Intermediates | Catalyst Solvent | Yield (%) | LC-MS ([M + H]$^+$) | $^1$H NMR |
|---|---|---|---|---|---|
| 500 | Int-B-32 + Int-A-42 | Bis(tri-tert-butylphosphine palladium(0) THF | 11% | | $^1$H NMR (DMSO-d$_6$) δ: 7.57-7.52 (1H), 7.33-7.28 (1H), 7.23-7.18 (1H), 7.11-7.05 (1H), 7.03-6.90 (2H), 6.55-6.29 (1H), 6.19-6.01 (1H), 4.75-4.65 (2H), 3.63-3.58 (3H), 2.46-2.35 (3H), 1.77-1.28 (6H) |
| 501 | Int-B-1 + 7-fluoro-4-(4,4,5,5-tetramethyl-1,3,2-dioxaborolan-2-yl)-1H-indazole | Bis(tri-tert-butylphosphine palladium(0) THF | 12% | | $^1$H NMR (DMSO-d$_6$) δ: 8.12-8.07 (m, 1H), 7.32 (dd, 1H), 7.20 (d, 1H), 7.19-7.12 (m, 1H), 6.85-6.79 (m, 1H), 2.52 (d, 3H), 1.55 (s, 6H) |
| 502 | Int-B-28 + Int-A-63 | Bis(tri-tert-butylphosphine palladium(0) THF | 74% | | $^1$H NMR (DMSO-d$_6$) δ: 7.90 (d, 1H), 7.55 (d, 1H), 7.43 (dd, 1H), 7.30 (d, 1H), 7.21 (s, 1H), 7.09-6.87 (m, 2H), 6.48 (s, 1H), 3.59 (d, 2H), 2.48 (s, 3H), 2.07 (s, 3H), 1.94-1.20 (m, 6H), 0.91-0.71 (m, 1H), 0.41-0.15 (m, 3H), −0.14 (d, 2H) |
| 503 | Int-B-48 + 3-methyl-7-(4,4,5,5-tetramethyl-1,3,2-dioxaborolan-2-yl)-1H-indole | Bis(tri-tert-butylphosphine palladium(0) THF | 65% | | $^1$H NMR (DMSO-d$_6$) δ: 10.47-10.43 (1H), 7.54-7.48 (1H), 7.32-7.16 (2H), 7.11-7.08 (1H), 7.08-6.95 (3H), 2.51-2.47 (3H), 2.31-2.27 (3H), 1.80-1.26 (6H) |
| 504 | Int-B-3 + 7-fluoro-4-(4-,4,5,5-tetramethyl-[1,3,2]dioxaborolan-2-yl)-1H-indole | Tetrakis-(triphenylphosphin)-palladium (0) Toluol/Ethanol | 17% | | $^1$H NMR (DMSO-d$_6$) δ: 11.73 (t, 1H), 7.44 (t, 1H), 7.02 (dd, 1H), 6.94 (dd, 1H), 6.78 (d, 1H), 6.71 (s, 1H), 6.17 (q, 1H), 2.44 (s, 3H), 1.98 (s, 3H), 1.53 (s, 3H), 1.44 (s, 3H) |
| 505 | Int-B-4 + 7-fluoro-4-(4,4,5,5-tetramethyl-[1,3,2]dioxaborolan-2-yl)-1H-indole | Tetrakis-(triphenylphosphin)-palladium (0) Toluol/Ethanol | 15% | | $^1$H NMR (DMSO-d$_6$) δ: 11.76-11.70 (1H), 7.44-7.35 (2H), 7.18-7.11 (1H), 7.07-6.91 (2H), 6.30-6.13 (1H), 2.49-2.39 (3H), 1.78-1.31 (6H) |
| 506 | Int-B-33 + 7-fluoro-4-(4,4,5,5-tetramethyl-[1,3,2]dioxaborolan-2-yl)-1H-indole | Tetrakis-(triphenylphosphin)-palladium (0) Toluol/Ethanol | 36% | | $^1$H NMR (DMSO-d$_6$) δ: 11.71 (t, 1H), 7.41 (t, 1H), 7.06 (s, 1H), 7.02 (dd, 1H), 6.87 (dd, 1H), 6.69 (s, 1H), 6.11 (q, 1H), 2.40 (s, 3H), 1.91 (s, 3H), 1.53 (s, 3H), 1.45 (s, 3H) |
| 507 | Int-B-48 + Int-A-15 | Bis(tri-tert-butylphosphine palladium(0) THF | 62% | | $^1$H NMR (DMSO-d$_6$) δ: 10.62-10.55 (1H), 7.33-7.21 (3H), 7.17-7.12 (2H), 7.01-6.81 (1H), 2.51-2.48 (3H), 2.30-2.23 (3H), 1.79-1.27 (6H) |
| 508 | Int-B-26 + Int-A-56 | Bis(tri-tert-butylphosphine palladium(0) THF | 10% | | $^1$H NMR (DMSO-d$_6$) δ: 8.08 (s, 1H), 7.75 (dt, 1H), 7.23 (d, 1H), 7.19 (dd, 1H), 7.08 (d, 1H), 6.48 (tt, 1H), 4.96 (td, 2H), 2.49 (d, 3H), 1.60 (s, 3H), 1.51 (s, 3H) |
| 509 | Int-B-32 + Int-A-59 | Bis(tri-tert-butylphosphine palladium(0) THF | 64% | | $^1$H NMR (DMSO-d$_6$) δ: 7.58-7.39 (1H), 7.35-7.23 (1H), 7.21-7.13 (1H), 7.10-7.03 (1H), 7.00-6.72 (2H), 6.08-5.92 (1H), 3.84-3.80 (3H), 3.62-3.55 (3H), 2.45-2.34 (3H), 1.76-1.28 (6H) |
| 510 | Int-B-3 + 4-(4,4,5,5-tetramethyl-1,3,2-dioxaborolan-2-yl)-1H-indazole | Bis(tri-tert-butylphosphine palladium(0) THF | 14% | | $^1$H NMR (DMSO-d$_6$) δ: 13.20 (s, 1H), 7.80 (s, 1H), 7.60 (s, 1H), 7.46 (dd, 1H), 7.11 (d, 1H), 6.81 (d, 1H), 6.78 (s, 1H), 2.47 (s, 3H), 2.00 (s, 3H), 1.53 (s, 3H), 1.46 (s, 3H) |

| Ex. # | Intermediates | Catalyst Solvent | Yield (%) | LC-MS ([M + H]$^+$) | $^1$H NMR |
|---|---|---|---|---|---|
| 511 | Int-B-1 + Int-A-69 | Bis(tri-tert-butylphosphine) palladium(0) THF | 53% | | $^1$H NMR (DMSO-d$_6$) δ: 11.38 (t, 1H), 7.54 (dd, 1H), 7.44 (t, 1H), 7.27-7.16 (m, 1H), 7.10 (d, 1H), 6.81 (dd, 1H), 6.32-6.28 (m, 1H), 2.49 (s, 3H), 1.57 (s, 3H), 1.50 (s, 3H) |
| 512 | Int-B-28 + Int-A-72 | Bis(tri-tert-butylphosphine) palladium(0) THF | 20% | | $^1$H NMR (DMSO-d$_6$) δ: 7.72-7.51 (m, 1H), 7.24 (d, 1H), 7.19 (s, 1H), 7.04 (d, 1H), 6.94 (t, 1H), 6.38 (s, 1H), 3.63 (s, 3H), 2.81 (s, 3H), 2.46 (s, 3H), 1.89-1.12 (m, 6H) |
| 513 | Int-B-3 + Int-A-69 | Bis(tri-tert-butylphosphine) palladium(0) THF | 89% | | $^1$H NMR (DMSO-d$_6$) δ: 11.35 (s, 1H), 7.50 (dd, 1H), 7.42 (t, 1H), 7.02 (d, 1H), 6.79 (d, 1H), 6.75 (s, 1H), 6.12 (t, 1H), 2.44 (s, 3H), 1.99 (s, 3H), 1.52 (s, 3H), 1.45 (s, 3H) |
| 514 | Int-B-28 + Int-A-44 | Bis(tri-tert-butylphosphine) palladium(0) THF | 41% | | $^1$H NMR (DMSO-d$_6$) δ: 7.62 (d, 1H), 7.31 (d, 1H), 7.25 (dd, 1H), 7.13 (s, 1H), 7.05 (dd, 2H), 6.87 (t, 1H), 6.04 (s, 1H), 3.48 (tt, 1H), 2.46 (s, 3H), 1.83-1.15 (m, 6H), 1.12-1.06 (m, 2H), 1.04-0.95 (m, 2H) |
| 515 | Int-B-28 + Int-A-71 | Bis(tri-tert-butylphosphine) palladium(0) THF | 5% | 416.1 | |
| 516 | Int-B-4 + Int-A-71 | Xphos/ Pd2dba3, 1,4-dioxane, tert-amyl alcohol | 3% | 434.2 | |
| 517 | Int-B-32 + Int-A-73 | Bis(tri-tert-butylphosphine) palladium(0) THF | 37% | | $^1$H NMR (DMSO-d$_6$) δ: 7.33-7.29 (1H), 7.27-7.23 (1H), 7.15-7.07 (1H), 6.99-6.96 (1H), 6.93-6.72 (1H), 6.11-5.91 (1H), 3.80-3.77 (3H), 3.62-3.58 (3H), 2.45-2.35 (3H), 1.77-1.29 (6H) |
| 518 | Int-B-3 + Int-A-73 | Bis(tri-tert-butylphosphine) palladium(0) THF | 17% | | $^1$H NMR (DMSO-d$_6$) δ: 7.40-7.36 (m, 1H), 7.35 (d, 1H), 6.92 (dd, 1H), 6.79 (d, 1H), 6.75 (s, 1H), 6.08 (d, 1H), 3.80 (s, 3H), 2.44 (s, 3H), 1.99 (s, 3H), 1.52 (s, 3H), 1.45 (s, 3H) |
| 519 | Int-B-33 + Int-A-73 | Bis(tri-tert-butylphosphine) palladium(0) THF | 7% | | $^1$H NMR (DMSO-d$_6$) δ: 7.38-7.34 (m, 1H), 7.33 (d, 1H), 7.05 (s, 1H), 6.85 (dd, 1H), 6.73 (s, 1H), 6.02 (d, 1H), 3.80 (s, 3H), 2.40 (s, 3H), 1.93 (s, 3H), 1.52 (s, 3H), 1.46 (s, 3H) |
| 520 | Int-B-34 + Int-A-73 | Bis(tri-tert-butylphosphine) palladium(0) THF | 19% | | $^1$H NMR (DMSO-d$_6$) δ: 7.36 (ddd, 1H), 7.33 (d, 1H), 6.89 (dd, 1H), 6.80 (s, 1H), 6.76 (s, 1H), 6.10 (d, 1H), 3.80 (s, 3H), 2.43 (d, 3H), 2.02 (s, 3H), 1.54 (s, 3H), 1.48 (s, 3H) |
| 521 | Int-B-28 + Int-A-73 | Bis(tri-tert-butylphosphine) palladium(0) THF | 36% | | $^1$H NMR (DMSO-d$_6$) δ: 7.38 (dd, 1H), 7.31 (d, 1H), 7.18 (s, 1H), 7.08-6.82 (m, 3H), 6.07 (s, 1H), 3.80 (s, 3H), 2.46 (s, 3H), 1.88-1.17 (m, 6H) |
| 522 | Int-B-48 + Int-A-73 | Bis(tri-tert-butylphosphine) palladium(0) THF | 30% | 430.2 | |
| 523 | Int-B-32 + Int-A-44 | Bis(tri-tert-butylphosphine) palladium(0) THF | 21% | | $^1$H NMR (DMSO-d$_6$) δ: 7.59-7.53 (1H), 7.26-7.23 (1H), 7.22-7.17 (1H), 7.10-7.03 (1H), 7.02-6.88 (2H), 6.05-5.90 (1H), 3.60-3.57 (3H), 3.48-3.44 (1H), 2.46-2.32 (3H), 1.80-1.26 (6H), 1.13-0.95 (4H) |
| 524 | Int-B-3 + 7-fluoro-4-(4,4,5,5-tetramethyl-1,3,2-dioxaborolan-2-yl)-1H-indazole | Bis(tri-tert-butylphosphine) palladium(0) THF | 15% | | $^1$H NMR (DMSO-d$_6$) δ: 7.91 (d, 1H), 7.29 (dd, 1H), 7.08 (dd, 1H), 6.81 (d, 1H), 6.79 (s, 1H), 2.46 (s, 3H), 2.00 (s, 3H), 1.52 (s, 3H), 1.46 (s, 3H) |
| 525 | Int-B-3 + Int-A-76 | Bis(tri-tert-butylphosphine) palladium(0) | 16% | | $^1$H NMR (DMSO-d$_6$) δ: 7.75 (d, 1H), 7.54 (d, 1H), 7.32 (d, 1H), 6.84-6.77 (m, 2H), 6.46 (d, 1H), 3.89 (s, |

-continued

| Ex. # | Intermediates | Catalyst Solvent | Yield (%) | LC-MS ([M + H]+) | 1H NMR |
|---|---|---|---|---|---|
| | | THF | | | 3H), 2.44 (s, 3H), 1.97 (s, 3H), 1.51 (s, 3H), 1.46 (s, 3H) |
| 526 | Int-B-52 + Int-A-2 | Bis(tri-tert-butylphosphine palladium(0) THF | 72% | | 1H NMR (DMSO-d6) δ: 7.66 (dd, 1H), 7.59 (d, 1H), 7.27-7.17 (m, 3H), 7.06 (t, 1H), 7.00 (s, 1H), 6.47 (s, 1H), 3.55 (s, 3H), 2.51 (s, 3H), 1.49 (s, 6H) |
| 527 | Int-B-52 + Int-A-15 | Bis(tri-tert-butylphosphine palladium(0) THF | 67% | | 1H NMR (DMSO-d6) δ: 10.46 (d, 1H), 7.24 (dd, 1H), 7.22-7.15 (m, 2H), 7.13-7.09 (m, 1H), 7.06-6.82 (m, 3H), 2.52 (s, 3H), 2.25 (s, 3H), 1.92-1.13 (m, 6H) |
| 528 | Int-B-52 + Int-A-12 | Bis(tri-tert-butylphosphine palladium(0) THF | 53% | | 1H NMR (DMSO-d6) δ: 7.88 (d, 1H), 7.58 (d, 1H), 7.43 (t, 1H), 7.30 (s, 1H), 7.22 (d, 1H), 7.17 (d, 1H), 6.99 (t, 1H), 6.94 (s, 1H), 6.48 (s, 1H), 3.49 (s, 3H), 2.50 (s, 3H), 1.78-1.20 (m, 6H) |
| 529 | Int-B-1 + A-74 | Int-Bis(tri-tert-butylphosphine palladium(0) THF | 46% | | 1H NMR (DMSO-d6) δ: 11.65-11.60 (m, 1H), 7.47 (t, 1H), 7.28 (d, 1H), 7.15 (d, 1H), 7.08 (d, 1H), 6.81 (dd, 1H), 6.41-6.36 (m, 1H), 2.49 (s, 3H), 1.57 (s, 3H), 1.50 (s, 3H) |
| 530 | Int-B-4 + Int-A-74 | Bis(tri-tert-butylphosphine palladium(0) THF | 27% | | 1H NMR (DMSO-d6) δ: 11.63-11.58 (1H), 7.45-7.38 (2H), 7.28-7.25 (1H), 7.17-7.13 (1H), 7.11-6.97 (1H), 6.32-6.16 (1H), 2.48-2.40 (3H), 1.79-1.29 (6H) |
| 531 | Int-B-4 + Int-A-75 | Xphos/ Pd2dba3, 1-4-dioxane, tert amyl alcohol | 44% | | 1H NMR (DMSO-d6) δ: 12.20-12.11 (1H), 7.72-7.67 (1H), 7.55-7.51 (1H), 7.50-7.46 (1H), 7.30-7.15 (2H), 6.44-6.27 (1H), 2.49-2.41 (3H), 1.78-1.24 (6H) |
| 532 | Int-B-4 + Int-A-73 | Xphos/ Pd2dba3, 1,4-dioxane, tert-amyl alcololol | 29% | | 1H NMR (DMSO-d6) δ: 7.45-7.38 (2H), 7.35-7.31 (1H), 7.20-7.11 (1H), 7.08-6.89 (1H), 6.21-6.05 (1H), 3.84-3.78 (3H), 2.50-2.40 (3H), 1.79-1.29 (6H) |
| 533 | Int-B-33 + Int-A-44 | Bis(tri-tert-butylphosphine palladium(0) THF | 17% | | 1H NMR (DMSO-d6) δ: 7.61 (dt, 1H), 7.33 (d, 1H), 7.28 (dd, 1H), 7.05 (s, 1H), 6.96 (dd, 1H), 6.68 (s, 1H), 6.00 (d, 1H), 3.49 (dq, 1H), 2.39 (s, 3H), 1.90 (s, 3H), 1.53 (s, 3H), 1.44 (s, 3H), 1.14-1.06 (m, 2H), 1.03-0.98 (m, 2H) |
| 534 | Int-B-3 30 Int-A-75 | Xphos/ Pd2dba3, 1,4-dioxane, tert-amyl alcohol | 91% | | 1H NMR (DMSO-d6) δ: 12.17-12.12 (m, 1H), 7.70 (d, 1H), 7.54 (t, 1H), 7.17 (d, 1H), 6.81 (t, 2H), 6.30 (t, 1H), 2.44 (s, 3H), 1.98 (s, 3H), 1.53 (s, 3H), 1.45 (s, 3H) |
| 535 | Int-B-4 + 7-fluoro-4-(4,4,5,5-tetramethyl-1,3,2-dioxaborolan-2-yl)-1H-indazole | Xphos/ Pd2dba3, 1,4-dioxane, tert-amyl alcohol | 25% | | 1H NMR (DMSO-d6) δ: 8.09-7.90 (1H), 7.49-7.44 (1H), 7.32-7.27 (1H), 7.21-7.06 (3H), 2.49-2.43 (3H), 1.78-1.31 (6H) |
| 536 | Int-B-4 + Int-A-77 | Xphos/ Pd2dba3, 1,4-dioxane, tert-amyl alcololol | 24% | | 1H NMR (DMSO-d6) δ: 7.49-7.43 (3H), 7.18-7.13 (1H), 7.10-6.93 (1H), 6.57-6.37 (1H), 3.90-3.84 (3H), 2.48-2.40 (3H), 1.81-1.28 (6H) MeO-omitted by water |
| 537 | Int-B-3 + Int-A-77 | Xphos/ Pd2dba3, 1,4-dioxane, tert-amyl alcohol (d, 3H) | 54% | | 1H NMR (DMSO-d6) δ: 7.47 (d, 1H), 7.44-7.39 (m, 1H), 6.95 (d, 1H), 6.83-6.77 (m, 2H), 6.39 (d, 1H), 3.88 (s, 3H), 3.49 (s, 3H), 2.45 (s, 3H), 2.00 (s, 3H), 1.51 (s, 3H), 1.43 |

The examples in Table 6 were synthesized in standard chemical reactions which are known to the person skilled in the art:

| Ex. # | Intermediates | Synthesis in analogy to | Yield (%) | $^1$H NMR |
|---|---|---|---|---|
| 202 | Ex. 445 + chloromethyl-cyclopropane | Example 35 | 38% | $^1$H NMR (DMSO-d$_6$) δ: 7.60 (d, 1H), 7.49 (d, 1H), 7.24 (t, 1H), 7.12 (d, 1H), 7.08 (d, 1H), 6.80 (dd, 1H), 6.31-6.25 (m, 1H), 4.09 (d, 2H), 2.51 (q, 3H), 1.59 (s, 3H), 1.50 (s, 3H), 1.29 (dtd, 1H), 0.58-0.49 (m, 2H), 0.47-0.38 (m, 2H) |
| 203 | Ex. 445 + tetrahydropyran-4-sulfonyl chloride | | 29% | $^1$H NMR (DMSO-d$_6$) δ: 7.96 (d, 1H), 7.65 (d, 1H), 7.49 (t, 1H), 7.39 (d, 1H), 7.21 (d, 1H), 6.82 (dd, 1H), 6.71 (d, 1H), 4.05 (tt, 1H), 3.92-3.86 (m, 2H), 3.30 (d, 2H), 2.54-2.48 (m, 3H), 1.70 (ddt, 4H), 1.57 (s, 3H), 1.52 (s, 3H) |
| 204 | Ex. 445 + 1-chloro-2-methoxy-ethane | Example 35 | 36% | $^1$H NMR (DMSO-d$_6$) δ: 7.57 (dd, 1H), 7.40 (q, 1H), 7.27-7.21 (m, 1H), 7.12 (s, 1H), 7.11-7.06 (m, 1H), 6.81 (dd, 1H), 6.27 (s, 1H), 4.38 (q, 2H), 3.70 (q, 2H), 3.28-3.23 (m, 3H), 2.49 (d, 3H), 1.58 (s, 3H), 1.50 (s, 3H) |
| 205 | Ex. 445 + cyclopropanesulfonyl chloride | | 20% | $^1$H NMR (DMSO-d$_6$) δ: 7.98 (dd, 1H), 7.66 (d, 1H), 7.49 (dd, 1H), 7.38 (d, 1H), 7.21 (d, 1H), 6.83 (dd, 1H), 6.69 (d, 1H), 3.15 (tt, 1H), 2.51 (d, 3H), 1.58 (s, 3H), 1.51 (s, 3H), 1.32-1.27 (m, 2H), 1.12 (dt, 2H) |
| 210 | Ex. 445 + cyclopropylmethane-sulfonyl chloride | | 28% | $^1$H NMR (DMSO-d$_6$) δ: 7.94 (d, 1H), 7.62 (d, 1H), 7.47 (t, 1H), 7.37 (d, 1H), 7.20 (d, 1H), 6.83 (dd, 1H), 6.70 (d, 1H), 3.61 (d, 2H), 2.52-2.48 (m, 3H), 1.58 (s, 3H), 1.52 (s, 3H), 0.82 (tt, 1H), 0.41-0.34 (m, 2H), −0.01 (td, 2H) |
| 223 | Ex. 445 + 2-(dimethylamine)-acetyl chloride (HCl-salt) | Example 4 | 19% | $^1$H NMR (DMSO-d$_6$) δ: 8.43 (d, 1H), 7.98 (d, 1H), 7.45 (t, 1H), 7.34 (d, 1H), 7.19 (d, 1H), 6.82 (dd, 1H), 6.63-6.58 (m, 1H), 3.81 (s, 2H), 2.51 (d, 3H), 2.36 (s, 6H), 1.59 (s, 3H), 1.50 (s, 3H) |
| 224 | Ex. 214 + Methanesulfonyl chloride | | 25% | $^1$H NMR (DMSO-d$_6$) δ: 7.97 (dd, 1H), 7.73 (d, 1H), 7.41 (t, 1H), 7.31 (d, 1H), 6.85 (dd, 1H), 6.74 (d, 1H), 3.55 (s, 3H), 2.52-2.50 (m, 3H), 1.58 (s, 3H), 1.52 (s, 3H) |
| 229 | Ex. 230 + 2.2-difluoropropanoic acid (T3P coupling) | | 49% | $^1$H NMR (DMSO-d$_6$) δ: 8.83 (t, 1H), 7.62-7.54 (m, 1H), 7.36 (d, 1H), 7.26 (dd, 1H), 7.15-7.06 (m, 2H), 6.79 (dd, 1H), 6.29 (dd, 1H), 4.36 (t, 2H), 3.60-3.51 (m, 2H), 2.49 (d, 3H), 1.60 (t, 3H), 1.58 (s, 3H), 1.50 (s, 3H) |
| 230 | Boc removal of Ex. 228 | | 36% | $^1$H NMR (DMSO-d$_6$) δ: 7.59 (d, 1H), 7.43 (dd, 1H), 7.28-7.21 (m, 1H), 7.14-7.06 (m, 2H), 6.80 (dd, 1H), 6.27 (d, 1H), 4.21 (td, 2H), 2.97 (s, 2H), 2.49 (d, 3H), 1.58 (s, 3H), 1.50 (s, 3H) |
| 258 | Demethylation of Ex. 233 (DL-Methionin) | | 9% | $^1$H NMR (DMSO-d$_6$) δ: 7.97 (s, 1H), 7.74 (d, 1H), 7.48 (dd, 1H), 7.20 (d, 2H), 6.83 (dd, 1H), 4.91 (t, 1H), 4.49 (t, 2H), 3.85 (q, 2H), 2.53 (s, 3H), 1.55 (s, 6H) |
| 259 | Ex. 252 + 1-chloro-2-methoxy-ethane | Example 35 | 42% | $^1$H NMR (DMSO-d$_6$) δ: 7.82-7.63 (m, 1H), 7.46 (dd, 1H), 7.22-7.18 (m, 1H), 7.16 (d, 1H), 7.12 (t, 1H), 6.94 (s, 1H), 6.82 (s, 1H), 4.63-4.28 (m, 2H), 3.71 (h, 2H), 3.24 (s, 3H), 2.47 (d, 3H), 1.58 (s, 3H), 1.52 (s, 3H) |
| 271 | Ex. 225 + methanesulfonyl chloride | | 32% | $^1$H NMR (DMSO-d$_6$) δ: 8.13 (d, 1H), 7.71 (dd, 1H), 7.53 (d, 2H), 7.25 (d, 1H), 6.83 (dd, 1H), 3.58 (s, 3H), 2.50 (s, 3H), 1.59 (s, 3H), 1.52 (s, 3H) |
| 289 | Ex. 225 + 1-chloro-2-methoxy-ethane | Example 35 | 15% | $^1$H NMR (DMSO-d$_6$) δ: 7.59 (d, 1H), 7.43 (dd, 1H), 7.24 (d, 1H), 6.99 (dd, 1H), 6.89 (s, 1H), 3.64 (t, 2H), 3.51 (t, 2H), 3.26 (s, 3H), 2.49 (d, 3H), 1.61 (s, 3H), 1.58 (s, 3H) |
| 312 | Ex. 225 + cyclopropylboronic acid | Example 2 | 49% | $^1$H NMR (DMSO-d$_6$) δ: 7.83-7.78 (m, 1H), 7.49 (dd, 1H), 7.27 (d, 1H), 7.18 (d, 1H), 6.97 (s, 1H), 6.81 (dd, 1H), 3.46 (tt, 1H), 2.48 (d, 3H), 1.57 (s, 3H), 1.52 (s, 3H), 1.28-1.23 (m, 2H), 1.19-1.13 (m, 2H) |

TABLE 7

| Ex. # | Intermediates | Synthesis in analogy to | yield (mol-%) | ¹H-NMR |
|---|---|---|---|---|
| 447 | Int-A-20 + Int-B-4 | Ex. 446 | 24% | ¹H NMR (400 MHz, DMSO-$d_6$): δ 7.34-7.40 (m, 2H), 7.14 (d, 2H), 6.91 (bs, 1H), 6.10 (s, 1H), 4.62 (s, 1H), 4.22 (d, 2H), 3.81 (q, 2H), 2.45 (s, 3H), 1.75 bs, 3H), 1.37 (bs, 3H). |
| 448 | Int-A-50 + Int-B-4 | Ex. 446 | 13% | ¹H NMR (400 MHz, DMSO-$d_6$): δ 8.38 (s, 1H), 7.81 (d, 1H), 7.44 (s, 1H), 7.33 (s, 1H), 7.20 (d, 1H), 3.75 (q, 2H), 1.78 (bs, 3H), 1.35 (bs, 3H), 1.15 (t, 3H); ($CH_3$- ommited by DMSO). |
| 449 | Int-A-21 + Int-B-4 | Ex. 446 | 32% | ¹H NMR (400 MHz, DMSO-$d_6$): δ 7.77 (bs, 1H), 7.56 (d, 1H), 7.24 (s, 1H), 7.17 (d, 1H), 7.07 (bs, 1H), 4.58 (s, 1H), 4.45 (d, 2H), 3.88 (q, 2H), 2.49 (s, 3H), 1.77 (bs, 3H), 1.37 (bs, 3H). |
| 451 | Int-A-20 + Int-B-40 | Ex. 450 | 61% | 1H NMR (400 MHz, dmso-d6): δ 7.39-7.35 (m, 2H), 7.14 (d1H), 6.95 (d, J = 8 Hz, 1H), 6.88-6.85 (m, 1H), 6.49 (s, 1H), 6.14 (s, 1H), 4.90 (t, 1H), 4.22 (t, 2H), 3.75-3.71 (m, 2H), 2.06 (s, 3H), 1.46 (s, 6H); ($CH_3$- ommited by DMSO). |
| 452 | Int-A-15 + Int-B-40 | Ex. 450 | 59% | 1H NMR (400 MHz, dmso-d6): δ 10.55 (s, 1H), 7.25-7.22 (m, 1H), 7.14-7.12 (m, 2H), 6.97-6.95 (m, 1H), 6.84-6.81 (m, 1H), 6.50 (s, 1H), 2.52 (s, 3H), 2.25 (s, 3H), 1.99 (s, 3H), 1.47 (bs, 6H). |
| 453 | Int-A-2 + Int-B-40 | Ex. 450 | 42% | 1H NMR (400 MHz, dmso-d6): δ 7.68-7.62 (m, 2H), 7.24-7.22 (m, 1H), 7.15-7.13 (m, 1H), 6.98-6.96 (m, 1H), 6.58-6.52 (m, 2H), 3.55 (s, 3H), 2.06 (s, 3H), 1.46 (bs, 6H); ($CH_3$- ommited by DMSO). |
| 454 | Int-A-23 + Int-B-4 | Ex. 446 | 15% | ¹H NMR (400 MHz, DMSO-$d_6$): δ 8.38 (s, 1H), 7.80 (d, 1H), 7.45 (bs, 1H), 7.34 (s, 1H), 7.20 (d, 1H), 3.55 (s, 3H), 2.49 (s, 3H), 1.78 (bs, 3H), 1.37 (bs, 3H). |
| 455 | Int-A-47 + Int-B-4 | Ex. 446 | 16% | ¹H NMR (400 MHz, DMSO-$d_6$): δ 7.96 (d, J = 8.4 Hz, 1H), 7.58 (s, 1H), 7.46 (t, 1H), 7.33 (bs, 1H), 7.16 (d, 2H), 6.54 (bs, 1H), 3.61 (q, 2H), 2.45 (s, 3H), 1.78 (bs, 3H), 1.37 (bs, 3H), 1.12 (t, 3H). |
| 456 | Int-A-51 + Int-B-4 | Ex. 446 | 20% | ¹H NMR (400 MHz, DMSO-$d_6$): T = 100° C.): δ 8.34 (bs, 1H), 8.09 (d, 1H), 7.73 (t, 1H), 7.45 (bs, 1H), 7.27 (s, 1H), 7.19 (d, 1H), 3.50 (s, 3H), 2.49 (s, 3H), 1.78 (bs, 3H), 1.48 (bs, 3H). |
| 457 | Int-A-22 + Int-B-40 | Ex. 450 | 53% | 1H NMR (400 MHz, dmso-d6): δ 8.38 (s, 1H), 8.00 (d, 1H), 7.73 (t, 1H), 7.43-7.41 (m, 1H), 7.19 (d, 1H), 7.01 (d, 1H), 6.61 (s, 1H), 3.52 (s, 3H), 2.52 (s, 3H), 2.07 (s, 3H), 1.47 (s, 6H). |

The molecular structures and chemical names of the Examples summarized in Tables 4, 5, 6 and 7 are given in Table 8 below:

| Ex. # | Structure | Name |
|---|---|---|
| 45 | 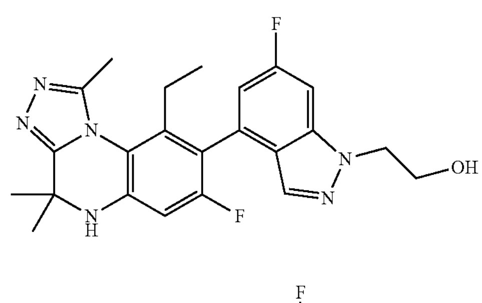 | 2-[4-(9-Ethyl-7-fluoro-1,4,4-trimethyl-5H-[1,2,4]triazolo[4,3-a]quinoxalin-8-yl)-6-fluoro-1H-indazol-1-yl]-ethanol |
| 46 | 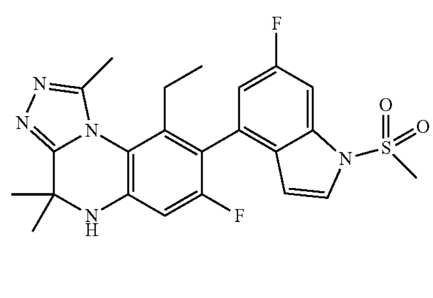 [SMILES: CCc1c(-c2cc(F)cc3c2ccn3S(C)(=O)=O)c(F)cc2c1-n1c(C)nnc1C(C)(C)N2] | 9-Ethyl-7-fluoro-8-(6-fluoro-1-methylsulfonyl-1H-indol-4-yl)-1,4,4-trimethyl-5H-[1,2,4]triazolo[4,3-a]quinoxaline |

-continued

| Ex. # | Structure | Name |
|---|---|---|
| 47 | 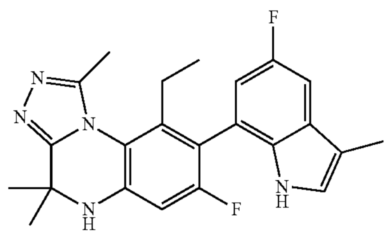 | 9-Ethyl-7-fluoro-8-(5-fluoro-3-methyl-1H-indol-7-yl)-1,4,4-trimethyl-5H-[1,2,4]triazolo[4,3-a]quinoxaline |
| 50 | 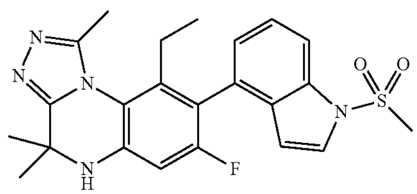 | 9-Ethyl-7-fluoro-1,4,4-trimethyl-8-(1-methylsulfonyl-1H-indol-4-yl)-5H-[1,2,4]triazolo[4,3-a]quinoxaline |
| 51 | 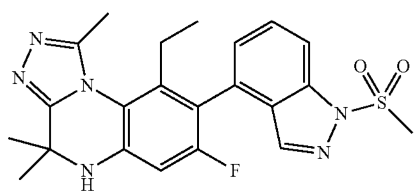 | 9-Ethyl-7-fluoro-1,4,4-trimethyl-8-(1-methylsulfonyl-1H-indazol-4-yl)-5H-[1,2,4]triazolo[4,3-a]quinoxaline |
| 52 | 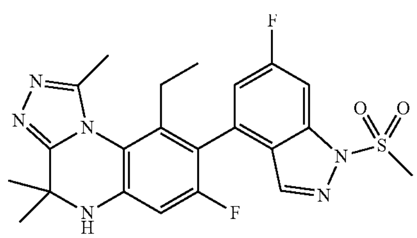 | 9-Ethyl-7-fluoro-8-(6-fluoro-1-methylsulfonyl-1H-indazol-4-yl)-1,4,4-trimethyl-5H-[1,2,4]triazolo[4,3-a]quinoxaline |
| 67 | 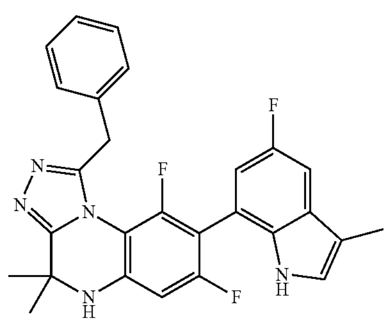 | 1-Benzyl-7,9-difluoro-8-(5-fluoro-3-methyl-1H-indol-7-yl)-4,4-dimethyl-5H-[1,2,4]triazolo[4,3-a]quinoxaline |
| 68 | 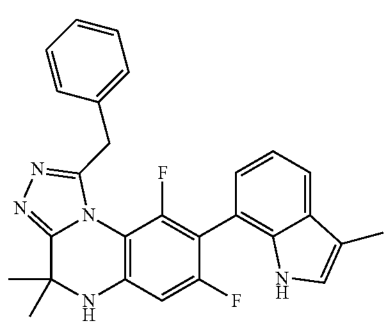 | 1-Benzyl-7,9-difluoro-4,4-dimethyl-8-(3-methyl-1H-indol-7-yl)-5H-[1,2,4]triazolo[4,3-a]quinoxaline |

-continued

| Ex. # | Structure | Name |
|---|---|---|
| 71 | 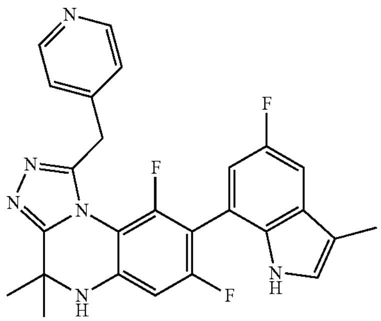 | 7,9-Difluoro-8-(5-fluoro-3-methyl-1H-indol-7-yl)-4,4-dimethyl-1-(pyridin-4-yl-methyl)-5H-[1,2,4]triazolo[4,3-a]quinoxaline |
| 72 | 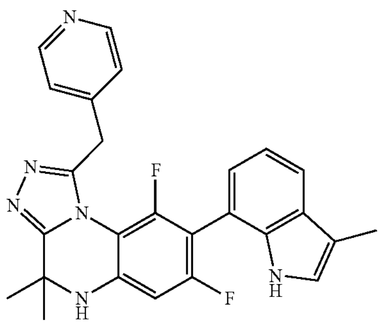 | 7,9-Difluoro-4,4-dimethyl-8-(3-methyl-1H-indol-7-yl)-1-(pyridin-4-yl-methyl)-5H-[1,2,4]triazolo[4,3-a]quinoxaline |
| 73 | 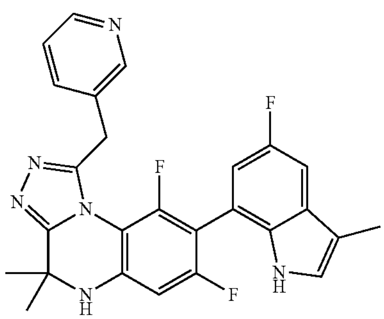 | 7,9-Difluoro-8-(5-fluoro-3-methyl-1H-indol-7-yl)-4,4-dimethyl-1-(pyridin-3-yl-methyl)-5H-[1,2,4]triazolo[4,3-a]quinoxaline |
| 74 | 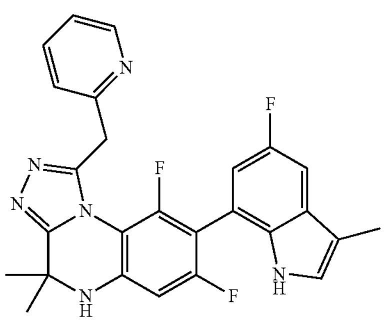 | 7,9-Difluoro-8-(5-fluoro-3-methyl-1H-indol-7-yl)-4,4-dimethyl-1-(pyridin-2-yl-methyl)-5H-[1,2,4]triazolo[4,3-a]quinoxaline |
| 75 | 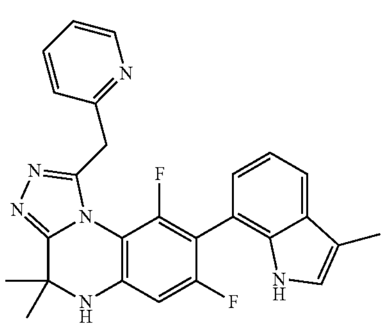 | 7,9-Difluoro-4,4-dimethyl-8-(3-methyl-1H-indol-7-yl)-1-(pyridin-2-yl-methyl)-5H-[1,2,4]triazolo[4,3-a]quinoxaline |

| Ex. # | Structure | Name |
|---|---|---|
| 80 | 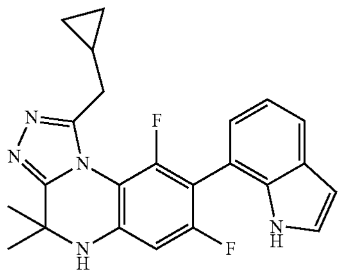 [SMILES: CC1(C)Nc2cc(F)c(-c3cccc4cc[nH]c34)c(F)c2-n2c(CC3CC3)nnc21] | 1-(Cyclopropyl-methyl)-7,9-difluoro-8-(1H-indol-7-yl)-4,4-dimethyl-5H-[1,2,4]triazolo[4,3-a]quinoxaline |
| 81 | 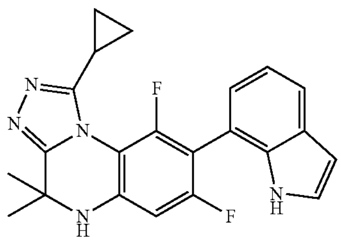 [SMILES: CC1(C)Nc2cc(F)c(-c3cccc4cc[nH]c34)c(F)c2-n2c(C3CC3)nnc21] | 1-Cyclopropyl-7,9-difluoro-8-(1H-indol-7-yl)-4,4-dimethyl-5H-[1,2,4]triazolo[4,3-a]quinoxaline |
| 82 | 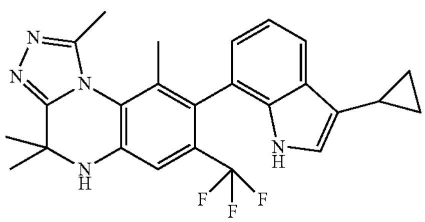 [SMILES: Cc1c(-c2cccc3c(C4CC4)c[nH]c23)c(C(F)(F)F)cc2c1-n1c(C)nnc1C(C)(C)N2] | 8-(3-Cyclopropyl-1H-indol-7-yl)-1,4,4,9-tetramethyl-7-(trifluoromethyl)-5H-[1,2,4]triazolo[4,3-a]quinoxaline |
| 83 | 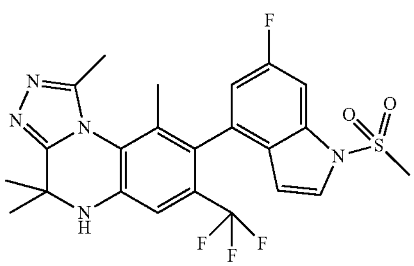 | 8-(6-Fluoro-1-methylsulfonyl-1H-indol-4-yl)-1,4,4,9-tetramethyl-7-(trifluoromethyl)-5H-[1,2,4]triazolo[4,3-a]quinoxaline |
| 84 | 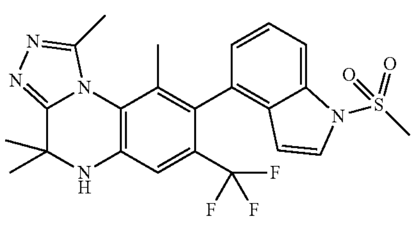 | 1,4,4,9-Tetramethyl-8-(1-methylsulfonyl-1H-indol-4-yl)-7-(trifluoromethyl)-5H-[1,2,4]triazolo[4,3-a]quinoxaline |
| 85 | 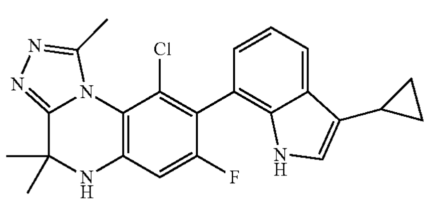 [SMILES: Cc1nnc2n1-c1c(cc(F)c(-c3cccc4c(C5CC5)c[nH]c34)c1Cl)NC2(C)C] | 9-Chloro-8-(3-cyclopropyl-1H-indol-7-yl)-7-fluoro-1,4,4-trimethyl-5H-[1,2,4]triazolo[4,3-a]quinoxaline |

| Ex. # | Structure | Name |
|---|---|---|
| 86 | 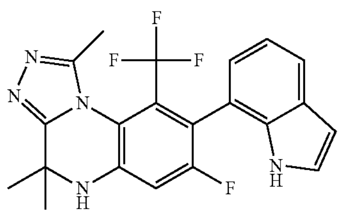 [SMILES: Cc1nnc2n1-c1c(cc(F)c(-c3cccc4cc[nH]c34)c1C(F)(F)F)NC2(C)C] | 7-Fluoro-8-(1H-indol-7-yl)-1,4,4-trimethyl-9-(trifluoromethyl)-5H-[1,2,4]triazolo[4,3-a]quinoxaline |
| 88 | 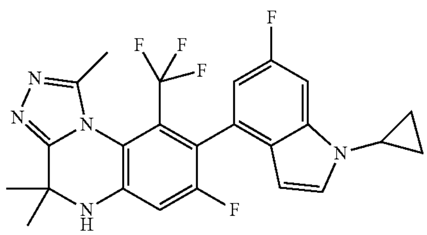 [SMILES: Cc1nnc2n1-c1c(cc(F)c(-c3cc(F)cc4c3ccn4C3CC3)c1C(F)(F)F)NC2(C)C] | 8-(1-Cyclopropyl-6-fluoro-1H-indol-4-yl)-7-fluoro-1,4,4-trimethyl-9-(trifluoromethyl)-5H-[1,2,4]triazolo[4,3-a]quinoxaline |
| 200 | 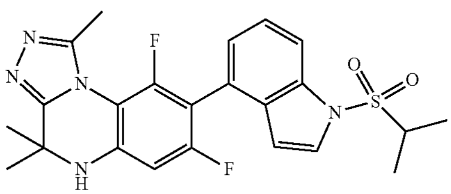 [SMILES: Cc1nnc2n1-c1c(cc(F)c(-c3cccc4c3ccn4S(=O)(=O)C(C)C)c1F)NC2(C)C] | 7,9-Difluoro-8-[1-(isopropylsulfonyl)-1H-indol-4-yl]-1,4,4-trimethyl-5H-[1,2,4]triazolo[4,3-a]quinoxaline |
| 201 | 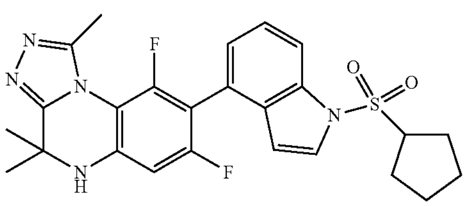 [SMILES: Cc1nnc2n1-c1c(cc(F)c(-c3cccc4c3ccn4S(=O)(=O)C3CCCC3)c1F)NC2(C)C] | 8-[1-(Cyclopentylsulfonyl)-1H-indol-4-yl]-7,9-difluoro-1,4,4-trimethyl-5H-[1,2,4]triazolo[4,3-a]quinoxaline |
| 202 | 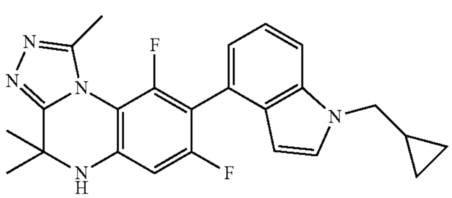 [SMILES: Cc1nnc2n1-c1c(cc(F)c(-c3cccc4c3ccn4CC3CC3)c1F)NC2(C)C] | 8-[1-(Cyclopropyl-methyl)-1H-indol-4-yl]-7,9-difluoro-1,4,4-trimethyl-5H-[1,2,4]triazolo[4,3-a]quinoxaline |
| 203 | 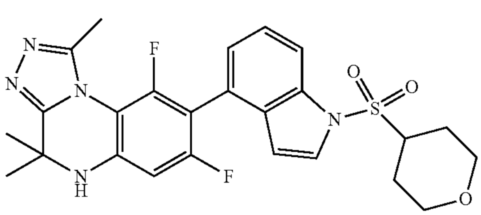 [SMILES: Cc1nnc2n1-c1c(cc(F)c(-c3cccc4c3ccn4S(=O)(=O)C3CCOCC3)c1F)NC2(C)C] | 7,9-Difluoro-1,4,4-trimethyl-8-[1-(tetrahydro-pyran-4-ylsulfonyl)-1H-indol-4-yl]-5H-[1,2,4]triazolo[4,3-a]quinoxaline |
| 204 | 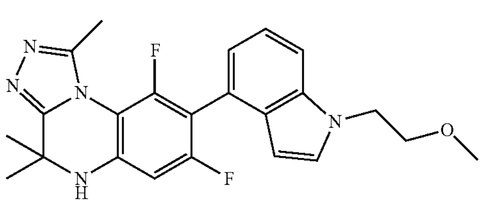 | 7,9-Difluoro-8-[1-(2-methoxy-ethyl)-1H-indol-4-yl]-1,4,4-trimethyl-5H-[1,2,4]triazolo[4,3-a]quinoxaline |

-continued

| Ex. # | Structure | Name |
|---|---|---|
| 205 | 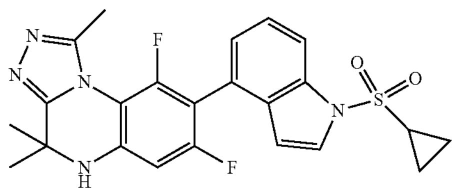 [SMILES: Cc1nnc2n1-c1c(cc(F)c(-c3cccc4c3ccn4S(=O)(=O)C3CC3)c1F)NC2(C)C] | 8-[1-(Cyclopropylsulfonyl)-1H-indol-4-yl]-7,9-difluoro-1,4,4-trimethyl-5H-[1,2,4]triazolo[4,3-a]quinoxaline |
| 207 | 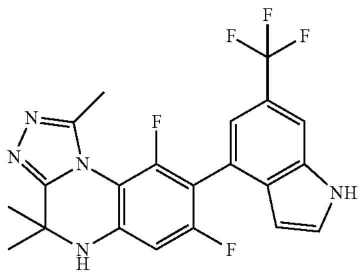 [SMILES: Cc1nnc2n1-c1c(cc(F)c(-c3cc(C(F)(F)F)cc4[nH]ccc34)c1F)NC2(C)C] | 7,9-Difluoro-1,4,4-trimethyl-8-[6-(trifluoromethyl)-1H-indol-4-yl]-5H-[1,2,4]triazolo[4,3-a]quinoxaline |
| 208 | 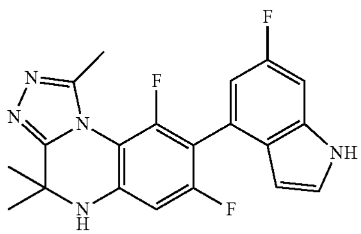 [SMILES: Cc1nnc2n1-c1c(cc(F)c(-c3cc(F)cc4[nH]ccc34)c1F)NC2(C)C] | 7,9-Difluoro-8-(6-fluoro-1H-indol-4-yl)-1,4,4-trimethyl-5H-[1,2,4]triazolo[4,3-a]quinoxaline |
| 210 | 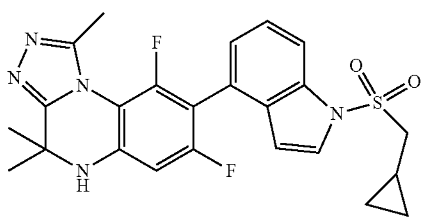 [SMILES: Cc1nnc2n1-c1c(cc(F)c(-c3cccc4c3ccn4S(=O)(=O)CC3CC3)c1F)NC2(C)C] | 8-[1-(Cyclopropyl-methylsulfonyl)-1H-indol-4-yl]-7,9-difluoro-1,4,4-trimethyl-5H-[1,2,4]triazolo[4,3-a]quinoxaline |
| 212 | 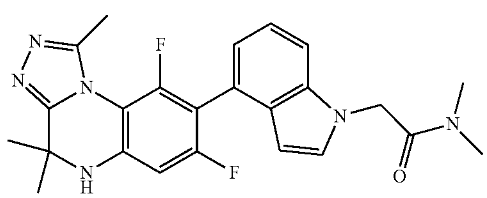 | 2-[4-(7,9-Difluoro-1,4,4-trimethyl-5H-[1,2,4]triazolo[4,3-a]quinoxalin-8-yl)-1H-indol-1-yl]-N,N-dimethyl-acetamide |
| 213 | 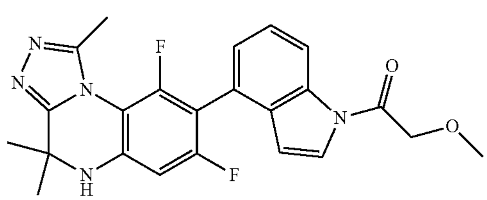 | 1-[4-(7,9-Difluoro-1,4,4-trimethyl-5H-[1,2,4]triazolo[4,3-a]quinoxalin-8-yl)-1H-indol-1-yl]-2-methoxy-ethanone |
| 214 | 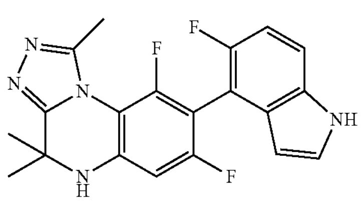 [SMILES: Cc1nnc2n1-c1c(cc(F)c(-c3c(F)ccc4[nH]ccc34)c1F)NC2(C)C] | 7,9-Difluoro-8-(5-fluoro-1H-indol-4-yl)-1,4,4-trimethyl-5H-[1,2,4]triazolo[4,3-a]quinoxaline |

| Ex. # | Structure | Name |
|---|---|---|
| 219 | 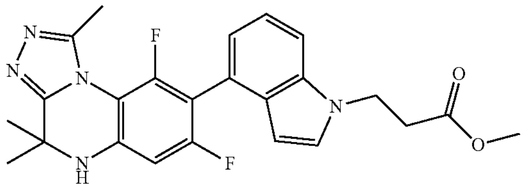 | 3-[4-(7,9-Difluoro-1,4,4-trimethyl-5H-[1,2,4]triazolo[4,3-a]quinoxalin-8-yl)-1H-indol-1-yl]-propionic acid methyl ester |
| 221 | 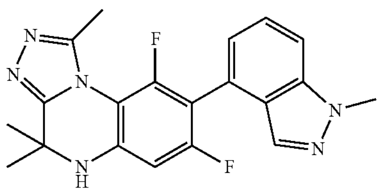 | 7,9-Difluoro-1,4,4-trimethyl-8-(1-methyl-1H-indazol-4-yl)-5H-[1,2,4]triazolo[4,3-a]quinoxaline |
| 222 | 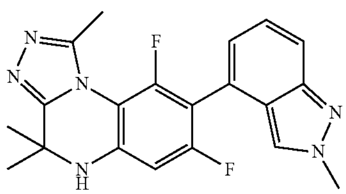 | 7,9-Difluoro-1,4,4-trimethyl-8-(2-methyl-2H-indazol-4-yl)-5H-[1,2,4]triazolo[4,3-a]quinoxaline |
| 223 | 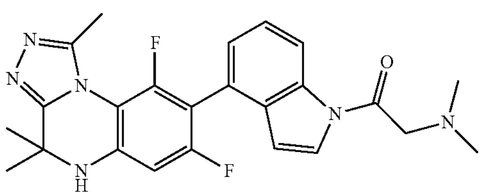 | 1-[4-(7,9-Difluoro-1,4,4-trimethyl-5H-[1,2,4]triazolo[4,3-a]quinoxalin-8-yl)-1H-indol-1-yl]-2-dimethylamino-ethanone |
| 224 | 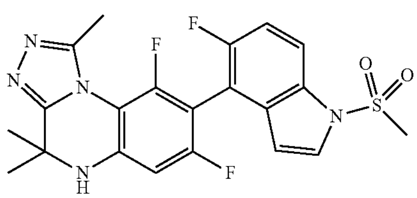 [SMILES: Cc1nnc2n1-c1c(cc(F)c(-c3c(F)ccc4c3ccn4S(C)(=O)=O)c1F)NC2(C)C] | 7,9-Difluoro-8-(5-fluoro-1-methylsulfonyl-1H-indol-4-yl)-1,4,4-trimethyl-5H-[1,2,4]triazolo[4,3-a]quinoxaline |
| 225 | 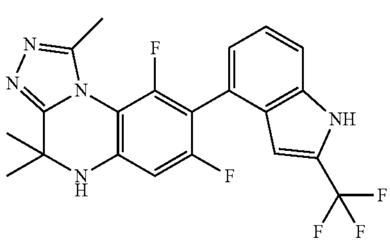 [SMILES: Cc1nnc2n1-c1c(cc(F)c(-c3cccc4[nH]c(C(F)(F)F)cc34)c1F)NC2(C)C] | 7,9-Difluoro-1,4,4-trimethyl-8-[2-(trifluoromethyl)-1H-indol-4-yl]-5H-[1,2,4]triazolo[4,3-a]quinoxaline |
| 228 | 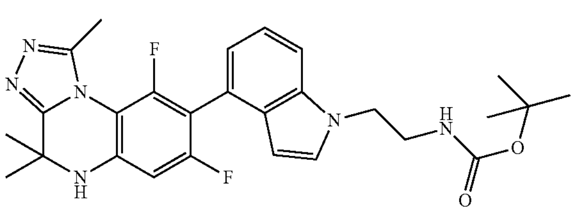 [SMILES: Cc1nnc2n1-c1c(cc(F)c(-c3cccc4c3ccn4CCNC(=O)OC(C)(C)C)c1F)NC2(C)C] | N-[2-[4-(7,9-Difluoro-1,4,4-trimethyl-5H-[1,2,4]triazolo[4,3-a]quinoxalin-8-yl)-1H-indol-1-yl]-ethyl]-carbarmic acid tert-butyl ester |

| Ex. # | Structure | Name |
|---|---|---|
| 229 | 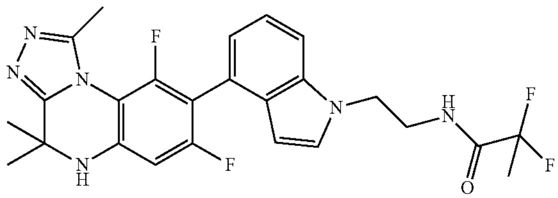 [SMILES: Cc1nnc2n1-c1c(cc(F)c(-c3cccc4c3ccn4CCNC(=O)C(C)(F)F)c1F)NC2(C)C] | N-[2-[4-(7,9-Difluoro-1,4,4-trimethyl-5H-[1,2,4]triazolo[4,3-a]quinoxalin-8-yl)-1H-indol-1-yl]-ethyl]-2,2-difluoro-propionamide |
| 230 | 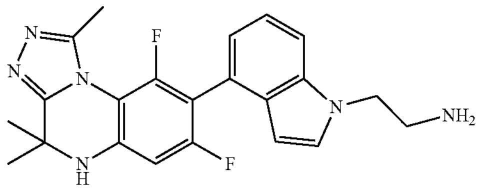 [SMILES: Cc1nnc2n1-c1c(cc(F)c(-c3cccc4c3ccn4CCN)c1F)NC2(C)C] | 2-[4-(7,9-Difluoro-1,4,4-trimethyl-5H-[1,2,4]triazolo[4,3-a]quinoxalin-8-yl)-1H-indol-1-yl]-ethyl-amine |
| 232 | 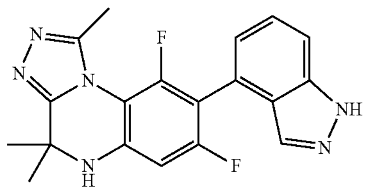 [SMILES: Cc1nnc2n1-c1c(cc(F)c(-c3cccc4[nH]ncc34)c1F)NC2(C)C] | 7,9-Difluoro-8-(1H-indazol-4-yl)-1,4,4-trimethyl-5H-[1,2,4]triazolo[4,3-a]quinoxaline |
| 233 | 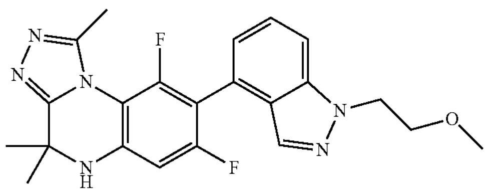 | 7,9-Difluoro-8-[1-(2-methoxy-ethyl)-1H-indazol-4-yl]-1,4,4-trimethyl-5H-[1,2,4]triazolo[4,3-a]quinoxaline |
| 234 | 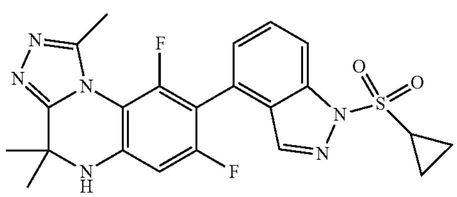 [SMILES: Cc1nnc2n1-c1c(cc(F)c(-c3cccc4c3cnn4S(=O)(=O)C3CC3)c1F)NC2(C)C] | 8-[1-(Cyclopropylsulfonyl)-1H-indazol-4-yl]-7,9-difluoro-1,4,4-trimethyl-5H-[1,2,4]triazolo[4,3-a]quinoxaline |
| 235 | 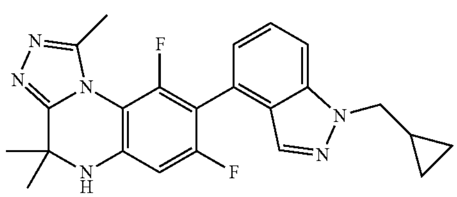 [SMILES: Cc1nnc2n1-c1c(cc(F)c(-c3cccc4c3cnn4CC3CC3)c1F)NC2(C)C] | 8-[1-(Cyclopropyl-methyl)-1H-indazol-4-yl]-7,9-difluoro-1,4,4-trimethyl-5H-[1,2,4]triazolo[4,3-a]quinoxaline |
| 236 | 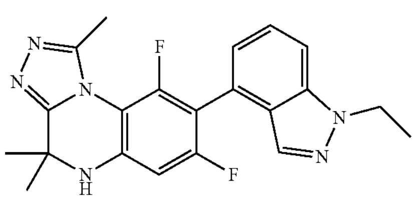 [SMILES: CCn1ncc2c(-c3c(F)cc4c(c3F)-n3c(C)nnc3C(C)(C)N4)cccc21] | 8-(1-Ethyl-1H-indazol-4-yl)-7,9-difluoro-1,4,4-trimethyl-5H-[1,2,4]triazolo[4,3-a]quinoxaline |
| 237 | 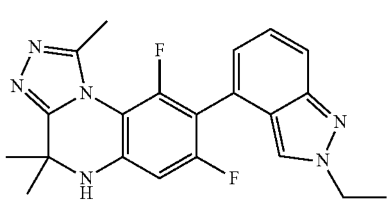 [SMILES: CCn1cc2c(-c3c(F)cc4c(c3F)-n3c(C)nnc3C(C)(C)N4)cccc2n1] | 8-(2-Ethyl-2H-indazol-4-yl)-7,9-difluoro-1,4,4-trimethyl-5H-[1,2,4]triazolo[4,3-a]quinoxaline |

-continued

| Ex. # | Structure | Name |
|---|---|---|
| 238 | 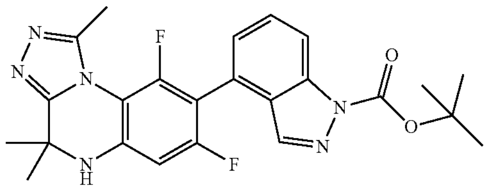 [SMILES: Cc1nnc2n1-c1c(cc(F)c(-c3cccc4c3cnn4C(=O)OC(C)(C)C)c1F)NC2(C)C] | 4-(7,9-Difluoro-1,4,4-trimethyl-5H-[1,2,4]triazolo[4,3-a]quinoxalin-8-yl)-1H-indazole-1-carboxylic acid tert-butyl ester |
| 239 | 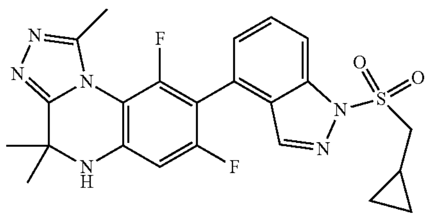 [SMILES: Cc1nnc2n1-c1c(cc(F)c(-c3cccc4c3cnn4S(=O)(=O)CC3CC3)c1F)NC2(C)C] | 8-[1-(Cyclopropyl-methylsulfonyl)-1H-indazol-4-yl]-7,9-difluoro-1,4,4-trimethyl-5H-[1,2,4]triazolo[4,3-a]quinoxaline |
| 240 | 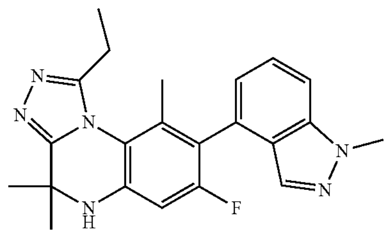 | 1-Ethyl-7-fluoro-4,4,9-trimethyl-8-(1-methyl-1H-indazol-4-yl)-5H-[1,2,4]triazolo[4,3-a]quinoxaline |
| 241 | 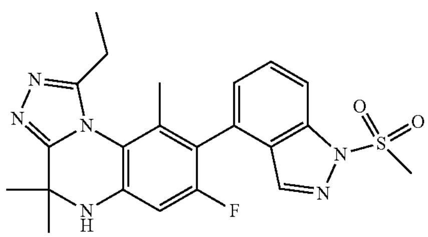 [SMILES: CCc1nnc2n1-c1c(cc(F)c(-c3cccc4c3cnn4S(C)(=O)=O)c1C)NC2(C)C] | 1-Ethyl-7-fluoro-4,4,9-trimethyl-8-(1-methylsulfonyl-1H-indazol-4-yl)-5H-[1,2,4]triazolo[4,3-a]quinoxaline |
| 242 | 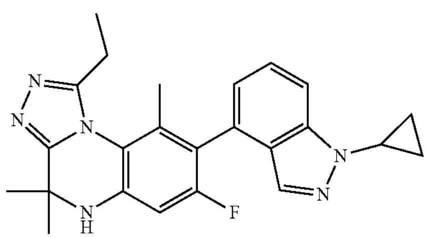 [SMILES: CCc1nnc2n1-c1c(cc(F)c(-c3cccc4c3cnn4C3CC3)c1C)NC2(C)C] | 8-(1-Cyclopropyl-1H-indazol-4-yl)-1-ethyl-7-fluoro-4,4,9-trimethyl-5H-[1,2,4]triazolo[4,3-a]quinoxaline |
| 243 | 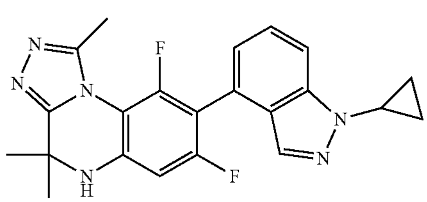 [SMILES: Cc1nnc2n1-c1c(cc(F)c(-c3cccc4c3cnn4C3CC3)c1F)NC2(C)C] | 8-(1-Cyclopropyl-1H-indazol-4-yl)-7,9-difluoro-1,4,4-trimethyl-5H-[1,2,4]triazolo[4,3-a]quinoxaline |
| 244 | 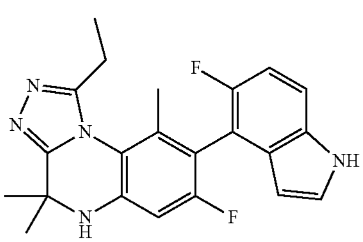 [SMILES: CCc1nnc2n1-c1c(cc(F)c(-c3c(F)ccc4[nH]ccc34)c1C)NC2(C)C] | 1-Ethyl-7-fluoro-8-(5-fluoro-1H-indol-4-yl)-4,4,9-trimethyl-5H-[1,2,4]triazolo[4,3-a]quinoxaline |

| Ex. # | Structure | Name |
|---|---|---|
| 247 | 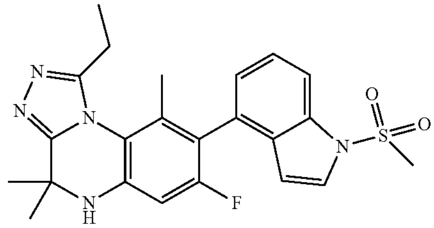 [SMILES: CCc1nnc2n1-c1c(cc(F)c(-c3cccc4c3ccn4S(C)(=O)=O)c1C)NC2(C)C] | 1-Ethyl-7-fluoro-4,4,9-trimethyl-8-(1-methylsulfonyl-1H-indol-4-yl)-5H-[1,2,4]triazolo[4,3-a]quinoxaline |
| 248 | 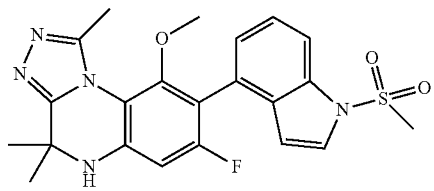 [SMILES: COc1c(-c2cccc3c2ccn3S(C)(=O)=O)c(F)cc2c1-n1c(C)nnc1C(C)(C)N2] | 7-Fluoro-9-methoxy-1,4,4-trimethyl-8-(1-methylsulfonyl-1H-indol-4-yl)-5H-[1,2,4]triazolo[4,3-a]quinoxaline |
| 249 | 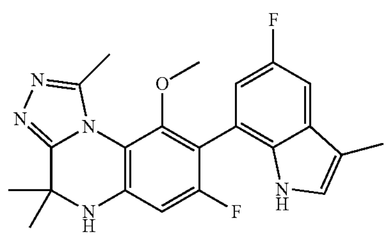 | 7-Fluoro-8-(5-fluoro-3-methyl-1H-indol-7-yl)-9-methoxy-1,4,4-trimethyl-5H-[1,2,4]triazolo[4,3-a]quinoxaline |
| 250 | 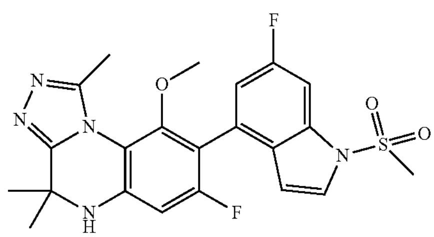 [SMILES: COc1c(-c2cc(F)cc3c2ccn3S(C)(=O)=O)c(F)cc2c1-n1c(C)nnc1C(C)(C)N2] | 7-Fluoro-8-(6-fluoro-1-methylsulfonyl-1H-indol-4-yl)-9-methoxy-1,4,4-trimethyl-5H-[1,2,4]triazolo[4,3-a]quinoxaline |
| 251 | 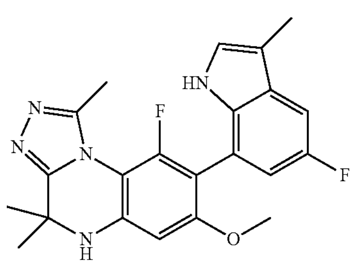 [SMILES: COc1cc2c(c(F)c1-c1cc(F)cc3c(C)c[nH]c13)-n1c(C)nnc1C(C)(C)N2] | 9-Fluoro-8-(5-fluoro-3-methyl-1H-indol-7-yl)-7-methoxy-1,4,4-trimethyl-5H-[1,2,4]triazolo[4,3-a]quinoxaline |
| 252 | 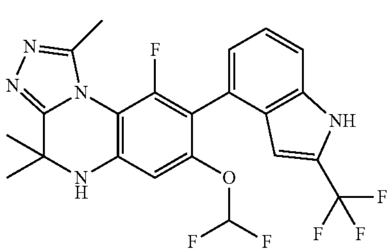 [SMILES: Cc1nnc2n1-c1c(cc(OC(F)F)c(-c3cccc4[nH]c(C(F)(F)F)cc34)c1F)NC2(C)C] | 7-(Difluoro-methoxy)-9-fluoro-1,4,4-trimethyl-8-[2-(trifluoromethyl)-1H-indol-4-yl]-5H-[1,2,4]triazolo[4,3-a]quinoxaline |

| Ex. # | Structure | Name |
|---|---|---|
| 253 | 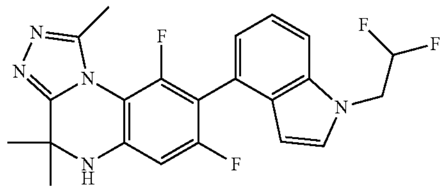 [SMILES: Cc1nnc2n1-c1c(cc(F)c(-c3cccc4c3ccn4CC(F)F)c1F)NC2(C)C] | 8-[1-(2,2-Difluoro-ethyl)-1H-indol-4-yl]-7,9-difluoro-1,4,4-trimethyl-5H-[1,2,4]triazolo[4,3-a]quinoxaline |
| 254 | 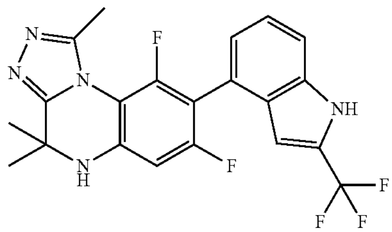 [SMILES: Cc1nnc2n1-c1c(cc(F)c(-c3cccc4[nH]c(C(F)(F)F)cc34)c1F)NC2(C)C] | 7-Chloro-9-fluoro-1,4,4-trimethyl-8-[2-(trifluoromethyl)-1H-indol-4-yl]-5H-[1,2,4]triazolo[4,3-a]quinoxaline |
| 255 | 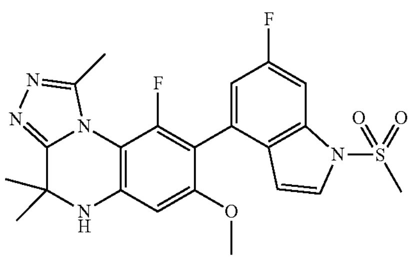 | 9-Fluoro-8-(6-fluoro-1-methylsulfonyl-1H-indol-4-yl)-7-methoxy-1,4,4-trimethyl-5H-[1,2,4]triazolo[4,3-a]quinoxaline |
| 256 | 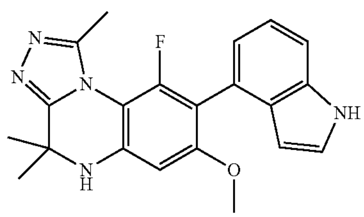 [SMILES: COc1cc2c(c(F)c1-c1cccc3[nH]ccc13)-n1c(C)nnc1C(C)(C)N2] | 9-Fluoro-8-(1H-indol-4-yl)-7-methoxy-1,4,4-trimethyl-5H-[1,2,4]triazolo[4,3-a]quinoxaline |
| 257 | 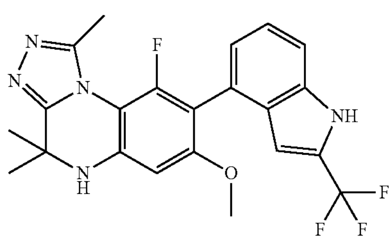 [SMILES: COc1cc2c(c(F)c1-c1cccc3[nH]c(C(F)(F)F)cc13)-n1c(C)nnc1C(C)(C)N2] | 9-Fluoro-7-methoxy-1,4,4-trimethyl-8-[2-(trifluoromethyl)-1H-indol-4-yl]-5H-[1,2,4]triazolo[4,3-a]quinoxaline |
| 258 | 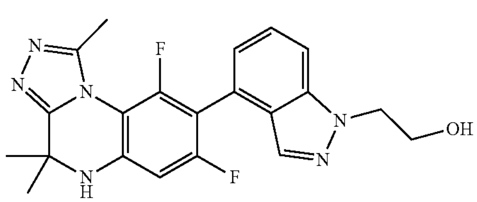 [SMILES: Cc1nnc2n1-c1c(cc(F)c(-c3cccc4c3cnn4CCO)c1F)NC2(C)C] | 2-[4-(7,9-Difluoro-1,4,4-trimethyl-5H-[1,2,4]triazolo[4,3-a]quinoxalin-8-yl)-1H-indazol-1-yl]-ethanol |
| 259 | 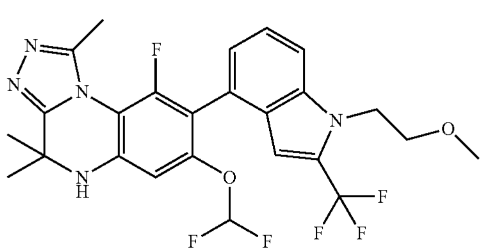 | 7-(Difluoro-methoxy)-9-fluoro-8-[1-(2-methoxy-ethyl)-2-(trifluoromethyl)-1H-indol-4-yl]-1,4,4-trimethyl-5H-[1,2,4]triazolo[4,3-a]quinoxaline |

-continued

| Ex. # | Structure | Name |
|---|---|---|
| 260 | 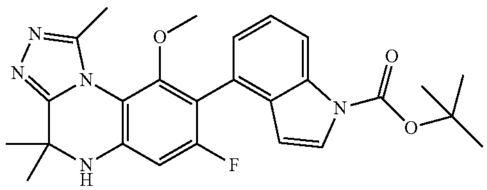 [SMILES: COc1c(-c2cccc3c2ccn3C(=O)OC(C)(C)C)c(F)cc2c1-n1c(C)nnc1C(C)(C)N2] | 4-(7-Fluoro-9-methoxy-1,4,4-trimethyl-5H-[1,2,4]triazolo[4,3-a]quinoxalin-8-yl)-1H-indole-1-carboxylic acid tert-butyl ester |
| 263 | 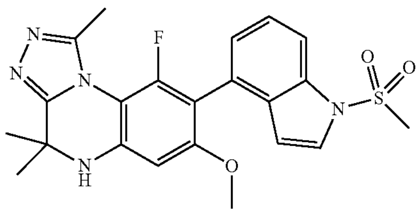 [SMILES: COc1cc2c(c(F)c1-c1cccc3c1ccn3S(C)(=O)=O)-n1c(C)nnc1C(C)(C)N2] | 9-Fluoro-7-methoxy-1,4,4-trimethyl-8-(1-methylsulfonyl-1H-indol-4-yl)-5H-[1,2,4]triazolo[4,3-a]quinoxaline |
| 264 | 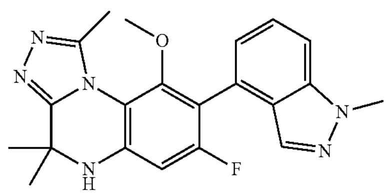 | 7-Fluoro-9-methoxy-1,4,4-trimethyl-8-(1-methyl-1H-indazol-4-yl)-5H-[1,2,4]triazolo[4,3-a]quinoxaline |
| 266 | 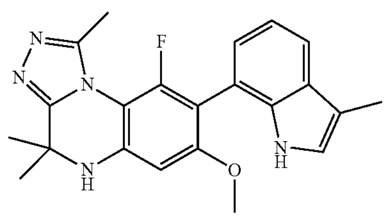 | 9-Fluoro-7-methoxy-1,4,4-trimethyl-8-(3-methyl-1H-indol-7-yl)-5H-[1,2,4]triazolo[4,3-a]quinoxaline |
| 267 | 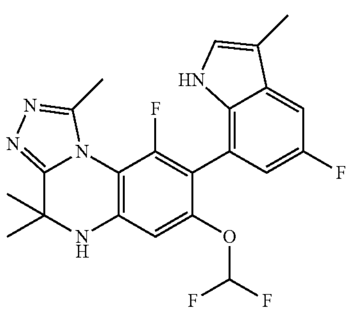 [SMILES: Cc1c[nH]c2c(-c3c(OC(F)F)cc4c(c3F)-n3c(C)nnc3C(C)(C)N4)cc(F)cc12] | 7-(Difluoro-methoxy)-9-fluoro-8-(5-fluoro-3-methyl-1H-indol-7-yl)-1,4,4-trimethyl-5H-[1,2,4]triazolo[4,3-a]quinoxaline |
| 268 | 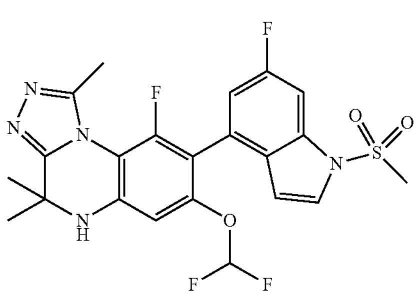 [SMILES: Cc1nnc2n1-c1c(cc(OC(F)F)c(-c3cc(F)cc4c3ccn4S(C)(=O)=O)c1F)NC2(C)C] | 7-(Difluoro-methoxy)-9-fluoro-8-(6-fluoro-1-methylsulfonyl-1H-indol-4-yl)-1,4,4-trimethyl-5H-[1,2,4]triazolo[4,3-a]quinoxaline |

-continued

| Ex. # | Structure | Name |
|---|---|---|
| 269 | 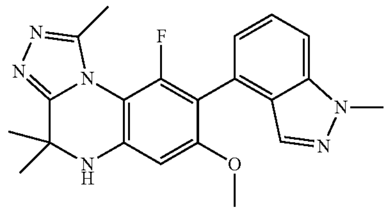 | 9-Fluoro-7-methoxy-1,4,4-trimethyl-8-(1-methyl-1H-indazol-4-yl)-5H-[1,2,4]triazolo[4,3-a]quinoxaline |
| 270 | 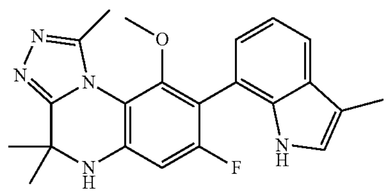 | 7-Fluoro-9-methoxy-1,4,4-trimethyl-8-(3-methyl-1H-indol-7-yl)-5H-[1,2,4]triazolo[4,3-a]quinoxaline |
| 271 | 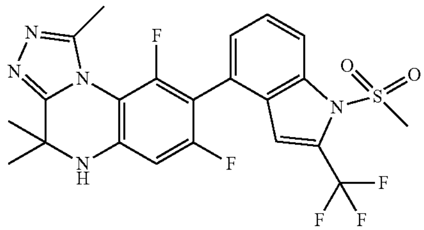 [SMILES: Cc1nnc2n1-c1c(cc(F)c(-c3cccc4c3cc(C(F)(F)F)n4S(C)(=O)=O)c1F)NC2(C)C] | 7,9-Difluoro-1,4,4-trimethyl-8-[1-methylsulfonyl-2-(trifluoromethyl)-1H-indol-4-yl]-5H-[1,2,4]triazolo[4,3-a]quinoxaline |
| 272 | 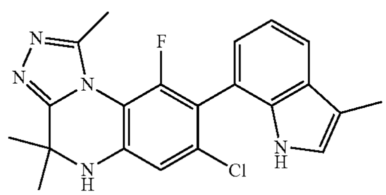 | 7-Chloro-9-fluoro-1,4,4-trimethyl-8-(3-methyl-1H-indol-7-yl)-5H-[1,2,4]triazolo[4,3-a]quinoxaline |
| 273 | 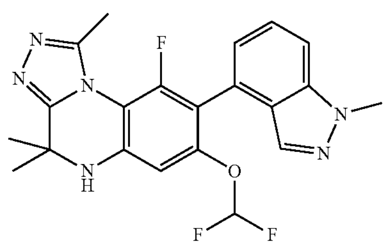 | 7-(Difluoro-methoxy)-9-fluoro-1,4,4-trimethyl-8-(1-methyl-1H-indazol-4-yl)-5H-[1,2,4]triazolo[4,3-a]quinoxaline |
| 275 | 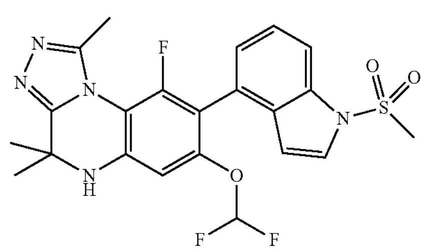 [SMILES: Cc1nnc2n1-c1c(cc(OC(F)F)c(-c3cccc4c3ccn4S(C)(=O)=O)c1F)NC2(C)C] | 7-(Difluoro-methoxy)-9-fluoro-1,4,4-trimethyl-8-(1-methylsulfonyl-1H-indol-4-yl)-5H-[1,2,4]triazolo[4,3-a]quinoxaline |
| 276 | 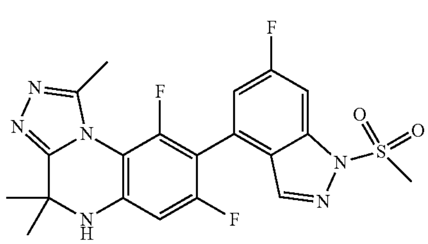 [SMILES: Cc1nnc2n1-c1c(cc(F)c(-c3cc(F)cc4c3cnn4S(C)(=O)=O)c1F)NC2(C)C] | 7,9-Difluoro-8-(6-fluoro-1-methylsulfonyl-1H-indazol-4-yl)-1,4,4-trimethyl-5H-[1,2,4]triazolo[4,3-a]quinoxaline |

| Ex. # | Structure | Name |
|---|---|---|
| 277 | 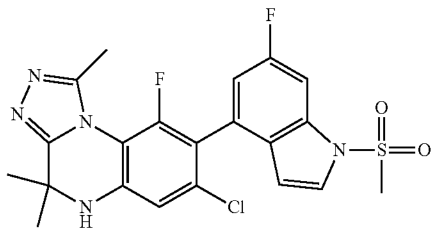 [SMILES: Cc1nnc2n1-c1c(cc(Cl)c(-c3cc(F)cc4c3ccn4S(C)(=O)=O)c1F)NC2(C)C] | 7-Chloro-9-fluoro-8-(6-fluoro-1-methylsulfonyl-1H-indol-4-yl)-1,4,4-trimethyl-5H-[1,2,4]triazolo[4,3-a]quinoxaline |
| 278 | 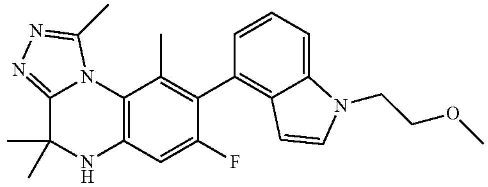 | 7-Fluoro-8-[1-(2-methoxy-ethyl)-1H-indol-4-yl]-1,4,4,9-tetramethyl-5H-[1,2,4]triazolo[4,3-a]quinoxaline |
| 279 | 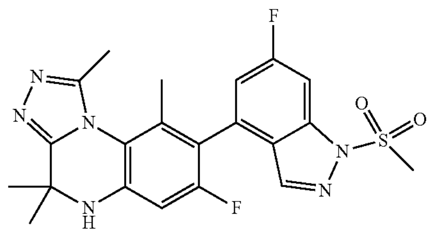 [SMILES: Cc1c(-c2cc(F)cc3c2cnn3S(C)(=O)=O)c(F)cc2c1-n1c(C)nnc1C(C)(C)N2] | 7-Fluoro-8-(6-fluoro-1-methylsulfonyl-1H-indazol-4-yl)-1,4,4,9-tetramethyl-5H-[1,2,4]triazolo[4,3-a]quinoxaline |
| 280 | 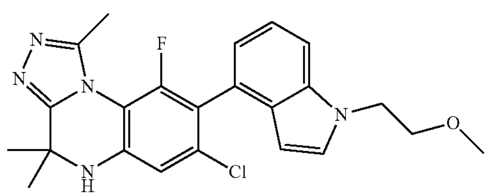 | 7-Chloro-9-fluoro-8-[1-(2-methoxy-ethyl)-1H-indol-4-yl]-1,4,4-trimethyl-5H-[1,2,4]triazolo[4,3-a]quinoxaline |
| 281 | 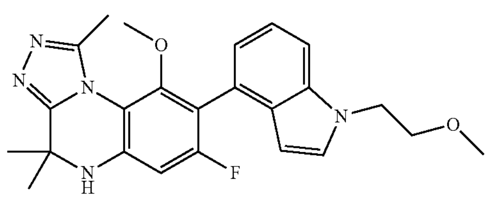 | 7-Fluoro-9-methoxy-8-[1-(2-methoxy-ethyl)-1H-indol-4-yl]-1,4,4-trimethyl-5H-[1,2,4]triazolo[4,3-a]quinoxaline |
| 282 | 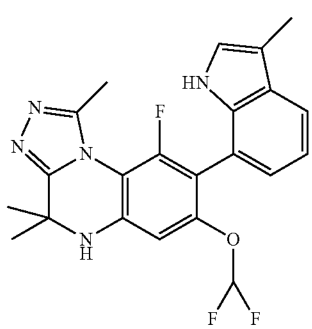 [SMILES: Cc1c[nH]c2c(-c3c(OC(F)F)cc4c(c3F)-n3c(C)nnc3C(C)(C)N4)cccc12] | 7-(Difluoro-methoxy)-9-fluoro-1,4,4-trimethyl-8-(3-methyl-1H-indol-7-yl)-5H-[1,2,4]triazolo[4,3-a]quinoxaline |

| Ex. # | Structure | Name |
|---|---|---|
| 283 | 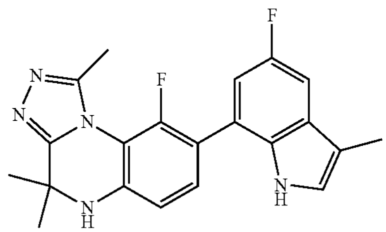 | 9-Fluoro-8-(5-fluoro-3-methyl-1H-indol-7-yl)-1,4,4-trimethyl-5H-[1,2,4]triazolo[4,3-a]quinoxaline |
| 284 | 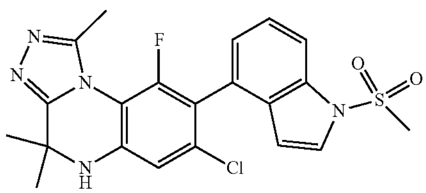 [SMILES: Cc1nnc2n1-c1c(cc(Cl)c(-c3cccc4c3ccn4S(C)(=O)=O)c1F)NC2(C)C] | 7-Chloro-9-fluoro-1,4,4-trimethyl-8-(1-methylsulfonyl-1H-indol-4-yl)-5H-[1,2,4]triazolo[4,3-a]quinoxaline |
| 285 | 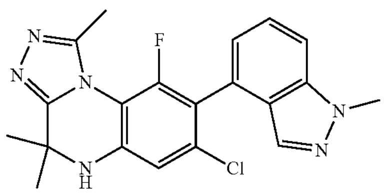 | 7-Chloro-9-fluoro-1,4,4-trimethyl-8-(1-methyl-1H-indazol-4-yl)-5H-[1,2,4]triazolo[4,3-a]quinoxaline |
| 286 | 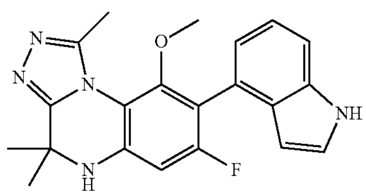 [SMILES: COc1c(-c2cccc3[nH]ccc23)c(F)cc2c1-n1c(C)nnc1C(C)(C)N2] | 7-Fluoro-8-(1H-indol-4-yl)-9-methoxy-1,4,4-trimethyl-5H-[1,2,4]triazolo[4,3-a]quinoxaline |
| 287 | 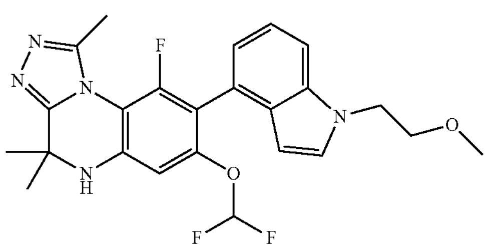 | 7-(Difluoro-methoxy)-9-fluoro-8-[1-(2-methoxy-ethyl)-1H-indol-4-yl]-1,4,4-trimethyl-5H-[1,2,4]triazolo[4,3-a]quinoxaline |
| 288 | 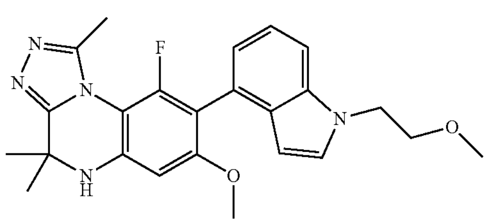 | 9-Fluoro-7-methoxy-8-[1-(2-methoxy-ethyl)-1H-indol-4-yl]-1,4,4-trimethyl-5H-[1,2,4]triazolo[4,3-a]quinoxaline |
| 289 | 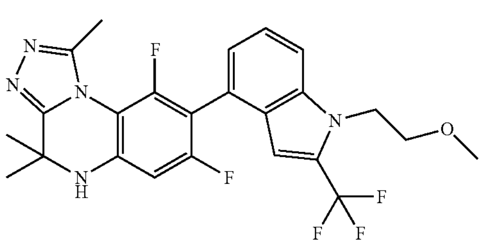 | 7,9-Difluoro-8-[1-(2-methoxy-ethyl)-2-(trifluoromethyl)-1H-indol-4-yl]-1,4,4-trimethyl-5H-[1,2,4]triazolo[4,3-a]quinoxaline |

| Ex. # | Structure | Name |
|---|---|---|
| 290 | 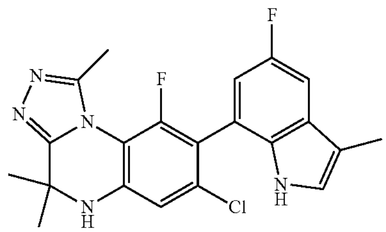 | 7-Chloro-9-fluoro-8-(5-fluoro-3-methyl-1H-indol-7-yl)-1,4,4-trimethyl-5H-[1,2,4]triazolo[4,3-a]quinoxaline |
| 292 | 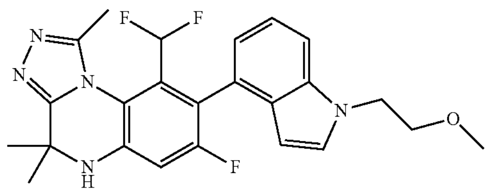 | 9-(Difluoro-methyl)-7-fluoro-8-[1-(2-methoxy-ethyl)-1H-indol-4-yl]-1,4,4-trimethyl-5H-[1,2,4]triazolo[4,3-a]quinoxaline |
| 293 | 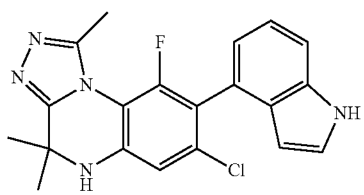 [SMILES: Cc1nnc2n1-c1c(cc(Cl)c(-c3cccc4[nH]ccc34)c1F)NC2(C)C] | 7-Chloro-9-fluoro-8-(1H-indol-4-yl)-1,4,4-trimethyl-5H-[1,2,4]triazolo[4,3-a]quinoxaline |
| 294 | 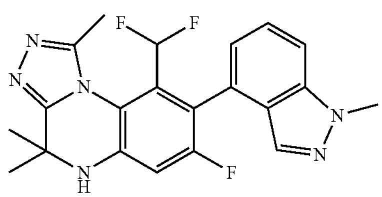 | 9-(Difluoro-methyl)-7-fluoro-1,4,4-trimethyl-8-(1-methyl-1H-indazol-4-yl)-5H-[1,2,4]triazolo[4,3-a]quinoxaline |
| 295 | 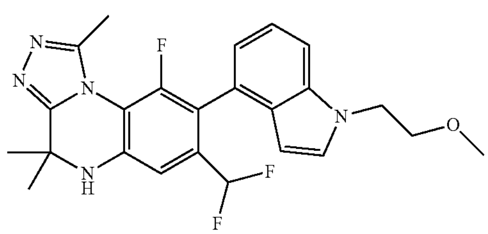 | 7-(Difluoro-methyl)-9-fluoro-8-[1-(2-methoxy-ethyl)-1H-indol-4-yl]-1,4,4-trimethyl-5H-[1,2,4]triazolo[4,3-a]quinoxaline |
| 296 | 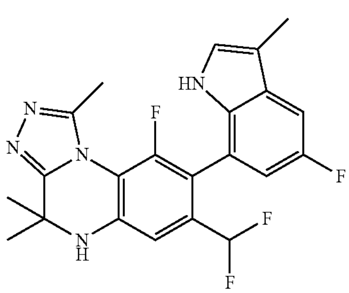 [SMILES: Cc1c[nH]c2c(-c3c(C(F)F)cc4c(c3F)-n3c(C)nnc3C(C)(C)N4)cc(F)cc12] | 7-(Difluoro-methyl)-9-fluoro-8-(5-fluoro-3-methyl-1H-indol-7-yl)-1,4,4-trimethyl-5H-[1,2,4]triazolo[4,3-a]quinoxaline |

| Ex. # | Structure | Name |
|---|---|---|
| 297 | 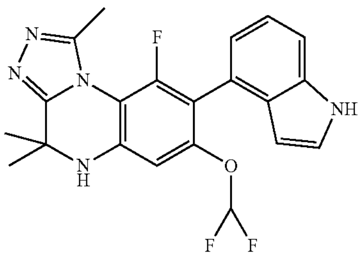 [SMILES: Cc1nnc2n1-c1c(cc(OC(F)F)c(-c3cccc4[nH]ccc34)c1F)NC2(C)C] | 7-(Difluoro-methoxy)-9-fluoro-8-(1H-indol-4-yl)-1,4,4-trimethyl-5H-[1,2,4]triazolo[4,3-a]quinoxaline |
| 298 | 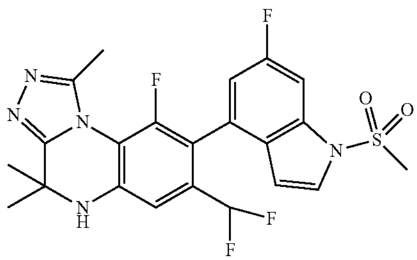 [SMILES: Cc1nnc2n1-c1c(cc(C(F)F)c(-c3cc(F)cc4c3ccn4S(C)(=O)=O)c1F)NC2(C)C] | 7-(Difluoro-methyl)-9-fluoro-8-(6-fluoro-1-methylsulfonyl-1H-indol-4-yl)-1,4,4-trimethyl-5H-[1,2,4]triazolo[4,3-a]quinoxaline |
| 299 | 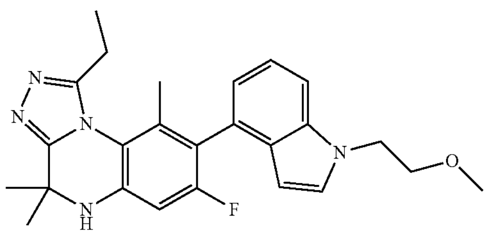 | 1-Ethyl-7-fluoro-8-[1-(2-methoxy-ethyl)-1H-indol-4-yl]-4,4,9-trimethyl-5H-[1,2,4]triazolo[4,3-a]quinoxaline |
| 302 | 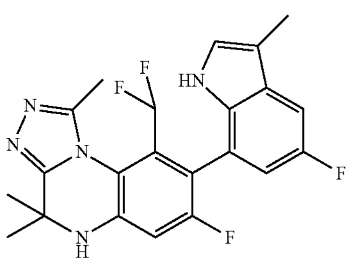 [SMILES: Cc1c[nH]c2c(-c3c(F)cc4c(c3C(F)F)-n3c(C)nnc3C(C)(C)N4)cc(F)cc12] | 9-(Difluoro-methyl)-7-fluoro-8-(5-fluoro-3-methyl-1H-indol-7-yl)-1,4,4-trimethyl-5H-[1,2,4]triazolo[4,3-a]quinoxaline |
| 306 | 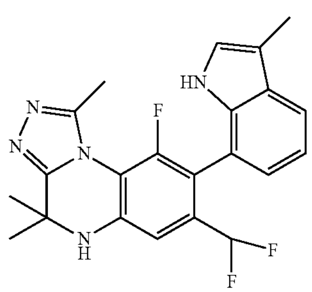 [SMILES: Cc1c[nH]c2c(-c3c(C(F)F)cc4c(c3F)-n3c(C)nnc3C(C)(C)N4)cccc12] | 7-(Difluoro-methyl)-9-fluoro-1,4,4-trimethyl-8-(3-methyl-1H-indol-7-yl)-5H-[1,2,4]triazolo[4,3-a]quinoxaline |
| 309 | 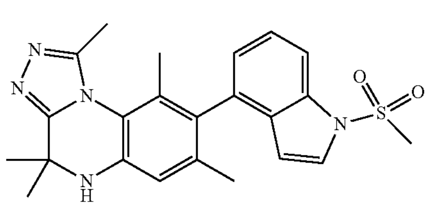 [SMILES: Cc1cc2c(c(C)c1-c1cccc3c1ccn3S(C)(=O)=O)-n1c(C)nnc1C(C)(C)N2] | 1,4,4,7,9-Pentamethyl-8-(1-methylsulfonyl-1H-indol-4-yl)-5H-[1,2,4]triazolo[4,3-a]quinoxaline |

| Ex. # | Structure | Name |
|---|---|---|
| 310 | 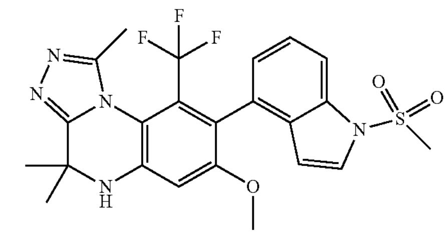 [SMILES: COc1cc2c(c(C(F)(F)F)c1-c1cccc3c1ccn3S(C)(=O)=O)-n1c(C)nnc1C(C)(C)N2] | 7-Methoxy-1,4,4-trimethyl-8-(1-methylsulfonyl-1H-indol-4-yl)-9-(trifluoromethyl)-5H-[1,2,4]triazolo[4,3-a]quinoxaline |
| 312 | 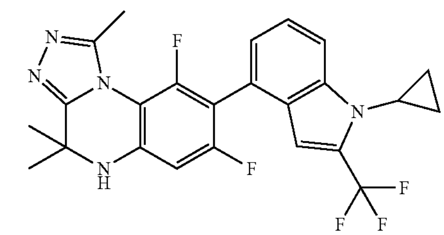 [SMILES: Cc1nnc2n1-c1c(cc(F)c(-c3cccc4c3cc(C(F)(F)F)n4C3CC3)c1F)NC2(C)C] | 8-[1-Cyclopropyl-2-(trifluoromethyl)-1H-indol-4-yl]-7,9-difluoro-1,4,4-trimethyl-5H-[1,2,4]triazolo[4,3-a]quinoxaline |
| 313 | 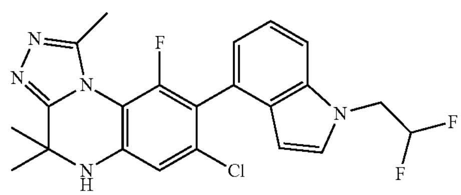 [SMILES: Cc1nnc2n1-c1c(cc(Cl)c(-c3cccc4c3ccn4CC(F)F)c1F)NC2(C)C] | 7-Chloro-8-[1-(2,2-difluoro-ethyl)-1H-indol-4-yl]-9-fluoro-1,4,4-trimethyl-5H-[1,2,4]triazolo[4,3-a]quinoxaline |
| 314 | 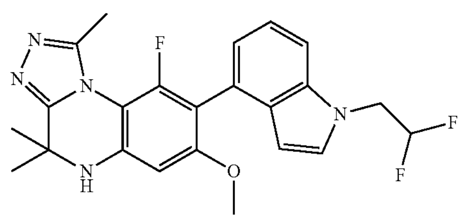 [SMILES: COc1cc2c(c(F)c1-c1cccc3c1ccn3CC(F)F)-n1c(C)nnc1C(C)(C)N2] | 8-[1-(2,2-Difluoro-ethyl)-1H-indol-4-yl]-9-fluoro-7-methoxy-1,4,4-trimethyl-5H-[1,2,4]triazolo[4,3-a]quinoxaline |
| 315 | 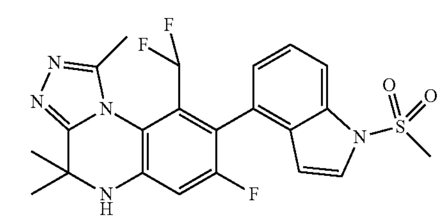 [SMILES: Cc1nnc2n1-c1c(cc(F)c(-c3cccc4c3ccn4S(C)(=O)=O)c1C(F)F)NC2(C)C] | 9-(Difluoro-methyl)-7-fluoro-1,4,4-trimethyl-8-(1-methylsulfonyl-1H-indol-4-yl)-5H-[1,2,4]triazolo[4,3-a]quinoxaline |
| 317 | 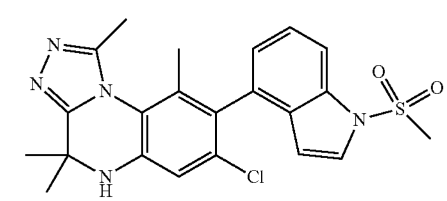 [SMILES: Cc1c(-c2cccc3c2ccn3S(C)(=O)=O)c(Cl)cc2c1-n1c(C)nnc1C(C)(C)N2] | 7-Chloro-1,4,4,9-tetramethyl-8-(1-methylsulfonyl-1H-indol-4-yl)-5H-[1,2,4]triazolo[4,3-a]quinoxaline |
| 318 | 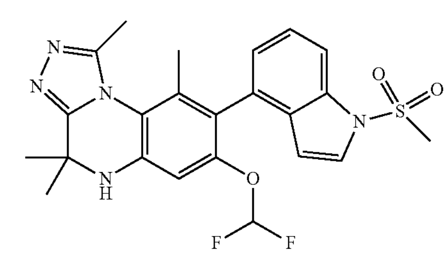 [SMILES: Cc1c(-c2cccc3c2ccn3S(C)(=O)=O)c(OC(F)F)cc2c1-n1c(C)nnc1C(C)(C)N2] | 7-(Difluoro-methoxy)-1,4,4,9-tetramethyl-8-(1-methylsulfonyl-1H-indol-4-yl)-5H-[1,2,4]triazolo[4,3-a]quinoxaline |

| Ex. # | Structure | Name |
|---|---|---|
| 319 | 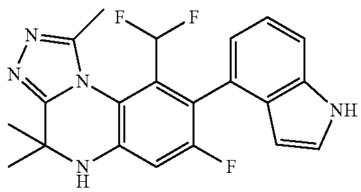 [SMILES: Cc1nnc2n1-c1c(cc(F)c(-c3cccc4[nH]ccc34)c1C(F)F)NC2(C)C] | 9-(Difluoro-methyl)-7-fluoro-8-(1H-indol-4-yl)-1,4,4-trimethyl-5H-[1,2,4]triazolo[4,3-a]quinoxaline |
| 320 | 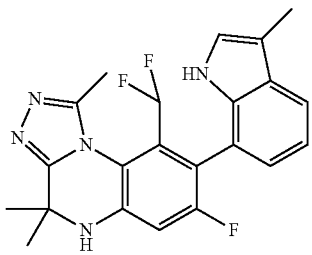 [SMILES: Cc1c[nH]c2c(-c3c(F)cc4c(c3C(F)F)-n3c(C)nnc3C(C)(C)N4)cccc12] | 9-(Difluoro-methyl)-7-fluoro-1,4,4-trimethyl-8-(3-methyl-1H-indol-7-yl)-5H-[1,2,4]triazolo[4,3-a]quinoxaline |
| 321 | 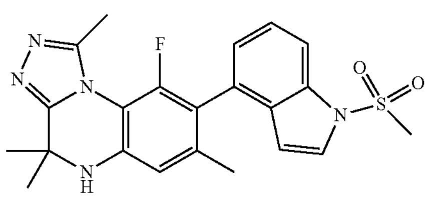 | 9-Fluoro-1,4,4,7-tetramethyl-8-(1-methylsulfonyl-1H-indol-4-yl)-5H-[1,2,4]triazolo[4,3-a]quinoxaline |
| 324 | 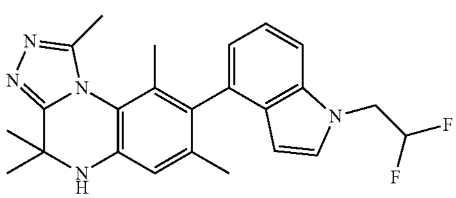 [SMILES: Cc1cc2c(c(C)c1-c1cccc3c1ccn3CC(F)F)-n1c(C)nnc1C(C)(C)N2] | 8-[1-(2,2-Difluoro-ethyl)-1H-indol-4-yl]-1,4,4,7,9-pentamethyl-5H-[1,2,4]triazolo[4,3-a]quinoxaline |
| 325 | 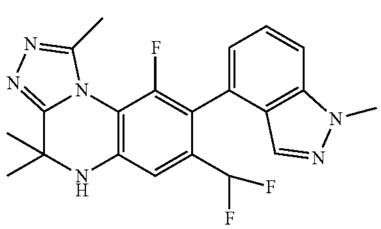 | 7-(Difluoro-methyl)-9-fluoro-1,4,4-trimethyl-8-(1-methyl-1H-indazol-4-yl)-5H-[1,2,4]triazolo[4,3-a]quinoxaline |
| 327 | 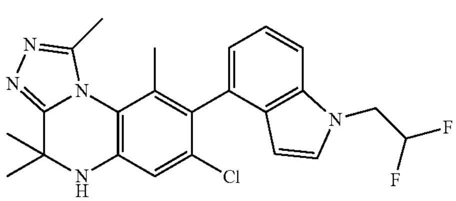 [SMILES: Cc1c(-c2cccc3c2ccn3CC(F)F)c(Cl)cc2c1-n1c(C)nnc1C(C)(C)N2] | 7-Chloro-8-[1-(2,2-difluoro-ethyl)-1H-indol-4-yl]-1,4,4,9-tetramethyl-5H-[1,2,4]triazolo[4,3-a]quinoxaline |
| 328 | 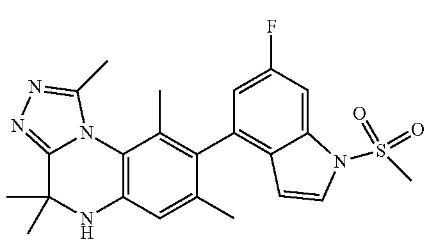 [SMILES: Cc1cc2c(c(C)c1-c1cc(F)cc3c1ccn3S(C)(=O)=O)-n1c(C)nnc1C(C)(C)N2] | 8-(6-Fluoro-1-methylsulfonyl-1H-indol-4-yl)-1,4,4,7,9-pentamethyl-5H-[1,2,4]triazolo[4,3-a]quinoxaline |

-continued

| Ex. # | Structure | Name |
|---|---|---|
| 329 | 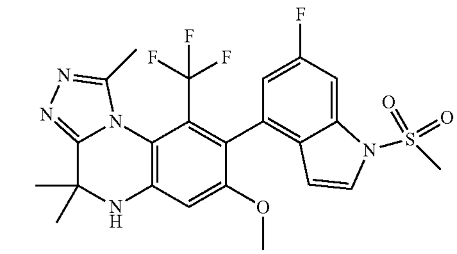 [SMILES: COc1cc2c(c(C(F)(F)F)c1-c1cc(F)cc3c1ccn3S(C)(=O)=O)-n1c(C)nnc1C(C)(C)N2] | 8-(6-Fluoro-1-methylsulfonyl-1H-indol-4-yl)-7-methoxy-1,4,4-trimethyl-9-(trifluoromethyl)-5H-[1,2,4]triazolo[4,3-a]quinoxaline |
| 330 | 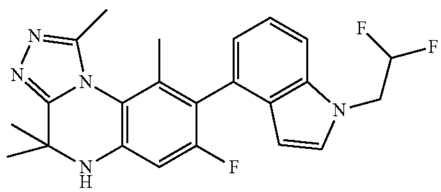 [SMILES: Cc1c(-c2cccc3c2ccn3CC(F)F)c(F)cc2c1-n1c(C)nnc1C(C)(C)N2] | 8-[1-(2,2-Difluoro-ethyl)-1H-indol-4-yl]-7-fluoro-1,4,4,9-tetramethyl-5H-[1,2,4]triazolo[4,3-a]quinoxaline |
| 331 | 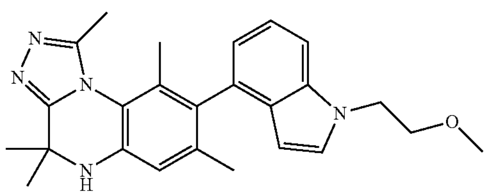 | 8-[1-(2-Methoxy-ethyl)-1H-indol-4-yl]-1,4,4,7,9-pentamethyl-5H-[1,2,4]triazolo[4,3-a]quinoxaline |
| 332 | 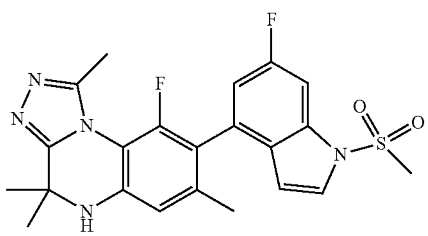 [SMILES: Cc1cc2c(c(F)c1-c1cc(F)cc3c1ccn3S(C)(=O)=O)-n1c(C)nnc1C(C)(C)N2] | 9-Fluoro-8-(6-fluoro-1-methylsulfonyl-1H-indol-4-yl)-1,4,4,7-tetramethyl-5H-[1,2,4]triazolo[4,3-a]quinoxaline |
| 333 | 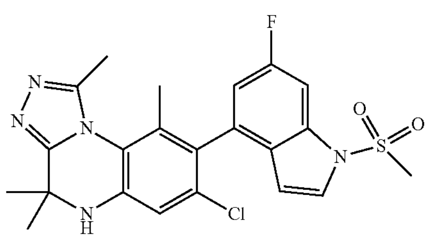 [SMILES: Cc1c(-c2cc(F)cc3c2ccn3S(C)(=O)=O)c(Cl)cc2c1-n1c(C)nnc1C(C)(C)N2] | 7-Chloro-8-(6-fluoro-1-methylsulfonyl-1H-indol-4-yl)-1,4,4,9-tetramethyl-5H-[1,2,4]triazolo[4,3-a]quinoxaline |
| 334 | 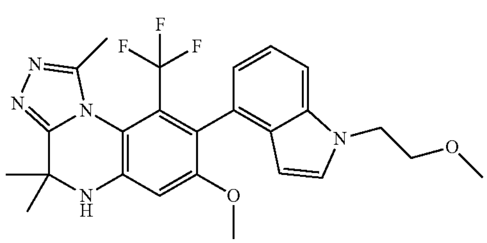 | 7-Methoxy-8-[1-(2-methoxy-ethyl)-1H-indol-4-yl]-1,4,4-trimethyl-9-(trifluoromethyl)-5H-[1,2,4]triazolo[4,3-a]quinoxaline |

| Ex. # | Structure | Name |
|---|---|---|
| 335 | 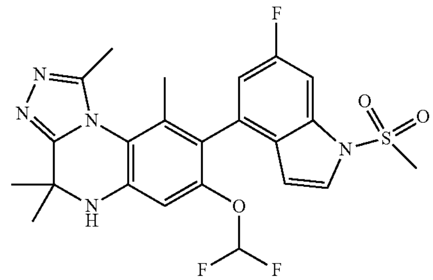 [SMILES: Cc1c(-c2cc(F)cc3c2ccn3S(C)(=O)=O)c(OC(F)F)cc2c1-n1c(C)nnc1C(C)(C)N2] | 7-(Difluoro-methoxy)-8-(6-fluoro-1-methylsulfonyl-1H-indol-4-yl)-1,4,4,9-tetramethyl-5H-[1,2,4]triazolo[4,3-a]quinoxaline |
| 336 | 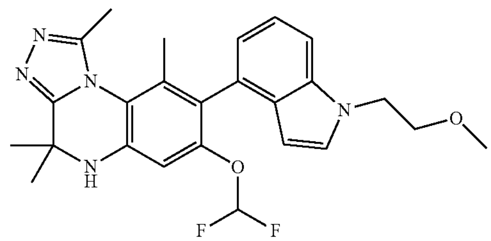 | 7-(Difluoro-methoxy)-8-[1-(2-methoxy-ethyl)-1H-indol-4-yl]-1,4,4,9-tetramethyl-5H-[1,2,4]triazolo[4,3-a]quinoxaline |
| 337 | 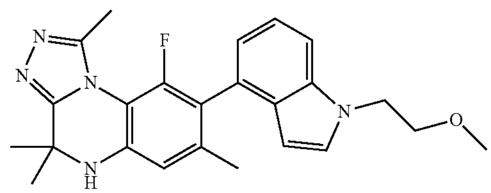 | 9-Fluoro-8-[1-(2-methoxy-ethyl)-1H-indol-4-yl]-1,4,4,7-tetramethyl-5H-[1,2,4]triazolo[4,3-a]quinoxaline |
| 338 | 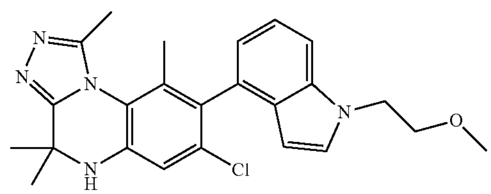 | 7-Chloro-8-[1-(2-methoxy-ethyl)-1H-indol-4-yl]-1,4,4,9-tetramethyl-5H-[1,2,4]triazolo[4,3-a]quinoxaline |
| 339 | 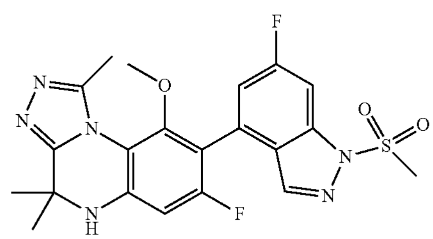 [SMILES: COc1c(-c2cc(F)cc3c2cnn3S(C)(=O)=O)c(F)cc2c1-n1c(C)nnc1C(C)(C)N2] | 7-Fluoro-8-(6-fluoro-1-methylsulfonyl-1H-indazol-4-yl)-9-methoxy-1,4,4-trimethyl-5H-[1,2,4]triazolo[4,3-a]quinoxaline |
| 341 | 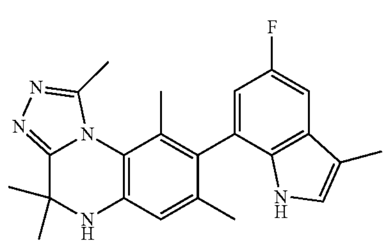 | 8-(5-Fluoro-3-methyl-1H-indol-7-yl)-1,4,4,7,9-pentamethyl-5H-[1,2,4]triazolo[4,3-a]quinoxaline |
| 342 | 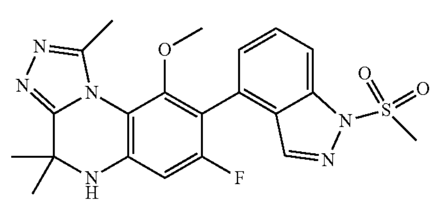 [SMILES: COc1c(-c2cccc3c2cnn3S(C)(=O)=O)c(F)cc2c1-n1c(C)nnc1C(C)(C)N2] | 7-Fluoro-9-methoxy-1,4,4-trimethyl-8-(1-methylsulfonyl-1H-indazol-4-yl)-5H-[1,2,4]triazolo[4,3-a]quinoxaline |

| Ex. # | Structure | Name |
|---|---|---|
| 343 | 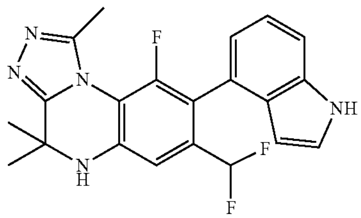 [SMILES: Cc1nnc2n1-c1c(cc(C(F)F)c(-c3cccc4[nH]ccc34)c1F)NC2(C)C] | 7-(Difluoro-methyl)-9-fluoro-8-(1H-indol-4-yl)-1,4,4-trimethyl-5H-[1,2,4]triazolo[4,3-a]quinoxaline |
| 344 | 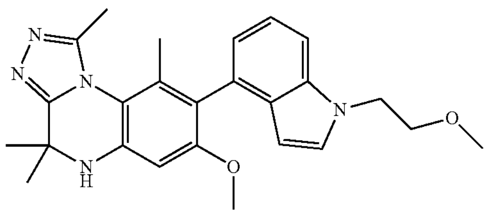 | 7-Methoxy-8-[1-(2-methoxy-ethyl)-1H-indol-4-yl]-1,4,4,9-tetramethyl-5H-[1,2,4]triazolo[4,3-a]quinoxaline |
| 345 | 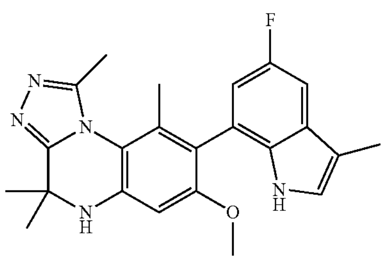 | 8-(5-Fluoro-3-methyl-1H-indol-7-yl)-7-methoxy-1,4,4,9-tetramethyl-5H-[1,2,4]triazolo[4,3-a]quinoxaline |
| 346 | 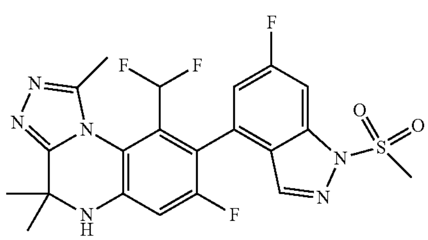 [SMILES: Cc1nnc2n1-c1c(cc(F)c(-c3cc(F)cc4c3cnn4S(C)(=O)=O)c1C(F)F)NC2(C)C] | 9-(Difluoro-methyl)-7-fluoro-8-(6-fluoro-1-methylsulfonyl-1H-indazol-4-yl)-1,4,4-trimethyl-5H-[1,2,4]triazolo[4,3-a]quinoxaline |
| 347 | 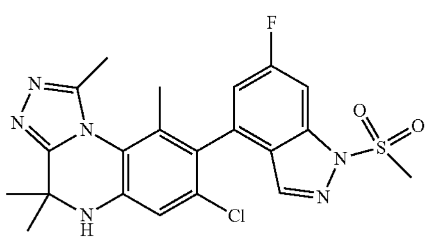 | 7-Chloro-8-(6-fluoro-1-methylsulfonyl-1H-indazol-4-yl)-1,4,4,9-tetramethyl-5H-[1,2,4]triazolo[4,3-a]quinoxaline |
| 348 | 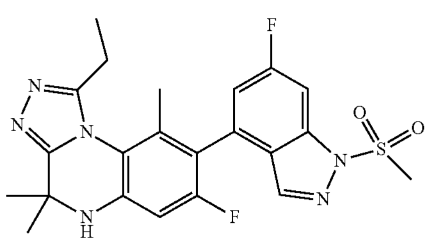 [SMILES: CCc1nnc2n1-c1c(cc(F)c(-c3cc(F)cc4c3cnn4S(C)(=O)=O)c1C)NC2(C)C] | 1-Ethyl-7-fluoro-8-(6-fluoro-1-methylsulfonyl-1H-indazol-4-yl)-4,4,9-trimethyl-5H-[1,2,4]triazolo[4,3-a]quinoxaline |

-continued

| Ex. # | Structure | Name |
|---|---|---|
| 351 | 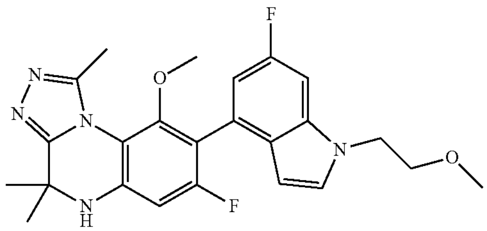 | 7-Fluoro-8-[6-fluoro-1-(2-methoxy-ethyl)-1H-indol-4-yl]-9-methoxy-1,4,4-trimethyl-5H-[1,2,4]triazolo[4,3-a]quinoxaline |
| 353 | 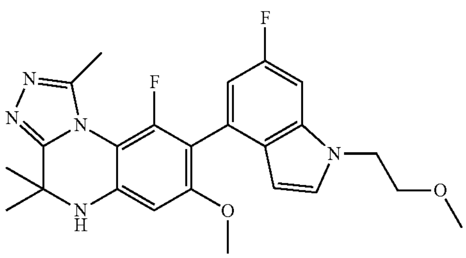 | 9-Fluoro-8-[6-fluoro-1-(2-methoxy-ethyl)-1H-indol-4-yl]-7-methoxy-1,4,4-trimethyl-5H-[1,2,4]triazolo[4,3-a]quinoxaline |
| 354 | 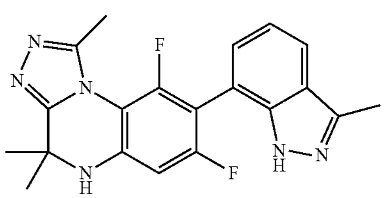 | 7,9-Difluoro-1,4,4-trimethyl-8-(3-methyl-1H-indazol-7-yl)-5H-[1,2,4]triazolo[4,3-a]quinoxaline |
| 356 | 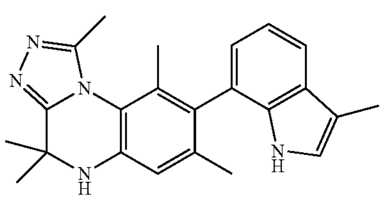 | 1,4,4,7,9-Pentamethyl-8-(3-methyl-1H-indol-7-yl)-5H-[1,2,4]triazolo[4,3-a]quinoxaline |
| 357 | 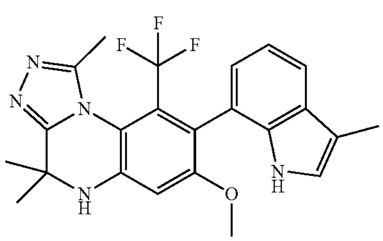 | 7-Methoxy-1,4,4-trimethyl-8-(3-methyl-1H-indol-7-yl)-9-(trifluoromethyl)-5H-[1,2,4]triazolo[4,3-a]quinoxaline |
| 358 | 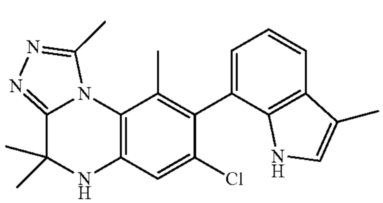 | 7-Chloro-1,4,4,9-tetramethyl-8-(3-methyl-1H-indol-7-yl)-5H-[1,2,4]triazolo[4,3-a]quinoxaline |
| 359 | 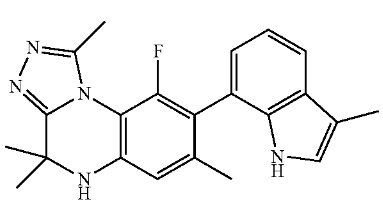 | 9-Fluoro-1,4,4,7-tetramethyl-8-(3-methyl-1H-indol-7-yl)-5H-[1,2,4]triazolo[4,3-a]quinoxaline |

| Ex. # | Structure | Name |
|---|---|---|
| 360 | 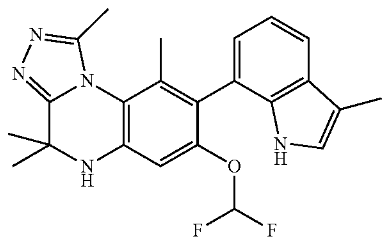 | 7-(Difluoro-methoxy)-1,4,4,9-tetramethyl-8-(3-methyl-1H-indol-7-yl)-5H-[1,2,4]triazolo[4,3-a]quinoxaline |
| 361 | 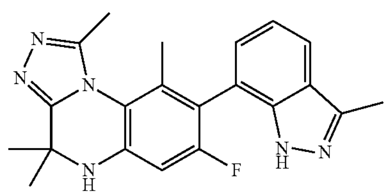 | 7-Fluoro-1,4,4,9-tetramethyl-8-(3-methyl-1H-indazol-7-yl)-5H-[1,2,4]triazolo[4,3-a]quinoxaline |
| 362 | 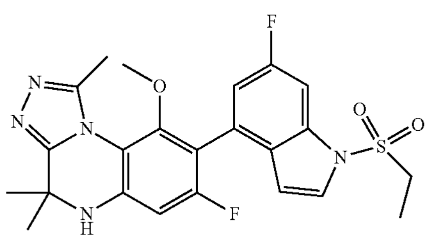 [SMILES: CCS(=O)(=O)n1ccc2c(-c3c(F)cc4c(c3OC)-n3c(C)nnc3C(C)(C)N4)cc(F)cc21] | 8-[1-(Ethylsulfonyl)-6-fluoro-1H-indol-4-yl]-7-fluoro-9-methoxy-1,4,4-trimethyl-5H-[1,2,4]triazolo[4,3-a]quinoxaline |
| 363 | 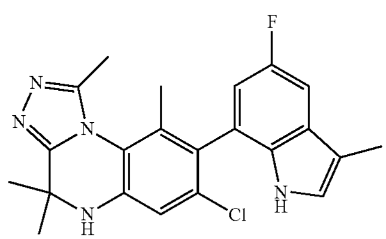 | 7-Chloro-8-(5-fluoro-3-methyl-1H-indol-7-yl)-1,4,4,9-tetramethyl-5H-[1,2,4]triazolo[4,3-a]quinoxaline |
| 364 | 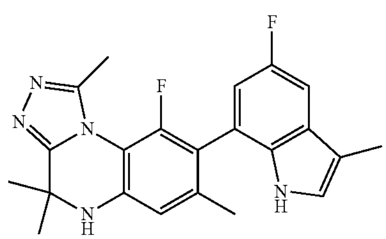 | 9-Fluoro-8-(5-fluoro-3-methyl-1H-indol-7-yl)-1,4,4,7-tetramethyl-5H-[1,2,4]triazolo[4,3-a]quinoxaline |
| 365 | 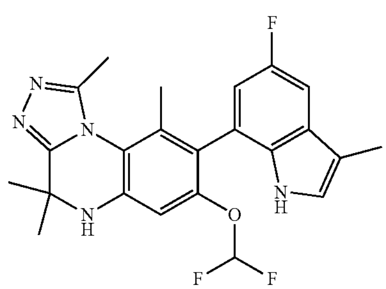 | 7-(Difluoro-methoxy)-8-(5-fluoro-3-methyl-1H-indol-7-yl)-1,4,4,9-tetramethyl-5H-[1,2,4]triazolo[4,3-a]quinoxaline |

| Ex. # | Structure | Name |
|---|---|---|
| 367 | 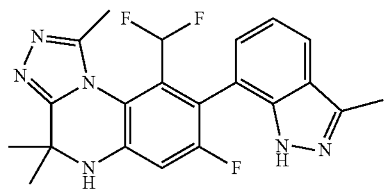 | 9-(Difluoro-methyl)-7-fluoro-1,4,4-trimethyl-8-(3-methyl-1H-indazol-7-yl)-5H-[1,2,4]triazolo[4,3-a]quinoxaline |
| 368 | 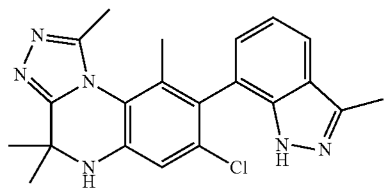 | 7-Chloro-1,4,4,9-tetramethyl-8-(3-methyl-1H-indazol-7-yl)-5H-[1,2,4]triazolo[4,3-a]quinoxaline |
| 369 | 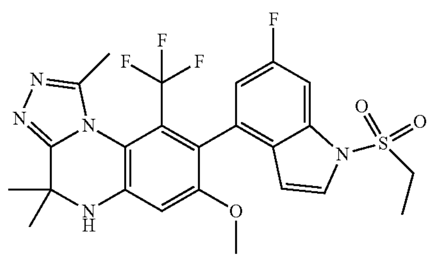 [SMILES: CCS(=O)(=O)n1ccc2c(-c3c(OC)cc4c(c3C(F)(F)F)-n3c(C)nnc3C(C)(C)N4)cc(F)cc21] | 8-[1-(Ethylsulfonyl)-6-fluoro-1H-indol-4-yl]-7-methoxy-1,4,4-trimethyl-9-(trifluoromethyl)-5H-[1,2,4]triazolo[4,3-a]quinoxaline |
| 370 | 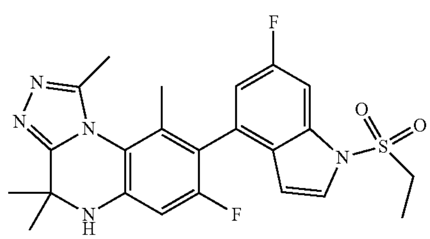 [SMILES: CCS(=O)(=O)n1ccc2c(-c3c(F)cc4c(c3C)-n3c(C)nnc3C(C)(C)N4)cc(F)cc21] | 8-[1-(Ethylsulfonyl)-6-fluoro-1H-indol-4-yl]-7-fluoro-1,4,4,9-tetramethyl-5H-[1,2,4]triazolo[4,3-a]quinoxaline |
| 371 | 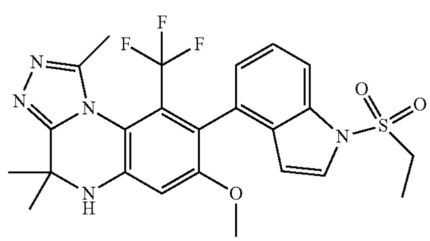 [SMILES: CCS(=O)(=O)n1ccc2c(-c3c(OC)cc4c(c3C(F)(F)F)-n3c(C)nnc3C(C)(C)N4)cccc21] | 8-[1-(Ethylsulfonyl)-1H-indol-4-yl]-7-methoxy-1,4,4-trimethyl-9-(trifluoromethyl)-5H-[1,2,4]triazolo[4,3-a]quinoxaline |
| 372 | 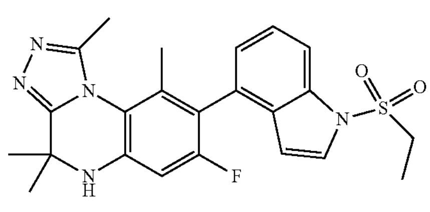 [SMILES: CCS(=O)(=O)n1ccc2c(-c3c(F)cc4c(c3C)-n3c(C)nnc3C(C)(C)N4)cccc21] | 8-[1-(Ethylsulfonyl)-1H-indol-4-yl]-7-fluoro-1,4,4,9-tetramethyl-5H-[1,2,4]triazolo[4,3-a]quinoxaline |
| 373 | 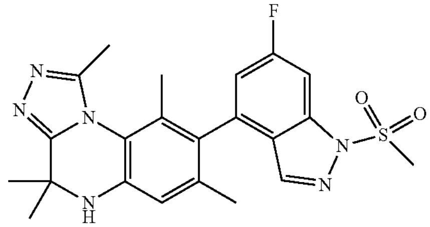 | 8-(6-Fluoro-1-methylsulfonyl-1H-indazol-4-yl)-1,4,4,7,9-pentamethyl-5H-[1,2,4]triazolo[4,3-a]quinoxaline |

-continued

| Ex. # | Structure | Name |
|---|---|---|
| 376 | 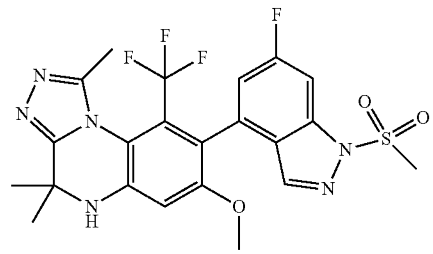 [SMILES: COc1cc2c(c(C(F)(F)F)c1-c1cc(F)cc3c1cnn3S(C)(=O)=O)-n1c(C)nnc1C(C)(C)N2] | 8-(6-Fluoro-1-methylsulfonyl-1H-indazol-4-yl)-7-methoxy-1,4,4-trimethyl-9-(trifluoromethyl)-5H-[1,2,4]triazolo[4,3-a]quinoxaline |
| 377 | 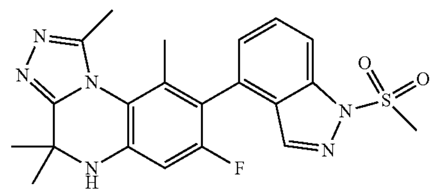 [SMILES: Cc1c(-c2cccc3c2cnn3S(C)(=O)=O)c(F)cc2c1-n1c(C)nnc1C(C)(C)N2] | 7-Fluoro-1,4,4,9-tetramethyl-8-(1-methylsulfonyl-1H-indazol-4-yl)-5H-[1,2,4]triazolo[4,3-a]quinoxaline |
| 379 | 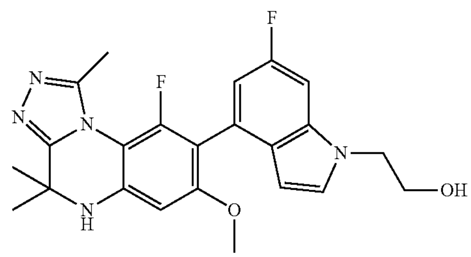 [SMILES: COc1cc2c(c(F)c1-c1cc(F)cc3c1ccn3CCO)-n1c(C)nnc1C(C)(C)N2] | 2-[6-Fluoro-4-(9-fluoro-7-methoxy-1,4,4-trimethyl-5H-[1,2,4]triazolo[4,3-a]quinoxalin-8-yl)-1H-indol-1-yl]-ethanol |
| 380 | 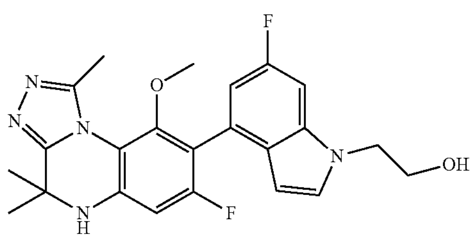 [SMILES: COc1c(-c2cc(F)cc3c2ccn3CCO)c(F)cc2c1-n1c(C)nnc1C(C)(C)N2] | 2-[6-Fluoro-4-(7-fluoro-9-methoxy-1,4,4-trimethyl-5H-[1,2,4]triazolo[4,3-a]quinoxalin-8-yl)-1H-indol-1-yl]-ethanol |
| 381 | 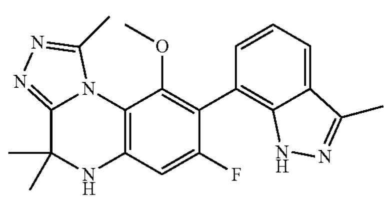 | 7-Fluoro-9-methoxy-1,4,4-trimethyl-8-(3-methyl-1H-indazol-7-yl)-5H-[1,2,4]triazolo[4,3-a]quinoxaline |
| 382 | 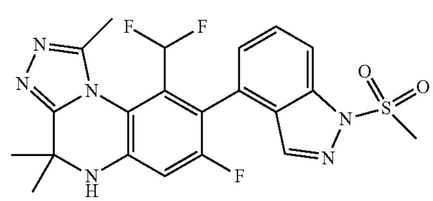 [SMILES: Cc1nnc2n1-c1c(cc(F)c(-c3cccc4c3cnn4S(C)(=O)=O)c1C(F)F)NC2(C)C] | 9-(Difluoro-methyl)-7-fluoro-1,4,4-trimethyl-8-(1-methylsulfonyl-1H-indazol-4-yl)-5H-[1,2,4]triazolo[4,3-a]quinoxaline |
| 383 | 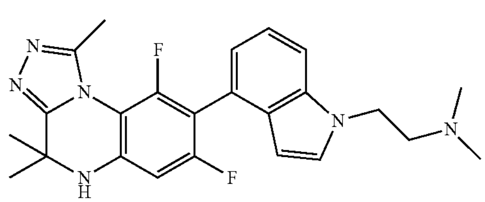 | [2-[4-(7,9-Difluoro-1,4,4-trimethyl-5H-[1,2,4]triazolo[4,3-a]quinoxalin-8-yl)-1H-indol-1-yl]-ethyl]-dimethyl-amine |

-continued

| Ex. # | Structure | Name |
|---|---|---|
| 384 | 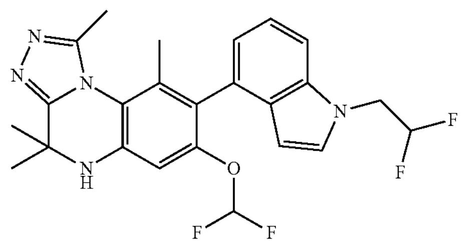 [SMILES: Cc1c(-c2cccc3c2ccn3CC(F)F)c(OC(F)F)cc2c1-n1c(C)nnc1C(C)(C)N2] | 8-[1-(2,2-Difluoro-ethyl)-1H-indol-4-yl]-7-(difluoro-methoxy)-1,4,4,9-tetramethyl-5H-[1,2,4]triazolo[4,3-a]quinoxaline |
| 385 | 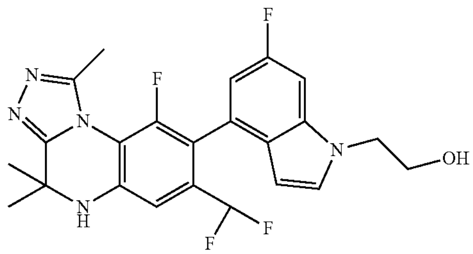 [SMILES: Cc1nnc2n1-c1c(cc(C(F)F)c(-c3cc(F)cc4c3ccn4CCO)c1F)NC2(C)C] | 2-[4-[7-(Difluoro-methyl)-9-fluoro-1,4,4-trimethyl-5H-[1,2,4]triazolo[4,3-a]quinoxalin-8-yl]-6-fluoro-1H-indol-1-yl]-ethanol |
| 386 | 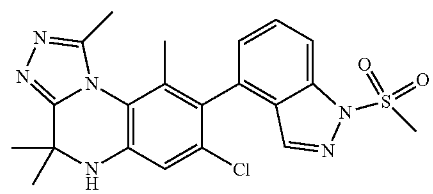 [SMILES: Cc1c(-c2cccc3c2cnn3S(C)(=O)=O)c(Cl)cc2c1-n1c(C)nnc1C(C)(C)N2] | 7-Chloro-1,4,4,9-tetramethyl-8-(1-methylsulfonyl-1H-indazol-4-yl)-5H-[1,2,4]triazolo[4,3-a]quinoxaline |
| 387 | 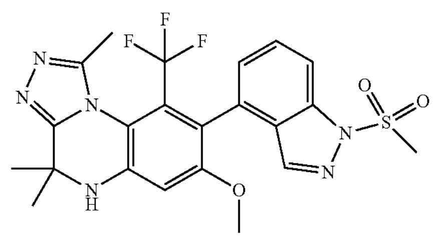 [SMILES: COc1cc2c(c(C(F)(F)F)c1-c1cccc3c1cnn3S(C)(=O)=O)-n1c(C)nnc1C(C)(C)N2] | 7-Methoxy-1,4,4-trimethyl-8-(1-methylsulfonyl-1H-indazol-4-yl)-9-(trifluoromethyl)-5H-[1,2,4]triazolo[4,3-a]quinoxaline |
| 388 | 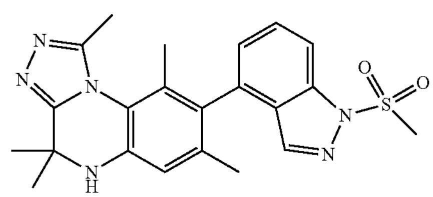 [SMILES: Cc1cc2c(c(C)c1-c1cccc3c1cnn3S(C)(=O)=O)-n1c(C)nnc1C(C)(C)N2] | 1,4,4,7,9-Pentamethyl-8-(1-methylsulfonyl-1H-indazol-4-yl)-5H-[1,2,4]triazolo[4,3-a]quinoxaline |
| 390 | 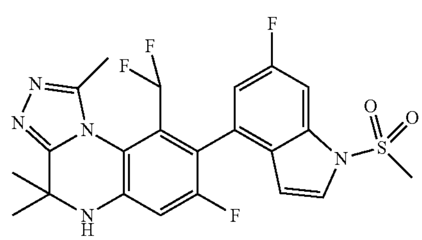 [SMILES: Cc1nnc2n1-c1c(cc(F)c(-c3cc(F)cc4c3ccn4S(C)(=O)=O)c1C(F)F)NC2(C)C] | 9-(Difluoro-methyl)-7-fluoro-8-(6-fluoro-1-methylsulfonyl-1H-indol-4-yl)-1,4,4-trimethyl-5H-[1,2,4]triazolo[4,3-a]quinoxaline |
| 392 | 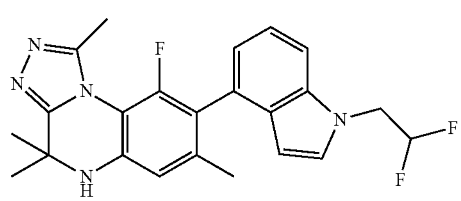 [SMILES: Cc1cc2c(c(F)c1-c1cccc3c1ccn3CC(F)F)-n1c(C)nnc1C(C)(C)N2] | 8-[1-(2,2-Difluoro-ethyl)-1H-indol-4-yl]-9-fluoro-1,4,4,7-tetramethyl-5H-[1,2,4]triazolo[4,3-a]quinoxaline |

| Ex. # | Structure | Name |
|---|---|---|
| 393 | 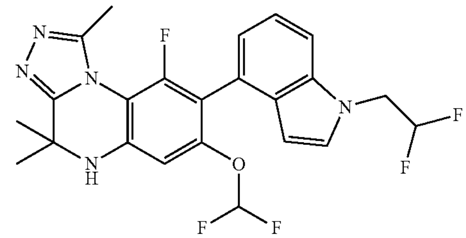 [SMILES: Cc1nnc2n1-c1c(cc(OC(F)F)c(-c3cccc4c3ccn4CC(F)F)c1F)NC2(C)C] | 8-[1-(2,2-Difluoro-ethyl)-1H-indol-4-yl]-7-(difluoro-methoxy)-9-fluoro-1,4,4-trimethyl-5H-[1,2,4]triazolo[4,3-a]quinoxaline |
| 394 | 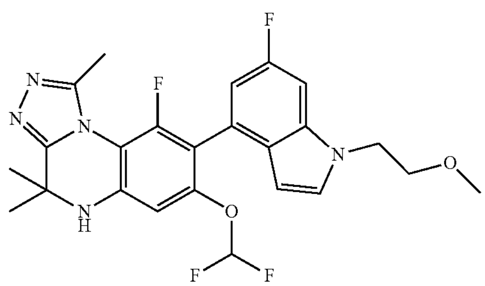 | 7-(Difluoro-methoxy)-9-fluoro-8-[6-fluoro-1-(2-methoxy-ethyl)-1H-indol-4-yl]-1,4,4-trimethyl-5H-[1,2,4]triazolo[4,3-a]quinoxaline |
| 395 | 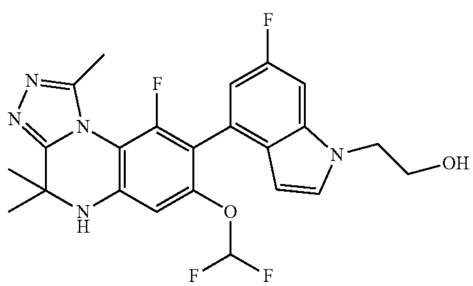 [SMILES: Cc1nnc2n1-c1c(cc(OC(F)F)c(-c3cc(F)cc4c3ccn4CCO)c1F)NC2(C)C] | 2-[4-[7-(Difluoro-methoxy)-9-fluoro-1,4,4-trimethyl-5H-[1,2,4]triazolo[4,3-a]quinoxalin-8-yl]-6-fluoro-1H-indol-1-yl]-ethanol |
| 396 | 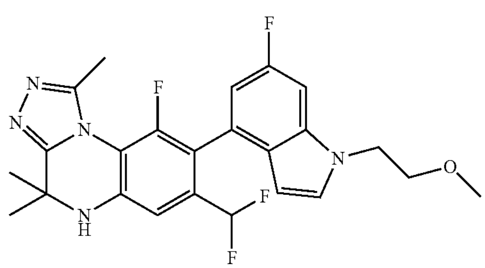 | 7-(Difluoro-methyl)-9-fluoro-8-[6-fluoro-1-(2-methoxy-ethyl)-1H-indol-4-yl]-1,4,4-trimethyl-5H-[1,2,4]triazolo[4,3-a]quinoxaline |
| 397 | 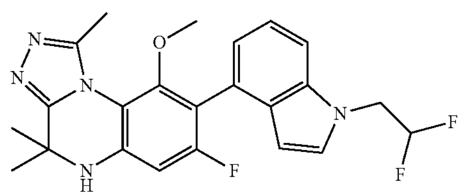 [SMILES: COc1c(-c2cccc3c2ccn3CC(F)F)c(F)cc2c1-n1c(C)nnc1C(C)(C)N2] | 8-[1-(2,2-Difluoro-ethyl)-1H-indol-4-yl]-7-fluoro-9-methoxy-1,4,4-trimethyl-5H-[1,2,4]triazolo[4,3-a]quinoxaline |
| 398 | 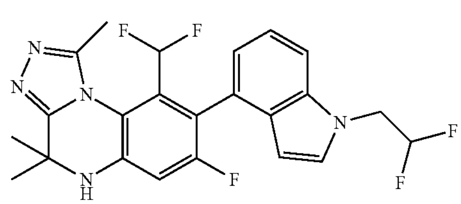 [SMILES: Cc1nnc2n1-c1c(cc(F)c(-c3cccc4c3ccn4CC(F)F)c1C(F)F)NC2(C)C] | 8-[1-(2,2-Difluoro-ethyl)-1H-indol-4-yl]-9-(difluoro-methyl)-7-fluoro-1,4,4-trimethyl-5H-[1,2,4]triazolo[4,3-a]quinoxaline |

| Ex. # | Structure | Name |
|---|---|---|
| 399 | 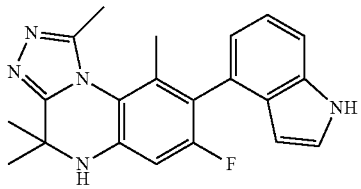 [SMILES: Cc1c(-c2cccc3[nH]ccc23)c(F)cc2c1-n1c(C)nnc1C(C)(C)N2] | 7-Fluoro-8-(1H-indol-4-yl)-1,4,4,9-tetramethyl-5H-[1,2,4]triazolo[4,3-a]quinoxaline |
| 400 | 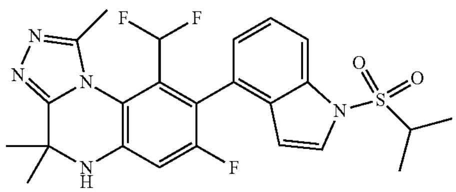 [SMILES: Cc1nnc2n1-c1c(cc(F)c(-c3cccc4c3ccn4S(=O)(=O)C(C)C)c1C(F)F)NC2(C)C] | 9-(Difluoro-methyl)-7-fluoro-8-[1-(isopropylsulfonyl)-1H-indol-4-yl]-1,4,4-trimethyl-5H-[1,2,4]triazolo[4,3-a]quinoxaline |
| 401 | 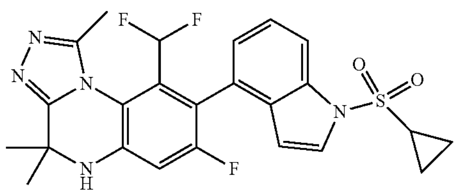 [SMILES: Cc1nnc2n1-c1c(cc(F)c(-c3cccc4c3ccn4S(=O)(=O)C3CC3)c1C(F)F)NC2(C)C] | 8-[1-(Cyclopropylsulfonyl)-1H-indol-4-yl]-9-(difluoro-methyl)-7-fluoro-1,4,4-trimethyl-5H-[1,2,4]triazolo[4,3-a]quinoxaline |
| 402 | 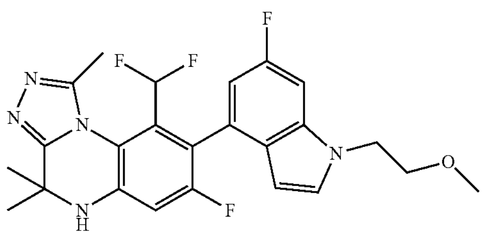 | 9-(Difluoro-methyl)-7-fluoro-8-[6-fluoro-1-(2-methoxy-ethyl)-1H-indol-4-yl]-1,4,4-trimethyl-5H-[1,2,4]triazolo[4,3-a]quinoxaline |
| 403 | 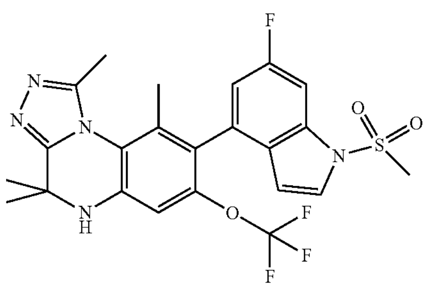 [SMILES: Cc1c(-c2cc(F)cc3c2ccn3S(C)(=O)=O)c(OC(F)(F)F)cc2c1-n1c(C)nnc1C(C)(C)N2] | 8-(6-Fluoro-1-methylsulfonyl-1H-indol-4-yl)-1,4,4,9-tetramethyl-7-(trifluoromethyloxy)-5H-[1,2,4]triazolo[4,3-a]quinoxaline |
| 404 | 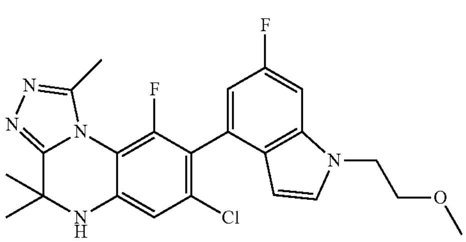 | 7-Chloro-9-fluoro-8-[6-fluoro-1-(2-methoxy-ethyl)-1H-indol-4-yl]-1,4,4-trimethyl-5H-[1,2,4]triazolo[4,3-a]quinoxaline |

| Ex. # | Structure | Name |
|---|---|---|
| 405 | 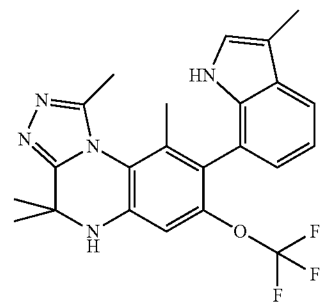 [SMILES: Cc1c(-c2cccc3c(C)c[nH]c23)c(OC(F)(F)F)cc2c1-n1c(C)nnc1C(C)(C)N2] | 1,4,4,9-Tetramethyl-8-(3-methyl-1H-indol-7-yl)-7-(trifluoromethyloxy)-5H-[1,2,4]triazolo[4,3-a]quinoxaline |
| 406 | 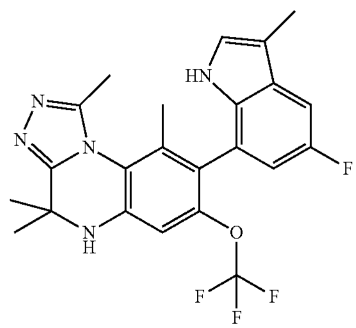 [SMILES: Cc1c(-c2cc(F)cc3c(C)c[nH]c23)c(OC(F)(F)F)cc2c1-n1c(C)nnc1C(C)(C)N2] | 8-(5-Fluoro-3-methyl-1H-indol-7-yl)-1,4,4,9-tetramethyl-7-(trifluoromethyloxy)-5H-[1,2,4]triazolo[4,3-a]quinoxaline |
| 407 | 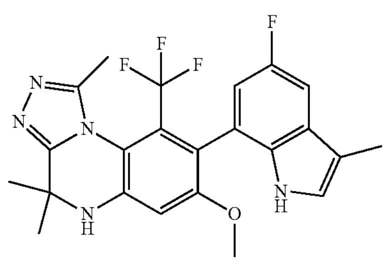 | 8-(5-Fluoro-3-methyl-1H-indol-7-yl)-7-methoxy-1,4,4-trimethyl-9-(trifluoromethyl)-5H-[1,2,4]triazolo[4,3-a]quinoxaline |
| 445 | 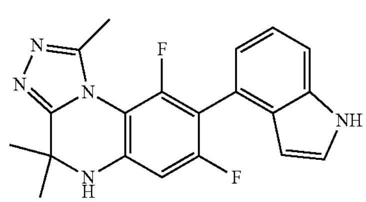 [SMILES: Cc1nnc2n1-c1c(cc(F)c(-c3cccc4[nH]ccc34)c1F)NC2(C)C] | 7,9-Difluoro-8-(1H-indol-4-yl)-1,4,4-trimethyl-5H-[1,2,4]triazolo[4,3-a]quinoxaline |
| 447 | 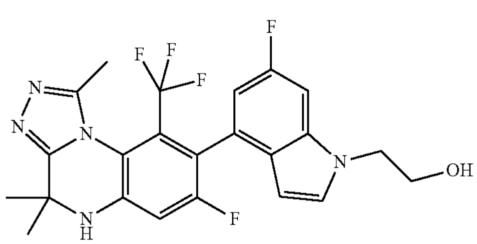 [SMILES: Cc1nnc2n1-c1c(cc(F)c(-c3cc(F)cc4c3ccn4CCO)c1C(F)(F)F)NC2(C)C] | 2-[6-Fluoro-4-[7-fluoro-1,4,4-trimethyl-9-(trifluoromethyl)-5H-[1,2,4]triazolo[4,3-a]quinoxalin-8-yl]-1H-indol-1-yl]-ethanol |
| 448 | 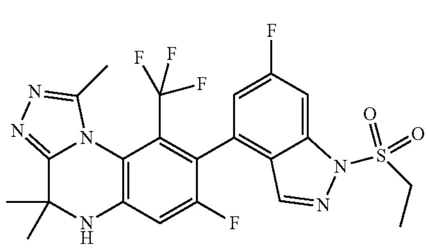 [SMILES: CCS(=O)(=O)n1ncc2c(-c3c(F)cc4c(c3C(F)(F)F)-n3c(C)nnc3C(C)(C)N4)cc(F)cc21] | 8-[1-(Ethylsulfonyl)-6-fluoro-1H-indazol-4-yl]-7-fluoro-1,4,4-trimethyl-9-(trifluoromethyl)-5H-[1,2,4]triazolo[4,3-a]quinoxaline |

| Ex. # | Structure | Name |
|---|---|---|
| 449 | 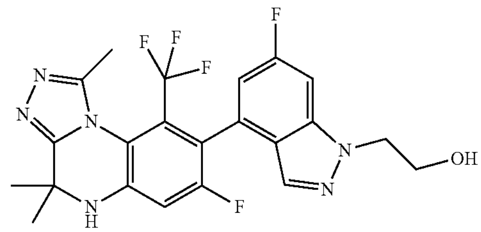 [SMILES: Cc1nnc2n1-c1c(cc(F)c(-c3cc(F)cc4c3cnn4CCO)c1C(F)(F)F)NC2(C)C] | 2-[6-Fluoro-4-[7-fluoro-1,4,4-trimethyl-9-(trifluoromethyl)-5H-[1,2,4]triazolo[4,3-a]quinoxalin-8-yl]-1H-indazol-1-yl]-ethanol |
| 451 | 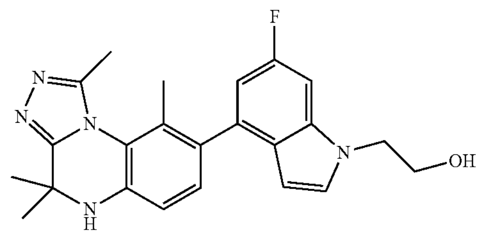 [SMILES: Cc1c(-c2cc(F)cc3c2ccn3CCO)ccc2c1-n1c(C)nnc1C(C)(C)N2] | 2-[6-Fluoro-4-(1,4,4,9-tetramethyl-5H-[1,2,4]triazolo[4,3-a]quinoxalin-8-yl)-1H-indol-1-yl]-ethanol |
| 452 | 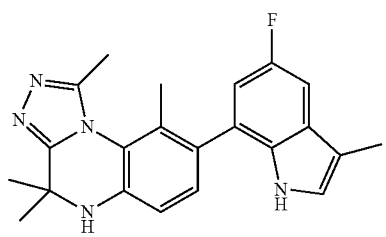 | 8-(5-Fluoro-3-methyl-1H-indol-7-yl)-1,4,4,9-tetramethyl-5H-[1,2,4]triazolo[4,3-a]quinoxaline |
| 453 | 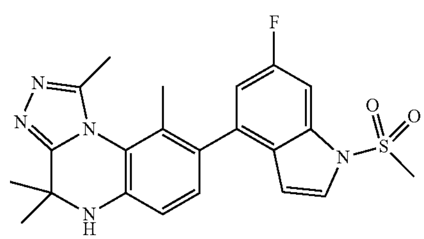 [SMILES: Cc1c(-c2cc(F)cc3c2ccn3S(C)(=O)=O)ccc2c1-n1c(C)nnc1C(C)(C)N2] | 8-(6-Fluoro-1-methylsulfonyl-1H-indol-4-yl)-1,4,4,9-tetramethyl-5H-[1,2,4]triazolo[4,3-a]quinoxaline |
| 454 | 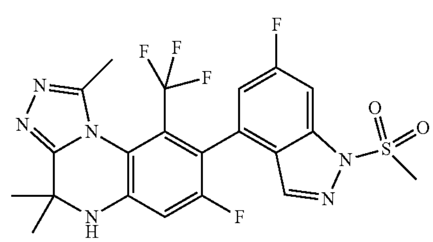 [SMILES: Cc1nnc2n1-c1c(cc(F)c(-c3cc(F)cc4c3cnn4S(C)(=O)=O)c1C(F)(F)F)NC2(C)C] | 7-Fluoro-8-(6-fluoro-1-methylsulfonyl-1H-indazol-4-yl)-1,4,4-trimethyl-9-(trifluoromethyl)-5H-[1,2,4]triazolo[4,3-a]quinoxaline |
| 455 | 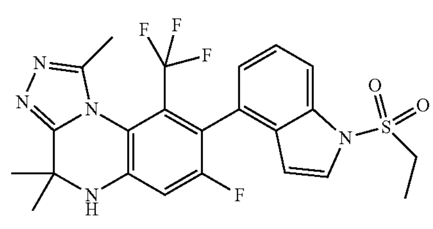 [SMILES: CCS(=O)(=O)n1ccc2c(-c3c(F)cc4c(c3C(F)(F)F)-n3c(C)nnc3C(C)(C)N4)cccc21] | 8-[1-(Ethylsulfonyl)-1H-indol-4-yl]-7-fluoro-1,4,4-trimethyl-9-(trifluoromethyl)-5H-[1,2,4]triazolo[4,3-a]quinoxaline |

-continued

| Ex. # | Structure | Name |
|---|---|---|
| 456 | 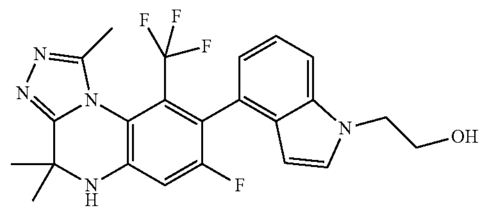 [SMILES: Cc1nnc2n1-c1c(cc(F)c(-c3cccc4c3ccn4CCO)c1C(F)(F)F)NC2(C)C] | 2-[4-[7-Fluoro-1,4,4-trimethyl-9-(trifluoromethyl)-5H-[1,2,4]triazolo[4,3-a]quinoxalin-8-yl]-1H-indol-1-yl]-ethanol |
| 457 | 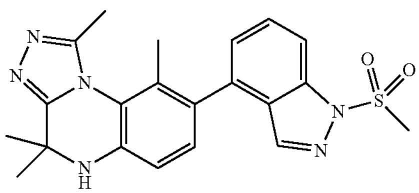 [SMILES: Cc1c(-c2cccc3c2cnn3S(C)(=O)=O)ccc2c1-n1c(C)nnc1C(C)(C)N2] | 1,4,4,9-Tetramethyl-8-(1-methylsulfonyl-1H-indazol-4-yl)-5H-[1,2,4]triazolo[4,3-a]quinoxaline |
| 458 | 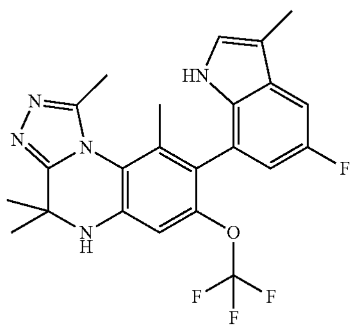 [SMILES: Cc1c(-c2cc(F)cc3c(C)c[nH]c23)c(OC(F)(F)F)cc2c1-n1c(C)nnc1C(C)(C)N2] | 8-(5-Fluoro-3-methyl-1H-indol-7-yl)-1,4,4,9-tetramethyl-7-(trifluoromethyloxy)-5H-[1,2,4]triazolo[4,3-a]quinoxaline |
| 459 | 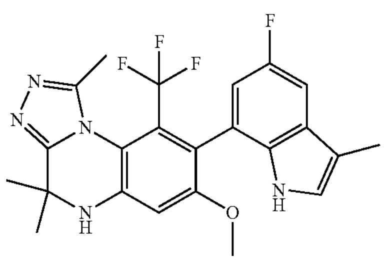 | 8-(5-Fluoro-3-methyl-1H-indol-7-yl)-7-methoxy-1,4,4-trimethyl-9-(trifluoromethyl)-5H-[1,2,4]triazolo[4,3-a]quinoxaline |
| 460 | 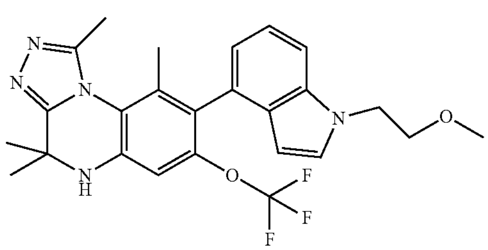 | 8-[1-(2-Methoxy-ethyl)-1H-indol-4-yl]-1,4,4,9-tetramethyl-7-(trifluoromethyloxy)-5H-[1,2,4]triazolo[4,3-a]quinoxaline |
| 461 | 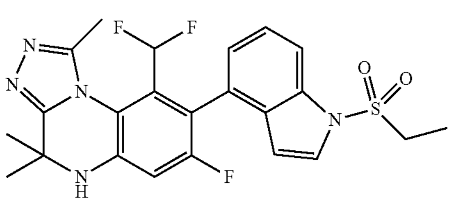 [SMILES: CCS(=O)(=O)n1ccc2c(-c3c(F)cc4c(c3C(F)F)-n3c(C)nnc3C(C)(C)N4)cccc21] | 9-(Difluoro-methyl)-8-[1-(ethylsulfonyl)-1H-indol-4-yl]-7-fluoro-1,4,4-trimethyl-5H-[1,2,4]triazolo[4,3-a]quinoxaline |

| Ex. # | Structure | Name |
|---|---|---|
| 462 | 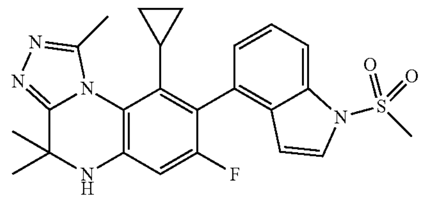 [SMILES: Cc1nnc2n1-c1c(cc(F)c(-c3cccc4c3ccn4S(C)(=O)=O)c1C1CC1)NC2(C)C] | 9-Cyclopropyl-7-fluoro-1,4,4-trimethyl-8-(1-methylsulfonyl-1H-indol-4-yl)-5H-[1,2,4]triazolo[4,3-a]quinoxaline |
| 463 | 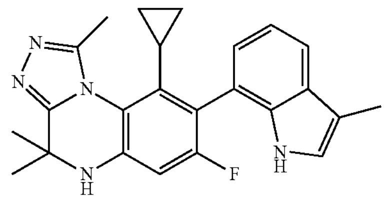 | 9-Cyclopropyl-7-fluoro-1,4,4-trimethyl-8-(3-methyl-1H-indol-7-yl)-5H-[1,2,4]triazolo[4,3-a]quinoxaline |
| 464 | 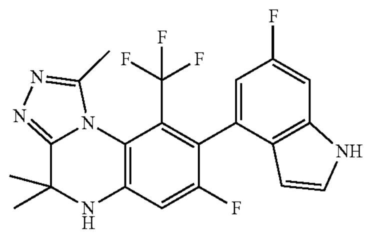 [SMILES: Cc1nnc2n1-c1c(cc(F)c(-c3cc(F)cc4[nH]ccc34)c1C(F)(F)F)NC2(C)C] | 7-Fluoro-8-(6-fluoro-1H-indol-4-yl)-1,4,4-trimethyl-9-(trifluoromethyl)-5H-[1,2,4]triazolo[4,3-a]quinoxaline |
| 465 | 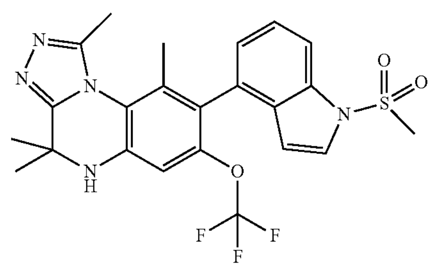 [SMILES: Cc1c(-c2cccc3c2ccn3S(C)(=O)=O)c(OC(F)(F)F)cc2c1-n1c(C)nnc1C(C)(C)N2] | 1,4,4,9-Tetramethyl-8-(1-methylsulfonyl-1H-indol-4-yl)-7-(trifluoromethyloxy)-5H-[1,2,4]triazolo[4,3-a]quinoxaline |
| 466 | 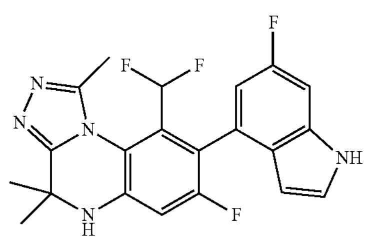 [SMILES: Cc1nnc2n1-c1c(cc(F)c(-c3cc(F)cc4[nH]ccc34)c1C(F)F)NC2(C)C] | 9-(Difluoro-methyl)-7-fluoro-8-(6-fluoro-1H-indol-4-yl)-1,4,4-trimethyl-5H-[1,2,4]triazolo[4,3-a]quinoxaline |
| 467 | 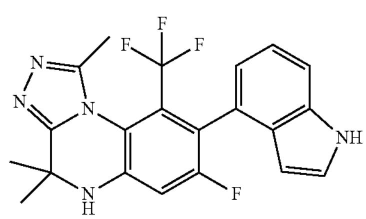 [SMILES: Cc1nnc2n1-c1c(cc(F)c(-c3cccc4[nH]ccc34)c1C(F)(F)F)NC2(C)C] | 7-Fluoro-8-(1H-indol-4-yl)-1,4,4-trimethyl-9-(trifluoromethyl)-5H-[1,2,4]triazolo[4,3-a]quinoxaline |
| 468 | 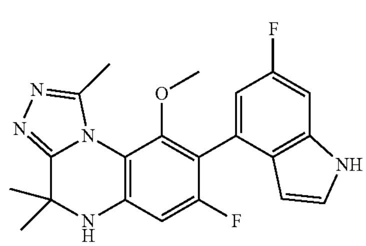 [SMILES: COc1c(-c2cc(F)cc3[nH]ccc23)c(F)cc2c1-n1c(C)nnc1C(C)(C)N2] | 7-Fluoro-8-(6-fluoro-1H-indol-4-yl)-9-methoxy-1,4,4-trimethyl-5H-[1,2,4]triazolo[4,3-a]quinoxaline |

| Ex. # | Structure | Name |
|---|---|---|
| 469 | 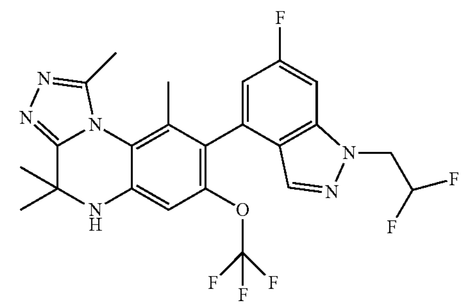 [SMILES: Cc1c(-c2cc(F)cc3c2cnn3CC(F)F)c(OC(F)(F)F)cc2c1-n1c(C)nnc1C(C)(C)N2] | 8-[1-(2,2-Difluoro-ethyl)-6-fluoro-1H-indazol-4-yl]-1,4,4,9-tetramethyl-7-(trifluoromethyloxy)-5H-[1,2,4]triazolo[4,3-a]quinoxaline |
| 470 | 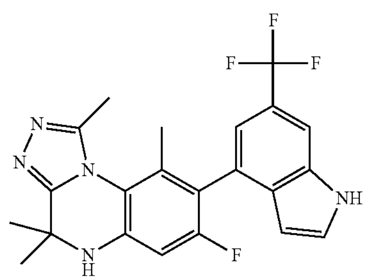 [SMILES: Cc1c(-c2cc(C(F)(F)F)cc3[nH]ccc23)c(F)cc2c1-n1c(C)nnc1C(C)(C)N2] | 7-Fluoro-1,4,4,9-tetramethyl-8-[6-(trifluoromethyl)-1H-indol-4-yl]-5H-[1,2,4]triazolo[4,3-a]quinoxaline |
| 471 | 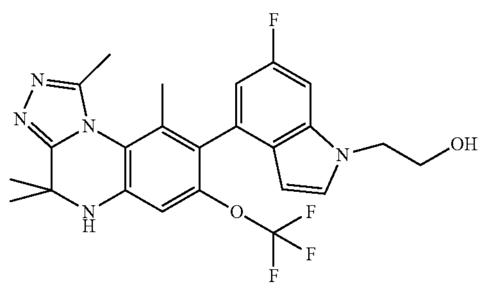 [SMILES: Cc1c(-c2cc(F)cc3c2ccn3CCO)c(OC(F)(F)F)cc2c1-n1c(C)nnc1C(C)(C)N2] | 2-[6-Fluoro-4-[1,4,4,9-tetramethyl-7-(trifluoromethyloxy)-5H-[1,2,4]triazolo[4,3-a]quinoxalin-8-yl]-1H-indol-1-yl]-ethanol |
| 472 | 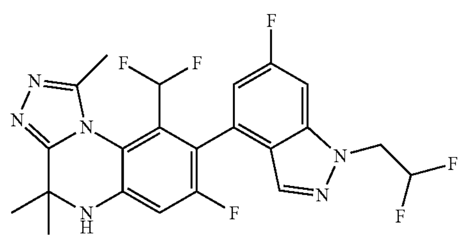 [SMILES: Cc1nnc2n1-c1c(cc(F)c(-c3cc(F)cc4c3cnn4CC(F)F)c1C(F)F)NC2(C)C] | 8-[1-(2,2-Difluoro-ethyl)-6-fluoro-1H-indazol-4-yl]-9-(difluoromethyl)-7-fluoro-1,4,4-trimethyl-5H-[1,2,4]triazolo[4,3-a]quinoxaline |
| 473 | 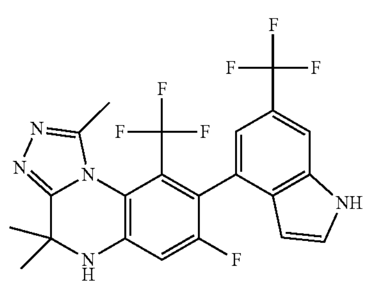 [SMILES: Cc1nnc2n1-c1c(cc(F)c(-c3cc(C(F)(F)F)cc4[nH]ccc34)c1C(F)(F)F)NC2(C)C] | 7-Fluoro-1,4,4-trimethyl-9-(trifluoromethyl)-8-[6-(trifluoromethyl)-1H-indol-4-yl]-5H-[1,2,4]triazolo[4,3-a]quinoxaline |

| Ex. # | Name |
|---|---|
| 474 | 7-Fluoro-9-methoxy-1,4,4-trimethyl-8-[6-(trifluoromethyl)-1H-indol-4-yl]-5H-[1,2,4]triazolo[4,3-a]quinoxaline |
| 475 | 7-Chloro-1,4,4,9-tetramethyl-8-[6-(trifluoromethyl)-1H-indol-4-yl]-5H-[1,2,4]triazolo[4,3-a]quinoxaline |
| 476 | 7-Fluoro-1,4,4-trimethyl-8-(6-methyl-1-methylsulfonyl-1H-indol-4-yl)-9-(trifluoromethyl)-5H-[1,2,4]triazolo[4,3-a]quinoxaline |
| 477 | 7-Fluoro-9-methoxy-1,4,4-trimethyl-8-(6-methyl-1-methylsulfonyl-1H-indol-4-yl)-5H-[1,2,4]triazolo[4,3-a]quinoxaline |
| 478 | 9-(Difluoro-methyl)-7-fluoro-1,4,4-trimethyl-8-(6-methyl-1-methylsulfonyl-1H-indol-4-yl)-5H-[1,2,4]triazolo[4,3-a]quinoxaline |
| 479 | 4-[7-Fluoro-1,4,4-trimethyl-9-(trifluoromethyl)-5H-[1,2,4]triazolo[4,3-a]quinoxalin-8-yl]-1H-indole-6-carbonitrile |

| Ex. # | Structure | Name |
|---|---|---|
| 480 | 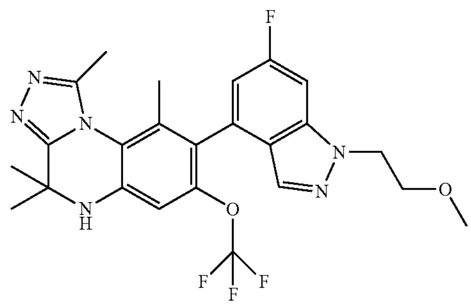 | 8-[6-Fluoro-1-(2-methoxy-ethyl)-1H-indazol-4-yl]-1,4,4,9-tetramethyl-7-(trifluoromethyloxy)-5H-[1,2,4]triazolo[4,3-a]quinoxaline |
| 481 | 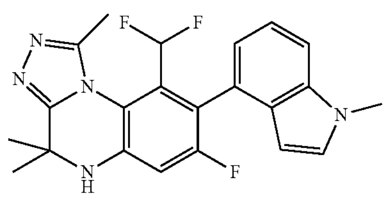 | 9-(Difluoro-methyl)-7-fluoro-1,4,4-trimethyl-8-(1-methyl-1H-indol-4-yl)-5H-[1,2,4]triazolo[4,3-a]quinoxaline |
| 482 | 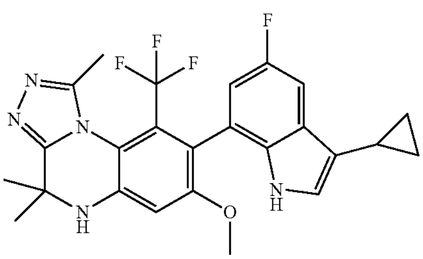 [SMILES: COc1cc2c(c(C(F)(F)F)c1-c1cc(F)cc3c(C4CC4)c[nH]c13)-n1c(C)nnc1C(C)(C)N2] | 8-(3-Cyclopropyl-5-fluoro-1H-indol-7-yl)-7-methoxy-1,4,4-trimethyl-9-(trifluoromethyl)-5H-[1,2,4]triazolo[4,3-a]quinoxaline |
| 483 | 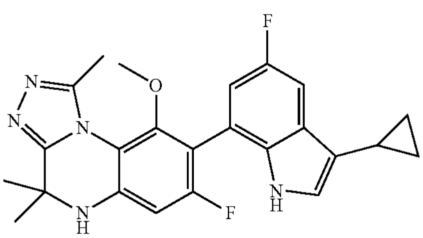 [SMILES: COc1c(-c2cc(F)cc3c(C4CC4)c[nH]c23)c(F)cc2c1-n1c(C)nnc1C(C)(C)N2] | 8-(3-Cyclopropyl-5-fluoro-1H-indol-7-yl)-7-fluoro-9-methoxy-1,4,4-trimethyl-5H-[1,2,4]triazolo[4,3-a]quinoxaline |
| 484 | 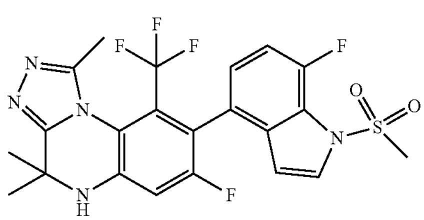 [SMILES: Cc1nnc2n1-c1c(cc(F)c(-c3ccc(F)c4c3ccn4S(C)(=O)=O)c1C(F)(F)F)NC2(C)C] | 7-Fluoro-8-(7-fluoro-1-methyl-sulfonyl-1H-indol-4-yl)-1,4,4-trimethyl-9-(trifluoromethyl)-5H-[1,2,4]triazolo[4,3-a]quinoxaline |
| 485 | 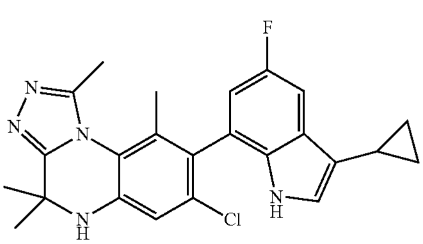 [SMILES: Cc1c(-c2cc(F)cc3c(C4CC4)c[nH]c23)c(Cl)cc2c1-n1c(C)nnc1C(C)(C)N2] | 7-Chloro-8-(3-cyclopropyl-5-fluoro-1H-indol-7-yl)-1,4,4,9-tetramethyl-5H-[1,2,4]triazolo[4,3-a]quinoxaline |

-continued

| Ex. # | Structure | Name |
|---|---|---|
| 486 | 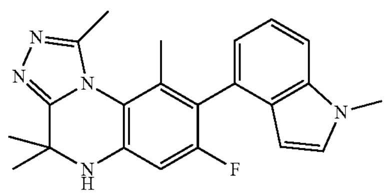 | 7-Fluoro-1,4,4,9-tetramethyl-8-(1-methyl-1H-indol-4-yl)-5H-[1,2,4]triazolo[4,3-a]quinoxaline |
| 487 | 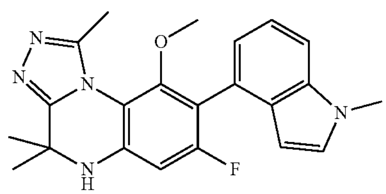 | 7-Fluoro-9-methoxy-1,4,4-trimethyl-8-(1-methyl-1H-indol-4-yl)-5H-[1,2,4]triazolo[4,3-a]quinoxaline |
| 488 | 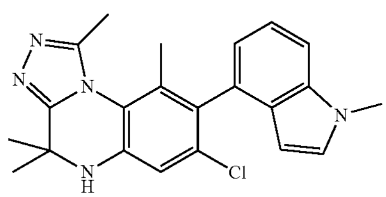 | 7-Chloro-1,4,4,9-tetramethyl-8-(1-methyl-1H-indol-4-yl)-5H-[1,2,4]triazolo[4,3-a]quinoxaline |
| 489 | 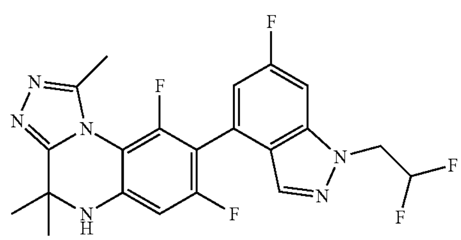 [SMILES: Cc1nnc2n1-c1c(cc(F)c(-c3cc(F)cc4c3cnn4CC(F)F)c1F)NC2(C)C] | 8-[1-(2,2-Difluoro-ethyl)-6-fluoro-1H-indazol-4-yl]-7,9-difluoro-1,4,4-trimethyl-5H-[1,2,4]triazolo[4,3-a]quinoxaline |
| 490 | 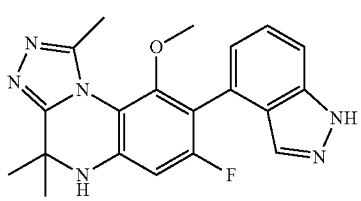 [SMILES: COc1c(-c2cccc3[nH]ncc23)c(F)cc2c1-n1c(C)nnc1C(C)(C)N2] | 7-Fluoro-8-(1H-indazol-4-yl)-9-methoxy-1,4,4-trimethyl-5H-[1,2,4]triazolo[4,3-a]quinoxaline |
| 491 | 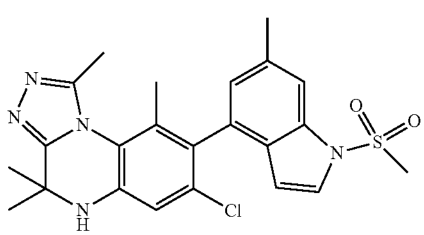 [SMILES: Cc1cc(-c2c(Cl)cc3c(c2C)-n2c(C)nnc2C(C)(C)N3)c2ccn(S(C)(=O)=O)c2c1] | 7-Chloro-1,4,4,9-tetramethyl-8-(6-methyl-1-methylsulfonyl-1H-indol-4-yl)-5H-[1,2,4]triazolo[4,3-a]quinoxaline |
| 492 | 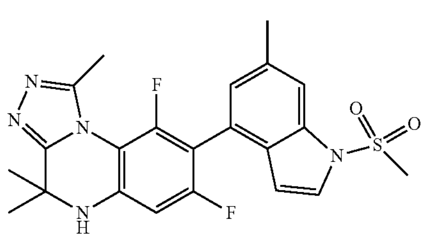 [SMILES: Cc1cc(-c2c(F)cc3c(c2F)-n2c(C)nnc2C(C)(C)N3)c2ccn(S(C)(=O)=O)c2c1] | 7,9-Difluoro-1,4,4-trimethyl-8-(6-methyl-1-methylsulfonyl-1H-indol-4-yl)-5H-[1,2,4]triazolo[4,3-a]quinoxaline |

-continued

| Ex. # | Structure | Name |
|---|---|---|
| 493 | 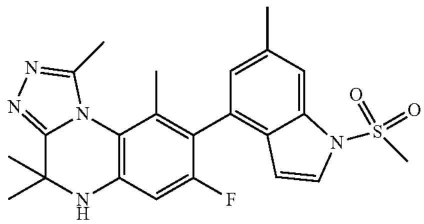 [SMILES: Cc1cc(-c2c(F)cc3c(c2C)-n2c(C)nnc2C(C)(C)N3)c2ccn(S(C)(=O)=O)c2c1] | 7-Fluoro-1,4,4,9-tetramethyl-8-(6-methyl-1-methylsulfonyl-1H-indol-4-yl)-5H-[1,2,4]triazolo[4,3-a]quinoxaline |
| 494 | 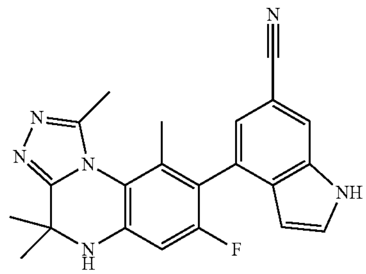 [SMILES: Cc1c(-c2cc(C#N)cc3[nH]ccc23)c(F)cc2c1-n1c(C)nnc1C(C)(C)N2] | 4-(7-Fluoro-1,4,4,9-tetramethyl-5H-[1,2,4]triazolo[4,3-a]quinoxalin-8-yl)-1H-indole-6-carbonitrile |
| 495 | 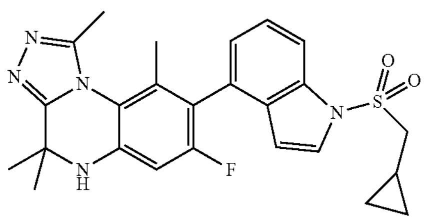 [SMILES: Cc1c(-c2cccc3c2ccn3S(=O)(=O)CC2CC2)c(F)cc2c1-n1c(C)nnc1C(C)(C)N2] | 8-[1-(Cyclopropyl-methylsulfonyl)-1H-indol-4-yl]-7-fluoro-1,4,4,9-tetramethyl-5H-[1,2,4]triazolo[4,3-a]quinoxaline |
| 496 | 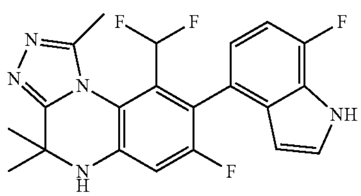 [SMILES: Cc1nnc2n1-c1c(cc(F)c(-c3ccc(F)c4[nH]ccc34)c1C(F)F)NC2(C)C] | 9-(Difluoro-methyl)-7-fluoro-8-(7-fluoro-1H-indol-4-yl)-1,4,4-trimethyl-5H-[1,2,4]triazolo[4,3-a]quinoxaline |
| 497 | 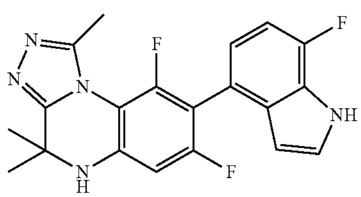 [SMILES: Cc1nnc2n1-c1c(cc(F)c(-c3ccc(F)c4[nH]ccc34)c1F)NC2(C)C] | 7,9-Difluoro-8-(7-fluoro-1H-indol-4-yl)-1,4,4-trimethyl-5H-[1,2,4]triazolo[4,3-a]quinoxaline |
| 498 | 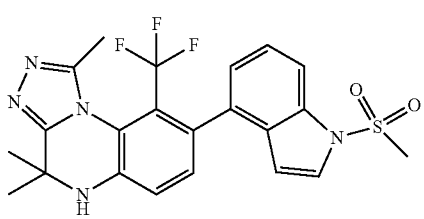 [SMILES: Cc1nnc2n1-c1c(ccc(-c3cccc4c3ccn4S(C)(=O)=O)c1C(F)(F)F)NC2(C)C] | 1,4,4-Trimethyl-8-(1-methylsulfonyl-1H-indol-4-yl)-9-(trifluoromethyl)-5H-[1,2,4]triazolo[4,3-a]quinoxaline |
| 499 | 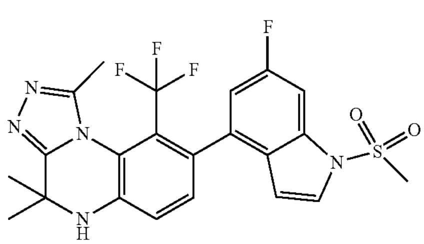 [SMILES: Cc1nnc2n1-c1c(ccc(-c3cc(F)cc4c3ccn4S(C)(=O)=O)c1C(F)(F)F)NC2(C)C] | 8-(6-Fluoro-1-methylsulfonyl-1H-indol-4-yl)-1,4,4-trimethyl-9-(trifluoromethyl)-5H-[1,2,4]triazolo[4,3-a]quinoxaline |

| Ex. # | Structure | Name |
|---|---|---|
| 500 | 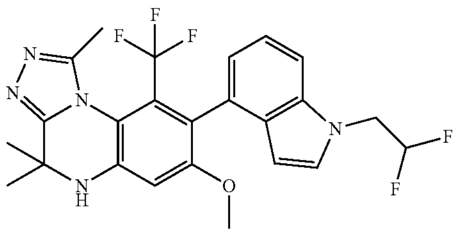 [SMILES: COc1cc2c(c(C(F)(F)F)c1-c1cccc3c1ccn3CC(F)F)-n1c(C)nnc1C(C)(C)N2] | 8-[1-(2,2-Difluoro-ethyl)-1H-indol-4-yl]-7-methoxy-1,4,4-trimethyl-9-(trifluoromethyl)-5H-[1,2,4]triazolo[4,3-a]quinoxaline |
| 501 | 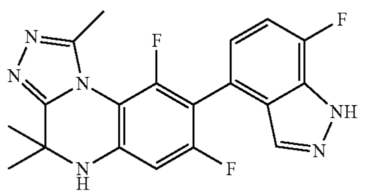 [SMILES: Cc1nnc2n1-c1c(cc(F)c(-c3ccc(F)c4[nH]ncc34)c1F)NC2(C)C] | 7,9-Difluoro-8-(7-fluoro-1H-indazol-4-yl)-1,4,4-trimethyl-5H-[1,2,4]triazolo[4,3-a]quinoxaline |
| 502 | 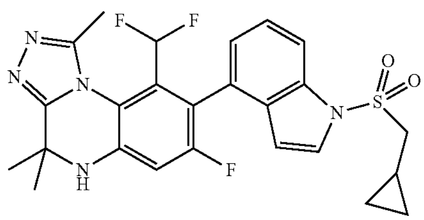 [SMILES: Cc1nnc2n1-c1c(cc(F)c(-c3cccc4c3ccn4S(=O)(=O)CC3CC3)c1C(F)F)NC2(C)C] | 8-[1-(Cyclopropyl-methylsulfonyl)-1H-indol-4-yl]-9-(difluoro-methyl)-7-fluoro-1,4,4-trimethyl-5H-[1,2,4]triazolo[4,3-a]quinoxaline |
| 503 | 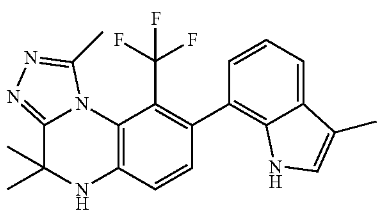 | 1,4,4-Trimethyl-8-(3-methyl-1H-indol-7-yl)-9-(trifluoromethyl)-5H-[1,2,4]triazolo[4,3-a]quinoxaline |
| 504 | 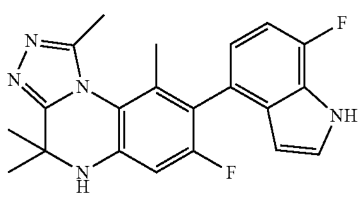 [SMILES: Cc1c(-c2ccc(F)c3[nH]ccc23)c(F)cc2c1-n1c(C)nnc1C(C)(C)N2] | 7-Fluoro-8-(7-fluoro-1H-indol-4-yl)-1,4,4,9-tetramethyl-5H-[1,2,4]triazolo[4,3-a]quinoxaline |
| 505 | 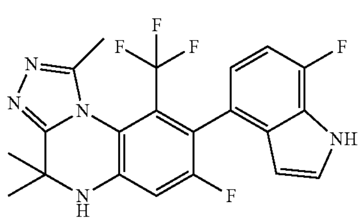 [SMILES: Cc1nnc2n1-c1c(cc(F)c(-c3ccc(F)c4[nH]ccc34)c1C(F)(F)F)NC2(C)C] | 7-Fluoro-8-(7-fluoro-1H-indol-4-yl)-1,4,4-trimethyl-9-(trifluoromethyl)-5H-[1,2,4]triazolo[4,3-a]quinoxaline |
| 506 | 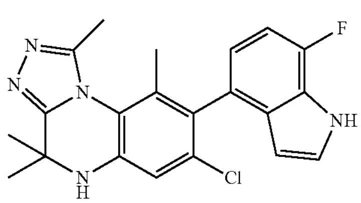 [SMILES: Cc1c(-c2ccc(F)c3[nH]ccc23)c(Cl)cc2c1-n1c(C)nnc1C(C)(C)N2] | 7-Chloro-8-(7-fluoro-1H-indol-4-yl)-1,4,4,9-tetramethyl-5H-[1,2,4]triazolo[4,3-a]quinoxaline |

-continued

| Ex. # | Structure | Name |
|---|---|---|
| 507 | 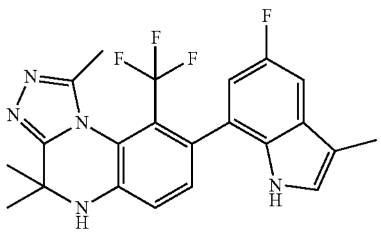 | 8-(5-Fluoro-3-methyl-1H-indol-7-yl)-1,4,4-trimethyl-9-(trifluoromethyl)-5H-[1,2,4]triazolo[4,3-a]quinoxaline |
| 508 | 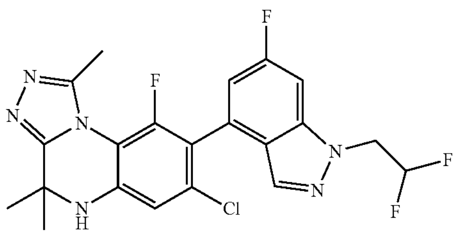 [SMILES: Cc1nnc2n1-c1c(cc(Cl)c(-c3cc(F)cc4c3cnn4CC(F)F)c1F)NC2(C)C] | 7-Chloro-8-[1-(2,2-difluoro-ethyl)-6-fluoro-1H-indazol-4-yl]-9-fluoro-1,4,4-trimethyl-5H-[1,2,4]triazolo[4,3-a]quinoxaline |
| 509 | 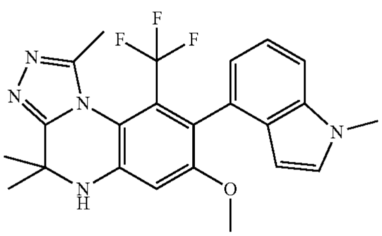 | 7-Methoxy-1,4,4-trimethyl-8-(1-methyl-1H-indol-4-yl)-9-(trifluoromethyl)-5H-[1,2,4]triazolo[4,3-a]quinoxaline |
| 510 | 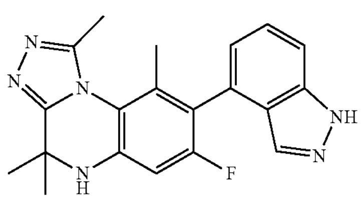 [SMILES: Cc1c(-c2cccc3[nH]ncc23)c(F)cc2c1-n1c(C)nnc1C(C)(C)N2] | 7-Fluoro-8-(1H-indazol-4-yl)-1,4,4,9-tetramethyl-5H-[1,2,4]triazolo[4,3-a]quinoxaline |
| 511 | 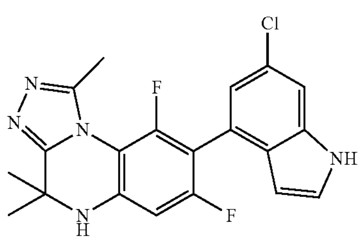 [SMILES: Cc1nnc2n1-c1c(cc(F)c(-c3cc(Cl)cc4[nH]ccc34)c1F)NC2(C)C] | 8-(6-Chloro-1H-indol-4-yl)-7,9-difluoro-1,4,4-trimethyl-5H-[1,2,4]triazolo[4,3-a]quinoxaline |
| 512 | 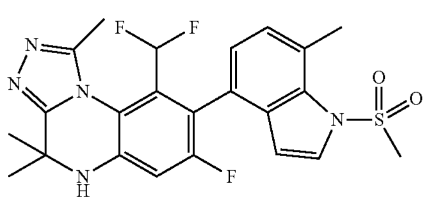 [SMILES: Cc1ccc(-c2c(F)cc3c(c2C(F)F)-n2c(C)nnc2C(C)(C)N3)c2ccn(S(C)(=O)=O)c12] | 9-(Difluoro-methyl)-7-fluoro-1,4,4-trimethyl-8-(7-methyl-1-methylsulfonyl-1H-indol-4-yl)-5H-[1,2,4]triazolo[4,3-a]quinoxaline |
| 513 | 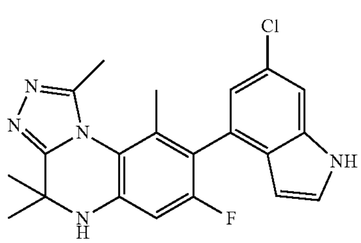 [SMILES: Cc1c(-c2cc(Cl)cc3[nH]ccc23)c(F)cc2c1-n1c(C)nnc1C(C)(C)N2] | 8-(6-Chloro-1H-indol-4-yl)-7-fluoro-1,4,4,9-tetramethyl-5H-[1,2,4]triazolo[4,3-a]quinoxaline |

| Ex. # | Structure | Name |
|---|---|---|
| 514 | 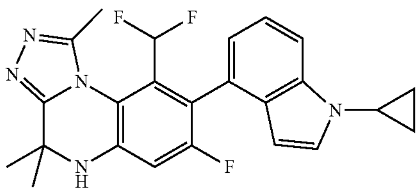 [SMILES: Cc1nnc2n1-c1c(cc(F)c(-c3cccc4c3ccn4C3CC3)c1C(F)F)NC2(C)C] | 8-(1-Cyclopropyl-1H-indol-4-yl)-9-(difluoro-methyl)-7-fluoro-1,4,4-trimethyl-5H-[1,2,4]triazolo[4,3-a]quinoxaline |
| 515 | 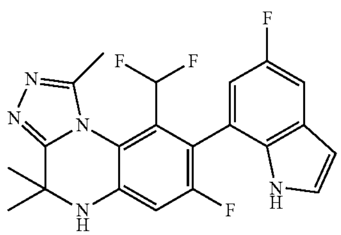 [SMILES: Cc1nnc2n1-c1c(cc(F)c(-c3cc(F)cc4cc[nH]c34)c1C(F)F)NC2(C)C] | 9-(Difluoro-methyl)-7-fluoro-8-(5-fluoro-1H-indol-7-yl)-1,4,4-trimethyl-5H-[1,2,4]triazolo[4,3-a]quinoxaline |
| 516 | 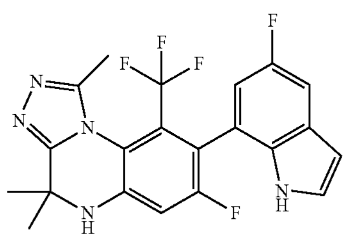 [SMILES: Cc1nnc2n1-c1c(cc(F)c(-c3cc(F)cc4cc[nH]c34)c1C(F)(F)F)NC2(C)C] | 7-Fluoro-8-(5-fluoro-1H-indol-7-yl)-1,4,4-trimethyl-9-(trifluoro-methyl)-5H-[1,2,4]triazolo[4,3-a]quinoxaline |
| 517 | 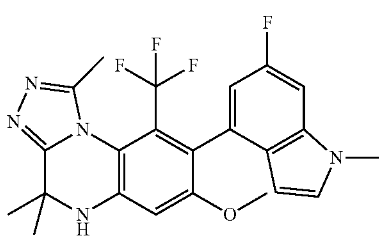 | 8-(6-Fluoro-1-methyl-1H-indol-4-yl)-7-methoxy-1,4,4-trimethyl-9-(trifluoromethyl)-5H-[1,2,4]triazolo[4,3-a]quinoxaline |
| 518 | 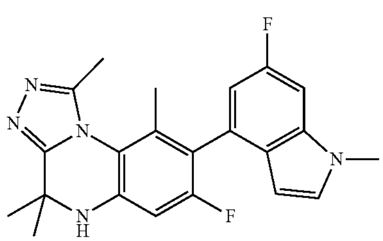 | 7-Fluoro-8-(6-fluoro-1-methyl-1H-indol-4-yl)-1,4,4,9-tetramethyl-5H-[1,2,4]triazolo[4,3-a]quinoxaline |
| 519 | 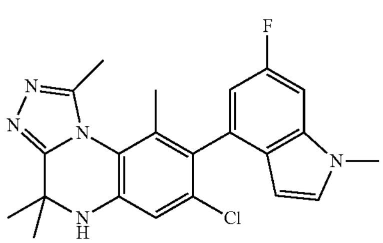 | 7-Chloro-8-(6-fluoro-1-methyl-1H-indol-4-yl)-1,4,4,9-tetramethyl-5H-[1,2,4]triazolo[4,3-a]quinoxaline |

| Ex. # | Structure | Name |
|---|---|---|
| 520 | 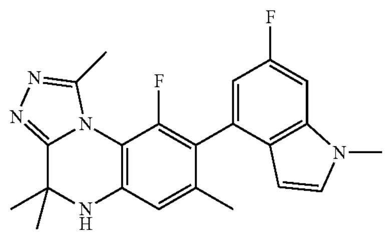 | 9-Fluoro-8-(6-fluoro-1-methyl-1H-indol-4-yl)-1,4,4,7-tetramethyl-5H-[1,2,4]triazolo[4,3-a]quinoxaline |
| 521 | 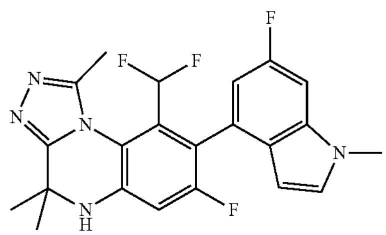 | 9-(Difluoro-methyl)-7-fluoro-8-(6-fluoro-1-methyl-1H-indol-4-yl)-1,4,4-trimethyl-5H-[1,2,4]triazolo[4,3-a]quinoxaline |
| 522 | 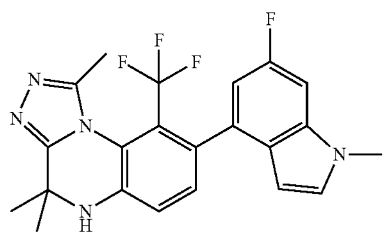 | 8-(6-Fluoro-1-methyl-1H-indol-4-yl)-1,4,4-trimethyl-9-(trifluoro-methyl)-5H-[1,2,4]triazolo[4,3-a]quinoxaline |
| 523 | 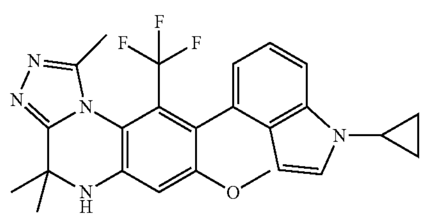 [SMILES: COc1cc2c(c(C(F)(F)F)c1-c1cccc3c1ccn3C1CC1)-n1c(C)nnc1C(C)(C)N2] | 8-(1-Cyclopropyl-1H-indol-4-yl)-7-methoxy-1,4,4-trimethyl-9-(trifluoromethyl)-5H-[1,2,4]triazolo[4,3-a]quinoxaline |
| 524 | 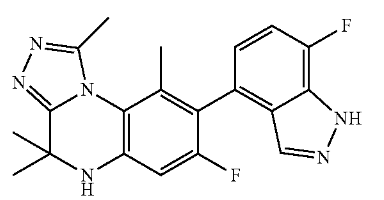 [SMILES: Cc1c(-c2ccc(F)c3[nH]ncc23)c(F)cc2c1-n1c(C)nnc1C(C)(C)N2] | 7-Fluoro-8-(7-fluoro-1H-indazol-4-yl)-1,4,4,9-tetramethyl-5H-[1,2,4]triazolo[4,3-a]quinoxaline |
| 525 | 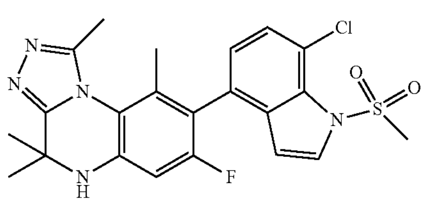 [SMILES: Cc1c(-c2ccc(Cl)c3c2ccn3S(C)(=O)=O)c(F)cc2c1-n1c(C)nnc1C(C)(C)N2] | 8-(7-Chloro-1-methylsulfonyl-1H-indol-4-yl)-7-fluoro-1,4,4,9-tetramethyl-5H-[1,2,4]triazolo[4,3-a]quinoxaline |
| 526 | 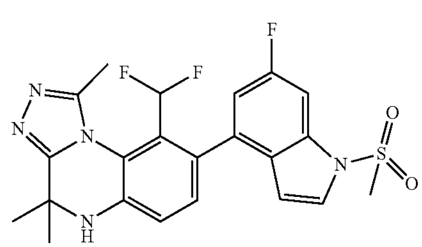 [SMILES: Cc1nnc2n1-c1c(ccc(-c3cc(F)cc4c3ccn4S(C)(=O)=O)c1C(F)F)NC2(C)C] | 9-(Difluoro-methyl)-8-(6-fluoro-1-methylsulfonyl-1H-indol-4-yl)-1,4,4-trimethyl-5H-[1,2,4]triazolo[4,3-a]quinoxaline |

-continued

| Ex. # | Structure | Name |
|---|---|---|
| 527 | 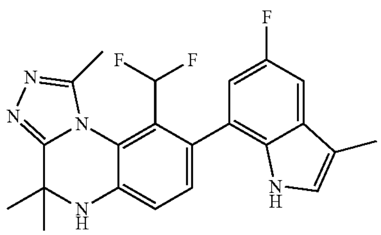 | 9-(Difluoro-methyl)-8-(5-fluoro-3-methyl-1H-indol-7-yl)-1,4,4-trimethyl-5H-[1,2,4]triazolo[4,3-a]quinoxaline |
| 528 | 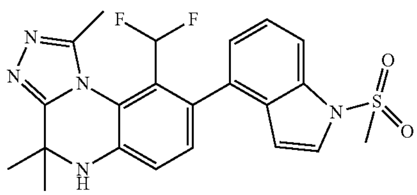 [SMILES: Cc1nnc2n1-c1c(ccc(-c3cccc4c3ccn4S(C)(=O)=O)c1C(F)F)NC2(C)C] | 9-(Difluoro-methyl)-1,4,4-trimethyl-8-(1-methylsulfonyl-1H-indol-4-yl)-5H-[1,2,4]triazolo[4,3-a]quinoxaline |
| 529 | 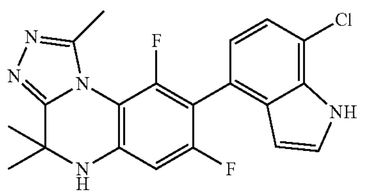 [SMILES: Cc1nnc2n1-c1c(cc(F)c(-c3ccc(Cl)c4[nH]ccc34)c1F)NC2(C)C] | 8-(7-Chloro-1H-indol-4-yl)-7,9-difluoro-1,4,4-trimethyl-5H-[1,2,4]triazolo[4,3-a]quinoxaline |
| 530 | 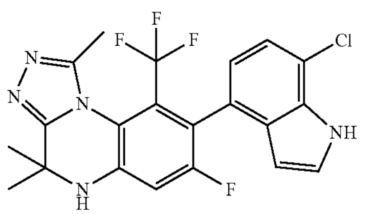 [SMILES: Cc1nnc2n1-c1c(cc(F)c(-c3ccc(Cl)c4[nH]ccc34)c1C(F)(F)F)NC2(C)C] | 8-(7-Chloro-1H-indol-4-yl)-7-fluoro-1,4,4-trimethyl-9-(trifluoromethyl)-5H-[1,2,4]triazolo[4,3-a]quinoxaline |
| 531 | 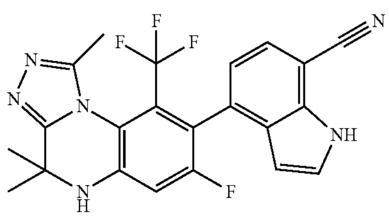 [SMILES: Cc1nnc2n1-c1c(cc(F)c(-c3ccc(C#N)c4[nH]ccc34)c1C(F)(F)F)NC2(C)C] | 4-[7-Fluoro-1,4,4-trimethyl-9-(trifluoromethyl)-5H-[1,2,4]triazolo[4,3-a]quinoxalin-8-yl]-1H-indole-7-carbonitrile |
| 532 | 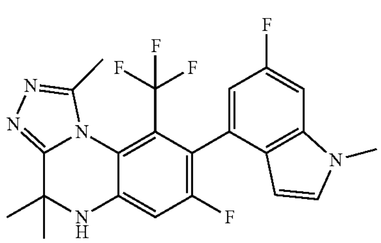 | 7-Fluoro-8-(6-fluoro-1-methyl-1H-indol-4-yl)-1,4,4-trimethyl-9-(trifluoromethyl)-5H-[1,2,4]triazolo[4,3-a]quinoxaline |
| 533 | 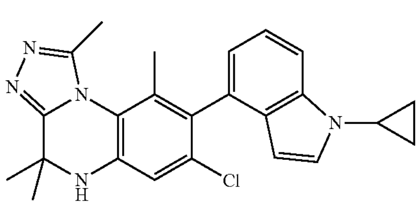 [SMILES: Cc1c(-c2cccc3c2ccn3C2CC2)c(Cl)cc2c1-n1c(C)nnc1C(C)(C)N2] | 7-Chloro-8-(1-cyclopropyl-1H-indol-4-yl)-1,4,4,9-tetramethyl-5H-[1,2,4]triazolo[4,3-a]quinoxaline |

-continued

| Ex. # | Structure | Name |
|---|---|---|
| 534 | 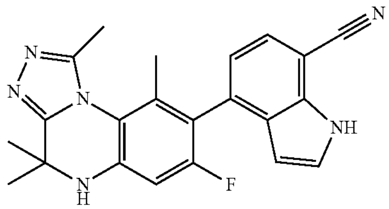 [SMILES: Cc1c(-c2ccc(C#N)c3[nH]ccc23)c(F)cc2c1-n1c(C)nnc1C(C)(C)N2] | 4-(7-Fluoro-1,4,4,9-tetramethyl-5H-[1,2,4]triazolo[4,3-a]quinoxalin-8-yl)-1H-indole-7-carbonitrile |
| 535 | 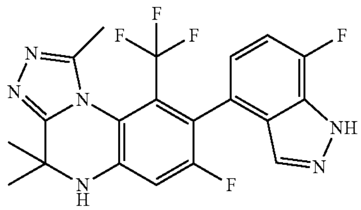 [SMILES: Cc1nnc2n1-c1c(cc(F)c(-c3ccc(F)c4[nH]ncc34)c1C(F)(F)F)NC2(C)C] | 7-Fluoro-8-(7-fluoro-1H-indazol-4-yl)-1,4,4-trimethyl-9-(trifluoromethyl)-5H-[1,2,4]triazolo[4,3-a]quinoxaline |
| 536 | 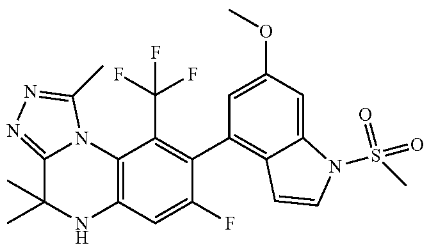 [SMILES: COc1cc(-c2c(F)cc3c(c2C(F)(F)F)-n2c(C)nnc2C(C)(C)N3)c2ccn(S(C)(=O)=O)c2c1] | 7-Fluoro-8-(6-methoxy-1-methylsulfonyl-1H-indol-4-yl)-1,4,4-trimethyl-9-(trifluoromethyl)-5H-[1,2,4]triazolo[4,3-a]quinoxaline |
| 537 | 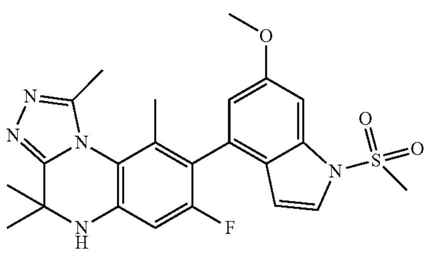 [SMILES: COc1cc(-c2c(F)cc3c(c2C)-n2c(C)nnc2C(C)(C)N3)c2ccn(S(C)(=O)=O)c2c1] | 7-Fluoro-8-(6-methoxy-1-methylsulfonyl-1H-indol-4-yl)-1,4,4,9-tetramethyl-5H-[1,2,4]triazolo[4,3-a]quinoxaline |

Biological Assays

Agonistic Mode of Action on the Glucocorticoid Receptor

The reporter cell line CHO-Gal4/GR consisted of a Chinese hamster ovary (CHO) cell line (Leibniz Institute DSMZ—German Collection of Microorganisms and Cell Cultures GmbH: ACC-110) containing a firefly luciferase gene under the control of the GR ligand binding domain fused to the DNA binding domain (DBD) of GAL4 (GAL4 DBD-GR) stably integrated into CHO cells. This cell line was established by stable transfection of CHO cells with a GAL4-UAS-Luciferase reporter construct. In a subsequent step the ligand binding domain of the GR cloned into pIRES2-EGFP-GAL4 containing the DNA binding domain of GAL4 from pFA-AT2 was transfected. This fusion construct activated firefly luciferase expression under the control of a multimerized GAL4 upstream activation sequence (UAS). The signal of the emitted luminescence was recorded by the FLIPR$^{TETRA}$. This allowed for specific detection of ligand-induced activation of the GR and therefore for the identification of compounds with agonistic properties. The GAL4/UAS reporter was premixed with a vector that constitutively expressed Renilla luciferase, which served as an internal positive control for transfection efficiency.

The complete culture medium for the assay was:
DMEM F-12 (1:1) MIXTURE (LONZA cat. N°: BE04-687F/U1) 500 mL
5 mL of 100 mM Sodium Pyruvate (LONZA cat. N°: BE12-115E)
25 mL of 7.5% Sodium Bicarbonate (LONZA cat. N° BE17-613E)
6.5 mL of 1 M Hepes (LONZA cat. N°: BE17-737E)
5 mL of 100× Penicillin/Streptomycin (LONZA cat. N° DE17-602E)
50 mL of Fetal Bovine Serum (Euroclone cat. N° ECS 0180L)
0.25 mL of 10 mg/mL Puromycin (InvivoGen cat.: ant-pr-1)
0.5 mL of 100 mg/mL Zeocin (InvivoGen cat.: ant-zn-1)

Cryo-preserved CHO-Gal4/GR cells were suspended in complete medium and 5000 cells/25 µl/well were seeded into the wells of 384-well polystyrene assay plates (Thermo Scientific, cat. #4332) and cultured at 37° C., 5% $CO_2$ and 95% humidity. After 24 hours growth medium was carefully removed and replaced by 30 µl Opti-MEM (GIBCO, cat. #31985062) as assay buffer. To test the compounds an 8-point half-log compound dilution curve was generated in 100% DMSO starting from a 2 mM stock and compounds were then diluted 1:50 in Opti-MEM. 10 µl of compounds were then added to the wells containing 30 µl Opti-MEM resulting in a final assay concentration range from 10 µM to 0.003 µM in 0.5% DMSO. Compounds were tested at 8 concentrations in quadruplicate data points. Cells were incubated for 6 hour with compounds and beclometasone (Sigma, cat. #Y0000351) as control compound at 37° C., 5% $CO_2$ and 95% humidity in a total volume of 40 µl. Finally, cells were lysed with 20 µl of Triton/Luciferin solution and the signal of the emitted luminescence was recorded at the FLIPR$^{TETRA}$ for 2 minutes.

The relative efficacy of a compound (% effect) was calculated based on the full effect of the agonist beclometasone:

% effect=((compound−min)/(max−min))×100
[min=Opti-MEM only, max=beclometasone]

To calculate EC50, max, min and slope factor for each compound a concentration response curve was fitted by plotting % effect versus compound concentration using a 4 parameter logistic equation:

$y=A+(B-A)/(1+((10C)/x)D)$ [$A$=min $y$, $B$=max $y$, $C$=log EC$_{50}$, $D$=slope]

Antagonistic Mode of Action on the Glucocorticoid Receptor

The reporter cell line CHO-Gal4/GR consisted of a Chinese hamster ovary (CHO) cell line (Leibniz Institute DSMZ—German Collection of Microorganisms and Cell Cultures GmbH: ACC-110) containing a firefly luciferase gene under the control of the GR ligand binding domain fused to the DNA binding domain (DBD) of GAL4 (GAL4 DBD-GR) stably integrated into CHO cells. This cell line was established by stable transfection of CHO cells with a GAL4-UAS-Luciferase reporter construct. In a subsequent step the ligand binding domain of the GR cloned into pIRES2-EGFP-GAL4 containing the DNA binding domain of GAL4 from pFA-AT2 was transfected. This fusion construct activated firefly luciferase expression under the control of a multimerized GAL4 upstream activation sequence (UAS). The signal of the emitted luminescence was recorded by the FLIPR$^{TETRA}$. This allowed for specific detection of antagonistic properties of compounds by measuring the ligand-induced inhibition of beclometasone-activated GR. The GAL4/UAS reporter was premixed with a vector that constitutively expressed Renilla luciferase, which served as an internal positive control for transfection efficiency.

The complete culture medium for the assay was:
DMEM F-12 (1:1) MIXTURE (LONZA cat. N°: BE04-687F/U1) 500 mL
5 mL of 100 mM Sodium Pyruvate (LONZA cat. N°: BE12-115E)
25 mL of 7.5% Sodium Bicarbonate (LONZA cat. N° BE17-613E)
6.5 mL of 1 M Hepes (LONZA cat. N°: BE17-737E)
5 mL of 100× Penicillin/Streptomycin (LONZA cat. N° DE17-602E)
50 mL of Fetal Bovine Serum (Euroclone cat. N° ECS 0180L)
0.25 mL of 10 mg/mL Puromycin (InvivoGen cat.: ant-pr-1)
0.5 mL of 100 mg/mL Zeocin (InvivoGen cat.: ant-zn-1)

Cryo-preserved CHO-Gal4/GR cells were suspended in complete medium and 5000 cells/25 µl/well were seeded into the wells of 384-well polystyrene assay plates (Thermo Scientific, cat. #4332) and cultured at 37° C., 5% $CO_2$ and 95% humidity. After 24 hours growth medium was carefully removed and replaced by 20 µl Opti-MEM (GIBCO, cat. #31985062) as assay buffer. For testing compounds an 8-point half-log compound dilution curve was generated in 100% DMSO starting from a 2 mM stock and compounds were then diluted 1:50 in Opti-MEM. To test the compounds in the antagonist mode 10 µl of compounds were then added to the wells containing 20 µl Opti-MEM and incubated for 10 min. After this pre-incubation 10 µl of the reference agonist beclometasone (Sigma, cat. #Y0000351) at an EC50 of 2.5 nM were added resulting in a final assay concentration range from 10 µM to 0.003 µM in 0.5% DMSO in a total volume of 40 µl. Compounds were tested at 8 concentrations in quadruplicate data points. Cells were incubated for 6 hour with compounds and mifepristone as control compound (Sigma, cat. #M8046) at 37° C., 5% $CO_2$ and 95% humidity. Finally, cells were lysed with 20 µl of Triton/Luciferin solution and the signal of the emitted luminescence was recorded at the FLIPR$^{TETRA}$ for 2 minutes.

The relative efficacy of a compound (% effect) was calculated based on the full effect of the antagonist mifepristone:

% effect=((compound−min)/(max−min))x−100
[min=Opti-MEM only, max=mifepristone]

To calculate IC50, max, min and slope factor for each compound a concentration response curve was fitted by plotting % effect versus compound concentration using a 4 parameter logistic equation:

$y=A+(B-A)/(1+((10C)/x)D)$ [$A$=min $y$, $B$=max $y$, $C$=log IC$_{50}$, $D$=slope]

In Table 9 below, the IC50 or EC50 ranges of the Examples are summarized which were observed in the agonistic assay or the antagonistic assay described above.

TABLE 9

(A < 100 nM; B = 100 nM-1 µM; C = 1 µM-15 µM; n.d. = not determined):

| Ex. # | IC50 or EC50 |
|---|---|
| 1 | A |
| 2 | A |
| 3 | A |
| 4 | A |
| 5 | B |
| 6 | C |
| 9 | B |
| 10 | B |
| 11 | B |
| 12 | C |
| 13 | B |
| 14 | n.d. |
| 15 | C |
| 16 | B |
| 17 | B |
| 18 | B |
| 19 | B |
| 20 | B |
| 21 | B |
| 22 | B |
| 23 | A |
| 24 | A |
| 25 | B |
| 26 | n.d. |
| 27 | A |
| 28 | A |
| 29 | A |
| 30 | A |
| 31 | A |
| 32 | n.d. |
| 33 | A |
| 34 | n.d. |
| 35 | B |
| 36 | B |
| 37 | A |

TABLE 9-continued (A < 100 nM; B = 100 nM-1 µM; C = 1 µM-15 µM; n.d. = not determined):

| Ex. # | IC50 or EC50 |
|---|---|
| 39 | B |
| 40 | A |
| 41 | A |
| 42 | A |
| 43 | A |
| 44 | B |
| 45 | B |
| 46 | A |
| 47 | A |
| 50 | n.d. |
| 51 | B |
| 52 | A |
| 67 | C |
| 68 | B |
| 69 | A |
| 70 | A |
| 71 | n.d. |
| 72 | n.d. |
| 73 | B |
| 74 | A |
| 75 | A |
| 76 | A |
| 77 | B |
| 78 | C |
| 79 | C |
| 80 | n.d. |
| 81 | n.d. |
| 82 | n.d. |
| 83 | C |
| 84 | n.d. |
| 85 | B |
| 86 | B |
| 87 | B |
| 88 | A |
| 89 | B |
| 200 | C |
| 201 | C |
| 202 | A |
| 203 | n.d. |
| 204 | B |
| 205 | B |
| 207 | B |
| 208 | A |
| 210 | A |
| 212 | C |
| 213 | A |
| 214 | A |
| 219 | C |
| 221 | B |
| 222 | C |
| 223 | A |
| 224 | B |
| 225 | A |
| 228 | C |
| 229 | C |
| 230 | n.d. |
| 232 | B |
| 233 | B |
| 234 | C |
| 235 | A |
| 236 | B |
| 237 | C |
| 238 | B |
| 239 | B |
| 240 | C |
| 241 | n.d. |
| 242 | C |
| 243 | B |
| 244 | C |
| 247 | C |
| 248 | B |
| 249 | A |
| 250 | A |
| 251 | B |
| 252 | B |
| 253 | B |
| 254 | B |
| 255 | C |
| 256 | C |
| 257 | B |
| 258 | n.d. |
| 259 | C |
| 260 | B |
| 263 | C |
| 264 | B |
| 266 | B |
| 267 | B |
| 268 | C |
| 269 | n.d. |
| 270 | B |
| 271 | C |
| 272 | B |
| 273 | C |
| 275 | C |
| 276 | B |
| 277 | n.d. |
| 278 | n.d. |
| 279 | A |
| 280 | C |
| 281 | B |
| 282 | B |
| 283 | n.d. |
| 284 | B |
| 285 | C |
| 286 | B |
| 287 | n.d. |
| 288 | C |
| 289 | C |
| 290 | B |
| 292 | B |
| 293 | n.d. |
| 294 | A |
| 295 | C |
| 296 | B |
| 297 | C |
| 298 | C |
| 299 | C |
| 302 | A |
| 306 | B |
| 309 | A |
| 310 | B |
| 312 | B |
| 313 | n.d. |
| 314 | C |
| 315 | B |
| 317 | C |
| 318 | B |
| 319 | n.d. |
| 320 | n.d. |
| 321 | C |
| 324 | B |
| 325 | n.d. |
| 327 | B |
| 328 | B |
| 329 | B |
| 330 | A |
| 331 | C |
| 332 | C |
| 333 | A |
| 334 | C |
| 335 | B |
| 336 | C |
| 337 | C |
| 338 | B |
| 339 | B |
| 341 | B |
| 342 | C |
| 343 | C |
| 344 | C |
| 345 | B |

TABLE 9-continued (A < 100 nM; B = 100 nM-1 μM; C = 1 μM-15 μM; n.d. = not determined):

| Ex. # | IC50 or EC50 |
|---|---|
| 346 | B |
| 347 | B |
| 348 | C |
| 351 | A |
| 353 | C |
| 354 | B |
| 356 | A |
| 357 | A |
| 358 | A |
| 359 | B |
| 360 | B |
| 361 | C |
| 362 | A |
| 363 | A |
| 364 | B |
| 365 | C |
| 367 | B |
| 368 | B |
| 369 | B |
| 370 | n.d. |
| 371 | B |
| 372 | A |
| 373 | B |
| 376 | C |
| 377 | B |
| 379 | n.d. |
| 380 | C |
| 381 | C |
| 382 | C |
| 383 | C |
| 384 | C |
| 385 | C |
| 386 | C |
| 387 | n.d. |
| 388 | n.d. |
| 390 | A |
| 392 | C |
| 393 | C |
| 394 | C |
| 395 | n.d. |
| 396 | C |
| 397 | B |
| 398 | B |
| 399 | A |
| 400 | C |
| 401 | B |
| 402 | B |
| 403 | A |
| 404 | B |
| 405 | B |
| 406 | B |
| 407 | A |
| 445 | A |
| 446 | B |
| 447 | B |
| 448 | B |
| 449 | A |
| 450 | B |
| 451 | B |
| 452 | A |
| 453 | A |
| 454 | B |
| 455 | A |
| 456 | B |
| 457 | B |
| 458 | B |
| 459 | A |
| 460 | B |
| 461 | A |
| 462 | A |
| 463 | A |
| 464 | n.d. |
| 465 | A |
| 466 | A |
| 467 | A |
| 468 | A |
| 469 | B |
| 470 | B |
| 471 | B |
| 472 | A |
| 473 | B |
| 474 | B |
| 475 | B |
| 476 | B |
| 477 | B |
| 478 | B |
| 479 | B |
| 480 | B |
| 481 | B |
| 482 | A |
| 483 | A |
| 484 | B |
| 485 | A |
| 486 | A |
| 487 | B |
| 488 | B |
| 489 | A |
| 490 | B |
| 491 | A |
| 492 | A |
| 493 | A |
| 494 | B |
| 495 | n.d. |
| 496 | A |
| 497 | B |
| 498 | B |
| 499 | B |
| 500 | B |
| 501 | B |
| 502 | B |
| 503 | B |
| 504 | B |
| 505 | B |
| 506 | B |
| 507 | A |
| 508 | B |
| 509 | B |
| 510 | B |
| 511 | A |
| 512 | C |
| 513 | B |
| 514 | B |
| 515 | B |
| 516 | B |
| 517 | B |
| 518 | A |
| 519 | A |
| 520 | B |
| 521 | A |
| 522 | B |
| 523 | B |
| 524 | B |
| 525 | B |
| 526 | B |
| 527 | A |
| 528 | B |
| 529 | B |
| 530 | B |
| 531 | B |
| 532 | A |
| 533 | A |
| 534 | B |
| 535 | n.d. |
| 536 | B |
| 537 | B |

The invention claimed is:
1. A compound according to general formula (I),

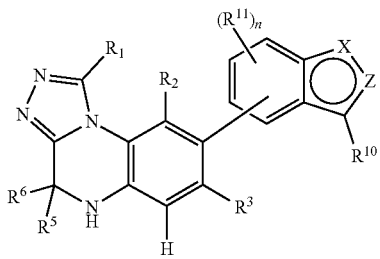

wherein
R¹ represents H; $C_{1-10}$-alkyl; $C_{3-10}$-cycloalkyl; 3 to 7 membered heterocycloalkyl; aryl; or 5 or 6-membered heteroaryl;
 wherein $C_{3-10}$-cycloalkyl, 3 to 7 membered heterocycloalkyl, aryl and 5 or 6-membered heteroaryl can optionally be bridged via $C_{1-6}$-alkylene;
R² represents H; F; Cl; Br; I; CN; $C_{1-10}$-alkyl; $C_{3-10}$-cycloalkyl; O—$C_{1-10}$-alkyl; N(H)($C_{1-10}$-alkyl), N($C_{1-10}$-alkyl)₂; C(O)—$C_{1-10}$-alkyl; C(O)—O—$C_{1-10}$-alkyl; C(O)—NH₂; C(O)—N(H)($C_{1-10}$-alkyl); C(O)—N($C_{1-10}$-alkyl)₂; O—$C_{3-10}$-cycloalkyl; N(H)($C_{3-10}$-cycloalkyl), N($C_{1-10}$-alkyl)($C_{3-10}$-cycloalkyl); C(O)—$C_{3-10}$-cycloalkyl; C(O)—O—$C_{3-10}$-cycloalkyl; C(O)—N(H)($C_{3-10}$-cycloalkyl) or C(O)—N($C_{1-10}$-alkyl)($C_{3-10}$-cycloalkyl);
 wherein $C_{3-10}$-cycloalkyl can optionally be bridged via $C_{1-6}$-alkylene;
R³ represents H; F; Cl; Br; I; CN; $C_{1-10}$-alkyl; $C_{3-10}$-cycloalkyl; O—$C_{1-10}$-alkyl; N(H)($C_{1-10}$-alkyl); N($C_{1-10}$-alkyl)₂; C(O)—$C_{1-10}$-alkyl; C(O)—O—$C_{1-10}$-alkyl; C(O)—NH₂; C(O)—N(H)($C_{1-10}$-alkyl); C(O)—N($C_{1-10}$-alkyl)₂; O—$C_{3-10}$-cycloalkyl; N(H)($C_{3-10}$-cycloalkyl), N($C_{1-10}$-alkyl)($C_{3-10}$-cycloalkyl); C(O)—$C_{3-10}$-cycloalkyl; C(O)—O—$C_{3-10}$-cycloalkyl; C(O)—N(H)($C_{3-10}$-cycloalkyl) or C(O)—N($C_{1-10}$-alkyl)($C_{3-10}$-cycloalkyl);
 wherein $C_{3-10}$-cycloalkyl can optionally be bridged via $C_{1-6}$-alkylene;
R⁵ and R⁶ represent independently from one another H or unsubstituted $C_{1-4}$-alkyl;
X represents N or NR⁷;
Z represents N, NR⁷ or CR⁹;
 with the proviso that
 when X represents NR⁷, Z represents N or CR⁹;
 when X represents N, Z represents NR⁷;
R⁷ represents H or L-R⁸; wherein
 L represents bond; S(O); S(O)₂; $C_{1-6}$-alkylene; C(O); $C_{1-6}$-alkylene-C(O); C(O)—O; $C_{1-6}$-alkylene-C(O)—O; $C_{1-6}$-alkylene-N(H)—C(O); $C_{1-6}$-alkylene-N($C_{1-10}$-alkyl)-C(O); $C_{1-6}$-alkylene-N(H)—C(O)—O; $C_{1-6}$-alkylene-N($C_{1-10}$-alkyl)-C(O)—O; O; NH or N($C_{1-10}$-alkyl);
R⁸ represents $C_{1-10}$-alkyl; $C_{3-10}$-cycloalkyl or 3 to 7 membered heterocycloalkyl;
 wherein $C_{3-10}$-cycloalkyl and 3 to 7 membered heterocycloalkyl can optionally be bridged via $C_{1-6}$-alkylene;
R⁹ and R¹⁰ represent independently from one another H; F; Cl; Br; I; CN; $C_{1-10}$-alkyl; $C_{3-10}$-cycloalkyl; 3 to 7 membered heterocycloalkyl; S(O)-($C_{1-10}$-alkyl); S(O)-($C_{3-10}$-cycloalkyl); S(O)-(3 to 7-membered heterocycloalkyl); S(O)₂—($C_{1-10}$-alkyl); S(O)₂—($C_{3-10}$-cycloalkyl); S(O)₂-(3 to 7-membered heterocycloalkyl); P(O)-($C_{1-10}$-alkyl)₂; P(O)($C_{1-10}$-alkyl)($C_{3-10}$-cycloalkyl); P(O)($C_{1-10}$-alkyl)(3 to 7-membered heterocycloalkyl); P(O)—(O—$C_{1-10}$-alkyl)₂; P(O)(O—$C_{1-10}$-alkyl)(O—$C_{3-10}$-cycloalkyl); P(O)(O—$C_{1-10}$-alkyl)(O-(3 to 7-membered heterocycloalkyl)); O—$C_{1-10}$-alkyl; S—$C_{1-10}$-alkyl; N(H)($C_{1-10}$-alkyl), N($C_{1-10}$-alkyl)₂; C(O)—$C_{1-10}$-alkyl; C(O)—O—$C_{1-10}$-alkyl; C(O)—NH₂; C(O)—N(H)($C_{1-10}$-alkyl); C(O)—N($C_{1-10}$-alkyl)₂; O—$C_{3-10}$-cycloalkyl; N(H)($C_{3-10}$-cycloalkyl), N($C_{1-10}$-alkyl)($C_{3-10}$-cycloalkyl); C(O)—$C_{3-10}$-cycloalkyl;
C(O)—O—$C_{3-10}$-cycloalkyl; C(O)—N(H)($C_{3-10}$-cycloalkyl); C(O)—N($C_{1-10}$-alkyl)($C_{3-10}$-cycloalkyl); O-3 to 7-membered heterocycloalkyl; N(H)(3 to 7-membered heterocycloalkyl), N($C_{1-10}$-alkyl)(3 to 7-membered heterocycloalkyl); C(O)-3 to 7-membered heterocycloalkyl; C(O)—O-(3 to 7-membered heterocycloalkyl); C(O)—N(H)(3 to 7-membered heterocycloalkyl) or C(O)—N($C_{1-10}$-alkyl)(3 to 7-membered heterocycloalkyl);
 wherein $C_{3-10}$-cycloalkyl and 3 to 7 membered heterocycloalkyl can optionally be bridged via $C_{1-6}$-alkylene;
R¹¹ represents F; Cl; Br; I; CN; $C_{1-10}$-alkyl; O—$C_{1-10}$-alkyl; NO₂; OH, NH₂; $C_{3-10}$-cycloalkyl; 3 to 7-membered heterocycloalkyl; S(O)-($C_{1-10}$-alkyl); S(O)-($C_{3-10}$-cycloalkyl); S(O)-(3 to 7-membered heterocycloalkyl); S(O)₂—($C_{1-10}$-alkyl); S(O)₂—($C_{3-10}$-cycloalkyl); S(O)₂-(3 to 7-membered heterocycloalkyl); P(O)-($C_{1-10}$-alkyl)₂; P(O)($C_{1-10}$-alkyl)($C_{3-10}$-cycloalkyl); P(O)($C_{1-10}$-alkyl)(3 to 7-membered heterocycloalkyl); P(O)—(O—$C_{1-10}$-alkyl)₂; P(O)(O—$C_{1-10}$-alkyl)(O—$C_{3-10}$-cycloalkyl); P(O)(O—$C_{1-10}$-alkyl)(O-(3 to 7-membered heterocycloalkyl)); O—$C_{1-10}$-alkyl; N(H)($C_{1-10}$-alkyl), N($C_{1-10}$-alkyl)₂; C(O)—$C_{1-10}$-alkyl; C(O)—O—$C_{1-10}$-alkyl; C(O)—NH₂; C(O)—N(H)($C_{1-10}$-alkyl); C(O)—N($C_{1-10}$-alkyl)₂; O—$C_{3-10}$-cycloalkyl; N(H)($C_{3-10}$-cycloalkyl), N($C_{1-10}$-alkyl)($C_{3-10}$-cycloalkyl); C(O)—$C_{3-10}$-cycloalkyl; C(O)—O—$C_{3-10}$-cycloalkyl; C(O)—N(H)($C_{3-10}$-cycloalkyl); C(O)—N($C_{1-10}$-alkyl)($C_{3-10}$-cycloalkyl); O-3 to 7-membered heterocycloalkyl; N(H)(3 to 7-membered heterocycloalkyl), N($C_{1-10}$-alkyl)(3 to 7-membered heterocycloalkyl); C(O)-3 to 7-membered heterocycloalkyl; C(O)—O-(3 to 7-membered heterocycloalkyl); C(O)—N(H)(3 to 7-membered heterocycloalkyl) or C(O)—N($C_{1-10}$-alkyl)(3 to 7-membered heterocycloalkyl);
 wherein $C_{3-10}$-cycloalkyl and 3 to 7 membered heterocycloalkyl can optionally be bridged via $C_{1-6}$-alkylene;
n represents 0, 1, 2 or 3;
wherein $C_{1-10}$-alkyl, $C_{1-4}$-alkyl and $C_{1-6}$-alkylene in each case independently from one another is linear or branched, saturated or unsaturated;
wherein $C_{1-10}$-alkyl, $C_{1-4}$-alkyl, $C_{1-6}$-alkylene, $C_{3-10}$-cycloalkyl and 3 to 7 membered heterocycloalkyl in each case independently from one another are unsubstituted or mono- or polysubstituted with one or more substituents selected from F; Cl; Br; I; CN; $C_{1-6}$-alkyl; CF₃; CF₂H; CFH₂; CF₂Cl; CFCl₂; C(O)—$C_{1-6}$-alkyl; C(O)—OH; C(O)—O$C_{1-6}$-alkyl; C(O)—NH₂; C(O)—N(H)($C_{1-6}$-alkyl); C(O)—N($C_{1-6}$-alkyl)₂; OH; =O; OCF₃; OCF₂H; OCFH₂; OCF₂Cl; OCFCl₂; O—$C_{1-6}$- alkyl; O—C(O)—C$_{1-6}$-alkyl; O—C(O)—O—C$_{1-6}$-alkyl; O—(CO)—N(H)(C$_{1-6}$-alkyl); O—C(O)—N(C$_{1-6}$-alkyl)$_2$; O—S(O)$_2$—NH$_2$; O—S(O)$_2$—N(H)(C$_{1-6}$-alkyl); O—S(O)$_2$—N(C$_{1-6}$-alkyl)$_2$; NH$_2$; N(H)(C$_{1-6}$-alkyl); N(C$_{1-6}$-alkyl)$_2$; N(H)—C(O)—C$_{1-6}$-alkyl; N(H)—C(O)—O—C$_{1-6}$-alkyl; N(H)—C(O)—NH$_2$; N(H)—C(O)—N(H)(C$_{1-6}$-alkyl); N(H)—C(O)—N(C$_{1-6}$-alkyl)$_2$; N(C$_{1-6}$-alkyl)-C(O)—C$_{1-6}$-alkyl; N(C$_{1-6}$-alkyl)-C(O)—O—C$_{1-6}$-alkyl; N(C$_{1-6}$-alkyl)-C(O)—NH$_2$; N(C$_{1-6}$-alkyl)-C(O)—N(H)(C$_{1-6}$-alkyl); N(C$_{1-6}$-alkyl)-C(O)—N(C$_{1-6}$-alkyl)$_2$; N(H)—S(O)$_2$OH; N(H)—S(O)$_2$—C$_{1-6}$-alkyl; N(H)—S(O)$_2$—O—C$_{1-6}$-alkyl; N(H)—S(O)$_2$—NH$_2$; N(H)—S(O)$_2$—N(H)(C$_{1-6}$-alkyl); N(H)—S(O)$_2$N(C$_{1-6}$-alkyl)$_2$; N(C$_{1-6}$-alkyl)-S(O)$_2$—OH; N(C$_{1-6}$-alkyl)-S(O)$_2$—C$_{1-6}$-alkyl; N(C$_{1-6}$-alkyl)-S(O)$_2$—O—C$_{1-6}$-alkyl; N(C$_{1-6}$-alkyl)-S(O)$_2$—NH$_2$; N(C$_{1-6}$-alkyl)-S(O)$_2$—N(H)(C$_{1-6}$-alkyl); N(C$_{1-6}$-alkyl)-S(O)$_2$—N(C$_{1-6}$-alkyl)$_2$; SCF$_3$; SCF$_2$H; SCFH$_2$; S—C$_{1-6}$-alkyl; S(O)—C$_{1-6}$-alkyl; S(O)$_2$—C$_{1-6}$-alkyl; S(O)$_2$—OH; S(O)$_2$—O—C$_{1-6}$-alkyl; S(O)$_2$—NH$_2$; S(O)$_2$—N(H)(C$_{1-6}$-alkyl); S(O)$_2$—N(C$_{1-6}$-alkyl)$_2$; C$_{3-6}$-cycloalkyl; 3 to 6-membered heterocycloalkyl; phenyl; 5 or 6-membered heteroaryl; O—C$_{3-6}$-cycloalkyl; O-(3 to 6-membered heterocycloalkyl); O-phenyl; O-(5 or 6-membered heteroaryl); C(O)—C$_{3-6}$-cycloalkyl; C(O)-(3 to 6-membered heterocycloalkyl); C(O)-phenyl; C(O)-(5 or 6-membered heteroaryl); S(O)$_2$—(C$_{3-6}$-cycloalkyl); S(O)$_2$-(3 to 6-membered heterocycloalkyl); S(O)$_2$-phenyl or S(O)$_2$-(5 or 6-membered heteroaryl);

wherein aryl and 5 or 6-membered heteroaryl in each case independently from one another are unsubstituted or mono- or polysubstituted with one or more substituents selected from F; Cl; Br; I; CN; C$_{1-6}$-alkyl; CF$_3$; CF$_2$H; CFH$_2$; CF$_2$Cl; CFCl$_2$; C$_{1-4}$-alkylene-CF$_3$; C$_{1-4}$-alkylene-CF$_2$H; C$_{1-4}$-alkylene-CFH$_2$; C(O)—C$_{1-6}$-alkyl; C(O)—OH; C(O)—OC$_{1-6}$-alkyl; C(O)—N(H)(OH); C(O)—NH$_2$; C(O)—N(H)(C$_{1-6}$-alkyl); C(O)—N(C$_{1-6}$-alkyl)$_2$; OH; OCF$_3$; OCF$_2$H; OCFH$_2$; OCF$_2$Cl; OCFCl$_2$; O—C$_{1-6}$-alkyl; O—C$_{3-6}$-cycloalkyl; O-(3 to 6-membered heterocycloalkyl); NH$_2$; N(H)(C$_{1-6}$-alkyl); N(C$_{1-6}$-alkyl)$_2$; N(H)—C(O)—C$_{1-6}$-alkyl; N(C$_{1-6}$-alkyl)-C(O)—C$_{1-6}$-alkyl; N(H)—C(O)—NH$_2$; N(H)—C(O)—N(H)(C$_{1-6}$-alkyl); N(H)—C(O)—N(C$_{1-6}$-alkyl)$_2$; N(C$_{1-6}$-alkyl)-C(O)—N(H)(C$_{1-6}$-alkyl); N(C$_{1-6}$-alkyl)-C(O)—N(C$_{1-6}$-alkyl)$_2$; N(H)—S(O)$_2$—C$_{1-6}$-alkyl; SCF$_3$; S—C$_{1-6}$-alkyl; S(O)—C$_{1-6}$-alkyl; S(O)$_2$—C$_{1-6}$-alkyl; S(O)$_2$—NH$_2$; S(O)$_2$—N(H)(C$_{1-6}$-alkyl); S(O)$_2$—N(C$_{1-6}$-alkyl)$_2$; C$_{3-6}$-cycloalkyl; C$_{1-4}$-alkylene-C$_{3-6}$-cycloalkyl; 3 to 6-membered heterocycloalkyl; C$_{1-4}$-alkylene-(3 to 6-membered heterocycloalkyl); phenyl or 5 or 6-membered heteroaryl;

in the form of the free compound or a physiologically acceptable salt thereof.

2. The compound according to claim 1, wherein $R^5$ and $R^6$ both represent CH$_3$.

3. The compound according to claim 1, which is according to general formula (II) or (III)

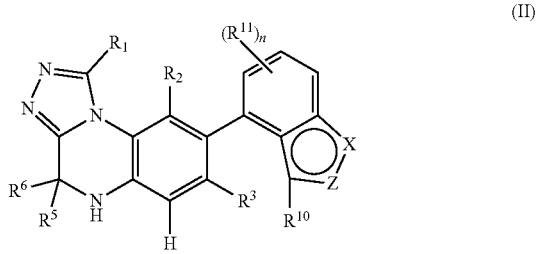

(II)

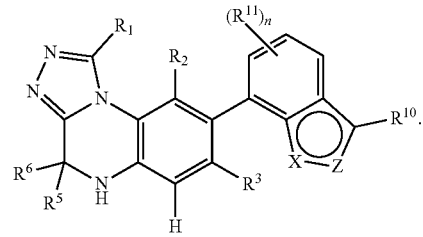

(III)

4. The compound according to claim 1, wherein X represents NR$^7$ and Z represents N or CR$^9$.

5. The compound according to claim 1, wherein
 $R^1$ represents H; C$_{1-6}$-alkyl; C$_{3-6}$-cycloalkyl; 3 to 6-membered heterocycloalkyl; phenyl; or 5 or 6-membered heteroaryl;
  wherein C$_{3-6}$-cycloalkyl, 3 to 6-membered heterocycloalkyl, phenyl and 5 or 6-membered heteroaryl can optionally be bridged via C$_{1-4}$-alkylene.

6. The compound according to claim 1, wherein
 $R^2$ represents H; F; Cl; Br; CN; C$_{1-6}$-alkyl; C$_{3-6}$-cycloalkyl; O—C$_{1-6}$-alkyl; C(O)—NH$_2$; C(O)—N(H)(C$_{1-6}$-alkyl); C(O)—N(C$_{1-6}$-alkyl)$_2$; C(O)—N(H)(C$_{3-6}$-cycloalkyl) or C(O)—N(C$_{1-6}$-alkyl)(C$_{3-6}$-cycloalkyl);
  wherein C$_{3-6}$-cycloalkyl can optionally be bridged via C$_{1-4}$-alkylene; and/or
 $R^3$ represents H; F; Cl; Br; CN; C$_{1-6}$-alkyl; C$_{3-6}$-cycloalkyl; O—C$_{1-6}$-alkyl; C(O)—NH$_2$; C(O)—N(H)(C$_{1-6}$-alkyl); C(O)—N(C$_{1-6}$-alkyl)$_2$; C(O)—N(H)(C$_{3-6}$-cycloalkyl) or C(O)—N(C$_{1-6}$-alkyl)(C$_{3-6}$-cycloalkyl);
  wherein C$_{3-6}$-cycloalkyl can optionally be bridged via C$_{1-4}$-alkylene.

7. The compound according to claim 1, wherein $R^7$ represents H.

8. The compound according to claim 1, wherein $R^7$ represents L-R$^8$; wherein
 L represents bond; S(O); S(O)$_2$; C$_{1-4}$-alkylene; C(O); C$_{1-4}$-alkylene-C(O); C(O)—O; C$_{1-4}$-alkylene-C(O)—O; C$_{1-4}$-alkylene-N(H)—C(O) or C$_{1-4}$-alkylene-N(H)—C(O)—O;
 $R^8$ represents C$_{1-6}$-alkyl; C$_{3-6}$-cycloalkyl or 3 to 6-membered heterocycloalkyl;
  wherein C$_{3-6}$-cycloalkyl and 3 to 6-membered heterocycloalkyl can optionally be bridged via C$_{1-4}$-alkylene.

9. The compound according to claim 1, wherein
 $R^9$ represents H; F; CN; methyl; ethyl; n-propyl; 2-propyl; CF$_3$; CH$_2$CF$_3$; CHF$_2$; CH$_2$CHF$_2$; CH$_2$F; CH$_2$CH$_2$F; S(O)—CH$_3$; S(O)—CH$_2$CH$_3$; S(O)—CH$_2$CH$_2$CH$_3$; S(O)—CH(CH$_3$)$_2$; S(O)$_2$—CH$_3$; S(O)$_2$—CH$_2$CH$_3$; S(O)$_2$—CH$_2$CH$_2$CH$_3$ or S(O)$_2$—CH(CH$_3$)$_2$.

10. The compound according to claim 1, wherein
 $R^{10}$ represents H; F; Cl; Br; CN; C$_{1-6}$-alkyl; C$_{3-6}$-cycloalkyl; 3 to 6-membered heterocycloalkyl; P(O)-(C$_{1-6}$-alkyl)$_2$; P(O)(C$_{1-6}$-alkyl)(C$_{3-6}$-cycloalkyl); P(O)(C$_{1-6}$-alkyl)(3 to 6-membered heterocycloalkyl) P(O)—(O—C$_{1-6}$-alkyl)$_2$; P(O)(O—C$_{1-6}$-alkyl)(O—C$_{3-6}$-cycloalkyl); P(O)(O—C$_{1-6}$-alkyl)(O-(3 to 6-membered heterocycloalkyl)).

11. The compound according to claim 1, wherein
 $R^{11}$ represents F; Cl; Br; I; CN; C$_{1-6}$-alkyl or O—C$_{1-6}$-alkyl;
 and/or
 n represents 0, 1 or 2.

12. A compound selected from the group consisting of:
1 7,9-Difluoro-8-(6-fluoro-1H-indol-4-yl)-1,4,4-trimethyl-5H-[1,2,4]triazolo[4,3-a]quinoxaline;
2 8-(1-Cyclopropyl-6-fluoro-1H-indol-4-yl)-7,9-difluoro-1,4,4-trimethyl-5H-[1,2,4]triazolo[4,3-a]quinoxaline;
3 7,9-Difluoro-8-(6-fluoro-1-methylsulfonyl-1H-indol-4-yl)-1,4,4-trimethyl-5H-[1,2,4]triazolo[4,3-a]quinoxaline;
4 1-[4-(7,9-Difluoro-1,4,4-trimethyl-5H-[1,2,4]triazolo[4,3-a]quinoxalin-8-yl)-6-fluoro-1H-indol-1-yl]-ethanone;
5 7,9-Difluoro-8-(6-fluoro-2-methyl-1H-indol-4-yl)-1,4,4-trimethyl-5H-[1,2,4]triazolo[4,3-a]quinoxaline;
6 4-(7,9-Difluoro-1,4,4-trimethyl-5H-[1,2,4]triazolo[4,3-a]quinoxalin-8-yl)-6-fluoro-1H-indole-2-carbonitrile;
9 7,9-Difluoro-8-(1H-indol-7-yl)-1,4,4-trimethyl-5H-[1,2,4]triazolo[4,3-a]quinoxaline;
10 7,9-Difluoro-1,4,4-trimethyl-8-[3-(trifluoromethyl)-1H-indol-7-yl]-5H-[1,2,4]triazolo[4,3-a]quinoxaline;
11 1-Ethyl-7,9-difluoro-8-(1H-indol-7-yl)-4,4-dimethyl-5H-[1,2,4]triazolo[4,3-a]quinoxaline;
12 7-(1-Ethyl-7,9-difluoro-4,4-dimethyl-5H-[1,2,4]triazolo[4,3-a]quinoxalin-8-yl)-1H-indole-3-carbonitrile;
13 1-Ethyl-7,9-difluoro-4,4-dimethyl-8-(3-prop-1-ynyl-1H-indol-7-yl)-5H-[1,2,4]triazolo[4,3-a]quinoxaline;
14 1-Ethyl-7,9-difluoro-8-(5-fluoro-1H-indol-7-yl)-4,4-dimethyl-5H-[1,2,4]triazolo[4,3-a]quinoxaline;
15 7-(1-Ethyl-7,9-difluoro-4,4-dimethyl-5H-[1,2,4]triazolo[4,3-a]quinoxalin-8-yl)-5-fluoro-1H-indole-3-carbonitrile;
16 1-Ethyl-7,9-difluoro-8-(5-fluoro-3-prop-1-ynyl-1H-indol-7-yl)-4,4-dimethyl-5H-[1,2,4]triazolo[4,3-a]quinoxaline;
17 7-(1-Ethyl-7,9-difluoro-4,4-dimethyl-5H-[1,2,4]triazolo[4,3-a]quinoxalin-8-yl)-5-methyl-1H-indole-3-carbonitrile;
18 8-[1-(Ethylsulfonyl)-6-fluoro-1H-indol-4-yl]-7,9-difluoro-1,4,4-trimethyl-5H-[1,2,4]triazolo[4,3-a]quinoxaline;
19 8-[1-(Cyclopropylsulfonyl)-6-fluoro-1H-indol-4-yl]-7,9-difluoro-1,4,4-trimethyl-5H-[1,2,4]triazolo[4,3-a]quinoxaline;
20 1-[4-(7,9-Difluoro-1,4,4-trimethyl-5H-[1,2,4]triazolo[4,3-a]quinoxalin-8-yl)-1H-indol-1-yl]-ethanone;
21 7,9-Difluoro-8-[6-fluoro-1-(2,2,2-trifluoro-ethyl)-1H-indol-4-yl]-1,4,4-trimethyl-5H-[1,2,4]triazolo[4,3-a]quinoxaline;
22 7,9-Difluoro-1,4,4-trimethyl-8-(1-methylsulfonyl-1H-indol-4-yl)-5H-[1,2,4]triazolo[4,3-a]quinoxaline;
23 7-Fluoro-8-[5-fluoro-3-(2,2,2-trifluoro-ethyl)-1H-indol-7-yl]-1,4,4,9-tetramethyl-5H-[1,2,4]triazolo[4,3-a]quinoxaline;
24 7-Fluoro-1,4,4,9-tetramethyl-8-[3-(2,2,2-trifluoro-ethyl)-1H-indol-7-yl]-5H-[1,2,4]triazolo[4,3-a]quinoxaline;
25 7-Fluoro-8-(1H-indol-7-yl)-1,4,4,9-tetramethyl-5H-[1,2,4]triazolo[4,3-a]quinoxaline;
26 7-Fluoro-8-(1H-indol-4-yl)-1,4,4,9-tetramethyl-5H-[1,2,4]triazolo[4,3-a]quinoxaline;
27 8-(1-Cyclopropyl-1H-indol-4-yl)-7-fluoro-1,4,4,9-tetramethyl-5H-[1,2,4]triazolo[4,3-a]quinoxaline;
28 7-Fluoro-1,4,4,9-tetramethyl-8-(3-prop-1-ynyl-1H-indol-7-yl)-5H-[1,2,4]triazolo[4,3-a]quinoxaline;
29 7-Fluoro-1,4,4-trimethyl-8-(3-methyl-1H-indol-7-yl)-9-(trifluoromethyl)-5H-[1,2,4]triazolo[4,3-a]quinoxaline;
30 9-Chloro-7-fluoro-8-(5-fluoro-3-methyl-1H-indol-7-yl)-1,4,4-trimethyl-5H-[1,2,4]triazolo[4,3-a]quinoxaline;
31 7-Fluoro-8-(5-fluoro-3-methyl-1H-indol-7-yl)-1,4,4,9-tetramethyl-5H-[1,2,4]triazolo[4,3-a]quinoxaline;
32 7-Fluoro-8-(5-fluoro-1H-indol-7-yl)-1,4,4,9-tetramethyl-5H-[1,2,4]triazolo[4,3-a]quinoxaline;
33 8-(3-Cyclopropyl-5-fluoro-1H-indol-7-yl)-7-fluoro-1,4,4,9-tetramethyl-5H-[1,2,4]triazolo[4,3-a]quinoxaline;
34 1-Ethyl-7-fluoro-8-(6-fluoro-1H-indol-4-yl)-4,4,9-trimethyl-5H-[1,2,4]triazolo[4,3-a]quinoxaline;
35 8-[1-(Cyclopropyl-methyl)-6-fluoro-1H-indol-4-yl]-1-ethyl-7-fluoro-4,4,9-trimethyl-5H-[1,2,4]triazolo[4,3-a]quinoxaline;
36 1-Ethyl-7-fluoro-8-[6-fluoro-1-(2-methoxy-ethyl)-1H-indol-4-yl]-4,4,9-trimethyl-5H-[1,2,4]triazolo[4,3-a]quinoxaline;
37 7-Fluoro-8-(6-fluoro-1-methylsulfonyl-1H-indol-4-yl)-1,4,4-trimethyl-9-(trifluoromethyl)-5H-[1,2,4]triazolo[4,3-a]quinoxaline;
39 4-[7-(7-Fluoro-1,4,4,9-tetramethyl-5H-[1,2,4]triazolo[4,3-a]quinoxalin-8-yl)-1H-indol-3-yl]-2-methyl-but-3-yn-2-ol;
40 [3-[7-(7-Fluoro-1,4,4,9-tetramethyl-5H-[1,2,4]triazolo[4,3-a]quinoxalin-8-yl)-1H-indol-3-y1]-1,1-dimethyl-prop-2-ynyl]-amine;
41 9-Chloro-8-(3-cyclobutyl-1H-indol-7-yl)-7-fluoro-1,4,4-trimethyl-5H-[1,2,4]triazolo[4,3-a]quinoxaline;
42 7-Fluoro-1,4,4,9-tetramethyl-8-(3-tetrahydro-furan-3-yl-1H-indol-7-yl)-5H-[1,2,4]triazolo[4,3-a]quinoxaline;
43 8-(3-Ethyl-5-fluoro-1H-indol-7-yl)-7,9-difluoro-1,4,4-trimethyl-5H-[1,2,4]triazolo[4,3-a]quinoxaline;
44 2-[4-(9-Ethyl-7-fluoro-1,4,4-trimethyl-5H-[1,2,4]triazolo[4,3-a]quinoxalin-8-yl)-6-fluoro-1H-indol-1-yl]-ethanol;
45 2-[4-(9-Ethyl-7-fluoro-1,4,4-trimethyl-5H-[1,2,4]triazolo[4,3-a]quinoxalin-8-yl)-6-fluoro-1H-indazol-1-yl]-ethanol;
46 9-Ethyl-7-fluoro-8-(6-fluoro-1-methylsulfonyl-1H-indol-4-yl)-1,4,4-trimethyl-5H-[1,2,4]triazolo[4,3-a]quinoxaline;
47 9-Ethyl-7-fluoro-8-(5-fluoro-3-methyl-1H-indol-7-yl)-1,4,4-trimethyl-5H-[1,2,4]triazolo[4,3-a]quinoxaline;
50 9-Ethyl-7-fluoro-1,4,4-trimethyl-8-(1-methylsulfonyl-1H-indol-4-yl)-5H-[1,2,4]triazolo[4,3-a]quinoxaline;
51 9-Ethyl-7-fluoro-1,4,4-trimethyl-8-(1-methylsulfonyl-1H-indazol-4-yl)-5H-[1,2,4]triazolo[4,3-a]quinoxaline;
52 9-Ethyl-7-fluoro-8-(6-fluoro-1-methylsulfonyl-1H-indazol-4-yl)-1,4,4-trimethyl-5H-[1,2,4]triazolo[4,3-a]quinoxaline;
67 1-Benzyl-7,9-difluoro-8-(5-fluoro-3-methyl-1H-indol-7-yl)-4,4-dimethyl-5H-[1,2,4]triazolo[4,3-a]quinoxaline;
68 1-Benzyl-7,9-difluoro-4,4-dimethyl-8-(3-methyl-1H-indol-7-yl)-5H-[1,2,4]triazolo[4,3-a]quinoxaline;
69 1-But-2-ynyl-7,9-difluoro-8-(5-fluoro-3-methyl-1H-indol-7-yl)-4,4-dimethyl-5H-[1,2,4]triazolo[4,3-a]quinoxaline;
70 1-But-2-ynyl-7,9-difluoro-4,4-dimethyl-8-(3-methyl-1H-indol-7-yl)-5H-[1,2,4]triazolo[4,3-a]quinoxaline;
71 7,9-Difluoro-8-(5-fluoro-3-methyl-1H-indol-7-yl)-4,4-dimethyl-1-(pyridin-4-yl-methyl)-5H-[1,2,4]triazolo[4,3-a]quinoxaline;

72 7,9-Difluoro-4,4-dimethyl-8-(3-methyl-1H-indol-7-yl)-1-(pyridin-4-yl-methyl)-5H-[1,2,4]triazolo[4,3-a]quinoxaline;

73 7,9-Difluoro-8-(5-fluoro-3-methyl-1H-indol-7-yl)-4,4-dimethyl-1-(pyridin-3-yl-methyl)-5H-[1,2,4]triazolo[4,3-a]quinoxaline;

74 7,9-Difluoro-8-(5-fluoro-3-methyl-1H-indol-7-yl)-4,4-dimethyl-1-(pyridin-2-yl-methyl)-5H-[1,2,4]triazolo[4,3-a]quinoxaline;

75 7,9-Difluoro-4,4-dimethyl-8-(3-methyl-1H-indol-7-yl)-1-(pyridin-2-yl-methyl)-5H-[1,2,4]triazolo[4,3-a]quinoxaline;

76 7-Fluoro-8-(5-fluoro-3-prop-1-ynyl-1H-indol-7-yl)-1-(methoxymethyl)-4,4,9-trimethyl-5H-[1,2,4]triazolo[4,3-a]quinoxaline;

77 [7-Fluoro-8-(5-fluoro-3-prop-1-ynyl-1H-indol-7-yl)-4,4,9-trimethyl-5H-[1,2,4]triazolo[4,3-a]quinoxalin-1-yl]-MeOH;

78 1-[7-Fluoro-8-(5-fluoro-3-prop-1-ynyl-1H-indol-7-yl)-4,4,9-trimethyl-5H-[1,2,4]triazolo[4,3-a]quinoxalin-1-yl]-ethanol;

79 7-Fluoro-8-(5-fluoro-3-prop-1-ynyl-1H-indol-7-yl)-1-(2-methoxy-ethyl)-4,4,9-trimethyl-5H-[1,2,4]triazolo[4,3-a]quinoxaline;

80 1-(Cyclopropyl-methyl)-7,9-difluoro-8-(1H-indol-7-yl)-4,4-dimethyl-5H-[1,2,4]triazolo[4,3-a]quinoxaline;

81 1-Cyclopropyl-7,9-difluoro-8-(1H-indol-7-yl)-4,4-dimethyl-5H-[1,2,4]triazolo[4,3-a]quinoxaline;

82 8-(3-Cyclopropyl-1H-indol-7-yl)-1,4,4,9-tetramethyl-7-(trifluoromethyl)-5H-[1,2,4]triazolo[4,3-a]quinoxaline;

83 8-(6-Fluoro-1-methylsulfonyl-1H-indol-4-yl)-1,4,4,9-tetramethyl-7-(trifluoromethyl)-5H-[1,2,4]triazolo[4,3-a]quinoxaline;

84 1,4,4,9-Tetramethyl-8-(1-methylsulfonyl-1H-indol-4-yl)-7-(trifluoromethyl)-5H-[1,2,4]triazolo[4,3-a]quinoxaline;

85 9-Chloro-8-(3-cyclopropyl-1H-indol-7-yl)-7-fluoro-1,4,4-trimethyl-5H-[1,2,4]triazolo[4,3-a]quinoxaline;

86 7-Fluoro-8-(1H-indol-7-yl)-1,4,4-trimethyl-9-(trifluoromethyl)-5H-[1,2,4]triazolo[4,3-a]quinoxaline;

87 8-(3-Cyclopropyl-5-fluoro-1H-indol-7-yl)-7-fluoro-1,4,4-trimethyl-9-(trifluoromethyl)-5H-[1,2,4]triazolo[4,3-a]quinoxaline;

88 8-(1-Cyclopropyl-6-fluoro-1H-indol-4-yl)-7-fluoro-1,4,4-trimethyl-9-(trifluoromethyl)-5H-[1,2,4]triazolo[4,3-a]quinoxaline;

89 7-[7-Fluoro-1,4,4-trimethyl-9-(trifluoromethyl)-5H-[1,2,4]triazolo[4,3-a]quinoxalin-8-yl]-1H-indole-3-carbonitrile;

200 7,9-Difluoro-8-[1-(isopropylsulfonyl)-1H-indol-4-yl]-1,4,4-trimethyl-5H-[1,2,4]triazolo[4,3-a]quinoxaline;

201 8-[1-(Cyclopentylsulfonyl)-1H-indol-4-yl]-7,9-difluoro-1,4,4-trimethyl-5H-[1,2,4]triazolo[4,3-a]quinoxaline;

202 8-[1-(Cyclopropyl-methyl)-1H-indol-4-yl]-7,9-difluoro-1,4,4-trimethyl-5H-[1,2,4]triazolo[4,3-a]quinoxaline;

203 7,9-Difluoro-1,4,4-trimethyl-8-[1-(tetrahydro-pyran-4-ylsulfonyl)-1H-indol-4-yl]-5H-[1,2,4]triazolo[4,3-a]quinoxaline;

204 7,9-Difluoro-8-[1-(2-methoxy-ethyl)-1H-indol-4-yl]-1,4,4-trimethyl-5H-[1,2,4]triazolo[4,3-a]quinoxaline;

205 8-[1-(Cyclopropylsulfonyl)-1H-indol-4-yl]-7,9-difluoro-1,4,4-trimethyl-5H-[1,2,4]triazolo[4,3-a]quinoxaline;

207 7,9-Difluoro-1,4,4-trimethyl-8-[6-(trifluoromethyl)-1H-indol-4-yl]-5H-[1,2,4]triazolo[4,3-a]quinoxaline;

208 7,9-Difluoro-8-(6-fluoro-1H-indol-4-yl)-1,4,4-trimethyl-5H-[1,2,4]triazolo[4,3-a]quinoxaline;

210 8-[1-(Cyclopropyl-methylsulfonyl)-1H-indol-4-yl]-7,9-difluoro-1,4,4-trimethyl-5H-[1,2,4]triazolo[4,3-a]quinoxaline;

212 2-[4-(7,9-Difluoro-1,4,4-trimethyl-5H-[1,2,4]triazolo[4,3-a]quinoxalin-8-yl)-1H-indol-1-yl]-N,N-dimethyl-acetamide;

213 1-[4-(7,9-Difluoro-1,4,4-trimethyl-5H-[1,2,4]triazolo[4,3-a]quinoxalin-8-yl)-1H-indol-1-yl]-2-methoxy-ethanone;

214 7,9-Difluoro-8-(5-fluoro-1H-indol-4-yl)-1,4,4-trimethyl-5H-[1,2,4]triazolo[4,3-a]quinoxaline;

219 3-[4-(7,9-Difluoro-1,4,4-trimethyl-5H-[1,2,4]triazolo[4,3-a]quinoxalin-8-yl)-1H-indol-1-yl]-propionic acid methyl ester;

221 7,9-Difluoro-1,4,4-trimethyl-8-(1-methyl-1H-indazol-4-yl)-5H-[1,2,4]triazolo[4,3-a]quinoxaline;

222 7,9-Difluoro-1,4,4-trimethyl-8-(2-methyl-2H-indazol-4-yl)-5H-[1,2,4]triazolo[4,3-a]quinoxaline;

223 1-[4-(7,9-Difluoro-1,4,4-trimethyl-5H-[1,2,4]triazolo[4,3-a]quinoxalin-8-yl)-1H-indol-1-yl]-2-dimethylamino-ethanone;

224 7,9-Difluoro-8-(5-fluoro-1-methylsulfonyl-1H-indol-4-yl)-1,4,4-trimethyl-5H-[1,2,4]triazolo[4,3-a]quinoxaline;

225 7,9-Difluoro-1,4,4-trimethyl-8-[2-(trifluoromethyl)-1H-indol-4-yl]-5H-[1,2,4]triazolo[4,3-a]quinoxaline;

228 N-[2-[4-(7,9-Difluoro-1,4,4-trimethyl-5H-[1,2,4]triazolo[4,3-a]quinoxalin-8-yl)-1H-indol-1-yl]-ethyl]-carbamic acid tert-butyl ester;

229 N-[2-[4-(7,9-Difluoro-1,4,4-trimethyl-5H-[1,2,4]triazolo[4,3-a]quinoxalin-8-yl)-1H-indol-1-yl]-ethyl]-2,2-difluoro-propionamide;

230 2-[4-(7,9-Difluoro-1,4,4-trimethyl-5H-[1,2,4]triazolo[4,3-a]quinoxalin-8-yl)-1H-indol-1-yl]-ethyl-amine;

232 7,9-Difluoro-8-(1H-indazol-4-yl)-1,4,4-trimethyl-5H-[1,2,4]triazolo[4,3-a]quinoxaline;

233 7,9-Difluoro-8-[1-(2-methoxy-ethyl)-1H-indazol-4-yl]-1,4,4-trimethyl-5H-[1,2,4]triazolo[4,3-a]quinoxaline;

234 8-[1-(Cyclopropylsulfonyl)-1H-indazol-4-yl]-7,9-difluoro-1,4,4-trimethyl-5H-[1,2,4]triazolo[4,3-a]quinoxaline;

235 8-[1-(Cyclopropyl-methyl)-1H-indazol-4-yl]-7,9-difluoro-1,4,4-trimethyl-5H-[1,2,4]triazolo[4,3-a]quinoxaline;

236 8-(1-Ethyl-1H-indazol-4-yl)-7,9-difluoro-1,4,4-trimethyl-5H-[1,2,4]triazolo[4,3-a]quinoxaline;

237 8-(2-Ethyl-2H-indazol-4-yl)-7,9-difluoro-1,4,4-trimethyl-5H-[1,2,4]triazolo[4,3-a]quinoxaline;

238 4-(7,9-Difluoro-1,4,4-trimethyl-5H-[1,2,4]triazolo[4,3-a]quinoxalin-8-yl)-1H-indazole-1-carboxylic acid tert-butyl ester;

239 8-[1-(Cyclopropyl-methylsulfonyl)-1H-indazol-4-yl]-7,9-difluoro-1,4,4-trimethyl-5H-[1,2,4]triazolo[4,3-a]quinoxaline;

240 1-Ethyl-7-fluoro-4,4,9-trimethyl-8-(1-methyl-1H-indazol-4-yl)-5H-[1,2,4]triazolo[4,3-a]quinoxaline;

241 1-Ethyl-7-fluoro-4,4,9-trimethyl-8-(1-methylsulfonyl-1H-indazol-4-yl)-5H-[1,2,4]triazolo[4,3-a]quinoxaline;

242 8-(1-Cyclopropyl-1H-indazol-4-yl)-1-ethyl-7-fluoro-4,4,9-trimethyl-5H-[1,2,4]triazolo[4,3-a]quinoxaline;

243 8-(1-Cyclopropyl-1H-indazol-4-yl)-7,9-difluoro-1,4,4-trimethyl-5H-[1,2,4]triazolo[4,3-a]quinoxaline;
244 1-Ethyl-7-fluoro-8-(5-fluoro-1H-indol-4-yl)-4,4,9-trimethyl-5H-[1,2,4]triazolo[4,3-a]quinoxaline;
247 1-Ethyl-7-fluoro-4,4,9-trimethyl-8-(1-methylsulfonyl-1H-indol-4-yl)-5H-[1,2,4]triazolo[4,3-a]quinoxaline;
248 7-Fluoro-9-methoxy-1,4,4-trimethyl-8-(1-methylsulfonyl-1H-indol-4-yl)-5H-[1,2,4]triazolo[4,3-a]quinoxaline;
249 7-Fluoro-8-(5-fluoro-3-methyl-1H-indol-7-yl)-9-methoxy-1,4,4-trimethyl-5H-[1,2,4]triazolo[4,3-a]quinoxaline;
250 7-Fluoro-8-(6-fluoro-1-methylsulfonyl-1H-indol-4-yl)-9-methoxy-1,4,4-trimethyl-5H-[1,2,4]triazolo[4,3-a]quinoxaline;
251 9-Fluoro-8-(5-fluoro-3-methyl-1H-indol-7-yl)-7-methoxy-1,4,4-trimethyl-5H-[1,2,4]triazolo[4,3-a]quinoxaline;
252 7-(Difluoro-methoxy)-9-fluoro-1,4,4-trimethyl-8-[2-(trifluoromethyl)-1H-indol-4-yl]-5H-[1,2,4]triazolo[4,3-a]quinoxaline;
253 8-[1-(2,2-Difluoro-ethyl)-1H-indol-4-yl]-7,9-difluoro-1,4,4-trimethyl-5H-[1,2,4]triazolo[4,3-a]quinoxaline;
254 7-Chloro-9-fluoro-1,4,4-trimethyl-8-[2-(trifluoromethyl)-1H-indol-4-yl]-5H-[1,2,4]triazolo[4,3-a]quinoxaline;
255 9-Fluoro-8-(6-fluoro-1-methylsulfonyl-1H-indol-4-yl)-7-methoxy-1,4,4-trimethyl-5H-[1,2,4]triazolo[4,3-a]quinoxaline;
256 9-Fluoro-8-(1H-indol-4-yl)-7-methoxy-1,4,4-trimethyl-5H-[1,2,4]triazolo[4,3-a]quinoxaline;
257 9-Fluoro-7-methoxy-1,4,4-trimethyl-8-[2-(trifluoromethyl)-1H-indol-4-yl]-5H-[1,2,4]triazolo[4,3-a]quinoxaline;
258 2-[4-(7,9-Difluoro-1,4,4-trimethyl-5H-[1,2,4]triazolo[4,3-a]quinoxalin-8-yl)-1H-indazol-1-yl]-ethanol;
259 7-(Difluoro-methoxy)-9-fluoro-8-[1-(2-methoxy-ethyl)-2-(trifluoromethyl)-1H-indol-4-yl]-1,4,4-trimethyl-5H-[1,2,4]triazolo[4,3-a]quinoxaline;
260 4-(7-Fluoro-9-methoxy-1,4,4-trimethyl-5H-[1,2,4]triazolo[4,3-a]quinoxalin-8-yl)-1H-indole-1-carboxylic acid tert-butyl ester;
263 9-Fluoro-7-methoxy-1,4,4-trimethyl-8-(1-methylsulfonyl-1H-indol-4-yl)-5H-[1,2,4]triazolo[4,3-a]quinoxaline;
264 7-Fluoro-9-methoxy-1,4,4-trimethyl-8-(1-methyl-1H-indazol-4-yl)-5H-[1,2,4]triazolo[4,3-a]quinoxaline;
266 9-Fluoro-7-methoxy-1,4,4-trimethyl-8-(3-methyl-1H-indol-7-yl)-5H-[1,2,4]triazolo[4,3-a]quinoxaline;
267 7-(Difluoro-methoxy)-9-fluoro-8-(5-fluoro-3-methyl-1H-indol-7-yl)-1,4,4-trimethyl-5H-[1,2,4]triazolo[4,3-a]quinoxaline;
268 7-(Difluoro-methoxy)-9-fluoro-8-(6-fluoro-1-methylsulfonyl-1H-indol-4-yl)-1,4,4-trimethyl-5H-[1,2,4]triazolo[4,3-a]quinoxaline;
269 9-Fluoro-7-methoxy-1,4,4-trimethyl-8-(1-methyl-1H-indazol-4-yl)-5H-[1,2,4]triazolo[4,3-a]quinoxaline;
270 7-Fluoro-9-methoxy-1,4,4-trimethyl-8-(3-methyl-1H-indol-7-yl)-5H-[1,2,4]triazolo[4,3-a]quinoxaline;
271 7,9-Difluoro-1,4,4-trimethyl-8-[1-methylsulfonyl-2-(trifluoromethyl)-1H-indol-4-yl]-5H-[1,2,4]triazolo[4,3-a]quinoxaline;
272 7-Chloro-9-fluoro-1,4,4-trimethyl-8-(3-methyl-1H-indol-7-yl)-5H-[1,2,4]triazolo[4,3-a]quinoxaline;
273 7-(Difluoro-methoxy)-9-fluoro-1,4,4-trimethyl-8-(1-methyl-1H-indazol-4-yl)-5H-[1,2,4]triazolo[4,3-a]quinoxaline;
275 7-(Difluoro-methoxy)-9-fluoro-1,4,4-trimethyl-8-(1-methylsulfonyl-1H-indol-4-yl)-5H-[1,2,4]triazolo[4,3-a]quinoxaline;
276 7,9-Difluoro-8-(6-fluoro-1-methylsulfonyl-1H-indazol-4-yl)-1,4,4-trimethyl-5H-[1,2,4]triazolo[4,3-a]quinoxaline;
277 7-Chloro-9-fluoro-8-(6-fluoro-1-methylsulfonyl-1H-indol-4-yl)-1,4,4-trimethyl-5H-[1,2,4]triazolo[4,3-a]quinoxaline;
278 7-Fluoro-8-[1-(2-methoxy-ethyl)-1H-indol-4-yl]-1,4,4,9-tetramethyl-5H-[1,2,4]triazolo[4,3-a]quinoxaline;
279 7-Fluoro-8-(6-fluoro-1-methylsulfonyl-1H-indazol-4-yl)-1,4,4,9-tetramethyl-5H-[1,2,4]triazolo[4,3-a]quinoxaline;
280 7-Chloro-9-fluoro-8-[1-(2-methoxy-ethyl)-1H-indol-4-yl]-1,4,4-trimethyl-5H-[1,2,4]triazolo[4,3-a]quinoxaline;
281 7-Fluoro-9-methoxy-8-[1-(2-methoxy-ethyl)-1H-indol-4-yl]-1,4,4-trimethyl-5H-[1,2,4]triazolo[4,3-a]quinoxaline;
282 7-(Difluoro-methoxy)-9-fluoro-1,4,4-trimethyl-8-(3-methyl-1H-indol-7-yl)-5H-[1,2,4]triazolo[4,3-a]quinoxaline;
283 9-Fluoro-8-(5-fluoro-3-methyl-1H-indol-7-yl)-1,4,4-trimethyl-5H-[1,2,4]triazolo[4,3-a]quinoxaline;
284 7-Chloro-9-fluoro-1,4,4-trimethyl-8-(1-methylsulfonyl-1H-indol-4-yl)-5H-[1,2,4]triazolo[4,3-a]quinoxaline;
285 7-Chloro-9-fluoro-1,4,4-trimethyl-8-(1-methyl-1H-indazol-4-yl)-5H-[1,2,4]triazolo[4,3-a]quinoxaline;
286 7-Fluoro-8-(1H-indol-4-yl)-9-methoxy-1,4,4-trimethyl-5H-[1,2,4]triazolo[4,3-a]quinoxaline;
287 7-(Difluoro-methoxy)-9-fluoro-8-[1-(2-methoxy-ethyl)-1H-indol-4-yl]-1,4,4-trimethyl-5H-[1,2,4]triazolo[4,3-a]quinoxaline;
288 9-Fluoro-7-methoxy-8-[1-(2-methoxy-ethyl)-1H-indol-4-yl]-1,4,4-trimethyl-5H-[1,2,4]triazolo[4,3-a]quinoxaline;
289 7,9-Difluoro-8-[1-(2-methoxy-ethyl)-2-(trifluoromethyl)-1H-indol-4-yl]-1,4,4-trimethyl-5H-[1,2,4]triazolo[4,3-a]quinoxaline;
290 7-Chloro-9-fluoro-8-(5-fluoro-3-methyl-1H-indol-7-yl)-1,4,4-trimethyl-5H-[1,2,4]triazolo[4,3-a]quinoxaline;
292 9-(Difluoro-methyl)-7-fluoro-8-[1-(2-methoxy-ethyl)-1H-indol-4-yl]-1,4,4-trimethyl-5H-[1,2,4]triazolo[4,3-a]quinoxaline;
293 7-Chloro-9-fluoro-8-(1H-indol-4-yl)-1,4,4-trimethyl-5H-[1,2,4]triazolo[4,3-a]quinoxaline;
294 9-(Difluoro-methyl)-7-fluoro-1,4,4-trimethyl-8-(1-methyl-1H-indazol-4-yl)-5H-[1,2,4]triazolo[4,3-a]quinoxaline;
295 7-(Difluoro-methyl)-9-fluoro-8-[1-(2-methoxy-ethyl)-1H-indol-4-yl]-1,4,4-trimethyl-5H-[1,2,4]triazolo[4,3-a]quinoxaline;
296 7-(Difluoro-methyl)-9-fluoro-8-(5-fluoro-3-methyl-1H-indol-7-yl)-1,4,4-trimethyl-5H-[1,2,4]triazolo[4,3-a]quinoxaline;
297 7-(Difluoro-methoxy)-9-fluoro-8-(1H-indol-4-yl)-1,4,4-trimethyl-5H-[1,2,4]triazolo[4,3-a]quinoxaline;

298 7-(Difluoro-methyl)-9-fluoro-8-(6-fluoro-1-methyl-sulfonyl-1H-indol-4-yl)-1,4,4-trimethyl-5H-[1,2,4]triazolo[4,3-a]quinoxaline;

299 1-Ethyl-7-fluoro-8-[1-(2-methoxy-ethyl)-1H-indol-4-yl]-4,4,9-trimethyl-5H-[1,2,4]triazolo[4,3-a]quinoxaline;

302 9-(Difluoro-methyl)-7-fluoro-8-(5-fluoro-3-methyl-1H-indol-7-yl)-1,4,4-trimethyl-5H-[1,2,4]triazolo[4,3-a]quinoxaline;

306 7-(Difluoro-methyl)-9-fluoro-1,4,4-trimethyl-8-(3-methyl-1H-indol-7-yl)-5H-[1,2,4]triazolo[4,3-a]quinoxaline;

309 1,4,4,7,9-Pentamethyl-8-(1-methylsulfonyl-1H-indol-4-yl)-5H-[1,2,4]triazolo[4,3-a]quinoxaline;

310 7-Methoxy-1,4,4-trimethyl-8-(1-methylsulfonyl-1H-indol-4-yl)-9-(trifluoromethyl)-5H-[1,2,4]triazolo[4,3-a]quinoxaline;

312 8-[1-Cyclopropyl-2-(trifluoromethyl)-1H-indol-4-yl]-7,9-difluoro-1,4,4-trimethyl-5H-[1,2,4]triazolo[4,3-a]quinoxaline;

313 7-Chloro-8-[1-(2,2-difluoro-ethyl)-1H-indol-4-yl]-9-fluoro-1,4,4-trimethyl-5H-[1,2,4]triazolo[4,3-a]quinoxaline;

314 8-[1-(2,2-Difluoro-ethyl)-1H-indol-4-yl]-9-fluoro-7-methoxy-1,4,4-trimethyl-5H-[1,2,4]triazolo[4,3-a]quinoxaline;

315 9-(Difluoro-methyl)-7-fluoro-1,4,4-trimethyl-8-(1-methylsulfonyl-1H-indol-4-yl)-5H-[1,2,4]triazolo[4,3-a]quinoxaline;

317 7-Chloro-1,4,4,9-tetramethyl-8-(1-methylsulfonyl-1H-indol-4-yl)-5H-[1,2,4]triazolo[4,3-a]quinoxaline;

318 7-(Difluoro-methoxy)-1,4,4,9-tetramethyl-8-(1-methylsulfonyl-1H-indol-4-yl)-5H-[1,2,4]triazolo[4,3-a]quinoxaline;

319 9-(Difluoro-methyl)-7-fluoro-8-(1H-indol-4-yl)-1,4,4-trimethyl-5H-[1,2,4]triazolo[4,3-a]quinoxaline;

320 9-(Difluoro-methyl)-7-fluoro-1,4,4-trimethyl-8-(3-methyl-1H-indol-7-yl)-5H-[1,2,4]triazolo[4,3-a]quinoxaline;

321 9-Fluoro-1,4,4,7-tetramethyl-8-(1-methylsulfonyl-1H-indol-4-yl)-5H-[1,2,4]triazolo[4,3-a]quinoxaline;

324 8-[1-(2,2-Difluoro-ethyl)-1H-indol-4-yl]-1,4,4,7,9-pentamethyl-5H-[1,2,4]triazolo[4,3-a]quinoxaline;

325 7-(Difluoro-methyl)-9-fluoro-1,4,4-trimethyl-8-(1-methyl-1H-indazol-4-yl)-5H-[1,2,4]triazolo[4,3-a]quinoxaline;

327 7-Chloro-8-[1-(2,2-difluoro-ethyl)-1H-indol-4-yl]-1,4,4,9-tetramethyl-5H-[1,2,4]triazolo[4,3-a]quinoxaline;

328 8-(6-Fluoro-1-methylsulfonyl-1H-indol-4-yl)-1,4,4,7,9-pentamethyl-5H-[1,2,4]triazolo[4,3-a]quinoxaline;

329 8-(6-Fluoro-1-methylsulfonyl-1H-indol-4-yl)-7-methoxy-1,4,4-trimethyl-9-(trifluoromethyl)-5H-[1,2,4]triazolo[4,3-a]quinoxaline;

330 8-[1-(2,2-Difluoro-ethyl)-1H-indol-4-yl]-7-fluoro-1,4,4,9-tetramethyl-5H-[1,2,4]triazolo[4,3-a]quinoxaline;

331 8-[1-(2-Methoxy-ethyl)-1H-indol-4-yl]-1,4,4,7,9-pentamethyl-5H-[1,2,4]triazolo[4,3-a]quinoxaline;

332 9-Fluoro-8-(6-fluoro-1-methylsulfonyl-1H-indol-4-yl)-1,4,4,7-tetramethyl-5H-[1,2,4]triazolo[4,3-a]quinoxaline;

333 7-Chloro-8-(6-fluoro-1-methylsulfonyl-1H-indol-4-yl)-1,4,4,9-tetramethyl-5H-[1,2,4]triazolo[4,3-a]quinoxaline;

334 7-Methoxy-8-[1-(2-methoxy-ethyl)-1H-indol-4-yl]-1,4,4-trimethyl-9-(trifluoromethyl)-5H-[1,2,4]triazolo[4,3-a]quinoxaline;

335 7-(Difluoro-methoxy)-8-(6-fluoro-1-methylsulfonyl-1H-indol-4-yl)-1,4,4,9-tetramethyl-5H-[1,2,4]triazolo[4,3-a]quinoxaline;

336 7-(Difluoro-methoxy)-8-[1-(2-methoxy-ethyl)-1H-indol-4-yl]-1,4,4,9-tetramethyl-5H-[1,2,4]triazolo[4,3-a]quinoxaline;

337 9-Fluoro-8-[1-(2-methoxy-ethyl)-1H-indol-4-yl]-1,4,4,7-tetramethyl-5H-[1,2,4]triazolo[4,3-a]quinoxaline;

338 7-Chloro-8-[1-(2-methoxy-ethyl)-1H-indol-4-yl]-1,4,4,9-tetramethyl-5H-[1,2,4]triazolo[4,3-a]quinoxaline;

339 7-Fluoro-8-(6-fluoro-1-methylsulfonyl-1H-indazol-4-yl)-9-methoxy-1,4,4-trimethyl-5H-[1,2,4]triazolo[4,3-a]quinoxaline;

341 8-(5-Fluoro-3-methyl-1H-indol-7-yl)-1,4,4,7,9-pentamethyl-5H-[1,2,4]triazolo[4,3-a]quinoxaline;

342 7-Fluoro-9-methoxy-1,4,4-trimethyl-8-(1-methylsulfonyl-1H-indazol-4-yl)-5H-[1,2,4]triazolo[4,3-a]quinoxaline;

343 7-(Difluoro-methyl)-9-fluoro-8-(1H-indol-4-yl)-1,4,4-trimethyl-5H-[1,2,4]triazolo[4,3-a]quinoxaline;

344 7-Methoxy-8-[1-(2-methoxy-ethyl)-1H-indol-4-yl]-1,4,4,9-tetramethyl-5H-[1,2,4]triazolo[4,3-a]quinoxaline;

345 8-(5-Fluoro-3-methyl-1H-indol-7-yl)-7-methoxy-1,4,4,9-tetramethyl-5H-[1,2,4]triazolo[4,3-a]quinoxaline;

346 9-(Difluoro-methyl)-7-fluoro-8-(6-fluoro-1-methylsulfonyl-1H-indazol-4-yl)-1,4,4-trimethyl-5H-[1,2,4]triazolo[4,3-a]quinoxaline;

347 7-Chloro-8-(6-fluoro-1-methylsulfonyl-1H-indazol-4-yl)-1,4,4,9-tetramethyl-5H-[1,2,4]triazolo[4,3-a]quinoxaline;

348 1-Ethyl-7-fluoro-8-(6-fluoro-1-methylsulfonyl-1H-indazol-4-yl)-4,4,9-trimethyl-5H-[1,2,4]triazolo[4,3-a]quinoxaline;

351 7-Fluoro-8-[6-fluoro-1-(2-methoxy-ethyl)-1H-indol-4-yl]-9-methoxy-1,4,4-trimethyl-5H-[1,2,4]triazolo[4,3-a]quinoxaline;

353 9-Fluoro-8-[6-fluoro-1-(2-methoxy-ethyl)-1H-indol-4-yl]-7-methoxy-1,4,4-trimethyl-5H-[1,2,4]triazolo[4,3-a]quinoxaline;

354 7,9-Difluoro-1,4,4-trimethyl-8-(3-methyl-1H-indazol-7-yl)-5H-[1,2,4]triazolo[4,3-a]quinoxaline;

356 1,4,4,7,9-Pentamethyl-8-(3-methyl-1H-indol-7-yl)-5H-[1,2,4]triazolo[4,3-a]quinoxaline;

357 7-Methoxy-1,4,4-trimethyl-8-(3-methyl-1H-indol-7-yl)-9-(trifluoromethyl)-5H-[1,2,4]triazolo[4,3-a]quinoxaline;

358 7-Chloro-1,4,4,9-tetramethyl-8-(3-methyl-1H-indol-7-yl)-5H-[1,2,4]triazolo[4,3-a]quinoxaline;

359 9-Fluoro-1,4,4,7-tetramethyl-8-(3-methyl-1H-indol-7-yl)-5H-[1,2,4]triazolo[4,3-a]quinoxaline;

360 7-(Difluoro-methoxy)-1,4,4,9-tetramethyl-8-(3-methyl-1H-indol-7-yl)-5H-[1,2,4]triazolo[4,3-a]quinoxaline;

361 7-Fluoro-1,4,4,9-tetramethyl-8-(3-methyl-1H-indazol-7-yl)-5H-[1,2,4]triazolo[4,3-a]quinoxaline;

362 8-[1-(Ethylsulfonyl)-6-fluoro-1H-indol-4-yl]-7-fluoro-9-methoxy-1,4,4-trimethyl-5H-[1,2,4]triazolo[4,3-a]quinoxaline;

363 7-Chloro-8-(5-fluoro-3-methyl-1H-indol-7-yl)-1,4,4,9-tetramethyl-5H-[1,2,4]triazolo[4,3-a]quinoxaline;

364 9-Fluoro-8-(5-fluoro-3-methyl-1H-indol-7-yl)-1,4,4,7-tetramethyl-5H-[1,2,4]triazolo[4,3-a]quinoxaline;

365 7-(Difluoro-methoxy)-8-(5-fluoro-3-methyl-1H-indol-7-yl)-1,4,4,9-tetramethyl-5H-[1,2,4]triazolo[4,3-a]quinoxaline;

367 9-(Difluoro-methyl)-7-fluoro-1,4,4-trimethyl-8-(3-methyl-1H-indazol-7-yl)-5H-[1,2,4]triazolo[4,3-a]quinoxaline;

368 7-Chloro-1,4,4,9-tetramethyl-8-(3-methyl-1H-indazol-7-yl)-5H-[1,2,4]triazolo[4,3-a]quinoxaline;

369 8-[1-(Ethylsulfonyl)-6-fluoro-1H-indol-4-yl]-7-methoxy-1,4,4-trimethyl-9-(trifluoromethyl)-5H-[1,2,4]triazolo[4,3-a]quinoxaline;

370 8-[1-(Ethylsulfonyl)-6-fluoro-1H-indol-4-yl]-7-fluoro-1,4,4,9-tetramethyl-5H-[1,2,4]triazolo[4,3-a]quinoxaline;

371 8-[1-(Ethylsulfonyl)-1H-indol-4-yl]-7-methoxy-1,4,4-trimethyl-9-(trifluoromethyl)-5H-[1,2,4]triazolo[4,3-a]quinoxaline;

372 8-[1-(Ethylsulfonyl)-1H-indol-4-yl]-7-fluoro-1,4,4,9-tetramethyl-5H-[1,2,4]triazolo[4,3-a]quinoxaline;

373 8-(6-Fluoro-1-methylsulfonyl-1H-indazol-4-yl)-1,4,4,7,9-pentamethyl-5H-[1,2,4]triazolo[4,3-a]quinoxaline;

376 8-(6-Fluoro-1-methylsulfonyl-1H-indazol-4-yl)-7-methoxy-1,4,4-trimethyl-9-(trifluoromethyl)-5H-[1,2,4]triazolo[4,3-a]quinoxaline;

377 7-Fluoro-1,4,4,9-tetramethyl-8-(1-methylsulfonyl-1H-indazol-4-yl)-5H-[1,2,4]triazolo[4,3-a]quinoxaline;

379 2-[6-Fluoro-4-(9-fluoro-7-methoxy-1,4,4-trimethyl-5H-[1,2,4]triazolo[4,3-a]quinoxalin-8-yl)-1H-indol-1-yl]-ethanol;

380 2-[6-Fluoro-4-(7-methoxy-9-methyl-1,4,4-trimethyl-5H-[1,2,4]triazolo[4,3-a]quinoxalin-8-yl)-1H-indol-1-yl]-ethanol;

381 7-Fluoro-9-methoxy-1,4,4-trimethyl-8-(3-methyl-1H-indazol-7-yl)-5H-[1,2,4]triazolo[4,3-a]quinoxaline;

382 9-(Difluoro-methyl)-7-fluoro-1,4,4-trimethyl-8-(1-methylsulfonyl-1H-indazol-4-yl)-5H-[1,2,4]triazolo[4,3-a]quinoxaline;

383 [2-[4-(7,9-Difluoro-1,4,4-trimethyl-5H-[1,2,4]triazolo[4,3-a]quinoxalin-8-yl)-1H-indol-1-yl]-ethyl]-dimethyl-amine;

384 8-[1-(2,2-Difluoro-ethyl)-1H-indol-4-yl]-7-(difluoromethoxy)-1,4,4,9-tetramethyl-5H-[1,2,4]triazolo[4,3-a]quinoxaline;

385 2-[4-[7-(Difluoro-methyl)-9-fluoro-1,4,4-trimethyl-5H-[1,2,4]triazolo[4,3-a]quinoxalin-8-yl]-6-fluoro-1H-indol-1-yl]-ethanol;

386 7-Chloro-1,4,4,9-tetramethyl-8-(1-methylsulfonyl-1H-indazol-4-yl)-5H-[1,2,4]triazolo[4,3-a]quinoxaline;

387 7-Methoxy-1,4,4-trimethyl-8-(1-methylsulfonyl-1H-indazol-4-yl)-9-(trifluoromethyl)-5H-[1,2,4]triazolo[4,3-a]quinoxaline;

388 1,4,4,7,9-Pentamethyl-8-(1-methylsulfonyl-1H-indazol-4-yl)-5H-[1,2,4]triazolo[4,3-a]quinoxaline;

390 9-(Difluoro-methyl)-7-fluoro-8-(6-fluoro-1-methylsulfonyl-1H-indol-4-yl)-1,4,4-trimethyl-5H-[1,2,4]triazolo[4,3-a]quinoxaline;

392 8-[1-(2,2-Difluoro-ethyl)-1H-indol-4-yl]-9-fluoro-1,4,4,7-tetramethyl-5H-[1,2,4]triazolo[4,3-a]quinoxaline;

393 8-[1-(2,2-Difluoro-ethyl)-1H-indol-4-yl]-7-(difluoromethoxy)-9-fluoro-1,4,4-trimethyl-5H-[1,2,4]triazolo[4,3-a]quinoxaline;

394 7-(Difluoro-methoxy)-9-fluoro-8-[6-fluoro-1-(2-methoxy-ethyl)-1H-indol-4-yl]-1,4,4-trimethyl-5H-[1,2,4]triazolo[4,3-a]quinoxaline;

395 2-[4-[7-(Difluoro-methoxy)-9-fluoro-1,4,4-trimethyl-5H-[1,2,4]triazolo[4,3-a]quinoxalin-8-yl]-6-fluoro-1H-indol-1-yl]-ethanol;

396 7-(Difluoro-methyl)-9-fluoro-8-[6-fluoro-1-(2-methoxy-ethyl)-1H-indol-4-yl]-1,4,4-trimethyl-5H-[1,2,4]triazolo[4,3-a]quinoxaline;

397 8-[1-(2,2-Difluoro-ethyl)-1H-indol-4-yl]-7-fluoro-9-methoxy-1,4,4-trimethyl-5H-[1,2,4]triazolo[4,3-a]quinoxaline;

398 8-[1-(2,2-Difluoro-ethyl)-1H-indol-4-yl]-9-(difluoromethyl)-7-fluoro-1,4,4-trimethyl-5H-[1,2,4]triazolo[4,3-a]quinoxaline;

399 7-Fluoro-8-(1H-indol-4-yl)-1,4,4,9-tetramethyl-5H-[1,2,4]triazolo[4,3-a]quinoxaline;

400 9-(Difluoro-methyl)-7-fluoro-8-[1-(isopropylsulfonyl)-1H-indol-4-yl]-1,4,4-trimethyl-5H-[1,2,4]triazolo[4,3-a]quinoxaline;

401 8-[1-(Cyclopropylsulfonyl)-1H-indol-4-yl]-9-(difluoro-methyl)-7-fluoro-1,4,4-trimethyl-5H-[1,2,4]triazolo[4,3-a]quinoxaline;

402 9-(Difluoro-methyl)-7-fluoro-8-[6-fluoro-1-(2-methoxy-ethyl)-1H-indol-4-yl]-1,4,4-trimethyl-5H-[1,2,4]triazolo[4,3-a]quinoxaline;

403 8-(6-Fluoro-1-methylsulfonyl-1H-indol-4-yl)-1,4,4,9-tetramethyl-7-(trifluoromethyloxy)-5H-[1,2,4]triazolo[4,3-a]quinoxaline;

404 7-Chloro-9-fluoro-8-[6-fluoro-1-(2-methoxy-ethyl)-1H-indol-4-yl]-1,4,4-trimethyl-5H-[1,2,4]triazolo[4,3-a]quinoxaline;

405 1,4,4,9-Tetramethyl-8-(3-methyl-1H-indol-7-yl)-7-(trifluoromethyloxy)-5H-[1,2,4]triazolo[4,3-a]quinoxaline;

406 8-(5-Fluoro-3-methyl-1H-indol-7-yl)-1,4,4,9-tetramethyl-7-(trifluoromethyloxy)-5H-[1,2,4]triazolo[4,3-a]quinoxaline;

407 8-(5-Fluoro-3-methyl-1H-indol-7-yl)-7-methoxy-1,4,4-trimethyl-9-(trifluoromethyl)-5H-[1,2,4]triazolo[4,3-a]quinoxaline;

445 7,9-Difluoro-8-(1H-indol-4-yl)-1,4,4-trimethyl-5H-[1,2,4]triazolo[4,3-a]quinoxaline;

446 7-Fluoro-1,4,4-trimethyl-8-(1-methylsulfonyl-1H-indazol-4-yl)-9-(trifluoromethyl)-5H-[1,2,4]triazolo[4,3-a]quinoxaline;

447 2-[6-Fluoro-4-[7-fluoro-1,4,4-trimethyl-9-(trifluoromethyl)-5H-[1,2,4]triazolo[4,3-a]quinoxalin-8-yl]-1H-indol-1-yl]-ethanol;

448 8-[1-(Ethylsulfonyl)-6-fluoro-1H-indazol-4-yl]-7-fluoro-1,4,4-trimethyl-9-(trifluoromethyl)-5H-[1,2,4]triazolo[4,3-a]quinoxaline;

449 2-[6-Fluoro-4-[7-fluoro-1,4,4-trimethyl-9-(trifluoromethyl)-5H-[1,2,4]triazolo[4,3-a]quinoxalin-8-yl]-1H-indazol-1-yl]-ethanol;

450 1,4,4,9-Tetramethyl-8-(1-methylsulfonyl-1H-indol-4-yl)-5H-[1,2,4]triazolo[4,3-a]quinoxaline;

451 2-[6-Fluoro-4-(1,4,4,9-tetramethyl-5H-[1,2,4]triazolo[4,3-a]quinoxalin-8-yl)-1H-indol-1-yl]-ethanol;

452 8-(5-Fluoro-3-methyl-1H-indol-7-yl)-1,4,4,9-tetramethyl-5H-[1,2,4]triazolo[4,3-a]quinoxaline;

453 8-(6-Fluoro-1-methylsulfonyl-1H-indol-4-yl)-1,4,4,9-tetramethyl-5H-[1,2,4]triazolo[4,3-a]quinoxaline;

454 7-Fluoro-8-(6-fluoro-1-methylsulfonyl-1H-indazol-4-yl)-1,4,4-trimethyl-9-(trifluoromethyl)-5H-[1,2,4]triazolo[4,3-a]quinoxaline;
455 8-[1-(Ethylsulfonyl)-1H-indol-4-yl]-7-fluoro-1,4,4-trimethyl-9-(trifluoromethyl)-5H-[1,2,4]triazolo[4,3-a]quinoxaline;
456 2-[4-[7-Fluoro-1,4,4-trimethyl-9-(trifluoromethyl)-5H-[1,2,4]triazolo[4,3-a]quinoxalin-8-yl]-1H-indol-1-yl]-ethanol;
457 1,4,4,9-Tetramethyl-8-(1-methylsulfonyl-1H-indazol-4-yl)-5H-[1,2,4]triazolo[4,3-a]quinoxaline;
458 8-(5-Fluoro-3-methyl-1H-indol-7-yl)-1,4,4,9-tetramethyl-7-(trifluoromethyloxy)-5H-[1,2,4]triazolo[4,3-a]quinoxaline;
459 8-(5-Fluoro-3-methyl-1H-indol-7-yl)-7-methoxy-1,4,4-trimethyl-9-(trifluoromethyl)-5H-[1,2,4]triazolo[4,3-a]quinoxaline;
460 8-[1-(2-Methoxy-ethyl)-1H-indol-4-yl]-1,4,4,9-tetramethyl-7-(trifluoromethyloxy)-5H-[1,2,4]triazolo[4,3-a]quinoxaline;
461 9-(Difluoro-methyl)-8-[1-(ethylsulfonyl)-1H-indol-4-yl]-7-fluoro-1,4,4-trimethyl-5H-[1,2,4]triazolo[4,3-a]quinoxaline;
462 9-Cyclopropyl-7-fluoro-1,4,4-trimethyl-8-(1-methylsulfonyl-1H-indol-4-yl)-5H-[1,2,4]triazolo[4,3-a]quinoxaline;
463 9-Cyclopropyl-7-fluoro-1,4,4-trimethyl-8-(3-methyl-1H-indol-7-yl)-5H-[1,2,4]triazolo[4,3-a]quinoxaline;
464 7-Fluoro-8-(6-fluoro-1H-indol-4-yl)-1,4,4-trimethyl-9-(trifluoromethyl)-5H-[1,2,4]triazolo[4,3-a]quinoxaline;
465 1,4,4,9-Tetramethyl-8-(1-methylsulfonyl-1H-indol-4-yl)-7-(trifluoromethyloxy)-5H-[1,2,4]triazolo[4,3-a]quinoxaline;
466 9-(Difluoro-methyl)-7-fluoro-8-(6-fluoro-1H-indol-4-yl)-1,4,4-trimethyl-5H-[1,2,4]triazolo[4,3-a]quinoxaline;
467 7-Fluoro-8-(1H-indol-4-yl)-1,4,4-trimethyl-9-(trifluoromethyl)-5H-[1,2,4]triazolo[4,3-a]quinoxaline;
468 7-Fluoro-8-(6-fluoro-1H-indol-4-yl)-9-methoxy-1,4,4-trimethyl-5H-[1,2,4]triazolo[4,3-a]quinoxaline;
469 8-[1-(2,2-Difluoro-ethyl)-6-fluoro-1H-indazol-4-yl]-1,4,4,9-tetramethyl-7-(trifluoromethyloxy)-5H-[1,2,4]triazolo[4,3-a]quinoxaline;
470 7-Fluoro-1,4,4,9-tetramethyl-8-[6-(trifluoromethyl)-1H-indol-4-yl]-5H-[1,2,4]triazolo[4,3-a]quinoxaline;
471 2-[6-Fluoro-4-[1,4,4,9-tetramethyl-7-(trifluoromethyloxy)-5H-[1,2,4]triazolo[4,3-a]quinoxalin-8-yl]-1H-indol-1-yl]-ethanol;
472 8-[1-(2,2-Difluoro-ethyl)-6-fluoro-1H-indazol-4-yl]-9-(difluoro-methyl)-7-fluoro-1,4,4-trimethyl-5H-[1,2,4]triazolo[4,3-a]quinoxaline;
473 7-Fluoro-1,4,4-trimethyl-9-(trifluoromethyl)-8-[6-(trifluoromethyl)-1H-indol-4-yl]-5H-[1,2,4]triazolo[4,3-a]quinoxaline;
474 7-Fluoro-9-methoxy-1,4,4-trimethyl-8-[6-(trifluoromethyl)-1H-indol-4-yl]-5H-[1,2,4]triazolo[4,3-a]quinoxaline;
475 7-Chloro-1,4,4,9-tetramethyl-8-[6-(trifluoromethyl)-1H-indol-4-yl]-5H-[1,2,4]triazolo[4,3-a]quinoxaline;
476 7-Fluoro-1,4,4-trimethyl-8-(6-methyl-1-methylsulfonyl-1H-indol-4-yl)-9-(trifluoromethyl)-5H-[1,2,4]triazolo[4,3-a]quinoxaline;
477 7-Fluoro-9-methoxy-1,4,4-trimethyl-8-(6-methyl-1-methylsulfonyl-1H-indol-4-yl)-5H-[1,2,4]triazolo[4,3-a]quinoxaline;
478 9-(Difluoro-methyl)-7-fluoro-1,4,4-trimethyl-8-(6-methyl-1-methylsulfonyl-1H-indol-4-yl)-5H-[1,2,4]triazolo[4,3-a]quinoxaline;
479 4-[7-Fluoro-1,4,4-trimethyl-9-(trifluoromethyl)-5H-[1,2,4]triazolo[4,3-a]quinoxalin-8-yl]-1H-indole-6-carbonitrile;
480 8-[6-Fluoro-1-(2-methoxy-ethyl)-1H-indazol-4-yl]-1,4,4,9-tetramethyl-7-(trifluoromethyloxy)-5H-[1,2,4]triazolo[4,3-a]quinoxaline;
481 9-(Difluoro-methyl)-7-fluoro-1,4,4-trimethyl-8-(1-methyl-1H-indol-4-yl)-5H-[1,2,4]triazolo[4,3-a]quinoxaline;
482 8-(3-Cyclopropyl-5-fluoro-1H-indol-7-yl)-7-methoxy-1,4,4-trimethyl-9-(trifluoromethyl)-5H-[1,2,4]triazolo[4,3-a]quinoxaline;
483 8-(3-Cyclopropyl-5-fluoro-1H-indol-7-yl)-7-fluoro-9-methoxy-1,4,4-trimethyl-5H-[1,2,4]triazolo[4,3-a]quinoxaline;
484 7-Fluoro-8-(7-fluoro-1-methylsulfonyl-1H-indol-4-yl)-1,4,4-trimethyl-9-(trifluoromethyl)-5H-[1,2,4]triazolo[4,3-a]quinoxaline;
485 7-Chloro-8-(3-cyclopropyl-5-fluoro-1H-indol-7-yl)-1,4,4,9-tetramethyl-5H-[1,2,4]triazolo[4,3-a]quinoxaline;
486 7-Fluoro-1,4,4,9-tetramethyl-8-(1-methyl-1H-indol-4-yl)-5H-[1,2,4]triazolo[4,3-a]quinoxaline;
487 7-Fluoro-9-methoxy-1,4,4-trimethyl-8-(1-methyl-1H-indol-4-yl)-5H-[1,2,4]triazolo[4,3-a]quinoxaline;
488 7-Chloro-1,4,4,9-tetramethyl-8-(1-methyl-1H-indol-4-yl)-5H-[1,2,4]triazolo[4,3-a]quinoxaline;
489 8-[1-(2,2-Difluoro-ethyl)-6-fluoro-1H-indazol-4-yl]-7,9-difluoro-1,4,4-trimethyl-5H-[1,2,4]triazolo[4,3-a]quinoxaline;
490 7-Fluoro-8-(1H-indazol-4-yl)-9-methoxy-1,4,4-trimethyl-5H-[1,2,4]triazolo[4,3-a]quinoxaline;
491 7-Chloro-1,4,4,9-tetramethyl-8-(6-methyl-1-methylsulfonyl-1H-indol-4-yl)-5H-[1,2,4]triazolo[4,3-a]quinoxaline;
492 7,9-Difluoro-1,4,4-trimethyl-8-(6-methyl-1-methylsulfonyl-1H-indol-4-yl)-5H-[1,2,4]triazolo[4,3-a]quinoxaline;
493 7-Fluoro-1,4,4,9-tetramethyl-8-(6-methyl-1-methylsulfonyl-1H-indol-4-yl)-5H-[1,2,4]triazolo[4,3-a]quinoxaline;
494 4-(7-Fluoro-1,4,4,9-tetramethyl-5H-[1,2,4]triazolo[4,3-a]quinoxalin-8-yl)-1H-indole-6-carbonitrile;
495 8-[1-(Cyclopropyl-methylsulfonyl)-1H-indol-4-yl]-7-fluoro-1,4,4,9-tetramethyl-5H-[1,2,4]triazolo[4,3-a]quinoxaline;
496 9-(Difluoro-methyl)-7-fluoro-8-(7-fluoro-1H-indol-4-yl)-1,4,4-trimethyl-5H-[1,2,4]triazolo[4,3-a]quinoxaline;
497 7,9-Difluoro-8-(7-fluoro-1H-indol-4-yl)-1,4,4-trimethyl-5H-[1,2,4]triazolo[4,3-a]quinoxaline;
498 1,4,4-Trimethyl-8-(1-methylsulfonyl-1H-indol-4-yl)-9-(trifluoromethyl)-5H-[1,2,4]triazolo[4,3-a]quinoxaline;
499 8-(6-Fluoro-1-methylsulfonyl-1H-indol-4-yl)-1,4,4-trimethyl-9-(trifluoromethyl)-5H-[1,2,4]triazolo[4,3-a]quinoxaline;
500 8-[1-(2,2-Difluoro-ethyl)-1H-indol-4-yl]-7-methoxy-1,4,4-trimethyl-9-(trifluoromethyl)-5H-[1,2,4]triazolo[4,3-a]quinoxaline;
501 7,9-Difluoro-8-(7-fluoro-1H-indazol-4-yl)-1,4,4-trimethyl-5H-[1,2,4]triazolo[4,3-a]quinoxaline;

502 8-[1-(Cyclopropyl-methylsulfonyl)-1H-indol-4-yl]-9-(difluoro-methyl)-7-fluoro-1,4,4-trimethyl-5H-[1,2,4]triazolo[4,3-a]quinoxaline;

503 1,4,4-Trimethyl-8-(3-methyl-1H-indol-7-yl)-9-(trifluoromethyl)-5H-[1,2,4]triazolo[4,3-a]quinoxaline;

504 7-Fluoro-8-(7-fluoro-1H-indol-4-yl)-1,4,4,9-tetramethyl-5H-[1,2,4]triazolo[4,3-a]quinoxaline;

505 7-Fluoro-8-(7-fluoro-1H-indol-4-yl)-1,4,4-trimethyl-9-(trifluoromethyl)-5H-[1,2,4]triazolo[4,3-a]quinoxaline;

506 7-Chloro-8-(7-fluoro-1H-indol-4-yl)-1,4,4,9-tetramethyl-5H-[1,2,4]triazolo[4,3-a]quinoxaline;

507 8-(5-Fluoro-3-methyl-1H-indol-7-yl)-1,4,4-trimethyl-9-(trifluoromethyl)-5H-[1,2,4]triazolo[4,3-a]quinoxaline;

508 7-Chloro-8-[1-(2,2-difluoro-ethyl)-6-fluoro-1H-indazol-4-yl]-9-fluoro-1,4,4-trimethyl-5H-[1,2,4]triazolo[4,3-a]quinoxaline;

509 7-Methoxy-1,4,4-trimethyl-8-(1-methyl-1H-indol-4-yl)-9-(trifluoromethyl)-5H-[1,2,4]triazolo[4,3-a]quinoxaline;

510 7-Fluoro-8-(1H-indazol-4-yl)-1,4,4,9-tetramethyl-5H-[1,2,4]triazolo[4,3-a]quinoxaline;

511 8-(6-Chloro-1H-indol-4-yl)-7,9-difluoro-1,4,4-trimethyl-5H-[1,2,4]triazolo[4,3-a]quinoxaline;

512 9-(Difluoro-methyl)-7-fluoro-1,4,4-trimethyl-8-(7-methyl-1-methylsulfonyl-1H-indol-4-yl)-5H-[1,2,4]triazolo[4,3-a]quinoxaline;

513 8-(6-Chloro-1H-indol-4-yl)-7-fluoro-1,4,4,9-tetramethyl-5H-[1,2,4]triazolo[4,3-a]quinoxaline;

514 8-(1-Cyclopropyl-1H-indol-4-yl)-9-(difluoromethyl)-7-fluoro-1,4,4-trimethyl-5H-[1,2,4]triazolo[4,3-a]quinoxaline;

515 9-(Difluoro-methyl)-7-fluoro-8-(5-fluoro-1H-indol-7-yl)-1,4,4-trimethyl-5H-[1,2,4]triazolo[4,3-a]quinoxaline;

516 7-Fluoro-8-(5-fluoro-1H-indol-7-yl)-1,4,4-trimethyl-9-(trifluoromethyl)-5H-[1,2,4]triazolo[4,3-a]quinoxaline;

517 8-(6-Fluoro-1-methyl-1H-indol-4-yl)-7-methoxy-1,4,4-trimethyl-9-(trifluoromethyl)-5H-[1,2,4]triazolo[4,3-a]quinoxaline;

518 7-Fluoro-8-(6-fluoro-1-methyl-1H-indol-4-yl)-1,4,4,9-tetramethyl-5H-[1,2,4]triazolo[4,3-a]quinoxaline;

519 7-Chloro-8-(6-fluoro-1-methyl-1H-indol-4-yl)-1,4,4,9-tetramethyl-5H-[1,2,4]triazolo[4,3-a]quinoxaline;

520 9-Fluoro-8-(6-fluoro-1-methyl-1H-indol-4-yl)-1,4,4,7-tetramethyl-5H-[1,2,4]triazolo[4,3-a]quinoxaline;

521 9-(Difluoro-methyl)-7-fluoro-8-(6-fluoro-1-methyl-1H-indol-4-yl)-1,4,4-trimethyl-5H-[1,2,4]triazolo[4,3-a]quinoxaline;

522 8-(6-Fluoro-1-methyl-1H-indol-4-yl)-1,4,4-trimethyl-9-(trifluoromethyl)-5H-[1,2,4]triazolo[4,3-a]quinoxaline;

523 8-(1-Cyclopropyl-1H-indol-4-yl)-7-methoxy-1,4,4-trimethyl-9-(trifluoromethyl)-5H-[1,2,4]triazolo[4,3-a]quinoxaline;

524 7-Fluoro-8-(7-fluoro-1H-indazol-4-yl)-1,4,4,9-tetramethyl-5H-[1,2,4]triazolo[4,3-a]quinoxaline;

525 8-(7-Chloro-1-methylsulfonyl-1H-indol-4-yl)-7-fluoro-1,4,4,9-tetramethyl-5H-[1,2,4]triazolo[4,3-a]quinoxaline;

526 9-(Difluoro-methyl)-8-(6-fluoro-1-methylsulfonyl-1H-indol-4-yl)-1,4,4-trimethyl-5H-[1,2,4]triazolo[4,3-a]quinoxaline;

527 9-(Difluoro-methyl)-8-(5-fluoro-3-methyl-1H-indol-7-yl)-1,4,4-trimethyl-5H-[1,2,4]triazolo[4,3-a]quinoxaline;

528 9-(Difluoro-methyl)-1,4,4-trimethyl-8-(1-methylsulfonyl-1H-indol-4-yl)-5H-[1,2,4]triazolo[4,3-a]quinoxaline;

529 8-(7-Chloro-1H-indol-4-yl)-7,9-difluoro-1,4,4-trimethyl-5H-[1,2,4]triazolo[4,3-a]quinoxaline;

530 8-(7-Chloro-1H-indol-4-yl)-7-fluoro-1,4,4-trimethyl-9-(trifluoromethyl)-5H-[1,2,4]triazolo[4,3-a]quinoxaline;

531 4-[7-Fluoro-1,4,4-trimethyl-9-(trifluoromethyl)-5H-[1,2,4]triazolo[4,3-a]quinoxalin-8-yl]-1H-indole-7-carbonitrile;

532 7-Fluoro-8-(6-fluoro-1-methyl-1H-indol-4-yl)-1,4,4-trimethyl-9-(trifluoromethyl)-5H-[1,2,4]triazolo[4,3-a]quinoxaline;

533 7-Chloro-8-(1-cyclopropyl-1H-indol-4-yl)-1,4,4,9-tetramethyl-5H-[1,2,4]triazolo[4,3-a]quinoxaline;

534 4-(7-Fluoro-1,4,4,9-tetramethyl-5H-[1,2,4]triazolo[4,3-a]quinoxalin-8-yl)-1H-indole-7-carbonitrile;

535 7-Fluoro-8-(7-fluoro-1H-indazol-4-yl)-1,4,4-trimethyl-9-(trifluoromethyl)-5H-[1,2,4]triazolo[4,3-a]quinoxaline;

536 7-Fluoro-8-(6-methoxy-1-methylsulfonyl-1H-indol-4-yl)-1,4,4-trimethyl-9-(trifluoromethyl)-5H-[1,2,4]triazolo[4,3-a]quinoxaline; and 537 7-Fluoro-8-(6-methoxy-1-methylsulfonyl-1H-indol-4-yl)-1,4,4,9-tetramethyl-5H-[1,2,4]triazolo[4,3-a]quinoxaline;

in the form of the free compound or a physiologically acceptable salt thereof.

13. A pharmaceutical dosage form comprising a compound according to claim 1.

14. A method for the treatment of pain and/or inflammation in a patient in need thereof, said method comprising administering to said patient an effective amount therefor of a compound according to claim 1.

15. The method according to claim 14, which is conducted for the treatment of inflammatory pain.

16. A pharmaceutical dosage form comprising a compound according to claim 12.

17. A method for the treatment of pain and/or inflammation in a patient in need thereof, said method comprising administering to said patient an effective amount therefor of a compound according to claim 12.

18. The method according to claim 17, which is conducted for the treatment of inflammatory pain.

* * * * *